United States Patent
Dasgupta et al.

(10) Patent No.: US 9,173,871 B2
(45) Date of Patent: *Nov. 3, 2015

(54) OXAZOLE AND THIAZOLE COMPOUNDS AS BETA-CATENIN MODULATORS AND USES THEREOF

(75) Inventors: Ramanuj Dasgupta, New York, NY (US); Foster Gonsalves, Brooklyn, NY (US); Susan Katherine Logan, New York, NY (US); Eugine Lee, New York, NY (US)

(73) Assignee: New York University, New York, NY (US)

( * ) Notice: Subject to any disclaimer, the term of this patent is extended or adjusted under 35 U.S.C. 154(b) by 413 days.

This patent is subject to a terminal disclaimer.

(21) Appl. No.: 13/448,737

(22) Filed: Apr. 17, 2012

(65) Prior Publication Data

US 2012/0264744 A1    Oct. 18, 2012

Related U.S. Application Data

(63) Continuation-in-part of application No. 12/322,070, filed on Jan. 28, 2009, now Pat. No. 8,252,823.

(60) Provisional application No. 61/062,772, filed on Jan. 28, 2008, provisional application No. 61/084,681, filed on Jul. 30, 2008, provisional application No. 61/147,715, filed on Jan. 27, 2009.

(51) Int. Cl.
*A61K 31/42* (2006.01)
*A61K 31/44* (2006.01)
(Continued)

(52) U.S. Cl.
CPC .............. *A61K 31/422* (2013.01); *A61K 31/426* (2013.01); *A61K 31/427* (2013.01); *C07D 263/32* (2013.01); *C07D 413/12* (2013.01)

(58) Field of Classification Search
CPC ........................... A61K 31/421; A61K 31/422
USPC ............................ 514/374, 299, 315, 252.13
See application file for complete search history.

(56) References Cited

U.S. PATENT DOCUMENTS 6,762,185 B1    7/2004    Kahn et al.
7,067,474 B1    6/2006    Birchmeier et al.
(Continued)

FOREIGN PATENT DOCUMENTS

JP    60-208971    10/1985
WO    2006116503    11/2006

OTHER PUBLICATIONS

Clemens et al., "Use of double-stranded RNA interference in Drosophila cell lines to dissect signal transduction pathways", Proceedings of National Academy of Sciences of the United States of America, 2000, vol. 97, No. 12, pp. 6499-6503.
(Continued)

*Primary Examiner* — Shengjun Wang
(74) *Attorney, Agent, or Firm* — Klauber & Jackson LLC

(57) ABSTRACT

A series of oxazole and thiazole compounds are shown herein to be small molecule inhibitors of the Wnt pathway that specifically target the activity of the stabilized pool of β-catenin. Oxazole and thiazole compounds are disclosed that have a formula represented by the following:

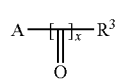

The compounds may be prepared as pharmaceutical compositions, and may be used for the prevention and treatment of a variety of conditions in mammals including humans, including by way of non-limiting example, cancer, and others.

19 Claims, 24 Drawing Sheets

Effect of candidate inhibitors on TOP12-LF in Clone 8 cells

(51) Int. Cl.
  *A61K 31/445* (2006.01)
  *A61K 31/497* (2006.01)
  *A61K 31/422* (2006.01)
  *A61K 31/426* (2006.01)
  *A61K 31/427* (2006.01)
  *C07D 263/32* (2006.01)
  *C07D 413/12* (2006.01)

(56) References Cited

U.S. PATENT DOCUMENTS

| | | |
|---|---|---|
| 8,252,823 B2 * | 8/2012 | Dasgupta et al. ............ 514/374 |
| 2005/0256076 A1 | 11/2005 | Bumcrot |
| 2006/0165699 A1 | 7/2006 | Colland et al. |
| 2011/0251144 A1 | 10/2011 | Moon et al. |

OTHER PUBLICATIONS

Dasgupta et al., "High-throughput RNAi screen in Drosophila", In Wnt Signaling, 2008, vol. II: Pathway Models, (E. Vincan, ed.), vol. 469, pp. 163-184.

Eggert et al., "Parallel chemical genetic and genome-wide RNAi screens identify cytokinesis inhibitors and targets", PLoS Biology, 2004, vol. 2, No. 12, pp. 2135-2143.

Kleino et al., "Pirk is a negative regulator of the Drosophila lmd pathway", The Journal of Immunology, 2008, vol. 180, pp. 5413-5422.

Perrimon et al., "Drug-target identification in Drosophila cells: combining high-throughput RNAi and small-molecule screens", Drug Discovery Today, 2007, vol. 12, Nos. 1-2, pp. 28-33.

Luu et al., "Wnt/Beta-catenin signaling pathway as novel cancer drug targets", Current Cancer Drug Targets, 2004, vol. 4, pp. 653-671.

Lepourcelet et al., "Small-molecule antagonists of the oncogenic Tcf/Beta-catenin protein complex", Cancer Cell, 2004, vol. 5, pp. 91-102.

Barker et al., "Mining the Wnt pathway for cancer therapeutics", Nature Reviews Drug Discovery, 2006, vol. 5, pp. 997-1014.

Watanabe et al., "Winning WNT: Race to Wnt signaling inhibitors", Proc Natl Academy Sciences, 2011, vol. 108, No. 15, pp. 5929-5930.

Gonsalves et al., "An RNAi-based chemical genetic screen identifies three small-molecule inhibitors of the Wnt/wingless signaling pathway", Proc Natl Academy Sciences, 2011, vol. 108, pp. 5954-5973 and Supplemental Information, pp. 1-8.

JP60-208971 Abstract, CAplus, AN 1986:148860t.

ACS registration RN 902585-79-9, 2006.

* cited by examiner

OXAZOLE AND THIAZOLE COMPOUNDS AS BETA-CATENIN MODULATORS AND USES THEREOF

RELATED APPLICATIONS

The present application is a Continuation in Part Application of U.S. application Ser. No. 12/322,070, filed Jan. 28, 2009 now U.S. Pat. No. 8,252,823, which claims priority from U.S. Provisional Application Ser. Nos. 61/062,772, filed Jan. 28, 2008; 61/084,681, filed Jul. 30, 2008; and 61/147,715, filed Jan. 27, 2009. The content of each of said applications is hereby incorporated by reference in its entirety. Priority under 35 U.S.C §§119 and 120 is claimed, and the entire content of each of the above applications is incorporated herein by reference in its entirety.

GOVERNMENT RIGHTS

This invention was made with government support under Grant No. W81XWH-04-1-0460 awarded by the Department of Defense. Accordingly, the United States Government has certain rights in the invention.

FIELD OF THE INVENTION

This invention relates to oxazole and thiazole compounds capable of modulating β-catenin activity and uses of such compounds to modulate the activity of the Wnt/wingless (wg) signaling pathway.

BACKGROUND OF THE INVENTION

Wnts/wingless (wg) are a family of conserved signaling molecules that have been shown to regulate a plethora of fundamental developmental and cell biological processes, including cell proliferation, differentiation and cell polarity [Miller et al. Oncogene 18, 7860-72 (1999); Polakis. Genes Dev 14, 1837-51 (2000); Wodarz et al. Annu Rev Cell Dev Biol 14, 59-88 (1998)]. Mutations in the Wnt genes or in those genes encoding regulators of the Wnt/wg signaling pathway can cause devastating birth defects, including debilitating abnormalities of the central nervous system, axial skeleton, limbs, and occasionally other organs [Ciruna et al. Nature 439, 220-4 (2006); Grove et al. Development 125, 2315-25 (1998); Jiang et al. Dev Dyn 235, 1152-66 (2006); Kokubu et al. Development 131, 5469-80 (2004); Miyoshi et al. Breast Cancer Res 5, 63-8 (2003); Shu et al. Development 129, 4831-42 (2002); Staal et al. Hematol J 1, 3-6 (2000)]. Aberrant Wnt signaling has also been linked to human disease, such as hepatic, colorectal, breast and skin cancers [Miyoshi et al. supra (2003); Miyoshi et al. Oncogene 21, 5548-56 (2002); Moon et al. Nat Rev Genet. 5, 691-701 (2004)]. Activating mutations of beta-catenin have also been found in around 5% of prostate cancers [Chesire et al., *The Prostate* 45, 323 (2000); Voeller et al., *Cancer research* 58, 2520 (1998)]. Mutation of APC has been found in 14% in one study [Gerstein et al., *Genes, chromosomes & cancer* 34, 9 (2002)] and 3% in another [Watanabe et al., *Japanese journal of clinical oncology* 26, 77 (1996)]. Over 20% of advanced prostate cancer, 77% of prostatic lymph node metastases and 85% of prostatic skeletal metastases have been reported to exhibit increased nuclear beta-catenin, as shown by immunohistochemistry [Chen et al., *Cancer* 101, 1345 (2004)]. The ligands of Wnt-pathway, Wnt1, Wnt2 and Wnt5a are, moreover, up-regulated in prostate cancer samples [Chen et al., *Cancer* 101, 1345 (2004); Katoh, *International journal of oncology* 19, 1003 (2001); Usui et al., *Nihon Sanka Fujinka Gakkai zasshi* 44, 703 (1992)]. Immunohistochemistry has revealed that one inhibitor of the Wnt-pathway, WIF1, was down-regulated in prostate cancer [Wissmann et al., *The Journal of pathology* 201, 204 (2003)].

Wnts/wg encode secreted glycoproteins that activate receptor-mediated pathways leading to numerous transcriptional and cellular responses [Wodarz et al. supra (1998); Moon et al. supra (2004); Nusse. Trends Genet. 15, 1-3 (1999)]. The main function of the canonical Wnt pathway is to stabilize the cytoplasmic pool of a key mediator, β-catenin (β-cat)/armadillo (arm), which is otherwise degraded by the proteosome pathway (See FIG. 1). Initially identified as a key player in stabilizing cell-cell adherens junctions, β-cat/arm is also known to act as a transcription factor by forming a complex with the LEF/TCF (Lymphoid Enhancer Factor/T Cell Factor) family of HMG-box (High mobility group) transcription factors. Upon Wnt stimulation, stabilized β-cat/arm translocates to the nucleus, wherein together with LEF/TCF transcription factors, it activates downstream target genes [Miller et al. supra (1999); Staal et al. supra (2000); Nusse. supra (1999); Schweizer et al. Proc Natl Acad Sci USA 100, 5846-51 (2003)]. Catenin responsive transcription (CRT), which is the activation of transcriptional targets of β-cat, has been shown to regulate many aspects of cell growth, proliferation, differentiation and death. The Wnt/wg pathway can also be activated by inhibiting negative regulators such as GSK-3β (Glycogen Synthase Kinase-313), APC (Adenomatous Polyposis Coli) and Axin that promote β-cat/arm degradation, or by introducing activating mutations in β-cat that render it incapable of interacting with the degradation complex, thus stabilizing its cytosolic pool [Logan et al. Annu Rev Cell Dev Biol 20, 781-810 (2004); Nusse et al. Cell Res 15, 28-32 (2005)]. Wnt/wg signaling can also activate an alternative "non-canonical" pathway that may lead to PKC (Protein Kinase C) and INK (c-Jun N-terminal Kinase) activation resulting in calcium release and cytoskeletal rearrangements [Miller et al. supra (1999)].

At the plasma membrane, Wnt proteins bind to their receptor, belonging to the Frizzled family of proteins and the co-receptor encoded by LDL-related-protein-5, 6 (LRP5, LRP6)/arrow (arr, in *Drosophila*) [Schweizer et al. BMC Cell Biol 4, 4 (2003); Tamai et al. Mol Cell 13, 149-56 (2004)]. In the absence of the Wnt stimulus, GSK-3β is known to phosphorylate β-cat/arm, which marks it for ubiquitination and subsequent proteosome-mediated degradation. Activation of the receptor/co-receptor complex upon Wnt binding initiates a signal transduction cascade, which results in phosphorylation and subsequent inactivation of GSK-3β24.

Recent evidence has uncovered a new branch in the canonical Wnt/wg pathway whereby β-cat/arm can be stabilized in a GSK-313 independent fashion suggesting that regulated degradation of β-cat/arm (by GSK-313) is not necessary for Wnt/wg signaling [Tolwinski et al. Dev Cell 4, 407-18 (2003); Tolwinski et al. Trends Genet. 20, 177-81 (2004)]. Specifically, upon Wg binding, Arr directly recruits Axin (a scaffold protein which acts as a negative regulator) to the plasma membrane and causes its degradation. As a consequence, Arm no longer binds Axin or the degradation complex, resulting in nuclear accumulation and signaling by β-cat/Arm42.

A large number of oxazole and thiazole compounds are commercially available.

In view of the above, a need exists for therapeutic agents, and corresponding pharmaceutical compositions and related methods of treatment that address conditions causally related to aberrant Wnt pathway activity and CRT activity, and it is toward the fulfillment and satisfaction of that need, that the present invention is directed.

SUMMARY OF THE INVENTION

Accordingly, the present invention provides a method for preventing, treating or ameliorating in a mammal a disease or condition that is causally related to the aberrant activity of the Wnt pathway in vivo, which comprises administering to the mammal an effective disease-treating or condition-treating amount of a compound according to formula I:

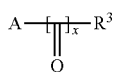

wherein A is $A^1$, $A^2$ or $A^3$;

$A^1$ is

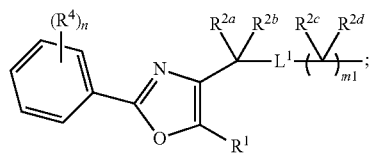

$A^2$ is

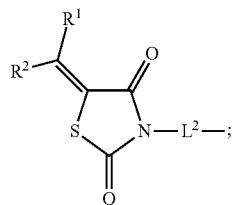

$A^3$ is
x is 1, when A is $A^1$ or $A^2$; or x is 0, when A is $A^3$;
$L^1$ is S, SO or $SO_2$;
m1 is 1, 2 or 3; n is 1, 2, 3, 4 or 5;
$L^2$ is substituted or unsubstituted $C_1$-$C_7$ alkylene or heteroalkylene;
each $R^1$, $R^{2a}$, $R^{2b}$, $R^{2c}$, and $R^{2d}$ is independently selected from hydrogen, halo, and substituted or unsubstituted $C_1$-$C_6$ alkyl;
$R^2$ is selected from aryl or heteroaryl, unsubstituted or substituted with one or more $R^4$;
$R^3$ is hydroxy, alkoxy, substituted or unsubstituted amino or cycloheteroalkyl; or when A is $A^3$, $R^3$ is $R^5$;

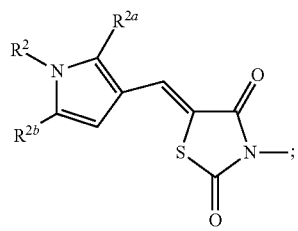

each $R^4$ and $R^{5a}$ is independently selected from H, alkyl, substituted alkyl, acyl, substituted acyl, substituted or unsubstituted acylamino, substituted or unsubstituted alkylamino, substituted or unsubstituted alkylthio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfonyl, substituted or unsubstituted sulfinyl, substituted or unsubstituted sulfanyl, substituted or unsubstituted aminosulfonyl, substituted or unsubstituted arylsulfonyl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol; and $R^5$ is selected from aryl or heteroaryl, unsubstituted or substituted with one or more $R^{5a}$;

or a pharmaceutically acceptable salt, solvate or prodrug thereof;

and stereoisomers, isotopic variants and tautomers thereof.

In one particular embodiment, with respect to compounds of formula I, $A^1$ is

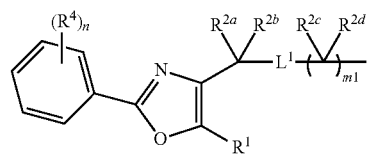

In one particular embodiment, with respect to compounds of formula I, $A^2$ is

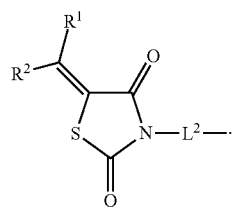

In one particular embodiment, with respect to compounds of formula I, $A^3$ is

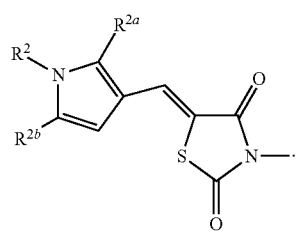

In one particular embodiment, with respect to compounds of formula I, the compound is according to formula IIa:

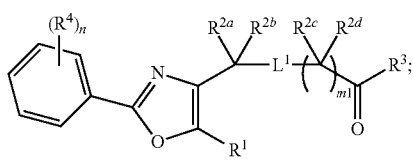

and wherein $L^1$, m1, n, $R^{2a}$, $R^{2b}$, $R^{2c}$, $R^{2d}$, $R^2$, $R^3$, and $R^4$ are as described for formula I.

In one particular embodiment, with respect to compounds of formula I, the compound is according to formula IIb:

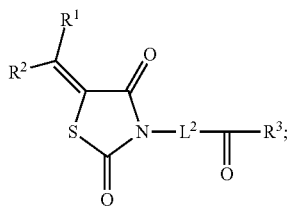

and wherein $L^2$, $R^1$, $R^2$, $R^3$, and $R^4$ are as described for formula I.

In one particular embodiment, with respect to compounds of formula I, the compound is according to formula IIc:

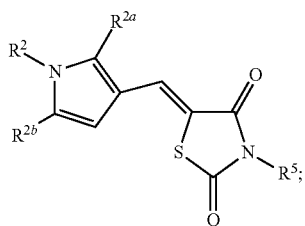

and wherein $R^{2a}$, $R^{2b}$, $R^2$, $R^4$, and $R^5$ are as described for formula I.

In a further aspect, the present invention provides pharmaceutical compositions comprising an oxazole or an thiazole compound of the invention, and a pharmaceutically acceptable carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect, this invention provides the compounds of the invention and other agents for use in the treatment of mammals susceptible to or afflicted with a condition from those listed herein, and particularly, such conditions as may be associated with alterations or aberrations in Wnt/wg pathway signaling.

In addition to the methods of treatment set forth above, the present invention extends to the use of any of the compounds of the invention for the preparation of medicaments that may be administered for such treatments, as well as to such compounds for the treatments disclosed and specified.

A further aspect and object of the invention, is to provide a method of treating a mammal susceptible to or afflicted with a condition from among those listed herein, and particularly, such condition as may be associated with e.g. altered Wnt/wg pathway signaling, by administering to such mammal an effective disease-treating or condition-treating amount of a compound or composition of the invention. Such conditions include, without limitation, a variety of hyperproliferative disorders and cancers, including prostate cancer, colorectal cancer, breast cancer, skin cancer (e.g., melanoma), hepatic cancer (e.g., hepatocellular cancer and hepatoblastoma), head and neck cancer, lung cancer (e.g., non-small cell lung cancer), gastric cancer, mesothelioma, Barrett's esophagus, synovial sarcoma, cervical cancer, endometrial ovarian cancer, Wilm's tumor, bladder cancer and leukemia. Additional support for this aspect of the invention is presented in the fact that most cancers of the skin, intestine, and breast epithelial tissue are a result of increased levels of the activated/signaling pool of β-catenin. Further to the above, evidence for the correlation between increased beta-catenin signaling and disease progression in prostate cancer is evident in the findings that over 20% of advanced prostate cancer, 77% of prostatic lymph node metastases and 85% of prostatic skeletal metastases are reported to have increased nuclear beta-catenin, as shown by immunohistochemistry [Chen et al., *Cancer* 101, 1345 (2004)]. The enhanced crosstalk between AR and beta-catenin pathways has, moreover, been shown in an in vivo model of castrate-resistant prostate cancer [Wang et al., *Cancer Res* 68, 9918 (2008)]. A number of birth defects are also associated with altered Wnt/wg pathway signaling, including debilitating abnormalities of the central nervous system, axial skeleton, limbs, and occasionally other organs.

Other objects and advantages will become apparent to those skilled in the art from a consideration of the ensuing detailed description, which proceeds with reference to the following illustrative drawings.

DETAILED DESCRIPTION OF THE INVENTION

General Introduction

Figure 1:
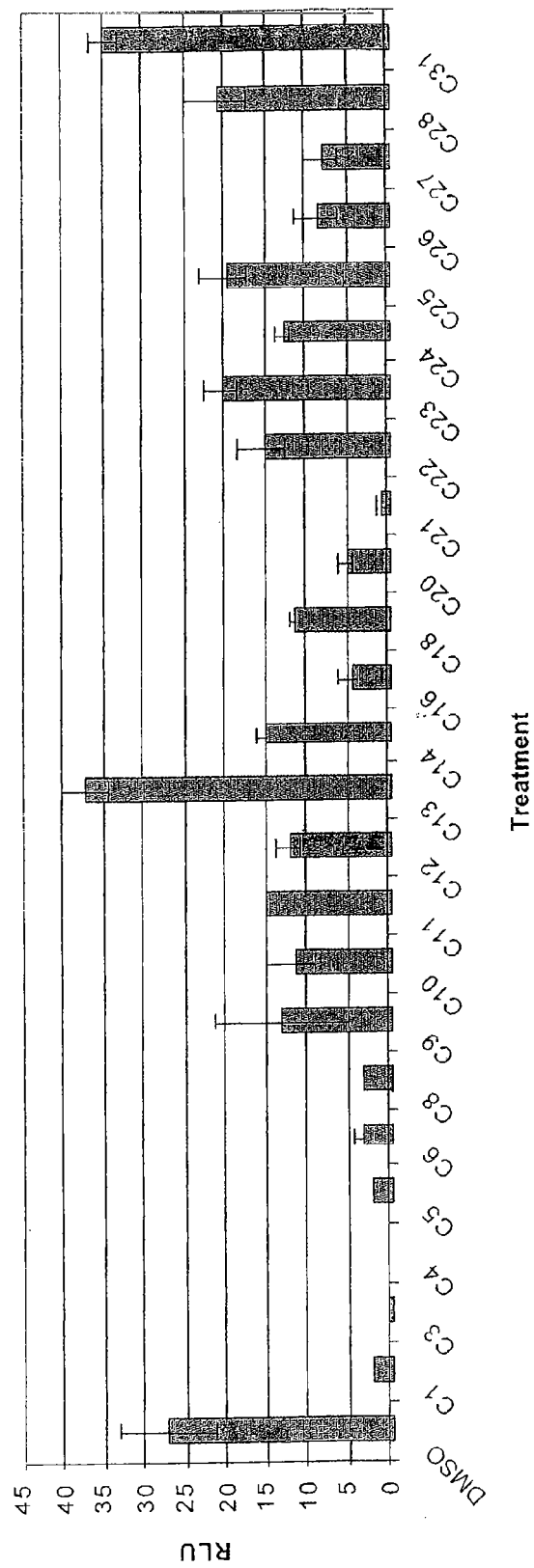
FIG. 1 shows a bar graph depicting the activity of candidate inhibitors on TOP12-LF in Clone 8 cells.

As indicated above, the Wnt pathway is one of a core set of evolutionarily conserved signaling pathways that regulates many aspects of metazoan development. Misregulation or aberrant regulation of the Wnt pathway can lead to adverse effects as demonstrated by the causal relationship identified between mutations in several components of the pathway and tumorigenesis of the liver, colon, breast and the skin [Wang et al., Cancer Res, 2008. 68(23): 9918-27; Beildeck et al., Exp Cell Res, 2010. 316(11): 1763-72; Yu et al., Prostate, 2009. 69(3): 249-62]. Activating mutations of beta-catenin have also been found in around 5% of prostate cancer [Chesire et al., *The Prostate* 45, 323 (2000); Voeller et al., *Cancer*

*research* 58, 2520 (1998)]. Mutation of APC, for example, has been found in 14% of prostate cancer in one study [Gerstein et al., *Genes, chromosomes & cancer* 34, 9 (2002)] and 3% of prostate cancer in another [Watanabe et al., *Japanese journal of clinical oncology* 26, 77 (1996)]. One of the most important effectors of the Wnt pathway is encoded by β-catenin (β-cat)/armadillo (arm). Induction by Wnt ligands leads to stabilization of cytosolic β-cat, which subsequently translocates into the nucleus to activate target genes that regulate many aspects of cell proliferation, growth, differentiation and death.

Since Catenin Responsive Transcription (CRT) has been implicated in the genesis of many cancers, this effector step of the pathway provides a good target for developing therapeutics that could modulate Wnt pathway activity, and more particularly, the nuclear activity of β-cat. Notably, the family of compounds disclosed herein comprises inhibitors that specifically target the activity of the signaling pool of β-catenin.

As indicated herein above, aberrant activation of Wnt signaling has been linked to or causally related with a variety of cancers, including: prostate cancer, colon cancer, rectal cancer, breast cancer, skin cancer (e.g., melanoma), liver cancer (e.g., hepatocellular cancer and hepatoblastoma), head and neck cancer, lung cancer (e.g., non-small cell lung cancer), gastric cancer, mesothelioma, Barrett's esophagus, synovial sarcoma, cervical cancer, endometrial ovarian cancer, Wilm's tumor, bladder cancer and leukemia. See, for example, Luu et al. (2004, Current Cancer Drug Targets 4:653), Lepourcelet et al. (2004, Cancer Cell 5:91), Barker and Clevers (2006, Nature Reviews Drug Discovery 5:997), and Watanabe and Dai (2011, Proc Natl Acad Sci 108:5929), the entire content of each of which is incorporated herein by reference.

In that a strong link has not been established between mutations in the Wnt pathway and prostate cancer, it is informative to review certain aspects of prostate development and prostate cancer development, progression, and treatment to provide insight as to various signaling pathways known to impact this organ. During development, androgens act through the Androgen Receptor (AR) to promote both prostate growth and differentiation. Indeed, maintenance of the prostate organ requires continuous AR and androgen signaling, without which, the prostate regresses. For this reason, aggressive prostate cancer is typically treated with agents that separately block androgen synthesis and inhibit the action of the androgen receptor. However, despite initial regression many cancers recur, making the treatment of what is then called castration-resistant prostate cancer the major challenge in the field. A breakthrough in understanding recurring, resistant disease was the finding that prostate cancer cells become addicted to the AR pathway, and up-regulation of the AR is the major determinate in aggressive castration-resistant prostate cancer [Chen et al., Nat Med, 2004. 10(1): 33-39]. In addition, recent studies show that even under conditions of androgen ablation therapy, prostate cancer cells are able to synthesize androgens locally, through upregulation of androgen synthetic enzymes that direct de novo androgen synthesis or convert adrenal androgens to higher affinity ligands, testosterone and dihydrotestosterone [Titus et al., Clin Cancer Res, 2005. 11(13): 4653-7; Stanbrough et al., Cancer Res, 2006. 66(5): 2815-25; Locke et al., Cancer Res, 2008. 68(15): 6407-15; Montgomery et al., Cancer Res, 2008. 68(11): 4447-54]. The versatility of prostate cancer in evading normal growth controls through altered AR function also encompasses additional mechanisms including generation of novel androgen regulated fusion proteins such as TMPRSS2/ERG [Tomlins et al., Science, 2005. 310(5748): 644-8], production of constitutively active AR splice variants [Dehm et al., Cancer Res, 2008. 68(13): 5469-77] and selection for activating mutations in AR in response to treatment [Steinkamp et al., Cancer Res, 2009. 69(10): 4434-42]. Thus, treatment approaches to develop more effective drugs include agents that block androgen binding to the AR (AR antagonists) such as the MDV3100 compound [Tran et al., Science, 2009. 324 (5928): 787-90; Scher et al., Lancet, 2010. 375(9724): 1437-46] or inhibit synthetic enzymes in the androgen synthesis pathway such as abiraterone acetate [Attard et al., Cancer Res, 2009. 69(12): 4937-40]. An additional promising compound blocks the N-terminal transcriptional regulatory domain of the AR [Andersen et al., Cancer Cell, 2010. 17(6): 535-46]. Despite the promise of these and other reagents, they extend life by only by 4-5 months [de Bono et al., N Engl J Med, 2011. 364(21): 1995-2005] and looking forward, the hope is that a variety of agents can be used synergistically or consecutively to further improve life expectancy.

In the interest of transforming this hope into reality, the present inventors have investigate further the role of the Wnt signaling pathway in prostate cancer by testing small molecule inhibitors of nuclear β-catenin to evaluate to evaluate their ability to repress prostate cancer growth by inhibiting AR function. As described herein, this approach takes advantage of the fact that the AR interacts with, and is transcriptionally regulated by β-catenin. As described herein, β-catenin is an effector of the Wnt family of proteins, an evolutionarily conserved group of signaling molecules that regulates developmental and biological processes [Wodarz et al., Annu Rev Cell Dev Biol, 1998. 14: 59-88; Miller et al., Oncogene, 1999. 18(55): 7860-72; Polakis, Genes Dev, 2000. 14(15): 1837-51]. Wnt signaling results in stabilization and activation of β-catenin, which translocates to the nucleus and together with the T-cell Factor (TCF) family of transcription factors, regulates expression of target genes. Aberrant Wnt/β-catenin signaling has been linked to a number of human cancers [Miyoshi et al., Breast Cancer Res, 2003. 5(2): 63-8; Moon et al., Nat Rev Genet, 2004. 5(9): 691-701] including prostate cancer [Wang et al., Cancer Res, 2008. 68(23): 9918-27; Beildeck et al., Exp Cell Res, 2010. 316(11): 1763-72; Yu et al., Prostate, 2009. 69(3): 249-62].

Seeking to take advantage of the synergy between the AR and β-catenin pathways, the present inventors have investigated the therapeutic efficacy of β-catenin inhibitors as putative prostate cancer agents. The synergy of these pathways occurs via direct and indirect interactions. In sum, the AR binds β-catenin directly to stimulate AR mediated gene transcription [Song et al., J Biol Chem, 2005. 280(45): 37853-67], and androgen causes nuclear translocation of β-catenin in cells that express AR [Mulholland et al., J Biol Chem, 2002. 277(20): 17933-43]. Importantly, the AR gene itself is a target of nuclear β-catenin action through TCF binding sites in the AR promoter [Yang et al., Oncogene, 2006. 25(24): 3436-44]. Further, crosstalk between the AR and β-catenin pathways occurs in castration-resistant prostate cancer [Wang et al., Cancer Res, 2008. 68(23): 9918-27]. Therefore, in theory, β-catenin inhibitors would modulate AR and its target genes as well as direct targets of β-catenin such as c-myc [He et al., Science, 1998. 281(5382): 1509-12], which acts as an oncogene in prostate cancer [Ellwood-Yen et al., Cancer Cell, 2003. 4(3): 223-38; Zhang et al., Prostate, 2000. 43(4): 278-85; Koh et al., Am J Pathol, 2011. 178(4): 1824-34].

As described herein, the present inventors tested the effects of iCRT3, iCRT5 and iCRT14 on prostate cancer cell growth with more extensive analysis performed with iCRT3 due to its specific and dramatic inhibition of prostate cancer cell growth. For simplicity, iCRT3 is referred to herein as C3 with respect to the Examples and drawings pertaining to prostate cancer cell growth. C3 inhibits the Wnt/β-catenin pathway as measured by the β-catenin-responsive luciferase reporter (dTF12) with an $IC_{50}$ of 8.2 nM [Gonsalves et al., Proc Natl Acad Sci USA, 2011. 108(15): 5954-63]. Results presented herein reveal that treatment of prostate cancer cells with C3 results in growth inhibition, diminished AR protein levels, and decreased transcription of AR target genes important in progression of androgen independent cells through the cell cycle [Wang et al., Cell, 2009. 138(2): 245-56]. C3 treatment also results in diminished levels of the c-myc oncogene, a well-characterized Wnt target and prostate cancer oncogene. These results demonstrate that C3 is an important new lead in the development of prostate cancer therapeutics.

An additional important aspect of the use of CRT inhibitors is their potential to target cancer stem cells. Recent studies have shown that small subpopulations of cancer cells, termed "cancer stem cells (CSCs)" or "tumor-initiating cells" based on their ability to self-renew as well as differentiate to a daughter cell type, play a critical role in both initiation and maintenance of tumors. It has been suggested that these cells are resistant to conventional chemotherapy and radiation, making it important to develop new therapeutic approaches to selectively target them [Chandler et al., Stem Cell Res Ther, 2010. 1(2): p. 13; Korkaya et al., Nat Cell Biol, 2010. 12(5): 419-21], perhaps by interfering with cell specific signaling pathways that regulate self-renewal. In prostate cancer, it is possible that CSCs survive after androgen ablation therapy, causing castration-resistant disease [Lawson et al., J Clin Invest, 2007. 117(8): 2044-50]. Growing evidence shows that Wnt/β-catenin signaling is highly active in CSCs, suggesting an important role in stem cell self-renewal [Bisson et al., Cell Res, 2009. 19(6): 683-97; Korkaya et al., PLoS Biol, 2009. 7(6): e1000121]. Together, these data suggest that small molecules such as C3 may target cancer stem cells or tumor initiating cells to inhibit tumor growth.

The physical and functional interaction of AR and β-catenin has been described in a number of reports [Song et al., J Biol Chem, 2005. 280(45): 37853-67; Mulholland et al., J Biol Chem, 2002. 277(20): 17933-43; Pawlowski et al., J Biol Chem, 2002. 277(23): 20702-10; Yang et al., J Biol Chem, 2002. 277(13): 11336-44] along with characterization of the interaction of β-catenin, TIF2/GRIP1 and AR [Song et al., J Biol Chem, 2005. 280(45): 37853-67; Li et al., J Biol Chem, 2004. 279(6): 4212-20]. Thus, while the idea of using small molecule inhibitors of β-catenin/TCF to inhibit both AR and β-catenin targets in prostate cancer may not be new, to the present inventors' knowledge, the proof of principle testing of such small molecules has not been performed. C3 interferes with β-catenin and TCF4 interaction [Gonsalves et al., Proc Natl Acad Sci USA, 2011. 108(15): 5954-63]. The present inventors show herein that C3 also interferes with AR and β-catenin interaction. Importantly, C3 treatment of androgen insensitive cell lines, which serve as a model of castration resistant disease, exhibit reduced AR mRNA and protein levels, resulting in decreased expression of genes involved in AR-dependent cell division [Wang et al., Cell, 2009. 138(2): 245-56], inhibition of cell proliferation and increased apoptosis. C3 also decreases levels of c-myc, a prostate oncogene [Ellwood-Yen et al., Cancer Cell, 2003. 4(3): 223-38; Zhang et al., Prostate, 2000. 43(4): 278-85; Iwata et al., PLoS One, 2010. 5(2): e9427] and β-catenin target gene, which might otherwise be challenging to inhibit. The idea that a single molecule could interfere specifically with multiple pathways dangerously upregulated in prostate cancer is an exciting multi-pronged approach to treatment.

DEFINITIONS

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' or 'Alkanoyl' refers to a radical —C(O)$R^{20}$, where $R^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_4$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)$R^{21}$, wherein $R^{21}$ is independently
  $C_1$-$C_8$ alkyl, substituted with halo or hydroxy; or
  $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Acylamino' refers to a radical —NR$^{22}$C(O)R$^{23}$, where $R^{22}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl and $R^{23}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino Particular exemplary 'acylamino' groups are —NR$^{24}$C(O)—$C_1$-$C_8$ alkyl, —NR$^{24}$C(O)—(CH$_2$)$_t$($C_6$-$C_{10}$ aryl), —NR$^{24}$C(O)—(CH$_2$)$_t$(5-10 membered heteroaryl), —NR$^{24}$C(O)—(CH$_2$)$_t$($C_3$-$C_{10}$ cycloalkyl), and —NR$^{24}$C(O)—(CH$_2$)$_t$(4-10 membered heterocycloalkyl), wherein t is an integer from 0 to 4, and each R$^{24}$ independently represents H or $C_1$-$C_8$ alkyl.

'Substituted Acylamino' refers to a radical —NR$^{25}$C(O)R$^{26}$, wherein:
  R$^{25}$ is independently
  H, $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is independently H, $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl;

provided at least one of $R^{25}$ and $R^{26}$ is other than H.

'Acyloxy' refers to a radical —OC(O)$R^{27}$, where $R^{27}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t(C_6$-$C_{10}$ aryl), —C(O)—$(CH_2)_t$(5-10 membered heteroaryl), —C(O)—$(CH_2)_t(C_3$-$C_{10}$ cycloalkyl), and —C(O)—$(CH_2)_t$(4-10 membered heterocycloalkyl), wherein t is an integer from 0 to 4.

'Substituted Acyloxy' refers to a radical —OC(O)$R^{28}$, wherein $R^{28}$ is independently $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —O$R^{29}$ where $R^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—$(CH_2)_t(C_6$-$C_{10}$ aryl), —O—$(CH_2)_t$(5-10 membered heteroaryl), —O—$(CH_2)_t(C_3$-$C_{10}$ cycloalkyl), and —O—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkoxycarbonyl' refers to a radical —C(O)—O$R^{30}$ where $R^{30}$ represents an $C_1$-$C_8$ alkyl, $C_3$-$C_{10}$ cycloalkyl, $C_3$-$C_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—$C_1$-$C_8$ alkyl, —C(O)O—$(CH_2)_t(C_6$-$C_{10}$ aryl), —C(O)O—$(CH_2)_t$(5-10 membered heteroaryl), —C(O)O—$(CH_2)_t(C_3$-$C_{10}$ cycloalkyl), and —C(O)O—$(CH_2)_t$(4-10 membered heterocycloalkyl), wherein t is an integer from 1 to 4.

'Substituted Alkoxycarbonyl' refers to a radical —C(O)—O$R^{31}$ where $R^{31}$ represents:

$C_1$-$C_8$ alkyl, $C_3$-$C_{10}$ cycloalkyl, $C_3$-$C_{10}$ cycloalkylalkyl, or 4-10 membered heterocycloalkylalkyl, each of which is substituted with halo, substituted or unsubstituted amino, or hydroxy; or $C_6$-$C_{10}$ aralkyl, or 5-10 membered heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Aryloxycarbonyl' refers to a radical —C(O)—O$R^{32}$ where $R^{32}$ represents an $C_6$-$C_{10}$ aryl, as defined herein. Exemplary "aryloxycarbonyl" groups is —C(O)O—$(C_6$-$C_{10}$ aryl).

'Substituted Aryloxycarbonyl' refers to a radical —C(O)—O$R^{33}$ where $R^{33}$ represents $C_6$-$C_{10}$ aryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Heteroaryloxycarbonyl' refers to a radical —C(O)—O$R^{34}$ where $R^{34}$ represents a 5-10 membered heteroaryl, as defined herein. An exemplary "aryloxycarbonyl" group is —C(O)O-(5-10 membered heteroaryl).

'Substituted Heteroaryloxycarbonyl' refers to a radical —C(O)—O$R^{35}$ where $R^{35}$ represents:

5-10 membered heteroaryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

"Alkoxycarbonylamino" refers to the group —N$R^{36}$C(O)O$R^{37}$, where $R^{36}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein, and $R^{37}$ is $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)$R^{20}$), alkoxy, alkoxycarbonyl, alkoxycarbonylamino (—NR-alkoxycarbonyl or —NH—C(O)—O$R^{27}$), amino, substituted amino, aminocarbonyl (carbamoyl or amido or —C(O)—NR"$_2$), aminocarbonylamino (—NR"-C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R''', —SO$_2$NR"R''', —C(O)R''', —C(O)OR''', —OC(O)R''', —NR'''(O)R''', —C(O)NR"R''', —NR"R''', or —(CR'''R'''')$_m$OR'''; wherein each R''' is independently selected from H, $C_1$-$C_8$ alkyl, —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R''' and R'''' independently represents H or $C_1$-$C_8$ alkyl.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

'Substituted alkylene' refers to those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Substituted alkenyl" refers to those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" refers to those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Amino' refers to the radical —NH$_2$.

'Substituted amino' refers to an amino group substituted with one or more of those groups recited in the definition of 'substituted' herein, and particularly refers to the group —N(R$^{38}$)$_2$ where each R$^{38}$ is independently selected from:
hydrogen, $C_1$-$C_8$ alkyl, $C_6$-$C_{10}$ aryl, 5-10 membered heteroaryl, 4-10 membered heterocycloalkyl, or $C_3$-$C_{10}$ cycloalkyl; or
$C_1$-$C_8$ alkyl, substituted with halo or hydroxy; or
—(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl) or —(CH$_2$)$_t$(4-10 membered heterocycloalkyl) wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or
both R$^{38}$ groups are joined to form an alkylene group.

When both R$^{38}$ groups are hydrogen, —N(R$^{38}$)$_2$ is an amino group. Exemplary 'substituted amino' groups are —NR$^{39}$—$C_1$-$C_8$ alkyl, —NR$^{39}$—(CH$_2$)$_t$($C_6$-$C_{10}$ aryl), —NR$^{39}$—(CH$_2$)$_t$(5-10 membered heteroaryl), —NR$^{39}$—(CH$_2$)$_t$($C_3$-$C_{10}$ cycloalkyl), and —NR$^{39}$—(CH$_2$)$_t$(4-10 membered heterocycloalkyl), wherein t is an integer from 0 to 4, each R$^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term "substituted amino" includes the groups alkylamino, substituted alkylamino, alkylarylamino, substituted alkylarylamino, arylamino, substituted arylamino, dialkylamino and substituted dialkylamino as defined below.

'Alkylamino' refers to the group —NHR$^{40}$, wherein R$^{40}$ is $C_1$-$C_8$ alkyl;

'Substituted Alkylamino' refers to the group —NHR$^{41}$, wherein R$^{41}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkylarylamino' refers to the group —NR$^{42}$R$^{43}$, wherein R$^{42}$ is aryl and R$^{43}$ is $C_1$-$C_8$ alkyl.

'Substituted Alkylarylamino' refers to the group —NR$^{44}$R$^{45}$, wherein R$^{44}$ is aryl and R$^{45}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Arylamino' means a radical —NHR$^{46}$ where R$^{46}$ is selected from $C_6$-$C_{10}$ aryl and 5-10 membered heteroaryl as defined herein.

'Substituted Arylamino' refers to the group —NHR$^{47}$, wherein R$^{47}$ is independently selected from $C_6$-$C_{10}$ aryl and 5-10 membered heteroaryl; and any aryl or heteroaryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Dialkylamino' refers to the group —NR$^{48}$R$^{49}$, wherein each of R$^{48}$ and R$^{49}$ are independently selected from $C_1$-$C_8$ alkyl.

'Substituted Dialkylamino' refers to the group —NR$^{50}$R$^{51}$, wherein each of R$^{59}$ and R$^{51}$ are independently selected from $C_1$-$C_8$ alkyl; and at least one of the alkyl groups is independently substituted with halo, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_{1-4}$ haloalkyl, unsubstituted $C_1$-$C_4$ hydroxyalkyl, or unsubstituted $C_1$-$C_4$ haloalkoxy or hydroxy.

'Diarylamino' refers to the group —NR$^{52}$R$^{53}$, wherein each of R$^{52}$ and R$^{53}$ are independently selected from $C_6$-$C_{10}$ aryl.

"Aminosulfonyl" or "Sulfonamide" refers to the radical —S(O$_2$)NH$_2$.

"Substituted aminosulfonyl" or "substituted sulfonamide" refers to a radical such as —S(O$_2$)N(R$^{54}$)$_2$ wherein each R$^{548}$ is independently selected from:

H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy;

provided that at least one R$^{54}$ is other than H.

Exemplary 'substituted aminosulfonyl' or 'substituted sulfonamide' groups are —S(O$_2$)N(R$^{55}$)—$C_1$-$C_8$ alkyl, —S(O$_2$)N(R$^{55}$)—(CH$_2$)$_t$($C_6$-$C_{10}$ aryl), —S(O$_2$)N(R$^{55}$)—(CH$_2$)$_t$(5-10 membered heteroaryl), —S(O$_2$)N(R$^{55}$)—(CH$_2$)$_t$($C_3$-$C_{10}$ cycloalkyl), and —S(O$_2$)N(R$^{55}$)—(CH$_2$)$_t$(4-10 membered heterocycloalkyl), wherein t is an integer from 0 to 4; each R$^{55}$ independently represents H or $C_1$-$C_8$ alkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

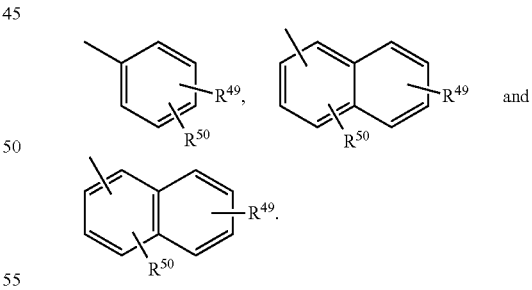

In these formulae one of R$^{56}$ and R$^{57}$ may be hydrogen and at least one of R$^{56}$ and R$^{57}$ is each independently selected from $C_1$-$C_8$ alkyl, $C_1$-$C_8$ haloalkyl, 4-10 membered heterocycloalkyl, alkanoyl, $C_1$-$C_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O or S. R$^{60}$, and $R^{61}$ are independently hydrogen, $C_1$-$C_8$ alkyl, $C_1$-$C_4$ haloalkyl, $C_3$-$C_{10}$ cycloalkyl, 4-10 membered heterocycloalkyl, $C_6$-$C_{10}$ aryl, substituted aryl, 5-10 membered heteroaryl.

"Fused Aryl" refers to an aryl having two of its ring carbon in common with a second aryl ring or with an aliphatic ring.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted $C_1$-$C_4$ alkyl, halo, cyano, unsubstituted $C_1$-$C_4$ alkoxy, unsubstituted $C_{1-4}$ haloalkyl, unsubstituted $C_1$-$C_4$ hydroxyalkyl, or unsubstituted $C_1$-$C_4$ haloalkoxy or hydroxy.

'Azido' refers to the radical —$N_3$.

'Carbamoyl or amido' refers to the radical —C(O)$NH_2$.

'Substituted Carbamoyl or substituted amido' refers to the radical —C(O)N($R^{62}$)$_2$ wherein each $R^{62}$ is independently
H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
$C_1$-$C_8$ alkyl substituted with halo or hydroxy; or
$C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy;
provided that at least one $R^{62}$ is other than H.
Exemplary 'Substituted Carbamoyl' groups are —C(O)$NR^{64}$—$C_1$-$C_8$ alkyl, —C(O)$NR^{64}$—(CH$_2$)$_t$($C_6$-$C_{10}$ aryl), —C(O)$N^{64}$—(CH$_2$)$_t$(5-10 membered heteroaryl), —C(O)$NR^{64}$—(CH$_2$)$_t$($C_3$-$C_{10}$ cycloalkyl), and —C(O)$NR^{64}$—(CH$_2$)$_t$(4-10 membered heterocycloalkyl), wherein t is an integer from 0 to 4, each $R^{64}$ independently represents H or $C_1$-$C_8$ alkyl and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Carboxy' refers to the radical —C(O)OH.

'Cycloalky' refers to cyclic non-aromatic hydrocarbyl groups having from 3 to 10 carbon atoms. Such cycloalkyl groups include, by way of example, single ring structures such as cyclopropyl, cyclobutyl, cyclopentyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent 'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

Heteroaryl means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

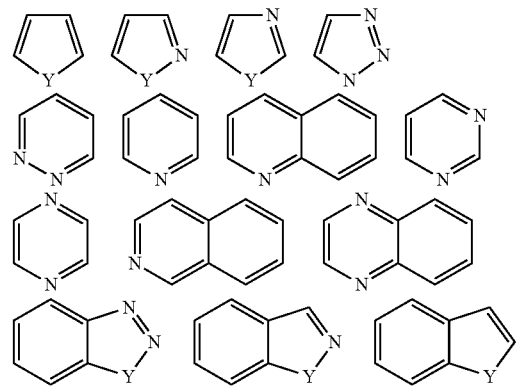

wherein each Y is selected from carbonyl, N, $NR^{65}$, O and S; and $R^{65}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative aryl having hetero atoms containing substitution include the following:

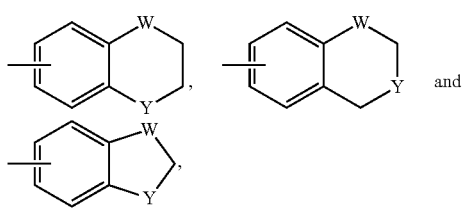

wherein each W is selected from $C(R^{66})_2$, $NR^{66}$, O and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

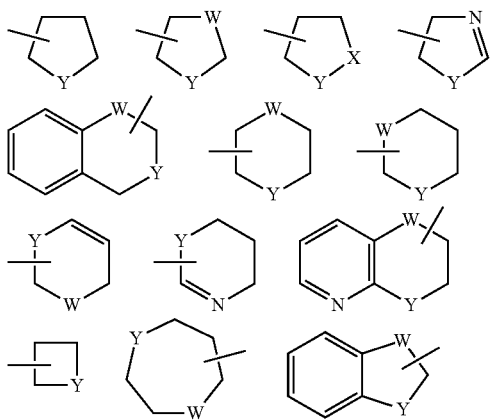

wherein each W is selected from $CR^{67}$, $C(R^{67})_2$, $NR^{67}$, O and S; and each Y is selected from $NR^{67}$, O and S; and $R^{67}$ is independently hydrogen, $C_1$-$C_8$ alkyl, $C_3$-$C_{10}$ cycloalkyl, 4-10 membered heterocycloalkyl, $C_6$-$C_{10}$ aryl, 5-10 membered heteroaryl, These heterocycloalkyl rings may be optionally substituted with one or more groups selected from the group consisting of: acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents may be selected from the group consisting of:

halogen, —$R^{68}$, —O$^-$, =O, —O$R^{68}$, —S$R^{68}$, —S$^-$, =S, —N$R^{68}R^{69}$, =N$R^{68}$, —CCl$_3$, —CF$_3$, —CN, —OCN, —SCN, —NO, —NO$_2$, =N$_2$, —N$_3$, —S(O)$_2$O, —S(O)$_2$OH, —S(O)$_2R^{68}$, —OS(O)$_2R^{68}$)$_2$, —P(O)(O$R^{68}$)(O), —OP(O)(O$R^{68}$)(O$R^{69}$), —C(O)$R^{68}$, —C(S)$R^{68}$, —C(O)O$R^{68}$, —C(O)N$R^{68}R^{69}$, —C(O)O$^-$, —C(S)O$R^{68}$, —N$R^{70}$C(O)N$R^{68}R^{69}$, —N$R^7$OC(S)N$R^{68}R^{69}$, —N$R^{71}$C(N$R^{70}$)N$R^{68}R^{69}$ and —C(N$R^{70}$)N$R^{68}R^{69}$;

wherein each $R^{68}$, $R^{69}$, $R^{79}$ and $R^{71}$ are independently:

hydrogen, $C_1$-$C_8$ alkyl, $C_6$-$C_{10}$ aryl, arylalkyl, $C_3$-$C_{10}$ cycloalkyl, 4-10 membered heterocycloalkyl, 5-10 membered heteroaryl, heteroarylalkyl; or $C_1$-$C_8$ alkyl substituted with halo or hydroxy; or $C_6$-$C_{10}$ aryl, 5-10 membered heteroaryl, $C_6$-$C_{10}$ cycloalkyl or 4-10 membered heterocycloalkyl each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from halo, cyano, nitro, trifluoromethyl, trifluoromethoxy, azido, —N$R^{72}$SO$_2R^{73}$, —SO$_2$N$R^{73}R^{72}$, —C(O)$R^{73}$, —C(O)O$R^{73}$, —OC(O)$R^{73}$, —N$R^{72}$C(O)$R^{73}$, —C(O)N$R^{73}R^{72}$, —N$R^{73}R^{72}$, —(C$R^{72}R^{72}$)$_m$O$R^{72}$, wherein, each $R^{73}$ is independently selected from H, $C_1$-$C_8$ alkyl, —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), and —(CH$_2$)$_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each R" independently represents H or $C_1$-$C_6$alkyl.

'Substituted sulfanyl' refers to the group —S$R^{74}$, wherein $R^{74}$ is selected from:

$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo, substituted or unsubstituted amino, or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfanyl' groups are —S—($C_1$-$C_8$ alkyl) and —S—($C_3$-$C_{10}$ cycloalkyl), —S—(CH$_2$)$_t$($C_6$-$C_{10}$ aryl), —S—(CH$_2$)$_t$(5-10 membered heteroaryl), —S—

$(CH_2)_t(C_3$-$C_{10}$ cycloalkyl), and —S—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —$SR^{75}$ where $R^{75}$ is a $C_1$-$C_8$ alkyl or group as defined herein. Representative examples include, but are not limited to, methylthio, ethylthio, propylthio and butylthio.

'Substituted Alkylthio' or 'substituted alkylsulfanyl' refers to the group —$SR^{76}$ SIC where $R^{76}$ is a $C_1$-$C_8$ alkyl, substituted with halo, substituted or unsubstituted amino, or hydroxy.

'Cycloalkylthio' or 'Cycloalkylsulfanyl' refers to a radical —$SR^{77}$ where $R^{77}$ is a $C_3$-$C_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —$SR^{78}$ where $R^{78}$ is a $C_3$-$C_{10}$ cycloalkyl, substituted with halo, substituted or unsubstituted amino, or hydroxy.

'Arylthio' or 'Arylsulfanyl' refers to a radical —$SR^{79}$ where $R^{79}$ is a $C_6$-$C_{10}$ aryl group as defined herein.

'Heteroarylthio' or 'Heteroarylsulfanyl' refers to a radical —$SR^{80}$ where $R^{80}$ is a 5-10 membered heteroaryl group as defined herein.

'Substituted sulfinyl' refers to the group —$S(O)R^{81}$, wherein $R^{81}$ is selected from:
  $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
  $C_1$-$C_8$ alkyl substituted with halo, substituted or unsubstituted amino, or hydroxy; or
  $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfinyl' groups are —$S(O)$—($C_1$-$C_8$ alkyl) and —$S(O)$—($C_3$-$C_{10}$ cycloalkyl), —$S(O)$—$(CH_2)_t(C_6$-$C_{10}$ aryl), —$S(O)$—$(CH_2)_t$(5-10 membered heteroaryl), —$S(O)$—$(CH_2)_t(C_3$-$C_{10}$ cycloalkyl), and —$S(O)$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —$S(O)R^{82}$ where $R^{82}$ is a $C_1$-$C_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —$S(O)R^{83}$ where $R^{83}$ is a $C_1$-$C_8$ alkyl group as defined herein, substituted with halo, substituted or unsubstituted amino, or hydroxy.

'Cycloalkylsulfinyl' refers to a radical —$S(O)R^{84}$ where $R^{84}$ is a $C_3$-$C_{10}$ cycloalkyl or group as defined herein. Representative examples include, but are not limited to, cyclopropylsulfinyl, cyclohexylsulfinyl, and cyclopentylsulfinyl Exemplary 'cycloalkylsulfinyl' groups are $S(O)$—$C_3$-$C_{10}$ cycloalkyl.

'Substituted cycloalkylsulfinyl' refers to the group —$S(O)R^{85}$ where $R^{85}$ is a $C_3$-$C_{10}$ cycloalkyl, substituted with halo, substituted or unsubstituted amino, or hydroxy.

'Arylsulfinyl' refers to a radical —$S(O)R^{86}$ where $R^{86}$ is a $C_6$-$C_{10}$ aryl group as defined herein.

'Heteroarylsulfinyl' refers to a radical —$S(O)R^{87}$ where $R^{87}$ is a 5-10 membered heteroaryl group as defined herein.

'Substituted sulfonyl' refers to the group —$S(O)_2R^{88}$, wherein $R^{88}$ is selected from:
  $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
  $C_1$-$C_8$ alkyl substituted with halo, substituted or unsubstituted amino, or hydroxy; or
  $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfonyl' groups are —$S(O)_2$—($C_1$-$C_8$ alkyl) and —$S(O)_2$—($C_3$-$C_{10}$ cycloalkyl), —$S(O)_2$—$(CH_2)_t(C_6$-$C_{10}$ aryl), —$S(O)_2$—$(CH_2)_t$(5-10 membered heteroaryl), —$S(O)_2$—$(CH_2)_t(C_3$-$C_{10}$ cycloalkyl), and —$S(O)_2$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —$S(O)_2R^{89}$ where $R^{89}$ is an $C_1$-$C_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —$S(O)_2R^{90}$ where $R^{90}$ is an $C_1$-$C_8$ alkyl group as defined herein, substituted with halo, substituted or unsubstituted amino, or hydroxy.

'Cycloalkylsulfonyl' refers to a radical —$S(O)_2R^{91}$ where $R^{91}$ is a $C_3$-$C_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —$S(O)_2R^{92}$ where $R^{92}$ is a $C_3$-$C_{10}$ cycloalkyl, substituted with halo, substituted or unsubstituted amino, or hydroxy.

'Arylsulfonyl' refers to a radical —$S(O)_2R^{93}$ where $R^{93}$ is an $C_6$-$C_{10}$ aryl group as defined herein.

'Heteroarylsulfonyl' refers to a radical —$S(O)_2R^{94}$ where $R^{94}$ is an 5-10 membered heteroaryl group as defined herein.

'Sulfo' or 'sulfonic acid' refers to a radical such as —$SO_3H$.

'Substituted sulfo' or 'sulfonic acid ester' refers to the group —$S(O)_2OR^{95}$, wherein $R^{95}$ is selected from:

$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo, substituted or unsubstituted amino, or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'Substituted sulfo' or 'sulfonic acid ester' groups are —S(O)$_2$—O—($C_1$-$C_8$ alkyl) and —S(O)$_2$—O—($C_3$-$C_{10}$ cycloalkyl), —S(O)$_2$—O—(CH$_2$)$_t$($C_6$-$C_{10}$ aryl), —S(O)$_2$—O—(CH$_2$)$_t$(5-10 membered heteroaryl), —S(O)$_2$—O—(CH$_2$)$_t$($C_3$-$C_{10}$ cycloalkyl), and —S(O)$_2$—O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Thiol' refers to the group —SH.

'Aminocarbonylamino' refers to the group —NR$^{96}$C(O)NR$^{96}$R$^{96}$ where each R$^{96}$ is independently hydrogen $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl, as defined herein; or where two R$^{96}$ groups, when attached to the same N, are joined to form an alkylene group.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

'Compounds of the present invention', and equivalent expressions, are meant to embrace the compounds as hereinbefore described, in particular compounds according to any of the formulae herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

'Cycloalkylalkyl' refers to a radical in which a cycloalkyl group is substituted for a hydrogen atom of an alkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

'Heterocycloalkylalkyl' refers to a radical in which a heterocycloalkyl group is substituted for a hydrogen atom of an alkyl group. Typical heterocycloalkylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

'Substituted cycloalkenyl' refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Ethenyl' refers to substituted or unsubstituted —(C=C)—.

'Ethylene' refers to substituted or unsubstituted —(C—C)—.

'Ethynyl' refers to —(C≡C)—.

'Hydrogen bond donor' group refers to a group containing O—H, or N—H functionality. Examples of 'hydrogen bond donor' groups include —OH, —NH$_2$, and —NH—R$^{97}$ and wherein R$^{97}$ is alkyl, acyl, cycloalkyl, aryl, or heteroaryl.

'Dihydroxyphosphoryl' refers to the radical —PO(OH)$_2$.

'Substituted dihydroxyphosphoryl' refers to those groups recited in the definition of "substituted" herein, and particularly refers to a dihydroxyphosphoryl radical wherein one or both of the hydroxyl groups are substituted. Suitable substituents are described in detail below.

'Aminohydroxyphosphoryl' refers to the radical —PO(OH)NH$_2$.

'Substituted aminohydroxyphosphoryl' refers to those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

'Nitrogen-Containing Heterocycloalkyl' group means a 4 to 7 membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

'Thioketo' refers to the group =S.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like.

The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

The term "cancer" is used herein refer to any cellular malignancy characterized by unregulated proliferation, lack of differentiation or dedifferentiation and the ability to invade local tissues and metastasize. Cancer can develop in any tissue of any organ. More specifically, cancer is intended to include, without limitation, prostate cancer, colon cancer, rectal cancer, breast cancer, skin cancer (e.g., melanoma), liver cancer (e.g., hepatocellular cancer and hepatoblastoma), head and neck cancer, lung cancer (e.g., non-small cell lung cancer), gastric cancer, mesothelioma, Barrett's esophagus, synovial sarcoma, cervical cancer, endometrial ovarian cancer, Wilm's tumor, bladder cancer and leukemia.

The term "prostate cancer" is used herein to refer to an uncontrolled (malignant) growth of cells in the prostate gland, which is located at the base of the urinary bladder and is responsible for forming part of the semen. Prostate cancer is typically classified by a Gleason score, a histological analysis of the grade or severity of the cancer.

The term "metastasis" is used herein to refer to a cancer that has spread beyond the tissue of origin, for example, the prostate. "Metastasis" is also intended to mean the process by which cancer spreads from one part of the body to another, the way it travels from the place at which it first arose as a primary tumor to distant locations in the body.

'Compounds of the present invention', and equivalent expressions, are meant to embrace compounds of the Formula (e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'.

When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides a method for preventing, treating or ameliorating in a mammal a disease or condition that is causally related to the aberrant activity of the Wnt signaling pathway in vivo, which comprises administering to the mammal an effective disease-treating or condition-treating amount of a compound according to formula I:

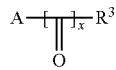

I wherein A is $A^1$, $A^2$ or $A^3$;

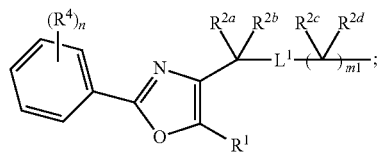

$A^1$ is

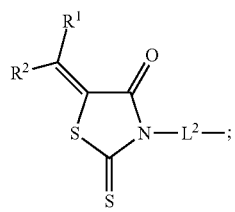

$A^2$ is

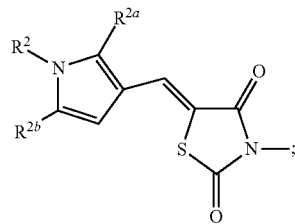

$A^3$ is x is 1, when A is $A^1$ or $A^2$; or x is 0, when A is $A^3$;

$L^1$ is S, SO or $SO_2$;

m1 is 1, 2 or 3; n is 1, 2, 3, 4 or 5;

$L^2$ is substituted or unsubstituted $C_1$-$C_7$ alkylene or heteroalkylene;

each $R^1$, $R^{2a}$, $R^{2b}$, $R^{2c}$, and $R^{2d}$ is independently selected from hydrogen, halo, and substituted or unsubstituted $C_1$-$C_6$ alkyl;

$R^2$ is selected from aryl or heteroaryl, unsubstituted or substituted with one or more $R^4$;

$R^3$ is hydroxy, alkoxy, substituted or unsubstituted amino or cycloheteroalkyl; or when A is $A^3$, $R^3$ is $R^5$;

each $R^4$ and $R^{5a}$ is independently selected from H, alkyl, substituted alkyl, acyl, substituted acyl, substituted or unsubstituted acylamino, substituted or unsubstituted alkylamino, substituted or unsubstituted alkylhio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfonyl, substituted or unsubstituted sulfinyl, substituted or unsubstituted sulfanyl, substituted or unsubstituted aminosulfonyl, substituted or unsubstituted arylsulfonyl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol; and $R^5$ is selected from aryl or heteroaryl, unsubstituted or substituted with one or more $R^{5a}$;

or a pharmaceutically acceptable salt, solvate or prodrug thereof;

and stereoisomers, isotopic variants and tautomers thereof.

In one particular embodiment, with respect to compounds of formula I, $A^1$ is

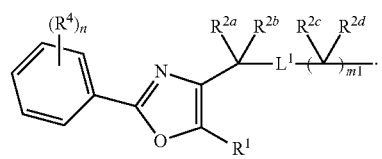

In one particular embodiment, with respect to compounds of formula I, $A^2$ is

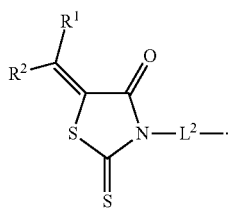

In one particular embodiment, with respect to compounds of formula I, $A^3$ is

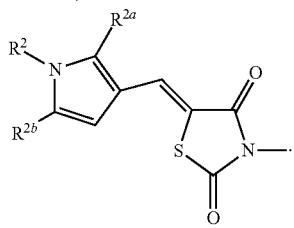

In one particular embodiment, with respect to compounds of formula I, the compound is according to formula IIa:

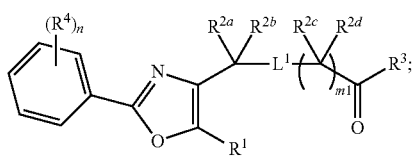

and wherein $L^1$, m1, n, $R^{2a}$, $R^{2b}$, $R^{2c}$, $R^{2d}$, $R^2$, $R^3$, and $R^4$ are as described for formula I.

In one particular embodiment, with respect to compounds of formula I, the compound is according to formula IIb:

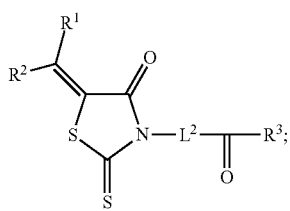

and wherein $L^2$, $R^1$, $R^2$, $R^3$, and $R^4$ are as described for formula I.

In one particular embodiment, with respect to compounds of formula I, the compound is according to formula IIc:

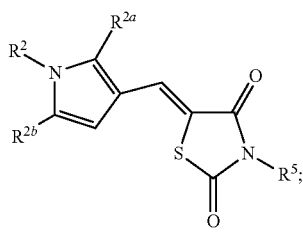

and wherein $R^{2a}$, $R^{2b}$, $R^2$, $R^4$, and $R^5$ are as described for formula.

In one particular embodiment, with respect to compounds of formula IIa; $L^1$ is S.

In one particular embodiment, with respect to compounds of formula IIa; $L^1$ is SO or $SO_2$.

In one particular embodiment, with respect to compounds of formula IIa or IIc; each of $R^{2a}$ and $R^{2b}$ is H.

In one particular embodiment, with respect to compounds of formula IIa or IIc; one of $R^{2a}$ and $R^{2b}$ is independently Me and the other is H.

In one particular embodiment, with respect to compounds of formula IIa or IIc; each of $R^{2a}$ and $R^{2b}$ is Me.

In one particular embodiment with respect to compounds of formula IIa; the subscript m1 is 1 or 2; and each of $R^{2c}$ and $R^{2d}$ is H.

In one particular embodiment, with respect to compounds of formula IIa; the subscript m1 is 1 or 2; and each of $R^{2c}$ and $R^{2d}$ is independently Me and the other is H.

In one particular embodiment, with respect to compounds of formula IIa; the subscript m1 is 1 or 2; and each of $R^{2c}$ and $R^{2d}$ is Me.

In one particular embodiment, with respect to compounds of formula IIa; $L^1$ is S; the subscript m1 is 1; and each of $R^{2a}$, $R^{2b}$, $R^{2c}$ and $R^{2d}$ is H.

In one particular embodiment, with respect to compounds of formula IIb; $L^2$ is —$CH_2$—, —$CH_2$—$CH_2$—, —$CH_2$—$CH_2$—$CH_2$—, or —$CH_2$—$CH_2$—$CH_2$—$CH_2$—.

In one particular embodiment, with respect to compounds of formula I, the compound is according to formula IIc.

In one particular embodiment, with respect to compounds of formula IIb or IIc, $R^2$ is phenyl, unsubstituted or substituted with one or more $R^4$.

In one particular embodiment, with respect to compounds of formula IIb or IIc, $R^2$ is heteroaryl, unsubstituted or substituted with one or more $R^4$.

In one particular embodiment, with respect to compounds of formula IIb or IIc, $R^2$ is pyridyl, furanyl, thiophenyl, or pyrrolidinyl, unsubstituted or substituted with one or more $R^4$.

In one particular embodiment, with respect to compounds of formula IIc, $R^5$ is phenyl, unsubstituted or substituted with one or more $R^4$.

In one particular embodiment, with respect to compounds of formula IIc, $R^5$ is heteroaryl, unsubstituted or substituted with one or more $R^4$.

In one particular embodiment, with respect to compounds of formula IIc, $R^5$ is pyridyl, furanyl, thiophenyl, or pyrrolidinyl, unsubstituted or substituted with one or more $R^4$.

In one particular embodiment, with respect to compounds of formula IIa or IIb; $R^1$ is H or substituted or unsubstituted $C_1$-$C_6$ alkyl.

In one particular embodiment, with respect to compounds of formula IIa or IIb; $R^1$ is halo.

In one particular embodiment, with respect to compounds of formula IIa or IIb; $R^1$ is Me.

In one particular embodiment, with respect to compounds of formula IIa or IIb; $R^3$ is OH.

In one particular embodiment, with respect to compounds of formula IIa or IIb; $R^3$ is alkoxy.

In one particular embodiment, with respect to compounds of formula IIa or IIb; $R^3$ is substituted or unsubstituted amino.

In one particular embodiment, with respect to compounds of formula IIa or IIb; $R^3$ is $NR^{3a}R^{3b}$; and each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ join together to form a cycloheteroalkyl heteroaryl ring.

In one particular embodiment, with respect to compounds of formula I, the compound is according to formulae IIIa, IIIb, IIIc, IIId, IIIe, or IIIf:

IIIa
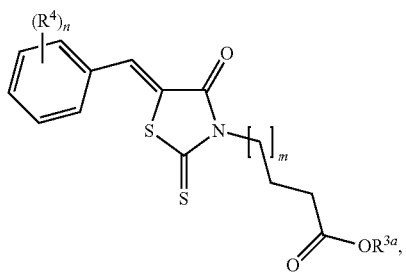

IIIb
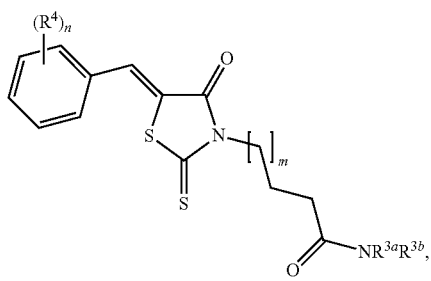

IIIc
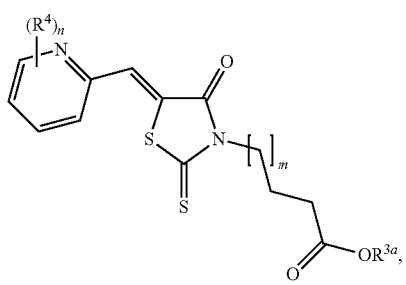

IIId
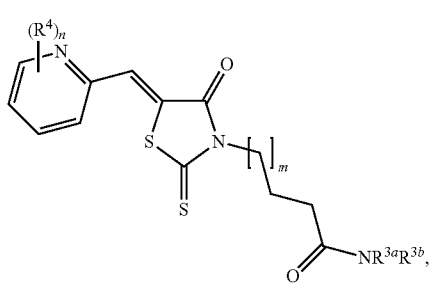

IIIe
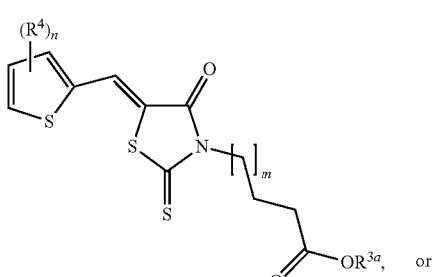 or

IIIf
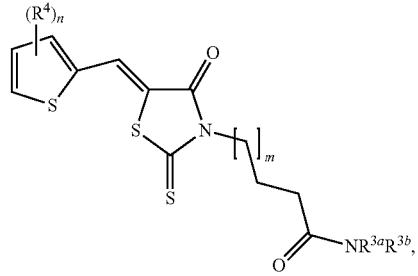

wherein n and $R^4$ are as described for formula I; $R^{3a}$ and $R^{3b}$ are as described above; and m is 0 or 1.

In one particular embodiment, with respect to compounds of formula I, the compound is according to formula IVa, IVb, or IVc:

IVa
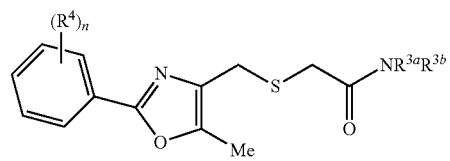

IVb
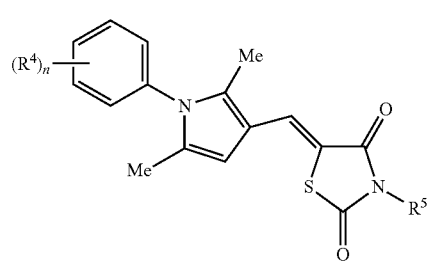

or

IVc
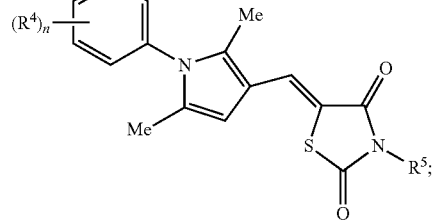

wherein n, $R^4$, and $R^5$ as described for formula I; and $R^{3a}$ and $R^{3b}$ as described above.

In one particular embodiment, with respect to compounds of formula IIa-IVc, each of $R^4$ is H.

In one particular embodiment, with respect to compounds of formula IIa-IVc, n, when present, is 1; and $R^4$ is alkyl, alkoxy, haloalkyl, or halo.

In one particular embodiment, with respect to compounds of formula IIa-IVc, n, when present, is 1 or 2; and $R^4$ is Me, Et, i-Pr, OMe, OEt, O-i-Pr, Cl, or F.

In one particular embodiment, with respect to compounds of formula IIa-IVc, n, when present, is 1 or 2; and $R^4$ is Me, OMe, SMe, or Et.

In one particular embodiment, with respect to compounds of formula I, the compound is according to formulae Va, Vb, Vc, Vd, Ve or Vf:

Va 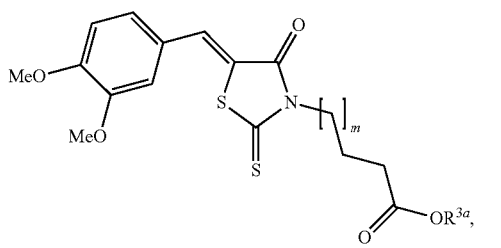

Vb 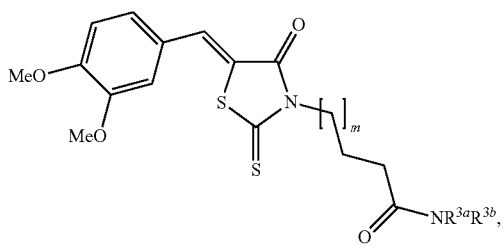

Vc 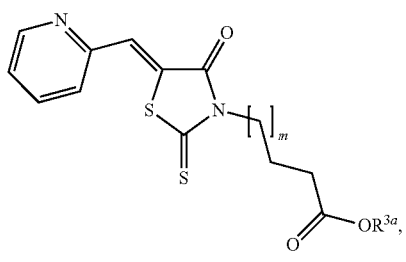

Vd 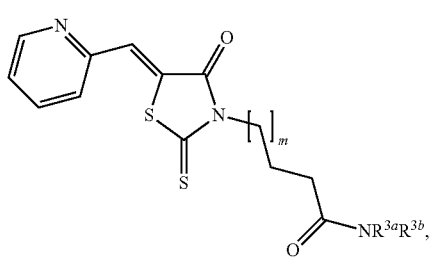

Ve 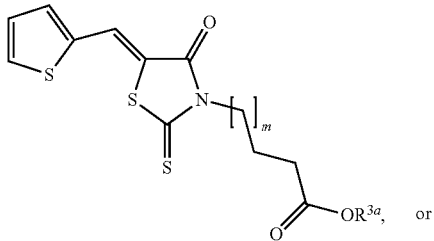

Vf 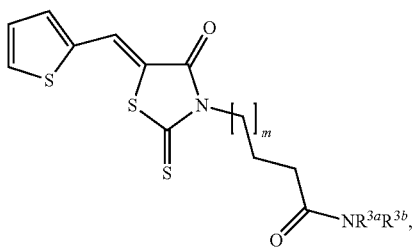

wherein $R^{3a}$ and $R^{3b}$ are as described above; and m is 0 or 1.

In one particular embodiment, with respect to compounds of formula IIIb, IIId, IIIf, IVa, Vb, Vd, or Vf, $R^{3a}$ is H.

In one particular embodiment, with respect to compounds of formula IIIb, IIId, IIIf, IVa, Vb, Vd, or Vf, $R^{3a}$ is substituted or unsubstituted alkyl.

In one particular embodiment, with respect to compounds of formula IIIb, IIId, IIIf, IVa, Vb, Vd, or Vf, $R^{3a}$ is substituted or unsubstituted benzyl.

In one particular embodiment, with respect to compounds of formula IIIb, IIId, IIIf, IVa, Vb, Vd, or Vf, $R^{3a}$ is substituted or unsubstituted phenethyl.

In one particular embodiment, with respect to compounds of formula IIIb, IIId, IIIf, IVa, Vb, Vd, or Vf, $R^{3a}$ is substituted or unsubstituted cycloalkyl.

In one particular embodiment, with respect to compounds of formula IIIb, IIId, IIIf, IVa, Vb, Vd, or Vf, $R^{3a}$ is cyclopropyl.

In one particular embodiment, with respect to compounds of formula IIIb, IIId, IIIf, IVa, Vb, Vd, or Vf; $R^{3b}$ is substituted or unsubstituted heteroaryl.

In one particular embodiment, with respect to compounds of formula IIIb, IIId, IIIf, IVa, Vb, Vd, or Vf; $R^{3b}$ is substituted or unsubstituted heterocycloalkyl.

In one particular embodiment, with respect to compounds of formula I, the compound is according to formula IIIb, IIId, IIIf, IVa, Vb, Vd, or Vf; and each of $R^{3a}$ and $R^{3b}$ is H.

In one particular embodiment, with respect to compounds of formula IIIb, IIId, IIIf, IVa, Vb, Vd, or Vf; one of $R^{3a}$ and $R^{3b}$ is substituted or unsubstituted alkyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted benzyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted phenethyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted cycloalkyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted cyclopropyl and the other is H.

In one particular embodiment, with respect to compounds of formula IIIb, IIId, IIIf, IVa, Vb, Vd, or Vf; one of $R^{3a}$ and $R^{3b}$ is substituted or unsubstituted cyclopentyl or cyclobutyl and the other is H.

In one particular embodiment, with respect to compounds of formula IIIb, IIId, IIIf, IVa, Vb, Vd, or Vf; $R^{3a}$ and $R^{3b}$ join together to form a cycloheteroalkyl heteroaryl ring.

In one particular embodiment, with respect to compounds of formula IIIb, IIId, IIIf, IVa, Vb, Vd, or Vf; $NR^{3a}R^{3b}$ is:

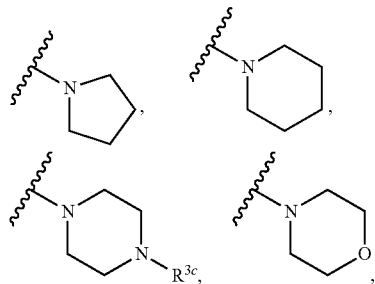

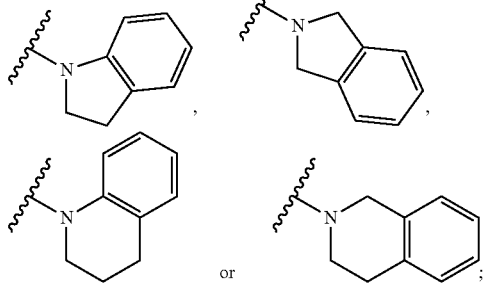

and wherein $R^{3c}$ is H or alkyl.

In one particular embodiment, with respect to compounds of formula I, the compound is according to formula VIa, VIb, or VIc:

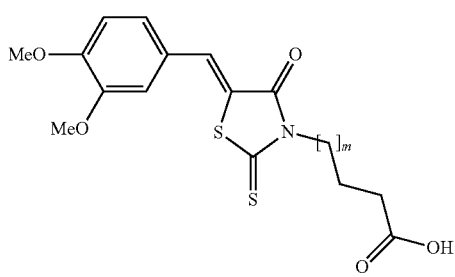

VIa

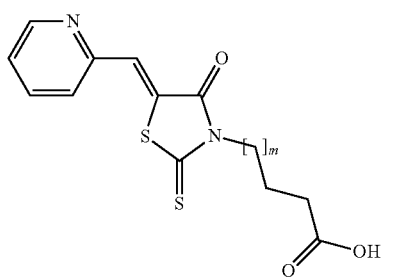

VIb

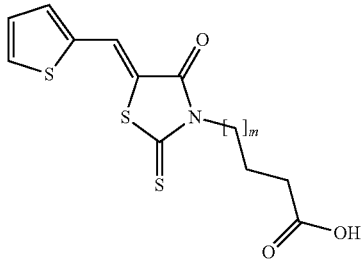

VIc and m is 0 or 1.

In one particular embodiment, with respect to compounds of formula IIIa-VIc, m, when present, is 0.

In one particular embodiment, with respect to compounds of formula IIIa-VIc, m, when present, is 1.

In one particular embodiment, with respect to compounds of formula IIIa-VIc, the compound is according to formula VIIa, VIIb, VIIc or VIId:

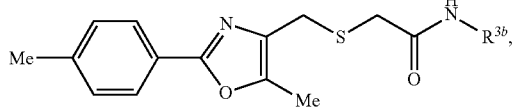

VIIa

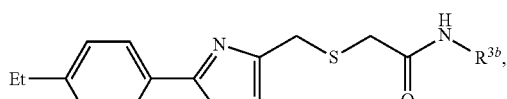

VIIb

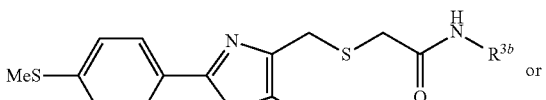

VIIc

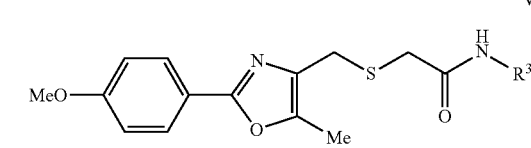

VIId wherein $R^{3b}$ is as described above.

In one particular embodiment, with respect to compounds of formula VIIIa, VIIb, VIIc or VIId; $R^{3b}$ is substituted or unsubstituted cycloalkyl, phenyl, benzyl, or phenethyl.

In one particular embodiment, with respect to compounds of formula VIIIa, VIIb, VIIc or VIId; $R^{3b}$ is substituted or unsubstituted heteroaryl, or heterocycloalkyl.

In one particular embodiment, with respect to compounds of formula I, the compound is according to formula VIIIa, VIIIb, VIIIc, or VIIId:

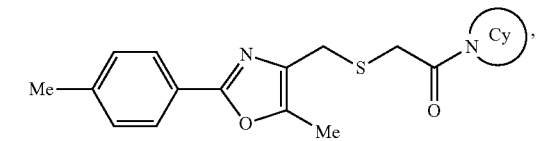

VIIIa

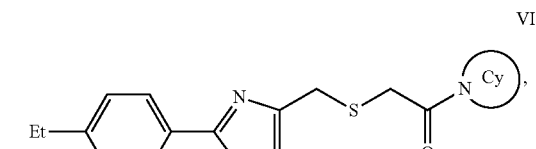

VIIIb

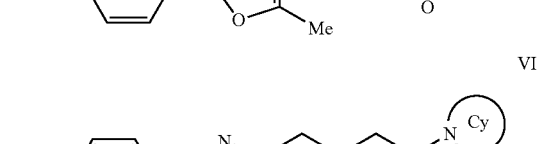

VIIIc

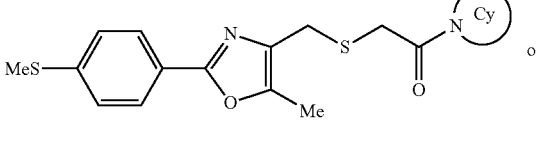

VIIId

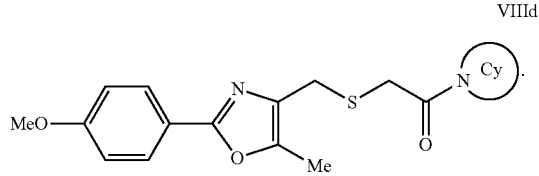

wherein Cy is

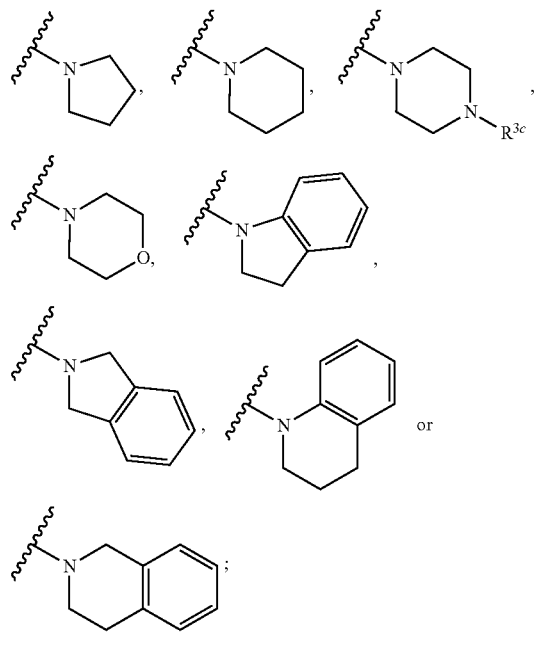

and wherein R³ᶜ is H or alkyl.

In one particular embodiment, with respect to compounds of formula I, the compound is according to formula IXa, IXb, IXc or IXd:

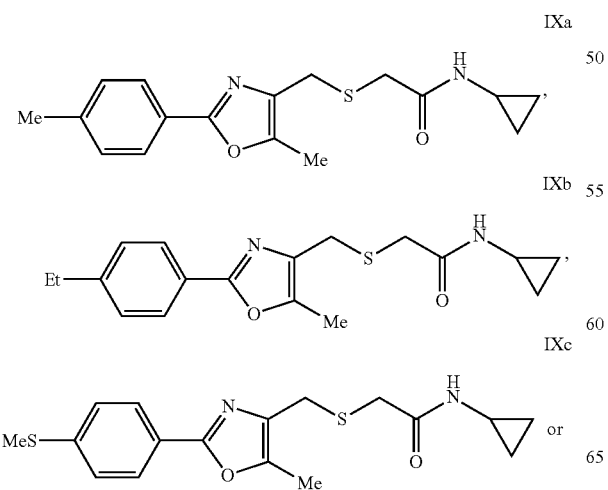

In one particular embodiment, with respect to compounds of formula I, the compound is according to formula Xa, Xb, Xc or Xd:

In one particular embodiment, with respect to compounds of formula I, the compound is according to formula XIa, XIb, XIc or XId:

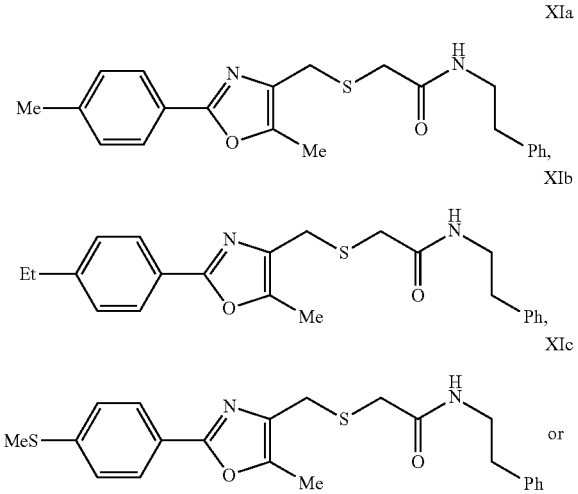

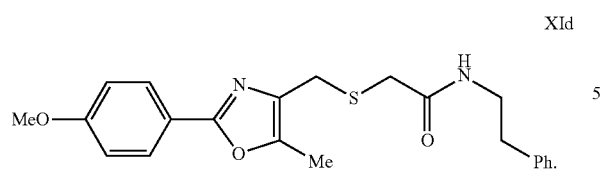

In one particular embodiment, with respect to compounds of formula I, the compound is according to formula XIIa, XIIb, XIIc or XIId:

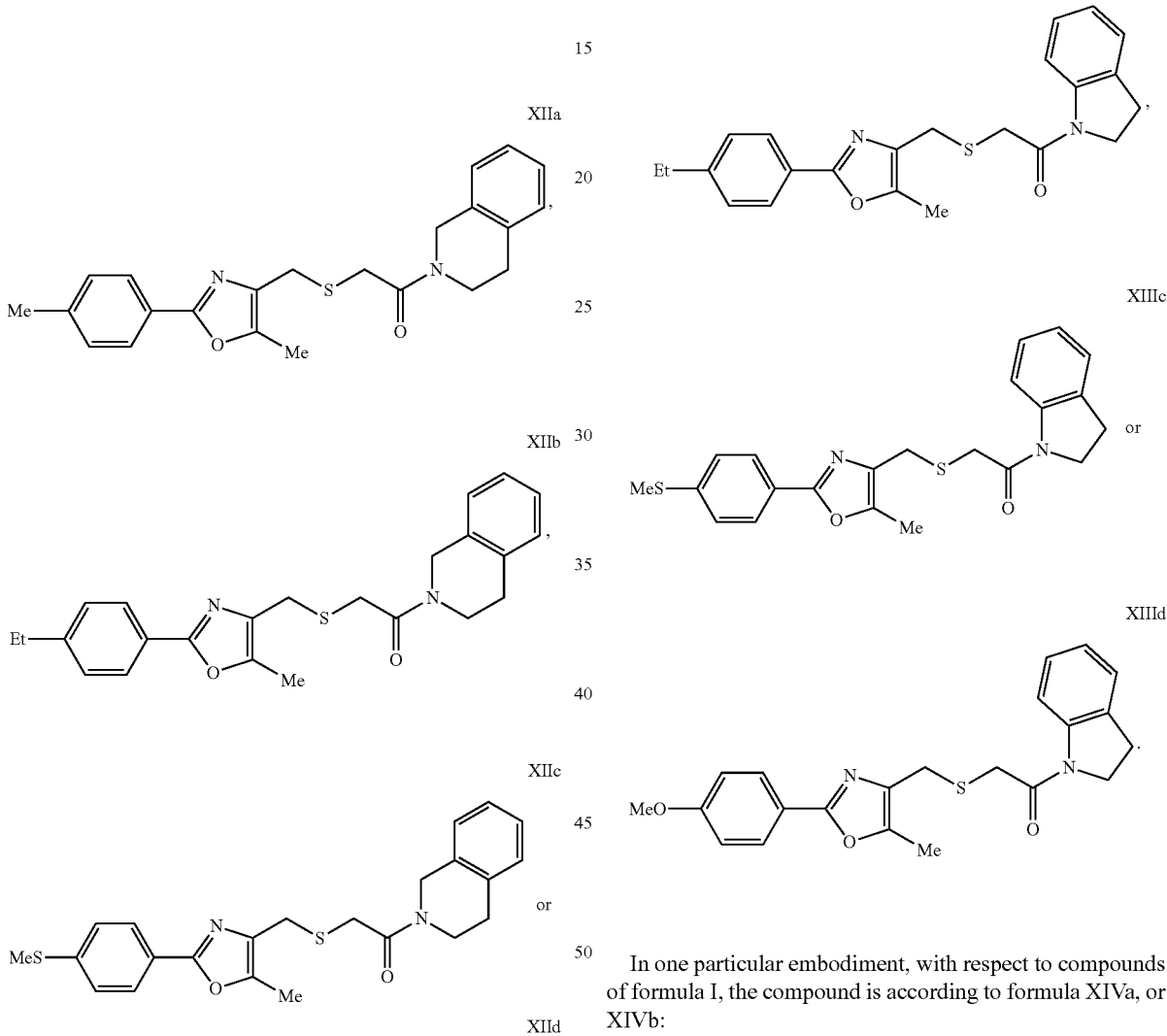

In one particular embodiment, with respect to compounds of formula I, the compound is according to formula XIIIa, XIIIb, XIIIc or XIIId:

In one particular embodiment, with respect to compounds of formula I, the compound is according to formula XIVa, or XIVb:

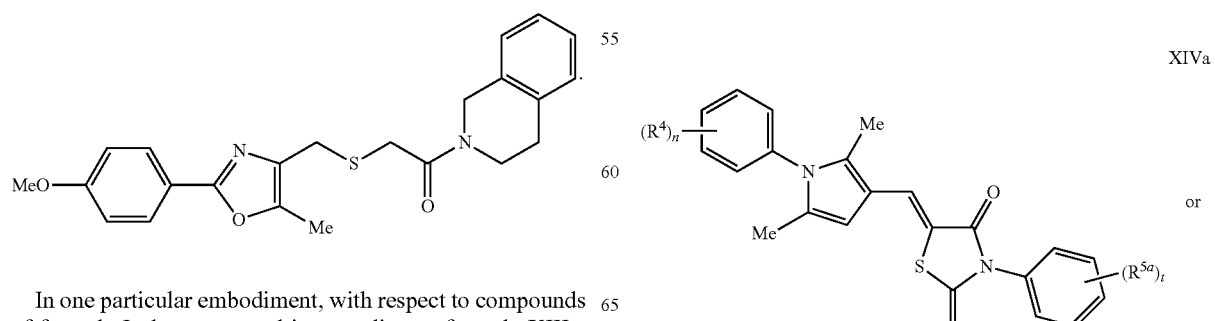

-continued

XIVb

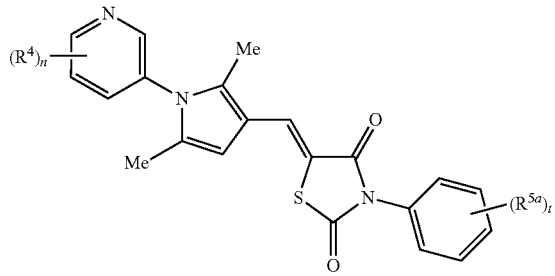

wherein each $R^4$ and $R^{5a}$ is independently selected from alkyl, alkoxy, haloalkyl, halo, hydroxy, carboxy, carbalkoxy, or nitro; and each n and t is independently 0, 1 or 2.

In one particular embodiment, with respect to compounds of formula XIVa, or XIVb, each $R^4$ is H.

In one particular embodiment, with respect to compounds of formula XIVa, or XIVb, n is 1 or 2; and each $R^4$ is independently Me, Et, i-Pr, OMe, OEt, O-i-Pr, Cl, or F.

In one particular embodiment, with respect to compounds of formula XIVa, or XIVb, each $R^{5a}$ is H.

In one particular embodiment, with respect to compounds of formula XIVa, or XIVb, t is 1 or 2; and each $R^{5a}$ is independently Me, Et, i-Pr, OMe, OEt, O-i-Pr, Cl, or F.

In one particular embodiment, with respect to compounds of formula I, the compound is according to formula XVa or XVb:

XVa

XVb

In one particular embodiment, with respect to compounds of formula I, the compound is selected from Table 1.

In one particular embodiment, with respect to compounds of formula I, the compound is selected from Table 2.

In one particular embodiment, with respect to compounds of formula I, the compound is selected from Table 3.

In one particular embodiment, with respect to compounds of formula I, the compound is selected from Table 4.

In one particular embodiment, with respect to compounds of formula I, the compound is selected from Table 5.

In one particular embodiment, with respect to compounds of formula I, the compound is selected from Table 6.

In one particular embodiment, with respect to compounds of formula I, the compound is selected from Table 7.

In one particular embodiment, with respect to compounds of formula I, the compound is selected from Table 8.

In one particular embodiment, with respect to compounds of formula I, the compound is selected from Table 9.

In one particular embodiment, with respect to compounds of formula I, the compound is selected from Table 10.

In one particular embodiment, with respect to compounds of formula I, the compound is selected from Table 11.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1

Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2

Capsules

A compound of the invention may be admixed as a dry powder with a starch diluent in an approximate 1:1 weight ratio. The mixture is filled into 250 mg capsules (125 mg of active amide compound per capsule).

Formulation 3

Liquid

A compound of the invention (125 mg), sucrose (1.75 g) and xanthan gum (4 mg) may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color would then be diluted with water and added with stirring. Sufficient water is then added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5

Injection

A compound of the invention may be dissolved or suspended in a buffered sterile saline injectable aqueous medium to a concentration of approximately 5 mg/ml.

Formulation 6

Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to aberrant activity of the Wnt/wg signaling pathway. Accordingly, the compounds and pharmaceutical compositions of this invention find use as therapeutics for preventing and/or treating a variety of cancers and hyperproliferative conditions in mammals, including humans. Thus, and as stated earlier, the present invention includes within its scope, and extends to, the recited methods of treatment, as well as to the compounds for use in such methods, and for the preparation of medicaments useful for such methods.

In a method of treatment aspect, this invention provides a method of treating a mammal susceptible to or afflicted with a condition associated with cancer and/or a hyperproliferative disorder, which method comprises administering an effective amount of one or more of the pharmaceutical compositions just described.

In yet another method of treatment aspect, this invention provides a method of treating a mammal susceptible to or afflicted with a condition that gives rise to increased cellular proliferation or a transformed phenotype, or that relates to dysregulation of Wnt/wg signaling. The present oxazoles and thiazoles have use as anti-proliferative agents that reduce proliferative levels (potentially to normal levels for a particular cell type), and/or anti-transformed phenotype agents that restore, at least in part, normal phenotypic properties of a particular cell type. Accordingly, the present oxazoles and thiazoles have use for the treatment of cancers and hyperproliferative disorders relating to aberrant Wnt/wg signaling.

In additional method of treatment aspects, this invention provides methods of treating a mammal susceptible to or afflicted with a cancer causally related or attributable to aberrant activity of the Wnt/wg signaling pathway. Such cancers include, without limitation, prostate cancer, colorectal cancer, breast cancer, skin cancer (e.g., melanoma), liver cancer (e.g., hepatocellular cancer and hepatoblastoma), head and neck cancer, lung cancer (e.g., non-small cell lung cancer), gastric cancer, mesothelioma, Barrett's esophagus, synovial sarcoma, cervical cancer, endometrial ovarian cancer, Wilm's tumor, bladder cancer and leukemia. Such methods comprise administering an effective condition-treating or condition-preventing amount of one or more of the pharmaceutical compositions just described.

With respect to prostate cancer, for example, compounds and compositions thereof and methods described herein are also envisioned as useful for targeting cancerous prostate cells that remain following radical prostatectomy, including micrometastases and thus, are useful for treating prostate cancer patients following surgical intervention. In addition, compounds and compositions thereof and methods described herein are envisioned as being useful in advance of surgical intervention to delay or prevent the need for surgery. For such purposes, direct delivery of the compounds or compositions thereof to the prostate tumor or in the vicinity of the tumor is envisioned as a particular delivery mode suitable for such an application.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as psoriasis, the regimen for treatment usually stretches over many months or years so oral dosing is preferred for patient convenience and tolerance. Psoriasis, for example, has been linked to Wnt signaling. Several basic and clinical studies using patient samples revealed an increase in nuclear β-catenin staining in many psoriatic samples. It has been suggested that a sustained low-level increase in Wnt/β-catenin signaling could be responsible for skin psoriatic lesions. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a hyperproliferative condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

General Synthetic Procedures

The compounds of this invention may be purchased from various commercial sources or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following schemes are presented with details as to the preparation of representative compounds that have been listed hereinabove. The compounds of the invention may be prepared from known or commercially available starting materials and reagents by one skilled in the art of organic synthesis.

Representative Scheme 1

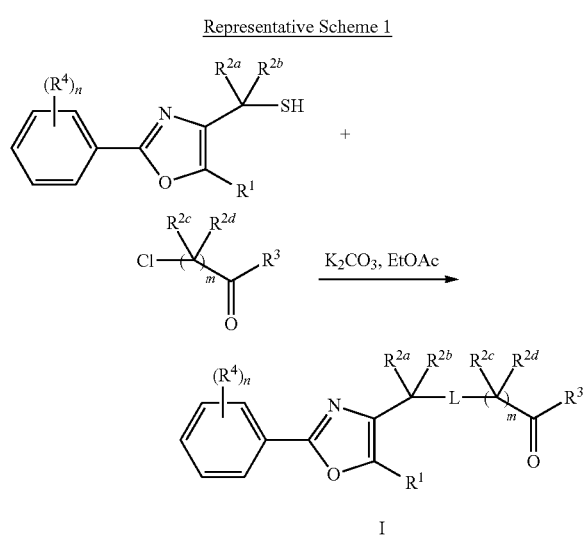

Representative Scheme 2

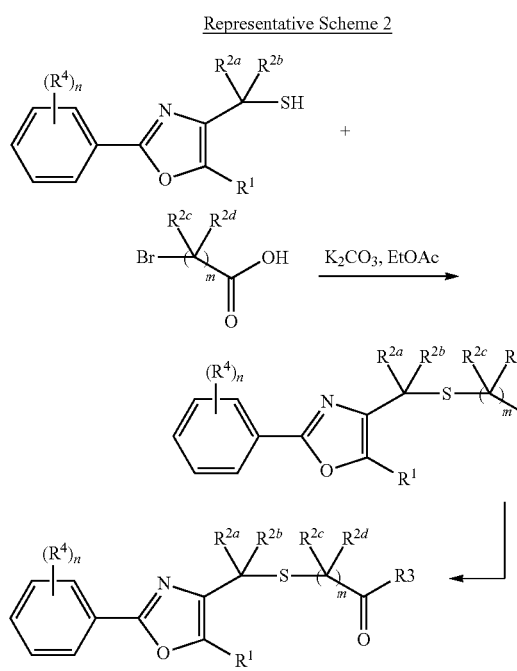

Representative Scheme 3

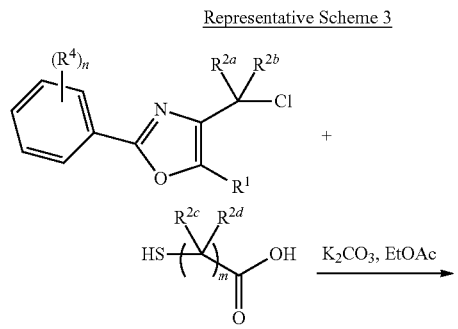

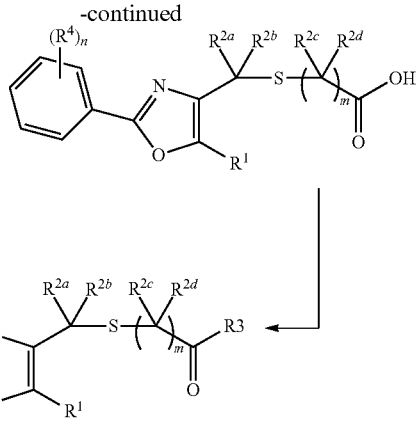

Example 1

Protocols/Methods for In Vitro Testing of Candidate Compounds

The present inventors employed a novel methodology that integrates a "sensitized" chemical genetic high-throughput screen (HTS) with RNA-interference (RNAi) screening technology in order to identify specific small molecule inhibitors of the Wnt pathway in Drosophila cells. As described herein, Drosophila Clone 8 cell-based assay systems developed by the present inventors to investigate the Wnt/wg pathway [DasGupta et al. Science 308, 826-33 (2005)] were used in a small molecule chemical genetic screen to identify specific inhibitors of the pathway. These cell-based assays, which are described in detail below, utilize a Wnt-responsive luciferase reporter dTF12, the activity of which can be determined using immunofluorescence-based visual detection means. The present inventors used the small-molecule library available from the Institute of Chemistry and Cellular Biology (ICCB-Longwood) at Harvard Medical School, Boston, for the screen.

More particularly, the method for testing and identifying compounds useful in the present invention begins with the activation of the signaling pathway by the introduction of dsRNAs specific for Axin, which is the scaffold protein that negatively regulates β-cat by promoting its GSK-3β-mediated degradation. The resultant activation of the Wnt signaling pathway is then detected by assessing the activity of the Wnt-responsive luciferase reporter gene in the cell-based assay system. Thereafter, candidate compounds are added to the cell-based assay system to assess their effect on the strongly induced Wg-reporter-gene (TOPFlash) activity that results from the dsRNA-mediated knockdown of Axin. This protocol significantly increases the specificity of the small-molecule inhibitors for CRT and serves to identify molecules that regulate Wnt signaling activity downstream of the Axin-mediated degradation complex. Although not wishing to be bound by theory, the prediction is that the candidate compounds act on the "activated" or stable pool of β-cat and potentially prevent its interaction with known components of the transcriptional-activator complex (such as pangolin (pan)/dTcf, pygopus (pygo), legless (lgs) or Bcl9, p300/CBP), or other proteins that may function to regulate the activity of stabilized cytosolic β-cat.

Methods and Materials
Primary Small Molecule Screen for the Wingless Signaling Pathway in *Drosophila* Clone 8 Cells
Day 1 (PM):
Set up transfection with Wg-reporter (dTF12), Normalization vector (PolIII-RL) and dsRNA against DAxin (dsRNA is specific towards *Drosophila* Axin and lacks any predicted off-targets).
1. Add 40,000 *Drosophila* Clone 8 cells (in 40 μL) in 384-well plate (white solid bottom, Corning Costar) using the multidrop.
2. Add 20 μL of Transfection mix in each well of a 384-well plate (Corning Costar) using the multidrop.
Transfection Mix:
TOP12x-Luc (DNA)=25 ng (0.25 μL of DNA @ 0.1 μg/μL)
PolIII-RLuc (DNA)=25 ng (0.25 μL of DNA @ 0.1 μg/μL)
dsRNA to DAxin=100 ng (5 μL of dsRNA @ 20 ng/μL)
Buffer EC=13.5 μL
Enhancer=0.8 μL
Effectene=0.25 μL
Total volume=20 μL
Incubate at 25° C. for 4 days to ensure complete knockdown of Axin.
Day 5 (PM):
Add small molecule library (Cybio Robot). Incubate 18 hrs.
Day 6 (AM):
Assay luminescence from the samples using the "Dual-Glo" luciferase kit (Promega Inc.). Specifically, aspirate supernatant and add 20 μL media+20 μL luciferase buffer using the multidrop. Read Firefly Luciferase activity on the EnVision (Perkin Elmer plate reader). Add 20 μL of Stop&Glo using the multidrop. Read Renilla luciferase activity on the EnVision (Perkin Elmer plate reader).
Epistasis Analysis:
Epistasis Analysis was conducted in a 96 well format following the protocol as described for the Primary Screen (above), except that, 80,000 Clone 8 cells were used per well. Small Molecule Compounds were used at a final concentration of 2.5 ng/ul.
Reporter Assay in Mammalian HEK 293 Cells:
HEK 293 cells were transfected with 50 ng each of the Wnt-responsive STF16 luciferase reporter and pCMV-RL normalization reporter using the Lipofectamine LTX (Invitrogen Inc.) in a 96 well plate format.
Transfection Mix Per Well
STF16-FLuc (DNA): 50 ng (0.54 of DNA @ 0.1 μg/μL)
CMV-RLuc (DNA): 50 ng (0.54 of DNA @ 0.1 μg/μL)
Lipofectamine-LTX: 0.25 μL
Serum Free Medium: 204
Cells were cultured in DMEM/10% FBS at 37° C. for 2 days following which, they were induced with Wnt3a conditioned media for 1 day and then treated with small molecule compounds to a final concentration of 2.5 ng/μl for approximately 18 hours. Luciferase reporter activity was then measured using the Dual-Glo system (Promega Inc.) on the Envision Plate Reader. Normalized luciferase activity in response to treatment with candidate small molecule compounds was compared to that obtained from cells treated with DMSO.
C57mg Transformation Assay:
The transformation assay was carried out in a 96 well format. C57 mg cells were cultured in DMEM/10% FBS supplemented with purified Wnt3a protein (R&D Systems) to a final concentration of 100 ng/μl. Small molecule compounds dissolved in DMSO were added to a final concentration of 10 ng/μl and 0.01% DMSO. Following incubation at 37° C. for 5 days, cells were fixed with 4% Formaldehyde in 1×PBS at RT for 30 min and washed subsequently with 1×PBS at room temperature (RT) for 5 minutes (×3). Cells were then permeabilized in Blocking buffer (0.1% Triton-X/1×PBS/5% Normal Goat Serum) at RT for 20 min, subsequent to which, cells were incubated with anti-β-cat at RT for 1 hour (diluted to 1:1000 in blocking buffer). Subsequently, cells were washed with 1×PBS at RT for 10 minutes (×3) and then incubated with secondary antibody and Alexa-Fluor 488 conjugated phalloidin in Blocking buffer at RT for 1 hour. Following a brief wash in 1×PBS, cells were imaged in PBS buffer using the Array-Scan imaging system.

Molecular validation of C57 mg transformation assay was performed by qPCR analysis of the Wnt-target gene, WISP1. First strand cDNA was prepared from C57 mg cells treated as above using Cells-to-cDNA kit (Ambion, Inc.) as directed by the manufacturer. Equal amounts of cDNA were used for qPCR analysis using primers specific for WISP1 and GAPDH (the endogenous control). Comparison of amplification kinetics of WISP1 from samples treated with compounds to those treated with DMSO (ddCt method) was used to study changes in Wnt-directed transcriptional activity in response to treatment with candidate small molecule compounds.

Figure 2:
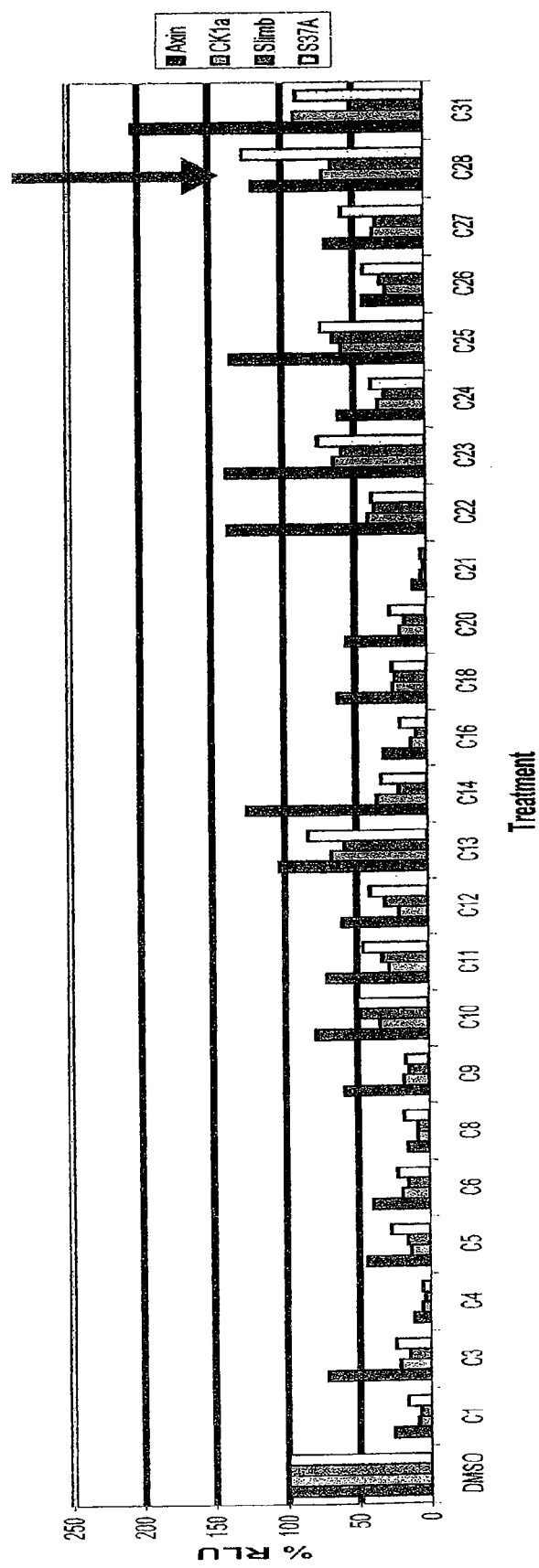
FIG. 2 shows a bar graph depicting the results of genetic epistasis analyses.

Unless otherwise indicated, all experiments described herein that call for supplemental Wnt3a utilize Wnt3a conditioned media prepared by harvesting media from L-cells stably transfected with a Wnt3a coding construct (available from ATCC #CRL-2647). The cells are cultured in DMEM containing 10% fetal bovine serum (FBS). The medium, harvested from adherent cells cultured to about 80% confluency over 4 days, is purified through a 0.2 μm filter and stored at 4° C. over several months without an appreciable loss in activity [Willert et al. Nature 423, 448-52 (2003)].
Results The Wnt signaling pathway was induced by the introduction of dsRNAs specific for Axin into Clone 8 cells comprising the Wg-responsive luciferase reporter-gene (dTF12). As described herein, Axin is a scaffold protein that negatively regulates Arm/β-cat by promoting its degradation. Thereafter, a selected set of a small molecule library was added to the Clone 8 cell-based assay system to assess the effect of individual compounds on (Axin dsRNA-mediated) activated CRT by monitoring the activity of the Wg-responsive luciferase reporter-gene (dTF12). The primary screen identified molecules that have a statistically significant effect on the activity of the dTF12-luciferase reporter gene, wherein a minimum of a 2.5-fold change in reporter activity was considered "significant" as a cut-off for hit-picking compounds for secondary screens. As shown in FIG. 1, addition of these compounds to the cells strongly repressed dTF12-reporter activity (>70-90%). Six of the strongest inhibitors are identified herein and, as indicated, share significant structural similarities suggesting that they constitute a family of compounds (i.e., a subset of oxazoles and thiazoles) that regulate a common aspect of the Wnt-pathway activity by potentially binding to the same target protein.
Epistatic Analyses:

Small molecule inhibitors identified in the primary screen may modulate Wnt signaling by affecting intermolecular interactions at any point downstream of Axin in the signaling cascade. Given that the oncogenic character of β-cat and therefore the Wnt pathway itself is caused by aberrant CRT (Park et al. Cancer Res 59, 4257-60 (1999); Lin et al. Proc Natl Acad Sci USA 97, 4262-6 (2000), a major focus of the present invention is to study those compounds which affect Wnt-responsiveness by regulating the transcriptional complex involved in CRT. The use of dsRNAs targeted to specific components of the Wnt pathway elucidates the level at which the compounds exert their inhibitory effect on the Wnt/Wg signaling pathway. This objective can be achieved by activating the Wnt pathway in Clone 8 cells using dsRNAs targeting other known negative regulators of the Wnt pathway, such as Slimb/βTrCP and SkpA, and assaying the effect of the compounds on the dTF12 reporter activity in these cells. Each of the aforementioned biomolecules functions to negatively regulate Wnt signaling downstream of Axin, so these analyses further delineate the stage in the Wnt pathway wherein the compound in question exerts its effect. The results of this experimental approach are presented in FIG. 2.

Figure 3:
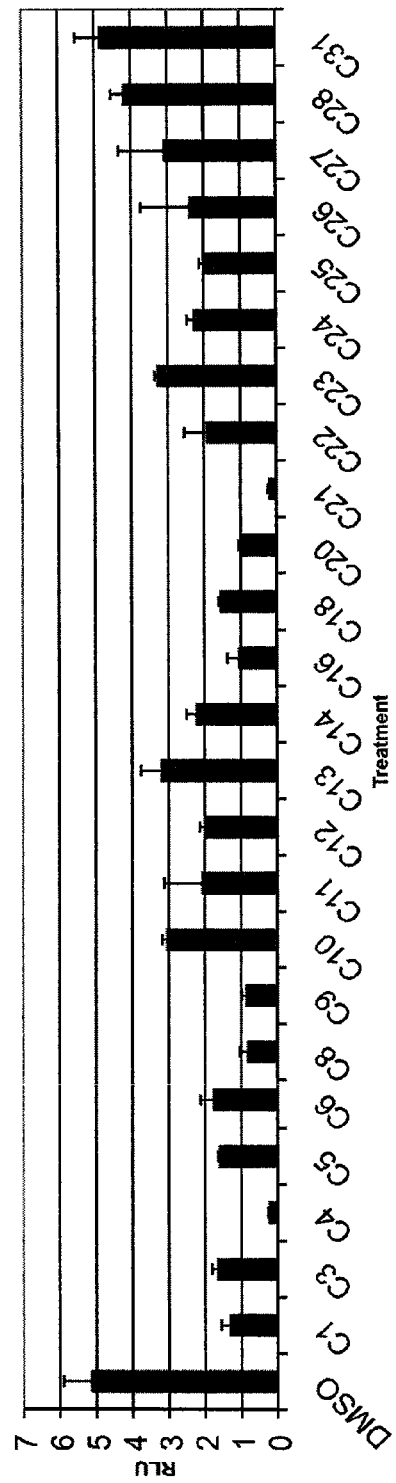
FIG. 3 shows a bar graph depicting the activity of candidate inhibitors on S37A β-catenin mediated TOP12-LF in Clone 8 cells.

To gain further evidence that the compounds exert their inhibitory effect in the nucleus, they have been tested in Clone 8 cells transfected with a construct coding for a degradation resistant form of β-cat, S37A β-cat [Orford et al. J Biol Chem 272, 24735-8 (1997)]. This mutant form of β-cat bears a Serine to Alanine mutation, thus rendering it refractory to GSK3β mediated phosphorylation and hence proteosome degradation. An inhibitory effect of the compounds on the activity of S37A β-cat thus provides further proof that the compounds exert their effect on Wnt responsiveness at the level of CRT. The concentration of the compounds for all of the above assays is kept constant at 2.5 ng/μl, which is the same as that used for the primary screen. As shown in FIG. 3, most of the compounds exert an inhibitory effect on Wnt signaling on the transcriptional level. Data depicted in FIG. 3 show that a majority of the compounds inhibit S37A-mediated reporter activity, thus lending further support to the notion that these putative inhibitors do indeed function by abrogating the activity of stabilized β-cat in the nucleus.

Figure 6:
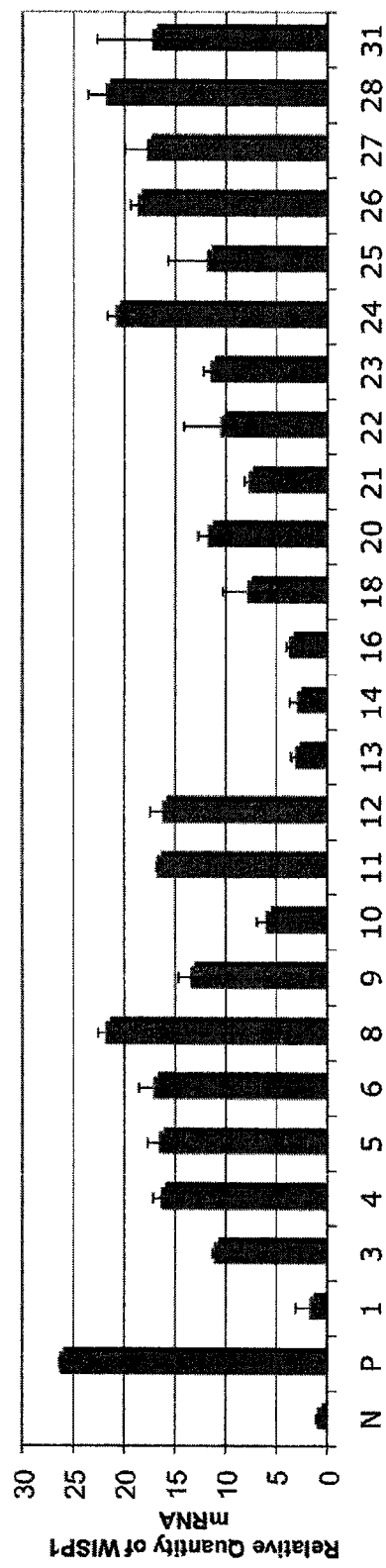
FIG. 6 shows a bar graph of quantitative analyses of Wnt3a transformed C57 mg cell phenotypes and rescue thereof by inhibitory compounds.

Reproducibility of Inhibitory Effect of Small Molecules in Mammalian Cells:

In order to confirm and corroborate the activity of CRT inhibitor compounds in a mammalian context, the present inventors have tested a subset of the inhibitors identified in the context of established mammalian cell lines. To this end, the present inventors have optimized culture conditions for screening for Wnt signaling modulators in mammalian HEK 293 cells in a 96-well plate format. Briefly, HEK 293 cells were transfected with pSTF16-LF along with the normalization reporter, pCMV-RL and the effect of the compounds on reporter activity in such cells was determined by quantifying the luminescence from the luciferase reporter gene as described in Dasgupta et al. [supra (2005)]. As shown in FIG. 6, the present inventors have been able to recapitulate the inhibitory effect of several candidate inhibitors in these cells using the Wnt responsive luciferase reporter, STF16-LF.

In that Wnt signaling has been shown to have a profound influence on both cell fate and cell proliferation in various developmental and pathogenic contexts [Clevers. Cell 127, 469-80 (2006)], the present inventors have begun to investigate the activity of a subset of the CRT inhibitors identified in the primary screen in the context of other available Wnt responsive cell lines. Such cell lines can be used to ascertain further the inhibitory activity of the putative small molecule inhibitors in a phenotypic context. Such Wnt responsive cell-specific phenotypes include an assessment of transformation of the C57 mg mammary epithelial cell line, neural differentiation capacity of G-Olig2 ES cells, E-cadherin expression in the HT-29 colon cancer cell line, and Wnt induced invasive capacity of the MCF-7 breast adenocarcinoma cell line.

The C57 mg cell line, which was isolated from mouse mammary epithelial tissue [Wong et al. Mol Cell Biol 14, 6278-86 (1994)], has previously been shown to undergo transformation when cultured in Wnt-conditioned media. Transformation of the cell line is evidenced by pronounced changes in morphology, typified by formation of chord-like bundles of cells or foci-forming colonies that break off and float in the media [Wong et al. supra, 1994]. This Wnt responsive phenotype provides a mammalian assay in which to evaluate the inhibitory effect of the small molecule inhibitors identified in the primary screen. Briefly, cells are cultured in Wnt3a conditioned media in the presence or absence of a small molecule inhibitor and morphological analysis conducted using automated microscopy.

The present inventors have established a phenotypic assay using the Wnt-responsive C57 mg mouse mammary epithelial cell line to ascertain the validity of the inhibitory compounds identified in the primary screen. Specifically, addition of Wnt3a conditioned media or purified Wnt3a protein results in cellular transformation, manifested by a pronounced change from an epithelial-cell like morphology to those resembling spindle shaped cells with chord like bundles. Addition of candidate small molecule compounds to such cells in the presence of Wnt3a results in significant inhibition of the transformation phenotype. The Array-Scan imagining system (Cellomics Inc.) is used to image such phenotypic changes in a 96-well plate format so as to gain a quantitative estimate of the degree of the inhibitory effect of the compounds on Wnt3a induced transformation in C57 mg cells. Quantitative analysis of the transformation phenotype is measured by the degree of actin fiber alignment (defined as anisotropy), which is expressed as the standard deviation (SD) of the angles projected by the actin fibers relative to the normal; low SD numbers reflect an increase in Wnt-responsive transformation. This approach allows for objective inferences on the cellular effects of the candidate inhibitors. See FIG. 5.

Figure 4:
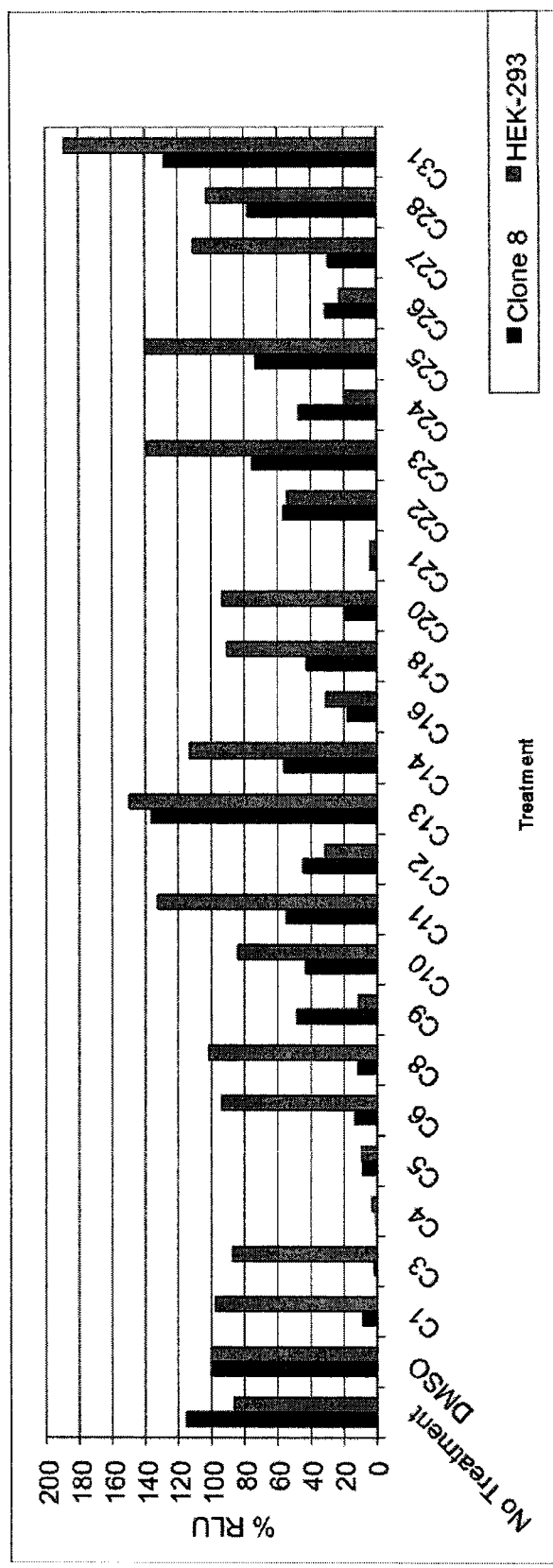
FIG. 4 shows a bar graph representation of the effect of several inhibitory compounds in mammalian HEK-293 cells.
Figure 5:
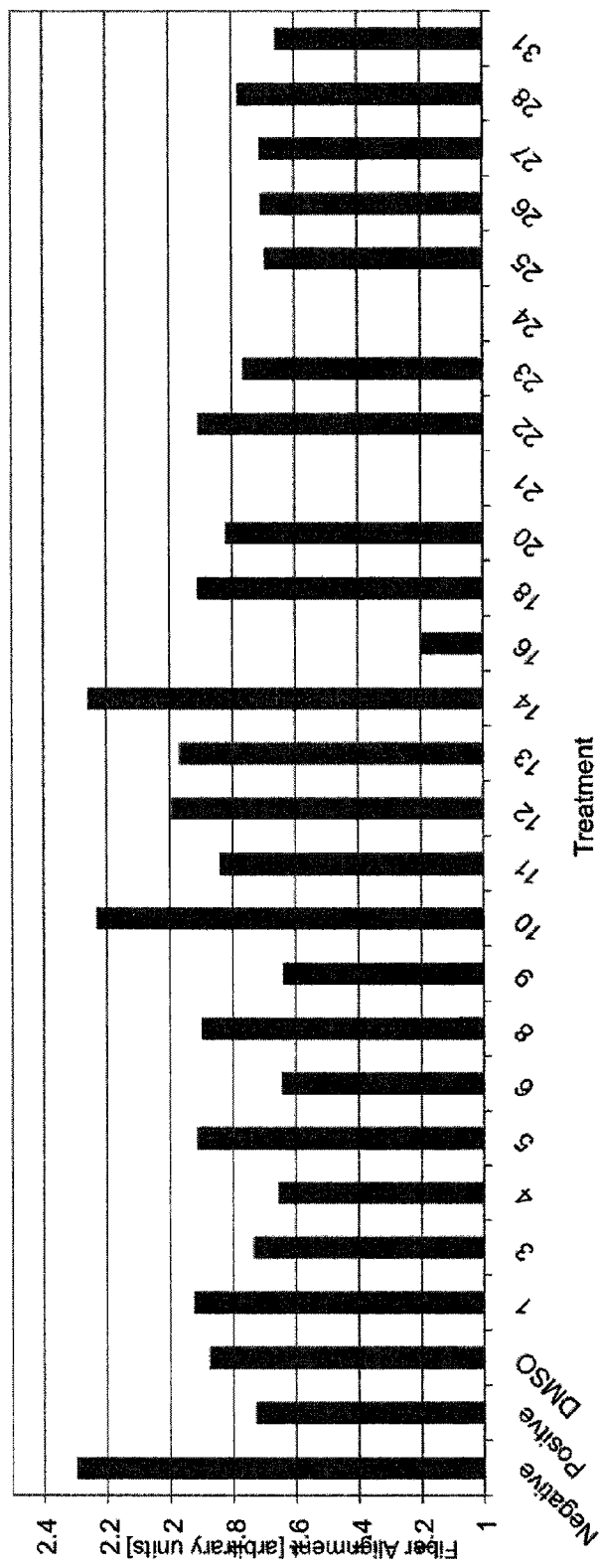
FIG. 5 shows photomicrographs of Wnt3a transformed C57 mg cell phenotypes and rescue thereof by inhibitory compounds.

As depicted in FIG. 5, compounds 10 and 14 show a significant inhibition of Wnt3a induced C57 mg transformation, whereas compounds 1, 5, 8, 11, 12, 13, 18 and 22 show a partial reduction in the degree of transformation. It should be noted that the degree of inhibitory effect of the compounds on Wnt-induced phenotypes may vary with different cellular types. For example, compounds 10 and 14 are poor inhibitors of TOP12-LF activity in HEK-293 cells (see FIG. 4), and yet seem to be potent inhibitors of Wnt3a-induced transformation in C57 mg cells. This could perhaps be due to their effect on the interaction of β-cat with different transcriptional co-factors in the nucleus that drive transcription of different targets. However to further validate the efficacy of candidate compounds in inhibiting Wnt-induced C57 mg transformation, the present inventors monitored changes in the expression of WISP1 mRNA by qRT-PCR. WISP1 is the key β-catenin target responsible for C57 mg transformation in response to Wnt signaling [Xu et al. Genes Dev. 14, 585-95 (2000)]. Reduction in the level of WISP1 mRNA correlates highly with the observed phenotypic rescue in response to Wnt exposure (FIG. 6).

The HT-29 colon cancer cell line has been shown to undergo β-cat/TCF dependent Epithelial Mesenchymal Transition (EMT) which can be monitored by changes in both morphology and downregulation of E-cadherin expression levels and upregulation of vimentin [Yang et al. Cell 127, 139-55 (2006)]. The HT-29 cell line, therefore, provides a model system for analysis of the candidate small molecule inhibitors in the context of a transformed colon cancer cell. Accordingly, the present inventors will treat HT-29 cells with candidate small molecules and assay E-cadherin and vimentin levels by western blotting as well as immunochemistry using commercially available antibodies. Furthermore, morphological analysis by compound differential contrast (DIC) microscopy will also be used to determine the effect of the compounds in inhibiting β-cat dependent EMT.

The MCF-7 breast cancer cell line exhibits a pronounced invasive capacity in response to Wnt signaling [Yook et al.

Nat Cell Biol 8, 1398-406 (2006)]. To utilize this cell line to assess the activity of Wnt inhibitor compounds identified, MCF-7 cells can be transduced with recombinant retroviral vectors coding for Wnt3a or β-cat-S33Y, a constitutively active form of β-cat [as described in Yook et al. supra, (2006)]. The retroviral vectors will be prepared from pPGS-β-cateninS33Y- or pPGS-Wnt3a-transfected 293 packaging cells. MCF-7 cells transduced with these retroviral vectors can be loaded onto the upper chamber of Matrigel (prepared in serum-free DMEM culture media) containing Transwells, which are subsequently cultured in complete media with inhibitory compounds or DMSO. The cultures will be incubated at 37° C. in a humidified chamber for 24-72 hrs. Following incubation of the cell-loaded Matrigel, non-invasive cells are scraped off and the invaded cells counted by simple light microscopy by fixing and staining with Trypan Blue [Valster et al. Methods 37, 208-15 (2005)]. Results derived from this assay will provide insights into the use of compounds as inhibitors of the metastatic potential of malignant cells in general and malignant breast cancer cells in particular.

G-Olig2 ES cells (available from ATCC) contain a GFP insertion in the gene for Olig 2, a neural lineage specific transcription factor. Neural differentiation, therefore, results in the upregulation of GFP-positive cells. Neural differentiation of G-Olig2 ES cells can be induced by treating these cells with synthetic Retinoic Acid (RA) following the appearance of Embryoid bodies in culture. It has previously been shown that Wnt signaling inhibits neural differentiation of ES cells [Bouhon et al. Brain Res Bull 68, 62-75 (2005)]. To assay the inhibitory effect of the candidate compounds, the present inventors will culture the above ES cells in Wnt3a conditioned media containing RA and individual compounds and determine the number of GFP positive cells by Flow Cytometry. The inhibitory effect on Wnt signaling will be reflected by a reduction in the number of GFP positive differentiated cells in cultures treated with DMSO+RA as compared to those treated with compound+RA.

Although the present Example is directed to screening in the context of an "activated" Wnt pathway, it will be appreciated that other components of the pathway that promote Wnt signaling can be targeted for RNAi mediated ablation and the result of such an approach would be an "inhibited" Wnt pathway. In either event, the cellular milieu of an "activated" or an "inhibited" Wnt pathway can be used as a genetic background in which to perform small molecule/compound chemical screens directed to the identification of small molecules/compounds such as those of the present invention, that modulate the activity of a specific component of a signaling pathway.

Example 2

Protocols/Methods for In Vitro and In Vivo Testing

Preliminary in vivo tests to assay the efficacy of the compounds will be performed in the zebrafish, Danio rerio, wherein increased Wnt signaling during zebrafish embryonic development results in axial specification defects and loss of anterior fates. This is commonly manifested by loss of or reduced eye-structures. To test the effectiveness of the compounds in inhibiting Wnt-signaling in a whole organismal context, one-cell embryos will be injected with synthetic Wnt8 mRNA and cultured in the presence of DMSO or individual compounds Inhibitory activity of the compounds will be assayed by quantifying the penetrance of the Wnt8 induced phenotype.

Upon successful in vivo validation of the compounds in an animal model system, their efficacy will be further tested in the clinically relevant mouse model system, viz. the $APC_{min}$ mouse. Loss of APC function results in an increase in the level of signaling competent β-catenin, which has been shown to be the causative factor in the induction of colon cancer in the above mouse model. Such mice will be administered candidate compounds and assayed for the regression of tumors resulting from increased Wnt signaling in the $APC_{min}$ mouse. Standardized protocols for tail-vein and/or tissue injections will be used.

Example 3

The colon carcinoma cell line, HCT-116 offers a pathologically-relevant system to examine the effects of candidate Wnt-inhibitors. HCT-116 cells bear a deletion of the S45 residue in β-cat, making it refractory to phosphorylation and degradation, thereby resulting in constitutive CRT. Wnt targets such as CycD1 and c-myc are thus overexpressed in this cell-type.

Figure 7:
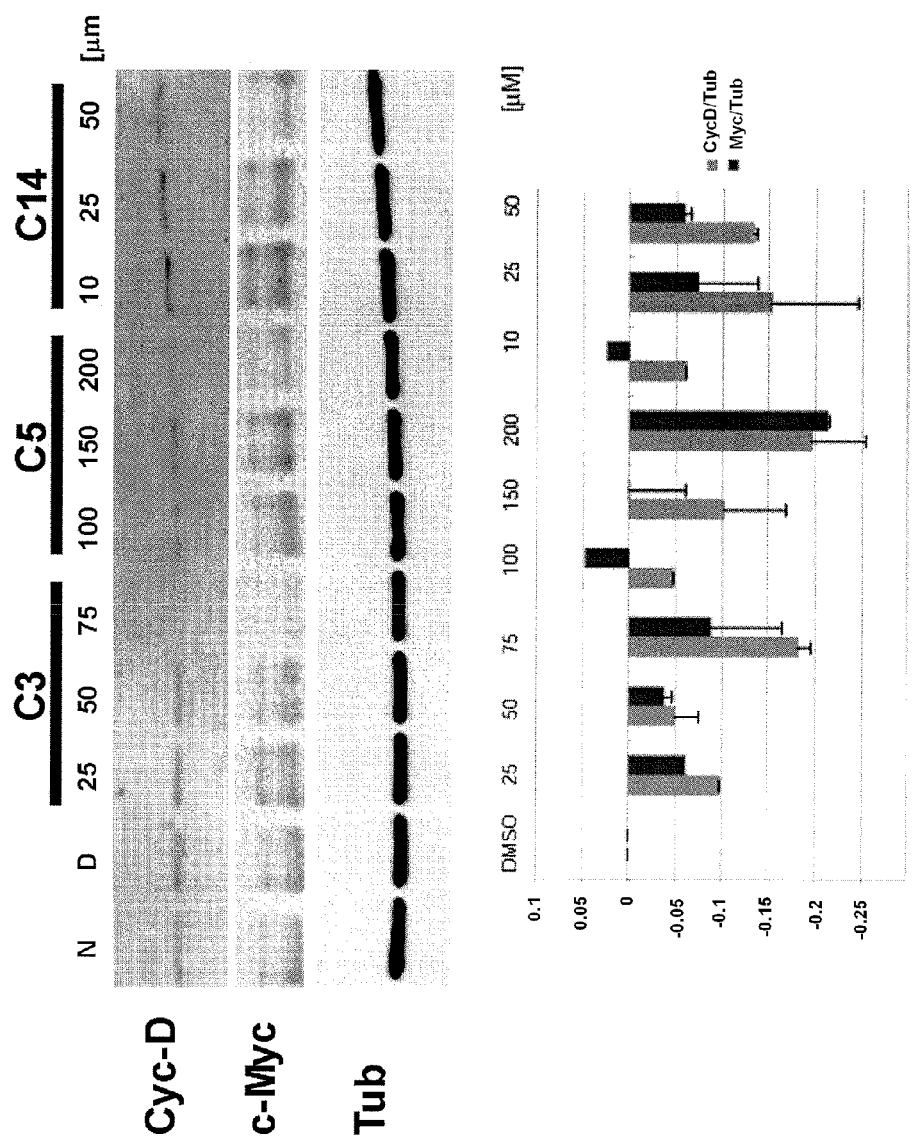
FIG. 7 shows inhibition of Wnt-target accumulation in HCT116 cells.
Figure 8:
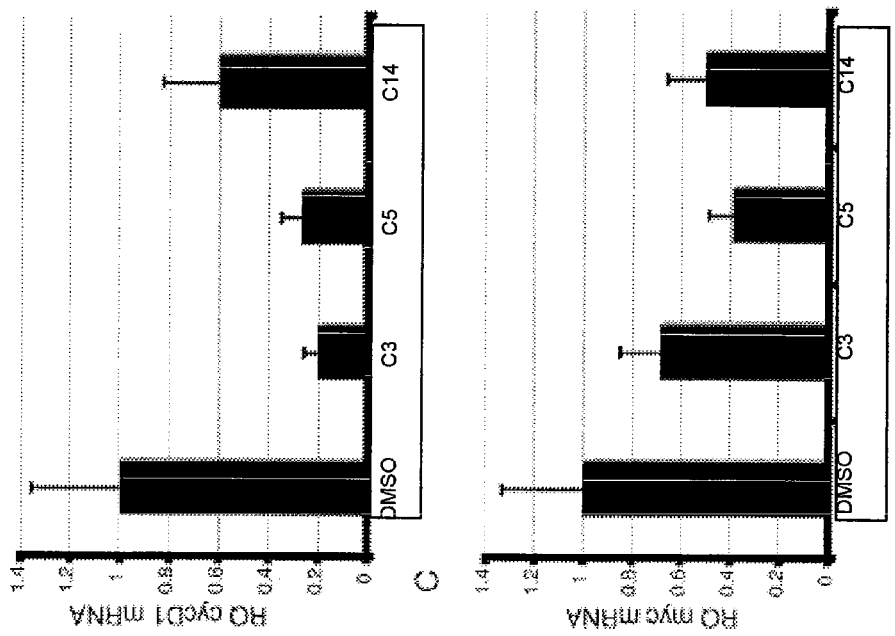
FIG. 8 shows transcriptional inhibition of Wnt-targets in HCT116 cells.
Figure 9:
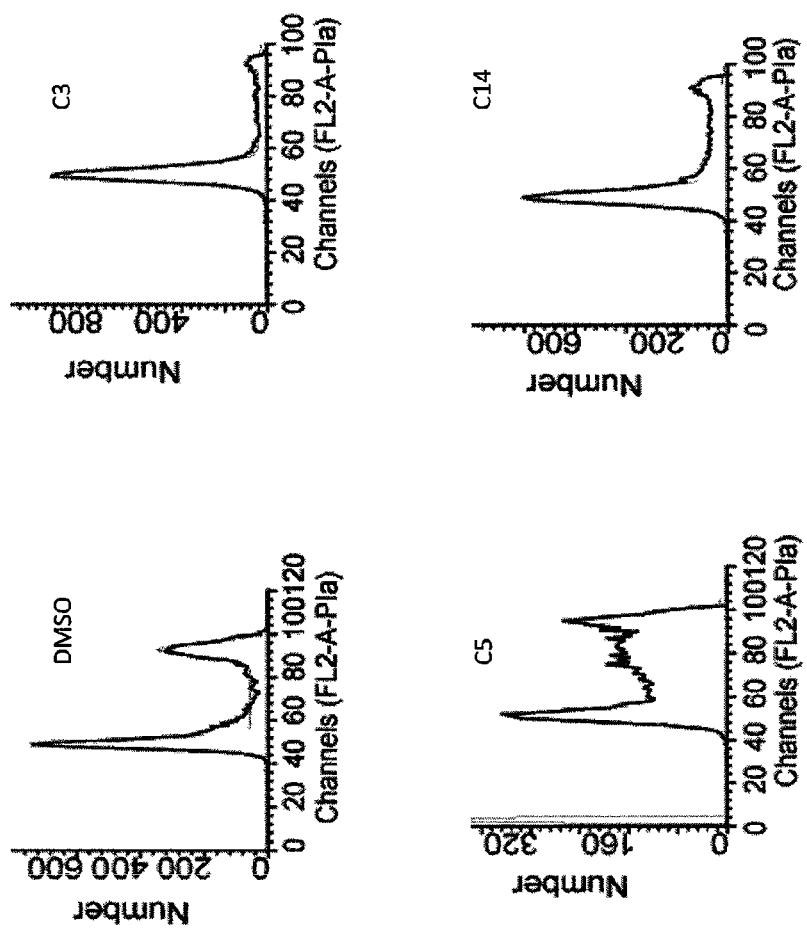
FIG. 9 shows that C3 & C14 cause G0/G1 arrest.
Figure 10:
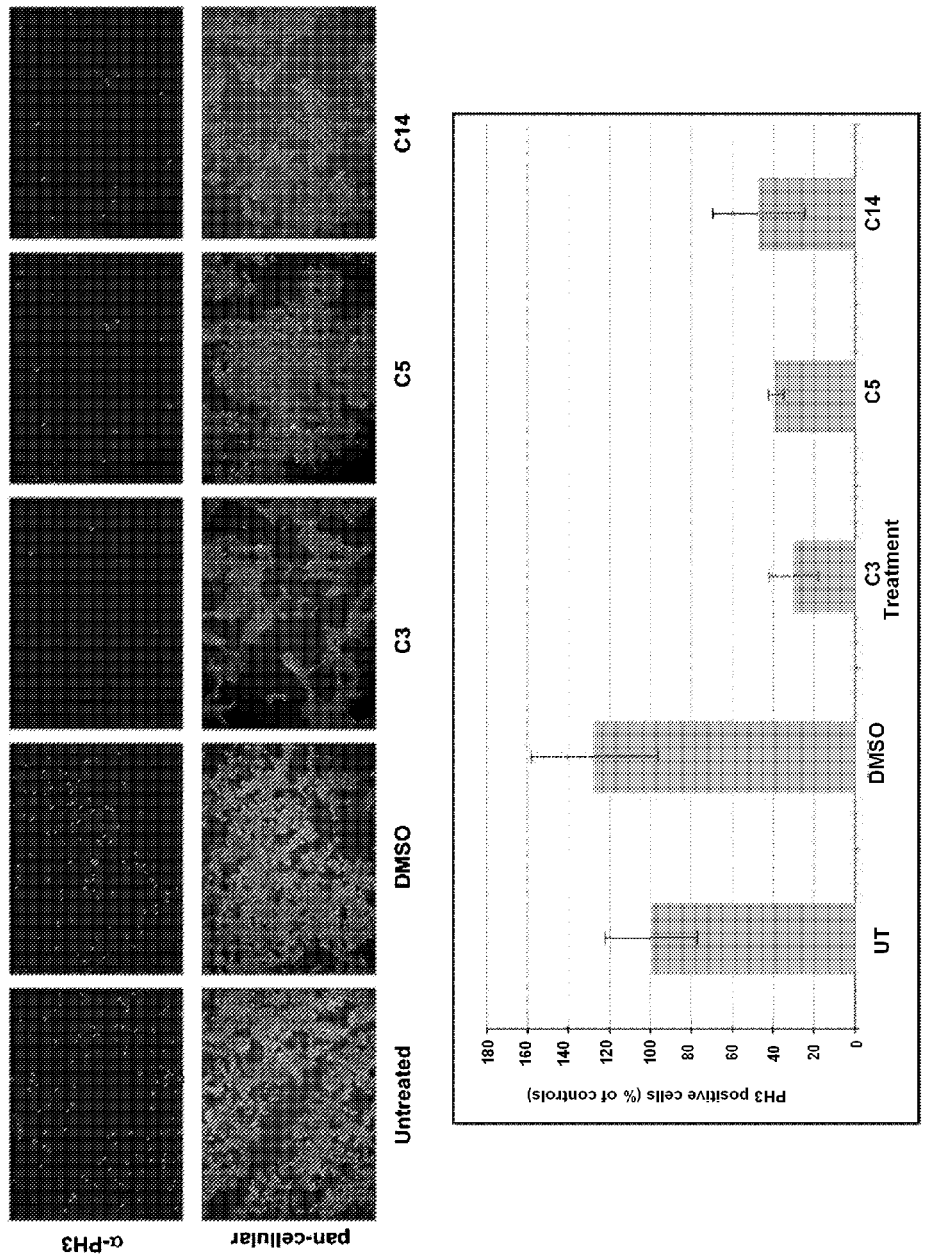
FIG. 10 shows Quantification of –αPH3 staining in compound treated HCT116 cells.

In order to test the inhibitory effect of candidate compounds on the transcription of endogenous Wnt/β-cat target genes in HCT116 cells, lysates were prepared from cells that were either treated with candidate small molecules or DMSO control. As shown in FIG. 7, the protein levels of CycD1 and c-myc were markedly reduced upon the addition of increasing concentrations of candidate compounds. qRT-PCR assays for the CycD1 and c-myc locus confirmed that the changes in their protein level reflected a change in their mRNA transcription (FIG. 8), further corroborating the effect of the candidate small molecules at the level of modulating CRT. Taken together, our analyses suggest a common theme of CRT-inhibition by these candidate compounds in a wide variety of Wnt-responsive heterologous cell types, thus making them ideal lead compounds for drug development for Wnt/CRT-related human disease. Finally, as predicted for the inhibition of target genes involved in cell cycle and cell proliferation, flow cytometry analyses of HCT116 cells treated with candidate compounds showed a G0/G1 arrest of the cell cycle (FIG. 9). Cell cycle arrest of compound treated HCT116 cells was further confirmed by the reduced number of phosphorylated Histone3 (PH3) positive cells, when cultured in the presence of candidate compounds (FIG. 10).

C3: Oxazole
C5: Thiazole

Example 4

Additional Protocols

HCT116 cells were obtained from ATCC(CCL-247) and cultured in McCoy's 5A medium supplemented with 10% Fetal Bovine Serum (FBS) at 37° C. with 5% $CO_2$. Target accumulation validations were performed by qPCR following treatment with the lead compounds. Briefly, cells were treated with specified concentrations of compounds for 1 day, and lysed in 50 ul of Cell Lysis Buffer (Ambion #AM8723) at 75° C./10'. First-strand cDNA was prepared using High-Capacity Reverse Transcription Kit (Applied Biosystems #4368814) as per the manufacturer's instructions. Real-time qPCR was carried out for CycD1, c-Myc and GAPDH2 (endogenous control) using pre-validated gene-specific primer pairs from Qiagen and the SYBr green PCR master mix from Applied Biosystems. Data analysis was performed using the MxPro-Mx3005P system from Stratagene using the ddCt method.

Flow Cytometry analysis was performed on HCT116 cells treated with candidate compounds for 16 hrs per standard protocols. Briefly, compound treated cells were harvested and washed in 1×PBS followed by fixation in 70% Ethanol at 4° C. for 16 hrs. Cells were then washed in 1×PBS and treated with RNAse at 37° C. for 30'. Following extensive washes in 1×PBS, cellular DNA was stained with 500 ug/ml of Propidium Iodide at room temperature for 10'. Cells were washed again in 1×PBS and analysed by flow cytometry on a FACScalibur machine (Beckson Dickinson) at the NYU flow cytometry core facility.

Example 5

Figure 11:
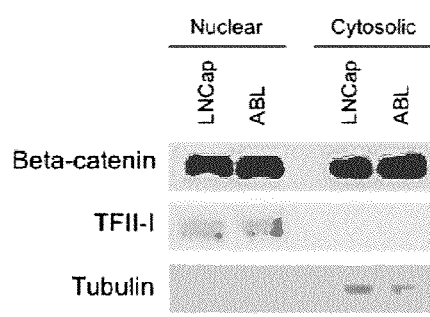
FIG. 11 depicts high levels of nuclear β-catenin expression in androgen-dependent LNCaP and androgen-independent LNCaP-abl cells. Cells were fractionated into cytoplasmic and nuclear components and analyzed for β-catenin expression by Western blot. Anti-TFII-I and tubulin antibodies were used as nuclear and cytoplasmic loading controls, respectively.

To determine if the β-catenin pathway is active in prostate cancer cells, levels of nuclear (transcriptionally active) β-catenin were assessed. FIG. 11 shows that β-catenin is equally abundant in the nucleus and cytoplasm of both androgen-dependent LNCaP cells [Horoszewicz et al., Cancer Res, 1983. 43(4): 1809-18] and an androgen-independent LNCaP cell derivative called LNCaP-abl (called ABL in the drawings) [Hobisch et al., Urol Int, 2000. 65(2): 73-9]. VCaP prostate cancer cells, derived from a vertebral metastatic lesion [Korenchuk et al., In Vivo, 2001. 15(2): 163-8] also exhibited high levels of nuclear β-catenin. These results indicate that the β-catenin pathway is constitutively active in a variety of cultured prostate cancer cells and suggest that androgen-dependent and androgen-independent cells would be susceptible to small molecule inhibitors of β-catenin.

Figure 12:
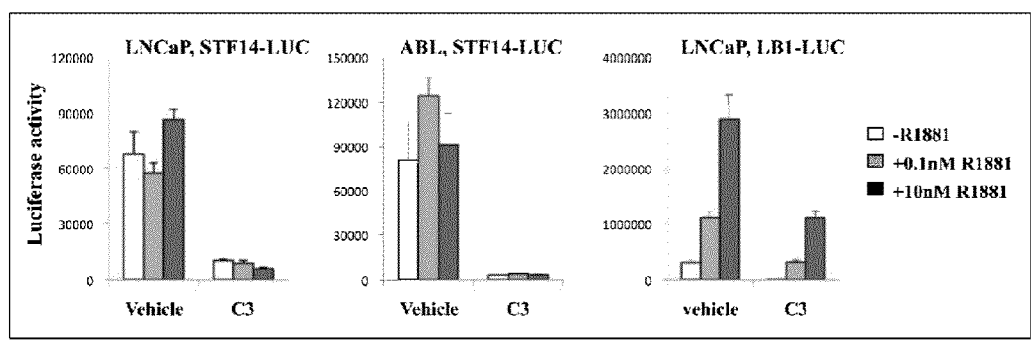
FIG. 12 shows that C3 inhibits Wnt and AR reporter gene activity in LNCaP and LNCaP-abl cells. LNCaP or LNCaP-abl (ABL) cells were cotransfected with 0.1 μg β-galactosidase and 0.2 μg S37A stabilized β-catenin together with the indicated luciferase reporter constructs; STF16-LUC (β-catenin reporter) and LB1-LUC (AR reporter). Cells were androgen-deprived in phenol-red free RPMI with 5% charcoal-stripped FBS for 24 hr after transfection, and either ethanol, 0.1 nM or 10 nM R1881 were added with or without 20 uM C3 for 24 hr. Luciferase activity was normalized to β-galactosidase expression.

While the C3 compound was previously demonstrated to inhibit Wnt/β-catenin mediated cell growth in colon cancer cells [Gonsalves et al., Proc Natl Acad Sci USA, 2011. 108 (15): 5954-63], the efficacy of C3 had not been tested in prostate cancer cells, nor had its effect on AR been determined. To test the impact of C3 on the β-catenin and AR pathways in prostate cancer cells, luciferase reporter assays were conducted in the presence of the constitutively active β-catenin S37A. FIG. 12 shows that C3 dramatically inhibits β-catenin and AR reporter genes, STF-16 as well as the androgen responsive pARR2Luc construct stably introduced into LNCaP cells (LB-1-LUC, [Link et al., Mol Cell Biol, 2005. 25(6): 2200-15]) in the presence and absence of the synthetic androgen, R1881.

Figure 13:
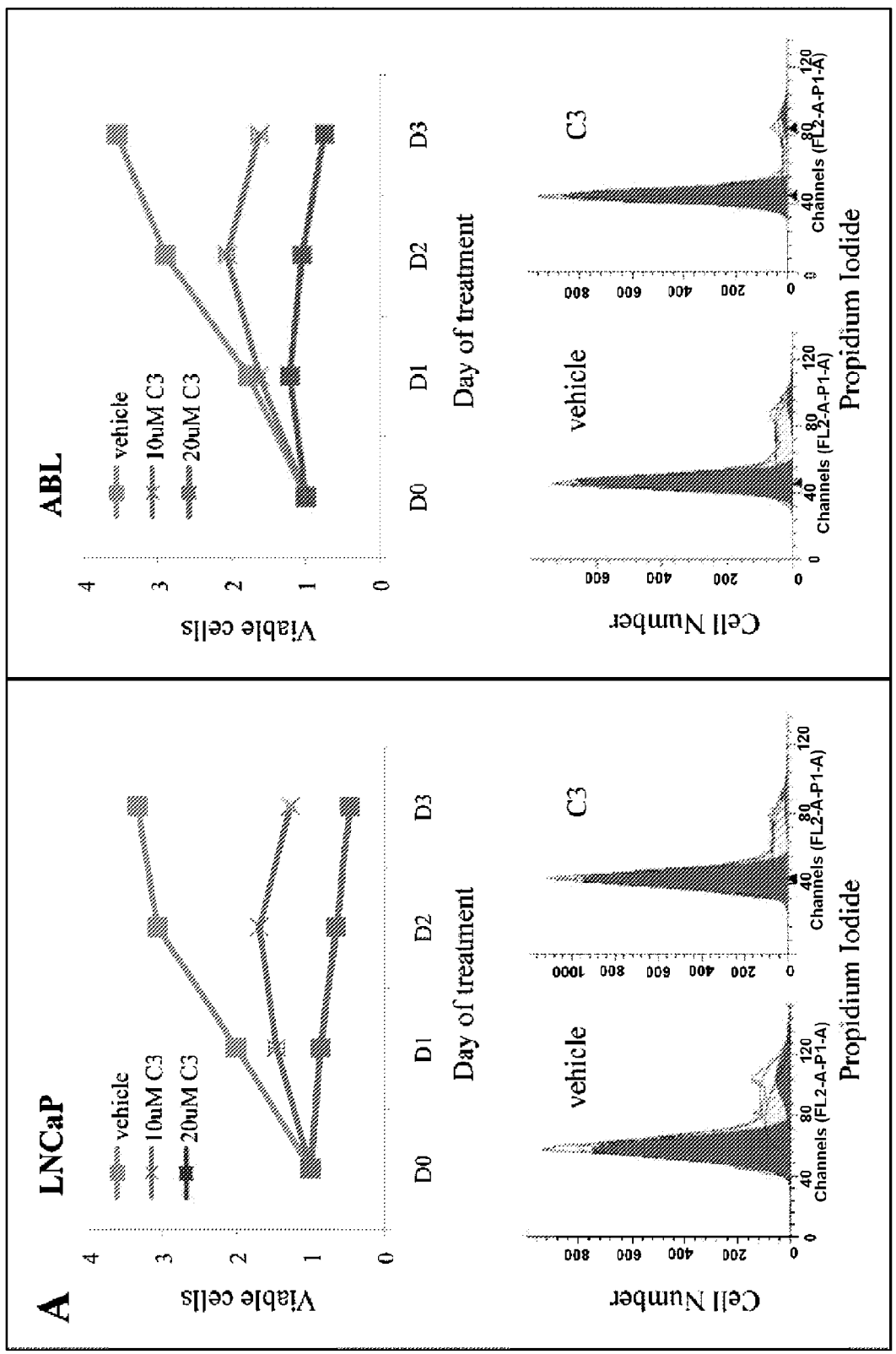
FIG. 13 shows that C3 induces growth arrest and apoptosis in LNCaP and LNCaP-abl cells. A) Cells were cultured in phenol-red free RPMI with either 5% charcoal-stripped FBS supplemented with 0.1 nM R1881 (LNCaP) or 10% charcoal-stripped FBS alone (LNCaP-abl). Upper panel; For the proliferation assay, cells were treated with DMSO, and 10 μM or 20 μM C3 everyday. Neutral red uptake assay was performed at the end of treatment to estimate the number of viable cells. Lower panel; Cells were treated with DMSO or 20 μM C3 for 24 hr and then fixed in ethanol. Fixed cells were stained with Propidium Iodide and analyzed for DNA content using flow cytometry. The first and the second red peak and the dashed area represent G0/G1, M and S-phase cell population, respectively. B) Cells were treated with DMSO or 20 μM C3 for 72 hr and then lysed and immunoblotted with indicated antibodies.
Figure 13:
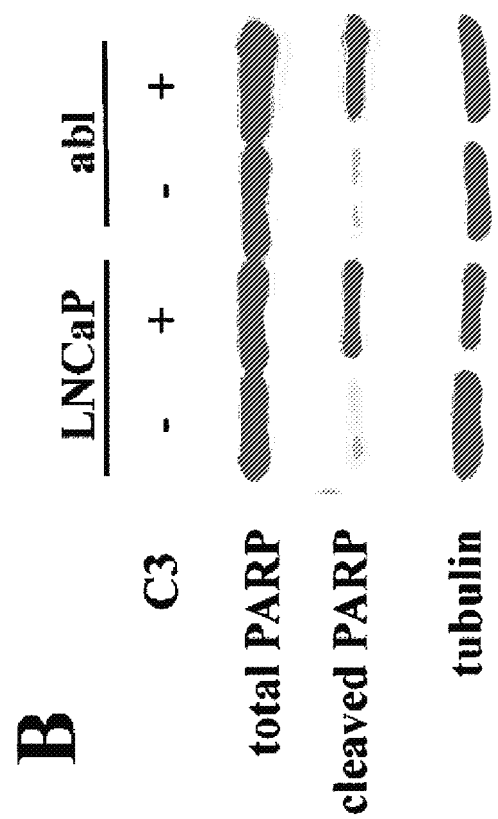

The fact that β-catenin is constitutively active in prostate cells (FIG. 11) and that C3 inhibits both Wnt and AR reporter gene activity (FIG. 12), suggests that C3 would inhibit prostate cell growth. To test this hypothesis LNCaP and LNCaP-abl cells were treated daily with either 20 μM C3 or vehicle. This treatment completely abolished growth of LNCaP, LNCaP-abl (FIG. 13) and VCaP cells and analysis of the cells by flow cytometry indicates that treatment with C3 results in growth arrest of the cells in the G0/G1 phase of the cell cycle (FIG. 13, lower panels). The FACS analysis conducted at 24 hours following C3 treatment did not show evidence of apoptotic cells despite growth inhibition and apparent diminished numbers of cells at day 3 (FIG. 13A). Therefore, to determine if cells were undergoing apoptosis at day 3, PARP cleavage was examined as a marker of apoptosis in LNCaP and LNCaP-abl cells treated with and without C3 (FIG. 13). Increased levels of PARP cleavage in C3 treated cells were observed, indicating that these cells are undergoing apoptosis (FIG. 13B).

Figure 14:
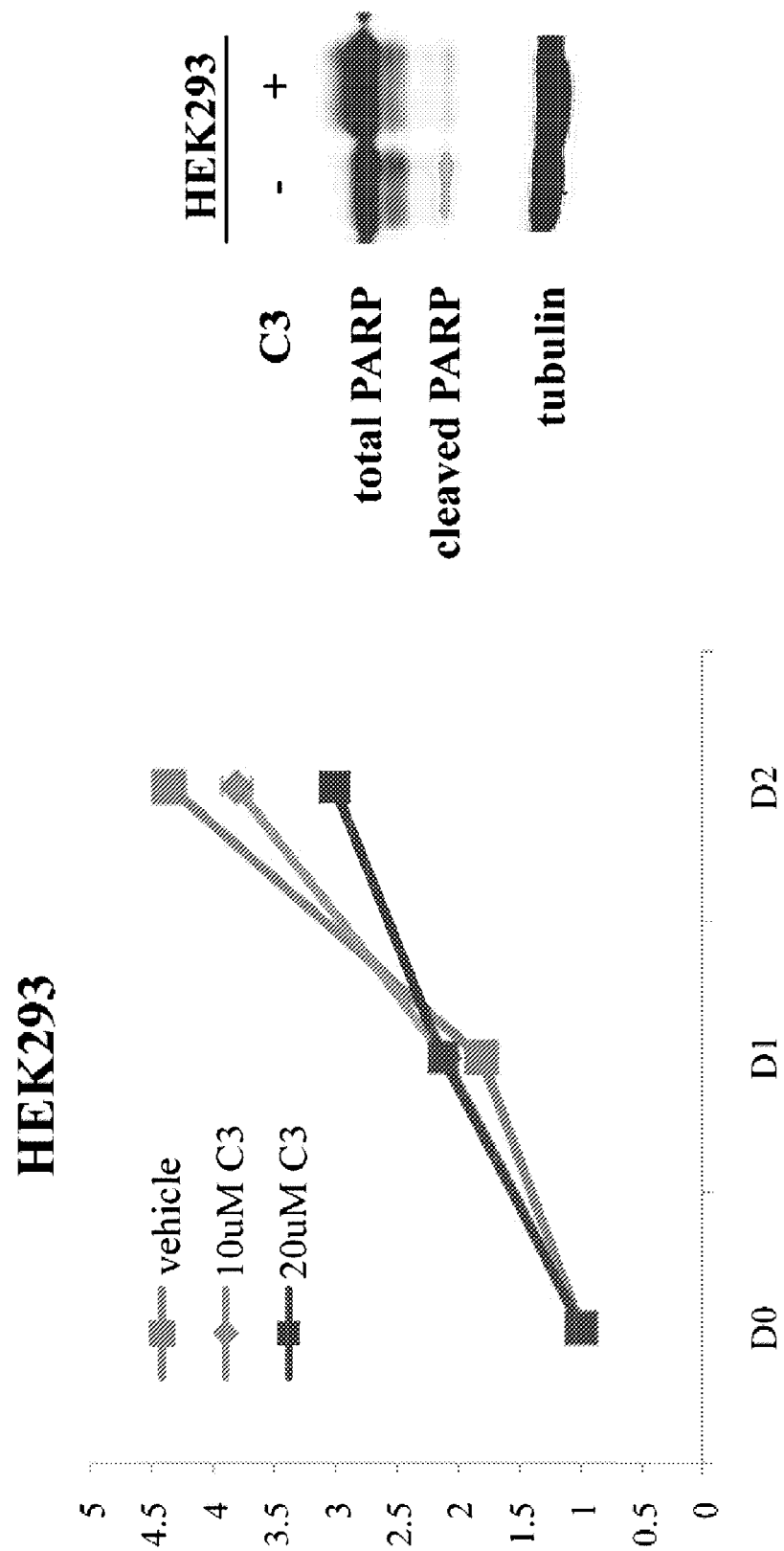
FIG. 14 shows that C3 does not induce apoptosis in HEK293 cells. Left panel; HEK293 cells were cultured in DMEM with 10% FBS. Cells were treated with DMSO, 10 μM or 20 μM C3 on a daily basis. Neutral red uptake assay was performed at the end of treatment to estimate the number of viable cells. Right panel; HEK293 cells were treated with DMSO or 20 μM C3 for 72 hr and then lysed and immunoblotted with indicated antibodies.

To determine if C3 is generally toxic, as opposed to inhibiting specific pathways in individual cell types, the effect of C3 on HEK 293 cells was examined. These cells do not have β-catenin or APC mutations and require Wnt ligand for activation of the pathway [Al-Fageeh et al., Oncogene, 2004. 23(28): 4839-46]. The results indicate that while higher levels of C3 somewhat slow 293 cell growth, the cells show basal levels of PARP cleavage (—C3) and this is not increased in the presence of C3 (+C3, FIG. 14) indicating that C3 does not induce apoptosis in 293 cells.

Figure 15:
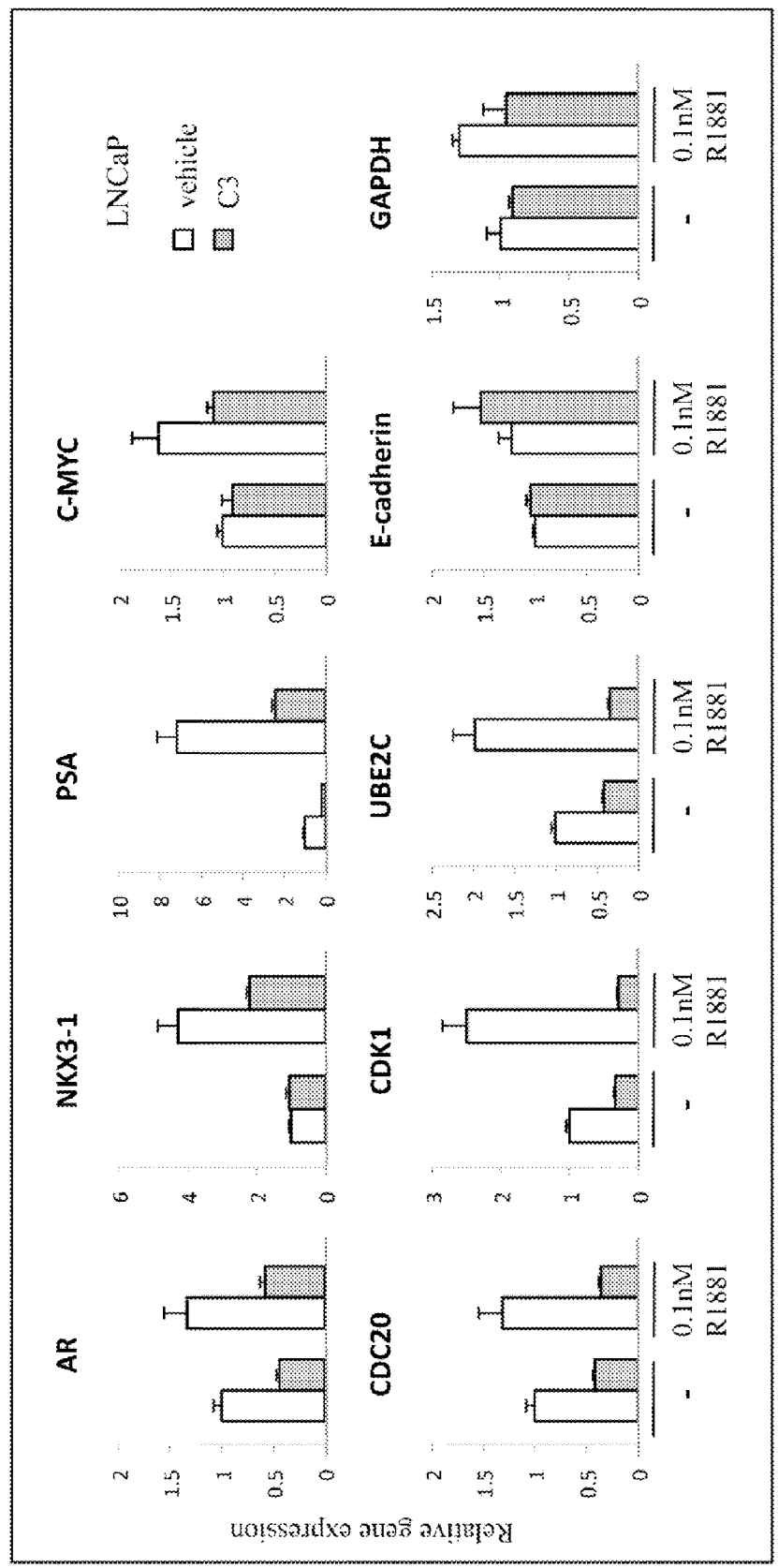
FIG. 15 shows that C3 inhibits expression of AR and β-catenin target genes. LNCaP cells were androgen-deprived in phenol-red free RPMI with 5% charcoal-stripped FBS for 48 hr and treated for 24 hr with DMSO or 20 μM C3 with or without 0.1 nM or 10 nM R1881. Samples are normalized to RPL19 and E-cadherin and GAPDH are included as controls.

While β-catenin can act as an AR coactivator [Song et al., J Biol Chem, 2005. 280(45): 37853-67], AR mRNA levels are also directly regulated by TCF binding sites in the AR promoter [Yang et al., Oncogene, 2006. 25(24): 3436-44]. Thus, the present inventors hypothesized that the dramatic effect of C3 on prostate cell growth is a consequence of transcriptional modulation of AR target genes as a result of decreased AR mRNA expression. To test this hypothesis, LNCaP cells were treated with vehicle or the synthetic androgen R1881 at growth promoting concentration of 0.1 nM in the presence or absence of C3, and Q-PCR was conducted on various target genes (FIG. 15). AR mRNA was quantified along with well-characterized AR target genes, Nkx3.1 and PSA. In addition, CDC20, CDK1 and UBE2C, M phase cell cycle regulatory genes that are AR targets in LNCaP-abl cells were examined [Wang et al., Cell, 2009. 138(2): 245-56]. Levels of c-myc were also examined since c-myc is a known Wnt/β-catenin target gene and assessment of information available through the Memorial Sloan Kettering cBio Cancer Genomics portal [Taylor et al., Cancer Cell, 2010. 18(1): 11-22] indicates that c-myc is upregulated in approximately two-thirds of all prostate tumors. The results indicate that AR, NRx3.1, CDC20, PSA, CDK1, c-myc and UBE2C are all diminished in response to C3 treatment in LNCaP cells (FIG. 15). E-cadherin and GAPDH are not affected by C3 treatment.

Because C3 markedly reduced AR target gene expression in LNCaP cells, experiments were performed to determine whether C3 also inhibited AR-mediated gene transcription in LNCaP-abl cells. To this end, cells were treated for 24 and 48 hours with C3 and Q-PCR and Western blot analysis were performed. Administration of a single dose of C3 at time 0 results in diminished AR, CDK1, UBE2C and c-myc mRNA that persists for 48 hours (FIG. 16A). Further, similar treatment followed by Western blot analysis of protein lysates indicates that C3 treatment results in diminished levels of AR, PSA, c-myc, CDK1 and UBE2C protein, especially at the 48-hour time point (FIG. 16B). Expression of tubulin (included as an internal loading control) and β-catenin were unaffected. Thus, treatment with C3 inhibits AR and β-catenin target genes in the androgen-dependent LNCaP cell line and its androgen-independent derivative, LNCaP-abl, suggesting that small molecule inhibitors of β-catenin specifically target the AR pathway to inhibit prostate cancer cell growth.

Figure 16:
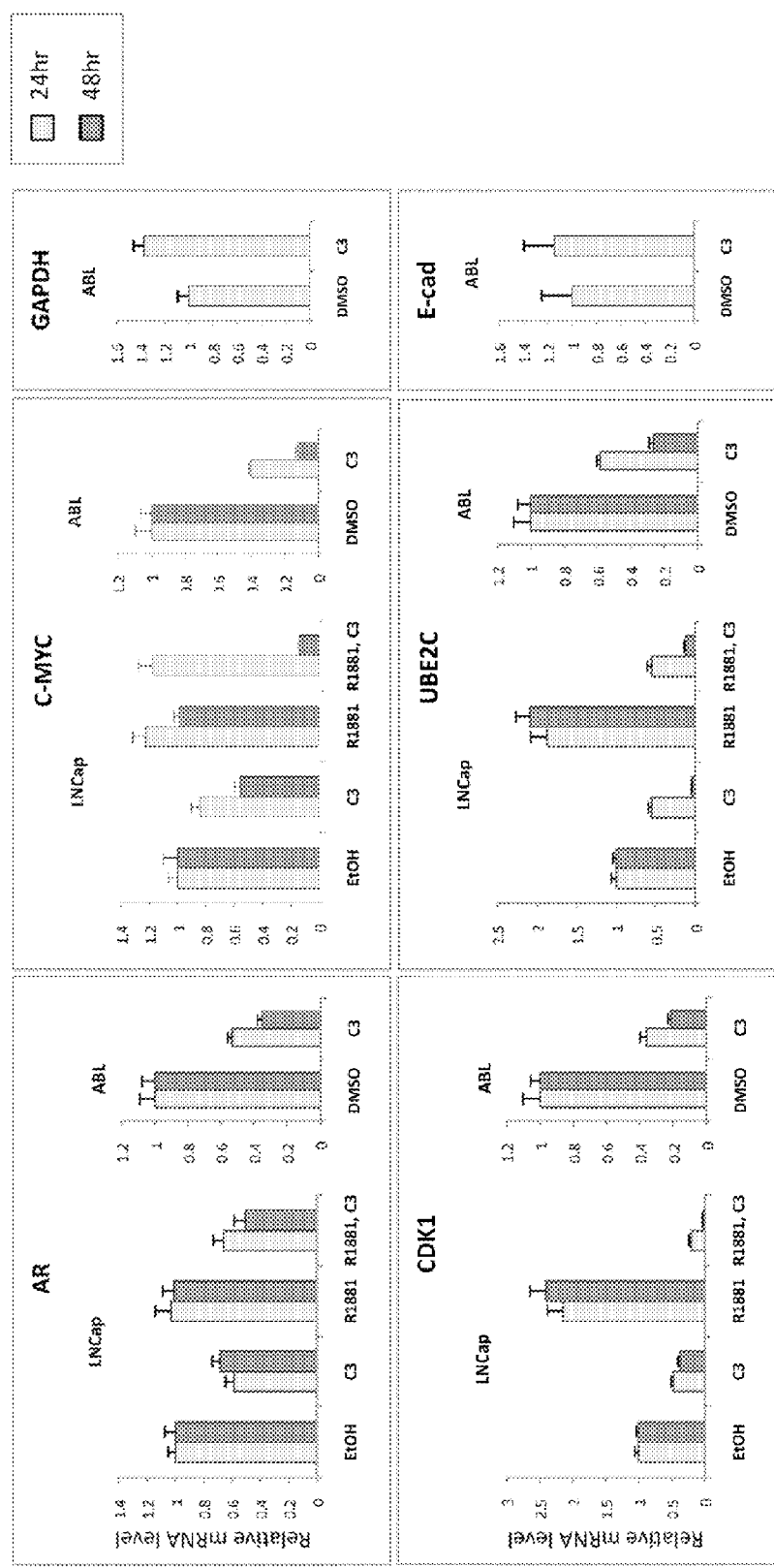
FIG. 16 shows a persistent effect of C3 on the expression of AR and β-catenin target genes. A) LNCaP or LNCaP-abl (ABL) cells were androgen-deprived in phenol-red free RPMI with 5% charcoal-stripped FBS for 48 hr and treated with DMSO or 20 μM C3 with or without 0.1 nM R1881 for up to 48 hr. ABL cells were treated similarly, but cultured in 5% charcoal-stripped phenol-red free RPMI. The mRNA was extracted at each time point and relative levels of indicated genes were analyzed by Q-PCR and normalized to RPL19. B) Protein from LNCaP cells was analyzed at each time point and immunoblotted with indicated antibodies.
Figure 16:
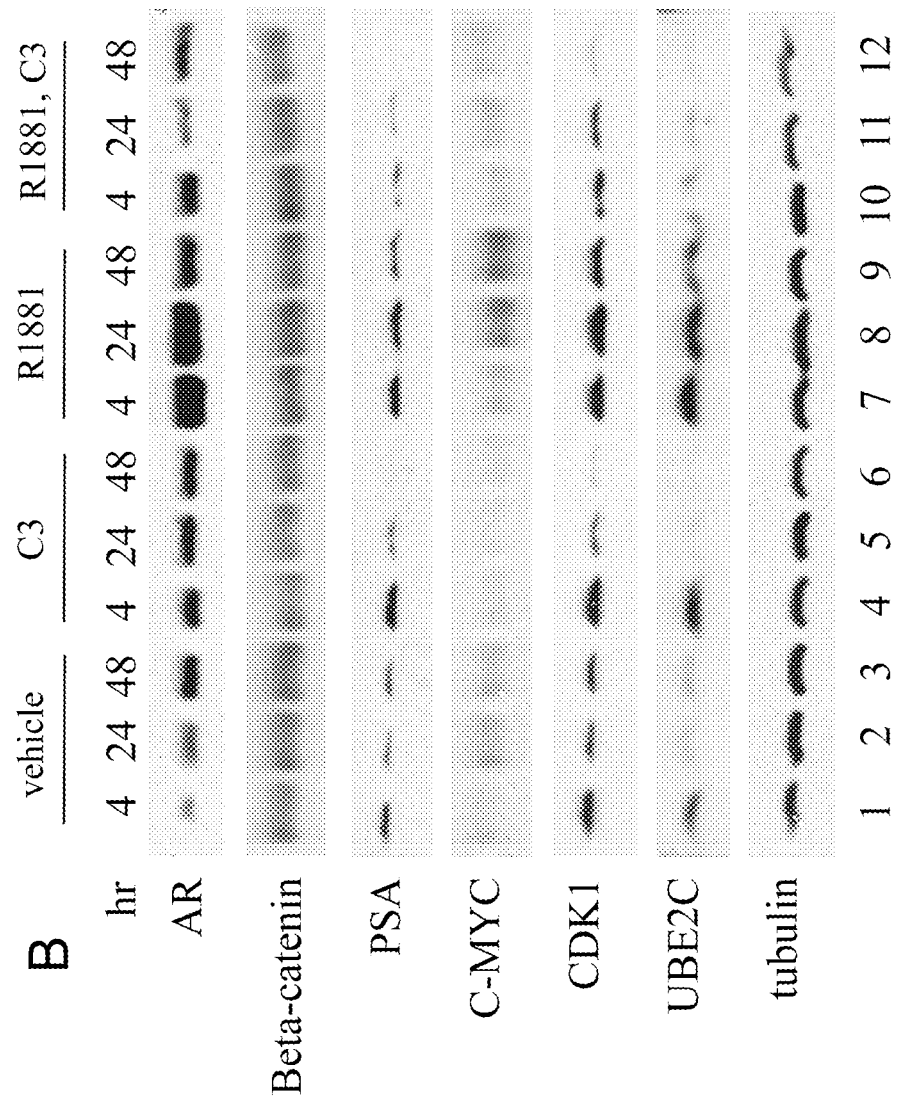
Figure 17:
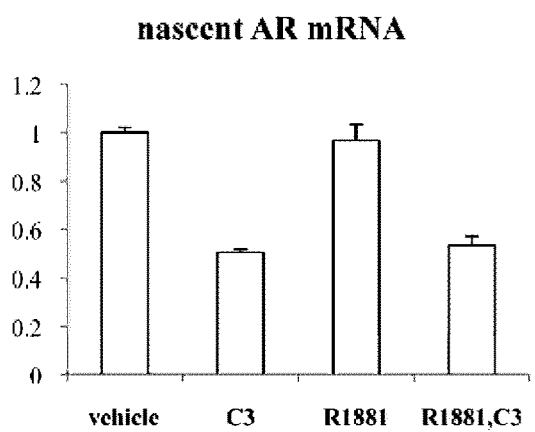
FIG. 17 shows that C3 inhibits transcription of AR nascent mRNA. LNCap cells were androgen-deprived for 48 hr and then treated with DMSO or 20 μM C3 with or without 0.1 nM R1881 for 4 hr. RNA was extracted, treated with deoxyribonuclease and subjected to cDNA synthesis. Relative levels of nascent AR mRNA were analyzed by Q-PCR using primers flanking exon/exon and exon/intron.

Experiments presented in FIGS. 15 and 16 indicate that C3 treatment results in decreased transcription of AR and AR target genes. If these effects occur directly through C3 interference with β-catenin and TCF4 interaction on the AR promoter, the effects are likely to be rapid. To evaluate AR mRNA levels shortly after C3 treatment newly synthesized transcript was examined using primers flanking an exon/exon and exon/intron boundary (FIG. 17). At four hours C3 treatment diminishes levels of AR mRNA in either the presence or absence of R1881.

Figure 18:
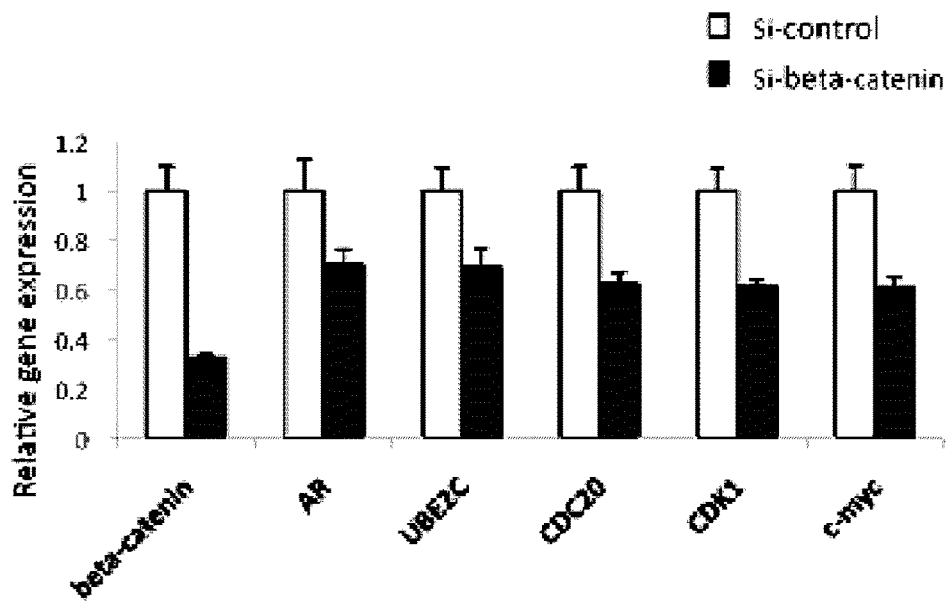
FIG. 18 reveals an effect of β-catenin knockdown on expression of AR and Wnt target genes in ABL cells. ABL cells were transfected with control or β-catenin siRNA and cultured in phenol-red free RPMI with 5% charcoal-stripped FBS for 48 hr. Relative mRNA levels of indicated genes were analyzed by Q-PCR.

To determine if the observed effects of C3 on AR-mediated gene transcription were dependent upon β-catenin, transcription of AR target genes in the presence and absence of β-catenin siRNA was evaluated. When β-catenin mRNA was depleted by approximately two-thirds in LNCaP-abl cells, AR and AR target genes promoting cell cycle progression through M-phase were decreased in a manner similar to that observed upon C3 treatment seen in FIG. 16, suggesting that AR expression is regulated through β-catenin, and/or that the AR/β-catenin protein complex is rate limiting for expression of these genes (FIG. 18).

Figure 19A:
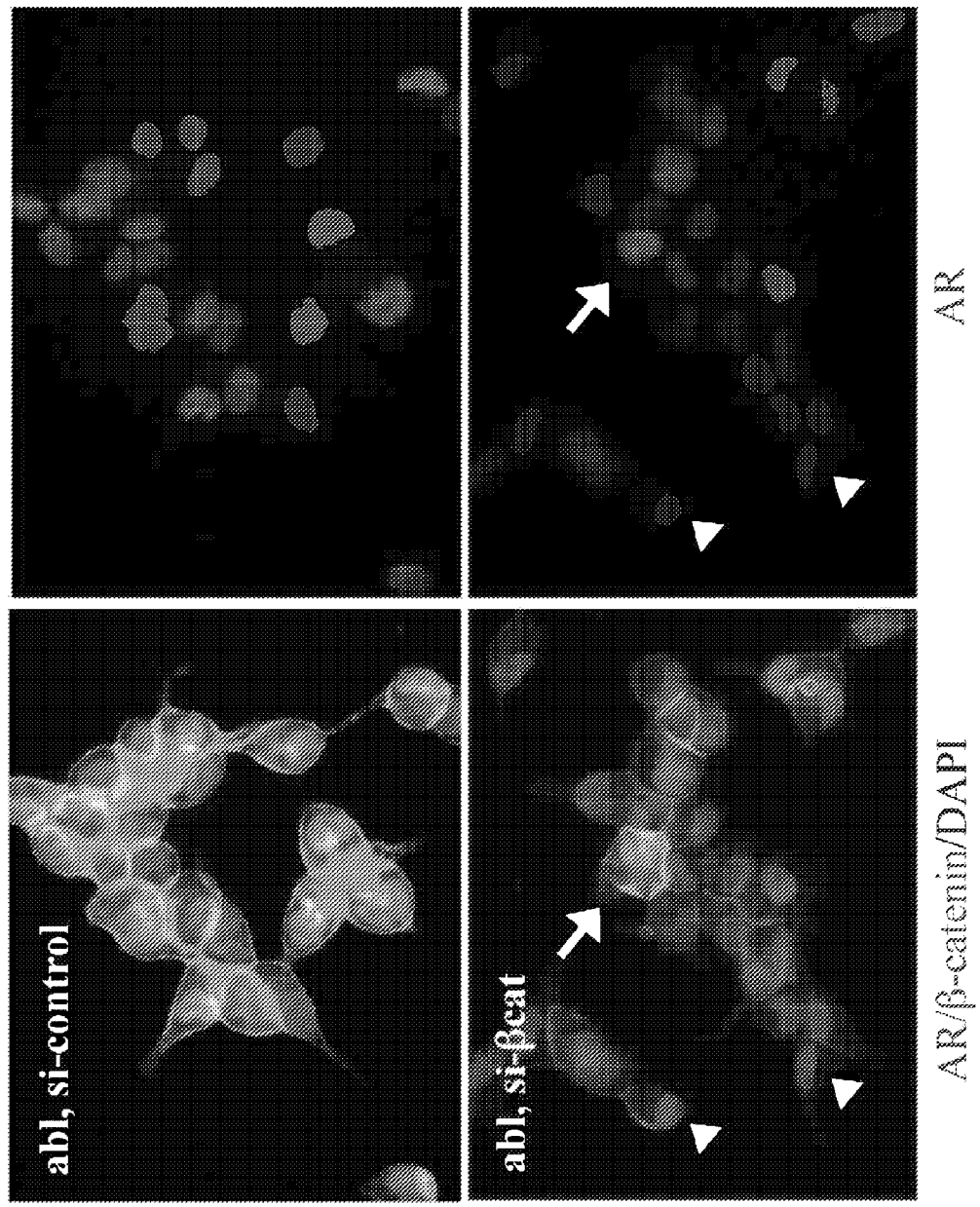
FIG. 19 reveals that (β-catenin mediates the inhibitory effect of C3 on AR expression in LNCaP. A) LNCaP-ABL cells were transfected with control or β-catenin siRNA and androgen-deprived in phenol-red free RPMI with 5% charcoal-stripped FBS for 24 hr and then treated with 0.1 nM R1881 for 24 hr. Cells were fixed with 4% paraformaldehyde and incubated with anti-AR (red), anti-β-catenin (green) antibodies, and DAPI solution (blue). Cells were observed by fluorescence microscopy. B) Cells were transfected as in A and Western blot analysis was performed with β-catenin or AR antibody. Tubulin is shown as an internal loading control.
Figure 19B:
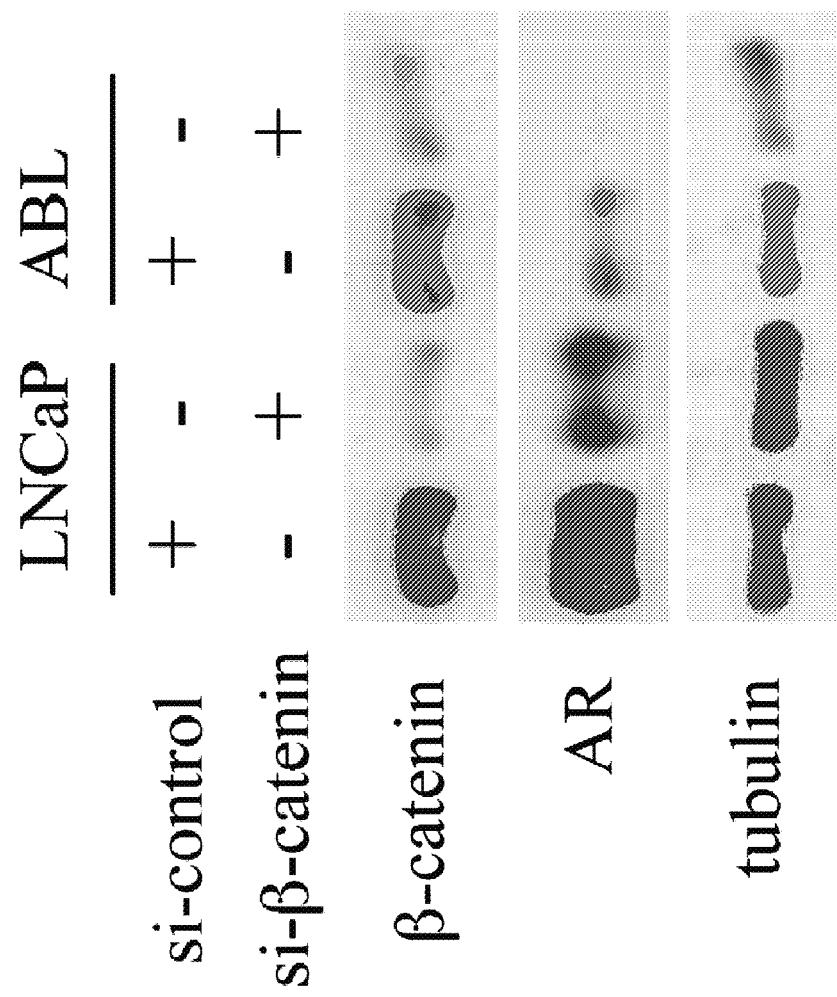

Experiments presented in FIGS. 15-18 indicate that C3 inhibits prostate cell growth by directly interfering with transcription of the AR. To examine the effect of loss of β-catenin on AR protein cells were treated with control siRNA or siRNA against β-catenin. The impact of β-catenin depletion is somewhat variable among cells (FIG. 19A; lower left panel), with some cells showing robust depletion of β-catenin (arrowheads) and others showing strong staining of β-catenin easily observable at the cell membrane (FIG. 19A; lower left panel; arrow). Interestingly, cells with endogenous levels of β-catenin clearly have higher levels of AR (FIG. 19A; lower right panel; arrow) than adjacent cells with lower levels of β-catenin (FIG. 19A; lower right panel; arrowheads), indicating that the cell specific expression of AR is regulated through β-catenin. These results were confirmed by Western blot analysis showing that depletion of β-catenin results in diminished levels of AR protein in both LNCaP and ABL cells (FIG. 19B).

An important objective in the initial screen for inhibitors of β-catenin responsive transcription (iCRT) was to isolate compounds that diminished the nuclear function of β-catenin without affecting β-catenin interaction with E-cadherin at the cell membrane. To verify that C3 does not affect membrane β-catenin in prostate cells, androgen-deprived LNCaP cells were treated with either DMSO (vehicle) or C3 and immunofluorescence was conducted to examine levels of β-catenin at the cell membrane. Importantly, cells treated with C3 show robust staining of membrane bound β-catenin, indicating that C3 does not affect the ability of β-catenin to interact with E-cadherin at the cell membrane.

Figure 20:
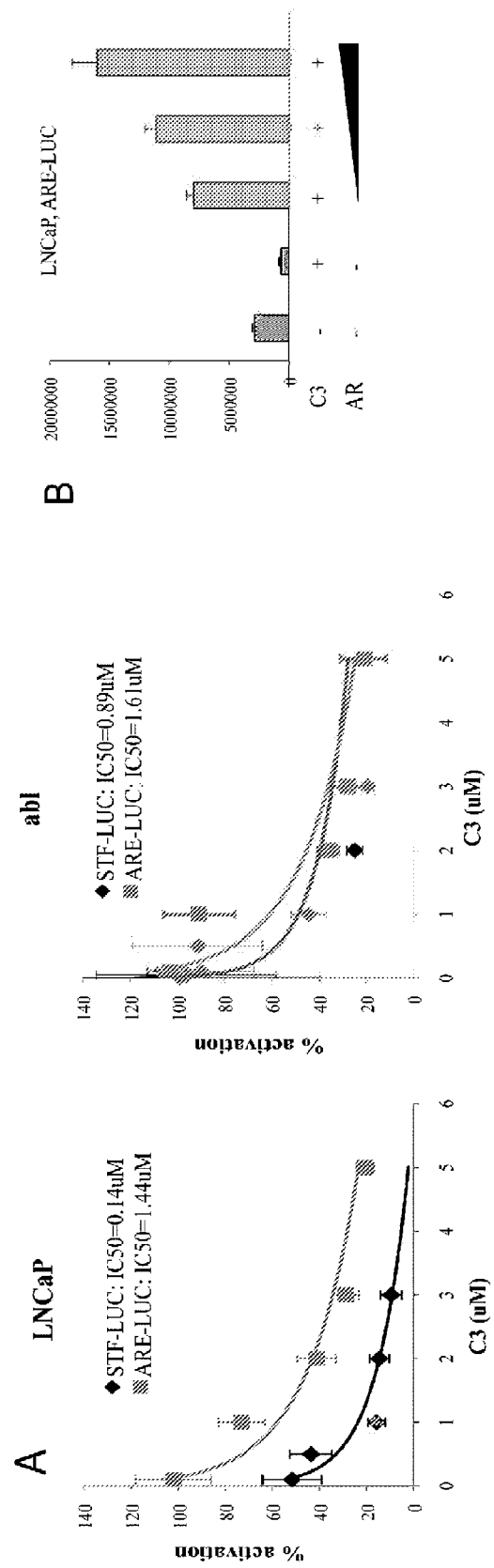
FIG. 20 shows A) Determination of the IC50 of C3 in prostate cancer cells. To determine the $IC_{50}$ for the β-catenin/Wnt-responsive reporter, cells were cotransfected with β-galactosidase (LacZ) and a constitutively active S37A stabilized β-catenin mutant construct together with the reporter construct, STF16-LUC. To determine the $IC_{50}$ for the AR-responsive construct, cells were cotransfected with LacZ and the AR responsive reporter construct, ARE-LUC. Luciferase activity in the presence of varying concentrations of C3 was analyzed by normalization to LacZ expression. B) AR overexpression circumvents C3 repression of AR-responsive transcription. LNCaP cells were cotransfected with 0.1 μg LacZ and 0.2 μg of the AR responsive reporter construct, ARE-LUC, together with 0, 0.05, 0.1 and 0.2 μg of an AR expression vector. Cells were androgen-deprived 24 hr after transfection, and 0.1 nM R1881 was added with or without 3 μM C3 for 24 hr. Luciferase activity was normalized to LacZ expression.

While the $IC_{50}$ for C3 has been determined in other cell types [Gonsalves et al., Proc Natl Acad Sci USA, 2011. 108 (15): 5954-63], it had not been determined in prostate cancer cells. Therefore, the concentration of C3 required to inhibit a Wnt/β-catenin responsive-reporter and an AR responsive reporter in LNCaP and LNCaP-abl cells was assessed (FIG. 20A). The present inventors determined that C3 inhibits the Wnt/β-catenin STF-LUC reporter with an $IC_{50}$ of 0.14 µM in LNCaP, and 0.89 µM in LNCaP-abl cells. The somewhat higher concentration needed in LNCaP-abl cells likely reflects greater activation of the β-catenin pathway in the LNCaP-abl cells through upregulation of the LEF1/TCF transcription factor as seen in other androgen-independent cell lines [Li et al., Cancer Res, 2009. 69(8): 3332-8]. The $IC_{50}$ needed to inhibit the ARE-LUC androgen responsive reporter gene was comparable between the two cell types at 1.44 and 1.61 µM (FIG. 20A). De-repression of ARE-LUC in AR transfected cells treated with C3 was also observed, suggesting that C3 acts through the AR pathway (FIG. 20B).

Figure 21:
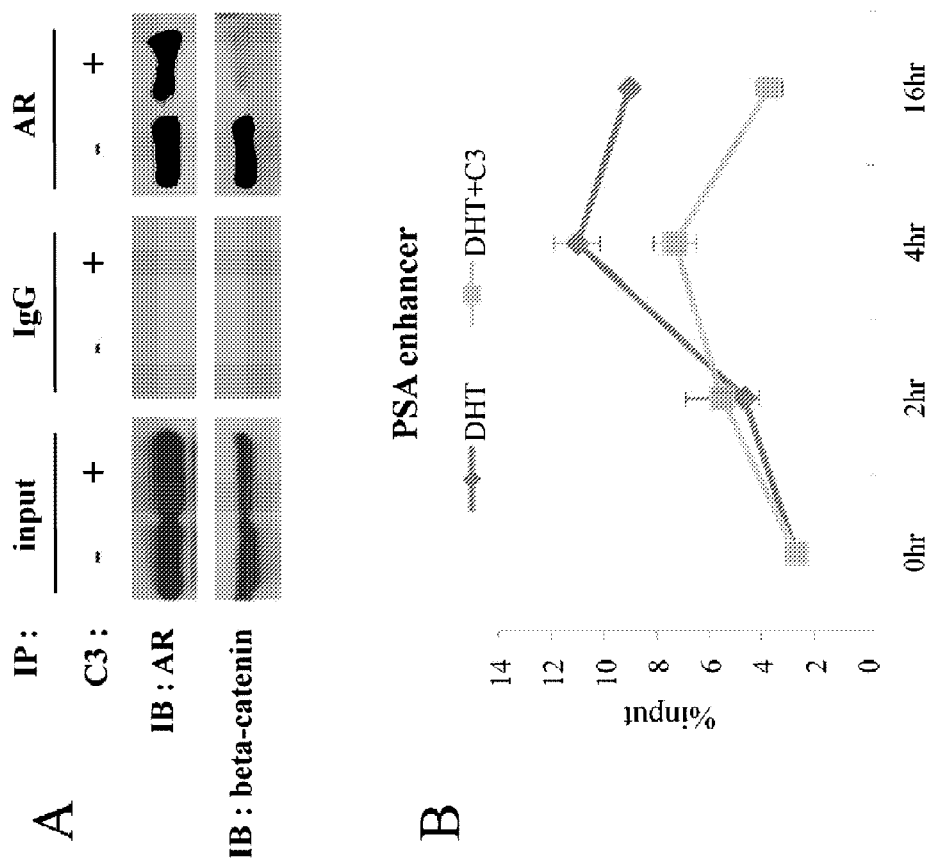
FIG. 21 shows that C3 inhibits AR and β-catenin interaction and β-catenin recruitment to the PSA enhancer. A) LNCaP cells were androgen-deprived for 48 hr and then treated with vehicle or 10 nM R1881 with or without 20 μM C3 for 4 hr. Nuclear extracts were immunoprecipitated with anti-AR antibody or normal mouse IgG followed by immunoblotting (IB) with indicated antibodies. B) LNCaP cells were hormone deprived for 3 days and then treated with vehicle or 100 nM DHT with or without 20 μM C3 for 2, 4 or 16 hr. Cells were crosslinked and chromatin was immunoprecipitated with β-catenin or IgG antibody. The precipitated DNA of the PSA enhancer was analyzed by Q-PCR. The results are presented as a percentage of input.

Literature reports suggest that the β-catenin binding site of AR overlaps with that of TCF4 [Song et al., J Biol Chem, 2005. 280(45): 37853-67; Yumoto et al., Proc Natl Acad Sci USA, 2012. 109(1): 143-8]. Therefore, the present inventors predict that C3 will not only inhibit AR transcription through interference with β-catenin/TCF interaction, but that it may also inhibit interaction with AR and β-catenin. To test this hypothesis, LNCaP cells were treated with 10 nM R1881 in the presence or absence of C3. It is noteworthy that AR protein is more stable at 10 nM R1881 (unlike the growth promoting concentration of 0.1 nM R1881 used in experiments above) and AR levels are comparable in the presence and absence of C3 (FIG. 21A, see input IB:AR). The results show that treatment with C3 greatly diminishes AR interaction with β-catenin (FIG. 21A). Further, chromatin immunoprecipitation assay (ChIP) shows that C3 treatment results in diminished β-catenin on the PSA enhancer (FIG. 21B) a region on which AR binding is well established.

Example 6

The results presented in Example 5 and related figures indicate that C3 (an iCRT) shows promise as a lead compound that can inhibit the AR through altered function of β-catenin in prostate cancer cells. To expand these results, the impact of C3 in an in vivo model of prostate tumorigenesis was tested. To this end, the effect of C3 in a mouse xenograft model of androgen-dependent and castration-resistant prostate cancer cell growth was evaluated. Sphere-forming assays to examine the impact of C3 on the self-renewing capacity of prostate cancer cells will also be conducted.

Determine the impact of C3 on prostate tumor growth in a xenograft model; analyze the blood levels of C3 and its metabolites over time: In that mice treated with 75 mg/Kg C3 injected 5 days a week for 5 weeks did not lose weight and histology of all major organs was normal, the present inventors have determined that C3 is not toxic. Importantly, given the role of the Wnt/β-catenin pathway as a regulator of intestinal stem cells [Korinek et al., Nat Genet, 1998. 19(4): 379-83; van de Wetering et al., Cell, 2002. 111(2): 241-50], no gut toxicity was observed. In addition, continuous injection of 20 mg/Kg by mini-pump for 5 weeks also showed no toxicity. To establish the most efficacious concentration of C3 (and its derivatives), the maximum tolerated dose (MTD) that yields no systemic toxicity was determined. Accordingly, mice were injected 5 days/week for 5 weeks at a range of concentrations between 50-125 mg/Kg and compared to vehicle-alone control. Toxicity was monitored by assessing mouse weight, blood counts and mortality. The MTD determination was performed at the fee-for-service, anti-tumor assessment facility at Memorial Sloan Kettering Cancer Center.

PK determination: For each of the compounds, mice will be administered a single dose (MTD mg/Kg for each compound), and blood samples will be obtained at pre-dose and at 0.5, 1, 1.5, 2, 4, 9, 12, 24 and 48 h after dosing to determine plasma levels of C3 and their metabolites by high-performance liquid chromatography and/or mass spectrometry. These studies provide information useful in determining the frequency/duration of compound administration in the in vivo mouse xenograft assays.

The cell types for xenograft studies include LNCaP, LNCaP-abl and VCaP, which have all been previously utilized for xenograft studies and are able to recur following castration [Korenchuk et al., In Vivo, 2001. 15(2): 163-8; Culig et al., Br J Cancer, 1999. 81(2): 242-51; Graff et al., J Biol Chem, 2000. 275(32): 24500-5]. VCaP cells harbor a wild type androgen receptor and are androgen-dependent for growth [van Bokhoven et al., Prostate, 2003. 57(3): 205-25]. Other characteristics of cells to be considered in such experiments include the mutational status of AR, pTEN, p53, ETS fusion, and the year derived. Following determination of the MTD, $5 \times 10^6$ cells are mixed with an equal volume of Matrigel (BD Biosciences) and injected subcutaneously into the right and left flank of a BALB/c nu/nu outbred mouse. When tumors reach an average of 50 mm³ (day 0), mice are randomized into two groups of 5 and treated by intraperitoneal injection at a concentration established by the MTD. To assay growth, tumors are measured with Vernier calipers, and the total volume determined by using the formula 0.52×width× height×depth. Tumor growth is measured twice weekly and animals are also weighed twice weekly to assess toxicity.

The effect of the compounds on proliferation and apoptosis in the tumors can also be assessed by immunohistochemical staining of the paraffin embedded tumor samples with antibodies against AR, Ki67 and phopho-histone H3 (proliferation), activated caspase 3 (apoptosis) and histone γ-H2AX and phospho-chk1 (senescence). Changes in expression of proteins that are products of AR target genes (prostate specific antigen, PSA; transmembrane protease serine 2, TMPRSS2; and the NKX3.1 transcription factor) and β-catenin target genes (c-myc, axin-2, cycD1) can also be assessed. Since human prostate cancer typically metastasizes to bone, the impact of C3 on proliferation and apoptosis of C4-2B cells that undergo metastasis [Thalmann et al., Prostate, 2000. 44(2): 91-103 July 1; 44(2)] and PCSD1 cells derived from a bone metastasis will also be assessed [Raheem et al., J Transl Med, 2011. 9: 185].

Establish the Impact of C3 on Tumor Recurrence and Growth of the Recurring Tumor:

To model castration-resistant prostate cancer, VCaP, LNCaP and LNCaP-abl xenograft tumors can be grown in animals depleted of endogenous androgens by surgical castration. See, for example, Korenchuk et al., In Vivo, 2001. 15(2): 163-8; Horoszewicz et al., Cancer Res, 1983. 43(4): 1809-18; and Culig et al., Br J Cancer, 1999. 81(2): 242-51, respectively with regard to the origin and properties of these cell lines. To determine if C3 has the potential to prevent recurrence, animals can be subjected to C3 or vehicle treatment immediately after castration for 5 days a week for 5 weeks, and tumor growth assayed as described above. The expectation is that tumors will recur in the vehicle treated, but not in C3 treated animals. To determine if C3 has the potential to augment the effects of androgen deprivation therapy in castration resistant prostate cancer, tumors will be permitted to recur and reach 50 mm$^3$ in another group of castrated animals. The animals can then be subjected to treatment with vehicle or C3 for 5 days a week for 5 weeks to determine if C3 has the potential to prevent growth under castrate conditions.

Figure 22:
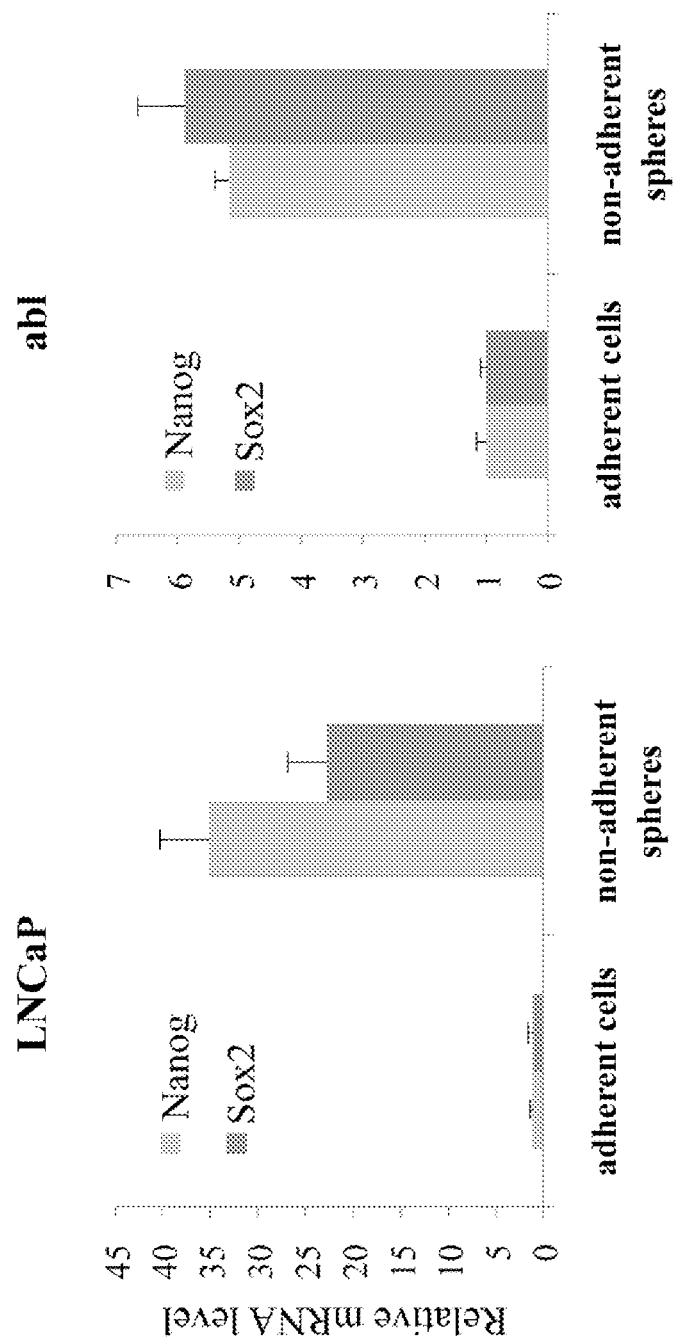
FIG. 22 shows that prostate cancer spheres express stemness markers. LNCaP and LNCaP-abl cells were cultured in non-adherent plates supplemented with EGF and bFGF for 14 days. RNA was extracted and subjected to cDNA synthesis. Q-PCR was used to analyze the relative mRNA levels of indicated stemness marker genes in spheres compared to cells cultured in adherent condition in 10% FBS RPMI media.

Determine the ability of C3 to target prostate cancer stem cells:

Increasing evidence shows that Wnt/β-catenin signaling is highly active in a cancer stem cell population, suggesting an important role in stem cell self-renewal [Bisson et al., Cell Res, 2009. 19(6): 683-97; Korkaya et al., PLoS Biol, 2009. 7(6): e1000121]. To investigate if inhibition of β-catenin responsive transcription by C3 decreases the stem cell population in prostate cancer cells, the in vitro sphere-forming assay can be used, which assesses stem/progenitor cell enrichment in multiple cell and tissue types [Bisson et al., Cell Res, 2009. 19(6): 683-97; Dontu et al., Genes Dev, 2003. 17(10): 1253-70]. Such assays have demonstrated the presence of a stem cell population in both LNCaP and VCaP cells [Bisson et al., Cell Res, 2009. 19(6): 683-97]. By analyzing sphere formation and their capability to be passaged for multiple generations, the present inventors can determine if C3 affects the self-renewal ability of prostate cancer stem cells, which property would facilitate effective targeting of this population of cells. FIG. 22 shows that LNCaP and LNCaP-abl cells show up-regulation of the Nanog and Sox2 genes associated with "stemness" when cells are grown in sphere formation assays. In addition, FACS can be performed to isolate CD133+/CD44+ cells that represent the stem cell population and determine if β-catenin target gene expression is higher in these cells than the parental cells. An assessment of CD133+/CD44+ cells can be performed to determine if these cells have higher renewal capacity and if they undergo apoptosis in response to C3.

Results

Figure 23:
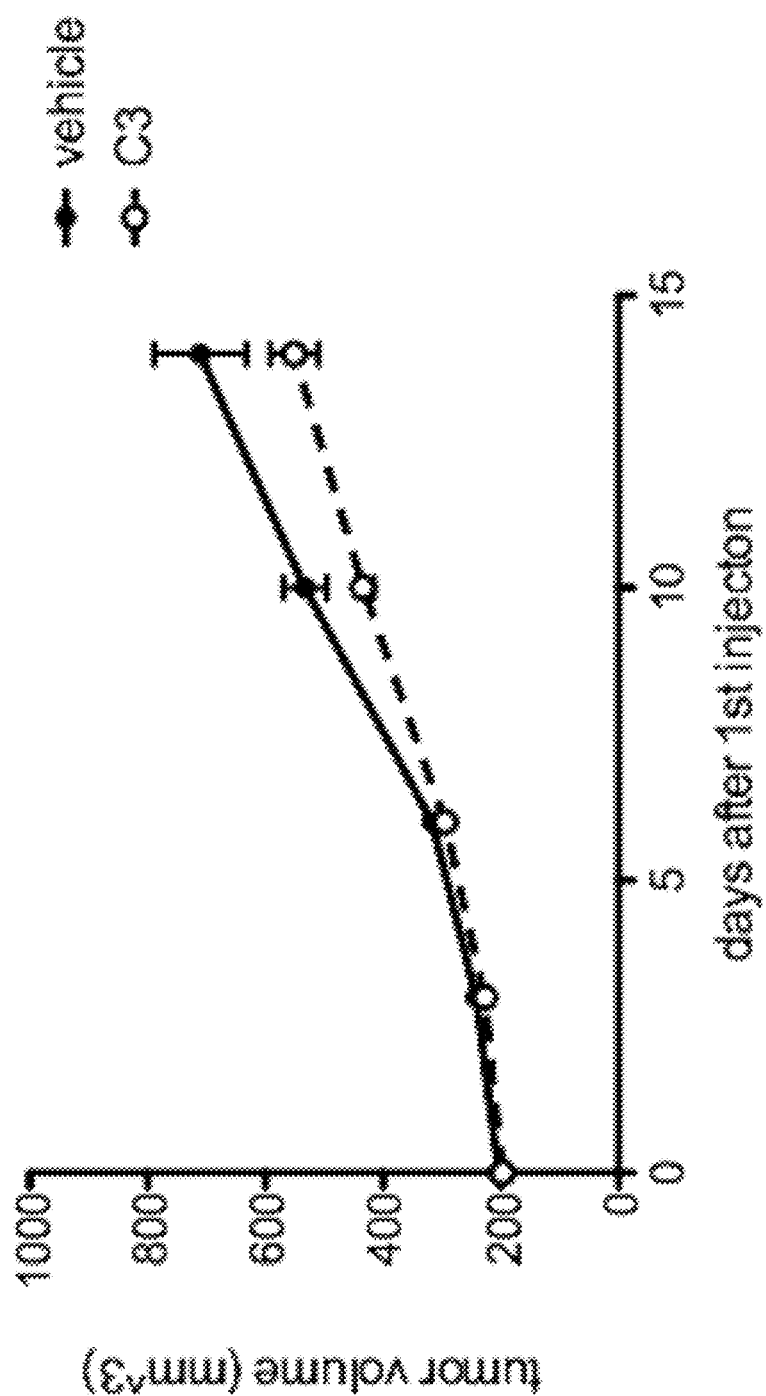
FIG. 23 shows that C3 inhibits tumor growth in a xenograft model of castration-resistant prostate cancer. Nude mice bearing LNCaP-abl tumors were treated with vehicle or C3 daily (100 mg/kg intraperitoneal injection for the first one week and intratumor injection for the rest of the experiment). Tumor volumes were measured twice weekly.

Methods: Rapidly cycling LNCaP-abl cells (15×10$^6$) were mixed with an equal volume of Matrigel and injected subcutaneously into the flank region of nude male mice. When tumors reach an average of al least 200 mm$^3$ (day 0), they were randomized into two groups of 5 and treated by intraperitoneal or intratumor injection of DMSO (vehicle) or C3 at a concentration of 100 mg/kg. To assess growth, tumors were measured twice weekly with Vernier calipers, and the total volume was determined. The results of this experiment are shown in FIG. 23. As shown therein, C3 reduced tumor volume to a statistically significant degree in this animal model of prostate cancer.

Example 7

Exemplary Compounds of the Invention

The following compounds, as exemplified in Tables 1-10, have been purchased, or can be purchased, or can be prepared according to the synthetic schemes described herein, or can be prepared according to the synthetic methods known to one skilled in the art.

TABLE 1

Oxazole amides (R$^3$ = NH-benzyl)

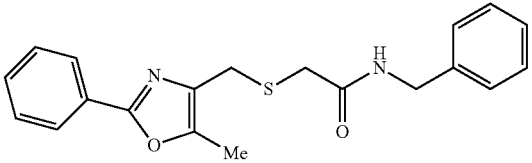 [SMILES: Cc1oc(-c2ccccc2)nc1CSCC(=O)NCc1ccccc1]

| ID | Structure | MW |
|---|---|---|
| IIa-1 | 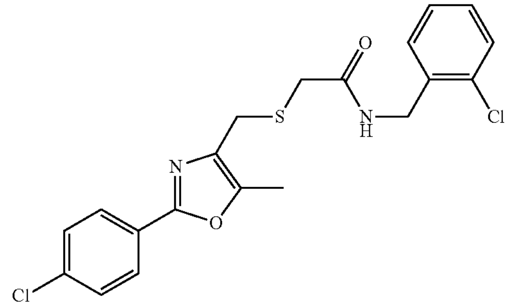 [SMILES: Cc1oc(-c2ccc(Cl)cc2)nc1CSCC(=O)NCc1ccccc1Cl] | 421.35 |

TABLE 1-continued
Oxazole amides ($R^3$ = NH-benzyl)
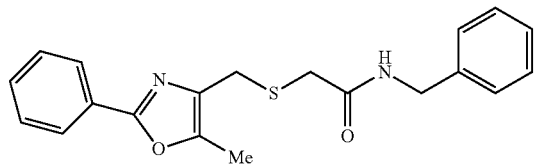
| ID | Structure | MW |
| --- | --- | --- |
| IIa-2 | 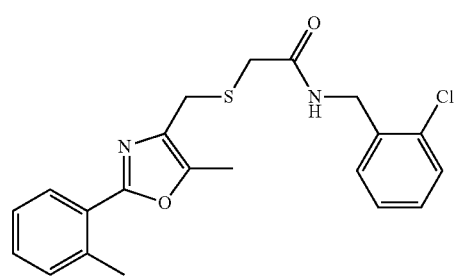 [SMILES: Cc1ccccc1-c1nc(CSCC(=O)NCc2ccccc2Cl)c(C)o1] | 400.93 |
| IIa-3 | 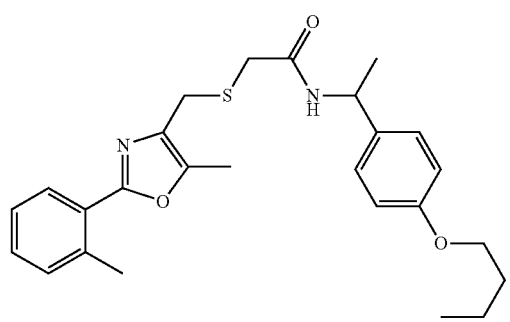 [SMILES: CCCCOc1ccc(C(C)NC(=O)CSCc2nc(-c3ccccc3C)oc2C)cc1] | 452.62 |
| IIa-4 | 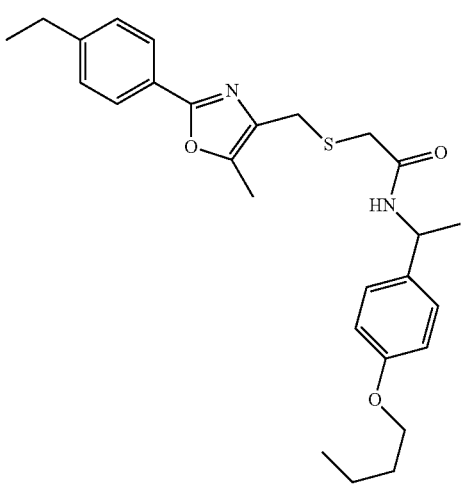 [SMILES: CCCCOc1ccc(C(C)NC(=O)CSCc2nc(-c3ccc(CC)cc3)oc2C)cc1] | 466.65 |

TABLE 1-continued

Oxazole amides (R³ = NH-benzyl)

| ID | Structure | MW |
|---|---|---|
| IIa-5 | 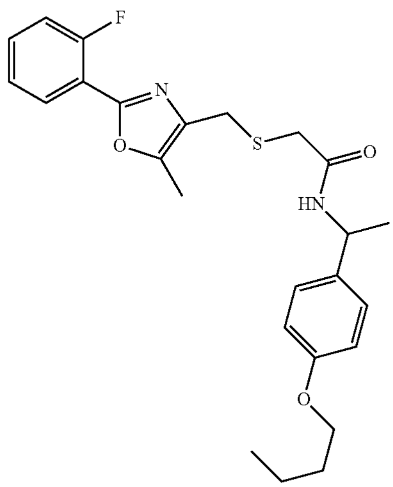 [SMILES: CCCCOc1ccc(C(C)NC(=O)CSCc2nc(-c3ccccc3F)oc2C)cc1] | 456.58 |
| IIa-6 | 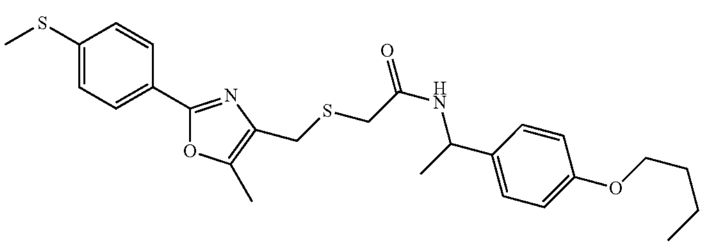 [SMILES: CCCCOc1ccc(C(C)NC(=O)CSCc2nc(-c3ccc(SC)cc3)oc2C)cc1] | 484.68 |
| IIa-7 | 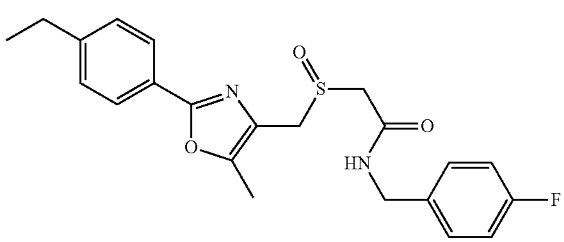 [SMILES: CCc1ccc(-c2nc(CS(=O)CC(=O)NCc3ccc(F)cc3)c(C)o2)cc1] | 414.50 |
| IIa-8 | 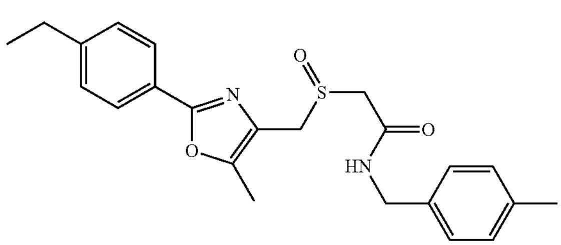 [SMILES: CCc1ccc(-c2nc(CS(=O)CC(=O)NCc3ccc(C)cc3)c(C)o2)cc1] | 410.54 |

TABLE 1-continued
Oxazole amides (R³ = NH-benzyl)
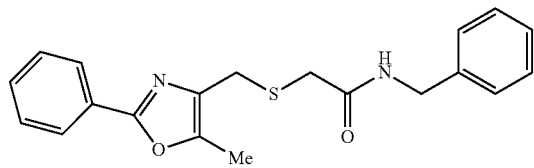
| ID | Structure | MW |
|---|---|---|
| IIa-9 | | 430.96 |
| IIa-10 | | 430.96 |
| IIa-11 | | 396.51 |
| IIa-12 | | 440.52 |

TABLE 1-continued

Oxazole amides (R³ = NH-benzyl)

| ID | Structure | MW |
|---|---|---|
| IIa-13 | 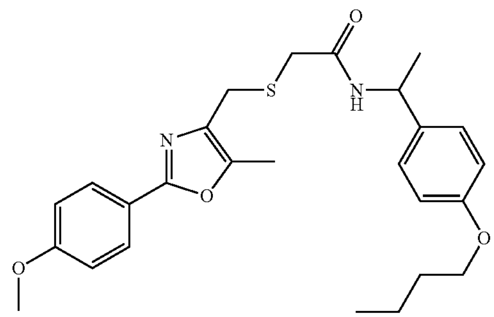 [SMILES: CCCCOc1ccc(C(C)NC(=O)CSCc2nc(-c3ccc(OC)cc3)oc2C)cc1] | 468.62 |
| IIa-14 | 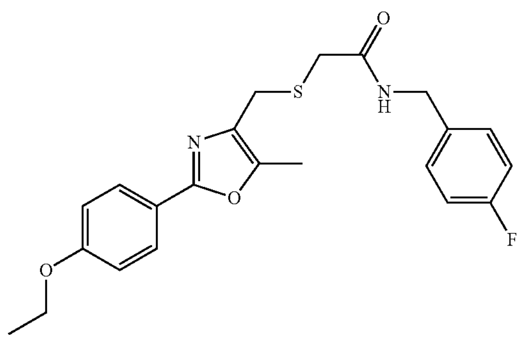 [SMILES: CCOc1ccc(-c2nc(CSCC(=O)NCc3ccc(F)cc3)c(C)o2)cc1] | 414.50 |
| IIa-15 | 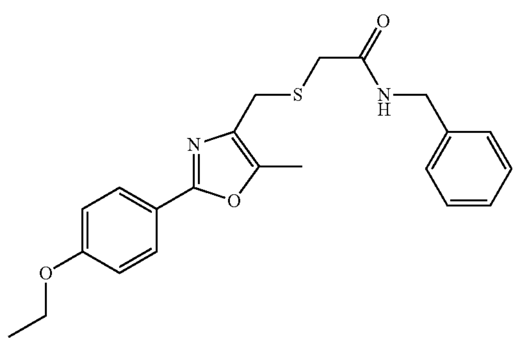 [SMILES: CCOc1ccc(-c2nc(CSCC(=O)NCc3ccccc3)c(C)o2)cc1] | 396.51 |
| IIa-16 | 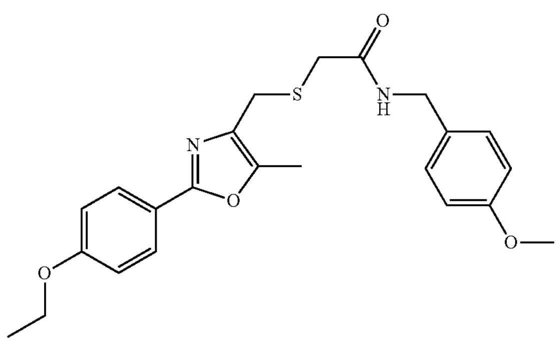 [SMILES: CCOc1ccc(-c2nc(CSCC(=O)NCc3ccc(OC)cc3)c(C)o2)cc1] | 426.54 |

TABLE 1-continued
Oxazole amides (R³ = NH-benzyl)
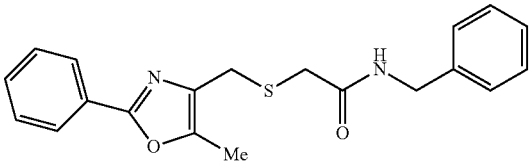
| ID | Structure | MW |
|---|---|---|
| IIa-17 | 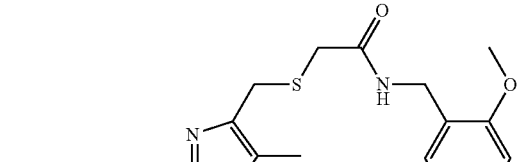 | 426.54 |
| IIa-18 | 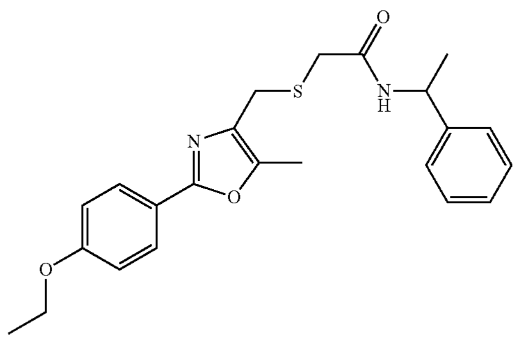 [SMILES: CCOc1ccc(-c2nc(CSCC(=O)NC(C)c3ccccc3)c(C)o2)cc1] | 410.54 |
| IIa-19 | 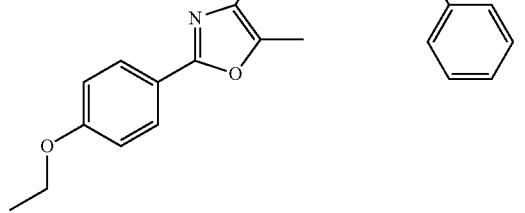 | 436.58 |
| IIa-20 | 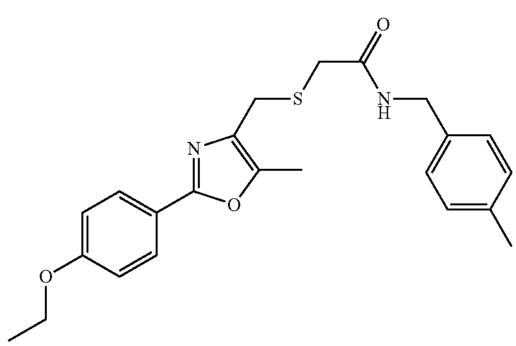 [SMILES: CCOc1ccc(-c2nc(CSCC(=O)NCc3ccc(C)cc3)c(C)o2)cc1] | 410.54 |

TABLE 1-continued
Oxazole amides (R³ = NH-benzyl)
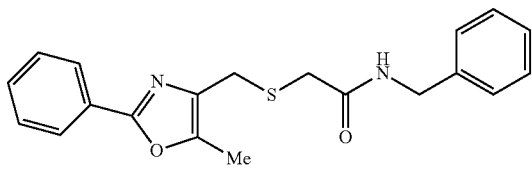
| ID | Structure | MW |
| --- | --- | --- |
| IIa-21 | 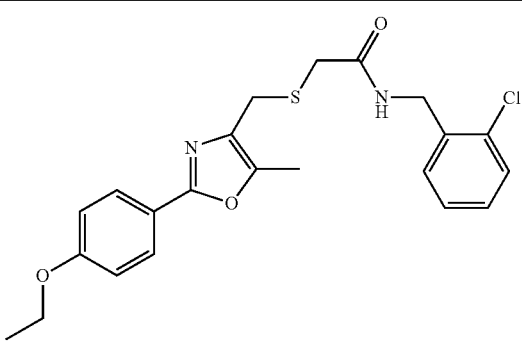 | 430.96 |
| IIa-22 | 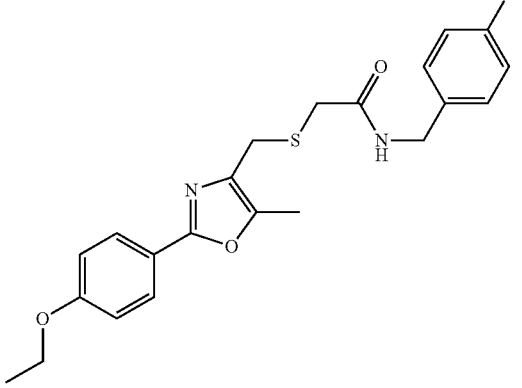 | 430.96 |
| IIa-23 | 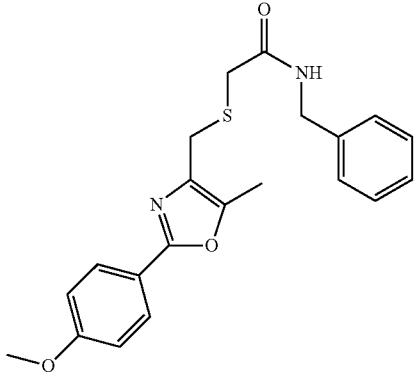 [SMILES: COc1ccc(-c2nc(CSCC(=O)NCc3ccccc3)c(C)o2)cc1] | 382.49 |

TABLE 1-continued
Oxazole amides (R³ = NH-benzyl)
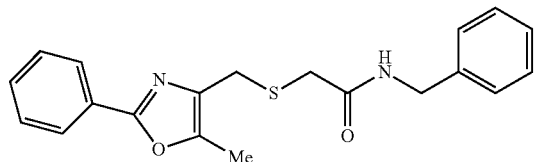
| ID | Structure | MW |
| --- | --- | --- |
| IIa-24 | 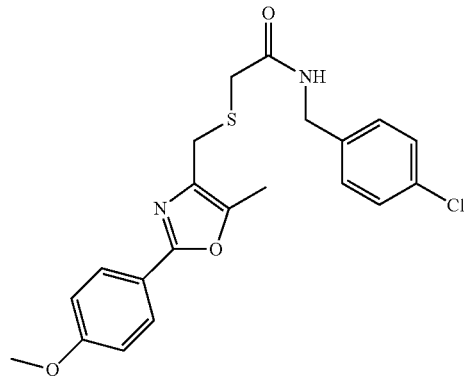 [SMILES: COc1ccc(-c2nc(CSCC(=O)NCc3ccc(Cl)cc3)c(C)o2)cc1] | 416.93 |
| IIa-25 | 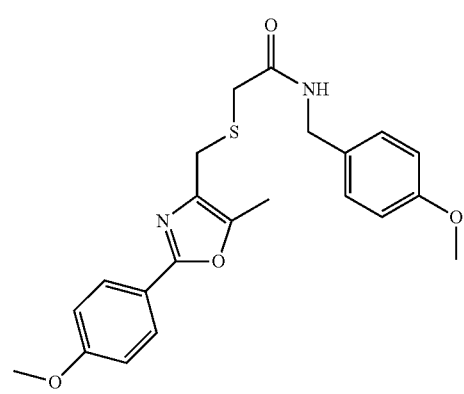 | 412.51 |
| IIa-26 | 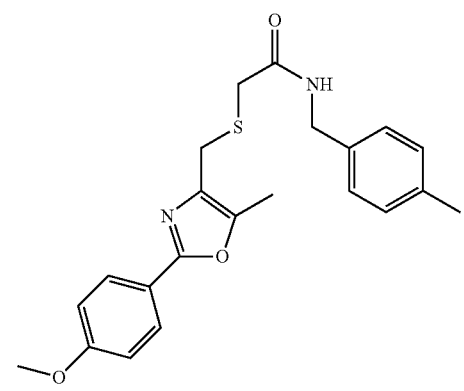 | 396.51 |

TABLE 1-continued

Oxazole amides (R³ = NH-benzyl)

| ID | Structure | MW |
|---|---|---|
| IIa-27 | | 426.50 |
| IIa-28 | | 396.51 |
| IIa-29 | | 412.51 |

TABLE 1-continued

Oxazole amides (R³ = NH-benzyl)

| ID | Structure | MW |
|---|---|---|
| IIa-30 | 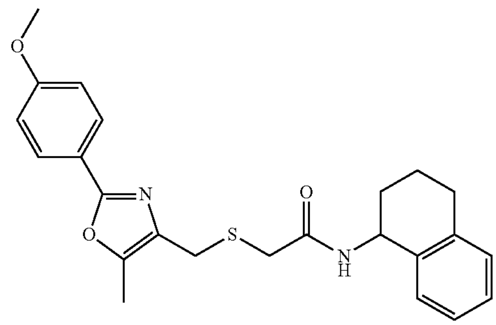 [SMILES: COc1ccc(-c2nc(CSCC(=O)NC3CCCc4ccccc43)c(C)o2)cc1] | 422.55 |
| IIa-31 | 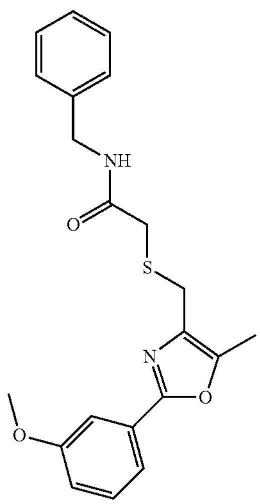 | 382.49 |
| IIa-32 | 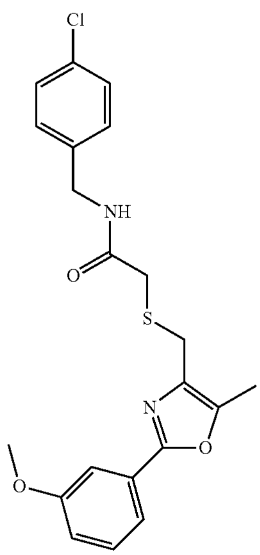 | 416.93 |

TABLE 1-continued
Oxazole amides (R³ = NH-benzyl)
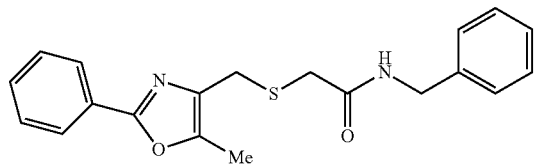
| ID | Structure | MW |
|---|---|---|
| IIa-33 | | 396.51 |
| IIa-34 | | 412.51 |

TABLE 1-continued
Oxazole amides (R³ = NH-benzyl)
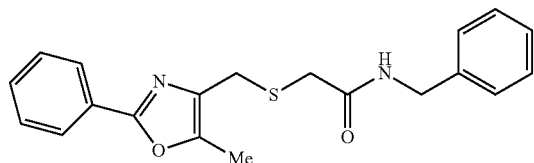
| ID | Structure | MW |
|---|---|---|
| IIa-35 | 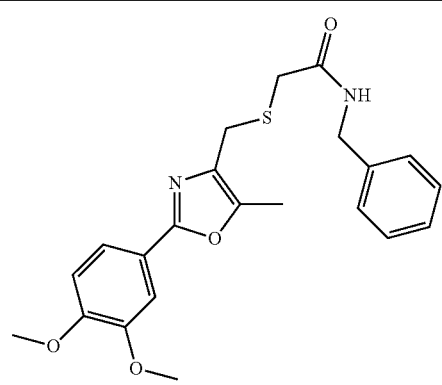 | 412.51 |
| IIa-36 | 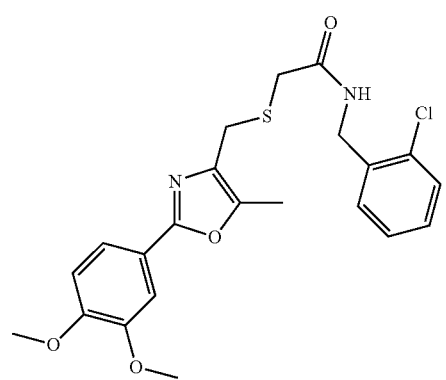 [SMILES: COc1ccc(-c2nc(CSCC(=O)NCc3ccccc3Cl)c(C)o2)cc1OC] | 446.96 |
| IIa-37 | 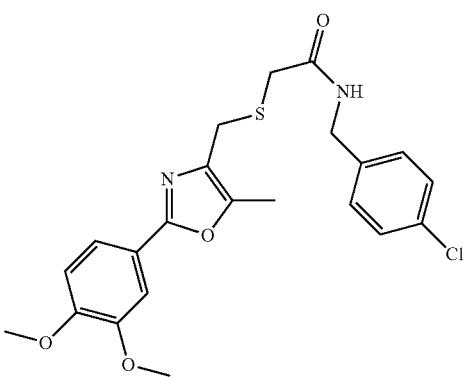 [SMILES: COc1ccc(-c2nc(CSCC(=O)NCc3ccc(Cl)cc3)c(C)o2)cc1OC] | 446.96 |

TABLE 1-continued
Oxazole amides (R³ = NH-benzyl)
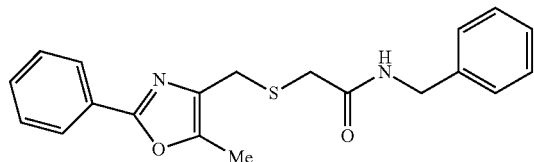
| ID | Structure | MW |
|---|---|---|
| IIa-38 | 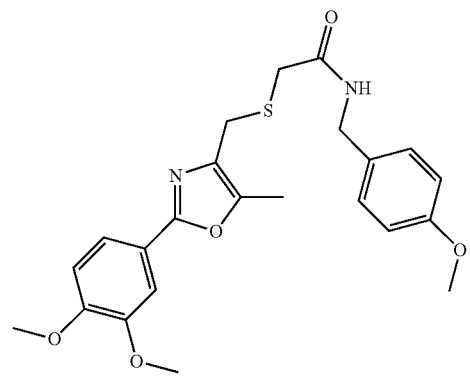 [SMILES: COc1ccc(CNC(=O)CSCc2nc(-c3ccc(OC)c(OC)c3)oc2C)cc1] | 442.54 |
| IIa-39 | | 456.52 |
| IIa-40 | 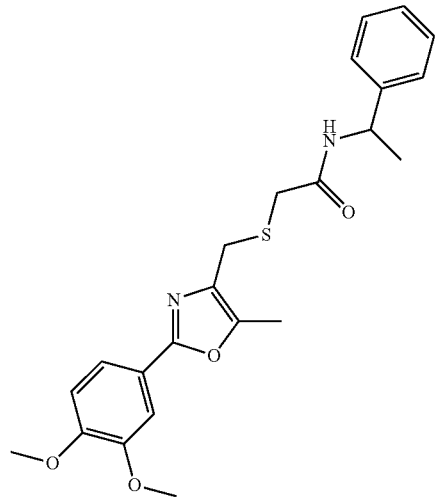 [SMILES: COc1ccc(-c2nc(CSCC(=O)NC(C)c3ccccc3)c(C)o2)cc1OC] | 426.54 |

TABLE 1-continued
Oxazole amides (R³ = NH-benzyl)
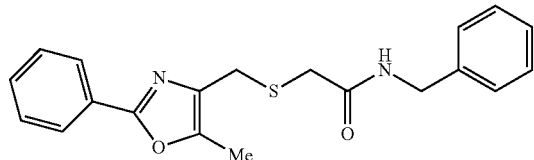
| ID | Structure | MW |
|---|---|---|
| IIa-41 | 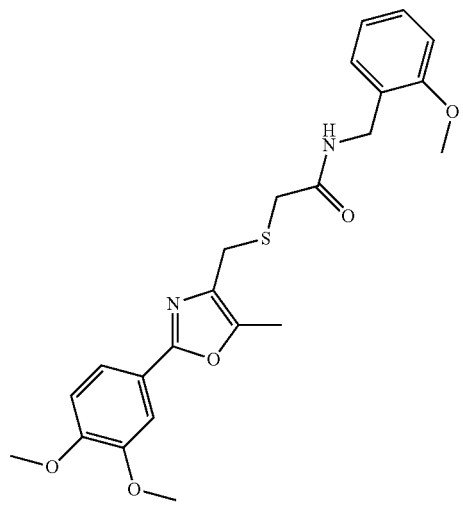 [SMILES: COc1ccccc1CNC(=O)CSCc1nc(-c2ccc(OC)c(OC)c2)oc1C] | 442.54 |
| IIa-42 | 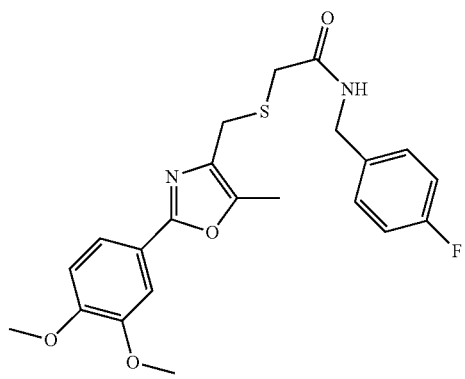 [SMILES: COc1ccc(-c2nc(CSCC(=O)NCc3ccc(F)cc3)c(C)o2)cc1OC] | 430.50 |
| IIa-43 | 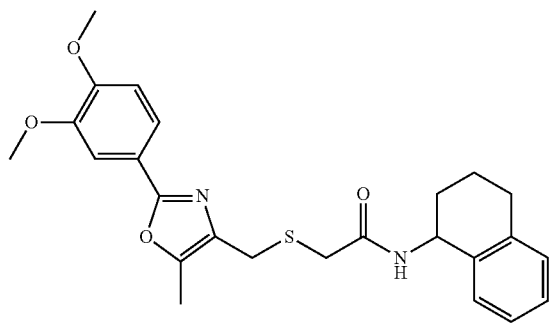 [SMILES: COc1ccc(-c2nc(CSCC(=O)NC3CCCc4ccccc43)c(C)o2)cc1OC] | 452.58 |

TABLE 1-continued
Oxazole amides (R³ = NH-benzyl)
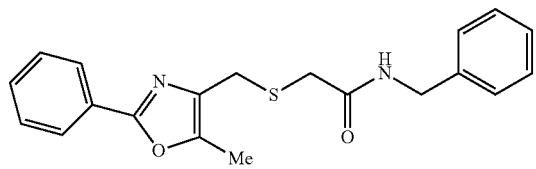
| ID | Structure | MW |
| --- | --- | --- |
| IIa-44 | 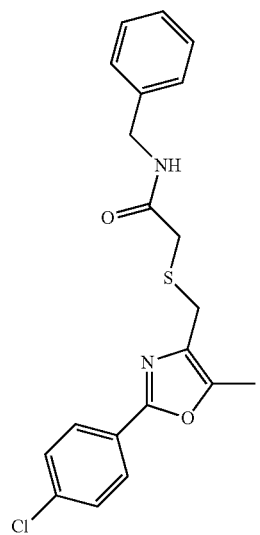 [SMILES: Cc1oc(-c2ccc(Cl)cc2)nc1CSCC(=O)NCc1ccccc1] | 386.90 |
| IIa-45 | 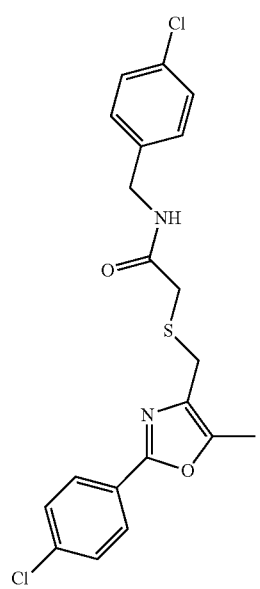 [SMILES: Cc1oc(-c2ccc(Cl)cc2)nc1CSCC(=O)NCc1ccc(Cl)cc1] | 421.35 |

TABLE 1-continued
Oxazole amides (R³ = NH-benzyl)
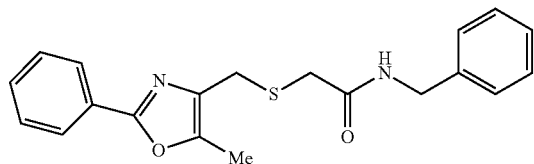
| ID | Structure | MW |
| --- | --- | --- |
| IIa-46 | 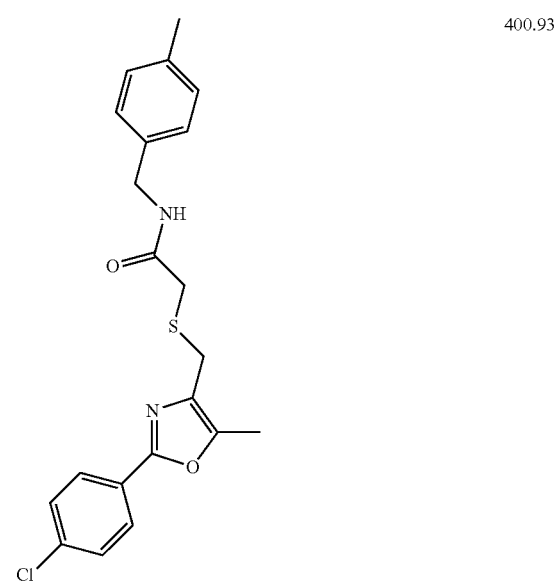 | 400.93 |
| IIa-47 | 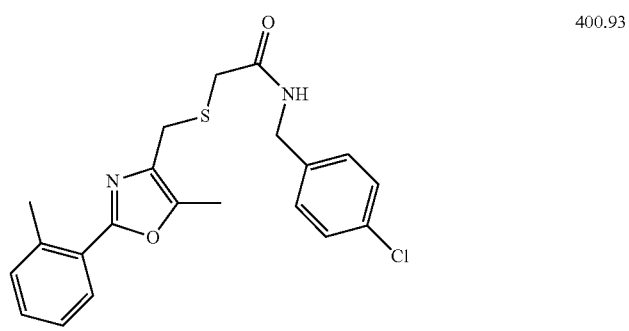 | 400.93 |
| IIa-48 | 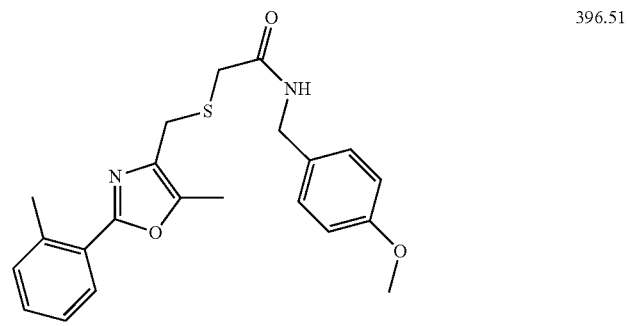 | 396.51 |

TABLE 1-continued
Oxazole amides (R³ = NH-benzyl)
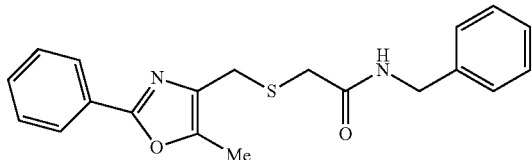
| ID | Structure | MW |
|---|---|---|
| IIa-49 | 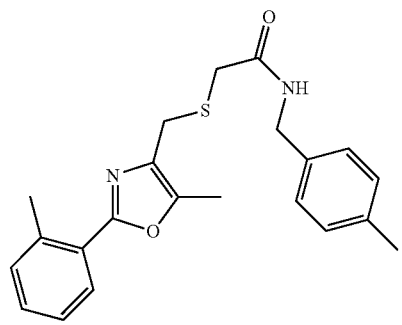 [SMILES: Cc1ccc(CNC(=O)CSCc2nc(-c3ccccc3C)oc2C)cc1] | 380.51 |
| IIa-50 | 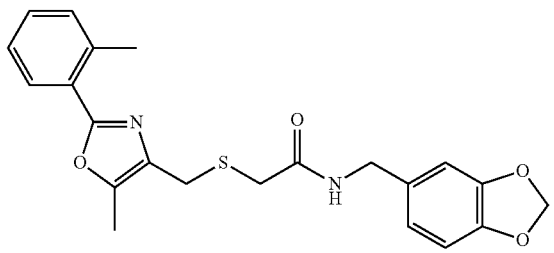 | 410.50 |
| IIa-51 | 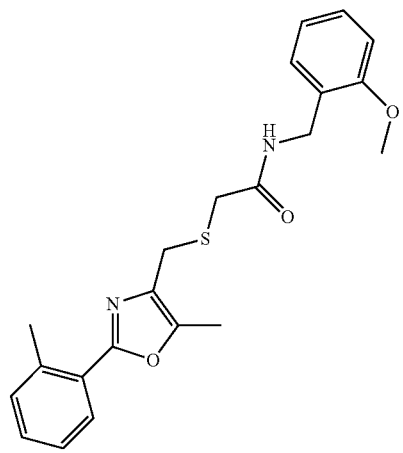 [SMILES: COc1ccccc1CNC(=O)CSCc1nc(-c2ccccc2C)oc1C] | 396.51 |
| IIa-52 | 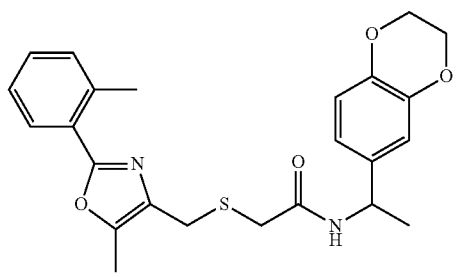 [SMILES: Cc1ccccc1-c1nc(CSCC(=O)NC(C)c2ccc3c(c2)OCCO3)c(C)o1] | 438.55 |

TABLE 1-continued

Oxazole amides (R³ = NH-benzyl)

| ID | Structure | MW |
|---|---|---|
| IIa-53 | | 421.35 |
| IIa-54 | | 400.93 |
| IIa-55 | | 430.91 |
| IIa-56 | | 416.93 |

TABLE 1-continued
Oxazole amides (R³ = NH-benzyl)
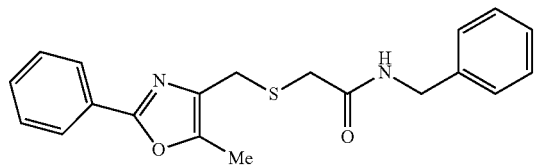
| ID | Structure | MW |
|---|---|---|
| IIa-57 | 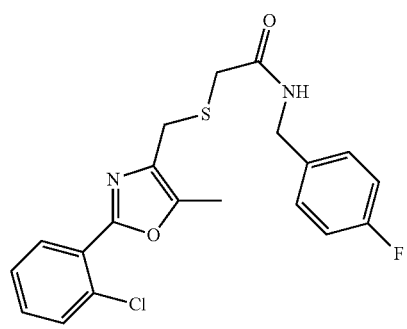 [SMILES: Cc1oc(-c2ccccc2Cl)nc1CSCC(=O)NCc1ccc(F)cc1] | 404.89 |
| IIa-58 | 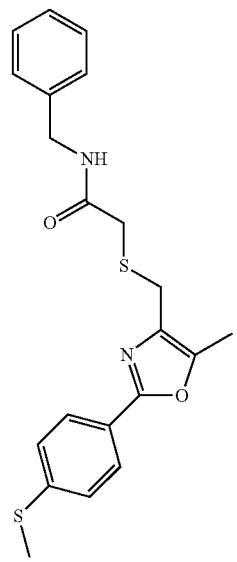 [SMILES: CSc1ccc(-c2nc(CSCC(=O)NCc3ccccc3)c(C)o2)cc1] | 398.55 |

TABLE 1-continued
Oxazole amides (R³ = NH-benzyl)
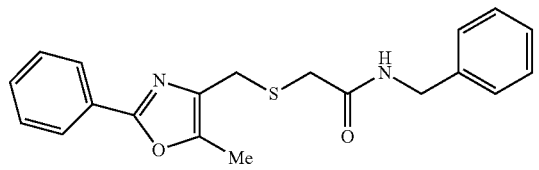
| ID | Structure | MW |
| --- | --- | --- |
| IIa-59 | | 432.99 |
| IIa-60 | | 432.99 |

TABLE 1-continued
Oxazole amides (R³ = NH-benzyl)
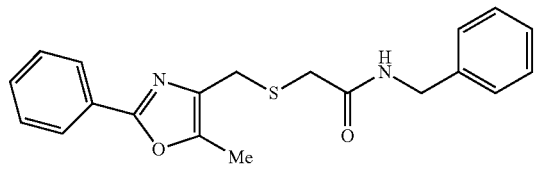
| ID | Structure | MW |
|---|---|---|
| IIa-61 | 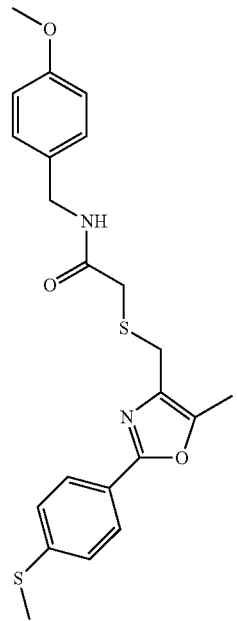 [SMILES: COc1ccc(CNC(=O)CSCc2nc(-c3ccc(SC)cc3)oc2C)cc1] | 428.58 |
| IIa-62 | 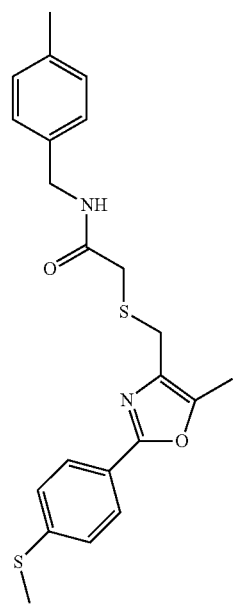 [SMILES: CSc1ccc(-c2nc(CSCC(=O)NCc3ccc(C)cc3)c(C)o2)cc1] | 412.58 |

TABLE 1-continued
Oxazole amides (R³ = NH-benzyl)
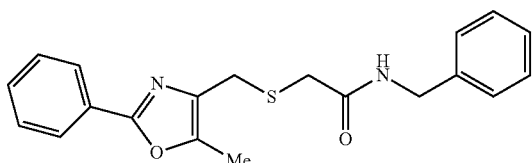
| ID | Structure | MW |
|---|---|---|
| IIa-63 | 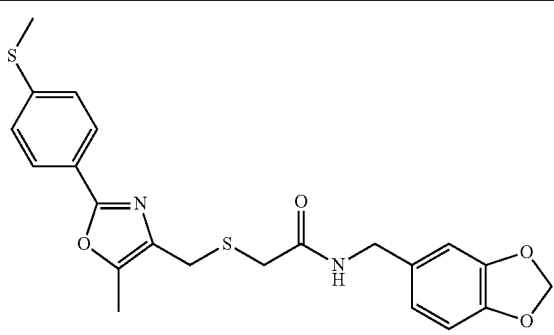 | 442.56 |
| IIa-64 | 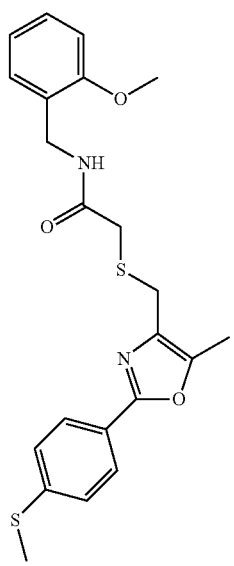 [SMILES: COc1ccccc1CNC(=O)CSCc1nc(-c2ccc(SC)cc2)oc1C] | 428.58 |
| IIa-65 | 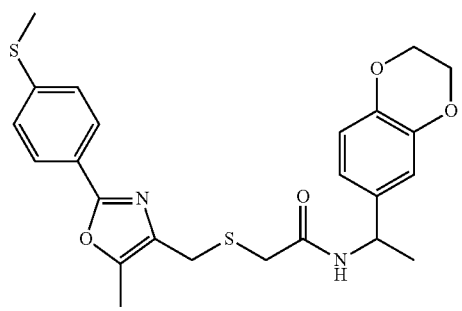 [SMILES: CSc1ccc(-c2nc(CSCC(=O)NC(C)c3ccc4c(c3)OCCO4)c(C)o2)cc1] | 470.61 |

TABLE 1-continued
Oxazole amides (R³ = NH-benzyl)
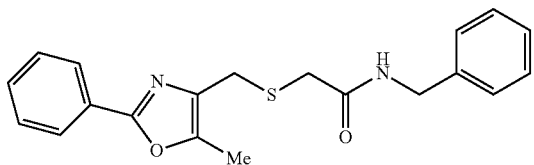
| ID | Structure | MW |
|---|---|---|
| IIa-66 | 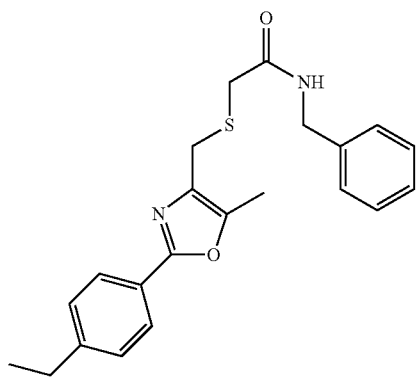 [SMILES: CCc1ccc(-c2nc(CSCC(=O)NCc3ccccc3)c(C)o2)cc1] | 380.51 |
| IIa-67 | 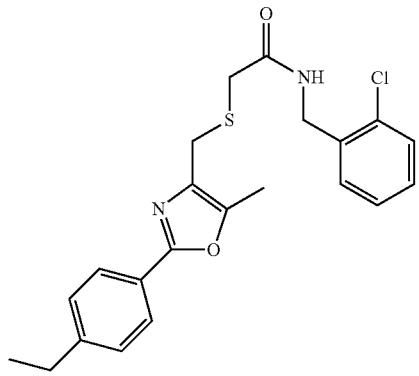 [SMILES: CCc1ccc(-c2nc(CSCC(=O)NCc3ccccc3Cl)c(C)o2)cc1] | 414.96 |
| IIa-68 | 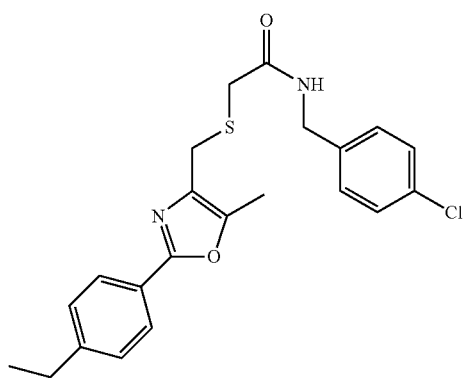 [SMILES: CCc1ccc(-c2nc(CSCC(=O)NCc3ccc(Cl)cc3)c(C)o2)cc1] | 414.96 |

TABLE 1-continued
Oxazole amides (R³ = NH-benzyl)
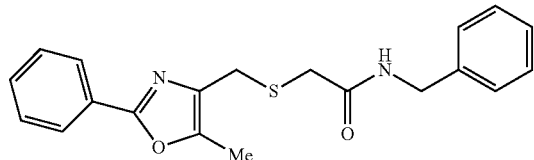
| ID | Structure | MW |
|---|---|---|
| IIa-69 | 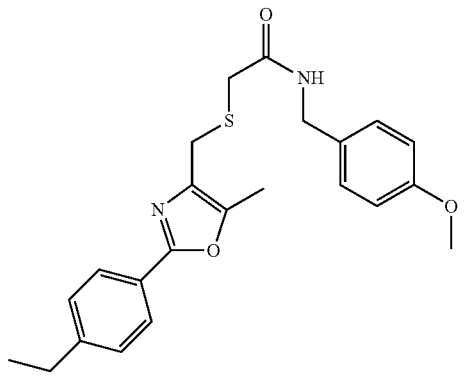 [SMILES: CCc1ccc(-c2nc(CSCC(=O)NCc3ccc(OC)cc3)c(C)o2)cc1] | 410.54 |
| IIa-70 | 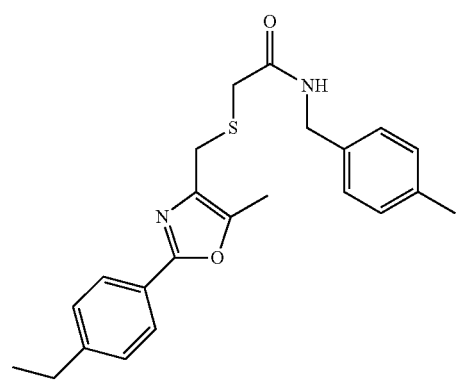 [SMILES: CCc1ccc(-c2nc(CSCC(=O)NCc3ccc(C)cc3)c(C)o2)cc1] | 394.54 |
| IIa-71 | 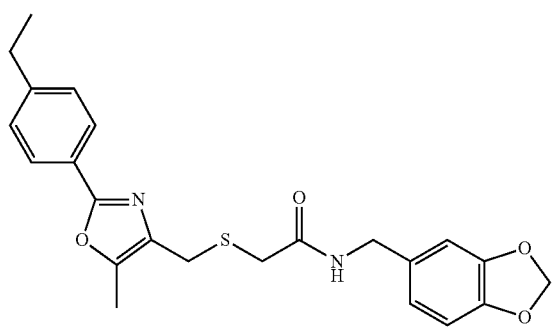 [SMILES: CCc1ccc(-c2nc(CSCC(=O)NCc3ccc4c(c3)OCO4)c(C)o2)cc1] | 424.52 |

TABLE 1-continued
Oxazole amides (R³ = NH-benzyl)
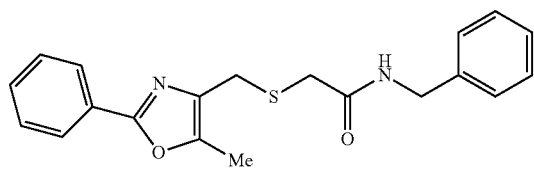
| ID | Structure | MW |
| --- | --- | --- |
| IIa-72 | 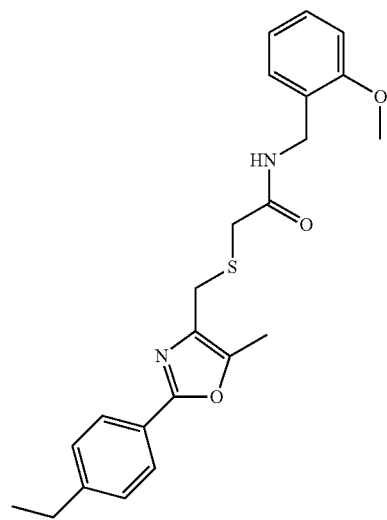 [SMILES: CCc1ccc(-c2nc(CSCC(=O)NCc3ccccc3OC)c(C)o2)cc1] | 410.54 |
| IIa-73 | 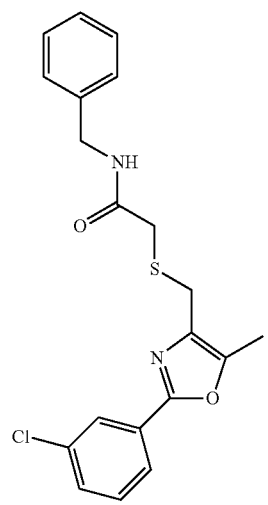 [SMILES: Cc1oc(-c2cccc(Cl)c2)nc1CSCC(=O)NCc1ccccc1] | 386.90 |

TABLE 1-continued
Oxazole amides (R³ = NH-benzyl)
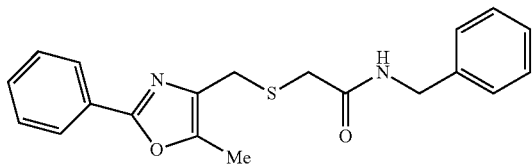
| ID | Structure | MW |
|---|---|---|
| IIa-74 | 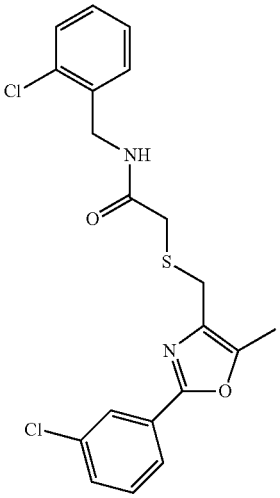 | 421.35 |
| IIa-75 | 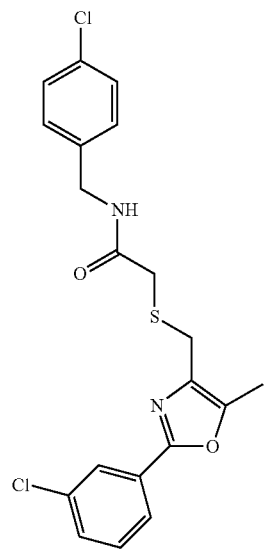 [SMILES: Cc1oc(-c2cccc(Cl)c2)nc1CSCC(=O)NCc1ccc(Cl)cc1] | 421.35 |

TABLE 1-continued
Oxazole amides (R³ = NH-benzyl)
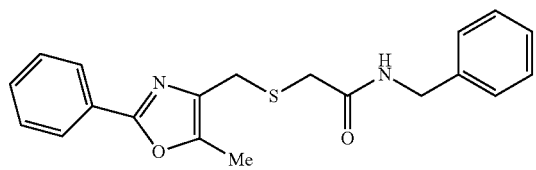
| ID | Structure | MW |
|---|---|---|
| IIa-76 | 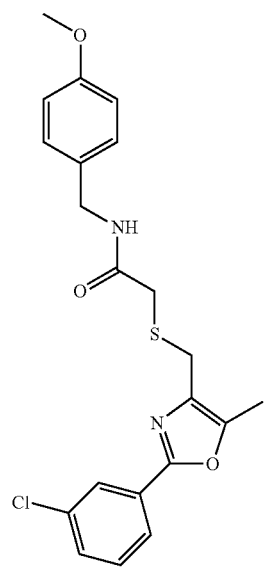 [SMILES: COc1ccc(CNC(=O)CSCc2nc(-c3cccc(Cl)c3)oc2C)cc1] | 416.93 |
| IIa-77 | 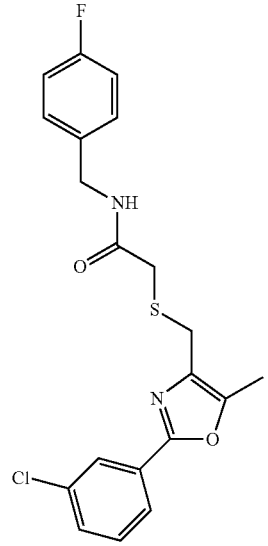 [SMILES: Cc1oc(-c2cccc(Cl)c2)nc1CSCC(=O)NCc1ccc(F)cc1] | 404.89 |

TABLE 1-continued
Oxazole amides (R³ = NH-benzyl)
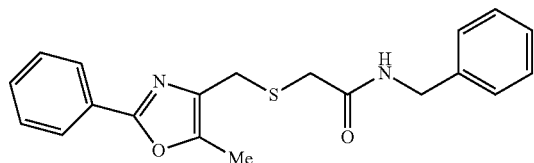
| ID | Structure | MW |
|---|---|---|
| IIa-78 | 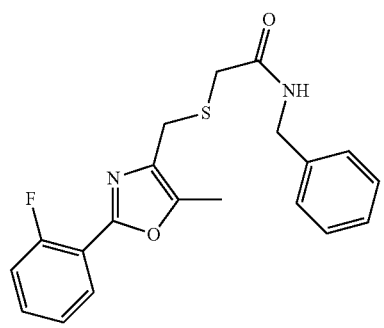 [SMILES: Cc1oc(-c2ccccc2F)nc1CSCC(=O)NCc1ccccc1] | 370.45 |
| IIa-79 | 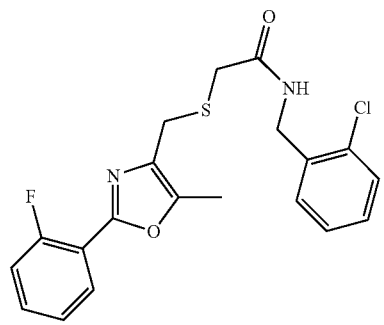 [SMILES: Cc1oc(-c2ccccc2F)nc1CSCC(=O)NCc1ccccc1Cl] | 404.89 |
| IIa-80 | 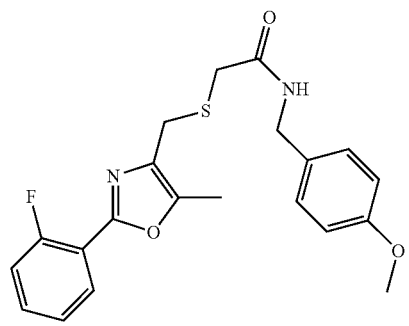 | 400.48 |
| IIa-81 | 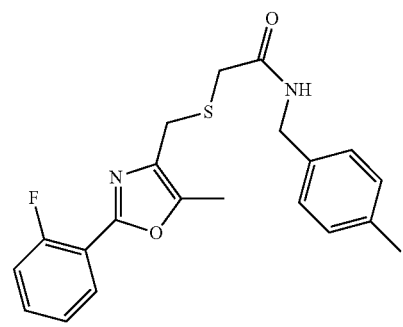 | 384.48 |

TABLE 1-continued
Oxazole amides (R³ = NH-benzyl)
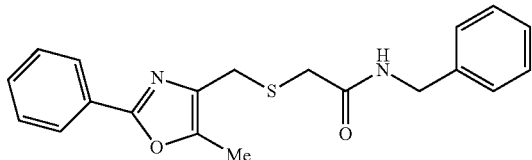
| ID | Structure | MW |
| --- | --- | --- |
| IIa-82 | 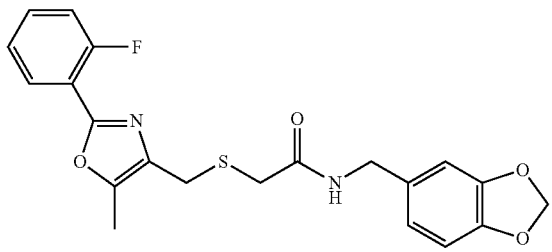 [SMILES: Cc1oc(-c2ccccc2F)nc1CSCC(=O)NCc1ccc2c(c1)OCO2] | 414.46 |
| IIa-83 | 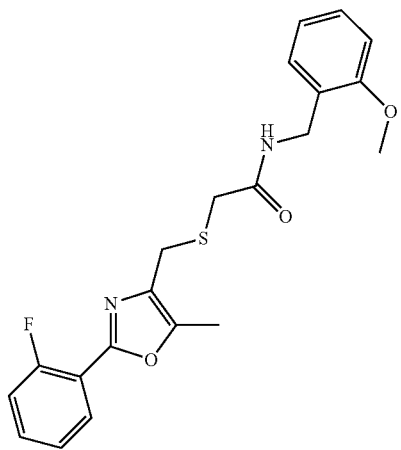 | 400.48 |
| IIa-84 | 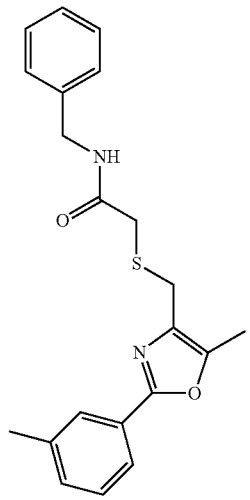 | 366.49 |

TABLE 1-continued
Oxazole amides (R³ = NH-benzyl)
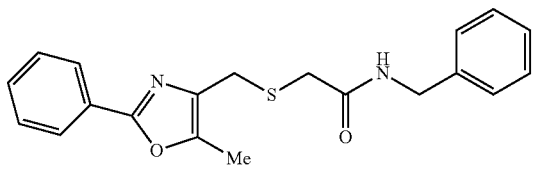
| ID | Structure | MW |
| --- | --- | --- |
| IIa-85 | 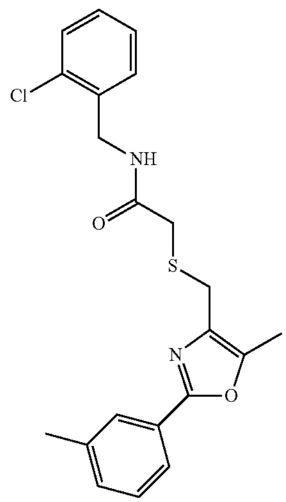 [SMILES: Cc1cccc(-c2nc(CSCC(=O)NCc3ccccc3Cl)c(C)o2)c1] | 400.93 |
| IIa-86 | 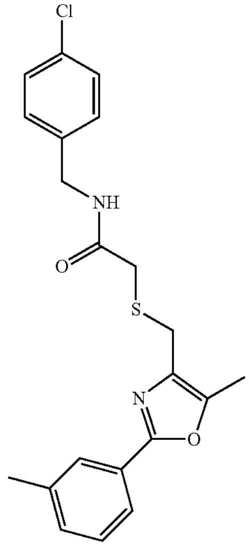 | 400.93 |

TABLE 1-continued
Oxazole amides (R³ = NH-benzyl)
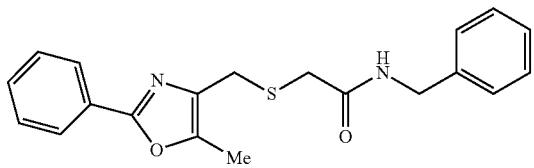
| ID | Structure | MW |
| --- | --- | --- |
| IIa-87 | 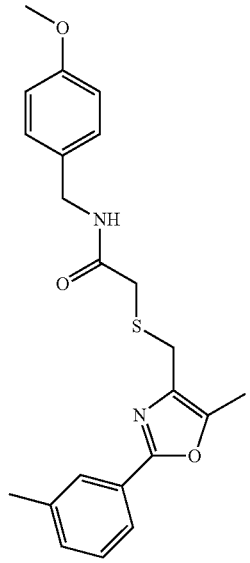 | 396.51 |
| IIa-88 | 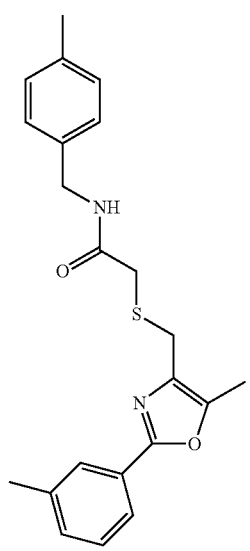 | 380.51 |

TABLE 1-continued
Oxazole amides (R³ = NH-benzyl)
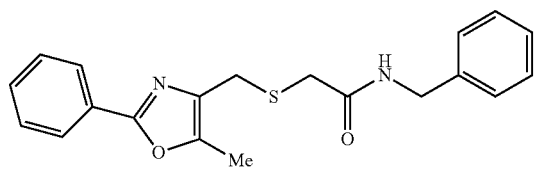
| ID | Structure | MW |
|---|---|---|
| IIa-89 | | 396.51 |
| IIa-90 | | 366.49 |
| IIa-91 | | 400.93 |

TABLE 1-continued

Oxazole amides (R³ = NH-benzyl)

| ID | Structure | MW |
|---|---|---|
| IIa-92 | | 400.93 |
| IIa-93 | | 396.51 |
| IIa-94 | | 380.51 |
| IIa-95 | | 410.50 |

TABLE 1-continued

Oxazole amides (R³ = NH-benzyl)

| ID | Structure | MW |
|---|---|---|
| IIa-96 | | 380.51 |
| IIa-97 | | 396.51 |
| IIa-98 | | 398.48 |

TABLE 1-continued
Oxazole amides (R³ = NH-benzyl)
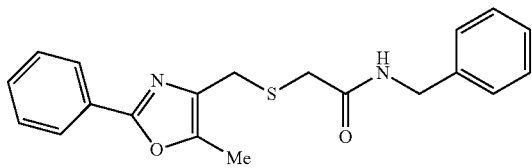
| ID | Structure | MW |
| --- | --- | --- |
| IIa-99 | | 432.93 |
| IIa-100 | 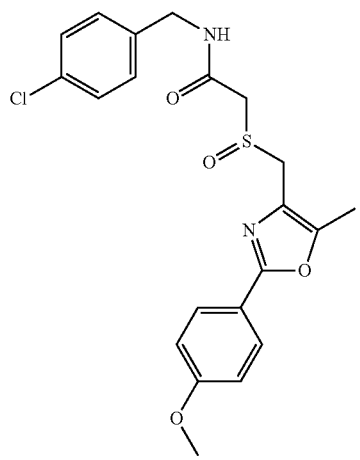 [SMILES: COc1ccc(-c2nc(CS(=O)CC(=O)NCc3ccc(Cl)cc3)c(C)o2)cc1] | 432.93 |

TABLE 1-continued
Oxazole amides (R³ = NH-benzyl)
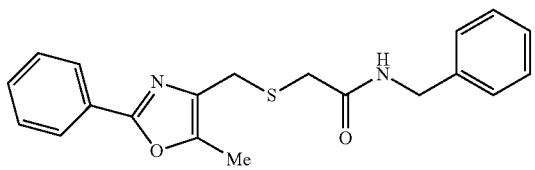
| ID | Structure | MW |
|---|---|---|
| IIa-101 | 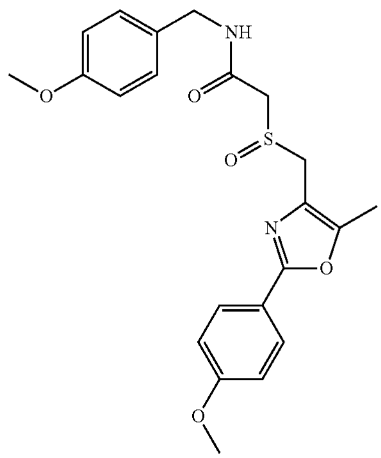 | 428.51 |
| IIa-102 | 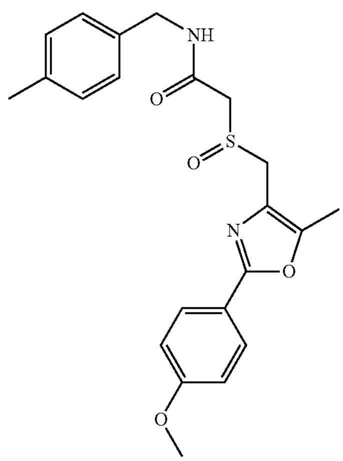 | 412.51 |
| IIa-103 | 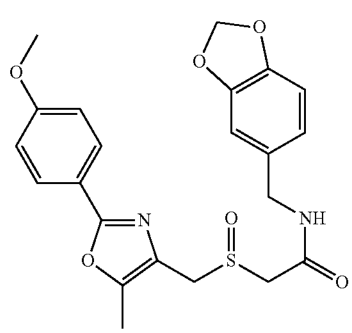 [SMILES: COc1ccc(-c2nc(CS(=O)CC(=O)NCc3ccc4c(c3)OCO4)c(C)o2)cc1] | 442.49 |

TABLE 1-continued
Oxazole amides (R³ = NH-benzyl)
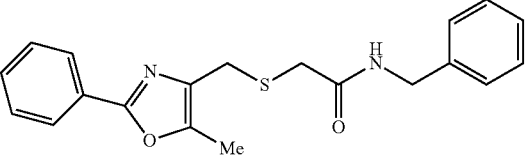
| ID | Structure | MW |
|---|---|---|
| IIa-104 | 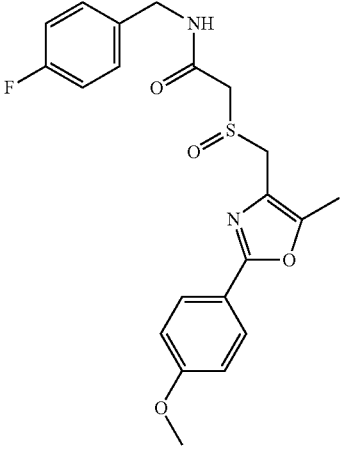 [SMILES: COc1ccc(-c2nc(CS(=O)CC(=O)NCc3ccc(F)cc3)c(C)o2)cc1] | 428.51 |
| IIa-105 | | 416.47 |
| IIa-106 | 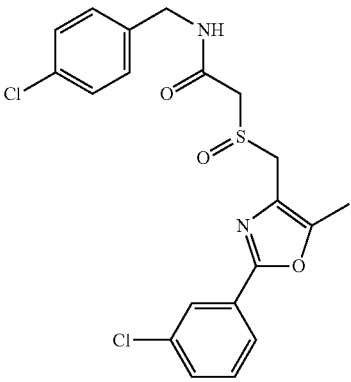 [SMILES: Cc1oc(-c2cccc(Cl)c2)nc1CS(=O)CC(=O)NCc1ccc(Cl)cc1] | 437.35 |

TABLE 1-continued
Oxazole amides (R³ = NH-benzyl)
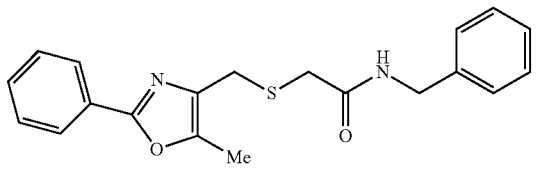
| ID | Structure | MW |
|---|---|---|
| IIa-107 | | 386.45 |
| IIa-108 | | 420.89 |
| IIa-109 | | 400.48 |

TABLE 1-continued
Oxazole amides (R³ = NH-benzyl)
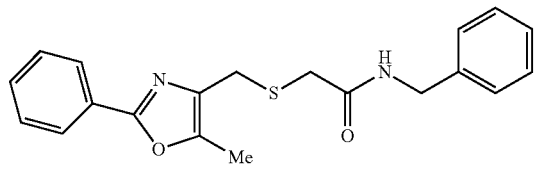
| ID | Structure | MW |
|---|---|---|
| IIa-110 | 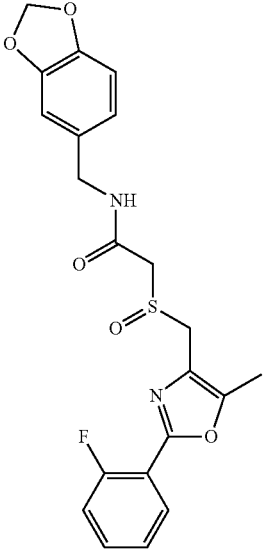 [SMILES: Cc1oc(-c2ccccc2F)nc1CS(=O)CC(=O)NCc1ccc2c(c1)OCO2] | 430.46 |
| IIa-111 | 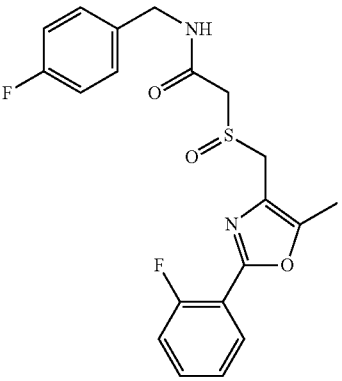 [SMILES: Cc1oc(-c2ccccc2F)nc1CS(=O)CC(=O)NCc1ccc(F)cc1] | 404.44 |
| IIa-112 | 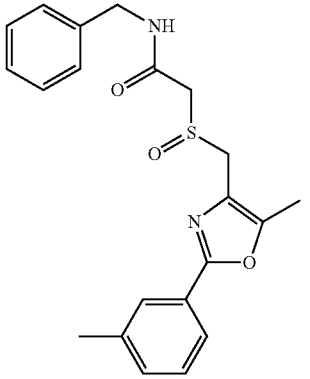 [SMILES: Cc1cccc(-c2nc(CS(=O)CC(=O)NCc3ccccc3)c(C)o2)c1] | 382.49 |

TABLE 1-continued
Oxazole amides (R³ = NH-benzyl)
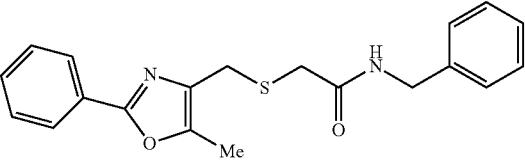
| ID | Structure | MW |
|---|---|---|
| IIa-113 | 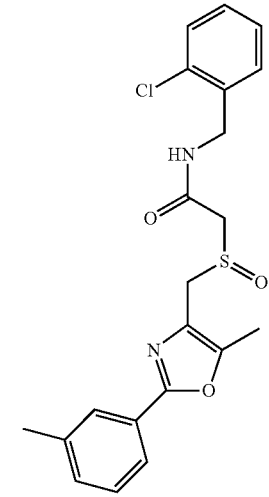 [SMILES: Cc1cccc(-c2nc(CS(=O)CC(=O)NCc3ccccc3Cl)c(C)o2)c1] | 416.93 |
| IIa-114 | | 416.93 |
| IIa-115 | 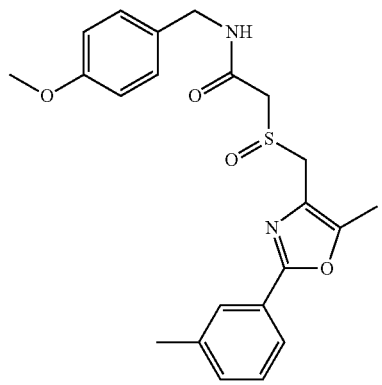 | 412.51 |

TABLE 1-continued
Oxazole amides (R³ = NH-benzyl)
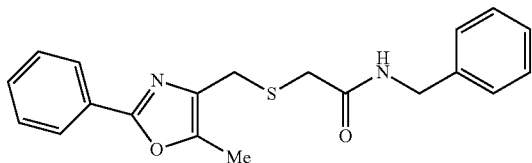
| ID | Structure | MW |
| --- | --- | --- |
| IIa-116 | 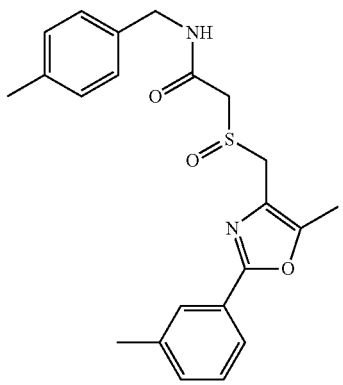 | 396.51 |
| IIa-117 | 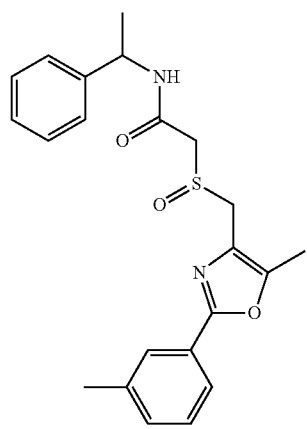 [SMILES: Cc1cccc(-c2nc(CS(=O)CC(=O)NC(C)c3ccccc3)c(C)o2)c1] | 396.51 |
| IIa-118 | 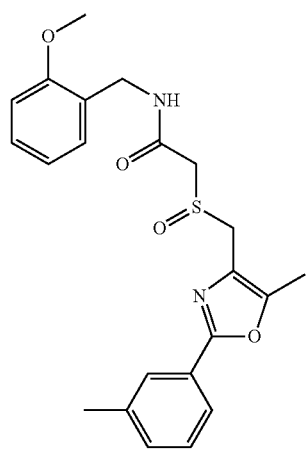 [SMILES: COc1ccccc1CNC(=O)CS(=O)Cc1nc(-c2cccc(C)c2)oc1C] | 412.51 |

TABLE 1-continued
Oxazole amides (R³ = NH-benzyl)
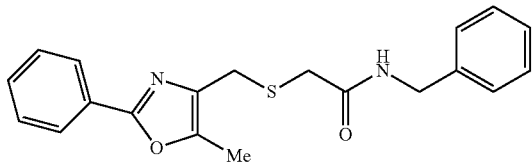
| ID | Structure | MW |
| --- | --- | --- |
| IIa-119 | | 400.48 |
| IIa-120 | | 382.49 |
| IIa-121 | | 416.93 |

TABLE 1-continued

Oxazole amides (R³ = NH-benzyl)

| ID | Structure | MW |
| --- | --- | --- |
| IIa-122 | | 416.93 |
| IIa-123 | | 412.51 |
| IIa-124 | | 396.51 |

TABLE 1-continued
Oxazole amides (R³ = NH-benzyl)
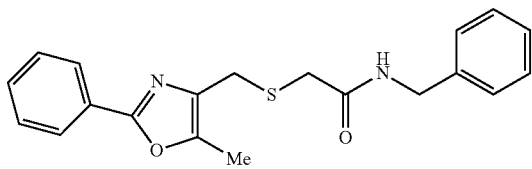
| ID | Structure | MW |
|---|---|---|
| IIa-125 | 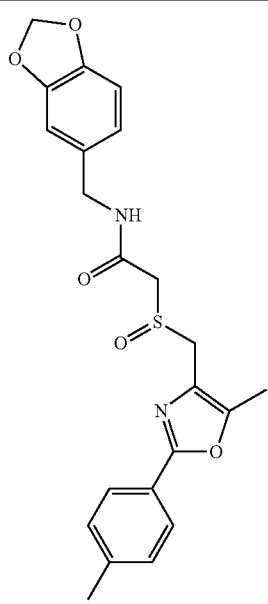 | 426.50 |
| IIa-126 | 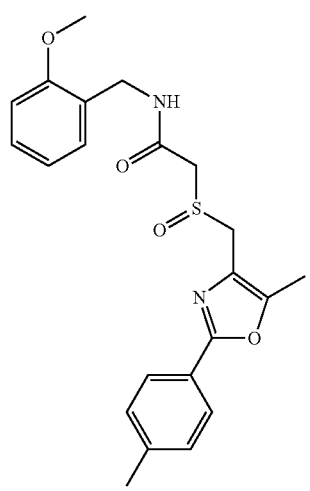 [SMILES: COc1ccccc1CNC(=O)CS(=O)Cc1nc(-c2ccc(C)cc2)oc1C] | 412.51 |

TABLE 1-continued
Oxazole amides (R³ = NH-benzyl)
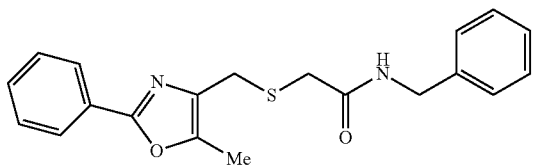
| ID | Structure | MW |
|---|---|---|
| IIa-127 | 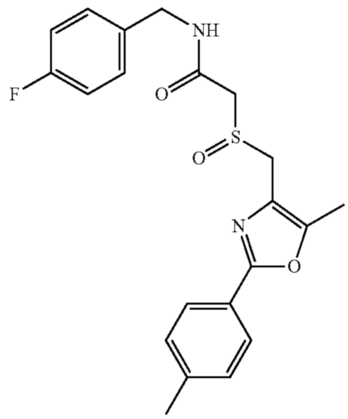 [SMILES: Cc1ccc(-c2nc(CS(=O)CC(=O)NCc3ccc(F)cc3)c(C)o2)cc1] | 400.48 |
| IIa-128 | 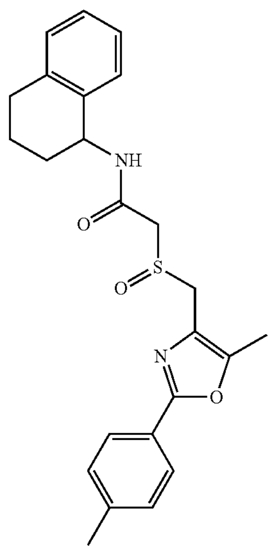 [SMILES: Cc1ccc(-c2nc(CS(=O)CC(=O)NC3CCCc4ccccc43)c(C)o2)cc1] | 422.55 |
| IIa-129 | 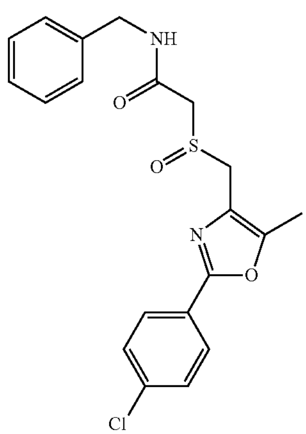 [SMILES: Cc1oc(-c2ccc(Cl)cc2)nc1CS(=O)CC(=O)NCc1ccccc1] | 402.90 |

TABLE 1-continued

Oxazole amides (R³ = NH-benzyl)

| ID | Structure | MW |
|---|---|---|
| IIa-130 | 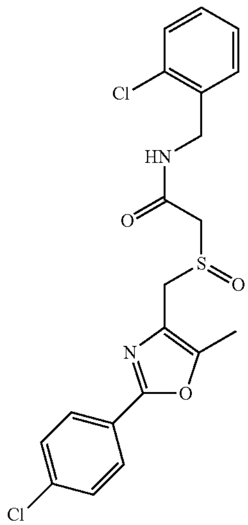 [SMILES: Cc1oc(-c2ccc(Cl)cc2)nc1CS(=O)CC(=O)NCc1ccccc1Cl] | 437.35 |
| IIa-131 | 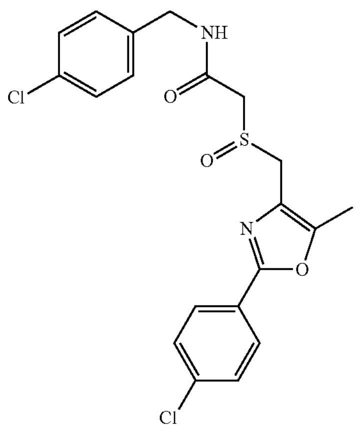 [SMILES: Cc1oc(-c2ccc(Cl)cc2)nc1CS(=O)CC(=O)NCc1ccc(Cl)cc1] | 437.35 |
| IIa-132 | 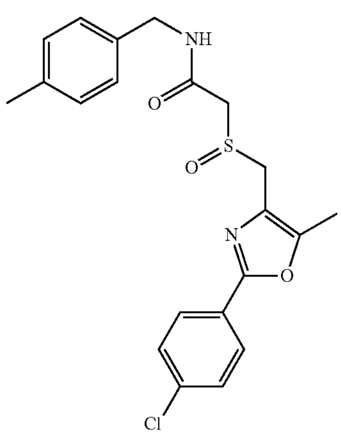 | 416.93 |

TABLE 1-continued
Oxazole amides (R³ = NH-benzyl)
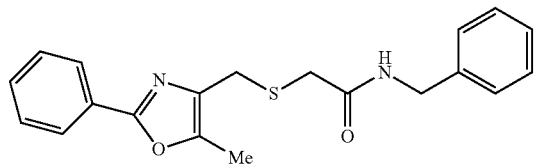
| ID | Structure | MW |
|---|---|---|
| IIa-133 | | 446.91 |
| IIa-134 | | 416.93 |

TABLE 1-continued
Oxazole amides (R³ = NH-benzyl)
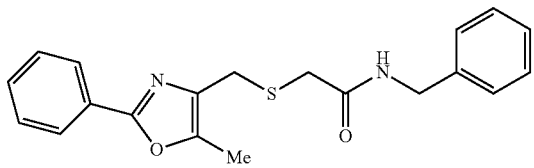
| ID | Structure | MW |
|---|---|---|
| IIa-135 | 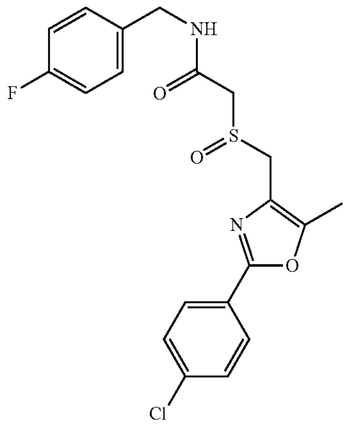 [SMILES: Cc1oc(-c2ccc(Cl)cc2)nc1CS(=O)CC(=O)NCc1ccc(F)cc1] | 420.89 |
| IIa-136 | 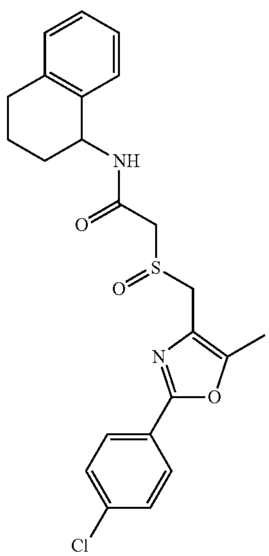 [SMILES: Cc1oc(-c2ccc(Cl)cc2)nc1CS(=O)CC(=O)NC1CCCc2ccccc21] | 442.97 |
| IIa-137 | 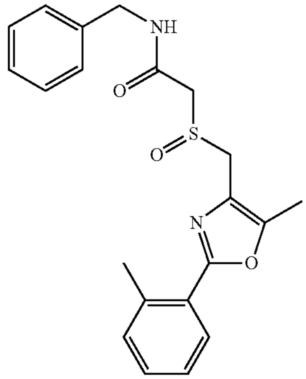 [SMILES: Cc1ccccc1-c1nc(CS(=O)CC(=O)NCc2ccccc2)c(C)o1] | 382.49 |

TABLE 1-continued
Oxazole amides (R³ = NH-benzyl)
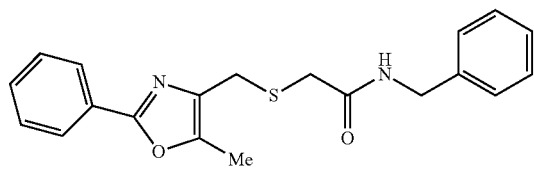
| ID | Structure | MW |
|---|---|---|
| IIa-138 | | 416.93 |
| IIa-139 | | 412.51 |
| IIa-140 | | 396.51 |

TABLE 1-continued
Oxazole amides (R³ = NH-benzyl)
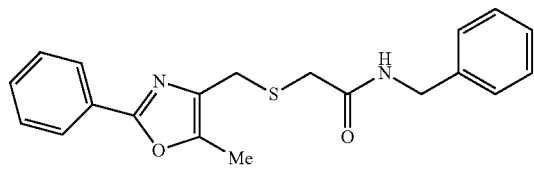
| ID | Structure | MW |
|---|---|---|
| IIa-141 | 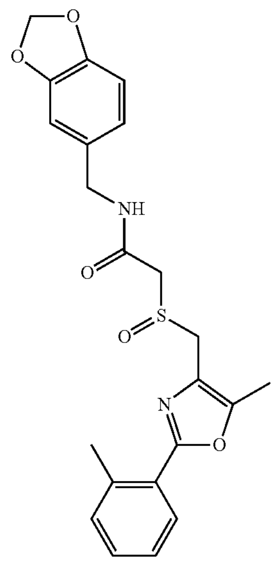 [SMILES: Cc1ccccc1-c1nc(CS(=O)CC(=O)NCc2ccc3c(c2)OCO3)c(C)o1] | 426.50 |
| IIa-142 | 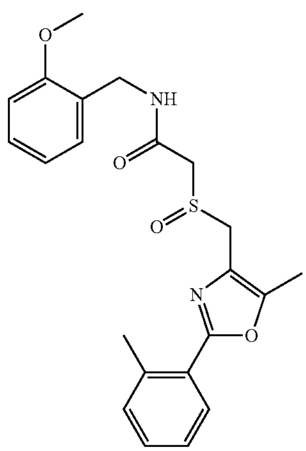 [SMILES: COc1ccccc1CNC(=O)CS(=O)Cc1nc(-c2ccccc2C)oc1C] | 412.51 |
| IIa-143 | 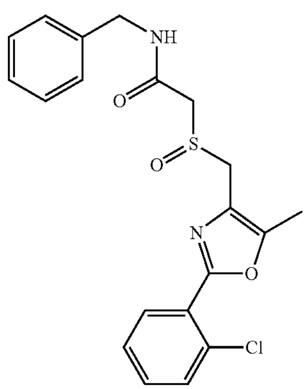 [SMILES: Cc1oc(-c2ccccc2Cl)nc1CS(=O)CC(=O)NCc1ccccc1] | 402.90 |

TABLE 1-continued
Oxazole amides (R³ = NH-benzyl)
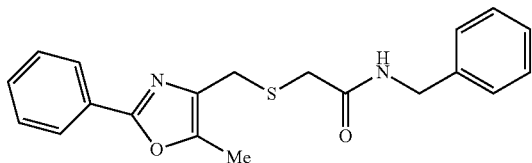
| ID | Structure | MW |
|---|---|---|
| IIa-144 | 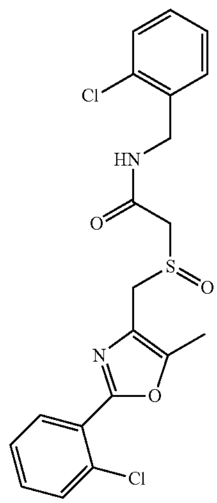 [SMILES: Cc1oc(-c2ccccc2Cl)nc1CS(=O)CC(=O)NCc1ccccc1Cl] | 437.35 |
| IIa-145 | 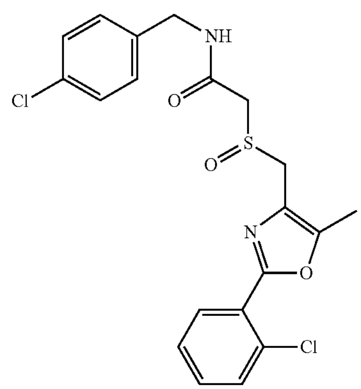 [SMILES: Cc1oc(-c2ccccc2Cl)nc1CS(=O)CC(=O)NCc1ccc(Cl)cc1] | 437.35 |
| IIa-146 | 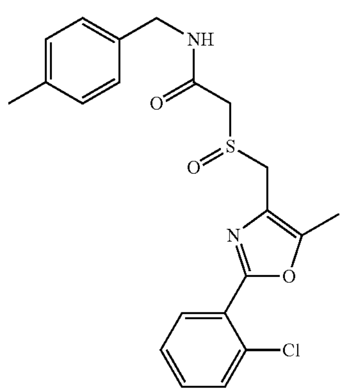 | 416.93 |

TABLE 1-continued
Oxazole amides (R³ = NH-benzyl)
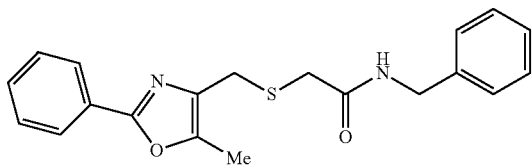
| ID | Structure | MW |
|---|---|---|
| IIa-147 | | 446.91 |
| IIa-148 | | 432.93 |
| IIa-149 | | 420.89 |

TABLE 1-continued
Oxazole amides (R³ = NH-benzyl)
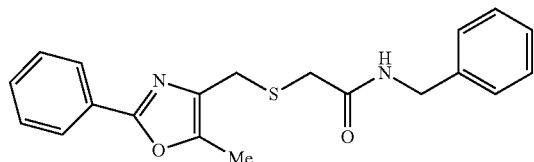
| ID | Structure | MW |
|---|---|---|
| IIa-150 | | 398.48 |
| IIa-151 | | 432.93 |
| IIa-152 | | 432.93 |

TABLE 1-continued
Oxazole amides (R³ = NH-benzyl)
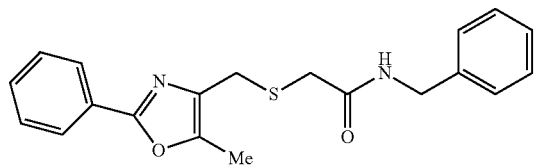
| ID | Structure | MW |
|---|---|---|
| IIa-153 | 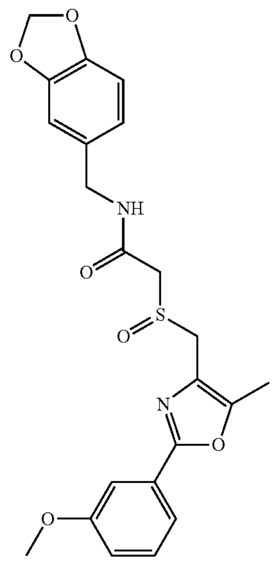 [SMILES: COc1cccc(-c2nc(CS(=O)CC(=O)NCc3ccc4c(c3)OCO4)c(C)o2)c1] | 442.49 |
| IIa-154 | 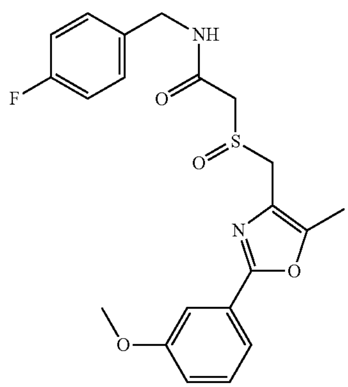 [SMILES: COc1cccc(-c2nc(CS(=O)CC(=O)NCc3ccc(F)cc3)c(C)o2)c1] | 416.47 |
| IIa-155 | 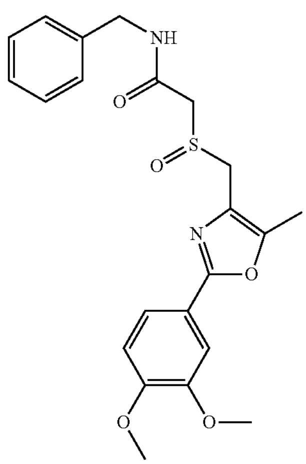 [SMILES: COc1ccc(-c2nc(CS(=O)CC(=O)NCc3ccccc3)c(C)o2)cc1OC] | 428.51 |

TABLE 1-continued
Oxazole amides (R³ = NH-benzyl)
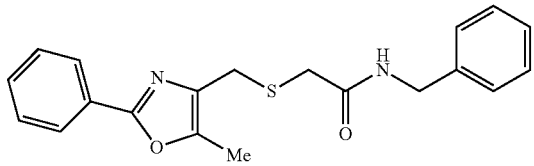
| ID | Structure | MW |
|---|---|---|
| IIa-156 | 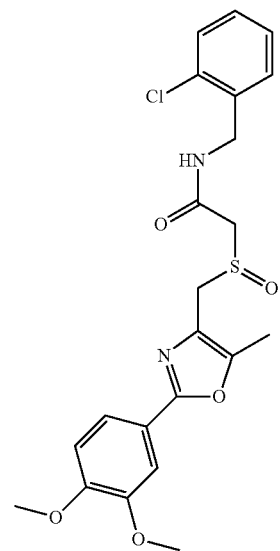 [SMILES: COc1ccc(-c2nc(CS(=O)CC(=O)NCc3ccccc3Cl)c(C)o2)cc1OC] | 462.96 |
| IIa-157 | 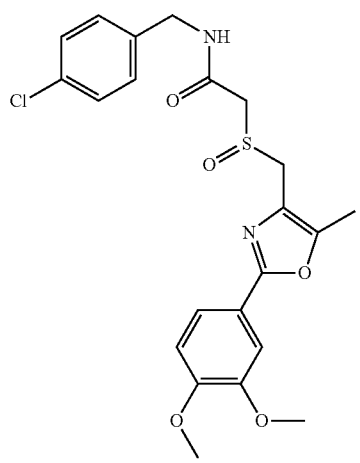 [SMILES: COc1ccc(-c2nc(CS(=O)CC(=O)NCc3ccc(Cl)cc3)c(C)o2)cc1OC] | 462.96 |

TABLE 1-continued
Oxazole amides (R³ = NH-benzyl)
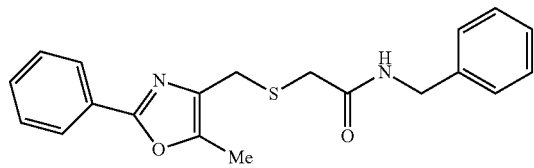
| ID | Structure | MW |
|---|---|---|
| IIa-158 | 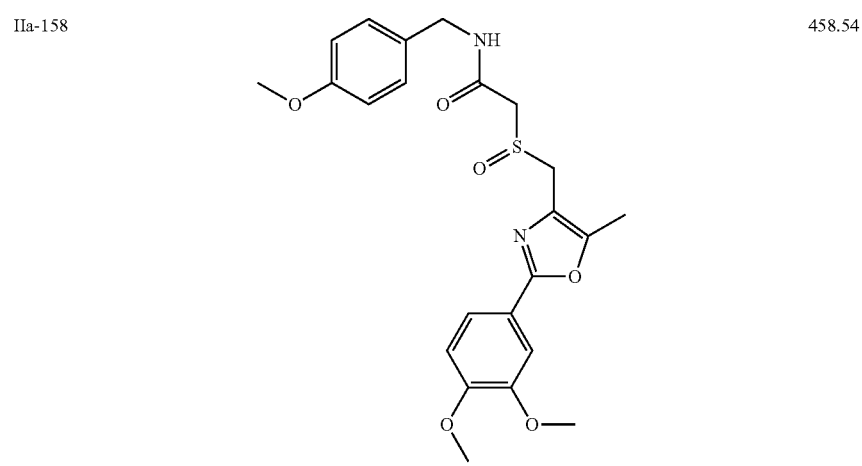 | 458.54 |
| IIa-159 | 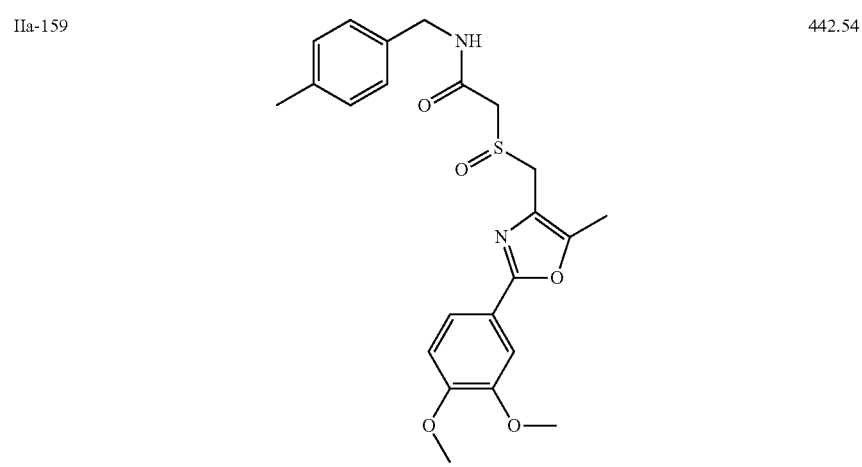 | 442.54 |

TABLE 1-continued
Oxazole amides (R³ = NH-benzyl)
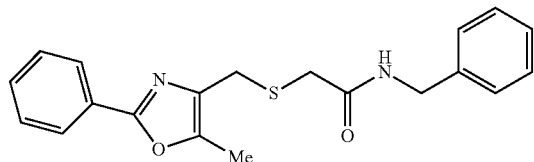
| ID | Structure | MW |
|---|---|---|
| IIa-160 | 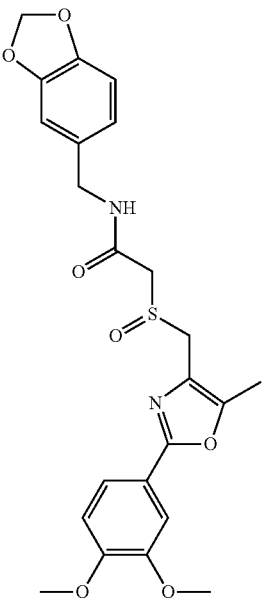 [SMILES: COc1ccc(-c2nc(CS(=O)CC(=O)NCc3ccc4c(c3)OCO4)c(C)o2)cc1OC] | 472.52 |
| IIa-161 | 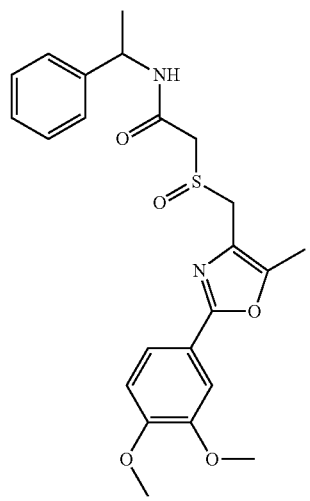 [SMILES: COc1ccc(-c2nc(CS(=O)CC(=O)NC(C)c3ccccc3)c(C)o2)cc1OC] | 442.54 |

TABLE 1-continued
Oxazole amides (R³ = NH-benzyl)
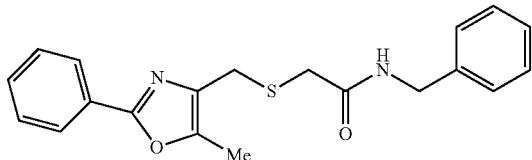
| ID | Structure | MW |
|---|---|---|
| IIa-162 | 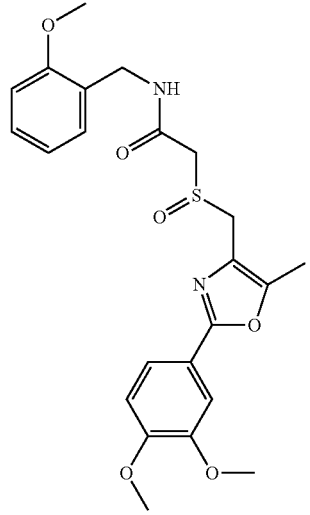 [SMILES: COc1ccccc1CNC(=O)CS(=O)Cc1nc(-c2ccc(OC)c(OC)c2)oc1C] | 458.54 |
| IIa-163 | 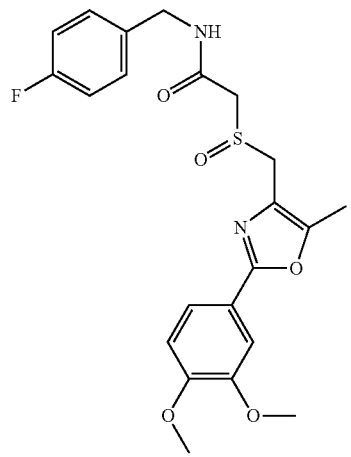 [SMILES: COc1ccc(-c2nc(CS(=O)CC(=O)NCc3ccc(F)cc3)c(C)o2)cc1OC] | 446.50 |

TABLE 1-continued
Oxazole amides (R³ = NH-benzyl)
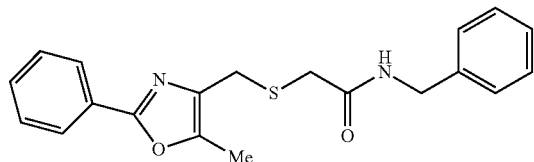
| ID | Structure | MW |
|---|---|---|
| IIa-164 | | 468.58 |
| IIa-165 | | 368.46 |
| IIa-166 | | 402.90 |

TABLE 1-continued
Oxazole amides (R³ = NH-benzyl)
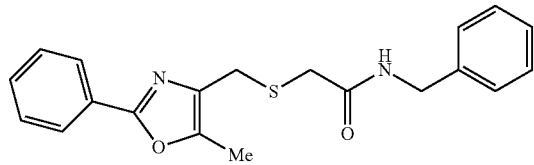
| ID | Structure | MW |
|---|---|---|
| IIa-167 | | 402.90 |
| IIa-168 | | 398.48 |
| IIa-169 | | 448.93 |

TABLE 1-continued

Oxazole amides (R³ = NH-benzyl)

| ID | Structure | MW |
|---|---|---|
| IIa-170 | | 432.47 |
| IIa-171 | | 432.93 |
| IIa-172 | | 398.48 |
| IIa-173 | | 432.93 |

TABLE 1-continued
Oxazole amides (R³ = NH-benzyl)
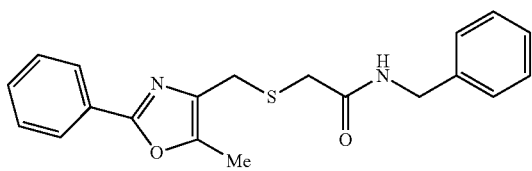
| ID | Structure | MW |
| --- | --- | --- |
| IIa-174 | 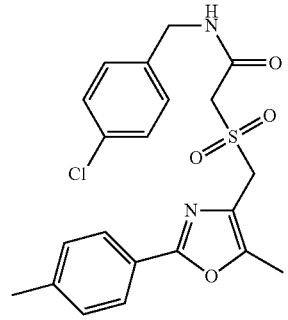 | 432.93 |
| IIa-175 | 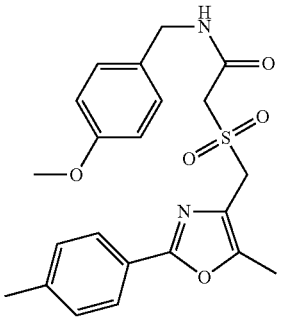 | 428.51 |
| IIa-176 | 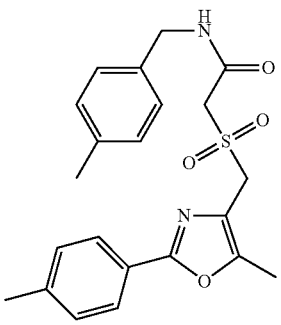 | 412.51 |

TABLE 1-continued
Oxazole amides (R³ = NH-benzyl)
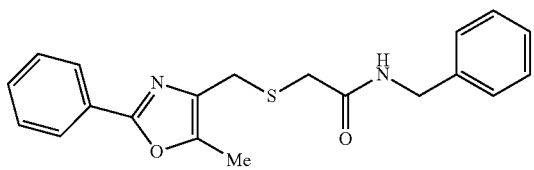
| ID | Structure | MW |
|---|---|---|
| IIa-177 | | 442.49 |
| IIa-178 | | 412.51 |
| IIa-179 | | 438.55 |

TABLE 1-continued
Oxazole amides (R³ = NH-benzyl)
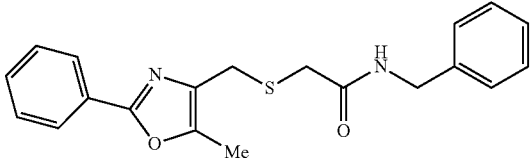
| ID | Structure | MW |
|---|---|---|
| IIa-180 | 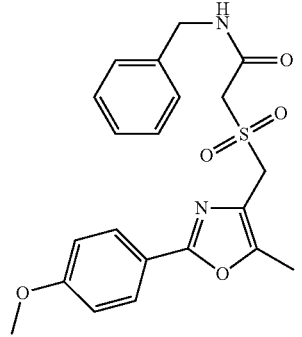 | 470.55 |
| IIa-181 | | 414.48 |
| IIa-182 | 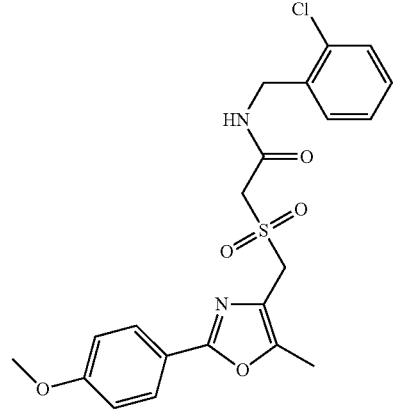 [SMILES: COc1ccc(-c2nc(CS(=O)(=O)CC(=O)NCc3ccccc3Cl)c(C)o2)cc1] | 448.93 |

TABLE 1-continued
Oxazole amides (R³ = NH-benzyl)
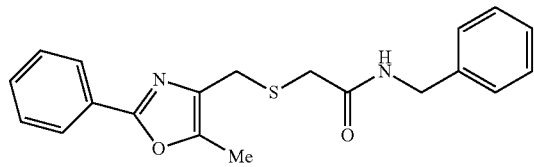
| ID | Structure | MW |
|---|---|---|
| IIa-183 | | 444.51 |
| IIa-184 | | 458.49 |
| IIa-185 | | 444.51 |

TABLE 1-continued
Oxazole amides (R³ = NH-benzyl)
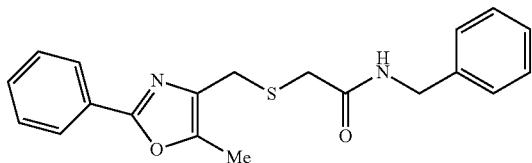
| ID | Structure | MW |
| --- | --- | --- |
| IIa-186 | 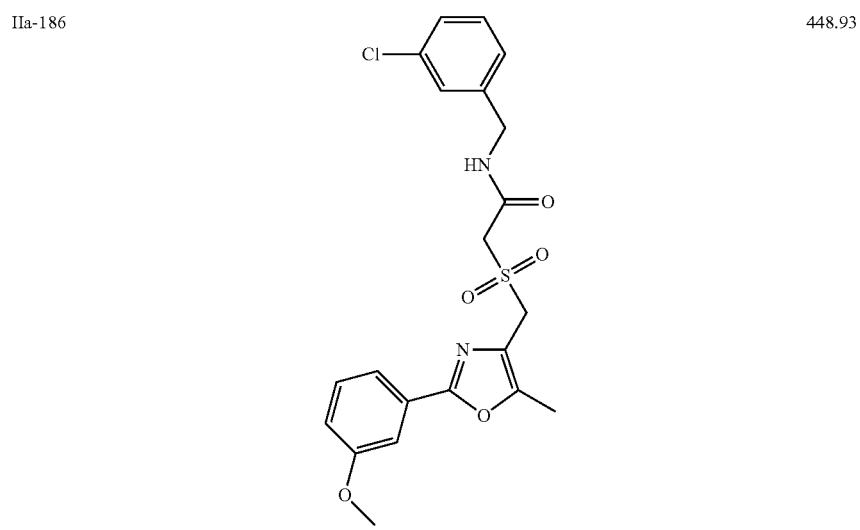 | 448.93 |
| IIa-187 | 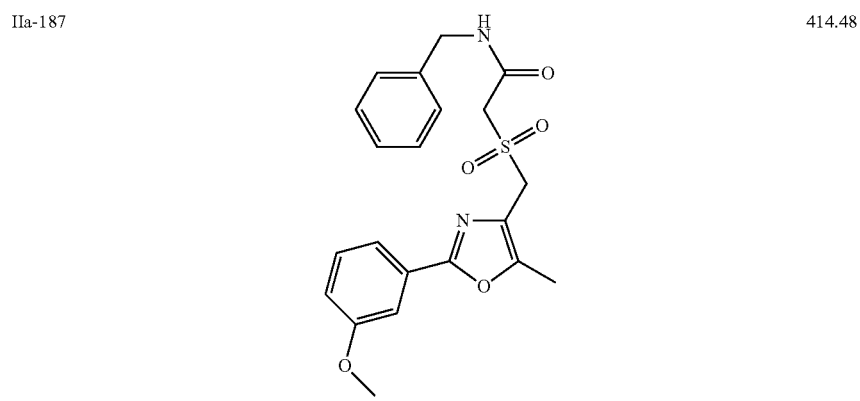 | 414.48 |

TABLE 1-continued
Oxazole amides (R³ = NH-benzyl)
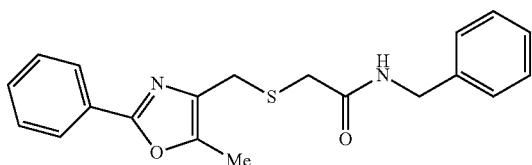
| ID | Structure | MW |
|---|---|---|
| IIa-188 | 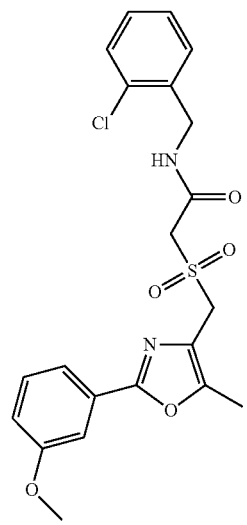 [SMILES: COc1cccc(-c2nc(CS(=O)(=O)CC(=O)NCc3ccccc3Cl)c(C)o2)c1] | 448.93 |
| IIa-189 | 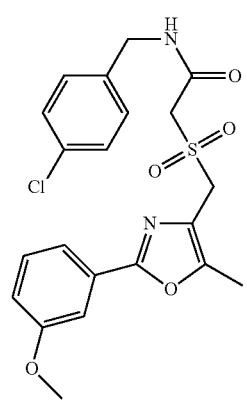 [SMILES: COc1cccc(-c2nc(CS(=O)(=O)CC(=O)NCc3ccc(Cl)cc3)c(C)o2)c1] | 448.93 |
| IIa-190 | 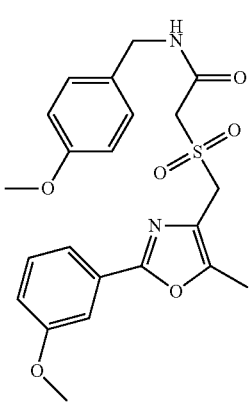 | 444.51 |

TABLE 1-continued
Oxazole amides (R³ = NH-benzyl)
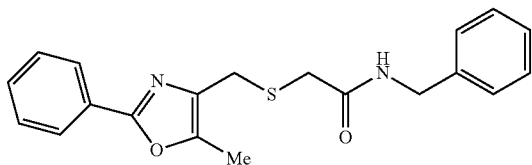
| ID | Structure | MW |
|---|---|---|
| IIa-191 | 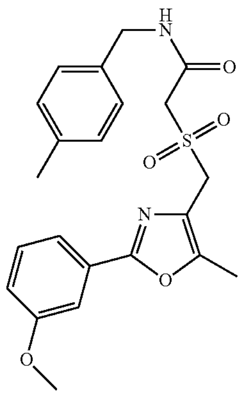 [SMILES: COc1cccc(-c2nc(CS(=O)(=O)CC(=O)NCc3ccc(C)cc3)c(C)o2)c1] | 428.51 |
| IIa-192 | 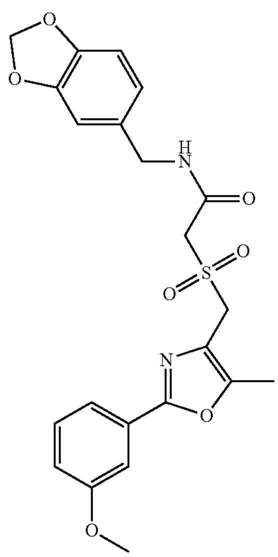 [SMILES: COc1cccc(-c2nc(CS(=O)(=O)CC(=O)NCc3ccc4c(c3)OCO4)c(C)o2)c1] | 458.49 |
| IIa-193 | 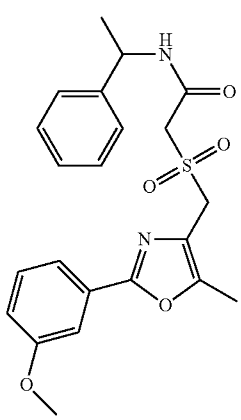 [SMILES: COc1cccc(-c2nc(CS(=O)(=O)CC(=O)NC(C)c3ccccc3)c(C)o2)c1] | 428.51 |

TABLE 1-continued
Oxazole amides (R³ = NH-benzyl)
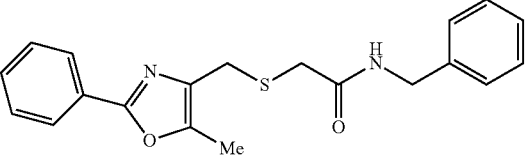
| ID | Structure | MW |
|---|---|---|
| IIa-194 | 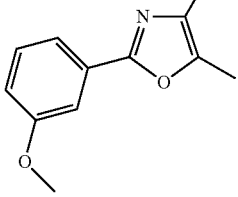 | 444.51 |
| IIa-195 | 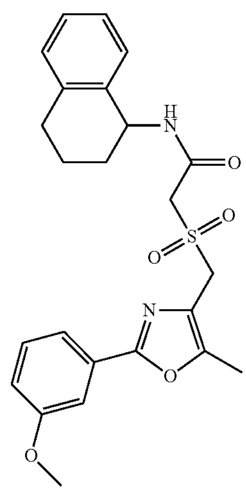 [SMILES: COc1cccc(-c2nc(CS(=O)(=O)CC(=O)NC3CCCc4ccccc43)c(C)o2)c1] | 454.55 |
| IIa-196 | 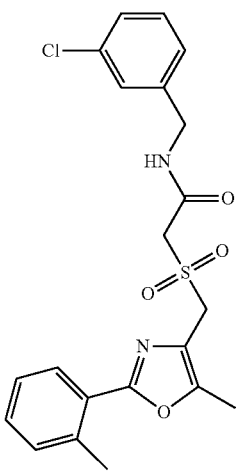 [SMILES: Cc1ccccc1-c1nc(CS(=O)(=O)CC(=O)NCc2cccc(Cl)c2)c(C)o1] | 432.93 |

TABLE 1-continued
Oxazole amides (R³ = NH-benzyl)
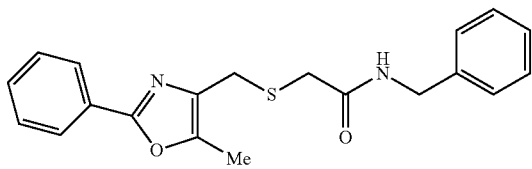
| ID | Structure | MW |
|---|---|---|
| IIa-197 | 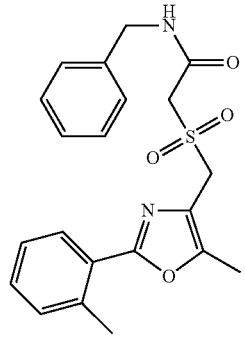 [SMILES: Cc1ccccc1-c1nc(CS(=O)(=O)CC(=O)NCc2ccccc2)c(C)o1] | 398.48 |
| IIa-198 | 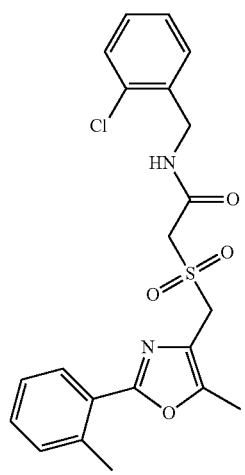 [SMILES: Cc1ccccc1-c1nc(CS(=O)(=O)CC(=O)NCc2ccccc2Cl)c(C)o1] | 432.93 |
| IIa-199 | 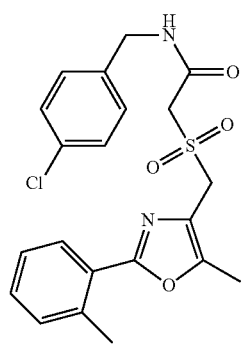 | 432.93 |

TABLE 1-continued
Oxazole amides (R³ = NH-benzyl)
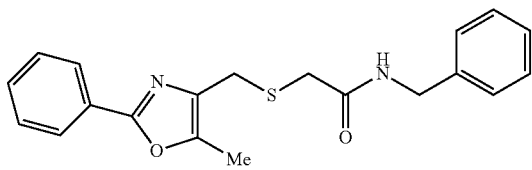
| ID | Structure | MW |
|---|---|---|
| IIa-200 | 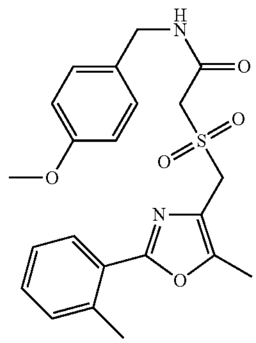 | 428.51 |
| IIa-201 | 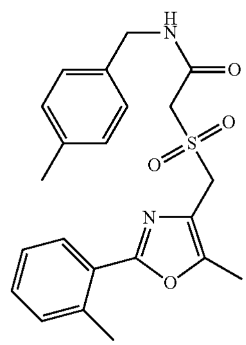 [SMILES: Cc1ccc(CNC(=O)CS(=O)(=O)Cc2nc(-c3ccccc3C)oc2C)cc1] | 412.51 |
| IIa-202 | 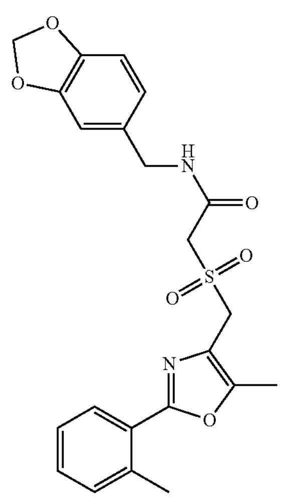 [SMILES: Cc1ccccc1-c1nc(CS(=O)(=O)CC(=O)NCc2ccc3c(c2)OCO3)c(C)o1] | 442.49 |

TABLE 1-continued
Oxazole amides (R³ = NH-benzyl)
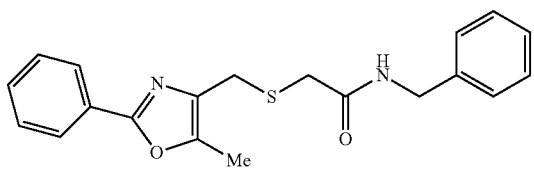
| ID | Structure | MW |
|---|---|---|
| IIa-203 | 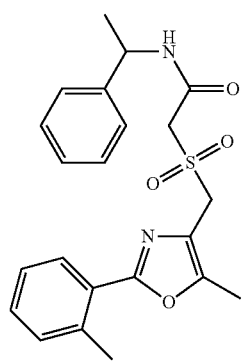 [SMILES: Cc1ccccc1-c1nc(CS(=O)(=O)CC(=O)NC(C)c2ccccc2)c(C)o1] | 412.51 |
| IIa-204 | 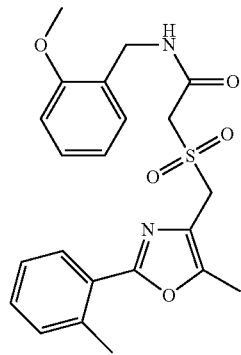 [SMILES: COc1ccccc1CNC(=O)CS(=O)(=O)Cc1nc(-c2ccccc2C)oc1C] | 428.51 |
| IIa-205 | 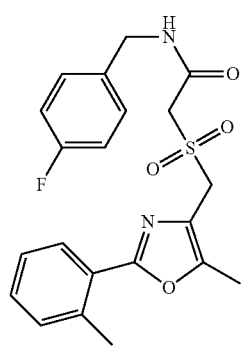 | 416.47 |

TABLE 1-continued

Oxazole amides (R³ = NH-benzyl)

| ID | Structure | MW |
|---|---|---|
| IIa-206 | | 436.89 |
| IIa-207 | | 416.47 |
| IIa-208 | | 418.90 |
| IIa-209 | | 436.89 |

TABLE 1-continued

Oxazole amides (R³ = NH-benzyl)

| ID | Structure | MW |
|---|---|---|
| IIa-210 | 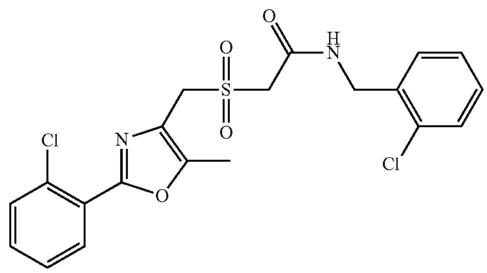 [SMILES: Cc1oc(-c2ccccc2Cl)nc1CS(=O)(=O)CC(=O)NCc1ccccc1Cl] | 453.35 |
| IIa-211 | 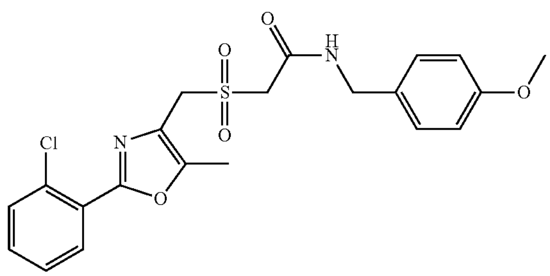 [SMILES: COc1ccc(CNC(=O)CS(=O)(=O)Cc2nc(-c3ccccc3Cl)oc2C)cc1] | 448.93 |
| IIa-212 | 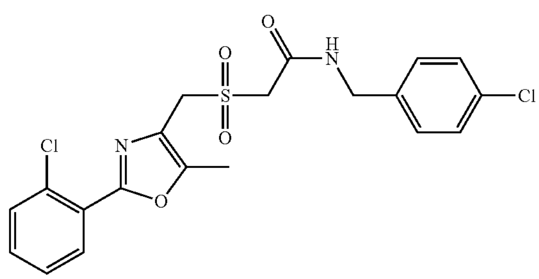 [SMILES: Cc1oc(-c2ccccc2Cl)nc1CS(=O)(=O)CC(=O)NCc1ccc(Cl)cc1] | 453.35 |
| IIa-213 | 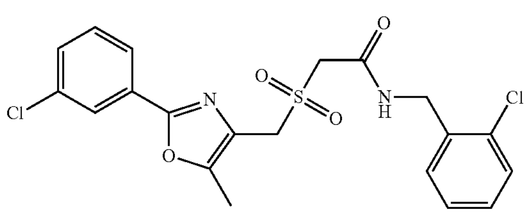 [SMILES: Cc1oc(-c2cccc(Cl)c2)nc1CS(=O)(=O)CC(=O)NCc1ccccc1Cl] | 453.35 |
| IIa-214 | 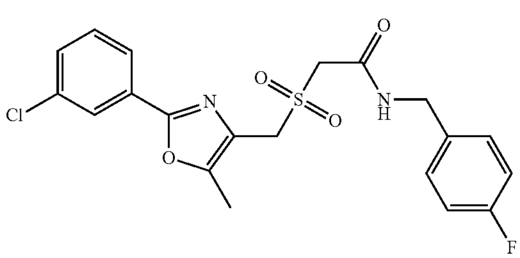 [SMILES: Cc1oc(-c2cccc(Cl)c2)nc1CS(=O)(=O)CC(=O)NCc1ccc(F)cc1] | 436.89 |

TABLE 1-continued

Oxazole amides (R³ = NH-benzyl)

| ID | Structure | MW |
|---|---|---|
| IIa-215 | 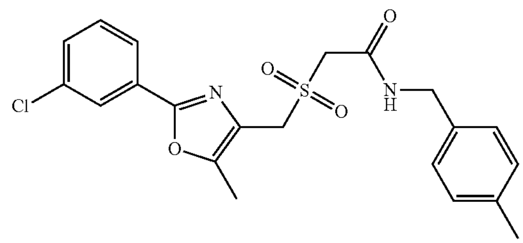 [SMILES: Cc1ccc(CNC(=O)CS(=O)(=O)Cc2nc(-c3cccc(Cl)c3)oc2C)cc1] | 432.93 |
| IIa-216 | 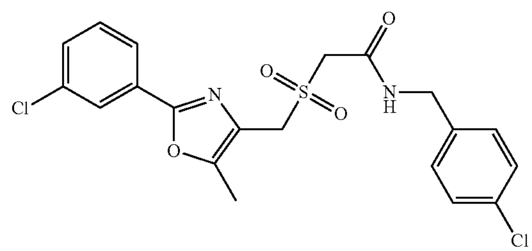 [SMILES: Cc1oc(-c2cccc(Cl)c2)nc1CS(=O)(=O)CC(=O)NCc1ccc(Cl)cc1] | 453.35 |
| IIa-217 | 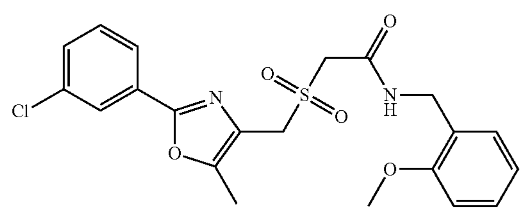 [SMILES: COc1ccccc1CNC(=O)CS(=O)(=O)Cc1nc(-c2cccc(Cl)c2)oc1C] | 448.93 |
| IIa-218 | 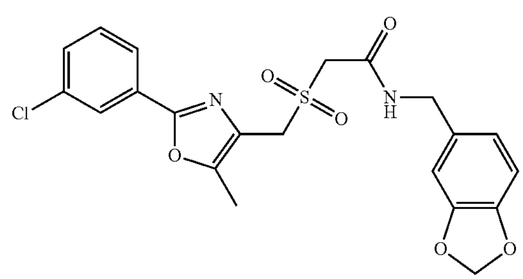 [SMILES: Cc1oc(-c2cccc(Cl)c2)nc1CS(=O)(=O)CC(=O)NCc1ccc2c(c1)OCO2] | 462.91 |
| IIa-219 | 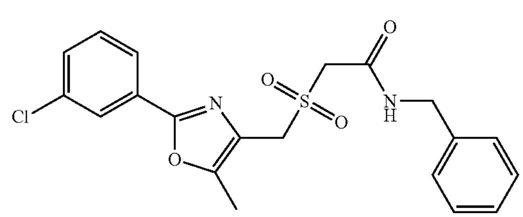 [SMILES: Cc1oc(-c2cccc(Cl)c2)nc1CS(=O)(=O)CC(=O)NCc1ccccc1] | 418.90 |

TABLE 1-continued

Oxazole amides (R³ = NH-benzyl)

| ID | Structure | MW |
|---|---|---|
| IIa-220 | 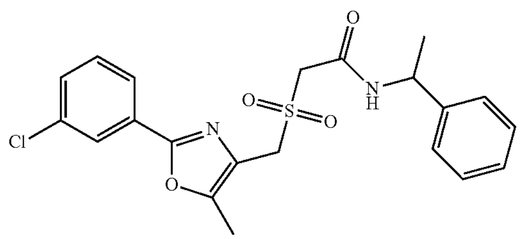 [SMILES: Cc1oc(-c2cccc(Cl)c2)nc1CS(=O)(=O)CC(=O)NC(C)c1ccccc1] | 432.93 |
| IIa-221 | 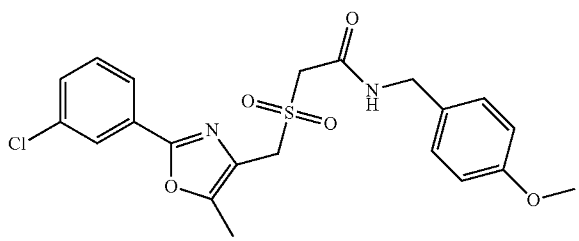 [SMILES: COc1ccc(CNC(=O)CS(=O)(=O)Cc2nc(-c3cccc(Cl)c3)oc2C)cc1] | 448.93 |
| IIa-222 | 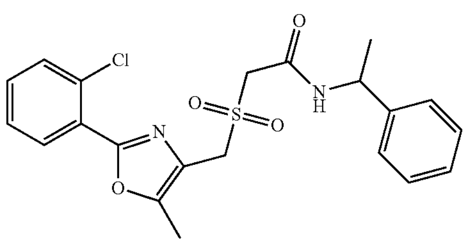 [SMILES: Cc1oc(-c2ccccc2Cl)nc1CS(=O)(=O)CC(=O)NC(C)c1ccccc1] | 432.93 |
| IIa-223 | 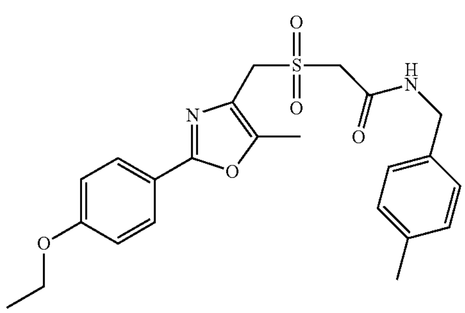 [SMILES: CCOc1ccc(-c2nc(CS(=O)(=O)CC(=O)NCc3ccc(C)cc3)c(C)o2)cc1] | 442.54 |
| IIa-224 | 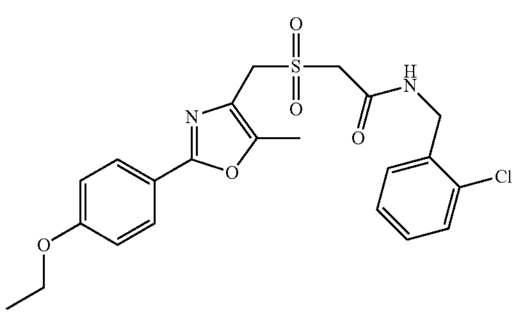 [SMILES: CCOc1ccc(-c2nc(CS(=O)(=O)CC(=O)NCc3ccccc3Cl)c(C)o2)cc1] | 462.96 |

TABLE 1-continued
Oxazole amides (R³ = NH-benzyl)
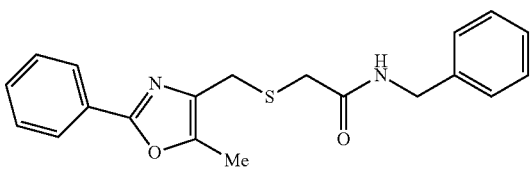
| ID | Structure | MW |
|---|---|---|
| IIa-225 | 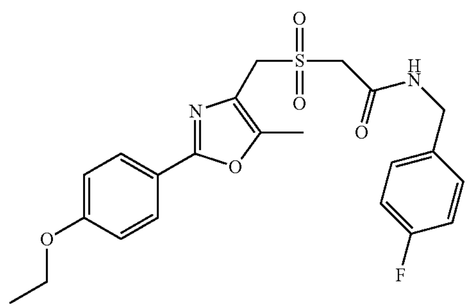 [SMILES: CCOc1ccc(-c2nc(CS(=O)(=O)CC(=O)NCc3ccc(F)cc3)c(C)o2)cc1] | 446.50 |
| IIa-226 | 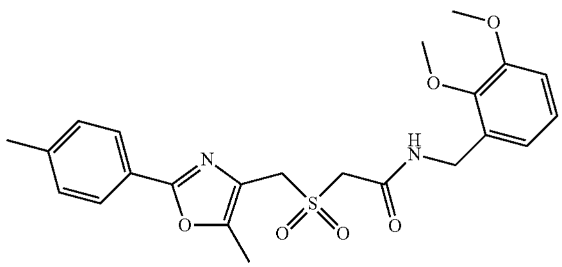 [SMILES: COc1cccc(CNC(=O)CS(=O)(=O)Cc2nc(-c3ccc(C)cc3)oc2C)c1OC] | 458.54 |
| IIa-227 | 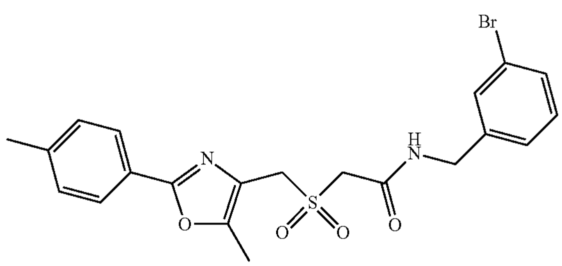 [SMILES: Cc1ccc(-c2nc(CS(=O)(=O)CC(=O)NCc3cccc(Br)c3)c(C)o2)cc1] | 477.38 |
| IIa-228 | 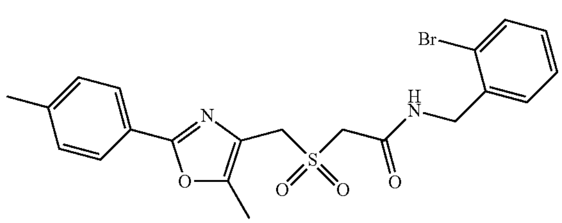 [SMILES: Cc1ccc(-c2nc(CS(=O)(=O)CC(=O)NCc3ccccc3Br)c(C)o2)cc1] | 477.38 |
| IIa-229 | 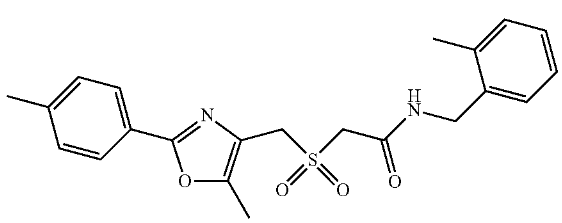 [SMILES: Cc1ccc(-c2nc(CS(=O)(=O)CC(=O)NCc3ccccc3C)c(C)o2)cc1] | 412.51 |

TABLE 1-continued
Oxazole amides (R³ = NH-benzyl)
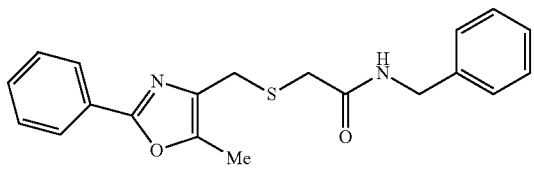
| ID | Structure | MW |
|---|---|---|
| IIa-230 | 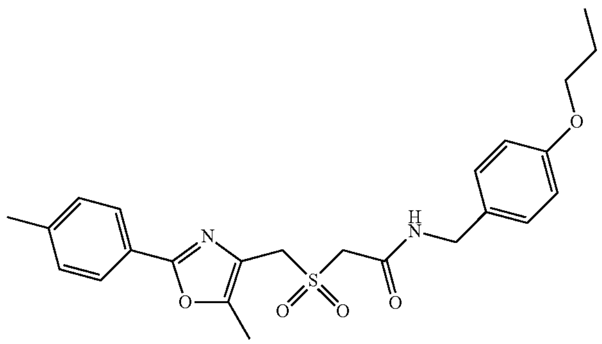 [SMILES: CCCOc1ccc(CNC(=O)CS(=O)(=O)Cc2nc(-c3ccc(C)cc3)oc2C)cc1] | 456.57 |
| IIa-231 | 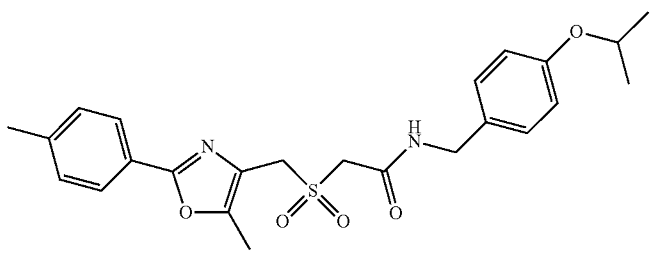 [SMILES: Cc1ccc(-c2nc(CS(=O)(=O)CC(=O)NCc3ccc(OC(C)C)cc3)c(C)o2)cc1] | 456.57 |
| IIa-232 | 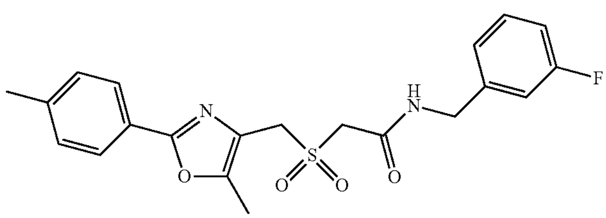 [SMILES: Cc1ccc(-c2nc(CS(=O)(=O)CC(=O)NCc3cccc(F)c3)c(C)o2)cc1] | 416.47 |
| IIa-233 | 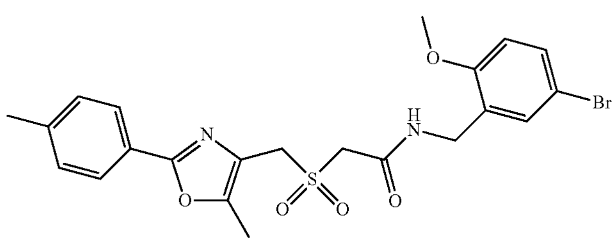 [SMILES: COc1ccc(Br)cc1CNC(=O)CS(=O)(=O)Cc1nc(-c2ccc(C)cc2)oc1C] | 507.41 |
| IIa-234 | 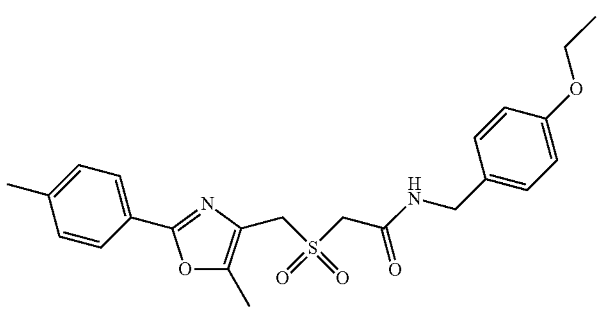 [SMILES: CCOc1ccc(CNC(=O)CS(=O)(=O)Cc2nc(-c3ccc(C)cc3)oc2C)cc1] | 442.54 |

TABLE 1-continued

Oxazole amides (R³ = NH-benzyl)

| ID | Structure | MW |
|---|---|---|
| IIa-235 | | 474.54 |
| IIa-236 | | 493.38 |
| IIa-237 | | 493.38 |
| IIa-238 | | 428.51 |
| IIa-239 | | 472.56 |

TABLE 1-continued

Oxazole amides (R³ = NH-benzyl)

| ID | Structure | MW |
|---|---|---|
| IIa-240 | 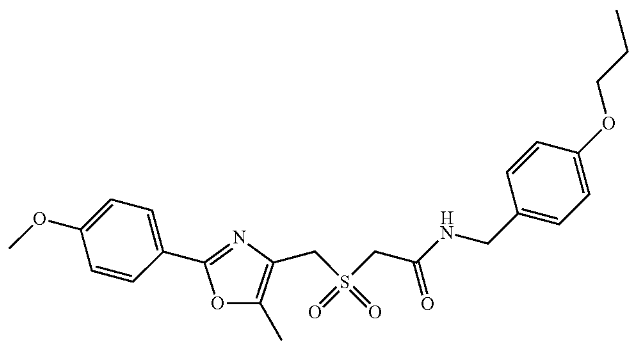 [SMILES: CCCOc1ccc(CNC(=O)CS(=O)(=O)Cc2nc(-c3ccc(OC)cc3)oc2C)cc1] | 472.56 |
| IIa-241 | 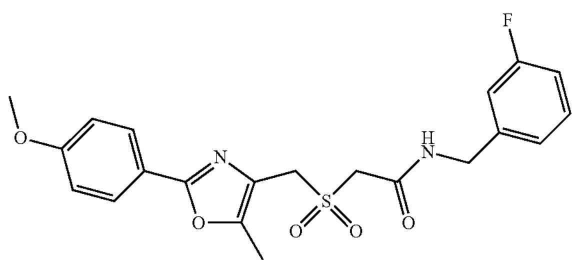 [SMILES: COc1ccc(-c2nc(CS(=O)(=O)CC(=O)NCc3cccc(F)c3)c(C)o2)cc1] | 432.47 |
| IIa-242 | 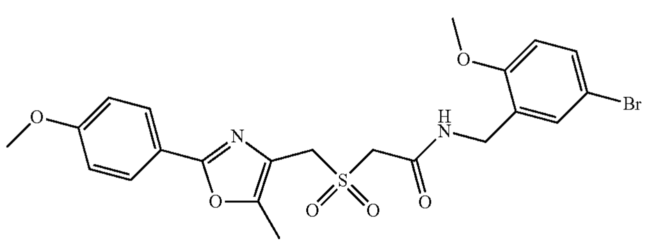 [SMILES: COc1ccc(-c2nc(CS(=O)(=O)CC(=O)NCc3cc(Br)ccc3OC)c(C)o2)cc1] | 523.41 |
| IIa-243 | 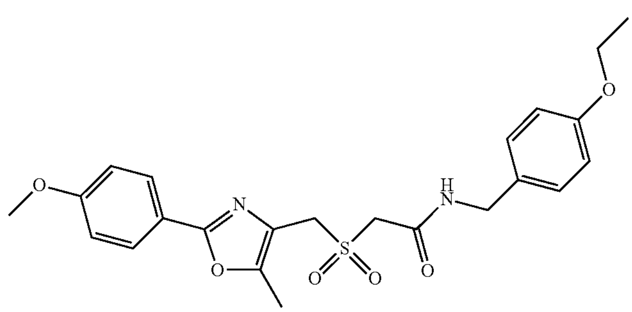 [SMILES: CCOc1ccc(CNC(=O)CS(=O)(=O)Cc2nc(-c3ccc(OC)cc3)oc2C)cc1] | 458.54 |
| IIa-244 | 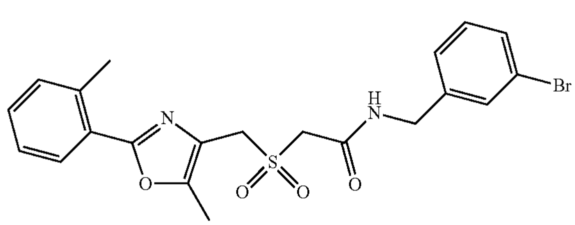 [SMILES: Cc1ccccc1-c1nc(CS(=O)(=O)CC(=O)NCc2cccc(Br)c2)c(C)o1] | 477.38 |

TABLE 1-continued
Oxazole amides (R³ = NH-benzyl)
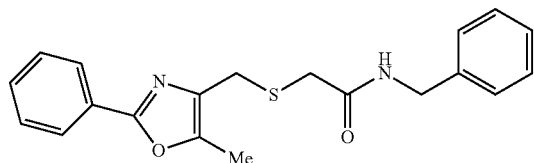
| ID | Structure | MW |
|---|---|---|
| IIa-245 | 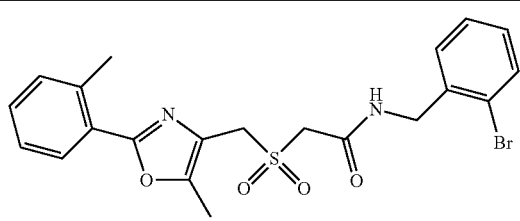 | 477.38 |
| IIa-246 | 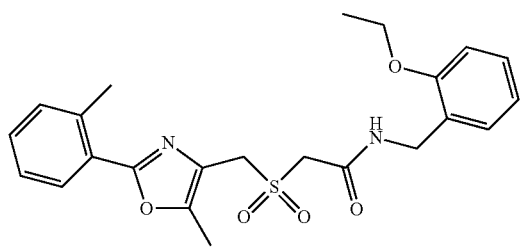 [SMILES: CCOc1ccccc1CNC(=O)CS(=O)(=O)Cc1nc(-c2ccccc2C)oc1C] | 442.54 |
| IIa-247 | 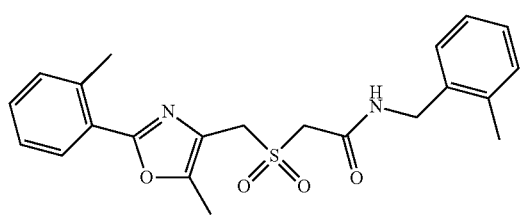 [SMILES: Cc1ccccc1CNC(=O)CS(=O)(=O)Cc1nc(-c2ccccc2C)oc1C] | 412.51 |
| IIa-248 | 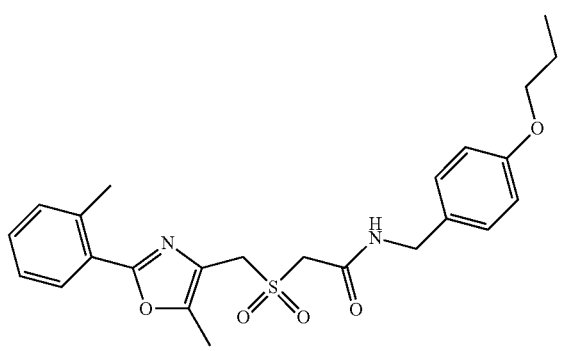 [SMILES: CCCOc1ccc(CNC(=O)CS(=O)(=O)Cc2nc(-c3ccccc3C)oc2C)cc1] | 456.57 |
| IIa-249 | 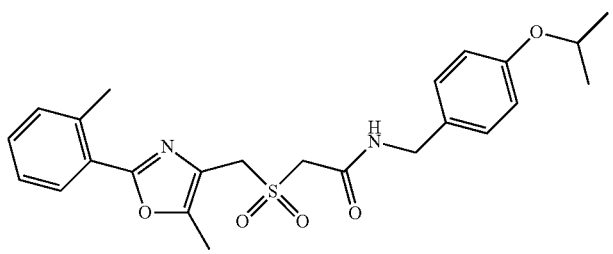 [SMILES: Cc1ccccc1-c1nc(CS(=O)(=O)CC(=O)NCc2ccc(OC(C)C)cc2)c(C)o1] | 456.57 |

TABLE 1-continued

Oxazole amides (R³ = NH-benzyl)

| ID | Structure | MW |
|---|---|---|
| IIa-250 | | 416.47 |
| IIa-251 | | 507.41 |
| IIa-252 | | 442.54 |
| IIa-253 | | 400.48 |

TABLE 1-continued
Oxazole amides (R³ = NH-benzyl)
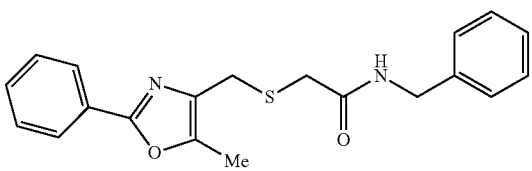
| ID | Structure | MW |
|---|---|---|
| IIa-254 | 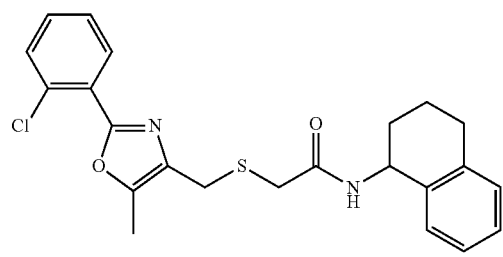 [SMILES: Cc1oc(-c2ccccc2Cl)nc1CSCC(=O)NC1CCCc2ccccc21] | 426.97 |
| IIa-255 | 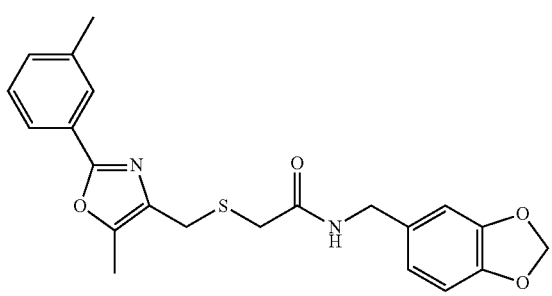 [SMILES: Cc1cccc(-c2nc(CSCC(=O)NCc3ccc4c(c3)OCO4)c(C)o2)c1] | 410.50 |
| IIa-256 | 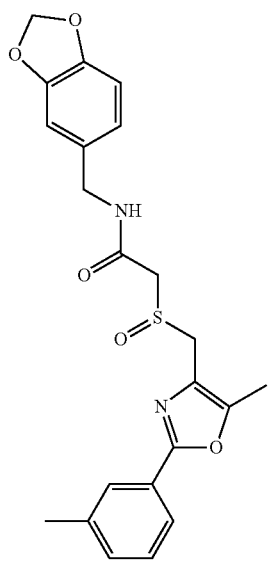 [SMILES: Cc1cccc(-c2nc(CS(=O)CC(=O)NCc3ccc4c(c3)OCO4)c(C)o2)c1] | 426.50 |

TABLE 1-continued
Oxazole amides (R³ = NH-benzyl)
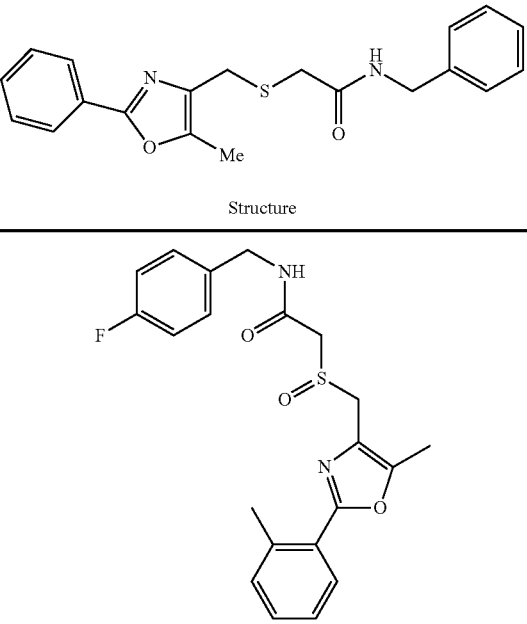
| ID | Structure | MW |
|---|---|---|
| IIa-257 | 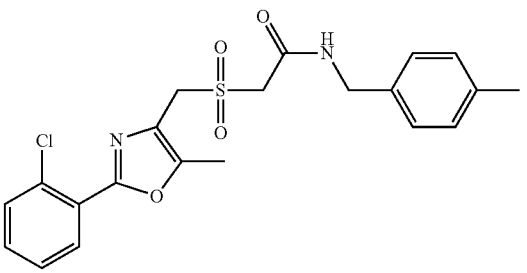 [SMILES: Cc1ccc(CNC(=O)CS(=O)(=O)Cc2nc(-c3ccccc3Cl)oc2C)cc1] | 400.48 |
| IIa-258 | 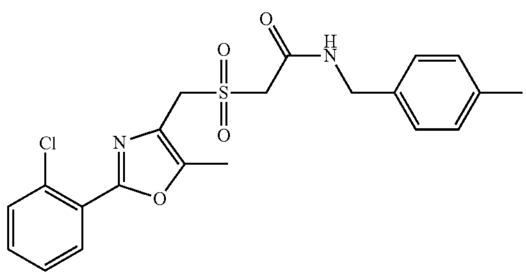 | 432.93 |
TABLE 2
Oxazole amides (R³ = NH-phenethyl)
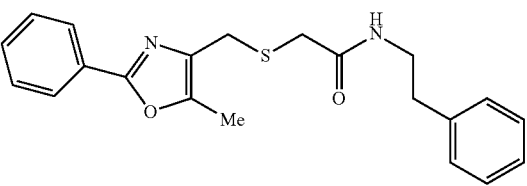 [SMILES: Cc1oc(-c2ccccc2)nc1CSCC(=O)NCCc1ccccc1]
| ID | Structure | MW |
|---|---|---|
| IIa-301 | 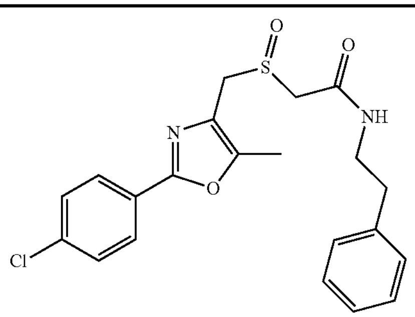 | 416.93 |

TABLE 2-continued

Oxazole amides (R³ = NH-phenethyl)

| ID | Structure | MW |
|---|---|---|
| IIa-302 | 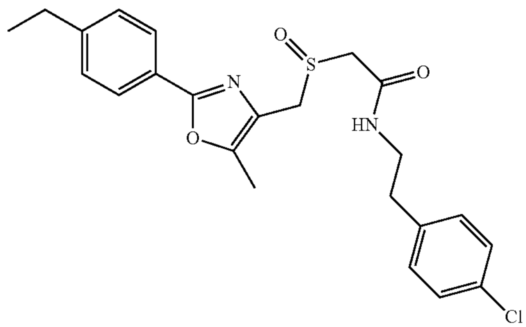 [SMILES: CCc1ccc(-c2nc(CS(=O)CC(=O)NCCc3ccc(Cl)cc3)c(C)o2)cc1] | 444.98 |
| IIa-303 | 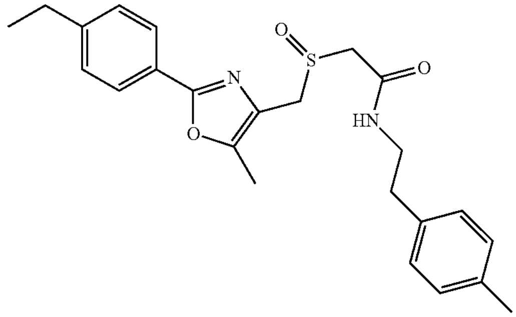 [SMILES: CCc1ccc(-c2nc(CS(=O)CC(=O)NCCc3ccc(C)cc3)c(C)o2)cc1] | 424.57 |
| IIa-304 | 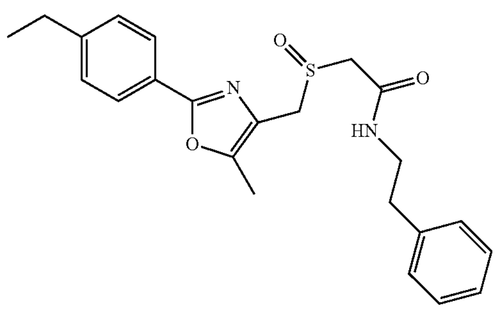 [SMILES: CCc1ccc(-c2nc(CS(=O)CC(=O)NCCc3ccccc3)c(C)o2)cc1] | 410.54 |
| IIa-305 | 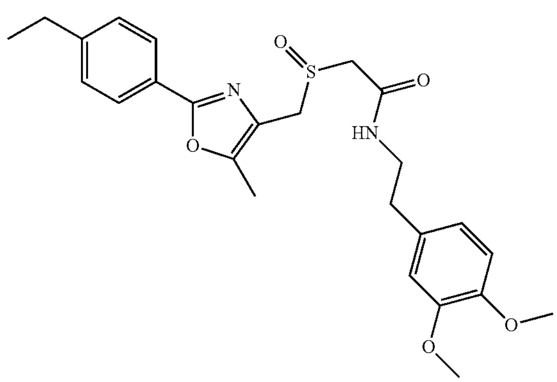 [SMILES: CCc1ccc(-c2nc(CS(=O)CC(=O)NCCc3ccc(OC)c(OC)c3)c(C)o2)cc1] | 470.59 |

TABLE 2-continued
Oxazole amides (R³ = NH-phenethyl)
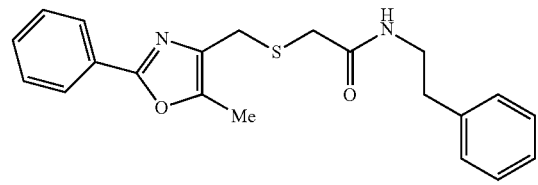
| ID | Structure | MW |
|---|---|---|
| IIa-306 | | 410.54 |
| IIa-307 | | 424.57 |
| IIa-308 | | 444.98 |

TABLE 2-continued

Oxazole amides (R³ = NH-phenethyl)

| ID | Structure | MW |
|---|---|---|
| IIa-309 | | 498.65 |
| IIa-310 | | 456.57 |
| IIa-311 | | 442.60 |

TABLE 2-continued
Oxazole amides (R³ = NH-phenethyl)
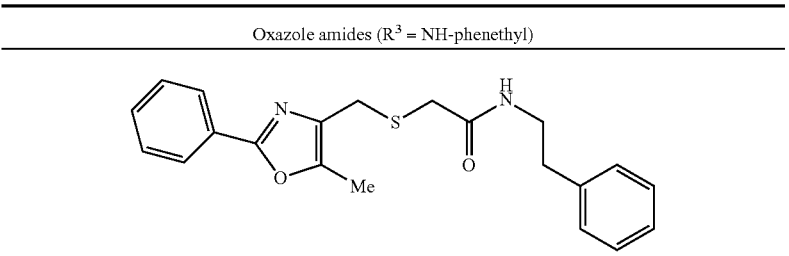
| ID | Structure | MW |
|---|---|---|
| IIa-312 | | 440.57 |
| IIa-313 | | 430.96 |

TABLE 2-continued
Oxazole amides (R³ = NH-phenethyl)
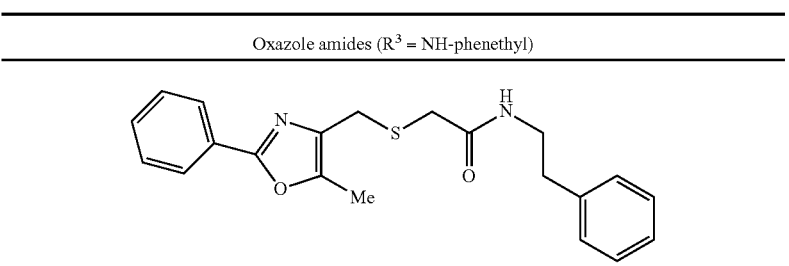
| ID | Structure | MW |
|---|---|---|
| IIa-314 | 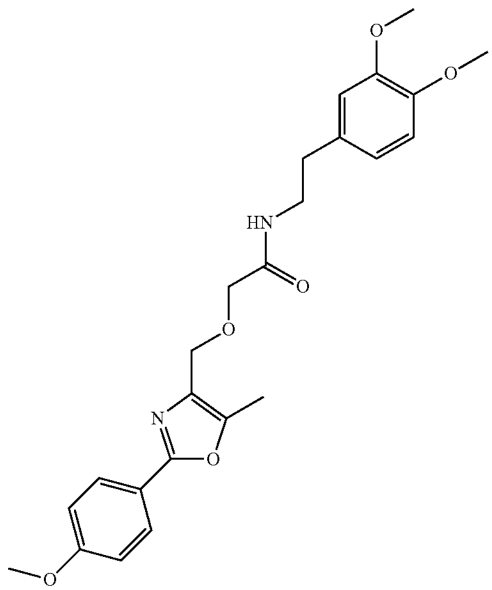 | 456.57 |
| IIa-315 | 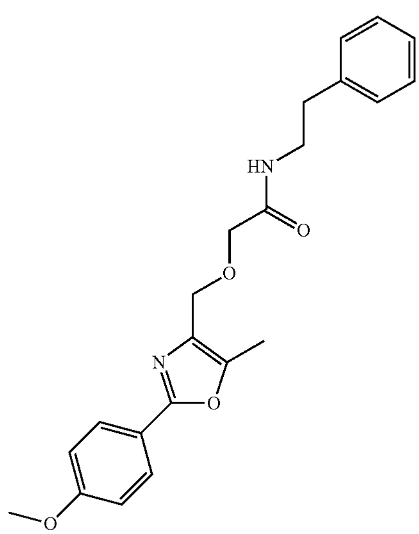 [SMILES: COc1ccc(-c2nc(COCC(=O)NCCc3ccccc3)c(C)o2)cc1] | 396.51 |

TABLE 2-continued
Oxazole amides (R³ = NH-phenethyl)
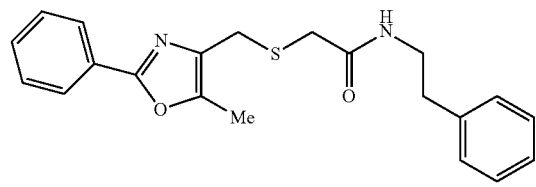
| ID | Structure | MW |
|---|---|---|
| IIa-316 | 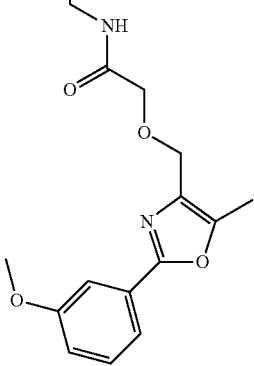 | 430.96 |
| IIa-317 | 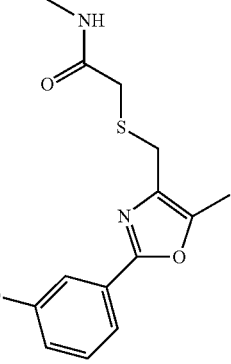 | 410.54 |

243

TABLE 2-continued

Oxazole amides (R³ = NH-phenethyl)

| ID | Structure | MW |
|---|---|---|
| IIa-318 | | 460.98 |
| IIa-319 | | 486.59 |

TABLE 2-continued
Oxazole amides (R³ = NH-phenethyl)
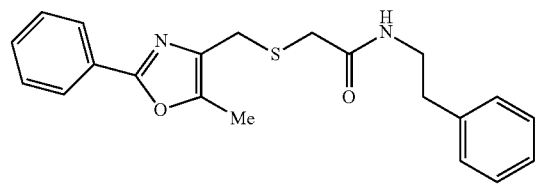
| ID | Structure | MW |
|---|---|---|
| IIa-320 | | 440.57 |
| IIa-321 | | 426.54 |

TABLE 2-continued
Oxazole amides (R³ = NH-phenethyl)
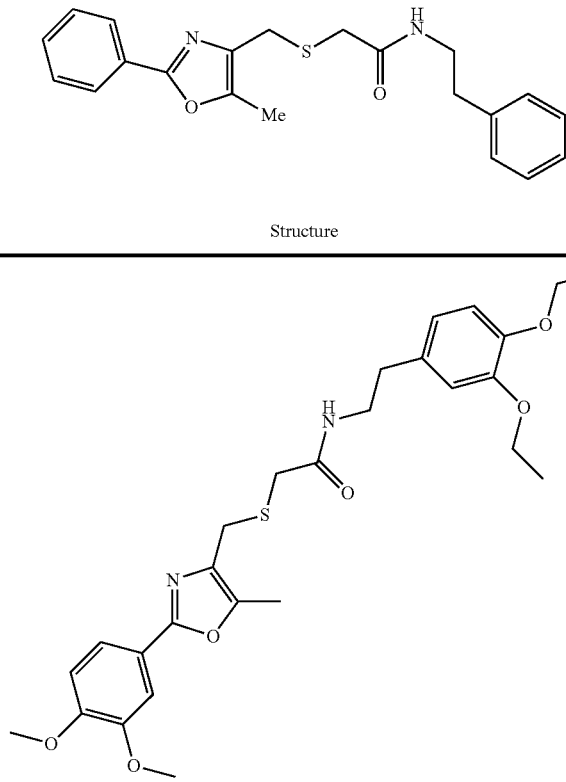
| ID | Structure | MW |
| --- | --- | --- |
| IIa-322 | 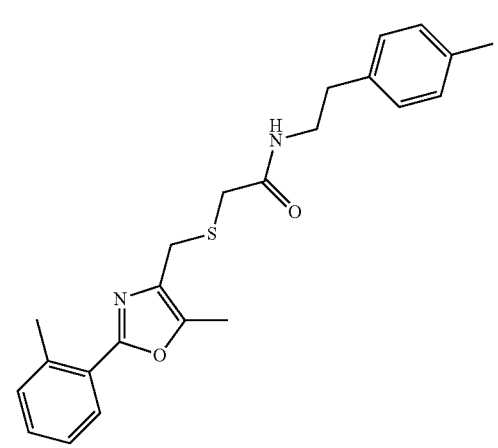 [SMILES: Cc1ccc(CCNC(=O)CSCc2nc(-c3ccccc3C)oc2C)cc1] | 514.65 |
| IIa-323 | | 394.54 |

TABLE 2-continued
Oxazole amides (R³ = NH-phenethyl)
| ID | Structure | MW |
|---|---|---|
| IIa-324 | 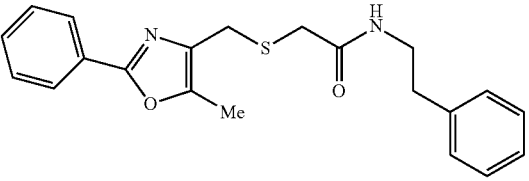 | 468.62 |
| IIa-325 | 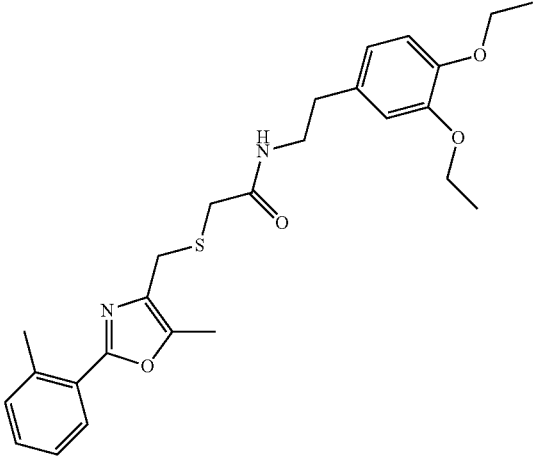 [SMILES: CCOc1ccc(CCNC(=O)CSCc2nc(-c3ccccc3C)oc2C)cc1OCC] | 435.38 |
| IIa-326 | 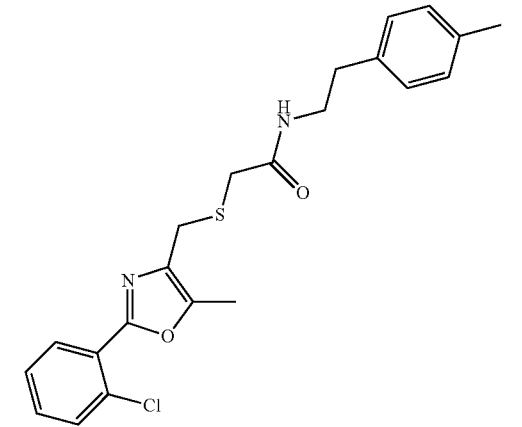 [SMILES: Cc1ccc(CCNC(=O)CSCc2nc(-c3ccccc3Cl)oc2C)cc1] | 414.96 |

TABLE 2-continued
Oxazole amides (R³ = NH-phenethyl)
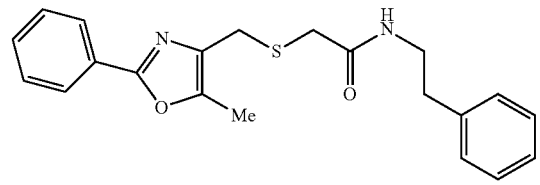
| ID | Structure | MW |
|---|---|---|
| IIa-327 | | 447.02 |
| IIa-328 | | 472.63 |

TABLE 2-continued
Oxazole amides (R³ = NH-phenethyl)
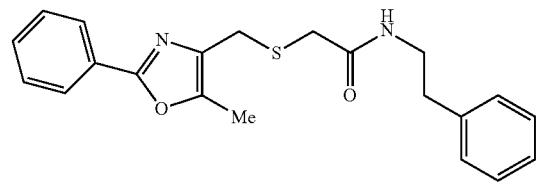
| ID | Structure | MW |
|---|---|---|
| IIa-329 | | 426.60 |
| IIa-330 | | 412.58 |

TABLE 2-continued
Oxazole amides (R³ = NH-phenethyl)
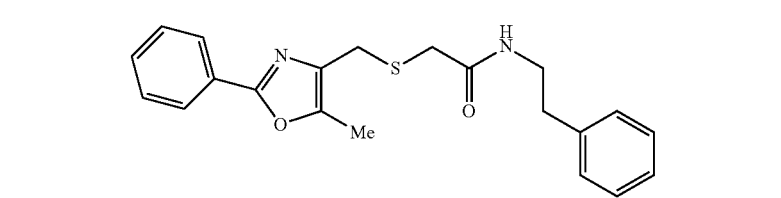
| ID | Structure | MW |
---
IIa-331 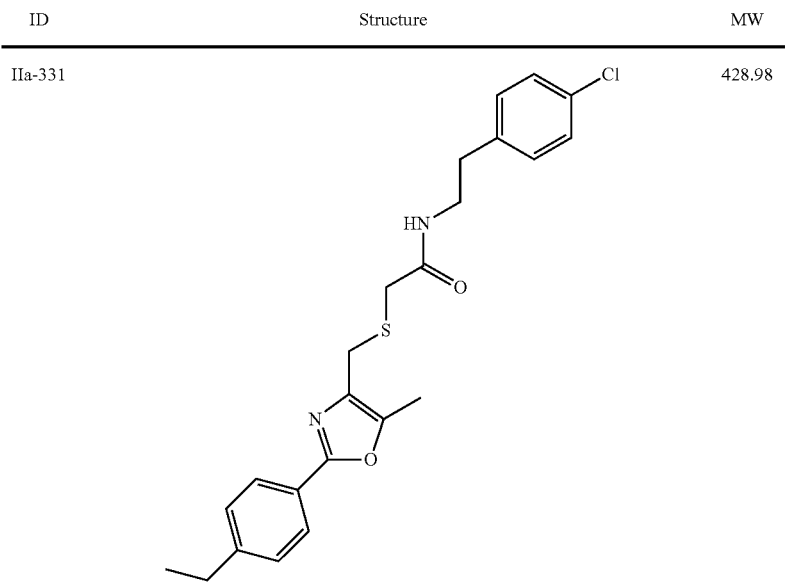 428.98
IIa-332 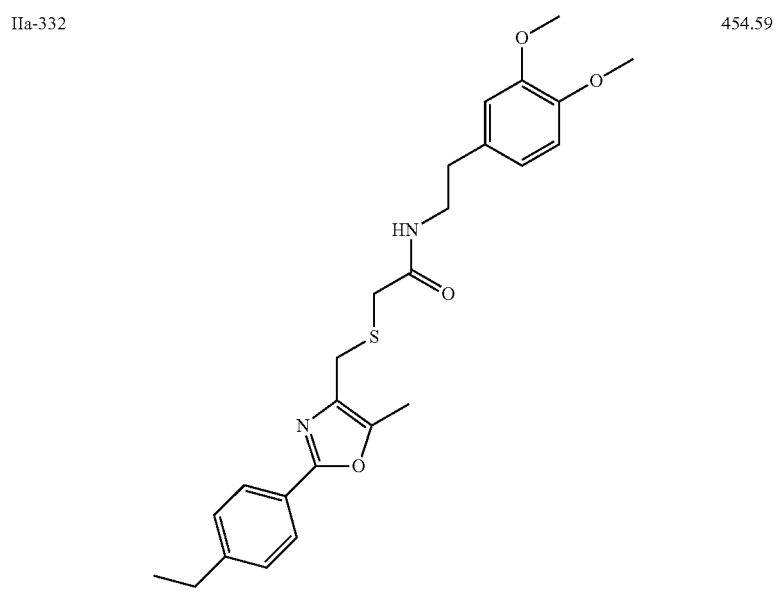 454.59

TABLE 2-continued
Oxazole amides (R³ = NH-phenethyl)
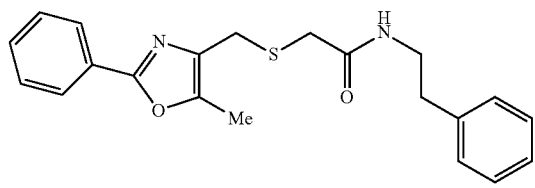
| ID | Structure | MW |
| --- | --- | --- |
| IIa-333 | | 394.54 |
| IIa-334 | | 482.65 |

TABLE 2-continued
Oxazole amides (R³ = NH-phenethyl)
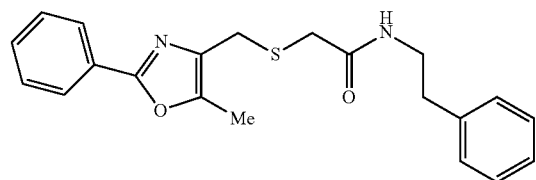
| ID | Structure | MW |
|---|---|---|
| IIa-335 | 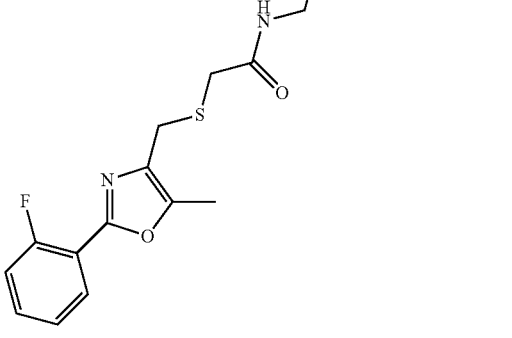 | 444.53 |
| IIa-336 |  | 384.48 |

TABLE 2-continued
Oxazole amides (R³ = NH-phenethyl)
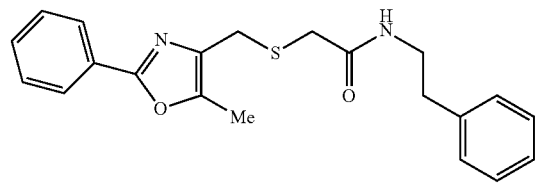
| ID | Structure | MW |
| --- | --- | --- |
| IIa-337 | | 414.96 |
| IIa-338 | 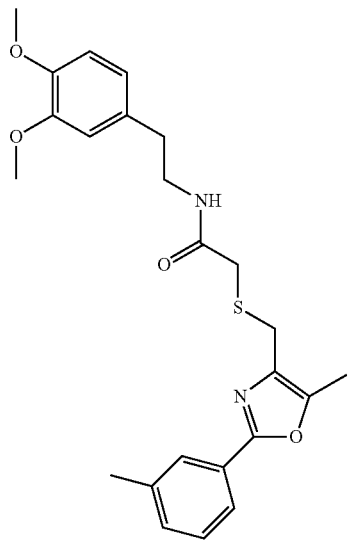 [SMILES: COc1ccc(CCNC(=O)CSCc2nc(-c3cccc(C)c3)oc2C)cc1OC] | 440.57 |

TABLE 2-continued
Oxazole amides (R³ = NH-phenethyl)
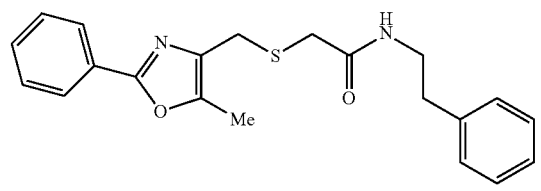
| ID | Structure | MW |
|---|---|---|
| IIa-339 | 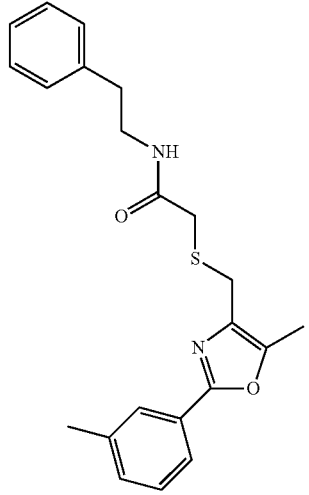 [SMILES: Cc1cccc(-c2nc(CSCC(=O)NCCc3ccccc3)c(C)o2)c1] | 380.51 |
| IIa-340 | 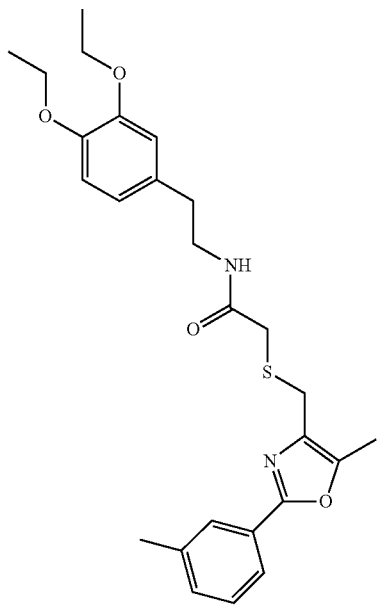 [SMILES: CCOc1ccc(CCNC(=O)CSCc2nc(-c3cccc(C)c3)oc2C)cc1OCC] | 468.62 |

TABLE 2-continued
Oxazole amides (R³ = NH-phenethyl)
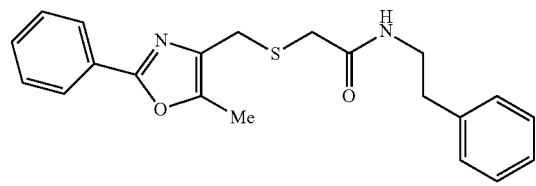
| ID | Structure | MW |
|---|---|---|
| IIa-341 | | 394.54 |
| IIa-342 | | 380.51 |

TABLE 2-continued
Oxazole amides (R³ = NH-phenethyl)
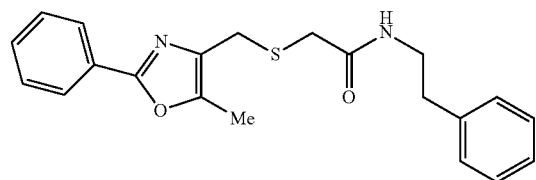
| ID | Structure | MW |
|---|---|---|
| IIa-343 | | 446.96 |
| IIa-344 | | 472.56 |

TABLE 2-continued
Oxazole amides (R³ = NH-phenethyl)
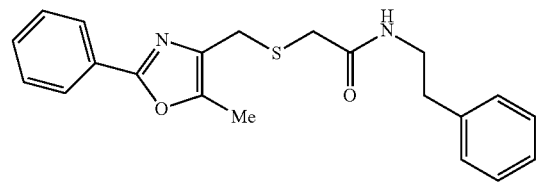
| ID | Structure | MW |
|---|---|---|
| IIa-345 | 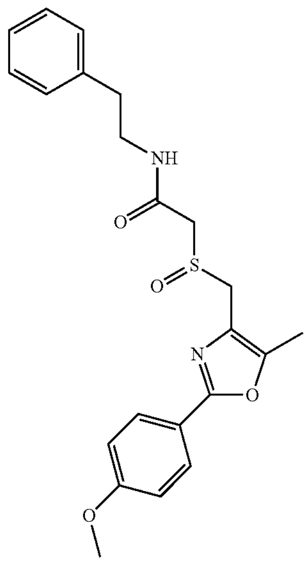 [SMILES: COc1ccc(-c2nc(CS(=O)CC(=O)NCCc3ccccc3)c(C)o2)cc1] | 412.51 |
| IIa-346 | 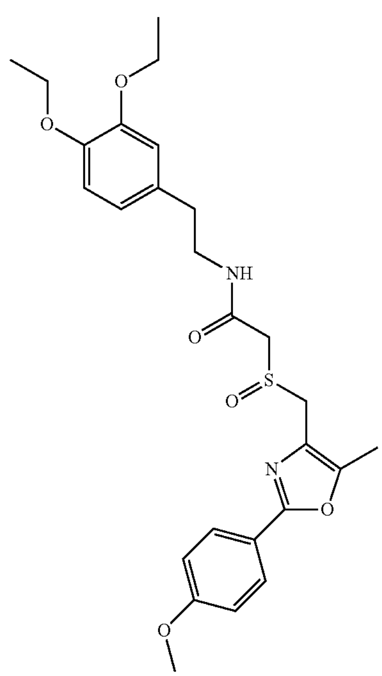 [SMILES: CCOc1ccc(CCNC(=O)CS(=O)Cc2nc(-c3ccc(OC)cc3)oc2C)cc1OCC] | 500.62 |

TABLE 2-continued
Oxazole amides (R³ = NH-phenethyl)
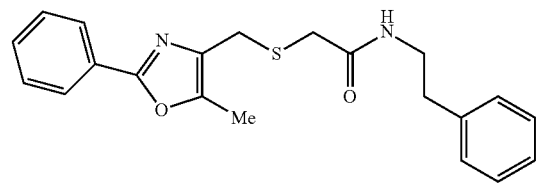
| ID | Structure | MW |
|---|---|---|
| IIa-347 | | 434.92 |
| IIa-348 | | 460.53 |

TABLE 2-continued
Oxazole amides (R³ = NH-phenethyl)
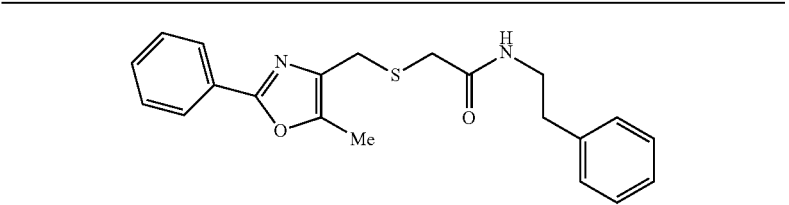
| ID | Structure | MW |
| --- | --- | --- |
| IIa-349 | 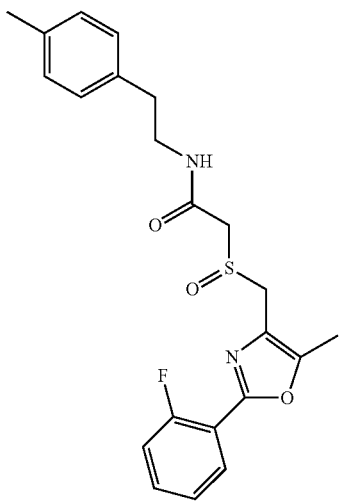 | 414.50 |
| IIa-350 | 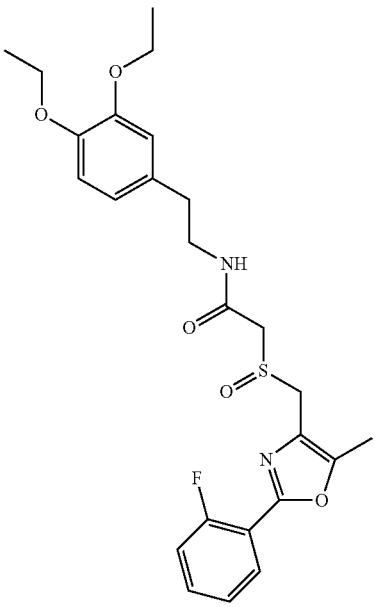 [SMILES: CCOc1ccc(CCNC(=O)CS(=O)Cc2nc(-c3ccccc3F)oc2C)cc1OCC] | 488.58 |

TABLE 2-continued
| Oxazole amides (R³ = NH-phenethyl) | | |
|---|---|---|
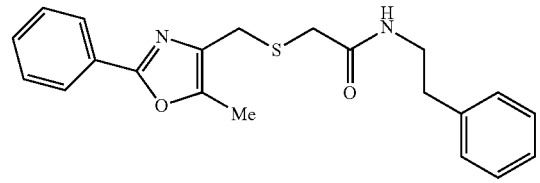
| ID | Structure | MW |
|---|---|---|
| IIa-351 | | 430.96 |
| IIa-352 | | 410.54 |

TABLE 2-continued
Oxazole amides (R³ = NH-phenethyl)
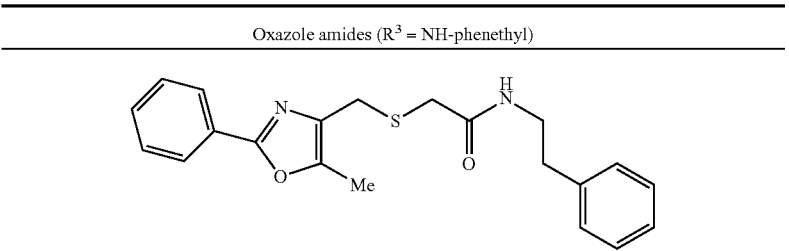
| ID | Structure | MW |
| --- | --- | --- |
| IIa-353 | 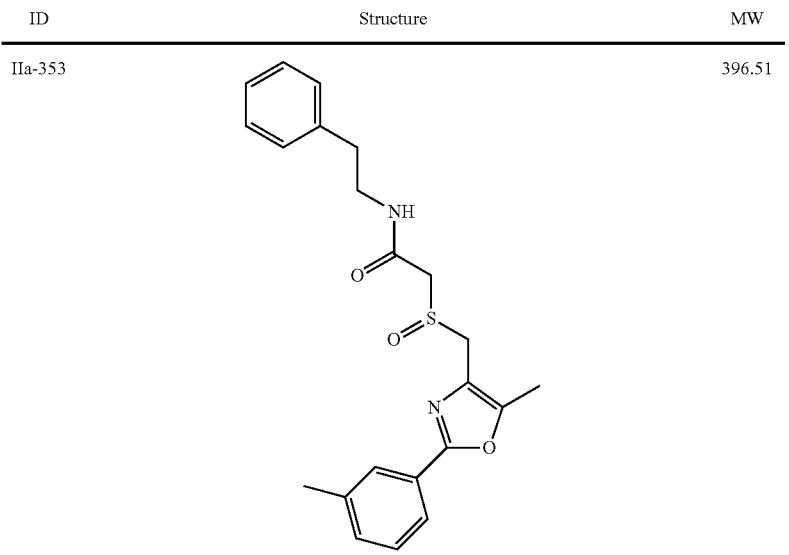 | 396.51 |
| IIa-354 | 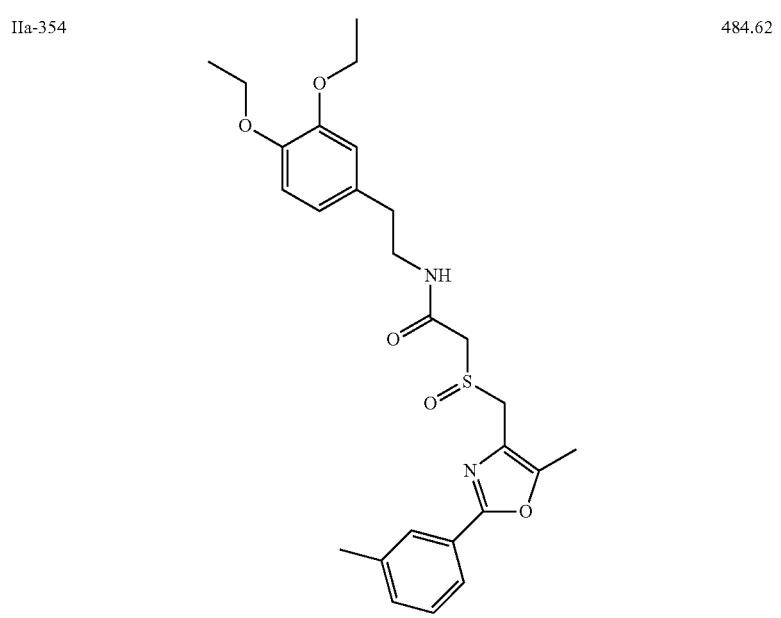 | 484.62 |

TABLE 2-continued

Oxazole amides (R³ = NH-phenethyl)

| ID | Structure | MW |
|---|---|---|
| IIa-355 | | 430.96 |
| IIa-356 | | 456.57 |

TABLE 2-continued
Oxazole amides (R³ = NH-phenethyl)
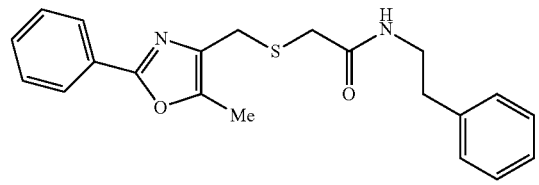
| ID | Structure | MW |
|---|---|---|
| IIa-357 | | 410.54 |
| IIa-358 | | 396.51 |

TABLE 2-continued
Oxazole amides (R³ = NH-phenethyl)
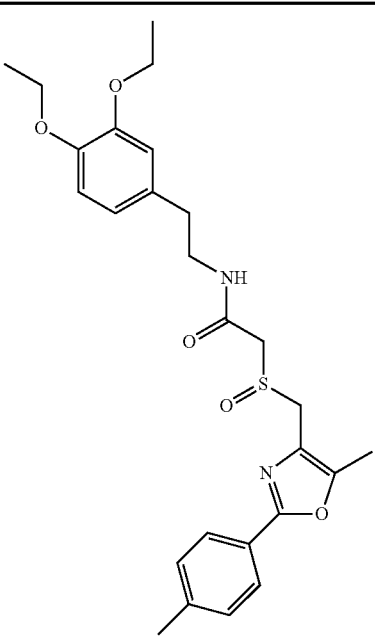
| ID | Structure | MW |
|---|---|---|
| IIa-359 | 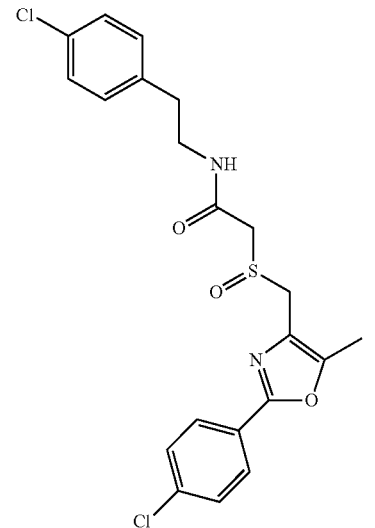 [SMILES: Cc1oc(-c2ccc(Cl)cc2)nc1CS(=O)CC(=O)NCCc1ccc(Cl)cc1] | 484.62 |
| IIa-360 | | 451.38 |

TABLE 2-continued

Oxazole amides (R³ = NH-phenethyl)

| ID | Structure | MW |
|---|---|---|
| IIa-361 | | 476.98 |
| IIa-362 | | 430.96 |

TABLE 2-continued
Oxazole amides (R³ = NH-phenethyl)
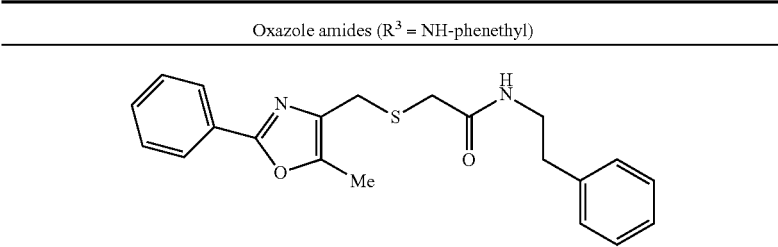
| ID | Structure | MW |
|---|---|---|
| IIa-363 | 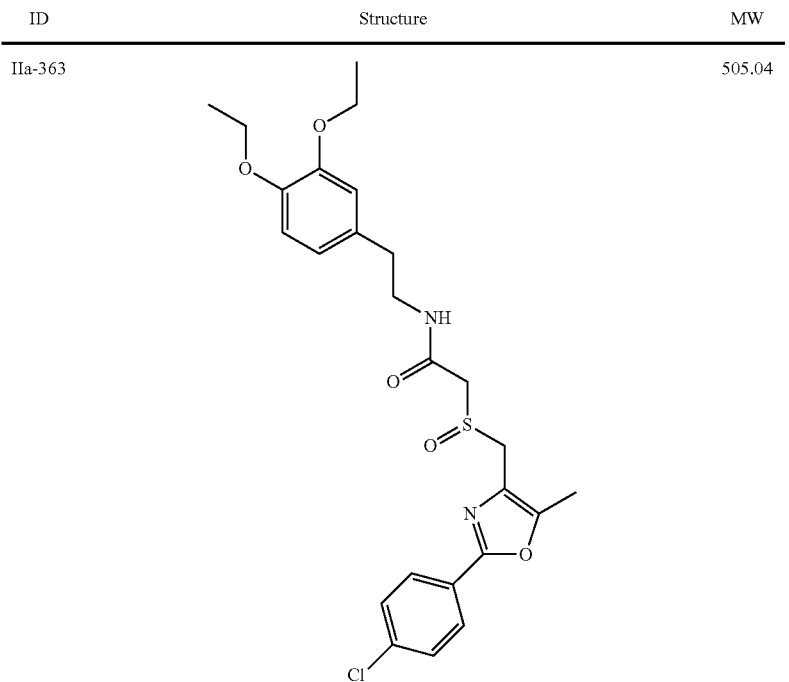 | 505.04 |
| IIa-364 | 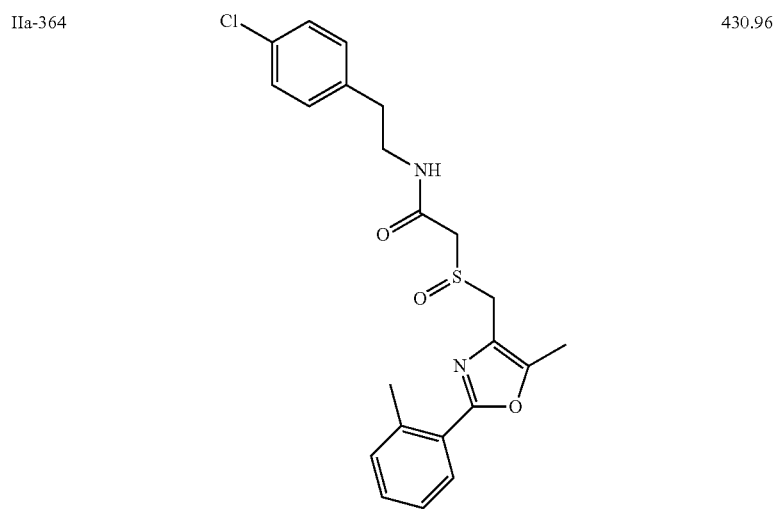 | 430.96 |

TABLE 2-continued
Oxazole amides (R³ = NH-phenethyl)
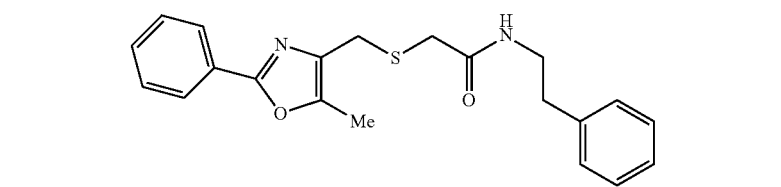
| ID | Structure | MW |
|---|---|---|
| IIa-365 | 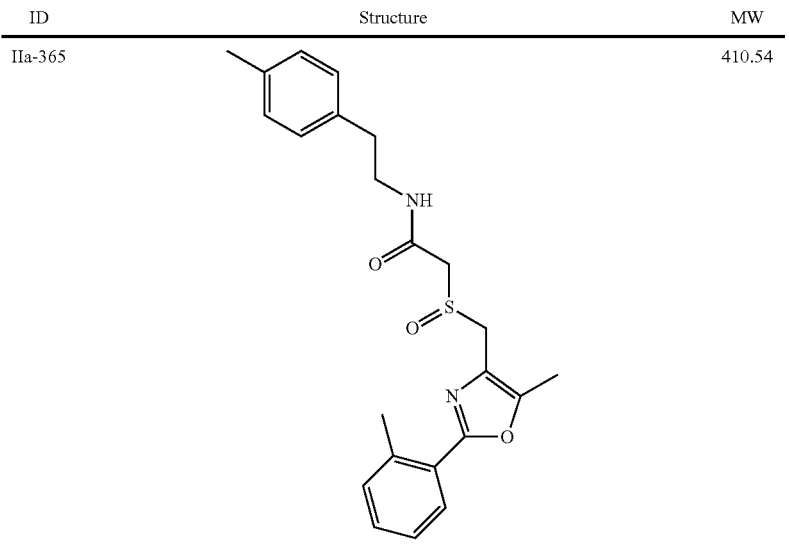 | 410.54 |
| IIa-366 | 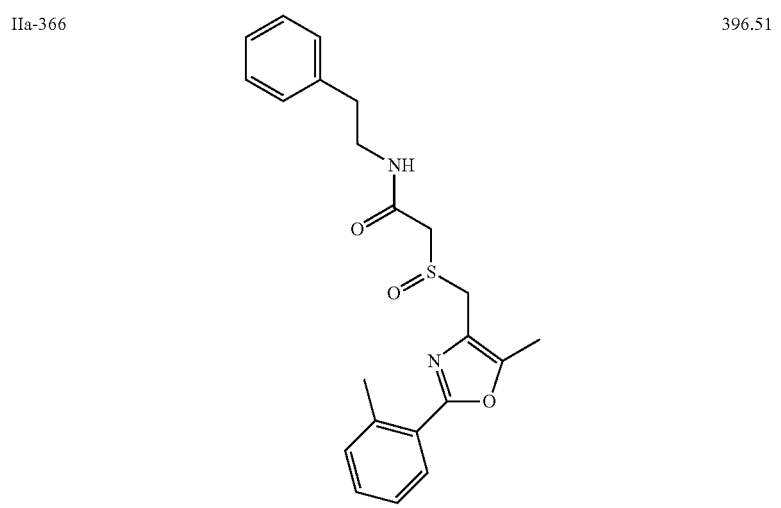 | 396.51 |

TABLE 2-continued
Oxazole amides (R³ = NH-phenethyl)
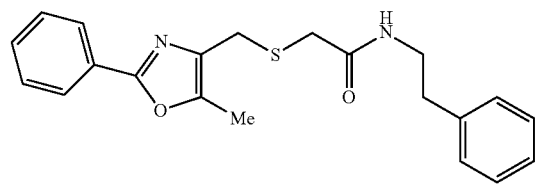
| ID | Structure | MW |
|---|---|---|
| IIa-367 | | 412.58 |
| IIa-368 | | 412.58 |

TABLE 2-continued
Oxazole amides (R³ = NH-phenethyl)
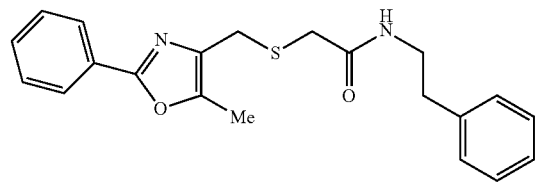
| ID | Structure | MW |
|---|---|---|
| IIa-369 | | 476.98 |
| IIa-370 | | 430.96 |

TABLE 2-continued
Oxazole amides (R³ = NH-phenethyl)
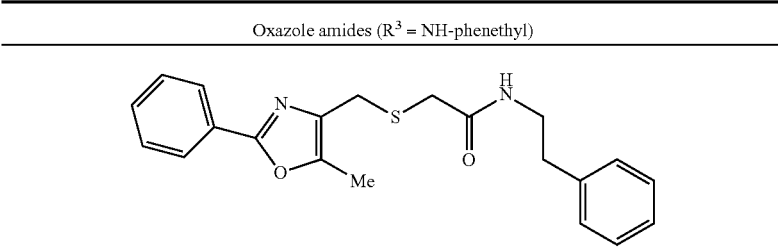
| ID | Structure | MW |
|---|---|---|
| IIa-371 | 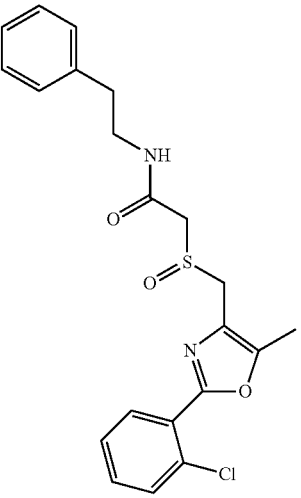 [SMILES: Cc1oc(-c2ccccc2Cl)nc1CS(=O)CC(=O)NCCc1ccccc1] | 416.93 |
| IIa-372 | 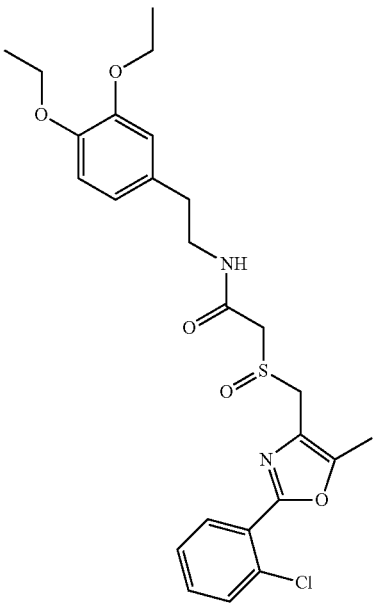 [SMILES: CCOc1ccc(CCNC(=O)CS(=O)Cc2nc(-c3ccccc3Cl)oc2C)cc1OCC] | 505.04 |

TABLE 2-continued
Oxazole amides (R³ = NH-phenethyl)
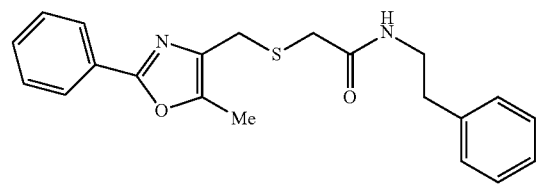
| ID | Structure | MW |
|---|---|---|
| IIa-373 | | 472.56 |
| IIa-374 | | 426.54 |

TABLE 2-continued
Oxazole amides (R³ = NH-phenethyl)
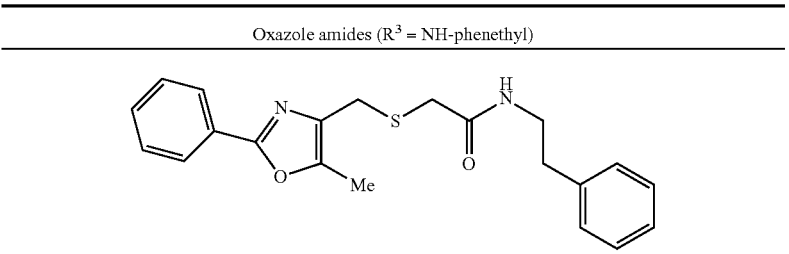
| ID | Structure | MW |
|---|---|---|
| IIa-375 | 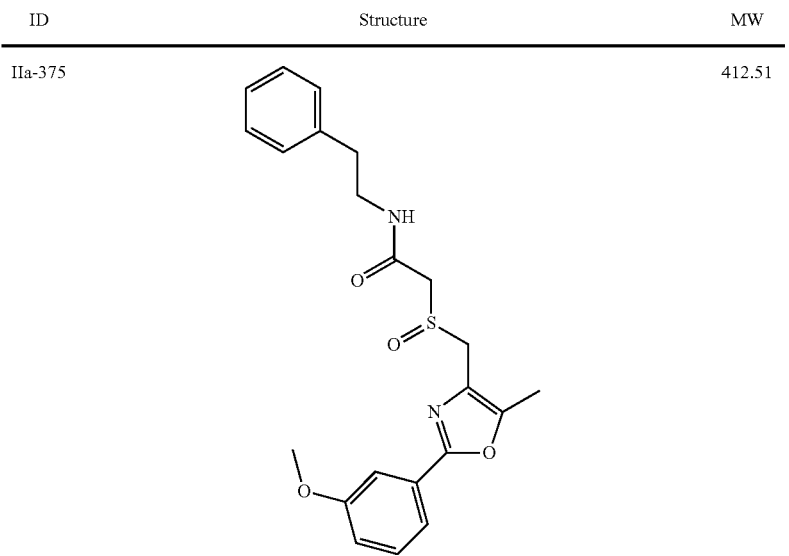 | 412.51 |
| IIa-376 | 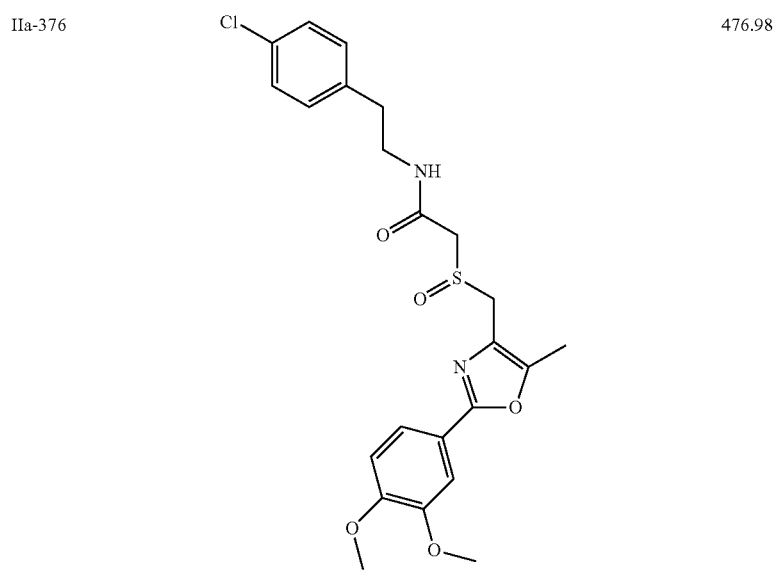 | 476.98 |

TABLE 2-continued
Oxazole amides (R³ = NH-phenethyl)
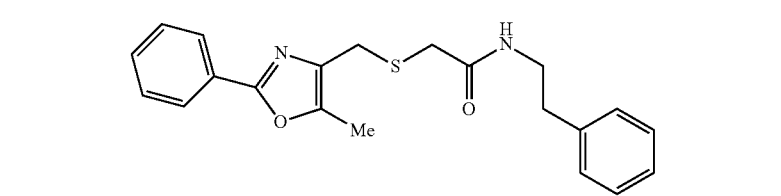
| ID | Structure | MW |
|---|---|---|
| IIa-377 | 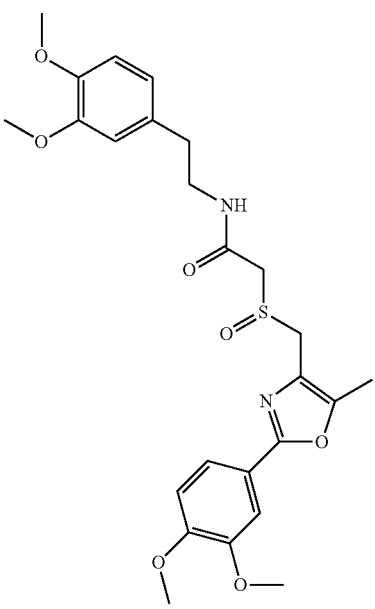 | 502.59 |
| IIa-378 | 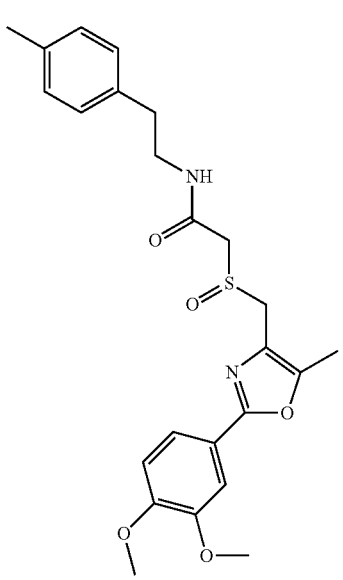 | 456.57 |

TABLE 2-continued
Oxazole amides (R³ = NH-phenethyl)
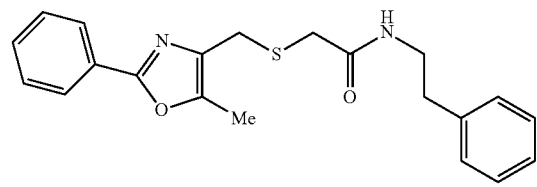
| ID | Structure | MW |
|---|---|---|
| IIa-379 | | 442.54 |
| IIa-380 | | 530.65 |

TABLE 2-continued
Oxazole amides (R³ = NH-phenethyl)
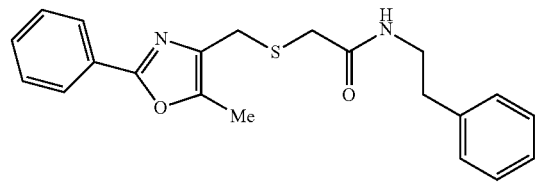
| ID | Structure | MW |
|---|---|---|
| IIa-381 | 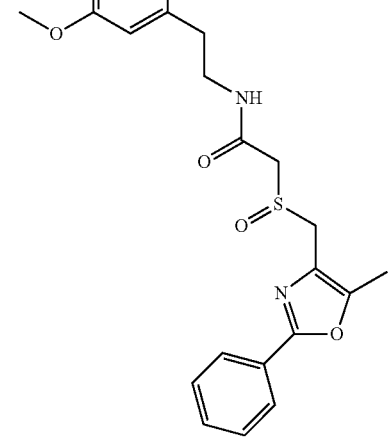 | 442.54 |
| IIa-382 | 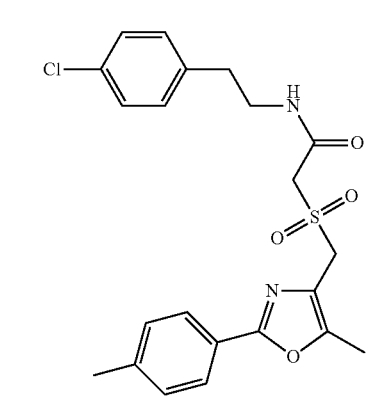 [SMILES: Cc1ccc(-c2nc(CS(=O)(=O)CC(=O)NCCc3ccc(Cl)cc3)c(C)o2)cc1] | 446.96 |
| IIa-383 | 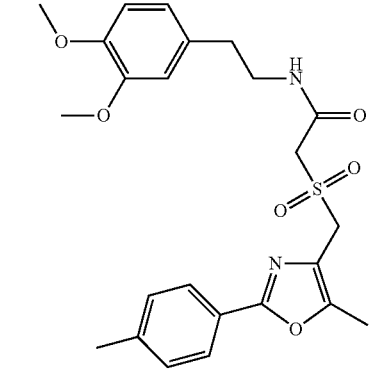 | 472.56 |

TABLE 2-continued
Oxazole amides (R³ = NH-phenethyl)
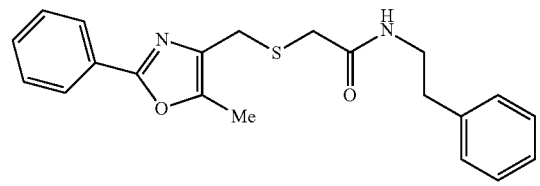
| ID | Structure | MW |
| --- | --- | --- |
| IIa-384 | | 412.51 |
| IIa-385 | | 426.54 |
| IIa-386 | | 426.54 |

TABLE 2-continued
Oxazole amides (R³ = NH-phenethyl)
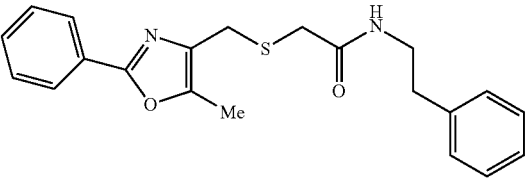
| ID | Structure | MW |
|---|---|---|
| IIa-387 | 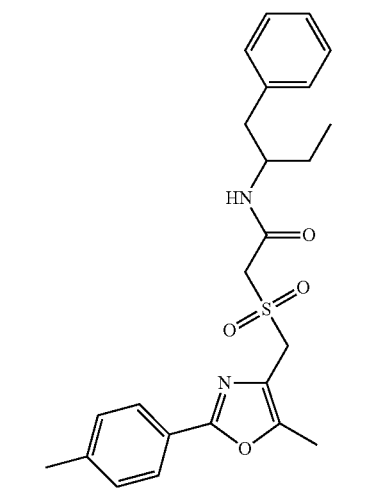 [SMILES: CCC(Cc1ccccc1)NC(=O)CS(=O)(=O)Cc1nc(-c2ccc(C)cc2)oc1C] | 440.57 |
| IIa-388 | | 456.57 |
| IIa-389 | 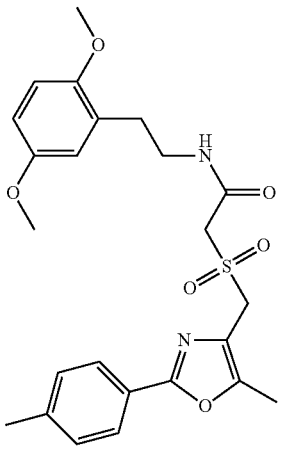 | 472.56 |

TABLE 2-continued
Oxazole amides (R³ = NH-phenethyl)
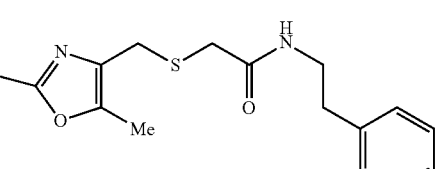
| ID | Structure | MW |
|---|---|---|
| IIa-390 | 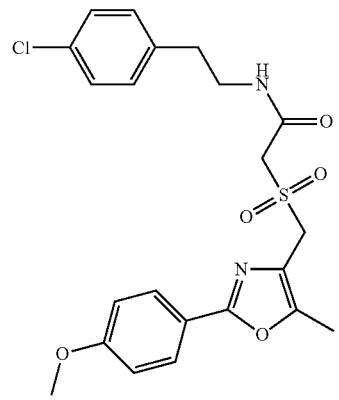 [SMILES: COc1ccc(-c2nc(CS(=O)(=O)CC(=O)NCCc3ccc(Cl)cc3)c(C)o2)cc1] | 458.60 |
| IIa-391 | 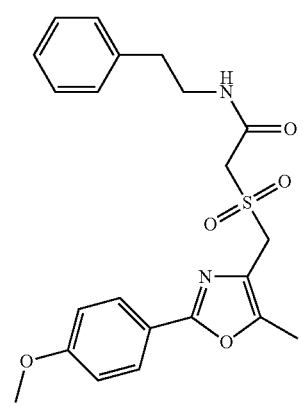 | 462.96 |
| IIa-392 | 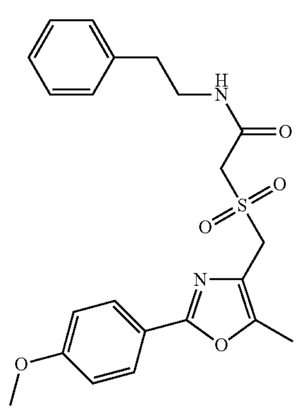 | 428.51 |

TABLE 2-continued

| Oxazole amides (R³ = NH-phenethyl) |

| ID | Structure | MW |
|---|---|---|
| IIa-393 | 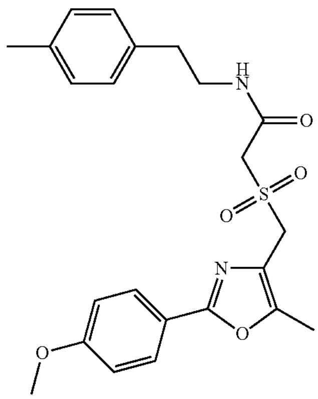 | 442.54 |
| IIa-394 | 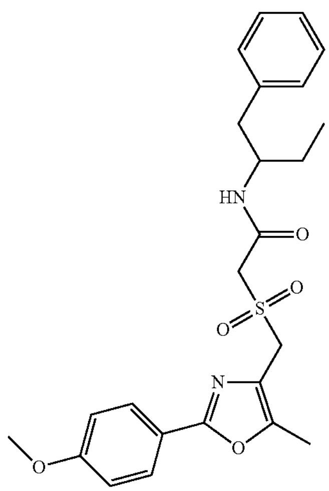 [SMILES: CCC(Cc1ccccc1)NC(=O)CS(=O)(=O)Cc1nc(-c2ccc(OC)cc2)oc1C] | 456.57 |
| IIa-395 | 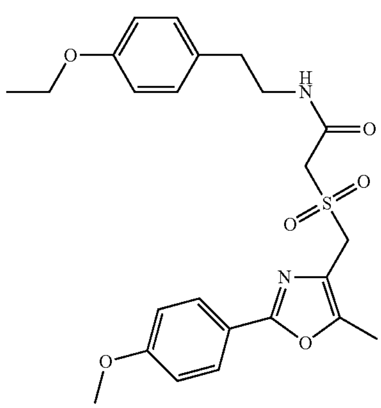 [SMILES: CCOc1ccc(CCNC(=O)CS(=O)(=O)Cc2nc(-c3ccc(OC)cc3)oc2C)cc1] | 472.56 |

TABLE 2-continued
Oxazole amides (R³ = NH-phenethyl)
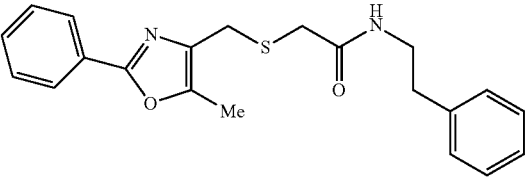
| ID | Structure | MW |
| --- | --- | --- |
| IIa-396 | 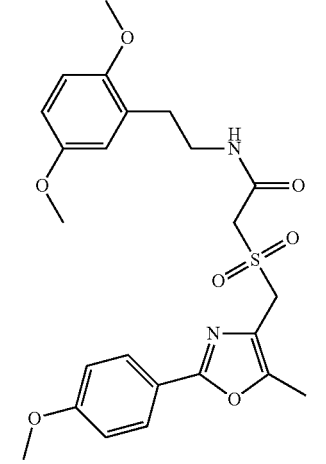 | 488.56 |
| IIa-397 | 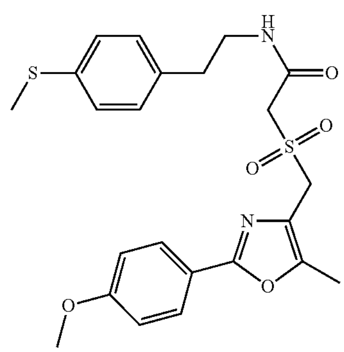 | 474.60 |
| IIa-398 | 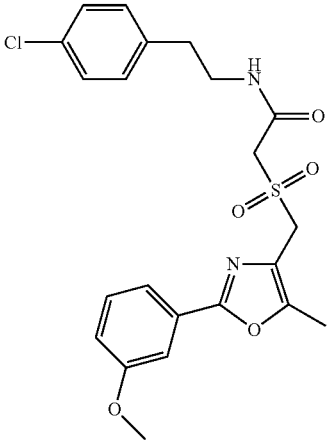 [SMILES: COc1cccc(-c2nc(CS(=O)(=O)CC(=O)NCCc3ccc(Cl)cc3)c(C)o2)c1] | 462.96 |

TABLE 2-continued
Oxazole amides (R³ = NH-phenethyl)
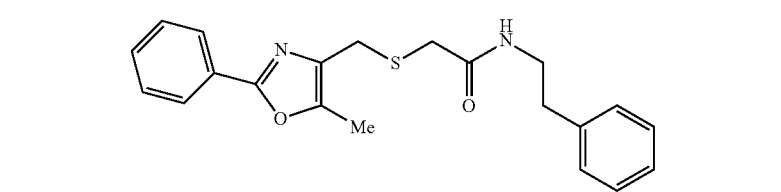
| ID | Structure | MW |
|---|---|---|
| IIa-399 | | 488.56 |
| IIa-400 | | 428.51 |
| IIa-401 | | 442.54 |

TABLE 2-continued
Oxazole amides ($R^3$ = NH-phenethyl)
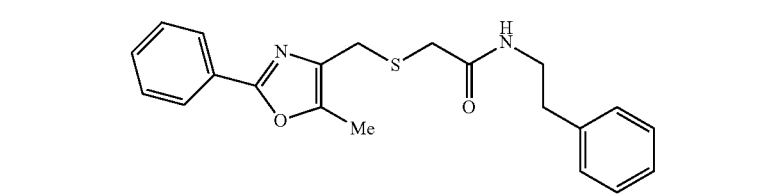
| ID | Structure | MW |
|---|---|---|
| IIa-402 | 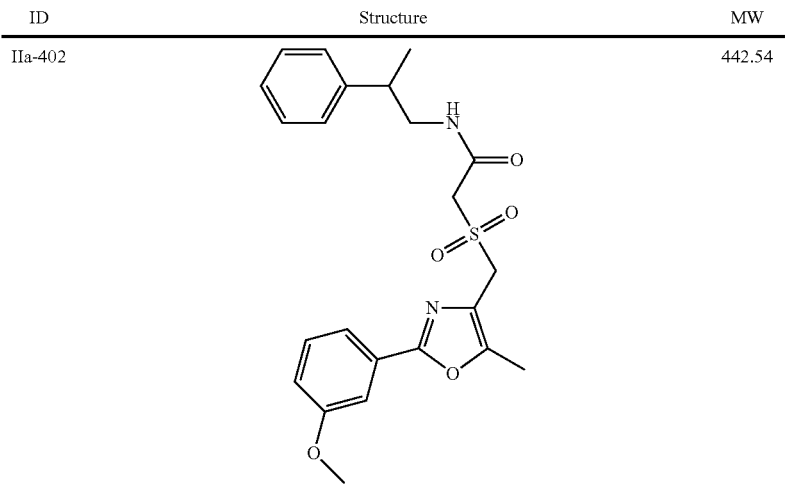 | 442.54 |
| IIa-403 | 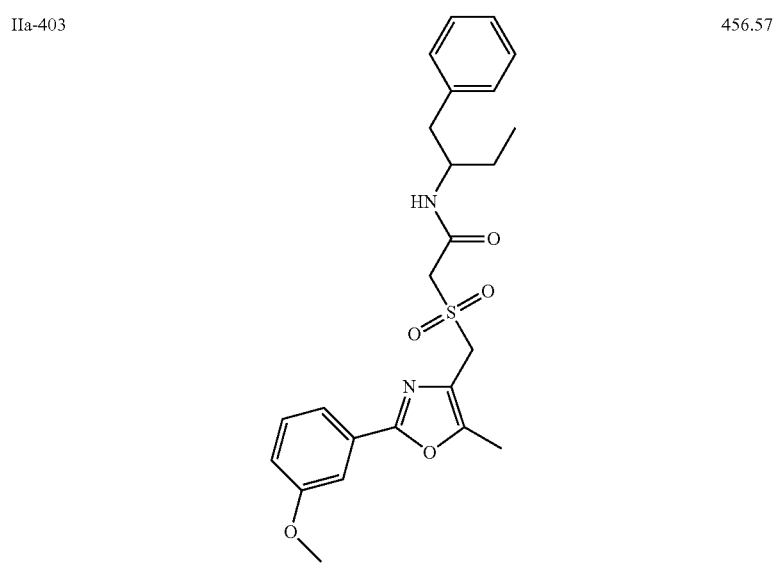 | 456.57 |

TABLE 2-continued
Oxazole amides (R³ = NH-phenethyl)
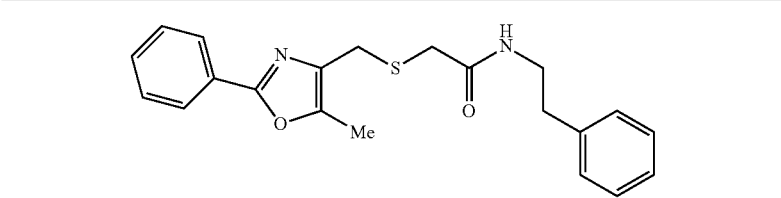
| ID | Structure | MW |
|---|---|---|
| IIa-404 | 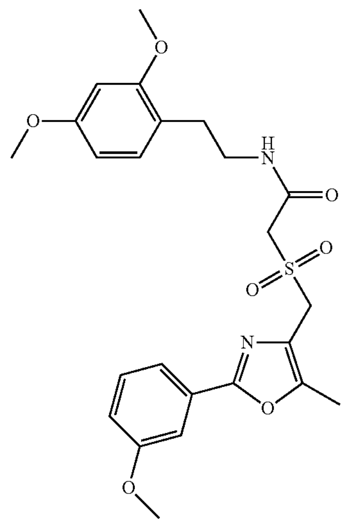 | 488.56 |
| IIa-405 | 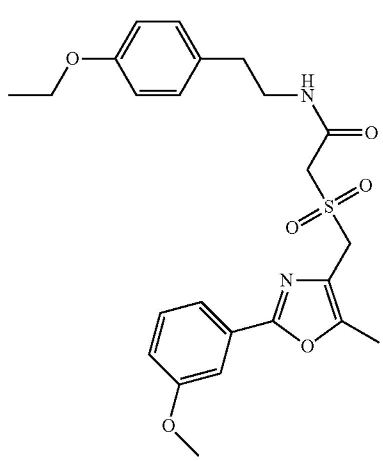 [SMILES: CCOc1ccc(CCNC(=O)CS(=O)(=O)Cc2nc(-c3cccc(OC)c3)oc2C)cc1] | 472.56 |

TABLE 2-continued

Oxazole amides (R³ = NH-phenethyl)

| ID | Structure | MW |
|---|---|---|
| IIa-406 | 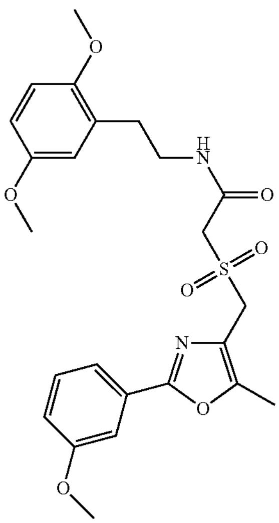 [SMILES: COc1cccc(-c2nc(CS(=O)(=O)CC(=O)NCCc3cc(OC)ccc3OC)c(C)o2)c1] | 488.56 |
| IIa-407 | 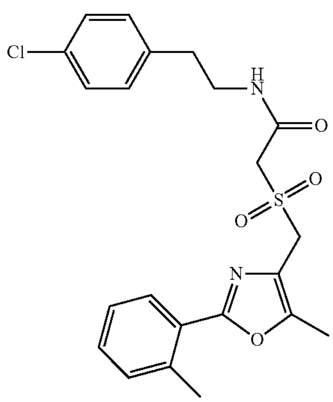 [SMILES: Cc1ccccc1-c1nc(CS(=O)(=O)CC(=O)NCCc2ccc(Cl)cc2)c(C)o1] | 446.96 |
| IIa-408 | 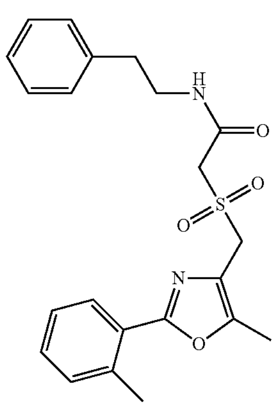 [SMILES: Cc1ccccc1-c1nc(CS(=O)(=O)CC(=O)NCCc2ccccc2)c(C)o1] | 412.51 |

TABLE 2-continued
Oxazole amides (R³ = NH-phenethyl)
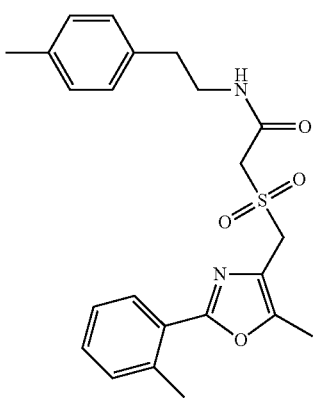
| ID | Structure | MW |
|---|---|---|
| IIa-409 | 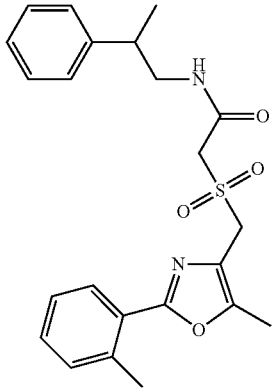 [SMILES: Cc1ccccc1-c1nc(CS(=O)(=O)CC(=O)NCC(C)c2ccccc2)c(C)o1] | 426.54 |
| IIa-410 | | 426.54 |
| IIa-411 | 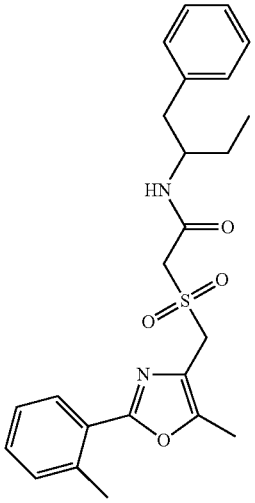 [SMILES: CCC(Cc1ccccc1)NC(=O)CS(=O)(=O)Cc1nc(-c2ccccc2C)oc1C] | 440.57 |

TABLE 2-continued

Oxazole amides (R³ = NH-phenethyl)

| ID | Structure | MW |
|---|---|---|
| IIa-412 | | 456.57 |
| IIa-413 | | 472.56 |
| IIa-414 | | 458.60 |

TABLE 2-continued

| Oxazole amides (R³ = NH-phenethyl) |
|---|

| ID | Structure | MW |
|---|---|---|
| IIa-415 | | 450.92 |
| IIa-416 | | 460.53 |
| IIa-417 | | 462.57 |

TABLE 2-continued

Oxazole amides (R³ = NH-phenethyl)

| ID | Structure | MW |
|---|---|---|
| IIa-418 | | 476.98 |
| IIa-419 | | 432.93 |
| IIa-420 | | 467.37 |
| IIa-421 | | 460.98 |

TABLE 2-continued
Oxazole amides (R³ = NH-phenethyl)
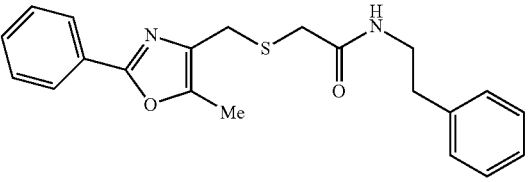
| ID | Structure | MW |
|---|---|---|
| IIa-422 | 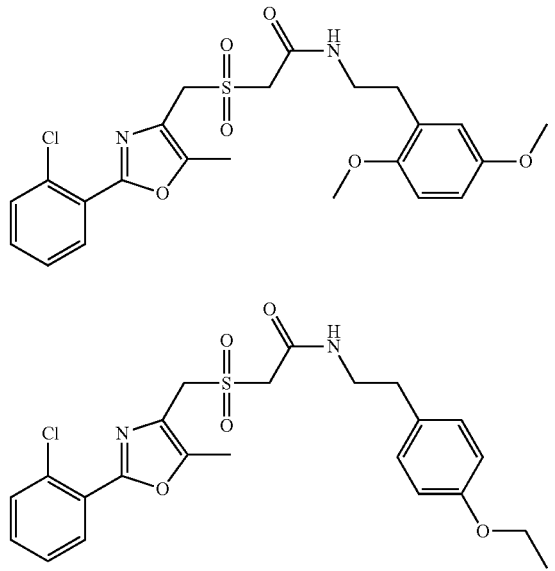 | 492.98 |
| IIa-423 | 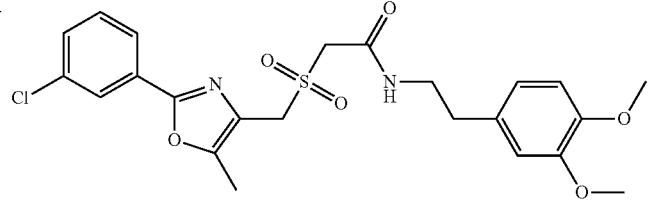 | 476.98 |
| IIa-424 | 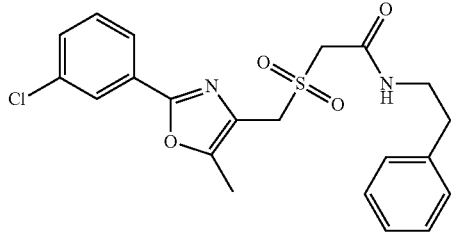 [SMILES: Cc1oc(-c2cccc(Cl)c2)nc1CS(=O)(=O)CC(=O)NCCc1ccccc1] | 492.98 |
| IIa-425 | 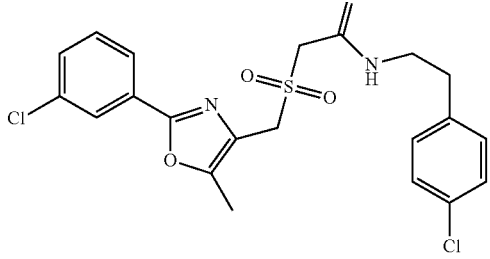 | 432.93 |
| IIa-426 | 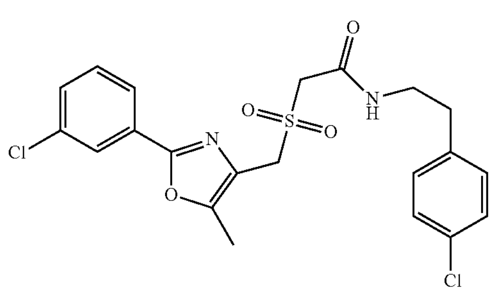 [SMILES: Cc1oc(-c2cccc(Cl)c2)nc1CS(=O)(=O)CC(=O)NCCc1ccc(Cl)cc1] | 467.37 |

TABLE 2-continued

Oxazole amides (R³ = NH-phenethyl)

| ID | Structure | MW |
|---|---|---|
| IIa-427 | 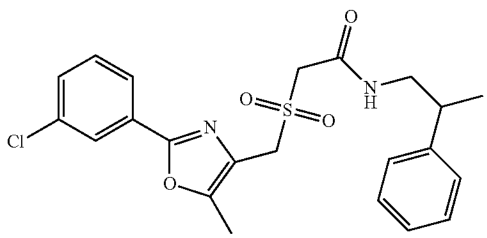 [SMILES: Cc1oc(-c2cccc(Cl)c2)nc1CS(=O)(=O)CC(=O)NCC(C)c1ccccc1] | 446.96 |
| IIa-428 | 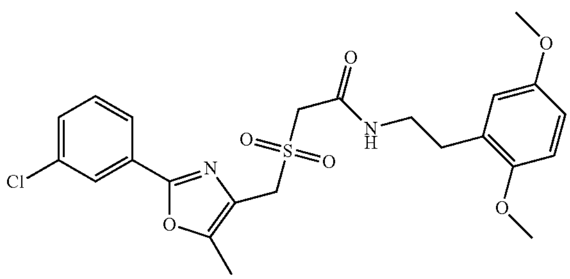 [SMILES: COc1ccc(OC)c(CCNC(=O)CS(=O)(=O)Cc2nc(-c3cccc(Cl)c3)oc2C)c1] | 492.98 |
| IIa-429 | 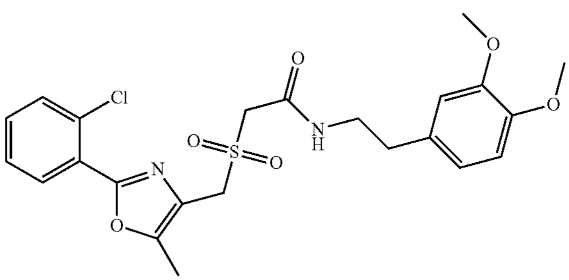 [SMILES: COc1ccc(CCNC(=O)CS(=O)(=O)Cc2nc(-c3ccccc3Cl)oc2C)cc1OC] | 492.98 |

TABLE 3

Oxazole amides (R³ = NH-Phenyl)

| ID | Structure | MW |
|---|---|---|
| IIa-501 | 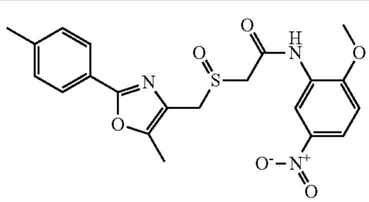 [SMILES: COc1ccc([N+](=O)[O-])cc1NC(=O)CS(=O)Cc1nc(-c2ccc(C)cc2)oc1C] | 443.48 |

TABLE 3-continued

Oxazole amides (R³ = NH-Phenyl)

| ID | Structure | MW |
|---|---|---|
| IIa-502 | 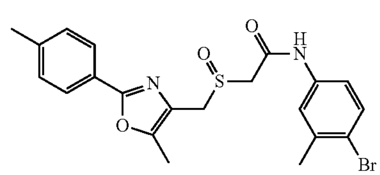 [SMILES: Cc1ccc(-c2nc(CS(=O)CC(=O)Nc3ccc(Br)c(C)c3)c(C)o2)cc1] | 461.38 |

TABLE 3-continued

Oxazole amides (R³ = NH-Phenyl)

| ID | Structure | MW |
|---|---|---|
| IIa-503 | 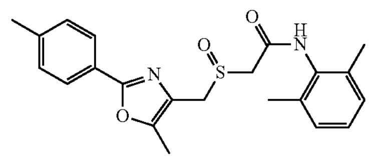 | 396.51 |
| IIa-504 | 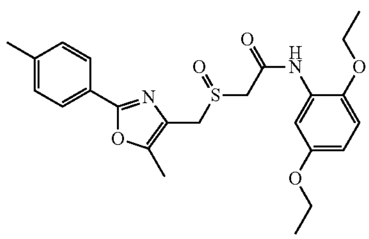 [SMILES: CCOc1ccc(OCC)c(NC(=O)CS(=O)Cc2nc(-c3ccc(C)cc3)oc2C)c1] | 456.57 |
| IIa-505 | 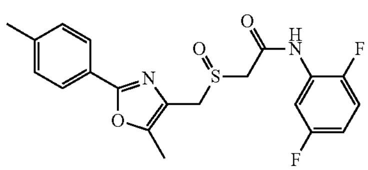 [SMILES: Cc1ccc(-c2nc(CS(=O)CC(=O)Nc3cc(F)ccc3F)c(C)o2)cc1] | 404.44 |
| IIa-506 | 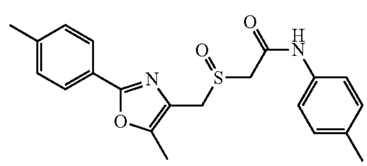 | 382.49 |
| IIa-507 | 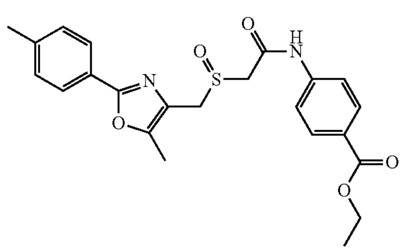 [SMILES: CCOC(=O)c1ccc(NC(=O)CS(=O)Cc2nc(-c3ccc(C)cc3)oc2C)cc1] | 440.52 |
| IIa-508 | 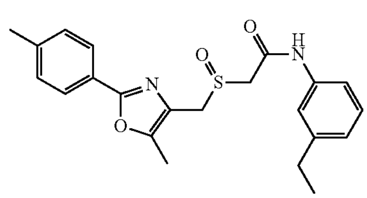 [SMILES: CCc1cccc(NC(=O)CS(=O)Cc2nc(-c3ccc(C)cc3)oc2C)c1] | 396.51 |
| IIa-509 | 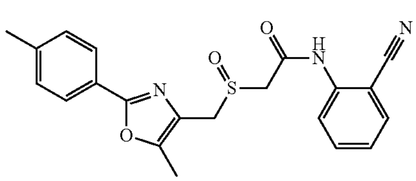 [SMILES: Cc1ccc(-c2nc(CS(=O)CC(=O)Nc3ccccc3C#N)c(C)o2)cc1] | 393.47 |
| IIa-510 | | 413.46 |
| IIa-511 | | 452.46 |
| IIa-512 | | 414.48 |
| IIa-513 | | 414.48 |

TABLE 3-continued

Oxazole amides (R³ = NH-Phenyl)

| ID | Structure | MW |
|---|---|---|
| IIa-514 | 2-Br phenyl amide, sulfone-CH2-oxazole(5-Me, 2-(4-methylphenyl)) | 463.35 |
| IIa-515 | 2-Cl phenyl amide, sulfone-CH2-oxazole(5-Me, 2-(4-methylphenyl)) | 418.90 |
| IIa-516 | 4-Cl phenyl amide, sulfone-CH2-oxazole(5-Me, 2-(4-methylphenyl)) | 418.90 |
| IIa-517 | 5-Cl-2,4-dimethoxy phenyl amide, sulfone-CH2-oxazole(5-Me, 2-(4-methylphenyl)) | 478.96 |
| IIa-518 | 2,3-dimethyl phenyl amide, sulfone-CH2-oxazole(5-Me, 2-(4-methylphenyl)) | 412.51 |
| IIa-519 | 2,6-dimethyl phenyl amide, sulfone-CH2-oxazole(5-Me, 2-(4-methylphenyl)) | 412.51 |

TABLE 3-continued

Oxazole amides (R³ = NH-Phenyl)

| ID | Structure | MW |
|---|---|---|
| IIa-520 | ethyl 3-[[[[2-(4-methylphenyl)-5-methyl-oxazol-4-yl]methylsulfonyl]acetyl]amino]benzoate | 456.52 |
| IIa-521 | methyl 2-[[[[2-(4-methylphenyl)-5-methyl-oxazol-4-yl]methylsulfonyl]acetyl]amino]benzoate | 442.49 |
| IIa-522 | N-(4-ethoxyphenyl)-2-[[2-(4-methylphenyl)-5-methyl-oxazol-4-yl]methylsulfonyl]acetamide | 428.51 |
| IIa-523 | N-(4-bromo-2-fluoro-phenyl)-2-[[2-(4-methylphenyl)-5-methyl-oxazol-4-yl]methylsulfonyl]acetamide | 481.34 |
| IIa-524 | 2-[[2-(4-methylphenyl)-5-methyl-oxazol-4-yl]methylsulfonyl]-N-(2-methylphenyl)acetamide | 398.48 |
| IIa-525 | N-(3-chloro-2-methyl-phenyl)-2-[[2-(4-methylphenyl)-5-methyl-oxazol-4-yl]methylsulfonyl]acetamide | 432.93 |

TABLE 3-continued

Oxazole amides (R³ = NH-Phenyl)

| ID | Structure | MW |
|---|---|---|
| IIa-526 | 3-Cl, 4-Me phenyl amide; sulfone linker; 2-(4-methylphenyl)-5-methyloxazole | 432.93 |
| IIa-527 | 2,5-dimethylphenyl amide; sulfone linker; 2-(4-methylphenyl)-5-methyloxazole | 412.51 |
| IIa-528 | 2,4-dimethylphenyl amide; sulfone linker; 2-(4-methylphenyl)-5-methyloxazole | 412.51 |
| IIa-529 | 4-(ethoxycarbonyl)phenyl amide; sulfone linker; 2-(4-methylphenyl)-5-methyloxazole | 456.52 |
| IIa-530 | 2,5-dimethoxyphenyl amide; sulfone linker; 2-(4-methylphenyl)-5-methyloxazole | 444.51 |
| IIa-531 | 2-Cl, 4-Me phenyl amide; sulfone linker; 2-(4-methylphenyl)-5-methyloxazole | 432.93 |

TABLE 3-continued
Oxazole amides (R³ = NH-Phenyl)
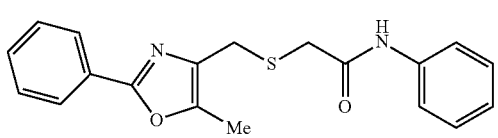
| ID | Structure | MW |
|---|---|---|
| IIa-532 | 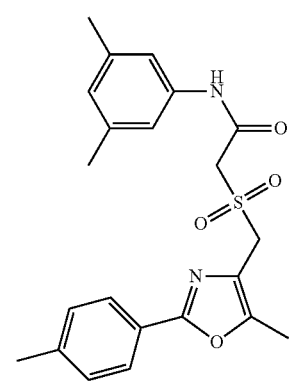 | 412.51 |
| IIa-533 | 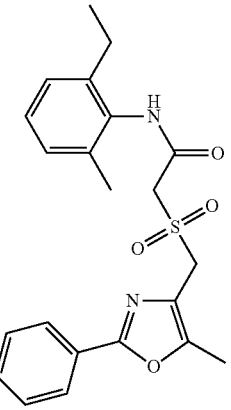 | 426.54 |
| IIa-534 | 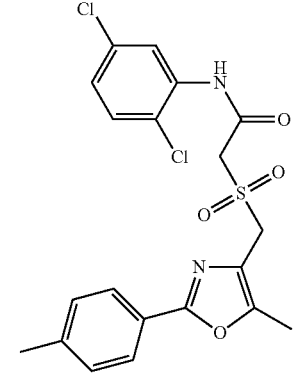 | 420.44 |
TABLE 3-continued
Oxazole amides (R³ = NH-Phenyl)
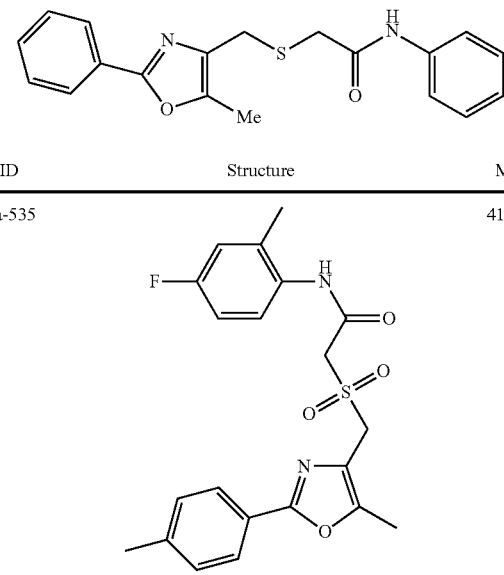
| ID | Structure | MW |
|---|---|---|
| IIa-535 | 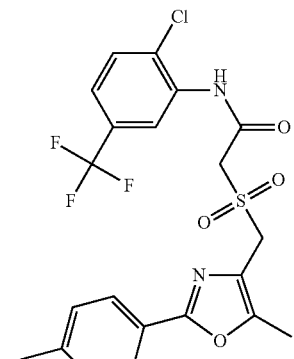 | 416.47 |
| IIa-536 | 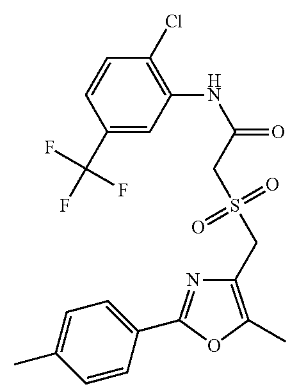 | 486.90 |
| IIa-537 | 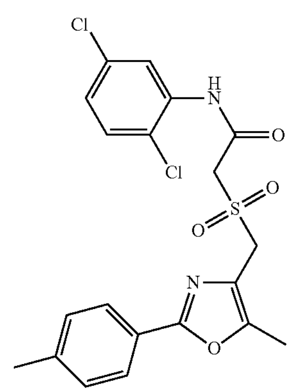 | 453.35 |

TABLE 3-continued

Oxazole amides (R³ = NH-Phenyl)

| ID | Structure | MW |
|---|---|---|
| IIa-538 | 4-Cl-phenyl amide, sulfonyl linker, 2-(4-methoxyphenyl)-5-methyloxazole | 434.90 |
| IIa-539 | 3-acetylphenyl amide, sulfonyl linker, 2-(4-methoxyphenyl)-5-methyloxazole | 442.49 |
| IIa-540 | 4-acetylphenyl amide, sulfonyl linker, 2-(3-methoxyphenyl)-5-methyloxazole | 442.49 |
| IIa-541 | 3-(trifluoromethyl)phenyl amide, sulfonyl linker, 2-(3-methoxyphenyl)-5-methyloxazole | 468.46 |
| IIa-542 | 2-Br-phenyl amide, sulfonyl linker, 2-(3-methoxyphenyl)-5-methyloxazole | 479.35 |
| IIa-543 | 2-Cl-phenyl amide, sulfonyl linker, 2-(3-methoxyphenyl)-5-methyloxazole | 434.90 |

TABLE 3-continued

Oxazole amides (R³ = NH-Phenyl)

| ID | Structure | MW |
|---|---|---|
| IIa-544 | 4-Cl-phenyl derivative | 434.90 |
| IIa-545 | 3,5-diCl-phenyl derivative | 469.35 |
| IIa-546 | 2,4-diF-phenyl derivative | 436.44 |
| IIa-547 | 2,3-diMe-phenyl derivative | 428.51 |
| IIa-548 | 2,6-diMe-phenyl derivative | 428.51 |
| IIa-549 | 3-(ethoxycarbonyl)phenyl derivative | 472.52 |

TABLE 3-continued

Oxazole amides (R³ = NH-Phenyl)

| ID | Structure | MW |
|---|---|---|
| IIa-550 | 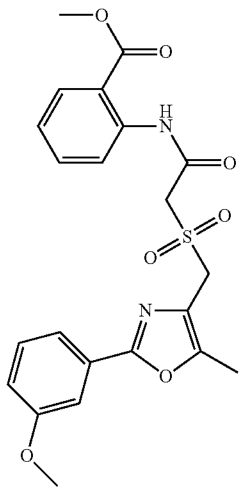 [SMILES: COC(=O)c1ccccc1NC(=O)CS(=O)(=O)Cc1nc(-c2cccc(OC)c2)oc1C] | 458.49 |
| IIa-551 | 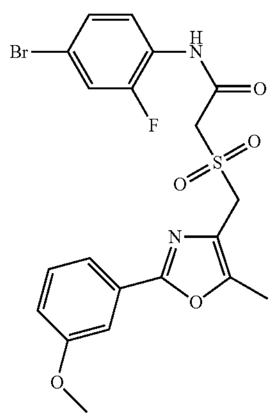 [SMILES: COc1cccc(-c2nc(CS(=O)(=O)CC(=O)Nc3ccc(Br)cc3F)c(C)o2)c1] | 497.34 |
| IIa-552 | 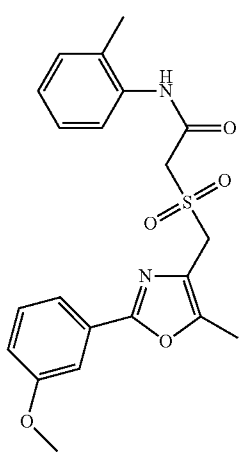 [SMILES: COc1cccc(-c2nc(CS(=O)(=O)CC(=O)Nc3ccccc3C)c(C)o2)c1] | 414.48 |
| IIa-553 | | 448.93 |
| IIa-554 | | 448.93 |
| IIa-555 | | 428.51 |

TABLE 3-continued

Oxazole amides (R³ = NH-Phenyl)

| ID | Structure | MW |
|---|---|---|
| IIa-556 | 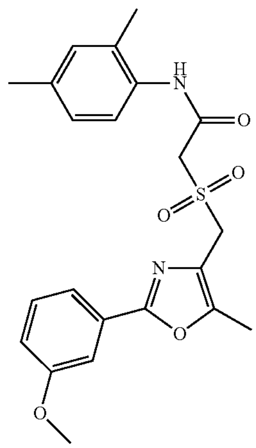 | 428.51 |
| IIa-557 | 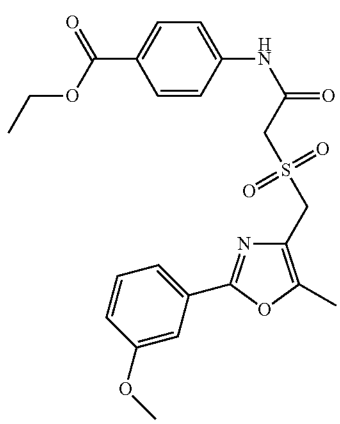 [SMILES: CCOC(=O)c1ccc(NC(=O)CS(=O)(=O)Cc2nc(-c3cccc(OC)c3)oc2C)cc1] | 472.52 |
| IIa-558 | 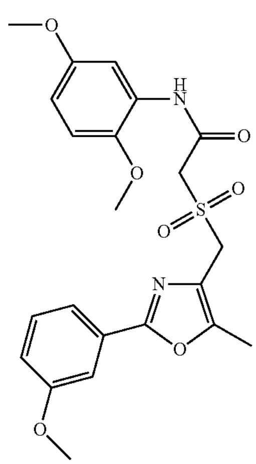 | 460.51 |
| IIa-559 | | 448.93 |
| IIa-560 | | 442.54 |
| IIa-561 | | 428.51 |

TABLE 3-continued

Oxazole amides (R³ = NH-Phenyl)

| ID | Structure | MW |
|---|---|---|
| IIa-562 | 3-acetylphenyl derivative | 442.49 |
| IIa-563 | 4-bromo-3-methylphenyl derivative | 493.38 |
| IIa-564 | 2-ethyl-6-methylphenyl derivative | 442.54 |
| IIa-565 | 2,5-difluorophenyl derivative | 436.44 |
| IIa-566 | 5-chloro-2-methoxyphenyl derivative | 464.93 |
| IIa-567 | 4-fluoro-2-methylphenyl derivative | 432.47 |

TABLE 3-continued
Oxazole amides (R³ = NH-Phenyl)
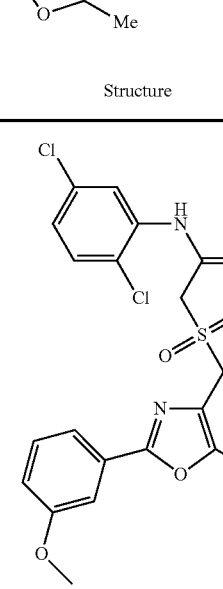
| ID | Structure | MW |
|---|---|---|
| IIa-568 | 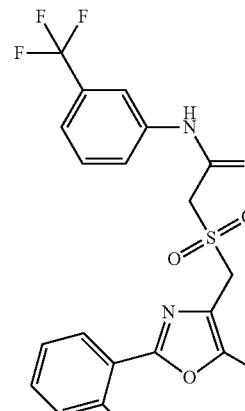 | 469.35 |
| IIa-569 | 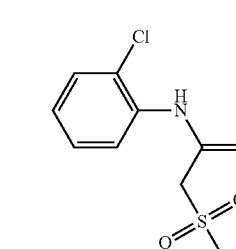 | 452.46 |
| IIa-570 | 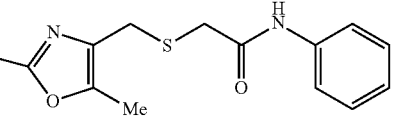 | 418.90 |
| IIa-571 | 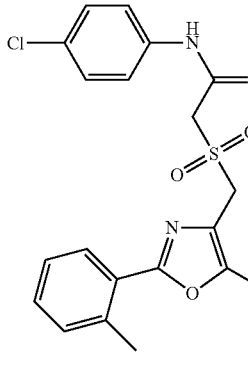 | 418.90 |
| IIa-572 | 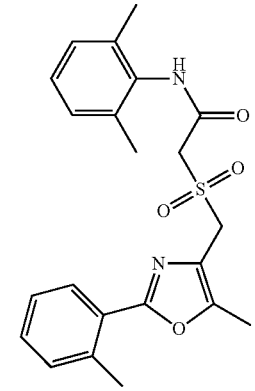 [SMILES: Cc1ccccc1-c1nc(CS(=O)(=O)CC(=O)Nc2c(C)cccc2C)c(C)o1] | 453.35 |
| IIa-573 | | 412.51 |

TABLE 3-continued
Oxazole amides (R³ = NH-Phenyl)
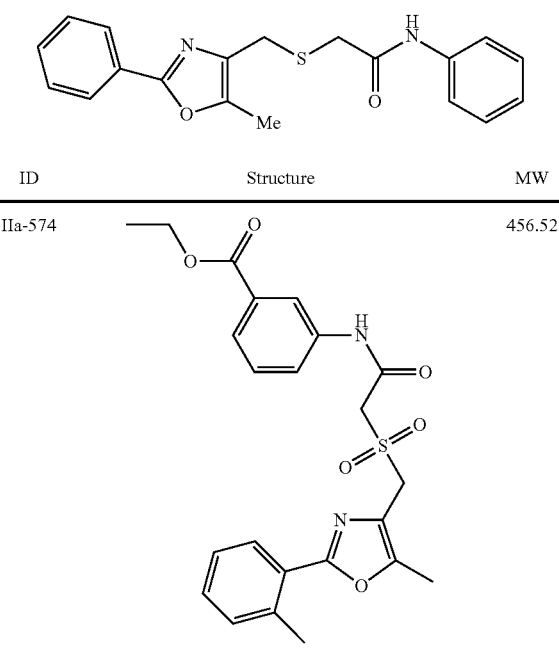
| ID | Structure | MW |
|---|---|---|
| IIa-574 | 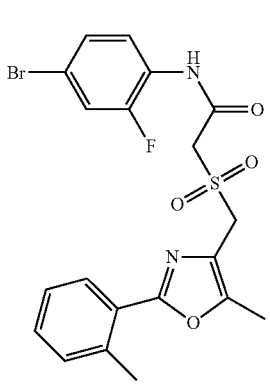 [SMILES: Cc1ccccc1-c1nc(CS(=O)(=O)CC(=O)Nc2ccc(Br)cc2F)c(C)o1] | 456.52 |
| IIa-575 | 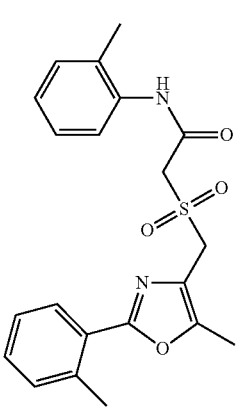 [SMILES: Cc1ccccc1NC(=O)CS(=O)(=O)Cc1nc(-c2ccccc2C)oc1C] | 481.34 |
| IIa-576 | 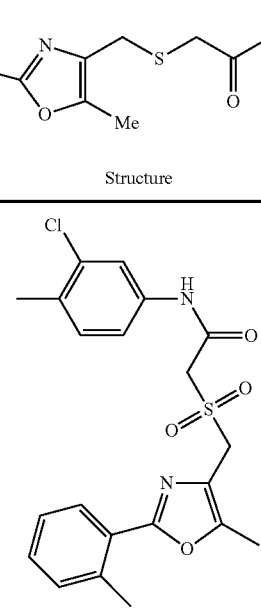 | 398.48 |
| IIa-577 | 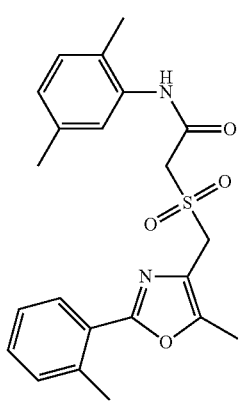 [SMILES: Cc1ccc(C)c(NC(=O)CS(=O)(=O)Cc2nc(-c3ccccc3C)oc2C)c1] | 432.93 |
| IIa-578 | 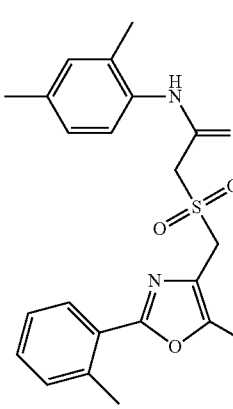 | 412.51 |
| IIa-579 | | 412.51 |

TABLE 3-continued
Oxazole amides (R³ = NH-Phenyl)
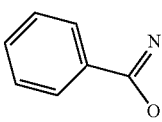
| ID | Structure | MW |
|---|---|---|
| IIa-580 | 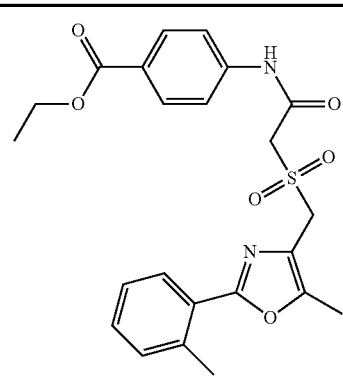 | 456.52 |
| IIa-581 | 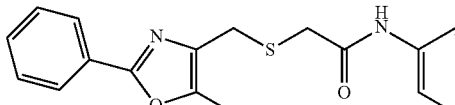 | 444.51 |
| IIa-582 | 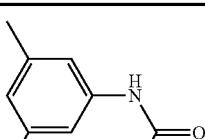 | 432.93 |
| IIa-583 | 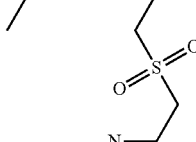 | 412.51 |
| IIa-584 | 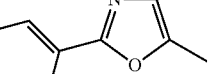 | 420.44 |
| IIa-585 | | 416.47 |

TABLE 3-continued

Oxazole amides (R³ = NH-Phenyl)

| ID | Structure | MW |
|---|---|---|
| IIa-586 | (2-chloro-5-trifluoromethylphenyl amide; sulfone linker to 5-methyl-2-(2-methylphenyl)oxazole) | 486.90 |
| IIa-587 | (2,5-dichlorophenyl amide; sulfone linker to 5-methyl-2-(2-methylphenyl)oxazole) | 453.35 |
| IIa-588 | (2,5-dimethylphenyl amide; thioether linker to 5-methyl-2-(3-methylphenyl)oxazole) | 380.51 |
| IIa-589 | (3-methoxyphenyl amide; thioether linker to 5-methyl-2-(3-methylphenyl)oxazole) | 382.49 |
| IIa-590 | (2,4-dichlorophenyl amide; thioether linker to 5-methyl-2-(3-methylphenyl)oxazole) | 421.35 |
| IIa-591 | (2-ethylphenyl amide; thioether linker to 5-methyl-2-(4-methylphenyl)oxazole) | 380.51 |
| IIa-592 | (2-bromophenyl amide; thioether linker to 5-methyl-2-(3-methylphenyl)oxazole) | 431.35 |

TABLE 4
Oxazole amides (R³ = NH-C₃-C₇cycloalkyl)
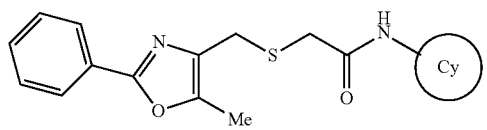 [SMILES: CNC(=O)CSCc1nc(-c2ccccc2)oc1C]
| ID | Structure | MW |
|---|---|---|
| IIa-601 | 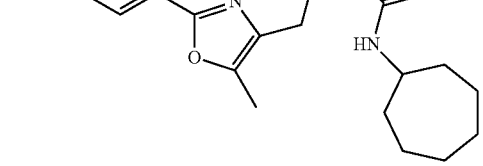 | 402.56 |
| IIa-602 |  | 388.53 |
| IIa-603 | 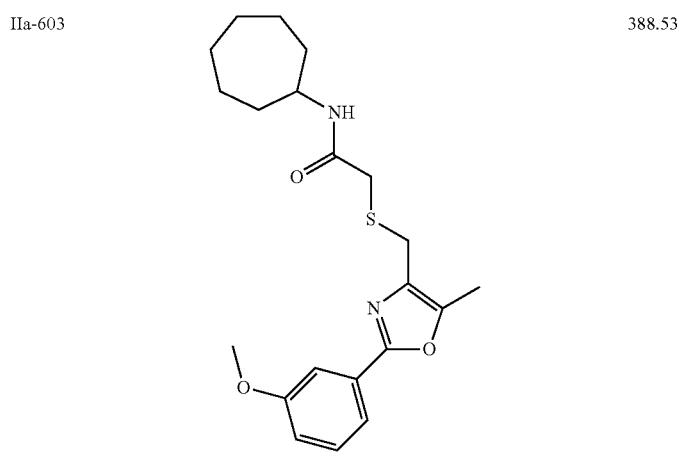 | 388.53 |

TABLE 4-continued

Oxazole amides (R³ = NH-C₃-C₇cycloalkyl)

| ID | Structure | MW |
|---|---|---|
| IIa-604 | 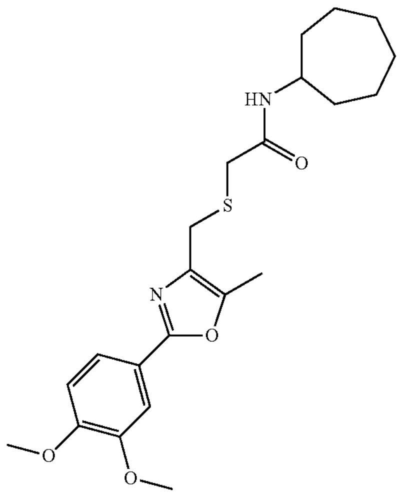 [SMILES: COc1ccc(-c2nc(CSCC(=O)NC3CCCCCC3)c(C)o2)cc1OC] | 418.56 |
| IIa-605 | 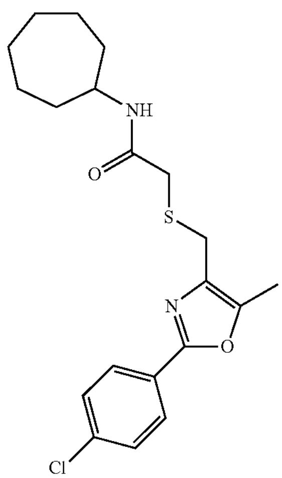 [SMILES: Cc1oc(-c2ccc(Cl)cc2)nc1CSCC(=O)NC1CCCCCC1] | 392.95 |
| IIa-606 | 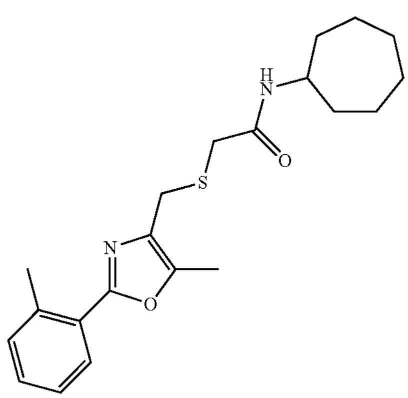 [SMILES: Cc1ccccc1-c1nc(CSCC(=O)NC2CCCCCC2)c(C)o1] | 372.53 |

TABLE 4-continued
Oxazole amides (R³ = NH-C₃-C₇cycloalkyl)
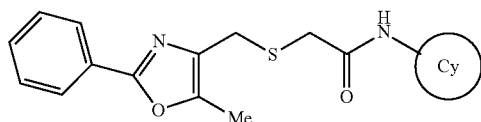
| ID | Structure | MW |
|---|---|---|
| IIa-607 | 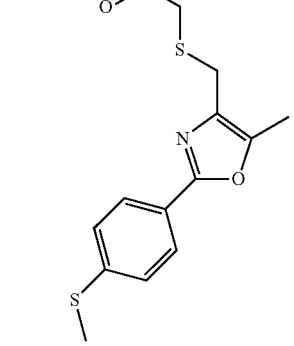 | 404.60 |
| IIa-608 | 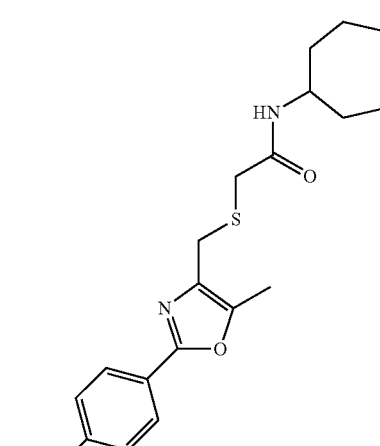 | 386.56 |
| IIa-609 | 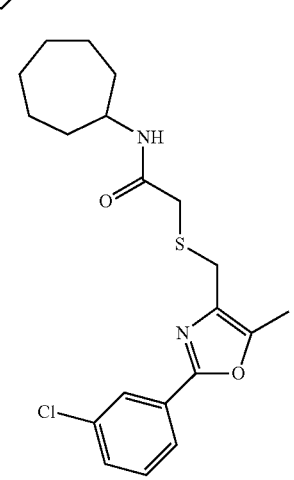 | 392.95 |

TABLE 4-continued
Oxazole amides ($R^3$ = NH-$C_3$-$C_7$cycloalkyl)
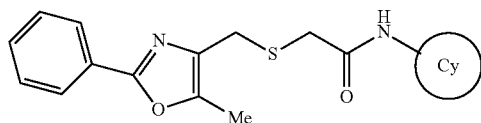
| ID | Structure | MW |
|---|---|---|
| IIa-610 | | 376.50 |
| IIa-611 | | 372.53 |
| IIa-612 | | 404.53 |

TABLE 4-continued

Oxazole amides ($R^3$ = NH-$C_3$-$C_7$cycloalkyl)

| ID | Structure | MW |
|---|---|---|
| IIa-613 | 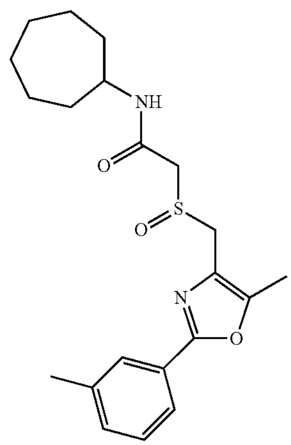 [SMILES: Cc1cccc(-c2nc(CS(=O)CC(=O)NC3CCCCCC3)c(C)o2)c1] | 388.53 |
| IIa-614 | 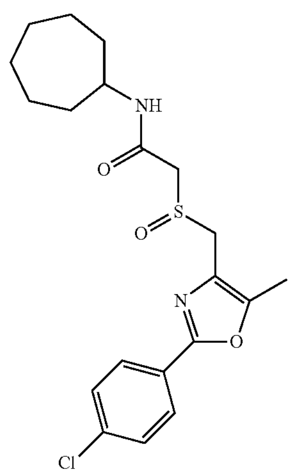 [SMILES: Cc1oc(-c2ccc(Cl)cc2)nc1CS(=O)CC(=O)NC1CCCCCC1] | 408.95 |
| IIa-615 | 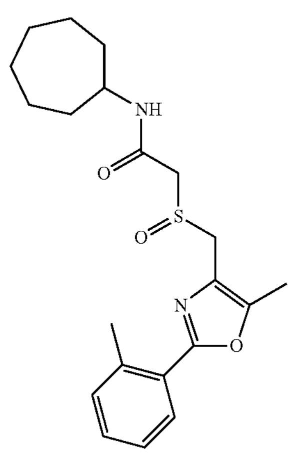 [SMILES: Cc1ccccc1-c1nc(CS(=O)CC(=O)NC2CCCCCC2)c(C)o1] | 388.53 |

TABLE 4-continued
Oxazole amides (R³ = NH-C₃-C₇cycloalkyl)
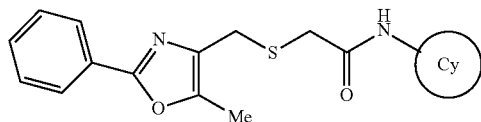
| ID | Structure | MW |
|---|---|---|
| IIa-616 | 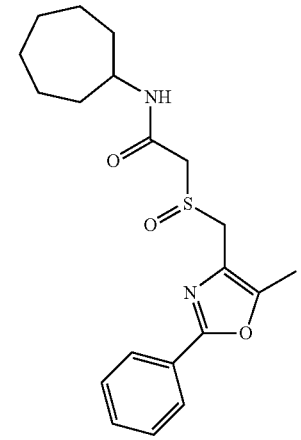 [SMILES: Cc1oc(-c2ccccc2)nc1CS(=O)CC(=O)NC1CCCCCC1] | 374.51 |
| IIa-617 | 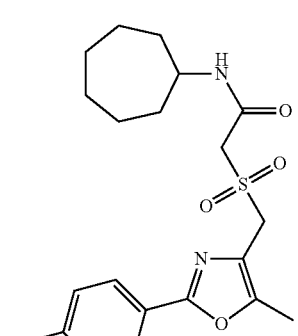 | 404.53 |
| IIa-618 | 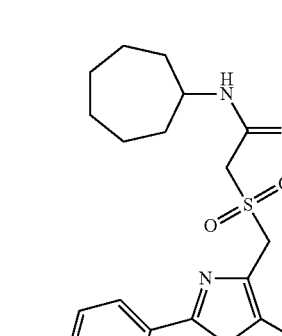 | 420.53 |

TABLE 4-continued
Oxazole amides (R³ = NH-C₃-C₇cycloalkyl)
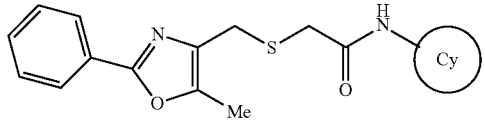
| ID | Structure | MW |
|---|---|---|
| IIa-619 | 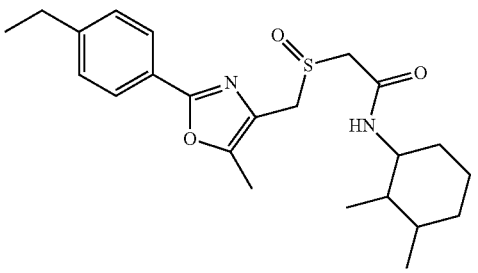 [SMILES: CCc1ccc(-c2nc(CS(=O)CC(=O)NC3CCCC(C)C3C)c(C)o2)cc1] | 420.53 |
| IIa-620 | 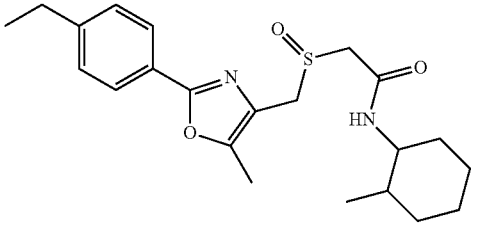 | 416.59 |
| IIa-621 | 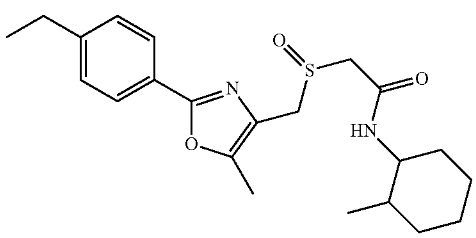 [SMILES: CCc1ccc(-c2nc(CS(=O)CC(=O)NC3CCCCC3C)c(C)o2)cc1] | 402.56 |
| IIa-622 | 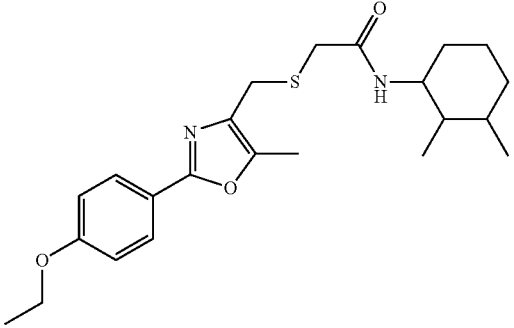 [SMILES: CCOc1ccc(-c2nc(CSCC(=O)NC3CCCC(C)C3C)c(C)o2)cc1] | 416.59 |

TABLE 4-continued
Oxazole amides (R³ = NH-C₃-C₇cycloalkyl)
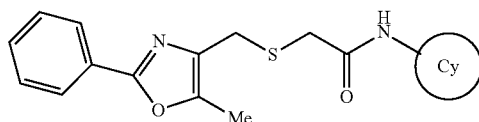
| ID | Structure | MW |
|---|---|---|
| IIa-623 | 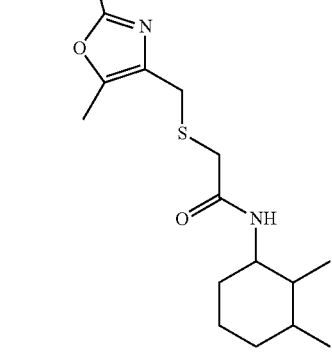 | 402.56 |
| IIa-624 | 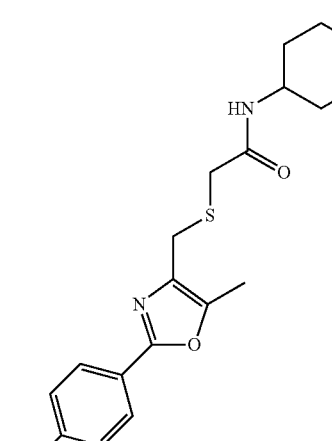 | 374.51 |
| IIa-625 | 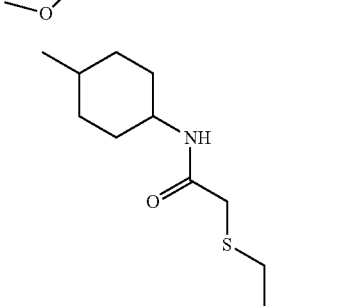 | 388.53 |

TABLE 4-continued
Oxazole amides (R³ = NH-C₃-C₇cycloalkyl)
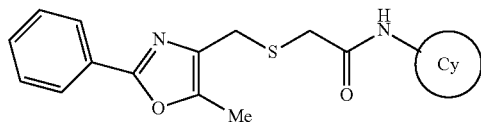
| ID | Structure | MW |
|---|---|---|
| IIa-626 | 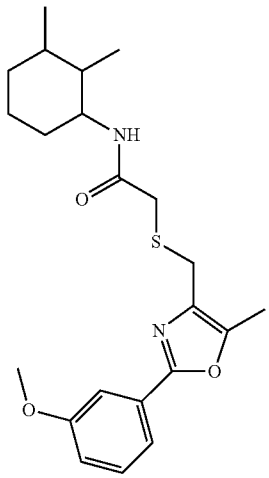 [SMILES: COc1cccc(-c2nc(CSCC(=O)NC3CCCC(C)C3C)c(C)o2)c1] | 402.56 |
| IIa-627 | 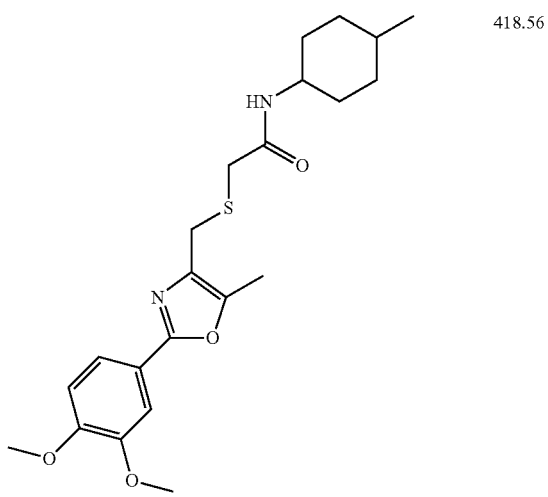 | 418.56 |

TABLE 4-continued
Oxazole amides (R³ = NH-C₃-C₇cycloalkyl)
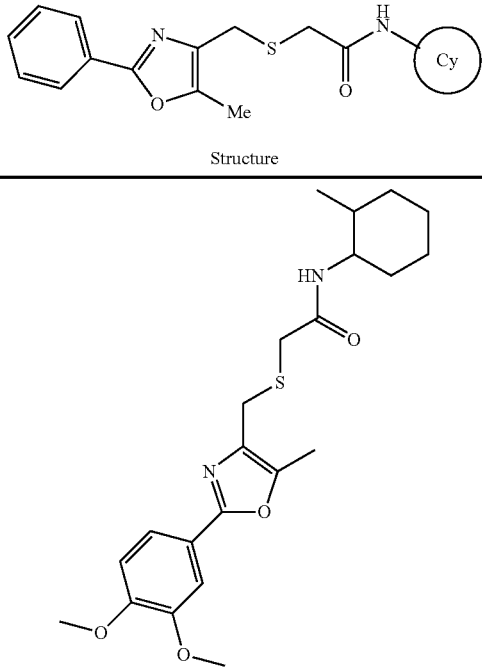
| ID | Structure | MW |
|---|---|---|
| IIa-628 | 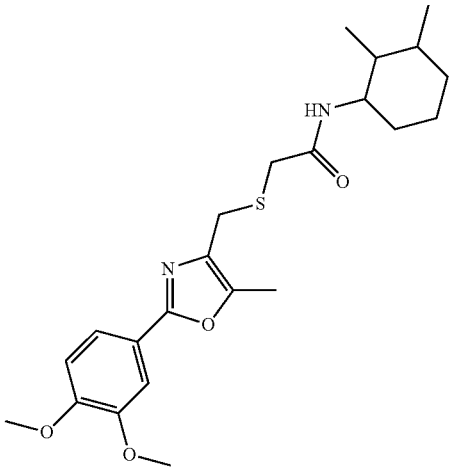 | 418.56 |
| IIa-629 | 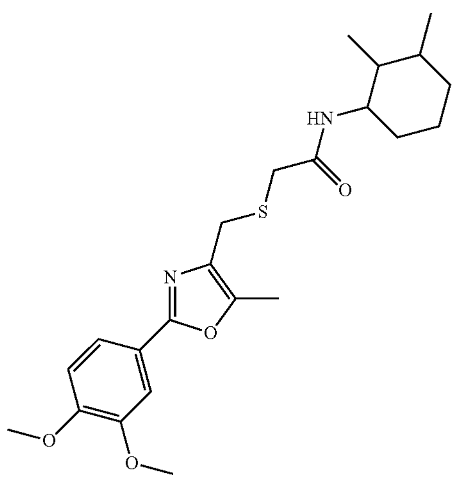 [SMILES: COc1ccc(-c2nc(CSCC(=O)NC3CCCC(C)C3C)c(C)o2)cc1OC] | 432.59 |
| IIa-630 | 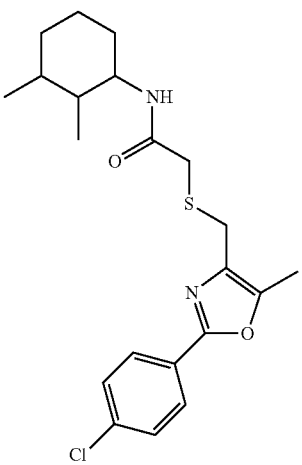 | 406.98 |

TABLE 4-continued
Oxazole amides (R³ = NH-C₃-C₇cycloalkyl)

| ID | Structure | MW |
|---|---|---|
| IIa-631 | 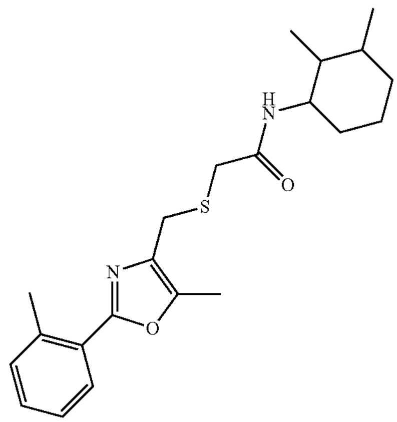 [SMILES: Cc1ccccc1-c1nc(CSCC(=O)NC2CCCC(C)C2C)c(C)o1] | 386.56 |
| IIa-632 | 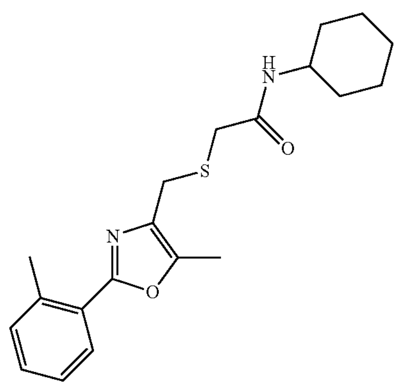 [SMILES: Cc1ccccc1-c1nc(CSCC(=O)NC2CCCCC2)c(C)o1] | 358.51 |
| IIa-633 | 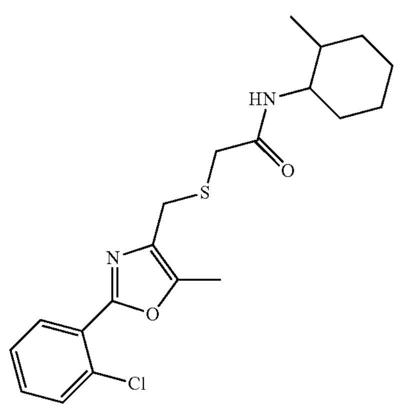 [SMILES: Cc1oc(-c2ccccc2Cl)nc1CSCC(=O)NC1CCCCC1C] | 392.95 |

TABLE 4-continued
Oxazole amides ($R^3$ = NH-$C_3$-$C_7$cycloalkyl)
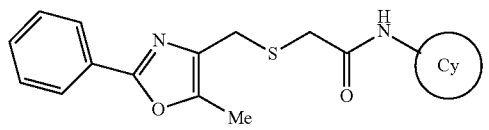
| ID | Structure | MW |
|---|---|---|
| IIa-634 | 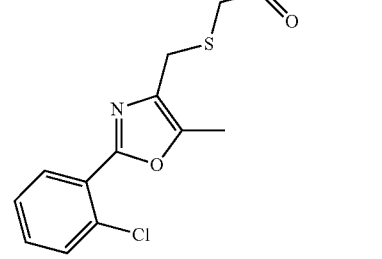 | 406.98 |
| IIa-635 | 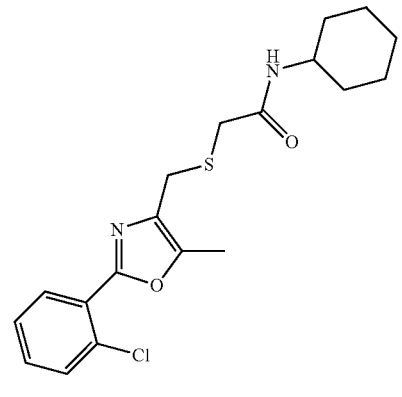 [SMILES: Cc1oc(-c2ccccc2Cl)nc1CSCC(=O)NC1CCCCC1] | 378.92 |
| IIa-636 | 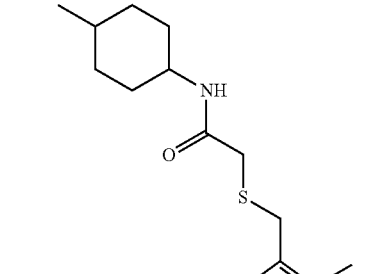 | 404.60 |

TABLE 4-continued
Oxazole amides (R³ = NH-C₃-C₇cycloalkyl)
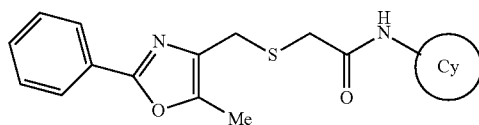
| ID | Structure | MW |
|---|---|---|
| IIa-637 | 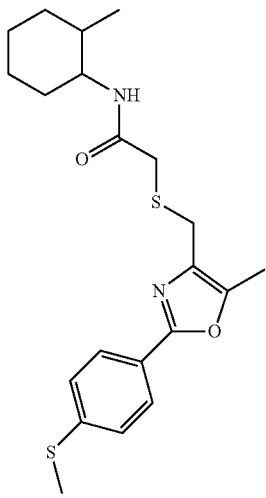 [SMILES: CSc1ccc(-c2nc(CSCC(=O)NC3CCCCC3C)c(C)o2)cc1] | 404.60 |
| IIa-638 | 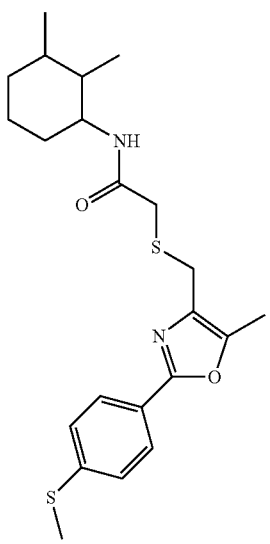 [SMILES: CSc1ccc(-c2nc(CSCC(=O)NC3CCCC(C)C3C)c(C)o2)cc1] | 418.62 |

TABLE 4-continued
Oxazole amides (R³ = NH-C₃-C₇cycloalkyl)
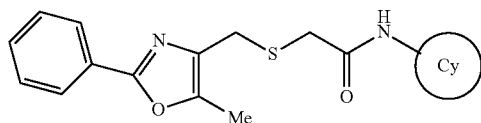
| ID | Structure | MW |
|---|---|---|
| IIa-639 | | 390.57 |
| IIa-640 | | 386.56 |
| IIa-641 | | 376.50 |

TABLE 4-continued
Oxazole amides (R³ = NH-C₃-C₇cycloalkyl)
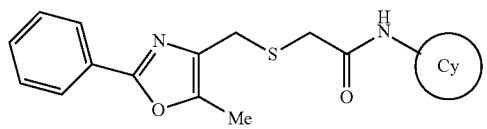
| ID | Structure | MW |
|---|---|---|
| IIa-642 | 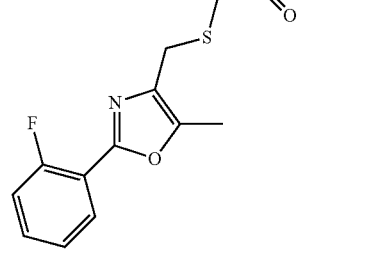 | 390.52 |
| IIa-643 | 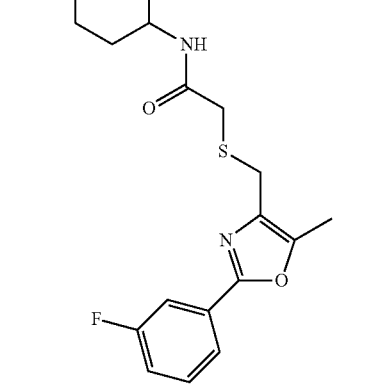 | 362.47 |
| IIa-644 | 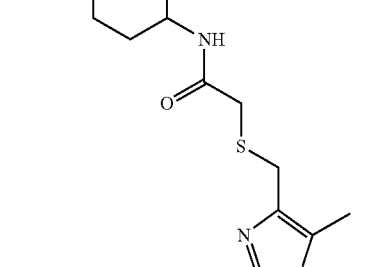 | 372.53 |

TABLE 4-continued

Oxazole amides ($R^3$ = NH-$C_3$-$C_7$cycloalkyl)

| ID | Structure | MW |
|---|---|---|
| IIa-645 | 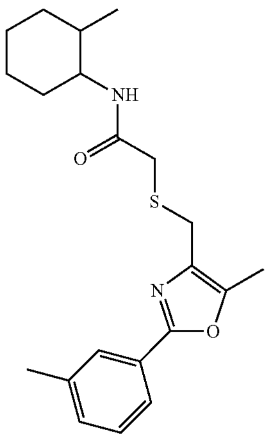 [SMILES: Cc1cccc(-c2nc(CSCC(=O)NC3CCCCC3C)c(C)o2)c1] | 372.53 |
| IIa-646 | 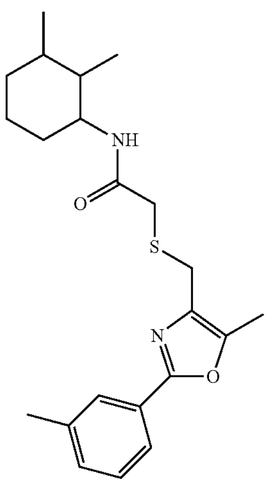 [SMILES: Cc1cccc(-c2nc(CSCC(=O)NC3CCCC(C)C3C)c(C)o2)c1] | 386.56 |
| IIa-647 | 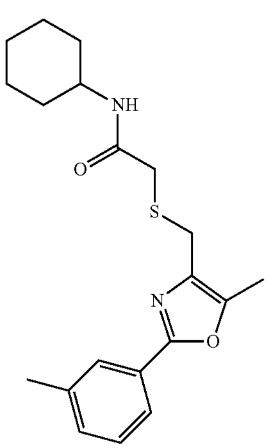 [SMILES: Cc1cccc(-c2nc(CSCC(=O)NC3CCCCC3)c(C)o2)c1] | 358.51 |

TABLE 4-continued
Oxazole amides (R³ = NH-C₃-C₇cycloalkyl)
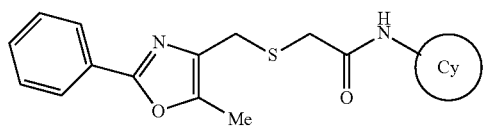
| ID | Structure | MW |
|---|---|---|
| IIa-648 | 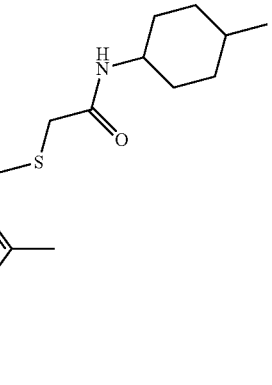 | 372.53 |
| IIa-649 | 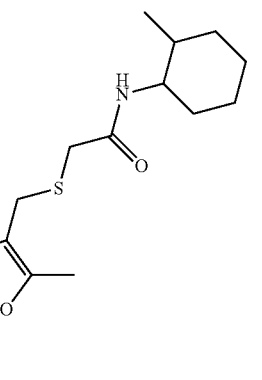 | 372.53 |
| IIa-650 | 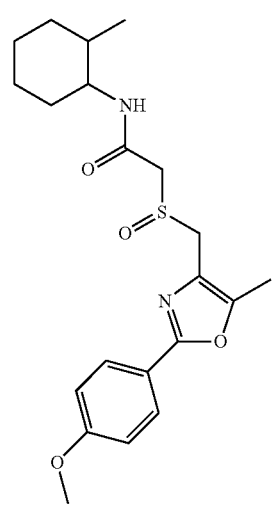 [SMILES: COc1ccc(-c2nc(CS(=O)CC(=O)NC3CCCCC3C)c(C)o2)cc1] | 404.53 |

TABLE 4-continued
Oxazole amides (R³ = NH-C₃-C₇cycloalkyl)
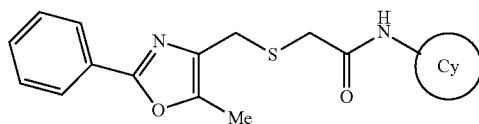
| ID | Structure | MW |
|---|---|---|
| IIa-651 | | 418.56 |
| IIa-652 | | 390.51 |
| IIa-653 | | 378.47 |

TABLE 4-continued
Oxazole amides (R³ = NH-C₃-C₇cycloalkyl)
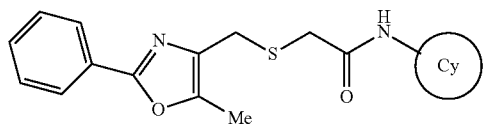
| ID | Structure | MW |
|---|---|---|
| IIa-654 | | 402.56 |
| IIa-655 | | 374.51 |
| IIa-656 | | 388.53 |

TABLE 4-continued
Oxazole amides (R³ = NH-C₃-C₇cycloalkyl)
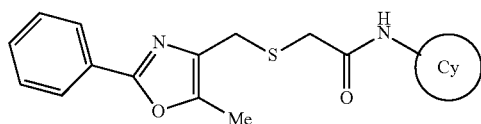
| ID | Structure | MW |
|---|---|---|
| IIa-657 | 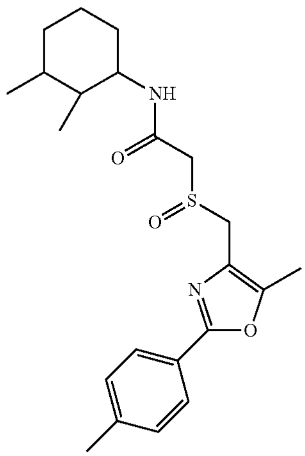 | 402.56 |
| IIa-658 | 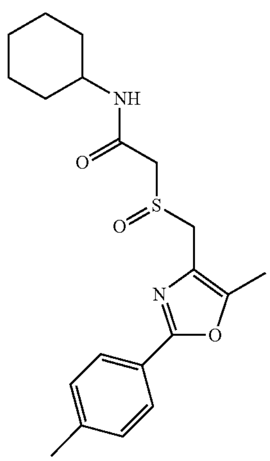 [SMILES: Cc1ccc(-c2nc(CS(=O)CC(=O)NC3CCCCC3)c(C)o2)cc1] | 374.51 |
| IIa-659 | 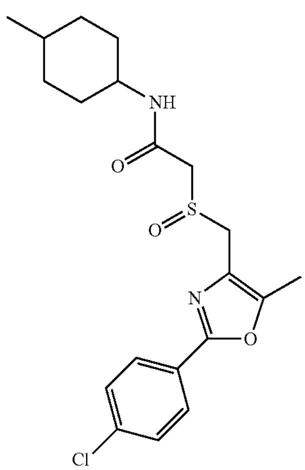 | 408.95 |

TABLE 4-continued
Oxazole amides (R³ = NH-C₃-C₇cycloalkyl)
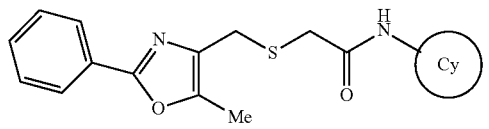
| ID | Structure | MW |
|---|---|---|
| IIa-660 | | 422.98 |
| IIa-661 | | 394.92 |
| IIa-662 | | 388.53 |

TABLE 4-continued
Oxazole amides (R³ = NH-C₃-C₇cycloalkyl)

| ID | Structure | MW |
|---|---|---|
| IIa-663 | 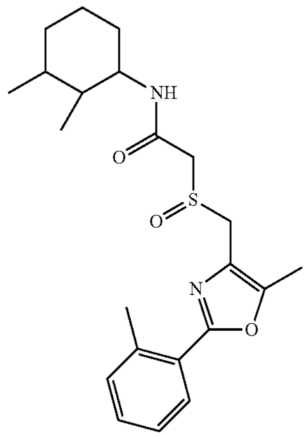 | 402.56 |
| IIa-664 | 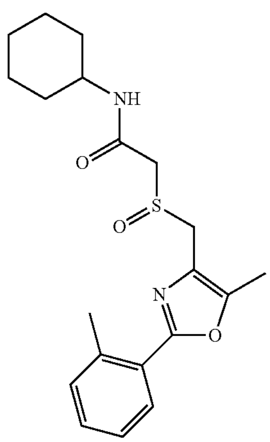 [SMILES: Cc1ccccc1-c1nc(CS(=O)CC(=O)NC2CCCCC2)c(C)o1] | 374.51 |
| IIa-665 | 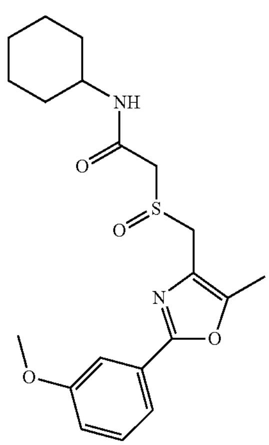 [SMILES: COc1cccc(-c2nc(CS(=O)CC(=O)NC3CCCCC3)c(C)o2)c1] | 390.51 |

TABLE 4-continued
Oxazole amides ($R^3$ = NH-$C_3$-$C_7$cycloalkyl)
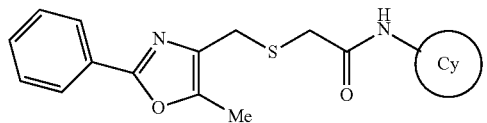
| ID | Structure | MW |
|---|---|---|
| IIa-666 | 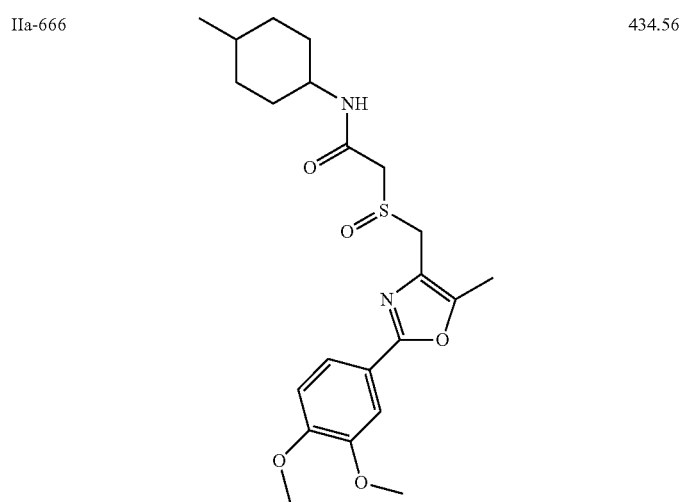 | 434.56 |
| IIa-667 | 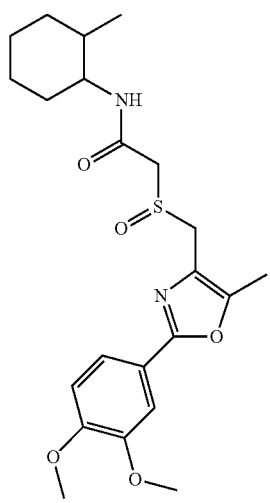 [SMILES: COc1ccc(-c2nc(CS(=O)CC(=O)NC3CCCCC3C)c(C)o2)cc1OC] | 434.56 |

TABLE 4-continued
Oxazole amides (R³ = NH-C₃-C₇cycloalkyl)
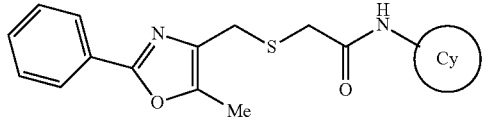
| ID | Structure | MW |
|---|---|---|
| IIa-668 | 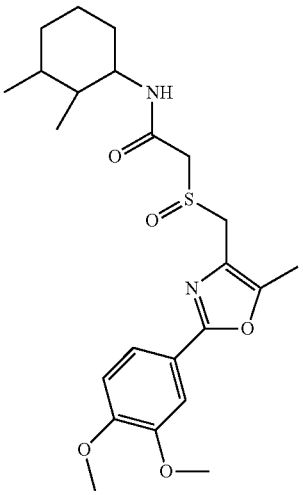 | 448.59 |
| IIa-669 | | 420.53 |
| IIa-670 | 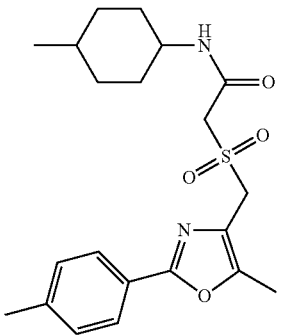 | 404.53 |

TABLE 4-continued
Oxazole amides (R³ = NH-C₃-C₇cycloalkyl)
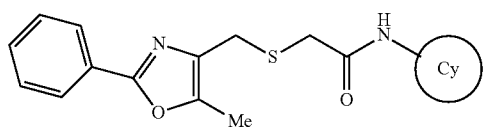
| ID | Structure | MW |
|---|---|---|
| IIa-671 | 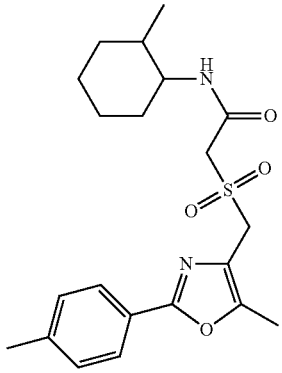 | 404.53 |
| IIa-672 | 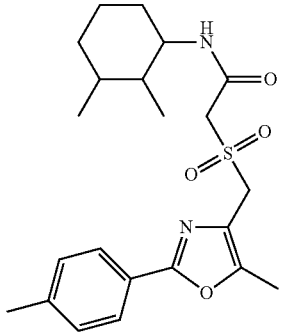 | 418.56 |
| IIa-673 | 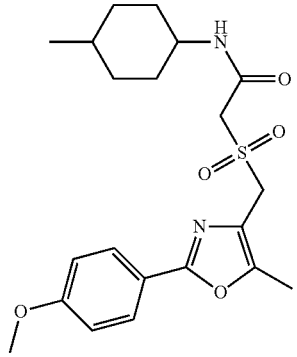 | 420.53 |

415
416
TABLE 4-continued
Oxazole amides (R³ = NH-C₃-C₇cycloalkyl)
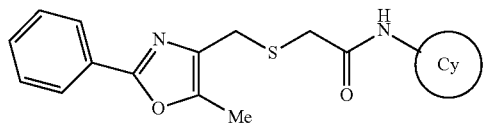
| ID | Structure | MW |
|---|---|---|
| IIa-674 | 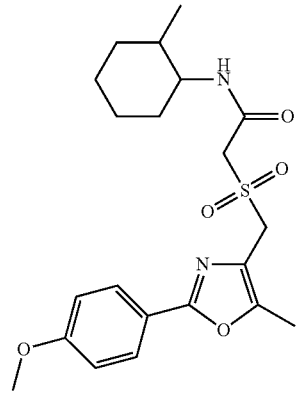 | 420.53 |
| IIa-675 | 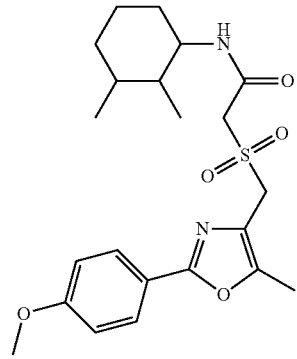 | 434.56 |
| IIa-676 | 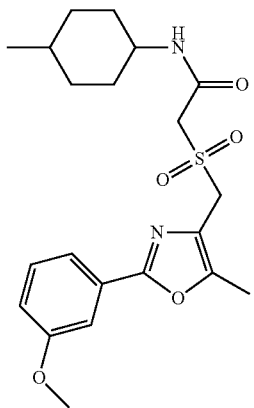 | 420.53 |

TABLE 4-continued

Oxazole amides (R³ = NH-C₃-C₇cycloalkyl)

| ID | Structure | MW |
|---|---|---|
| IIa-677 | | 420.53 |
| IIa-678 | | 434.56 |
| IIa-679 | | 404.53 |

TABLE 4-continued
Oxazole amides ($R^3$ = NH-$C_3$-$C_7$cycloalkyl)
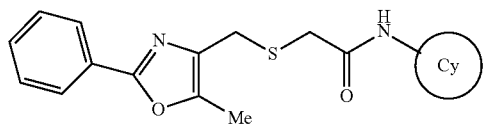
| ID | Structure | MW |
|---|---|---|
| IIa-680 | | 418.56 |
| IIa-681 | | 422.52 |
| IIa-682 | | 424.95 |
| IIa-683 | | 438.98 |

TABLE 4-continued

Oxazole amides (R³ = NH-C₃-C₇cycloalkyl)

| ID | Structure | MW |
|---|---|---|
| IIa-684 | 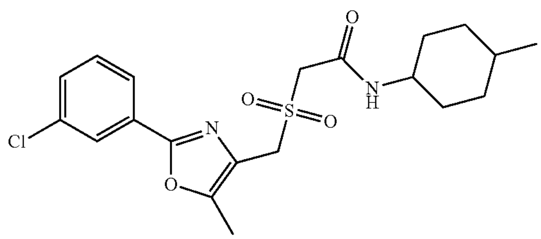 [SMILES: Cc1oc(-c2cccc(Cl)c2)nc1CS(=O)(=O)CC(=O)NC1CCC(C)CC1] | 424.95 |
| IIa-685 | 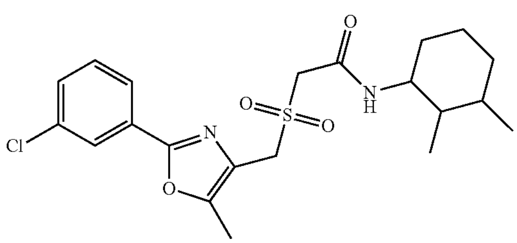 [SMILES: Cc1oc(-c2cccc(Cl)c2)nc1CS(=O)(=O)CC(=O)NC1CCCC(C)C1C] | 438.98 |
| IIa-686 | 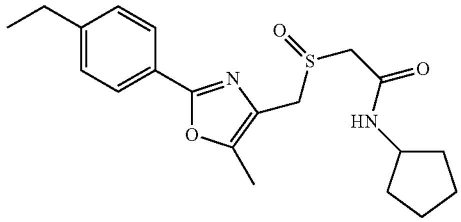 [SMILES: CCc1ccc(-c2nc(CS(=O)CC(=O)NC3CCCC3)c(C)o2)cc1] | 374.51 |
| IIa-687 | 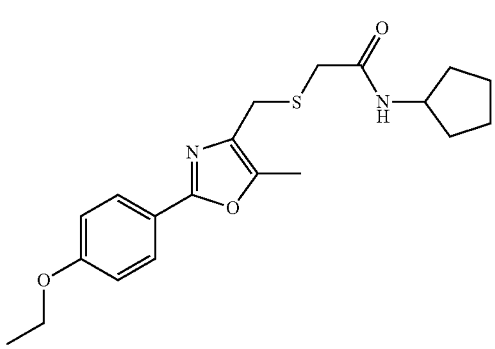 [SMILES: CCOc1ccc(-c2nc(CSCC(=O)NC3CCCC3)c(C)o2)cc1] | 374.51 |

TABLE 4-continued

| Oxazole amides (R³ = NH-C₃-C₇cycloalkyl) | | |
|---|---|---|
| ID | Structure | MW |
| IIa-688 | | 360.48 |
| IIa-689 | | 390.51 |
| IIa-690 | | 364.90 |

TABLE 4-continued
Oxazole amides (R³ = NH-C₃-C₇cycloalkyl)
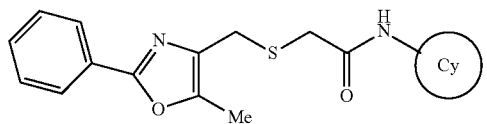
| ID | Structure | MW |
|---|---|---|
| IIa-691 | | 376.54 |
| IIa-692 | | 358.51 |
| IIa-693 | | 364.90 |

TABLE 4-continued

Oxazole amides (R³ = NH-C₃-C₇cycloalkyl)

| ID | Structure | MW |
|---|---|---|
| IIa-694 | | 348.44 |
| IIa-695 | | 344.48 |
| IIa-696 | | 376.48 |

TABLE 4-continued
Oxazole amides ($R^3$ = NH-$C_3$-$C_7$cycloalkyl)
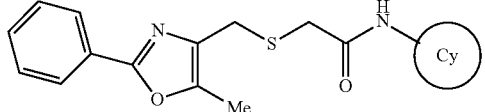
| ID | Structure | MW |
|---|---|---|
| IIa-697 | 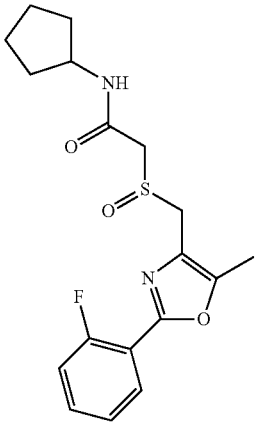 [SMILES: Cc1oc(-c2ccccc2F)nc1CS(=O)CC(=O)NC1CCCC1] | 364.44 |
| IIa-698 | 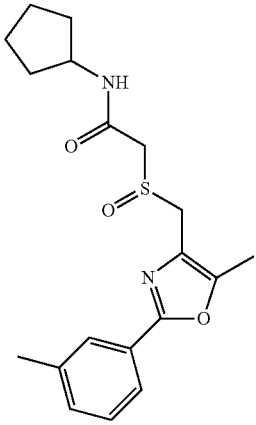 [SMILES: Cc1cccc(-c2nc(CS(=O)CC(=O)NC3CCCC3)c(C)o2)c1] | 360.48 |
| IIa-699 | | 360.48 |

TABLE 4-continued

Oxazole amides (R³ = NH-C₃-C₇cycloalkyl)

| ID | Structure | MW |
|---|---|---|
| IIa-700 | | 380.90 |
| IIa-701 | | 360.48 |
| IIa-702 | | 376.48 |

TABLE 4-continued
Oxazole amides (R³ = NH-C₃-C₇cycloalkyl)
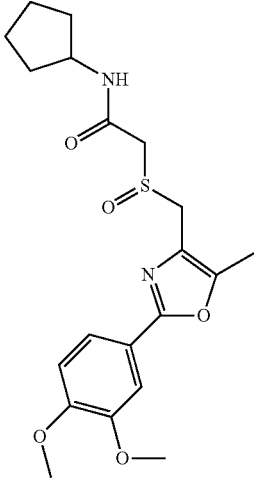 [SMILES: COc1ccc(-c2nc(CS(=O)CC(=O)NC3CCCC3)c(C)o2)cc1OC]
| ID | Structure | MW |
|---|---|---|
| IIa-703 | 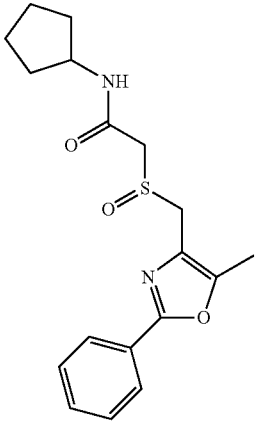 | 406.50 |
| IIa-704 | 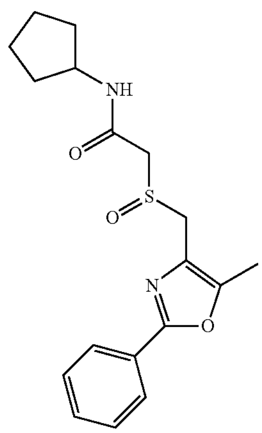 [SMILES: Cc1oc(-c2ccccc2)nc1CS(=O)CC(=O)NC1CCCC1] | 346.45 |
| IIa-705 | 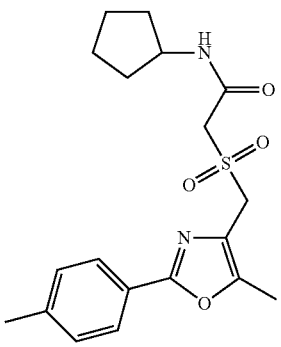 | 376.48 |

TABLE 4-continued
Oxazole amides (R³ = NH-C₃-C₇cycloalkyl)
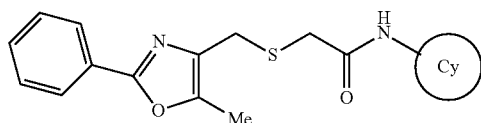
| ID | Structure | MW |
|---|---|---|
| IIa-706 | | 392.48 |
| IIa-707 | | 376.48 |
| IIa-708 | | 380.44 |

TABLE 4-continued

Oxazole amides (R³ = NH-C₃-C₇cycloalkyl)

| ID | Structure | MW |
|---|---|---|
| IIa-709 | 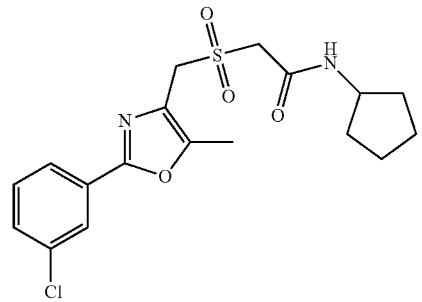 [SMILES: Cc1oc(-c2cccc(Cl)c2)nc1CS(=O)(=O)CC(=O)NC1CCCC1] | 396.90 |
| IIa-710 | 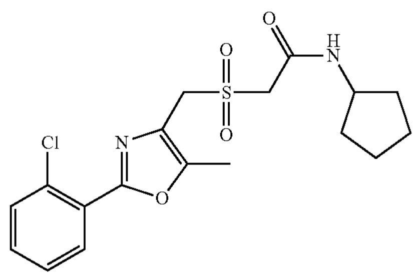 [SMILES: Cc1oc(-c2ccccc2Cl)nc1CS(=O)(=O)CC(=O)NC1CCCC1] | 396.90 |
| IIa-711 | 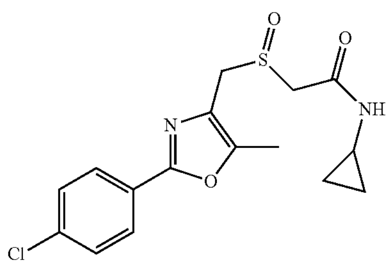 [SMILES: Cc1oc(-c2ccc(Cl)cc2)nc1CS(=O)CC(=O)NC1CC1] | 352.84 |
| IIa-712 | 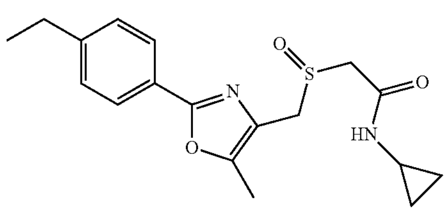 [SMILES: CCc1ccc(-c2nc(CS(=O)CC(=O)NC3CC3)c(C)o2)cc1] | 346.45 |
| IIa-713 | 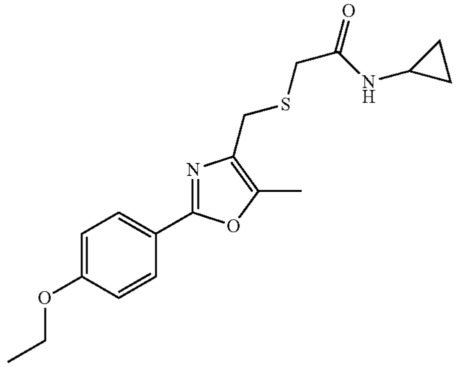 [SMILES: CCOc1ccc(-c2nc(CSCC(=O)NC3CC3)c(C)o2)cc1] | 346.45 |

TABLE 4-continued
Oxazole amides (R³ = NH-C₃-C₇cycloalkyl)
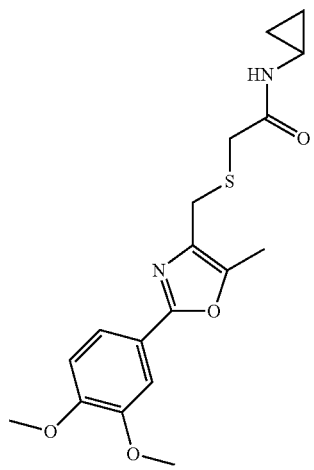 [SMILES: COc1ccc(-c2nc(CSCC(=O)NC3CC3)c(C)o2)cc1OC]
| ID | Structure | MW |
|---|---|---|
| IIa-714 | 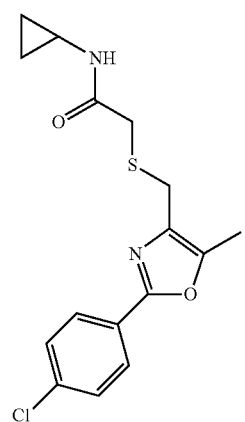 [SMILES: Cc1oc(-c2ccc(Cl)cc2)nc1CSCC(=O)NC1CC1] | 362.45 |
| IIa-715 | | 336.84 |
| IIa-716 | 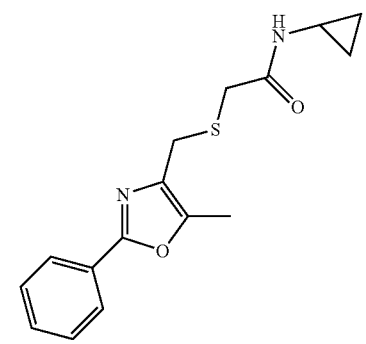 [SMILES: Cc1oc(-c2ccccc2)nc1CSCC(=O)NC1CC1] | 316.43 |

TABLE 4-continued
Oxazole amides (R³ = NH-C₃-C₇cycloalkyl)
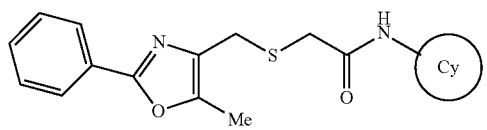
| ID | Structure | MW |
|---|---|---|
| IIa-717 | 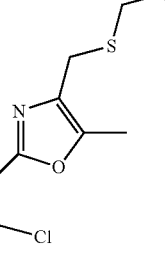 | 336.84 |
| IIa-718 | 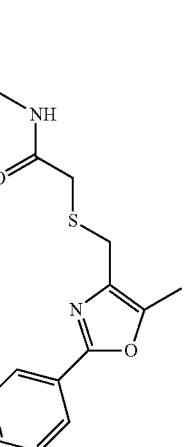 | 348.49 |
| IIa-719 | 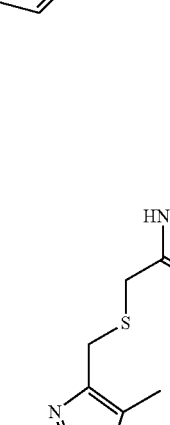 | 330.45 |

TABLE 4-continued
Oxazole amides ($R^3$ = NH-$C_3$-$C_7$cycloalkyl)
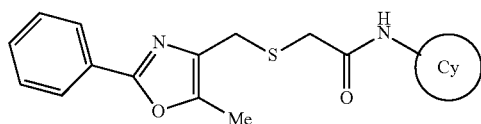
| ID | Structure | MW |
|---|---|---|
| IIa-720 | | 320.39 |
| IIa-721 | | 316.43 |
| IIa-722 | | 316.43 |

TABLE 4-continued
Oxazole amides (R³ = NH-C₃-C₇cycloalkyl)
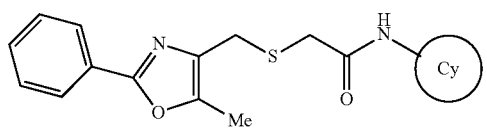
| ID | Structure | MW |
|---|---|---|
| IIa-723 | 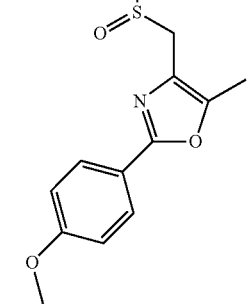 | 348.42 |
| IIa-724 | 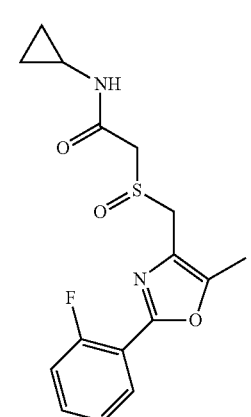 | 336.39 |
| IIa-725 | 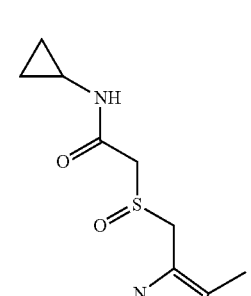 | 332.42 |

447
448
TABLE 4-continued
Oxazole amides (R³ = NH-C₃-C₇cycloalkyl)
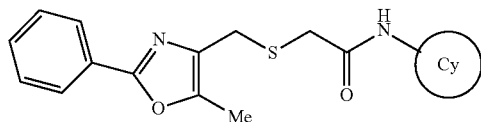
| ID | Structure | MW |
|---|---|---|
| IIa-726 | 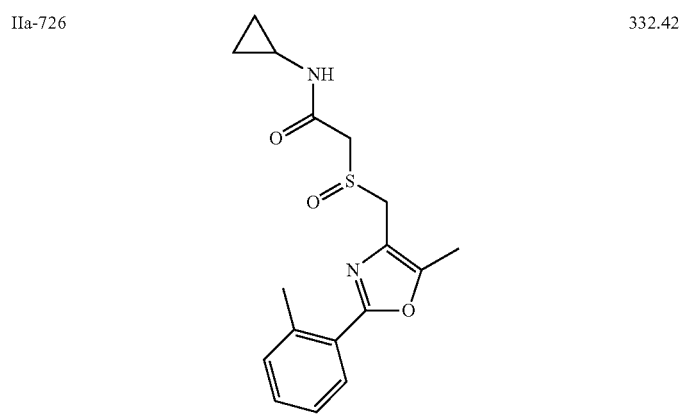 | 332.42 |
| IIa-727 | 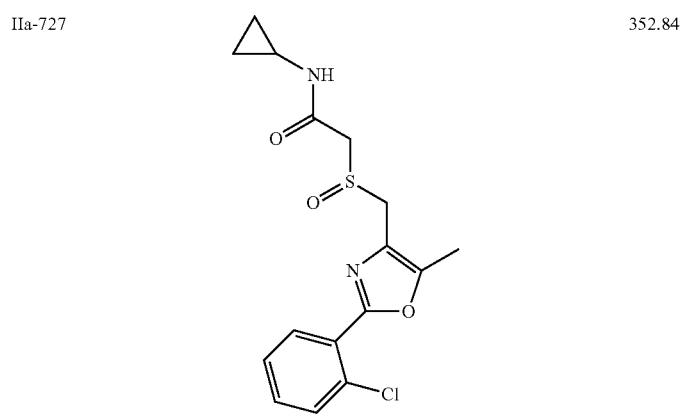 | 352.84 |
| IIa-728 | 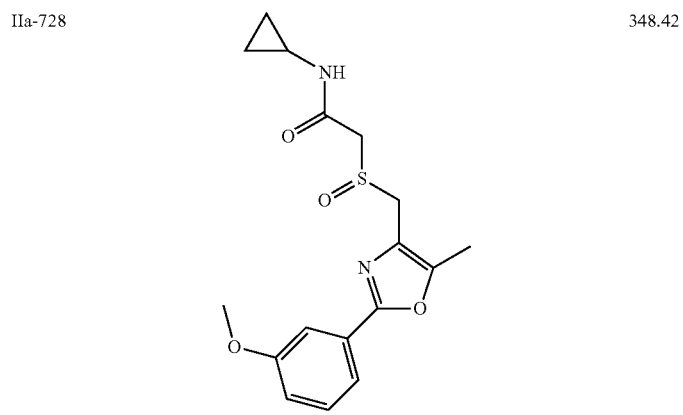 | 348.42 |

TABLE 4-continued
Oxazole amides (R³ = NH-C₃-C₇cycloalkyl)
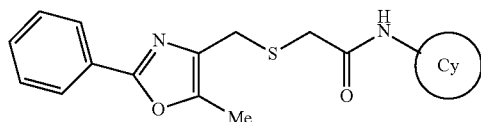
| ID | Structure | MW |
|---|---|---|
| IIa-729 | | 348.42 |
| IIa-730 | | 364.42 |
| IIa-731 | | 348.42 |
| IIa-732 | | 368.84 |

451
452
TABLE 4-continued
Oxazole amides (R³ = NH-C₃-C₇cycloalkyl)
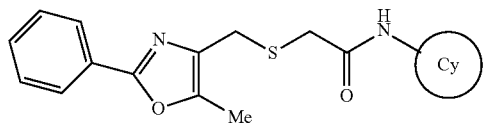
| ID | Structure | MW |
|---|---|---|
| IIa-733 | 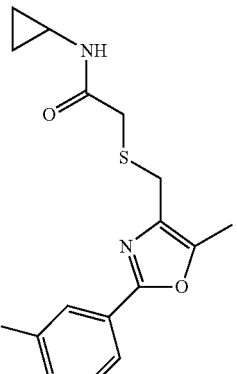 | 336.84 |
TABLE 5
Oxazole amides (R³ = NH-C₃C₇cycloalkyl)
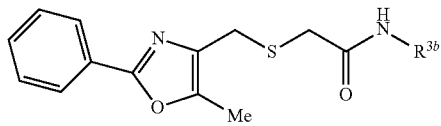
| ID | Structure | MW |
|---|---|---|
| IIa-1001 | 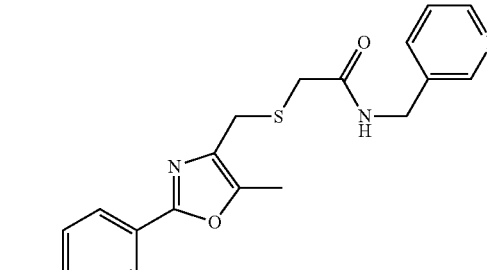 | 387.89 |
| IIa-1002 | 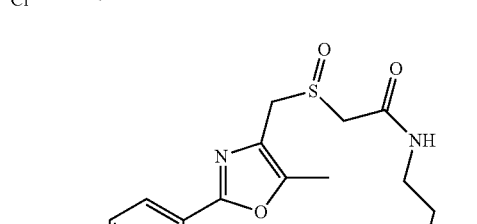 | 368.89 |

TABLE 5-continued
Oxazole amides (R³ = NH-C₃C₇cycloalkyl)
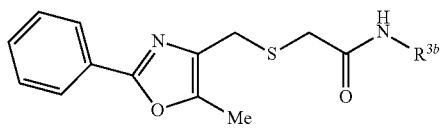
| ID | Structure | MW |
|---|---|---|
| IIa-1003 | | 400.88 |
| IIa-1004 | | 461.58 |
| IIa-1005 | | 416.59 |
| IIa-1006 | | 445.63 |

TABLE 5-continued
Oxazole amides (R³ = NH-C₃C₇cycloalkyl)

| ID | Structure | MW |
|---|---|---|
| IIa-1007 | 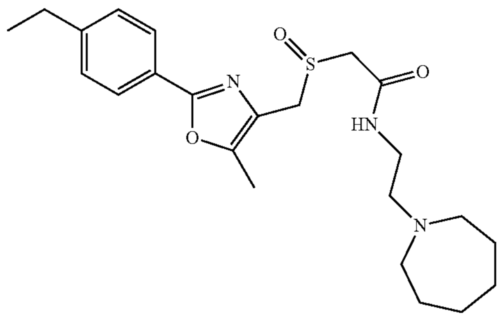 [SMILES: CCc1ccc(-c2nc(CS(=O)CC(=O)NCCN3CCCCCC3)c(C)o2)cc1] | 431.60 |
| IIa-1008 | 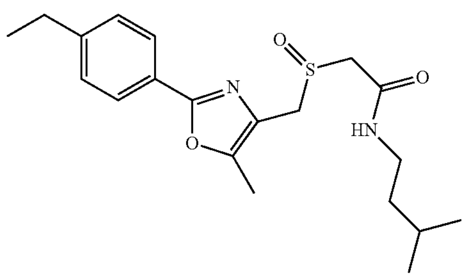 [SMILES: CCc1ccc(-c2nc(CS(=O)CC(=O)NCCC(C)C)c(C)o2)cc1] | 376.52 |
| IIa-1009 | 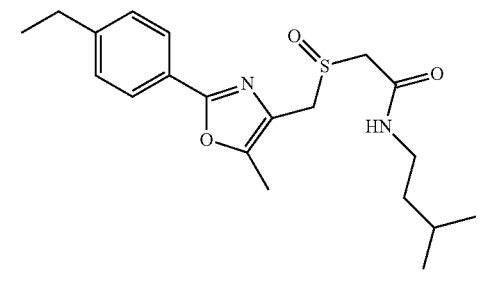 | 394.49 |
| IIa-1010 | 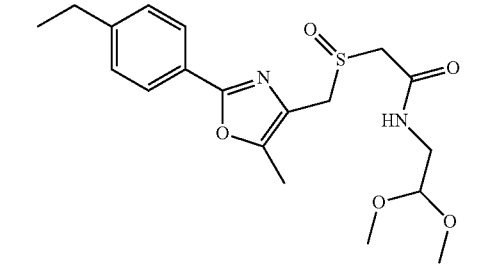 [SMILES: CCc1ccc(-c2nc(CS(=O)CC(=O)NCC(OC)OC)c(C)o2)cc1] | 348.47 |
| IIa-1011 | 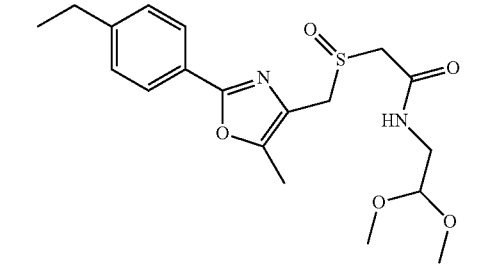 [SMILES: CCc1ccc(-c2nc(CS(=O)CC(=O)NCC(OC)OC)c(C)o2)cc1] | 433.57 |

TABLE 5-continued
Oxazole amides (R³ = NH-C₃C₇cycloalkyl)
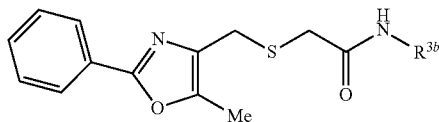
| ID | Structure | MW |
| --- | --- | --- |
| IIa-1012 | 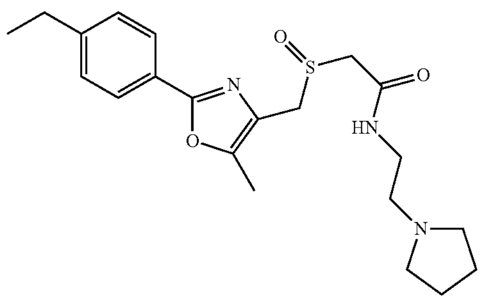 [SMILES: CCc1ccc(-c2nc(CS(=O)CC(=O)NCCN3CCCC3)c(C)o2)cc1] | 403.55 |
| IIa-1013 | 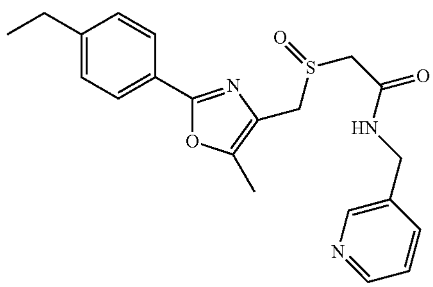 | 397.50 |
| IIa-1014 | 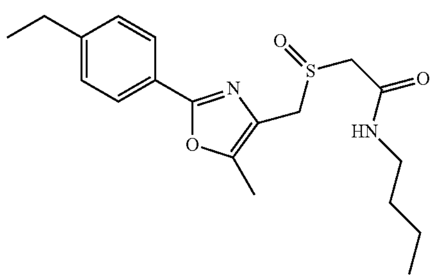 [SMILES: CCCCNC(=O)CS(=O)Cc1nc(-c2ccc(CC)cc2)oc1C] | 362.49 |
| IIa-1015 | 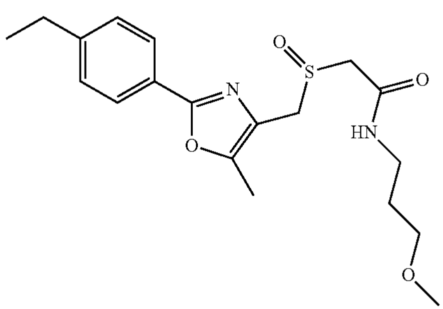 [SMILES: CCc1ccc(-c2nc(CS(=O)CC(=O)NCCCOC)c(C)o2)cc1] | 378.49 |

TABLE 5-continued
Oxazole amides ($R^3$ = NH-$C_3C_7$cycloalkyl)
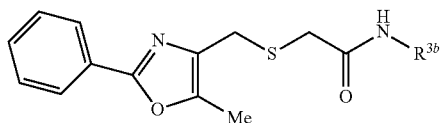
| ID | Structure | MW |
|---|---|---|
| IIa-1016 | 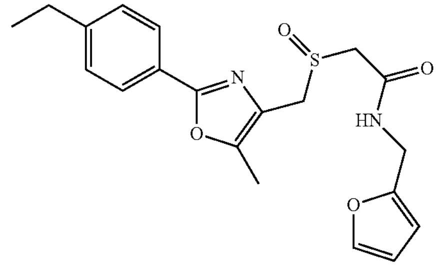 [SMILES: CCc1ccc(-c2nc(CS(=O)CC(=O)NCc3ccco3)c(C)o2)cc1] | 386.47 |
| IIa-1017 | 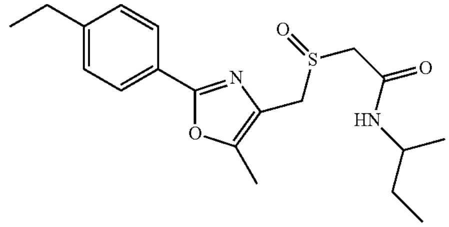 [SMILES: CCc1ccc(-c2nc(CS(=O)CC(=O)NC(C)CC)c(C)o2)cc1] | 362.49 |
| IIa-1018 | 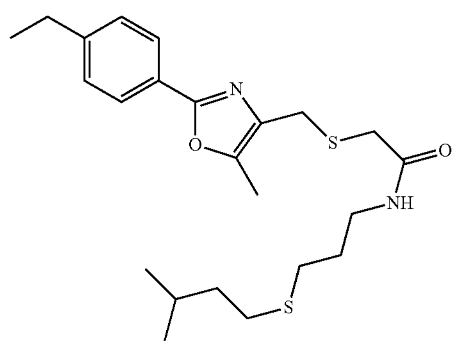 [SMILES: CCc1ccc(-c2nc(CSCC(=O)NCCCSCCC(C)C)c(C)o2)cc1] | 434.67 |
| IIa-1019 | 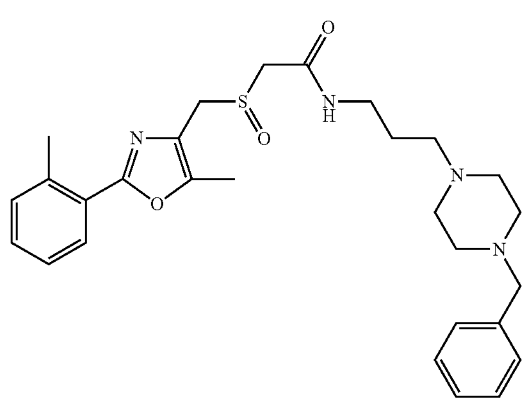 [SMILES: Cc1ccccc1-c1nc(CS(=O)CC(=O)NCCCN2CCN(Cc3ccccc3)CC2)c(C)o1] | 508.69 |

TABLE 5-continued

Oxazole amides (R³ = NH-C₃C₇cycloalkyl)

| ID | Structure | MW |
|---|---|---|
| IIa-1020 | 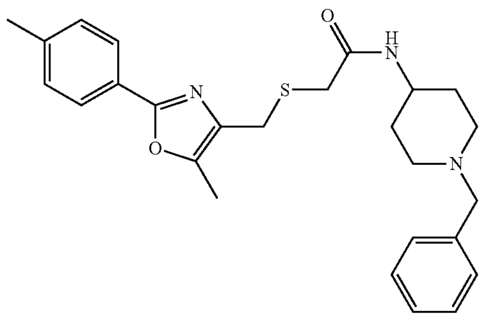 [SMILES: Cc1ccc(-c2nc(CSCC(=O)NC3CCN(Cc4ccccc4)CC3)c(C)o2)cc1] | 449.62 |
| IIa-1021 | 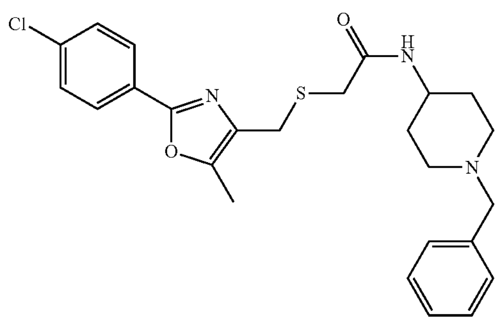 [SMILES: Cc1oc(-c2ccc(Cl)cc2)nc1CSCC(=O)NC1CCN(Cc2ccccc2)CC1] | 470.04 |
| IIa-1022 | 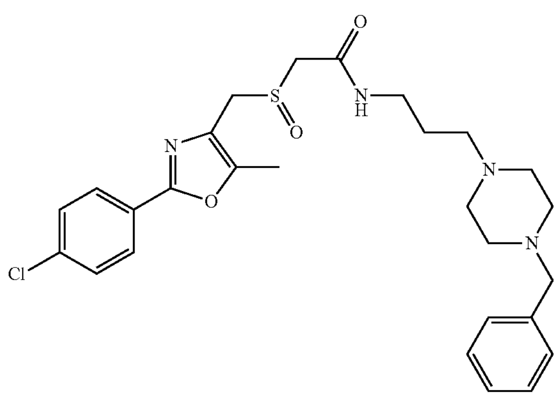 [SMILES: Cc1oc(-c2ccc(Cl)cc2)nc1CS(=O)CC(=O)NCCCN1CCN(Cc2ccccc2)CC1] | 529.11 |
| IIa-1023 | 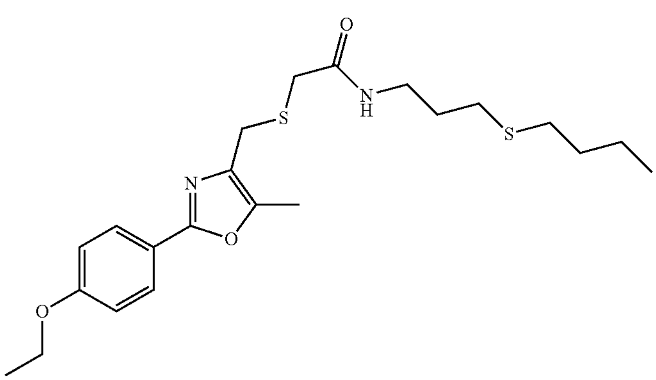 [SMILES: CCCCSCCCNC(=O)CSCc1nc(-c2ccc(OCC)cc2)oc1C] | 436.64 |

TABLE 5-continued
Oxazole amides ($R^3$ = NH-$C_3C_7$cycloalkyl)
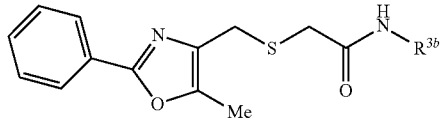
| ID | Structure | MW |
|---|---|---|
| IIa-1024 | 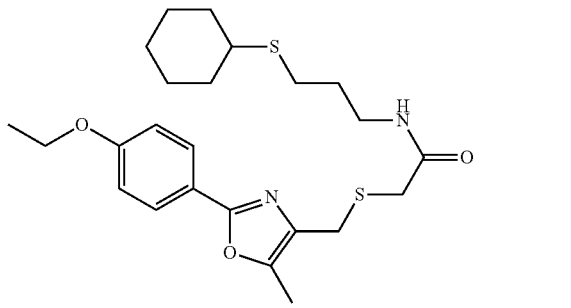 [SMILES: CCOc1ccc(-c2nc(CSCC(=O)NCCCSC3CCCCC3)c(C)o2)cc1] | 462.68 |
| IIa-1025 | 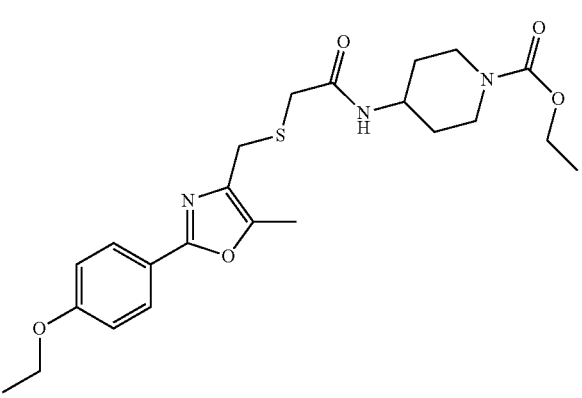 [SMILES: CCOC(=O)N1CCC(NC(=O)CSCc2nc(-c3ccc(OCC)cc3)oc2C)CC1] | 508.69 |
| IIa-1026 | 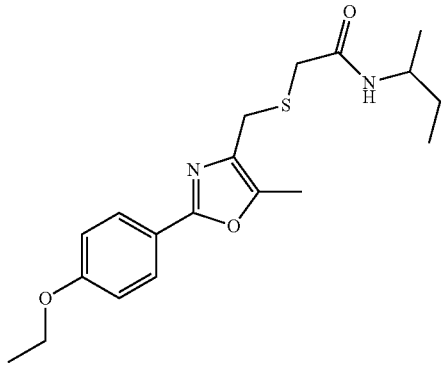 [SMILES: CCOc1ccc(-c2nc(CSCC(=O)NC(C)CC)c(C)o2)cc1] | 461.58 |
| IIa-1027 | | 362.49 |

TABLE 5-continued
Oxazole amides (R³ = NH-C₃C₇cycloalkyl)
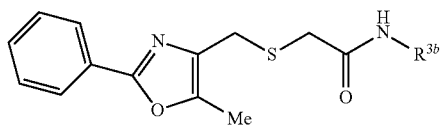
| ID | Structure | MW |
|---|---|---|
| IIa-1028 | | 348.47 |
| IIa-1029 | | 403.55 |
| IIa-1030 | | 529.11 |

TABLE 5-continued
Oxazole amides (R³ = NH-C₃C₇cycloalkyl)
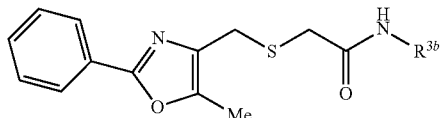
| ID | Structure | MW |
|---|---|---|
| IIa-1031 | 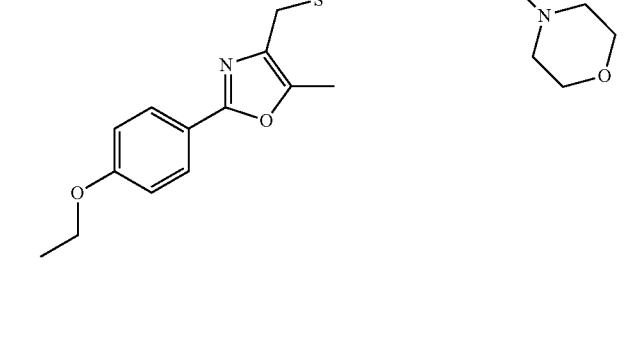 | 433.57 |
| IIa-1032 | 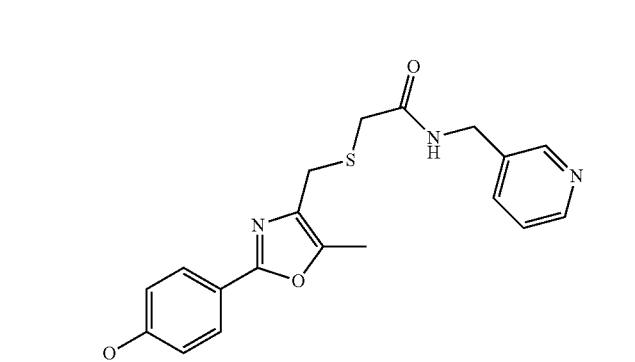 | 397.50 |
| IIa-1033 | 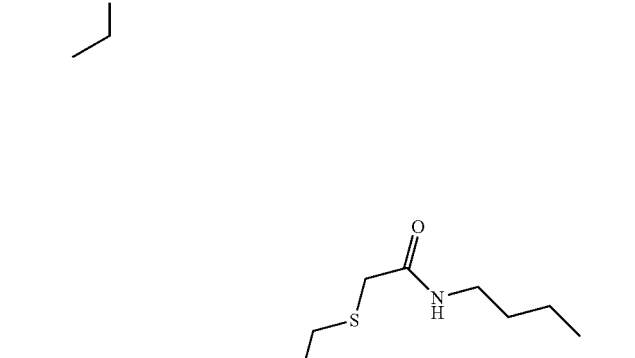 | 362.49 |

TABLE 5-continued

Oxazole amides (R³ = NH-C₃C₇cycloalkyl)

| ID | Structure | MW |
|---|---|---|
| IIa-1034 | | 386.47 |
| IIa-1035 | | 406.55 |
| IIa-1036 | | 376.52 |

TABLE 5-continued

Oxazole amides (R³ = NH-C₃C₇cycloalkyl)

| ID | Structure | MW |
| --- | --- | --- |
| IIa-1037 | 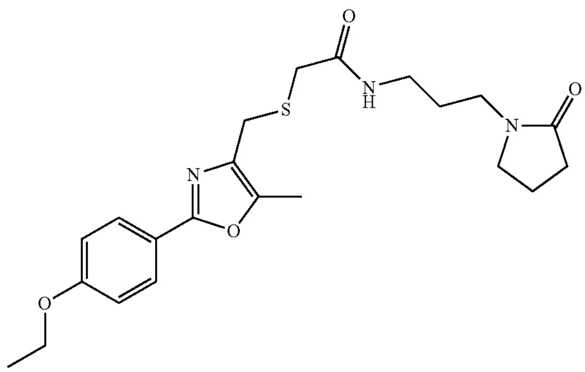 [SMILES: CCOc1ccc(-c2nc(CSCC(=O)NCCCN3CCCC3=O)c(C)o2)cc1] | 431.56 |
| IIa-1038 | 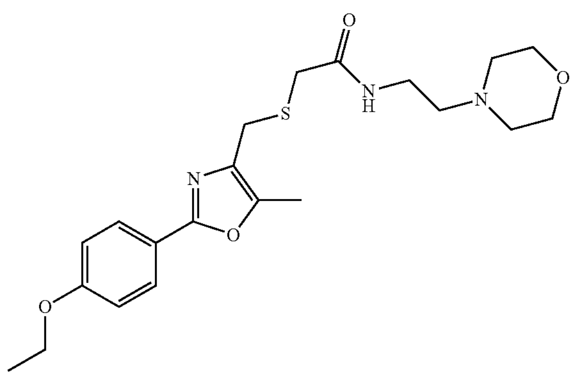 [SMILES: CCOc1ccc(-c2nc(CSCC(=O)NCCN3CCOCC3)c(C)o2)cc1] | 419.55 |
| IIa-1039 | 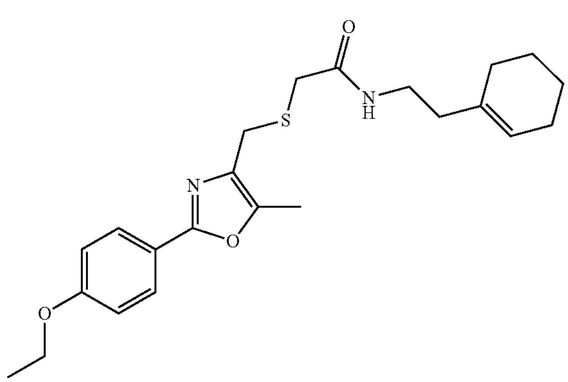 [SMILES: CCOc1ccc(-c2nc(CSCC(=O)NCCC3=CCCCC3)c(C)o2)cc1] | 414.57 |

TABLE 5-continued
Oxazole amides (R³ = NH-C₃C₇cycloalkyl)
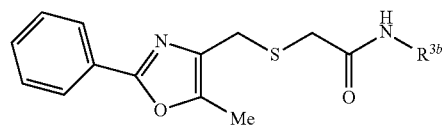
| ID | Structure | MW |
|---|---|---|
| IIa-1040 | 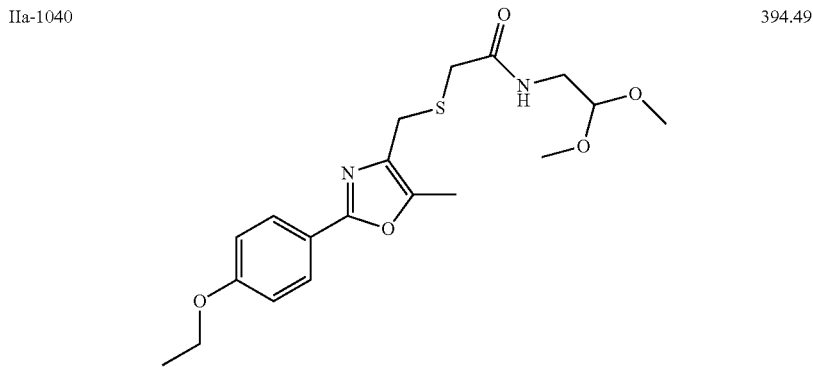 | 394.49 |
| IIa-1041 | 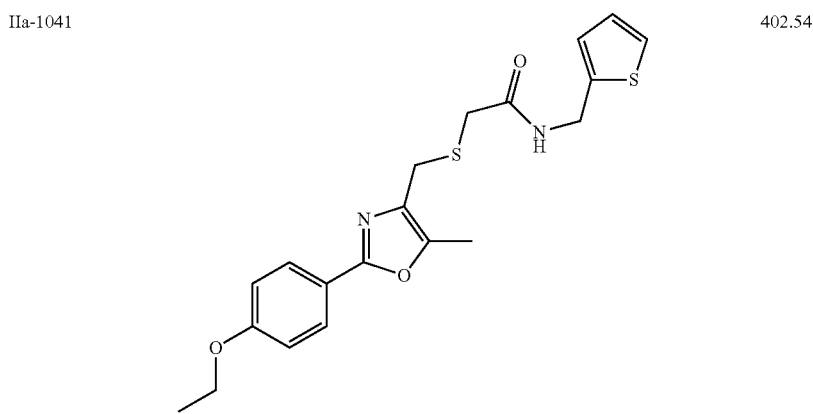 | 402.54 |
| IIa-1042 | 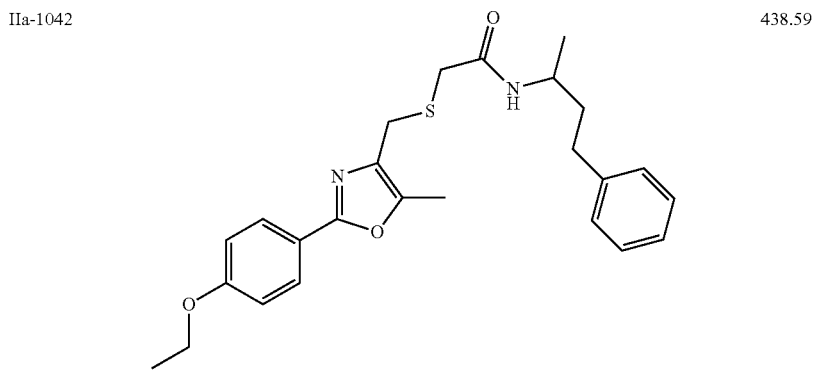 | 438.59 |

TABLE 5-continued

Oxazole amides (R³ = NH-C₃C₇cycloalkyl)

| ID | Structure | MW |
|---|---|---|
| IIa-1043 | | 422.55 |
| IIa-1044 | | 417.57 |
| IIa-1045 | | 348.47 |

TABLE 5-continued
Oxazole amides (R³ = NH-C₃C₇cycloalkyl)
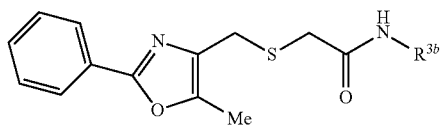
| ID | Structure | MW |
|---|---|---|
| IIa-1046 | | 390.51 |
| IIa-1047 | | 508.69 |
| IIa-1048 | | 392.52 |

TABLE 5-continued

Oxazole amides (R³ = NH-C₃C₇cycloalkyl)

![Generic structure: 2-phenyl-5-methyl-oxazole-4-CH2-S-CH2-C(=O)-NH-R^{3b}]

| ID | Structure | MW |
|---|---|---|
| IIa-1049 | [2-(3,4-dimethoxyphenyl)-5-methyloxazol-4-yl]methylthio-CH2-C(=O)-NH-(1-benzylpiperidin-4-yl) | 495.65 |
| IIa-1050 | [2-(4-ethoxyphenyl)-5-methyloxazol-4-yl]methylthio-CH2-C(=O)-NH-(CH2)3-(4-methylpiperazin-1-yl) | 446.62 |
| IIa-1051 | [2-(4-ethoxyphenyl)-5-methyloxazol-4-yl]methylthio-CH2-C(=O)-NH-CH2CH2-OMe | 364.47 |

TABLE 5-continued
Oxazole amides (R³ = NH-C₃C₇cycloalkyl)
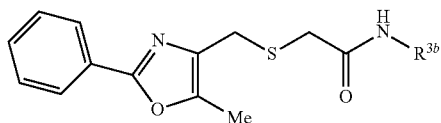
| ID | Structure | MW |
|---|---|---|
| IIa-1052 | | 479.65 |
| IIa-1053 | | 453.61 |
| IIa-1054 | | 375.47 |
| IIa-1055 | | 369.45 |

TABLE 5-continued
Oxazole amides (R³ = NH-C₃C₇cycloalkyl)
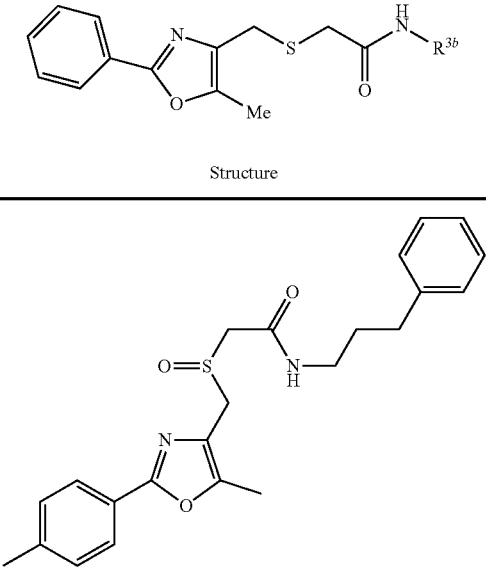
| ID | Structure | MW |
|---|---|---|
| IIa-1056 | 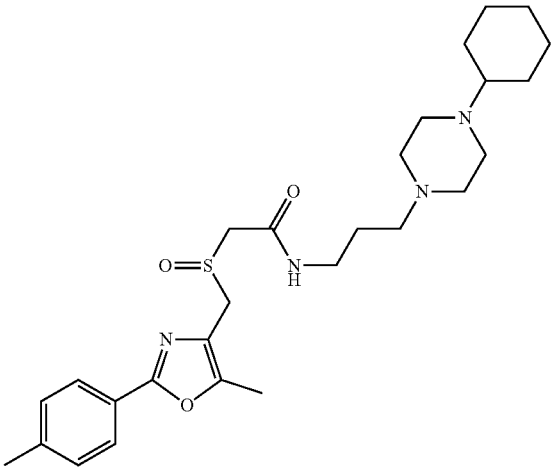 [SMILES: Cc1ccc(-c2nc(CS(=O)CC(=O)NCCCN3CCN(C4CCCCC4)CC3)c(C)o2)cc1] | 410.54 |
| IIa-1057 | | 500.71 |
| IIa-1058 | 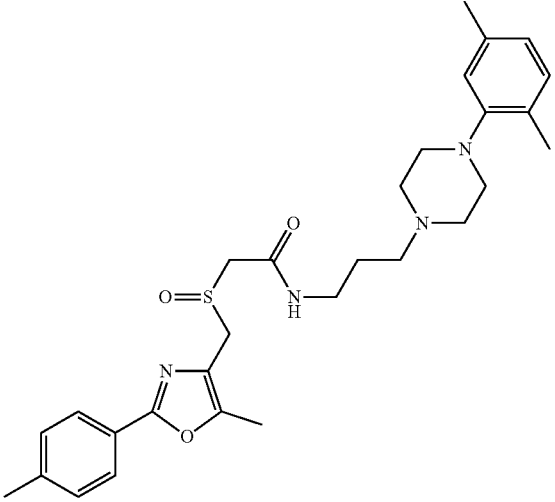 | 522.72 |

TABLE 5-continued
Oxazole amides (R³ = NH-C₃C₇cycloalkyl)
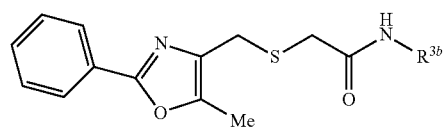
| ID | Structure | MW |
|---|---|---|
| IIa-1059 | | 447.56 |
| IIa-1060 | | 408.52 |
| IIa-1061 | | 383.47 |

TABLE 5-continued
Oxazole amides (R³ = NH-C₃C₇cycloalkyl)
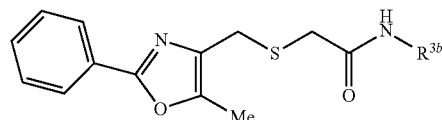
| ID | Structure | MW |
|---|---|---|
| IIa-1062 | 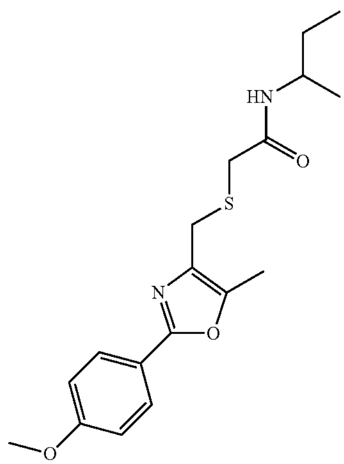 [SMILES: CCC(C)NC(=O)CSCc1nc(-c2ccc(OC)cc2)oc1C] | 348.47 |
| IIa-1063 | 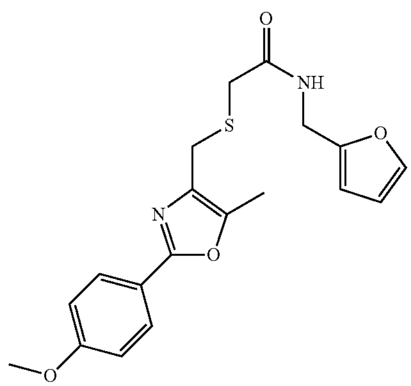 | 372.45 |
| IIa-1064 | 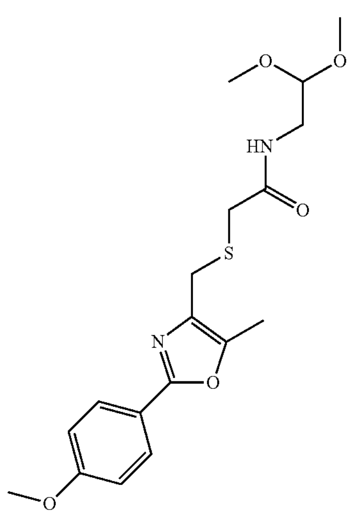 | 380.47 |

TABLE 5-continued
Oxazole amides (R³ = NH-C₃C₇cycloalkyl)
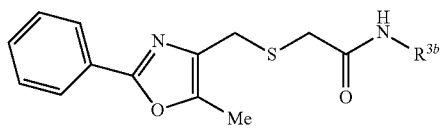
| ID | Structure | MW |
|---|---|---|
| IIa-1065 | | 419.55 |
| IIa-1066 | | 362.49 |
| IIa-1067 | | 376.48 |

491
492
TABLE 5-continued
Oxazole amides (R³ = NH-C₃C₇cycloalkyl)
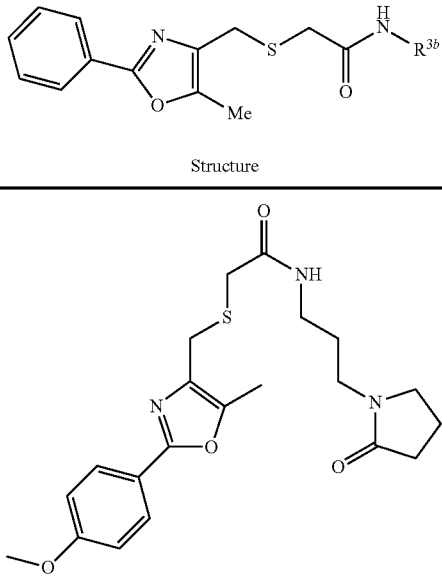
| ID | Structure | MW |
|---|---|---|
| IIa-1068 | 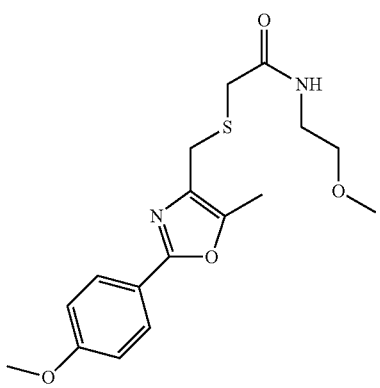 | 417.53 |
| IIa-1069 | | 350.44 |
| IIa-1070 | 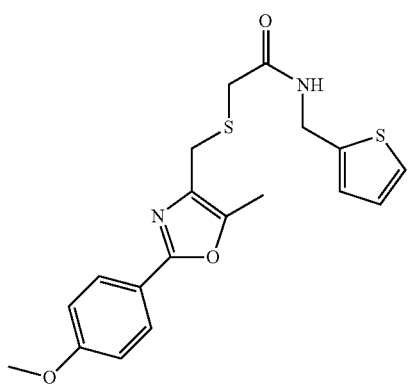 [SMILES: COc1ccc(-c2nc(CSCC(=O)NCc3cccs3)c(C)o2)cc1] | 388.51 |

TABLE 5-continued
Oxazole amides ($R^3$ = NH-$C_3C_7$cycloalkyl)
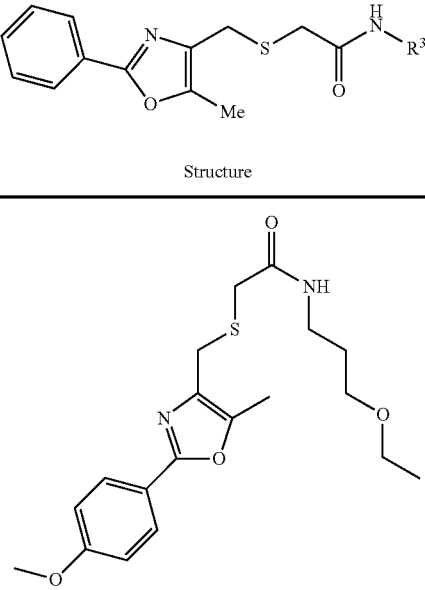
| ID | Structure | MW |
|---|---|---|
| IIa-1071 | 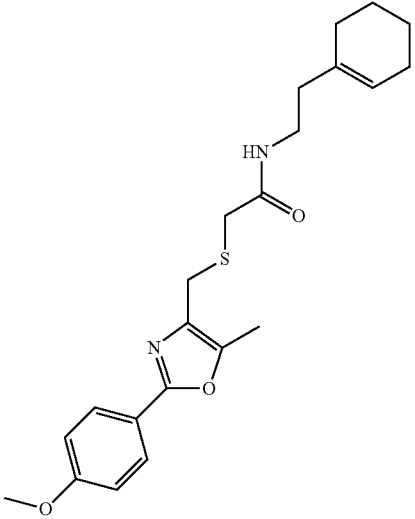 [SMILES: COc1ccc(-c2nc(CSCC(=O)NCCC3=CCCCC3)c(C)o2)cc1] | 378.49 |
| IIa-1072 | 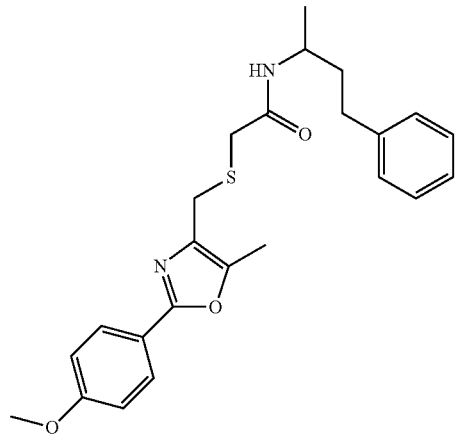 | 400.54 |
| IIa-1073 | 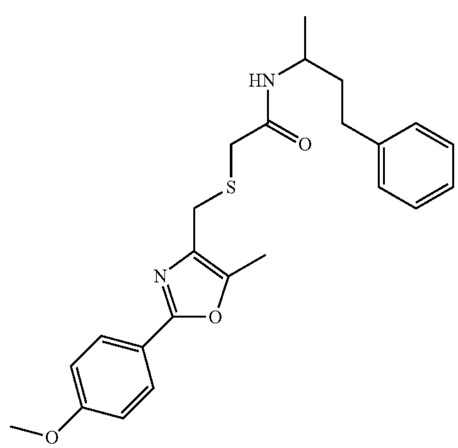 [SMILES: COc1ccc(-c2nc(CSCC(=O)NC(C)CCc3ccccc3)c(C)o2)cc1] | 424.57 |

TABLE 5-continued
Oxazole amides (R³ = NH-C₃C₇cycloalkyl)
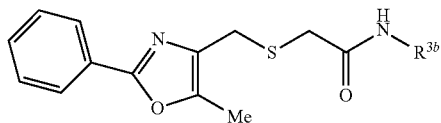
| ID | Structure | MW |
|---|---|---|
| IIa-1074 | | 364.47 |
| IIa-1075 | | 392.52 |
| IIa-1076 | | 348.47 |

TABLE 5-continued
Oxazole amides (R³ = NH-C₃C₇cycloalkyl)
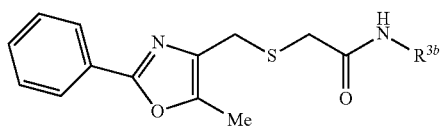
| ID | Structure | MW |
|---|---|---|
| IIa-1077 | | 515.08 |
| IIa-1078 | | 439.58 |

TABLE 5-continued
Oxazole amides (R³ = NH-C₃C₇cycloalkyl)
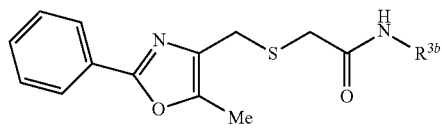
| ID | Structure | MW |
|---|---|---|
| IIa-1079 | 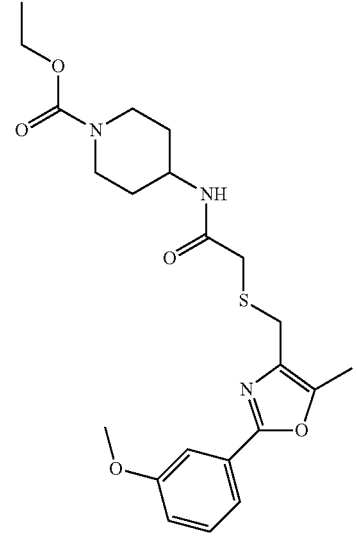 [SMILES: CCOC(=O)N1CCC(NC(=O)CSCc2nc(-c3cccc(OC)c3)oc2C)CC1] | 447.56 |
| IIa-1080 | 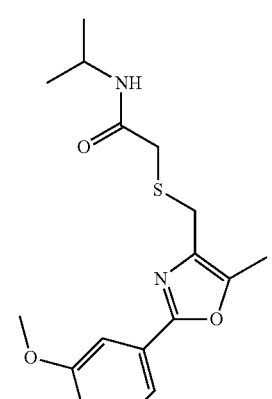 | 334.44 |
| IIa-1081 | 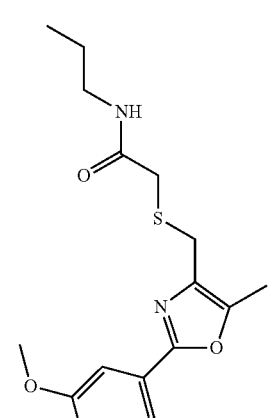 | 334.44 |

TABLE 5-continued
Oxazole amides (R³ = NH-C₃C₇cycloalkyl)
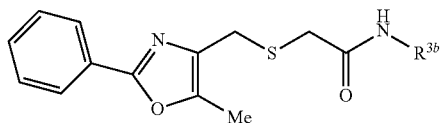
| ID | Structure | MW |
|---|---|---|
| IIa-1082 | | 376.48 |
| IIa-1083 | | 378.49 |

TABLE 5-continued
Oxazole amides (R³ = NH-C₃C₇cycloalkyl)
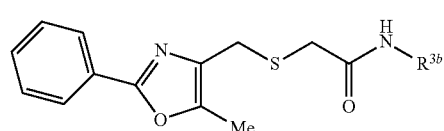
| ID | Structure | MW |
|---|---|---|
| IIa-1084 | 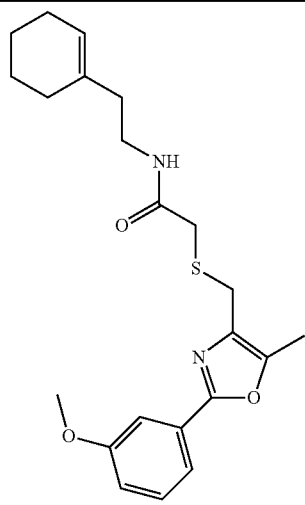 | 400.54 |
| IIa-1085 | 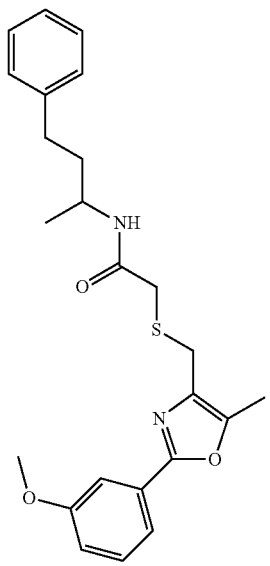 [SMILES: COc1cccc(-c2nc(CSCC(=O)NC(C)CCc3ccccc3)c(C)o2)c1] | 424.57 |

TABLE 5-continued
Oxazole amides ($R^3$ = NH-$C_3C_7$cycloalkyl)
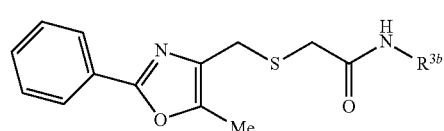
| ID | Structure | MW |
|---|---|---|
| IIa-1086 | | 364.47 |
| IIa-1087 | | 405.52 |

TABLE 5-continued
Oxazole amides (R³ = NH-C₃C₇cycloalkyl)
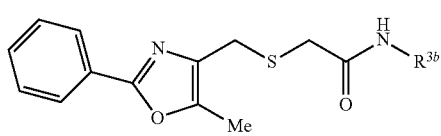
| ID | Structure | MW |
|---|---|---|
| IIa-1088 | | 348.47 |
| IIa-1089 | | 389.52 |

TABLE 5-continued
Oxazole amides (R³ = NH-C₃C₇cycloalkyl)
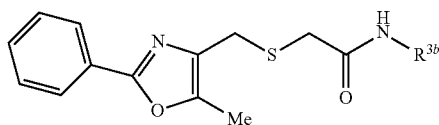
| ID | Structure | MW |
|---|---|---|
| IIa-1090 | 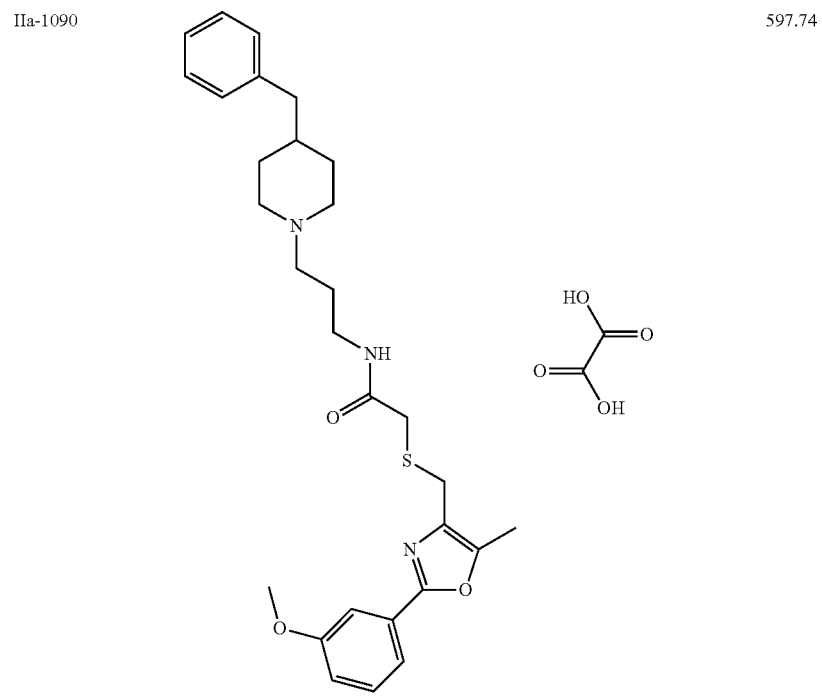 | 597.74 |
| IIa-1091 | 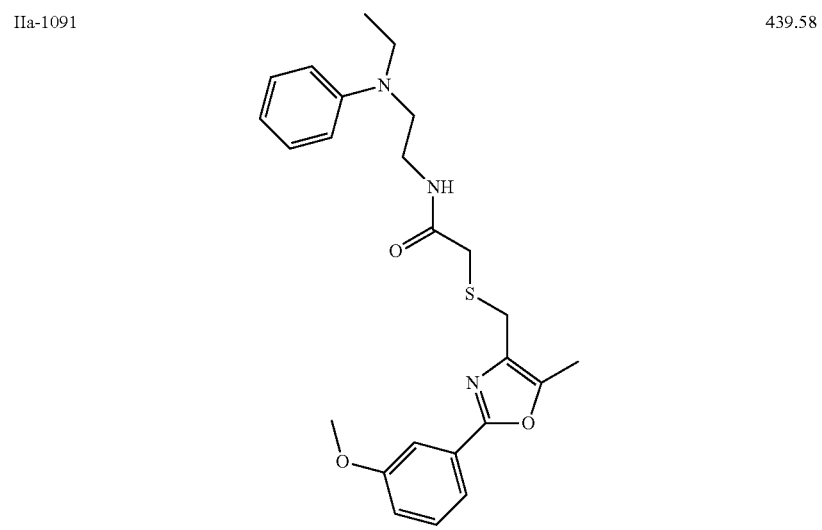 | 439.58 |

TABLE 5-continued
Oxazole amides (R³ = NH-C₃C₇cycloalkyl)
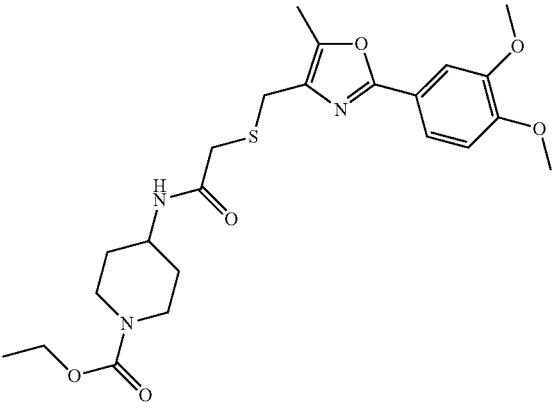 [SMILES: CCOC(=O)N1CCC(NC(=O)CSCc2nc(-c3ccc(OC)c(OC)c3)oc2C)CC1]
| ID | Structure | MW |
|---|---|---|
| IIa-1092 | 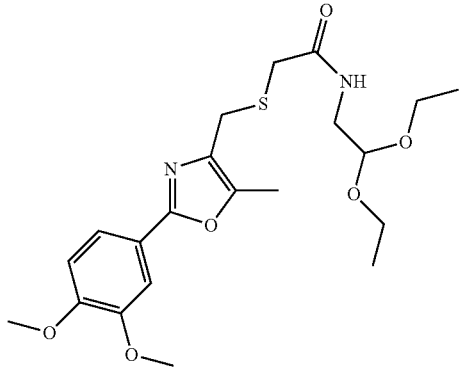 [SMILES: CCOC(CNC(=O)CSCc1nc(-c2ccc(OC)c(OC)c2)oc1C)OCC] | 477.58 |
| IIa-1093 | | 438.55 |
| IIa-1094 | 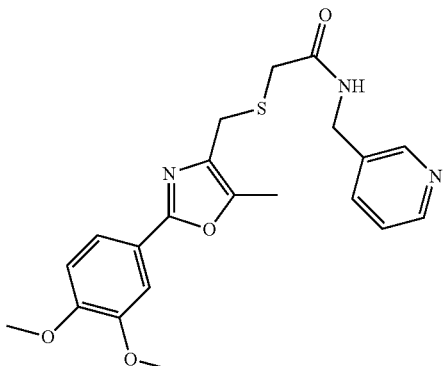 | 413.50 |

TABLE 5-continued
Oxazole amides (R³ = NH-C₃C₇cycloalkyl)
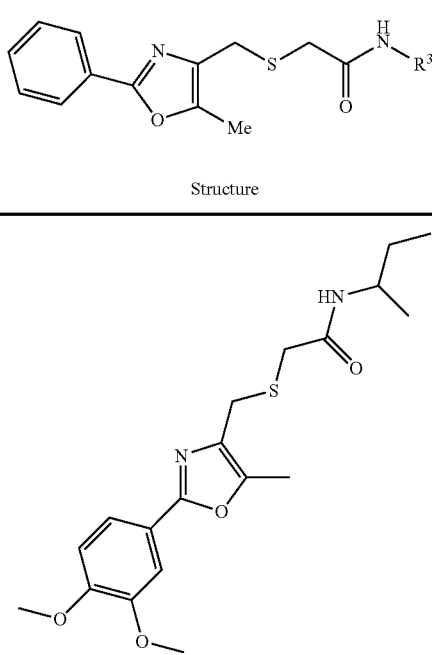
| ID | Structure | MW |
|----|-----------|-----|
| IIa-1095 | 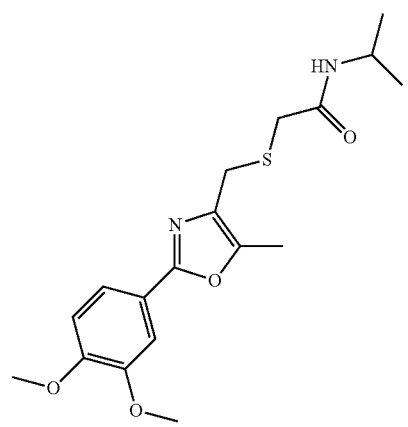 [SMILES: COc1ccc(-c2nc(CSCC(=O)NC(C)C)c(C)o2)cc1OC] | 378.49 |
| IIa-1096 | | 364.47 |
| IIa-1097 | 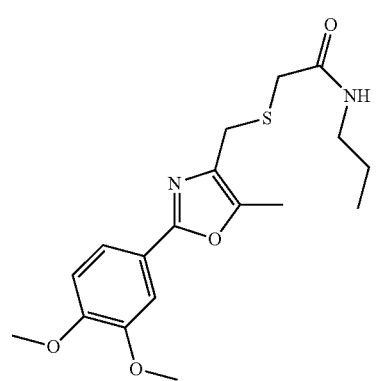 [SMILES: CCCNC(=O)CSCc1nc(-c2ccc(OC)c(OC)c2)oc1C] | 364.47 |

TABLE 5-continued
Oxazole amides ($R^3$ = NH-$C_3C_7$cycloalkyl)
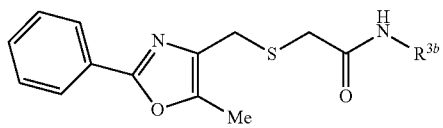
| ID | Structure | MW |
|---|---|---|
| IIa-1098 | 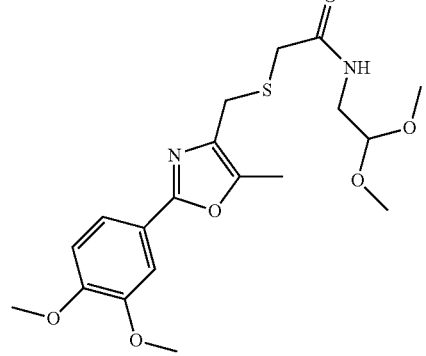 | 410.49 |
| IIa-1099 | 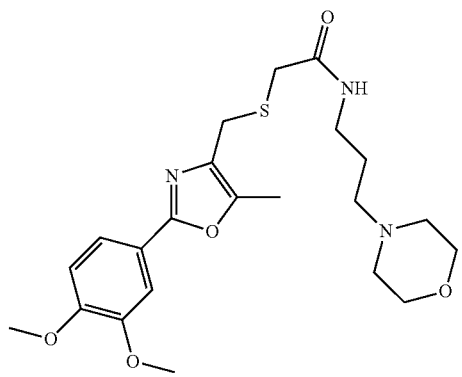 [SMILES: COc1ccc(-c2nc(CSCC(=O)NCCCN3CCOCC3)c(C)o2)cc1OC] | 449.57 |
| IIa-1100 | 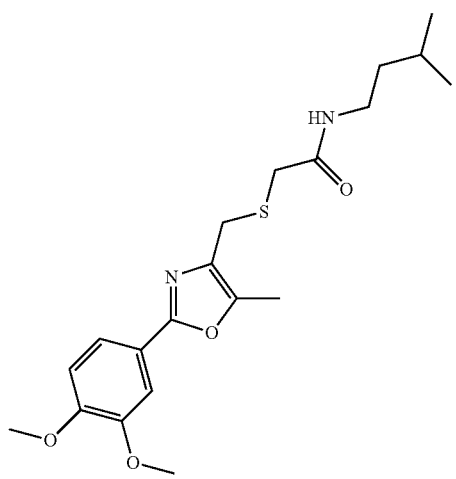 [SMILES: COc1ccc(-c2nc(CSCC(=O)NCCC(C)C)c(C)o2)cc1OC] | 392.52 |

TABLE 5-continued
Oxazole amides (R³ = NH-C₃C₇cycloalkyl)
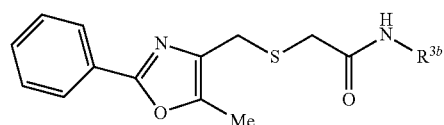
| ID | Structure | MW |
|---|---|---|
| IIa-1101 | | 447.56 |
| IIa-1102 | | 380.47 |
| IIa-1103 | | 408.52 |

TABLE 5-continued
Oxazole amides (R³ = NH-C₃C₇cycloalkyl)
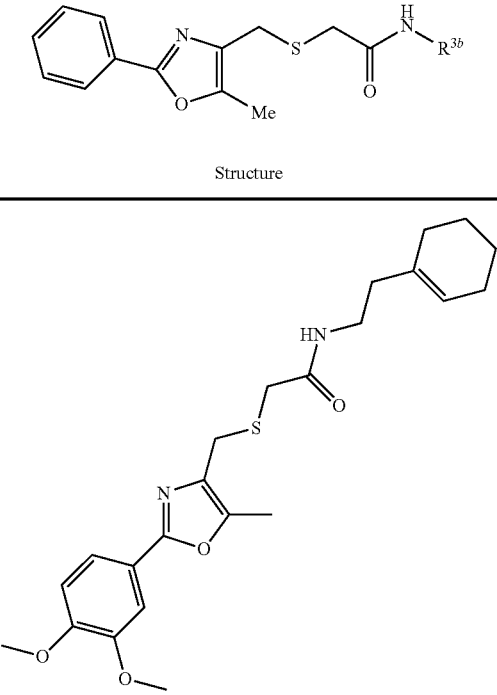
| ID | Structure | MW |
|---|---|---|
| IIa-1104 | 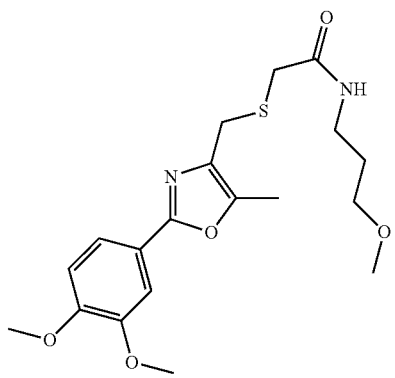 | 430.57 |
| IIa-1105 | 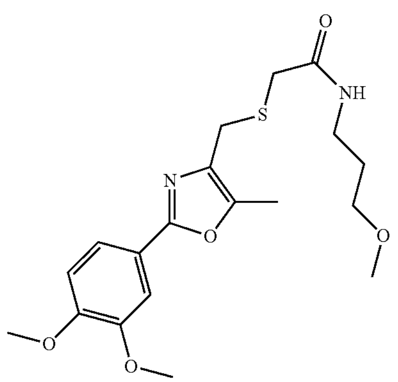 [SMILES: COCCCNC(=O)CSCc1nc(-c2ccc(OC)c(OC)c2)oc1C] | 394.49 |
| IIa-1106 | 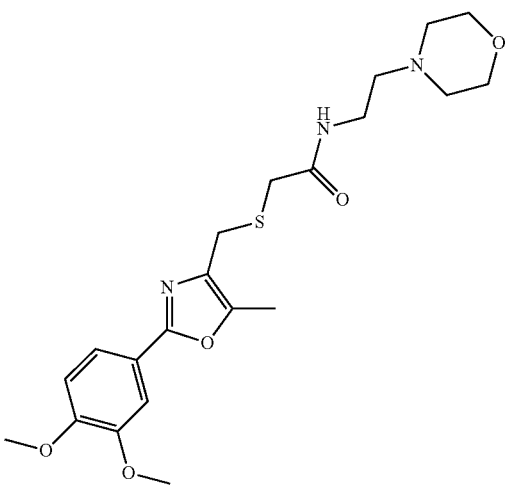 [SMILES: COc1ccc(-c2nc(CSCC(=O)NCCN3CCOCC3)c(C)o2)cc1OC] | 435.55 |

TABLE 5-continued
Oxazole amides (R³ = NH-C₃C₇cycloalkyl)
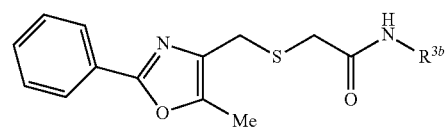
| ID | Structure | MW |
|---|---|---|
| IIa-1107 | | 378.49 |
| IIa-1108 | | 475.66 |
| IIa-1109 | | 461.63 |

TABLE 5-continued
Oxazole amides (R³ = NH-C₃C₇cycloalkyl)
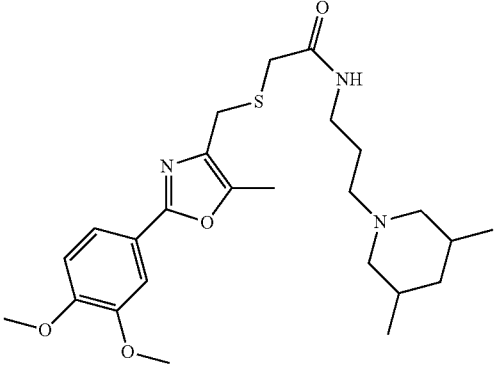
| ID | Structure | MW |
|---|---|---|
| IIa-1110 | 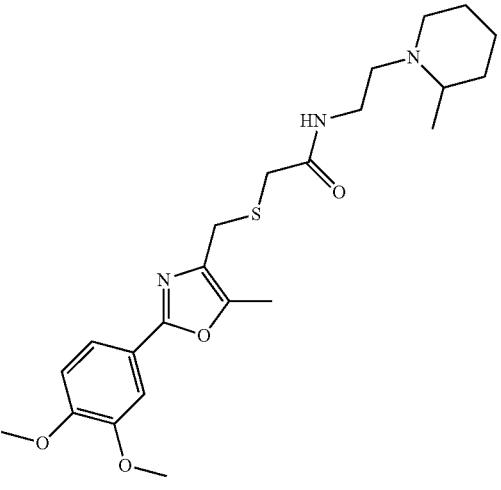 [SMILES: COc1ccc(-c2nc(CSCC(=O)NCCN3CCCCC3C)c(C)o2)cc1OC] | 475.66 |
| IIa-1111 | | 447.60 |
| IIa-1112 | 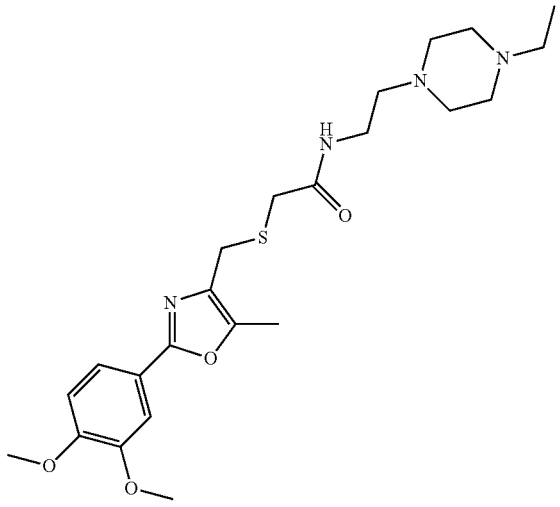 [SMILES: CCN1CCN(CCNC(=O)CSCc2nc(-c3ccc(OC)c(OC)c3)oc2C)CC1] | 462.62 |

TABLE 5-continued
Oxazole amides (R³ = NH-C₃C₇cycloalkyl)
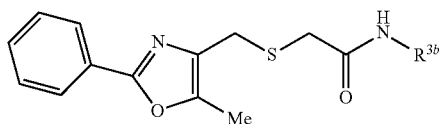
| ID | Structure | MW |
|---|---|---|
| IIa-1113 | | 542.68 |
| IIa-1114 | | 545.11 |

TABLE 5-continued
Oxazole amides (R³ = NH-C₃C₇cycloalkyl)
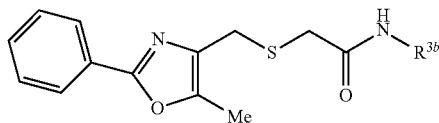
| ID | Structure | MW |
|---|---|---|
| IIa-1115 | 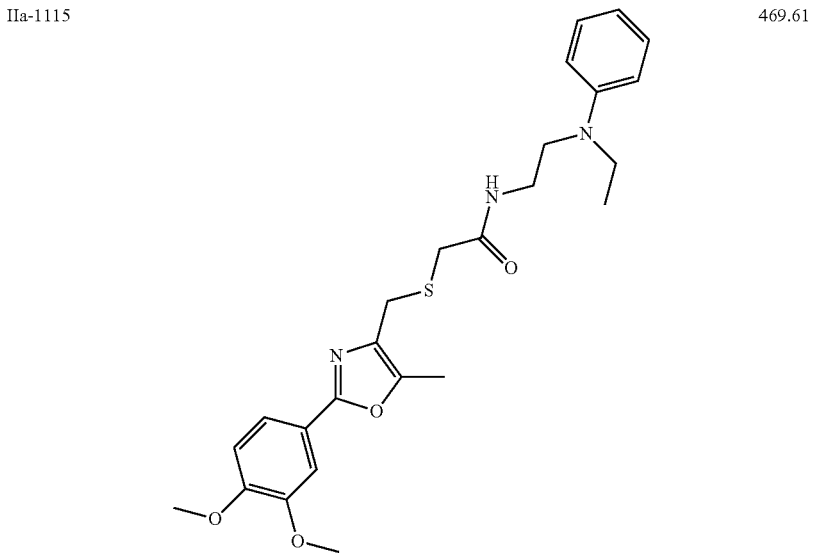 | 469.61 |
| IIa-1116 | 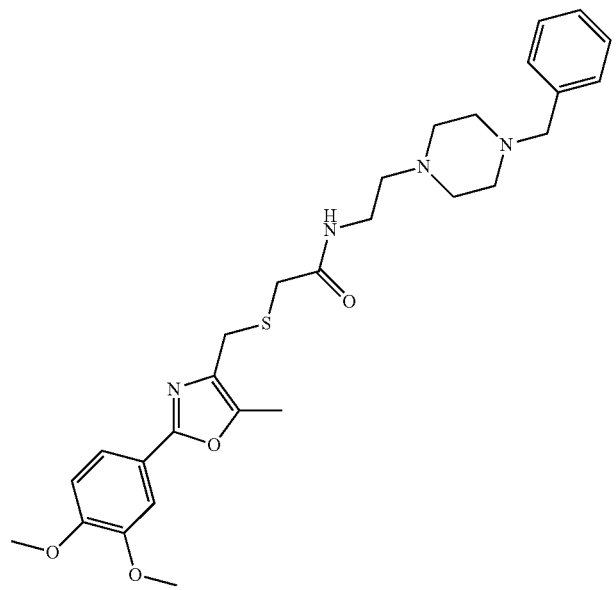 [SMILES: COc1ccc(-c2nc(CSCC(=O)NCCN3CCN(Cc4ccccc4)CC3)c(C)o2)cc1OC] | 524.69 |

TABLE 5-continued
Oxazole amides (R³ = NH-C₃C₇cycloalkyl)
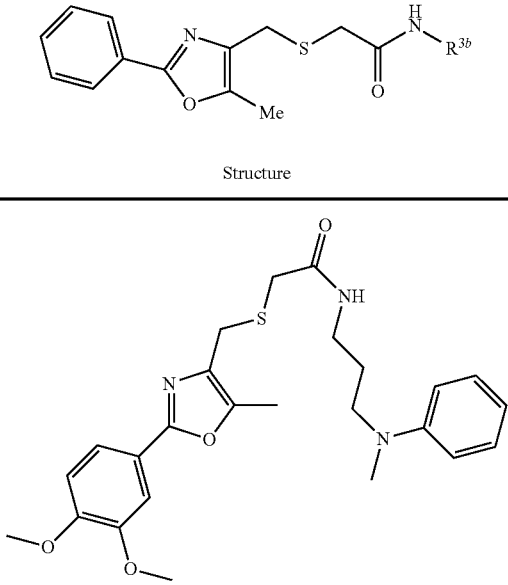
| ID | Structure | MW |
| --- | --- | --- |
| IIa-1117 | 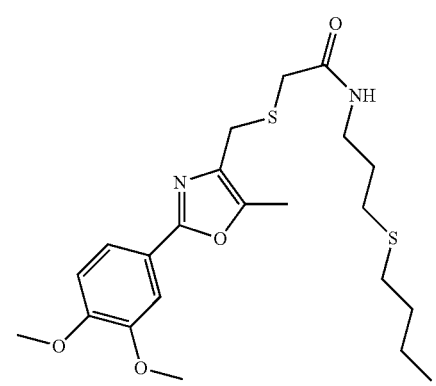 [SMILES: CCCCSCCCNC(=O)CSCc1nc(-c2ccc(OC)c(OC)c2)oc1C] | 469.61 |
| IIa-1118 | | 452.64 |
| IIa-1119 | 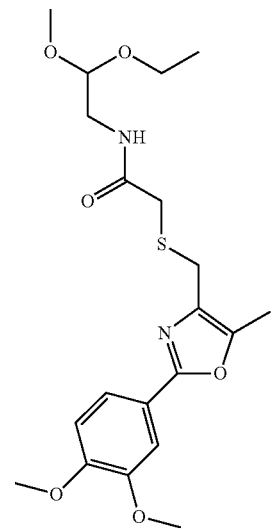 | 412.94 |

TABLE 5-continued
Oxazole amides (R³ = NH-C₃C₇cycloalkyl)
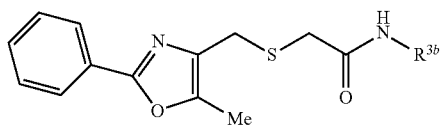
| ID | Structure | MW |
|---|---|---|
| IIa-1120 | 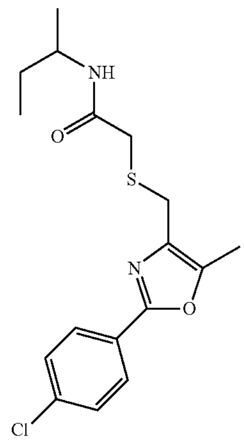 [SMILES: CCC(C)NC(=O)CSCc1nc(-c2ccc(Cl)cc2)oc1C] | 352.89 |
| IIa-1121 | 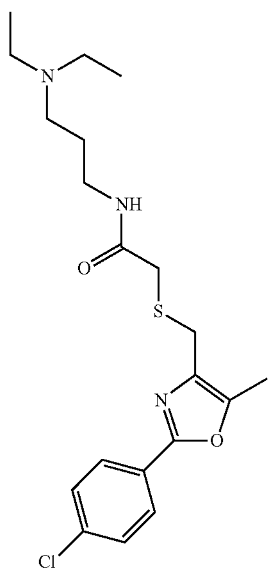 [SMILES: CCN(CC)CCCNC(=O)CSCc1nc(-c2ccc(Cl)cc2)oc1C] | 409.98 |
| IIa-1122 | 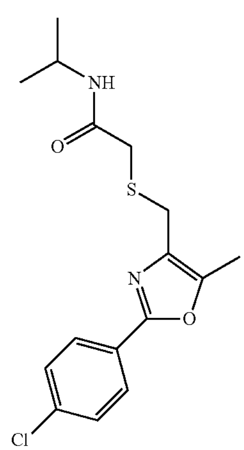 [SMILES: Cc1oc(-c2ccc(Cl)cc2)nc1CSCC(=O)NC(C)C] | 338.86 |

TABLE 5-continued
Oxazole amides (R³ = NH-C₃C₇cycloalkyl)
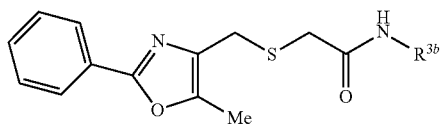
| ID | Structure | MW |
|---|---|---|
| IIa-1123 | 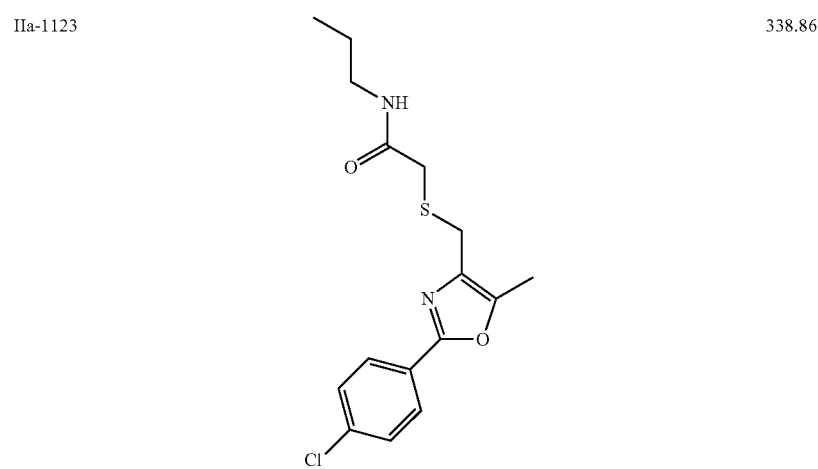 | 338.86 |
| IIa-1124 | 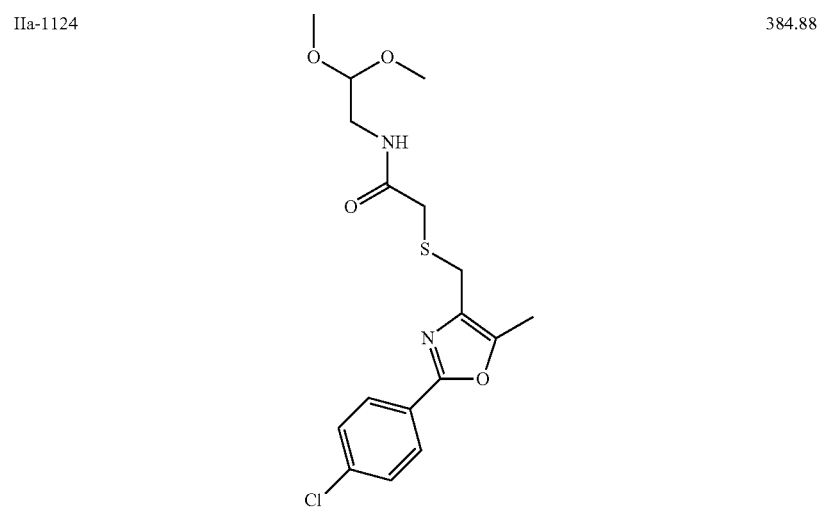 | 384.88 |

TABLE 5-continued
Oxazole amides (R³ = NH-C₃C₇cycloalkyl)
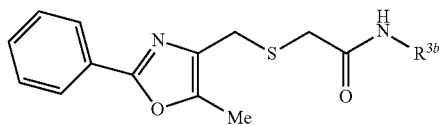
| ID | Structure | MW |
|---|---|---|
| IIa-1125 | 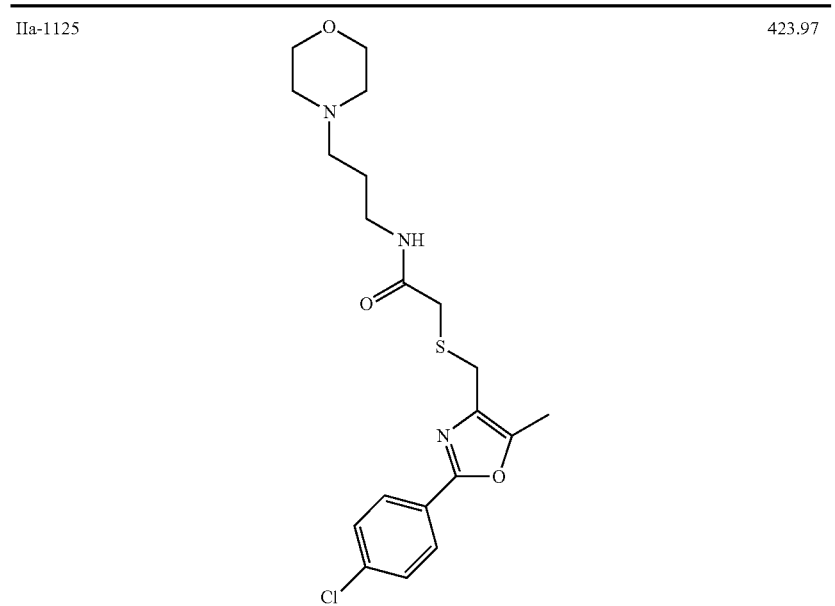 | 423.97 |
| IIa-1126 | 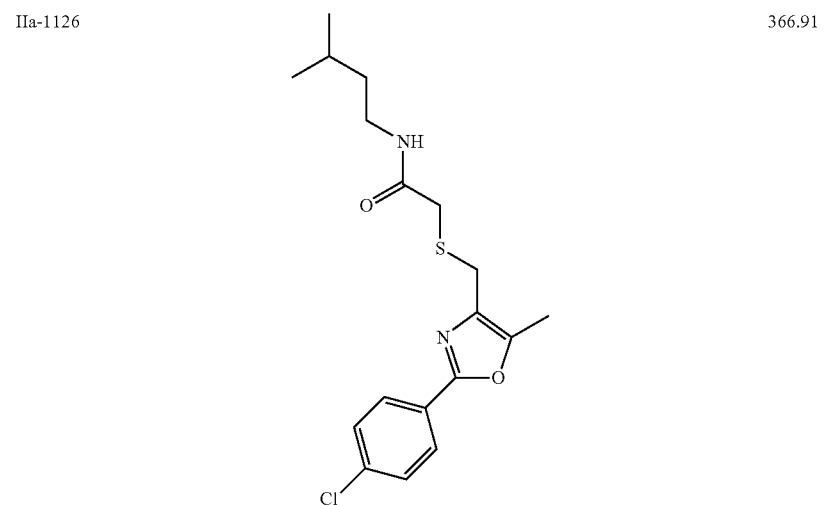 | 366.91 |

TABLE 5-continued
Oxazole amides (R³ = NH-C₃C₇cycloalkyl)
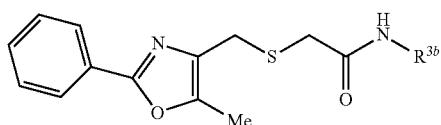
| ID | Structure | MW |
|---|---|---|
| IIa-1127 | | 380.90 |
| IIa-1128 | | 354.86 |

TABLE 5-continued
Oxazole amides (R³ = NH-C₃C₇cycloalkyl)
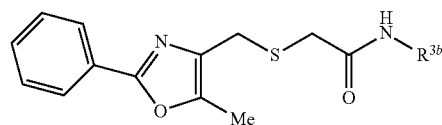
| ID | Structure | MW |
|---|---|---|
| IIa-1129 | | 382.91 |
| IIa-1130 | | 368.89 |

TABLE 5-continued
Oxazole amides (R³ = NH-C₃C₇cycloalkyl)
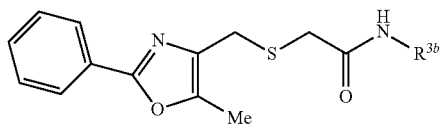
| ID | Structure | MW |
| --- | --- | --- |
| IIa-1131 | | 396.94 |
| IIa-1132 | | 409.94 |

TABLE 5-continued
Oxazole amides (R³ = NH-C₃C₇cycloalkyl)

| ID | Structure | MW |
|---|---|---|
| IIa-1133 | 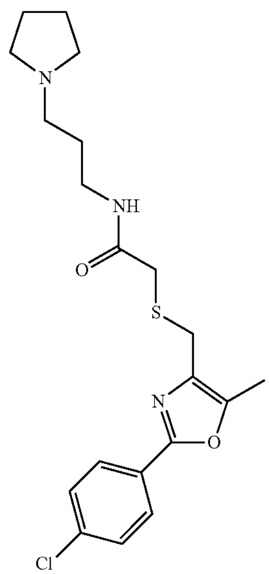 [SMILES: Cc1oc(-c2ccc(Cl)cc2)nc1CSCC(=O)NCCCN1CCCC1] | 407.97 |
| IIa-1134 | 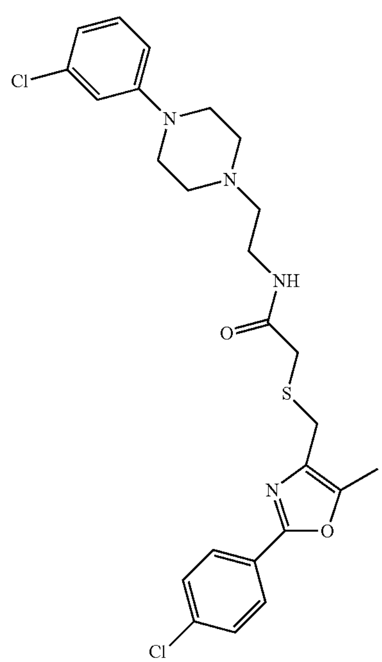 [SMILES: Cc1oc(-c2ccc(Cl)cc2)nc1CSCC(=O)NCCN1CCN(c2cccc(Cl)c2)CC1] | 519.50 |

TABLE 5-continued
Oxazole amides (R³ = NH-C₃C₇cycloalkyl)
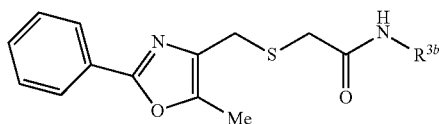
| ID | Structure | MW |
|---|---|---|
| IIa-1135 | | 444.00 |
| IIa-1136 | | 453.07 |

TABLE 5-continued
Oxazole amides (R³ = NH-C₃C₇cycloalkyl)
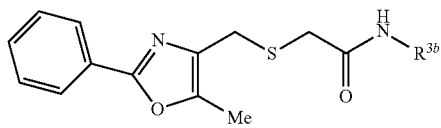
| ID | Structure | MW |
|---|---|---|
| IIa-1137 | 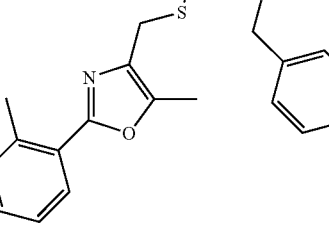 | 367.47 |
| IIa-1138 | 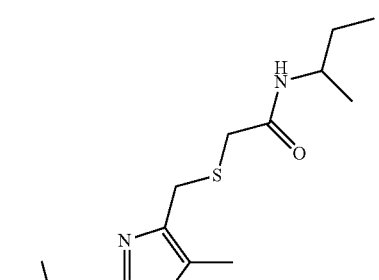 | 332.47 |
| IIa-1139 | 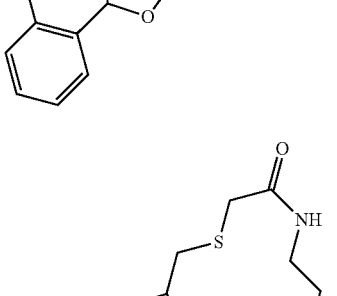 | 334.44 |
| IIa-1140 | 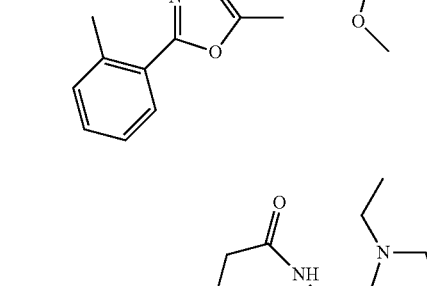 | 387.55 |

TABLE 5-continued
Oxazole amides (R³ = NH-C₃C₇cycloalkyl)
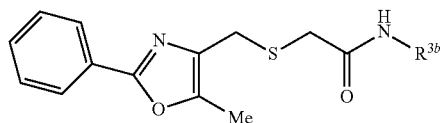
| ID | Structure | MW |
|---|---|---|
| IIa-1141 | | 372.51 |
| IIa-1142 | | 362.49 |
| IIa-1143 | | 348.47 |
| IIa-1144 | | 376.52 |

TABLE 5-continued
Oxazole amides (R³ = NH-C₃C₇cycloalkyl)
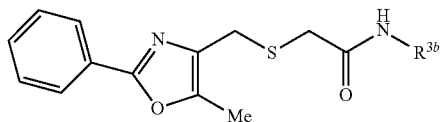
| ID | Structure | MW |
|---|---|---|
| IIa-1145 | 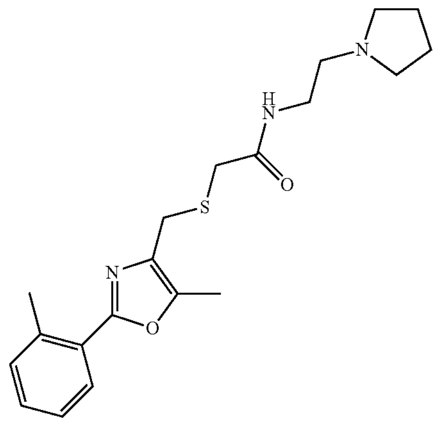 [SMILES: Cc1ccccc1-c1nc(CSCC(=O)NCCN2CCCC2)c(C)o1] | 373.52 |
| IIa-1146 | 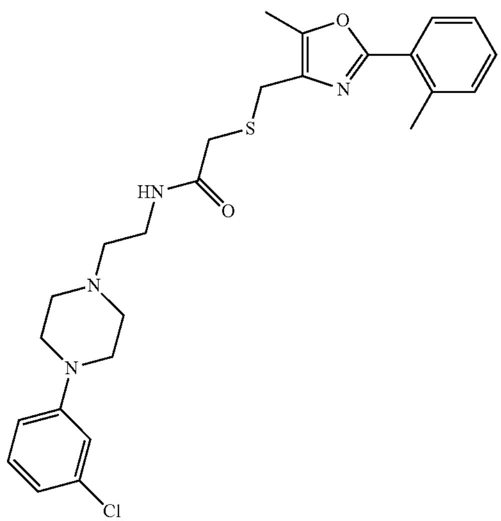 [SMILES: Cc1ccccc1-c1nc(CSCC(=O)NCCN2CCN(c3cccc(Cl)c3)CC2)c(C)o1] | 499.08 |
| IIa-1147 | 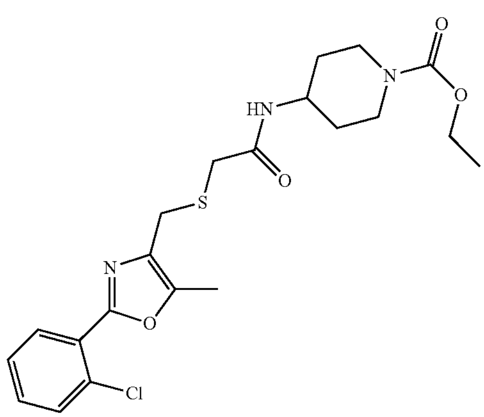 [SMILES: CCOC(=O)N1CCC(NC(=O)CSCc2nc(-c3ccccc3Cl)oc2C)CC1] | 451.98 |

TABLE 5-continued
Oxazole amides (R³ = NH-C₃C₇cycloalkyl)
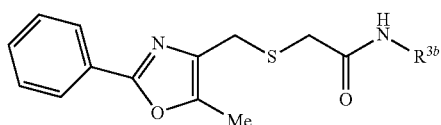
| ID | Structure | MW |
|---|---|---|
| IIa-1148 | 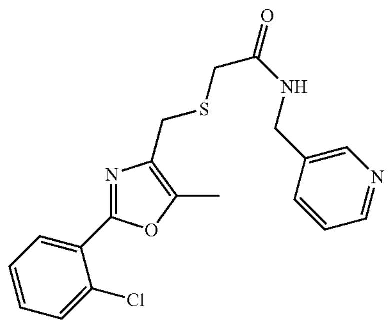 [SMILES: Cc1oc(-c2ccccc2Cl)nc1CSCC(=O)NCc1cccnc1] | 387.89 |
| IIa-1149 | 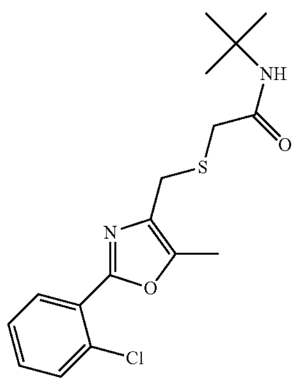 [SMILES: Cc1oc(-c2ccccc2Cl)nc1CSCC(=O)NC(C)(C)C] | 352.89 |
| IIa-1150 | 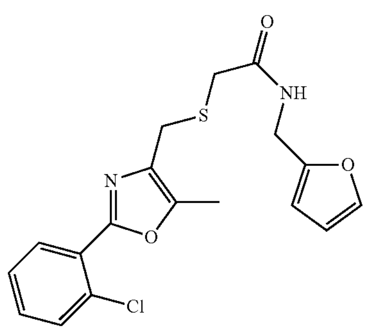 [SMILES: Cc1oc(-c2ccccc2Cl)nc1CSCC(=O)NCc1cccs1] | 376.86 |
| IIa-1151 | 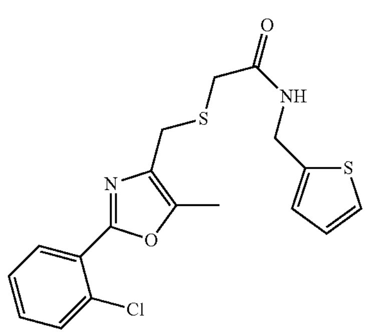 | 392.93 |

TABLE 5-continued
Oxazole amides ($R^3$ = NH-$C_3C_7$cycloalkyl)
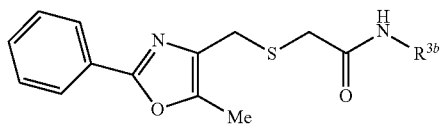
| ID | Structure | MW |
|---|---|---|
| IIa-1152 | 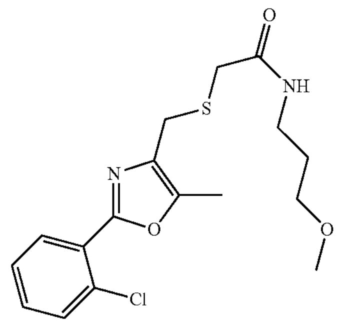 [SMILES: COCCCNC(=O)CSCc1nc(-c2ccccc2Cl)oc1C] | 368.89 |
| IIa-1153 | 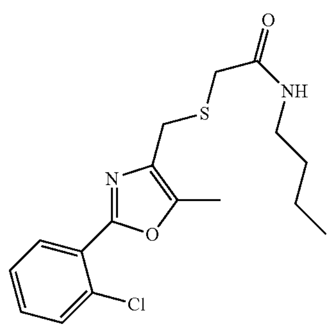 [SMILES: CCCCNC(=O)CSCc1nc(-c2ccccc2Cl)oc1C] | 352.89 |
| IIa-1154 | 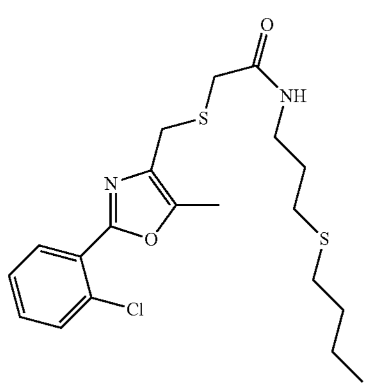 [SMILES: CCCCSCCCNC(=O)CSCc1nc(-c2ccccc2Cl)oc1C] | 427.03 |

TABLE 5-continued
Oxazole amides (R³ = NH-C₃C₇cycloalkyl)
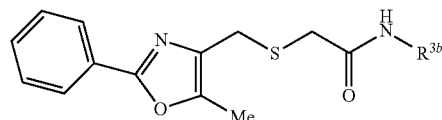
| ID | Structure | MW |
|---|---|---|
| IIa-1155 | 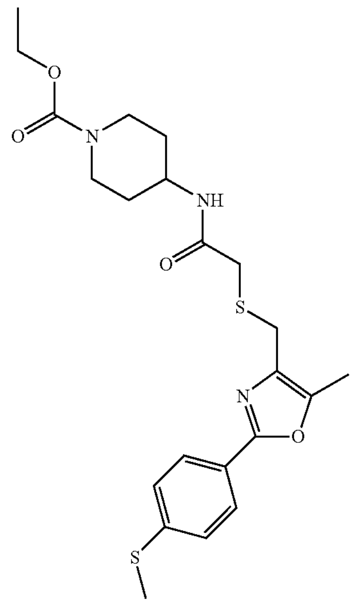 [SMILES: CCOC(=O)N1CCC(NC(=O)CSCc2nc(-c3ccc(SC)cc3)oc2C)CC1] | 463.62 |
| IIa-1156 | 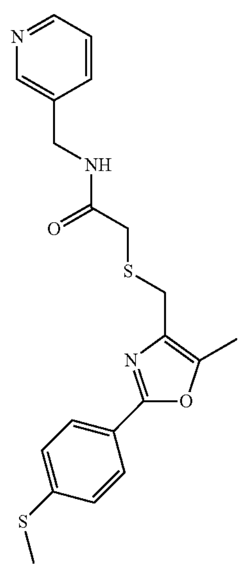 [SMILES: CSc1ccc(-c2nc(CSCC(=O)NCc3cccnc3)c(C)o2)cc1] | 399.54 |

TABLE 5-continued
Oxazole amides ($R^3$ = NH-$C_3C_7$cycloalkyl)
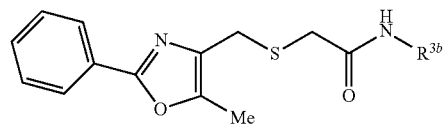
| ID | Structure | MW |
|---|---|---|
| IIa-1157 | 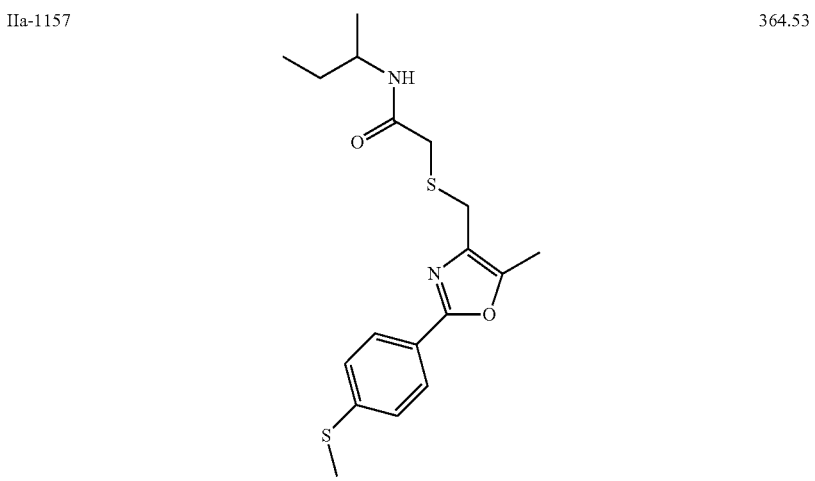 | 364.53 |
| IIa-1158 | 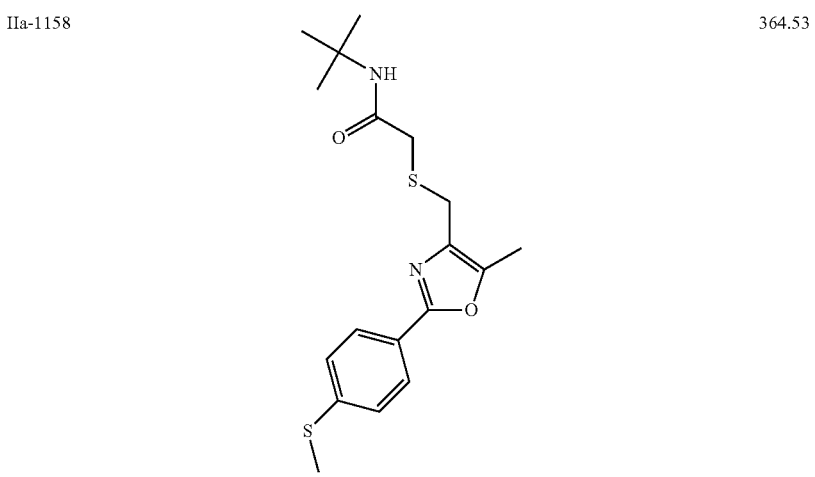 | 364.53 |

TABLE 5-continued
Oxazole amides (R³ = NH-C₃C₇cycloalkyl)
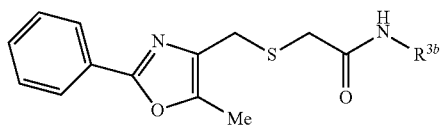
| ID | Structure | MW |
|---|---|---|
| IIa-1159 | | 379.55 |
| IIa-1160 | | 388.51 |

TABLE 5-continued
Oxazole amides (R³ = NH-C₃C₇cycloalkyl)
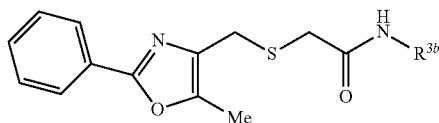
| ID | Structure | MW |
|---|---|---|
| IIa-1161 | 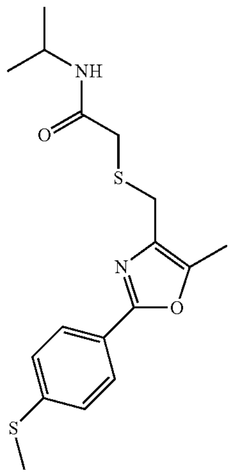 [SMILES: CSc1ccc(-c2nc(CSCC(=O)NC(C)C)c(C)o2)cc1] | 350.51 |
| IIa-1162 | 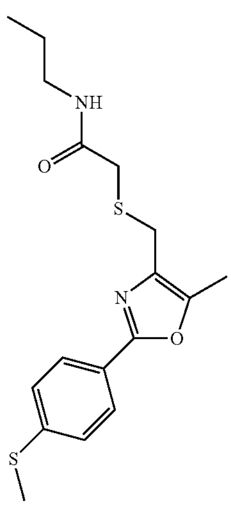 [SMILES: CCCNC(=O)CSCc1nc(-c2ccc(SC)cc2)oc1C] | 350.51 |

TABLE 5-continued
Oxazole amides ($R^3$ = NH-$C_3C_7$cycloalkyl)
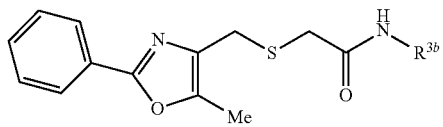
| ID | Structure | MW |
|---|---|---|
| IIa-1163 | 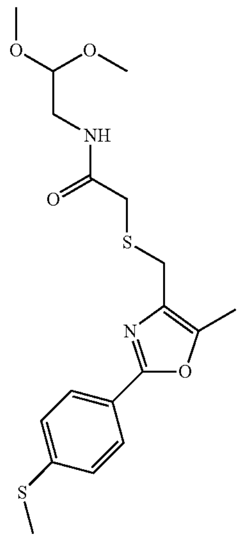 [SMILES: COC(CNC(=O)CSCc1nc(-c2ccc(SC)cc2)oc1C)OC] | 396.53 |
| IIa-1164 | 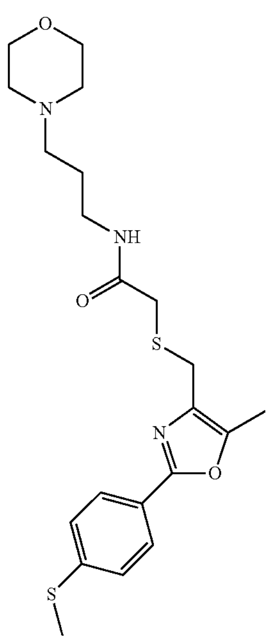 [SMILES: CSc1ccc(-c2nc(CSCC(=O)NCCCN3CCOCC3)c(C)o2)cc1] | 435.61 |

TABLE 5-continued
Oxazole amides ($R^3$ = NH-$C_3C_7$cycloalkyl)
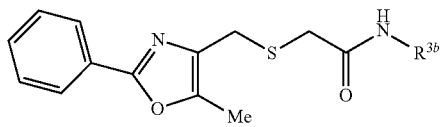
| ID | Structure | MW |
|---|---|---|
| IIa-1165 | | 378.56 |
| IIa-1166 | | 392.54 |

TABLE 5-continued
Oxazole amides (R³ = NH-C₃C₇cycloalkyl)
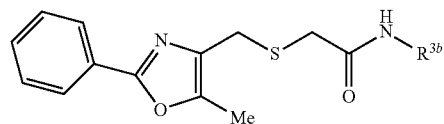
| ID | Structure | MW |
|---|---|---|
| IIa-1167 | | 433.60 |
| IIa-1168 | | 366.50 |

TABLE 5-continued
Oxazole amides ($R^3$ = NH-$C_3C_7$cycloalkyl)
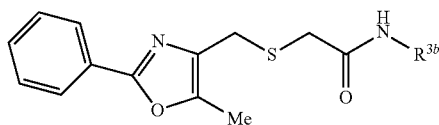
| ID | Structure | MW |
|---|---|---|
| IIa-1169 | | 419.61 |
| IIa-1170 | | 404.58 |

TABLE 5-continued
Oxazole amides (R³ = NH-C₃C₇cycloalkyl)
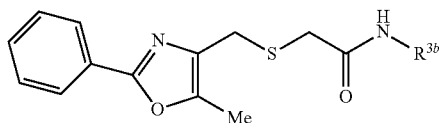
| ID | Structure | MW |
|---|---|---|
| IIa-1171 | 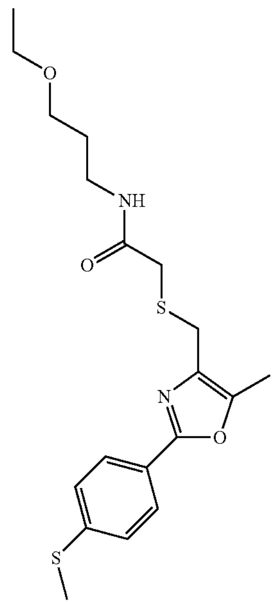 [SMILES: CCOCCCNC(=O)CSCc1nc(-c2ccc(SC)cc2)oc1C] | 394.56 |
| IIa-1172 | 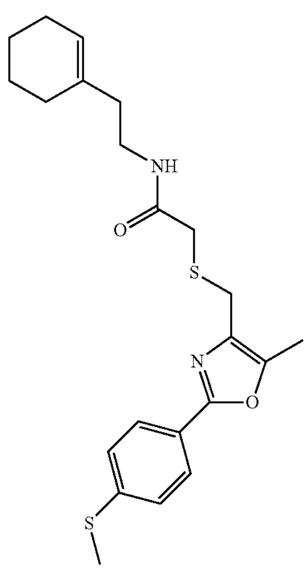 [SMILES: CSc1ccc(-c2nc(CSCC(=O)NCCC3=CCCCC3)c(C)o2)cc1] | 416.61 |

TABLE 5-continued
Oxazole amides ($R^3$ = NH-$C_3C_7$cycloalkyl)
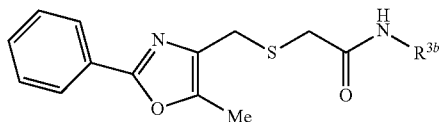
| ID | Structure | MW |
|---|---|---|
| IIa-1173 | 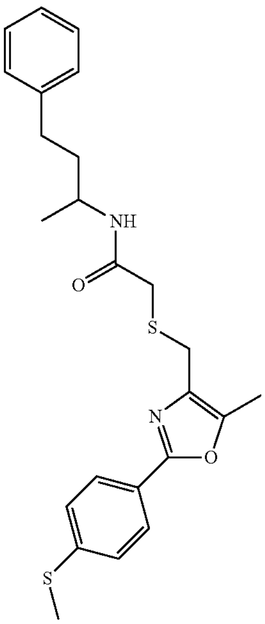 [SMILES: CSc1ccc(-c2nc(CSCC(=O)NC(C)CCc3ccccc3)c(C)o2)cc1] | 440.63 |
| IIa-1174 | 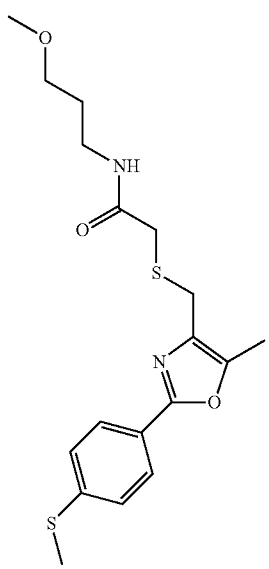 | 380.53 |

TABLE 5-continued
Oxazole amides (R³ = NH-C₃C₇cycloalkyl)
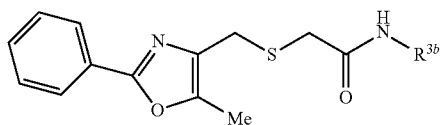
| ID | Structure | MW |
|---|---|---|
| IIa-1175 | 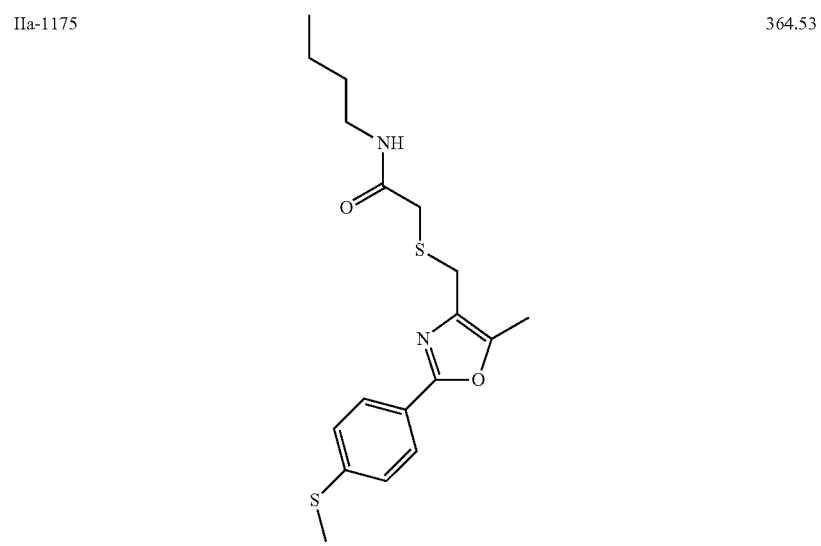 | 364.53 |
| IIa-1176 | 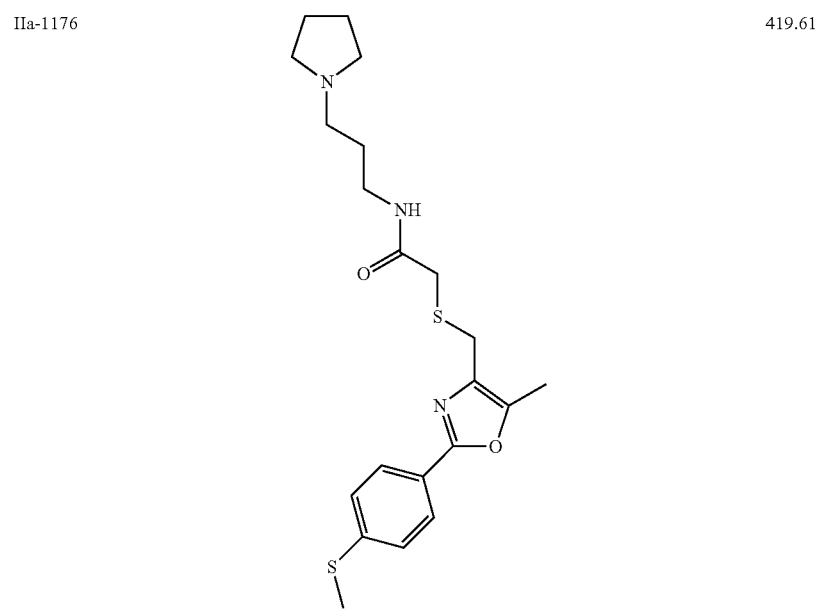 | 419.61 |

TABLE 5-continued
Oxazole amides (R³ = NH-C₃C₇cycloalkyl)
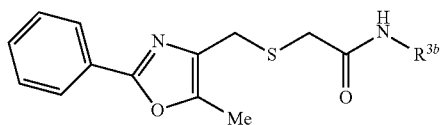
| ID | Structure | MW |
|---|---|---|
| IIa-1177 | | 405.59 |
| IIa-1178 | | 455.65 |

TABLE 5-continued
Oxazole amides (R³ = NH-C₃C₇cycloalkyl)
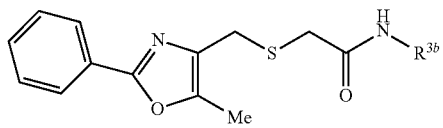
| ID | Structure | MW |
|---|---|---|
| IIa-1179 | 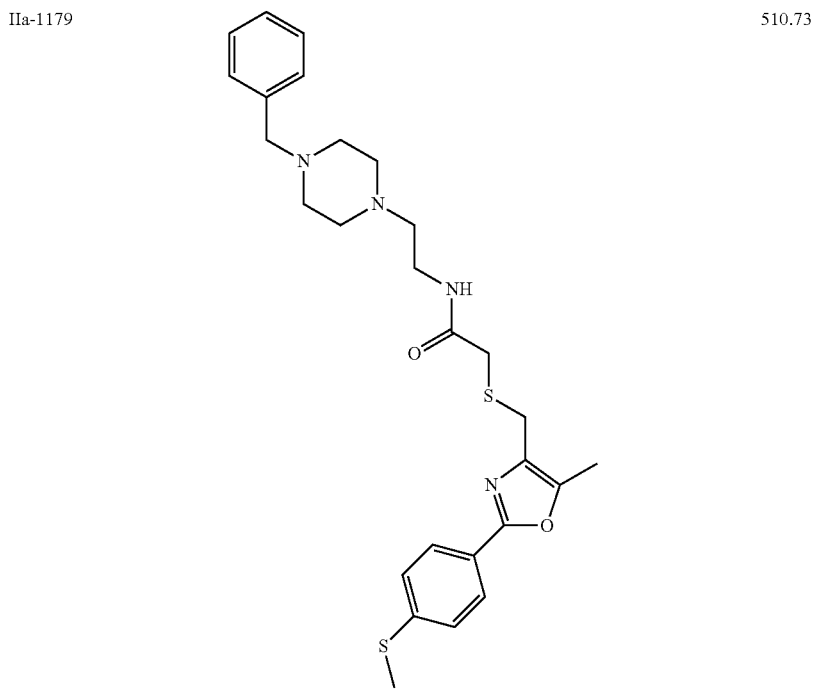 | 510.73 |
| IIa-1180 | 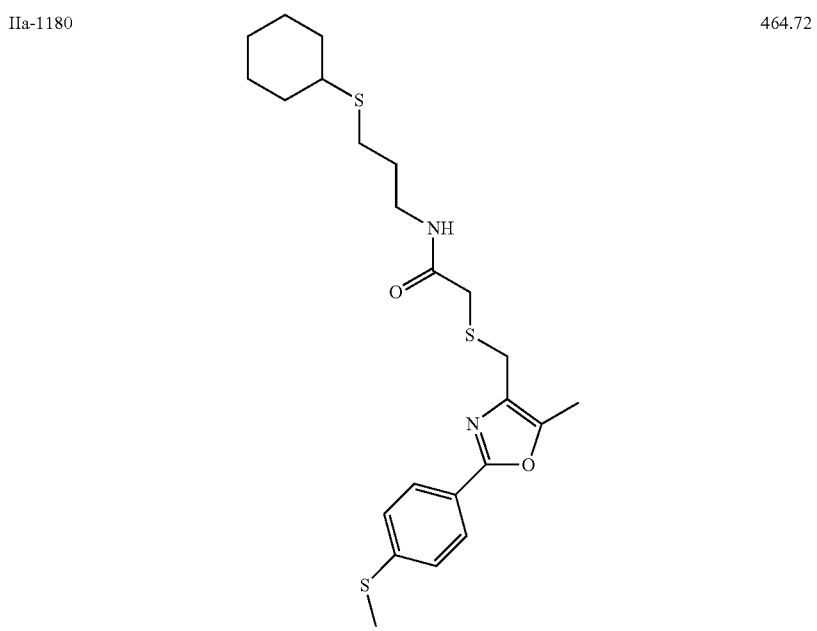 | 464.72 |

TABLE 5-continued
Oxazole amides (R³ = NH-C₃C₇cycloalkyl)
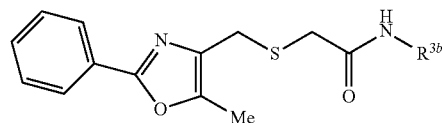
| ID | Structure | MW |
| --- | --- | --- |
| IIa-1181 | | 346.50 |
| IIa-1182 | | 346.50 |
| IIa-1183 | | 361.51 |

TABLE 5-continued
Oxazole amides (R³ = NH-C₃C₇cycloalkyl)
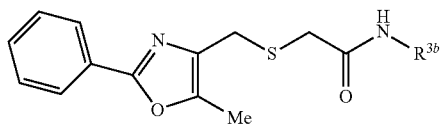
| ID | Structure | MW |
|---|---|---|
| IIa-1184 | | 370.47 |
| IIa-1185 | | 378.49 |
| IIa-1186 | | 415.56 |

TABLE 5-continued
Oxazole amides (R³ = NH-C₃C₇cycloalkyl)
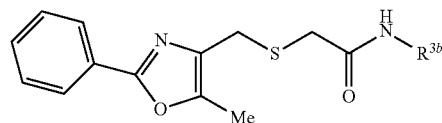
| ID | Structure | MW |
|---|---|---|
| IIa-1187 | 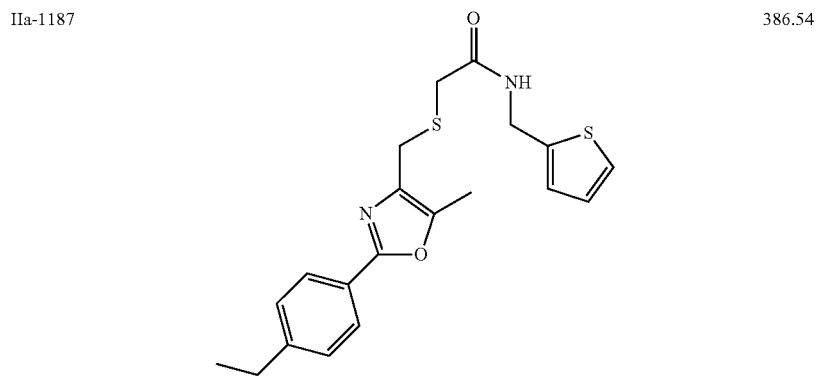 | 386.54 |
| IIa-1188 | 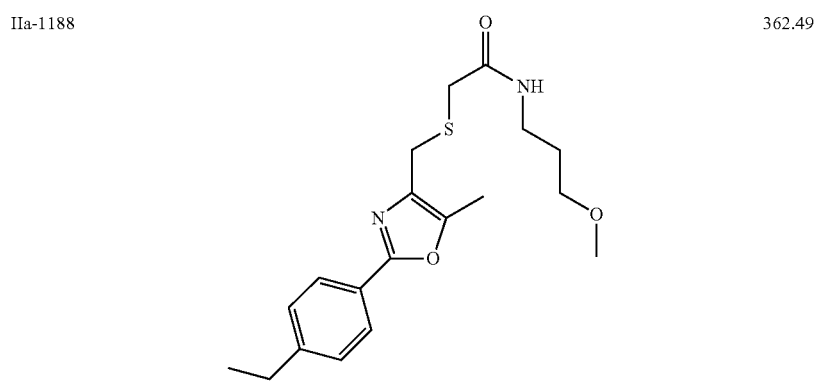 | 362.49 |
| IIa-1189 | 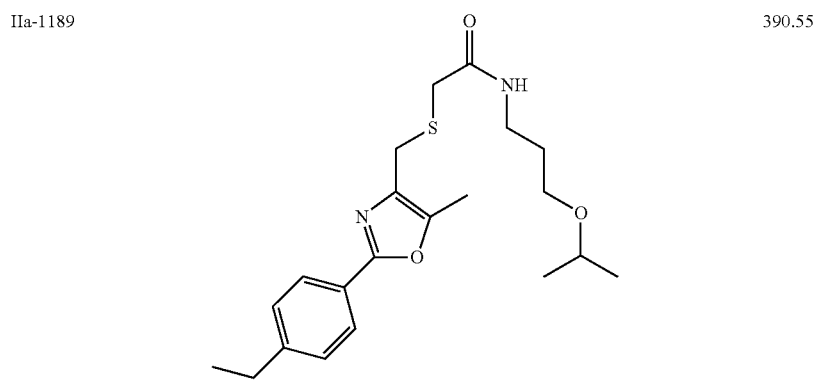 | 390.55 |

TABLE 5-continued
Oxazole amides (R³ = NH-C₃C₇cycloalkyl)
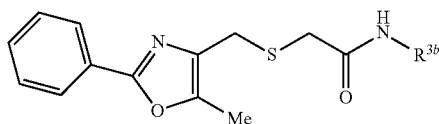
| ID | Structure | MW |
|---|---|---|
| IIa-1190 | 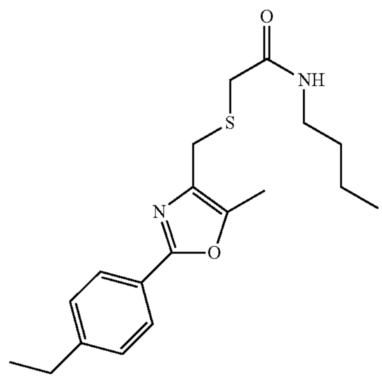 [SMILES: CCCCNC(=O)CSCc1nc(-c2ccc(CC)cc2)oc1C] | 346.50 |
| IIa-1191 | 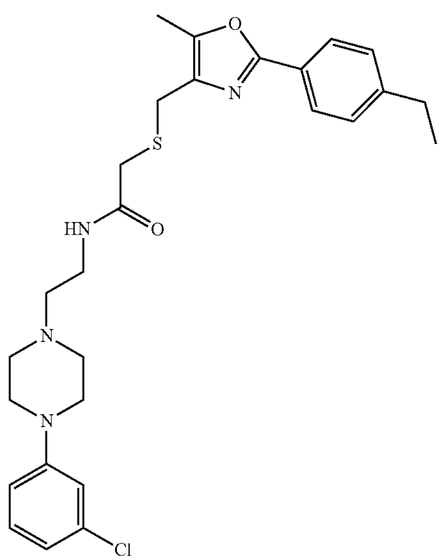 [SMILES: CCc1ccc(-c2nc(CSCC(=O)NCCN3CCN(c4cccc(Cl)c4)CC3)c(C)o2)cc1] | 513.11 |
| IIa-1192 | 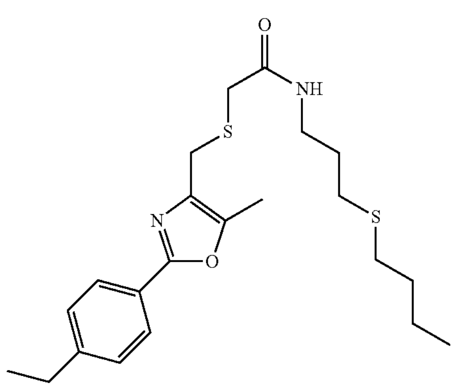 [SMILES: CCCCSCCCNC(=O)CSCc1nc(-c2ccc(CC)cc2)oc1C] | 420.64 |

TABLE 5-continued
Oxazole amides (R³ = NH-C₃C₇cycloalkyl)
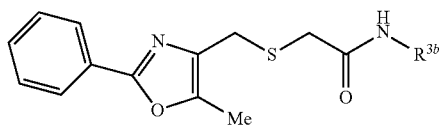
| ID | Structure | MW |
|---|---|---|
| IIa-1193 | | 446.68 |
| IIa-1194 | | 384.88 |
| IIa-1195 | | 366.91 |

TABLE 5-continued
Oxazole amides ($R^3$ = NH-$C_3C_7$cycloalkyl)
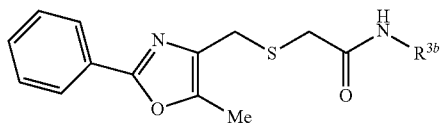
| ID | Structure | MW |
|---|---|---|
| IIa-1196 | 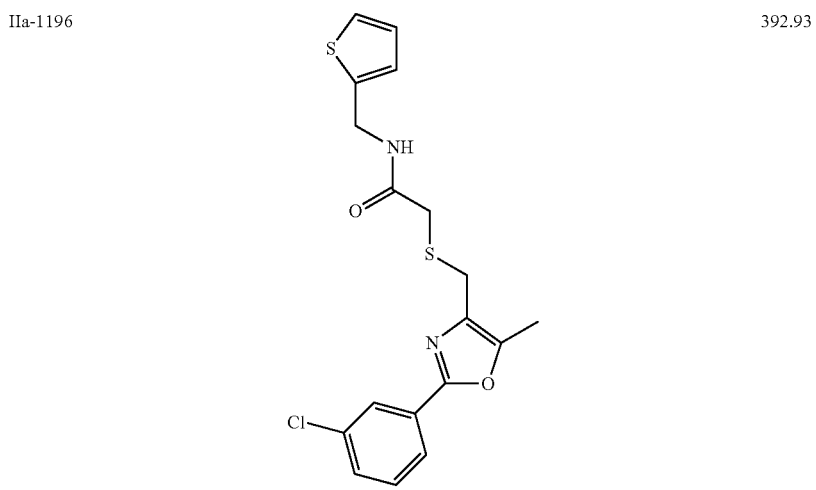 | 392.93 |
| IIa-1197 | 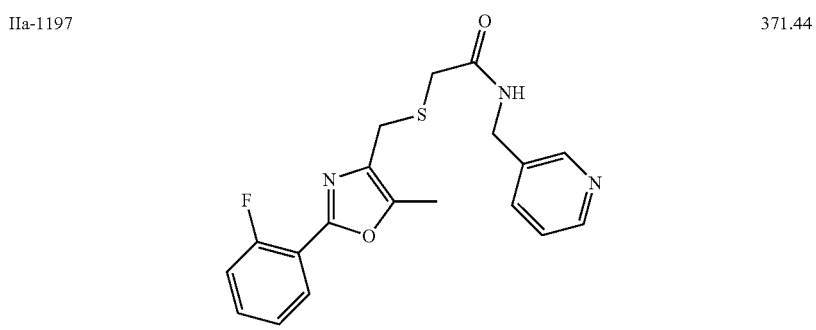 | 371.44 |
| IIa-1198 | 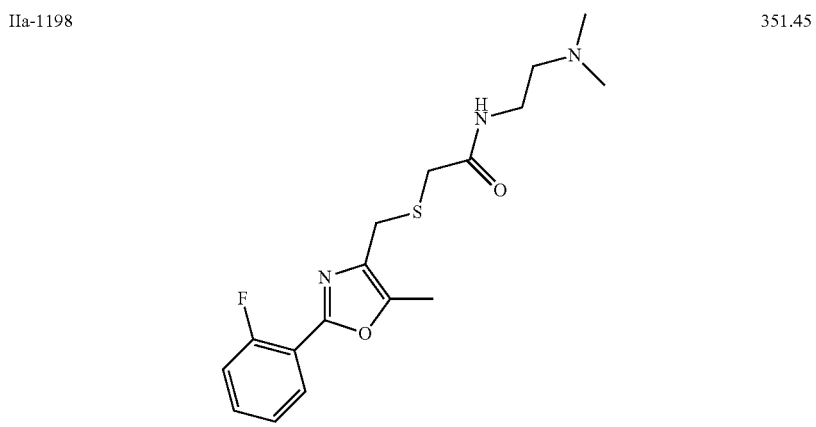 | 351.45 |

TABLE 5-continued
Oxazole amides ($R^3$ = NH-$C_3C_7$cycloalkyl)
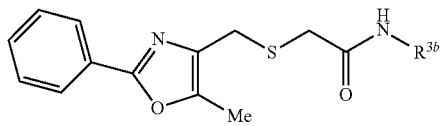
| ID | Structure | MW |
|---|---|---|
| IIa-1199 | | 360.41 |
| IIa-1200 | | 350.46 |
| IIa-1201 | | 364.44 |
| IIa-1202 | | 405.49 |

TABLE 5-continued
Oxazole amides (R³ = NH-C₃C₇cycloalkyl)
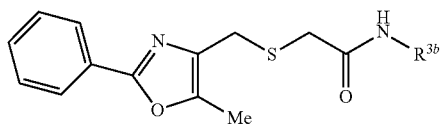
| ID | Structure | MW |
|---|---|---|
| IIa-1203 | | 338.40 |
| IIa-1204 | | 366.46 |
| IIa-1205 | | 352.43 |
| IIa-1206 | | 377.48 |

TABLE 5-continued
Oxazole amides ($R^3$ = NH-$C_3C_7$cycloalkyl)
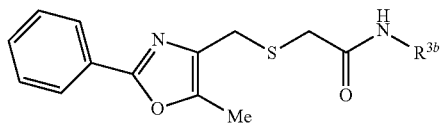
| ID | Structure | MW |
|---|---|---|
| IIa-1207 | | 410.58 |
| IIa-1208 | | 367.47 |
| IIa-1209 | | 332.47 |

TABLE 5-continued
Oxazole amides (R³ = NH-C₃C₇cycloalkyl)
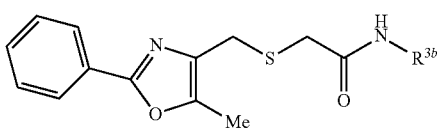
| ID | Structure | MW |
|---|---|---|
| IIa-1210 | | 403.55 |
| IIa-1211 | | 334.44 |

TABLE 5-continued
Oxazole amides (R³ = NH-C₃C₇cycloalkyl)
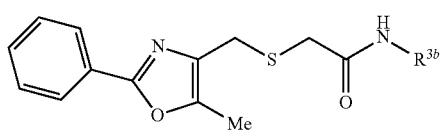
| ID | Structure | MW |
|---|---|---|
| IIa-1212 | 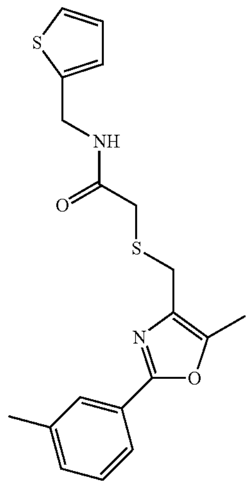 | 372.51 |
| IIa-1213 | 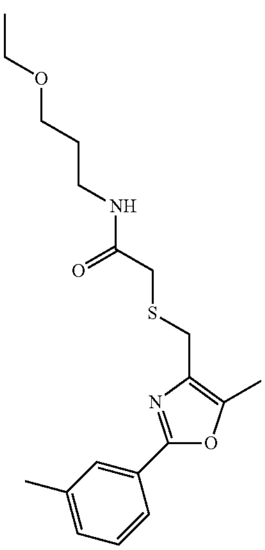 [SMILES: CCOCCCNC(=O)CSCc1nc(-c2cccc(C)c2)oc1C] | 362.49 |

TABLE 5-continued
Oxazole amides (R³ = NH-C₃C₇cycloalkyl)
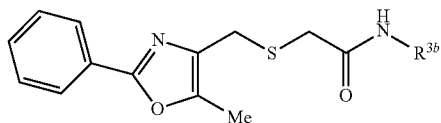
| ID | Structure | MW |
|---|---|---|
| IIa-1214 | | 332.47 |
| IIa-1215 | | 401.58 |

TABLE 5-continued
Oxazole amides (R³ = NH-C₃C₇cycloalkyl)
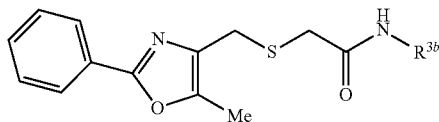
| ID | Structure | MW |
|---|---|---|
| IIa-1216 | | 499.08 |
| IIa-1217 | | 431.56 |
| IIa-1218 | | 392.52 |

TABLE 5-continued
Oxazole amides (R³ = NH-C₃C₇cycloalkyl)
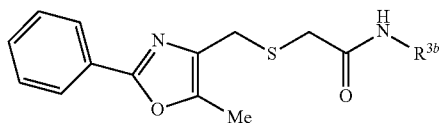
| ID | Structure | MW |
|---|---|---|
| IIa-1219 | 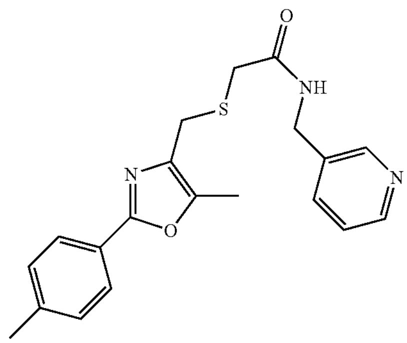 [SMILES: Cc1ccc(-c2nc(CSCC(=O)NCc3cccnc3)c(C)o2)cc1] | 367.47 |
| IIa-1220 | 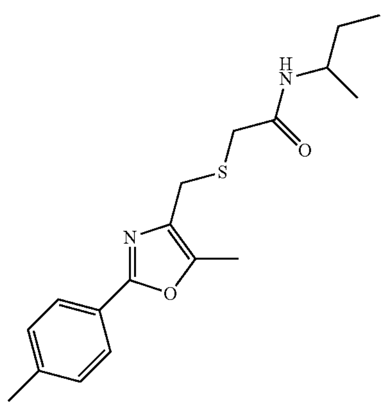 [SMILES: CCC(C)NC(=O)CSCc1nc(-c2ccc(C)cc2)oc1C] | 332.47 |
| IIa-1221 | 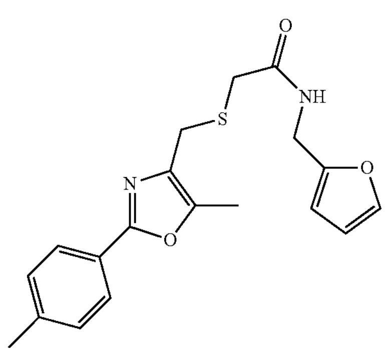 [SMILES: Cc1ccc(-c2nc(CSCC(=O)NCc3ccco3)c(C)o2)cc1] | 356.45 |

TABLE 5-continued
Oxazole amides (R³ = NH-C₃C₇cycloalkyl)
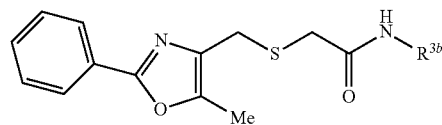
| ID | Structure | MW |
|---|---|---|
| IIa-1222 | 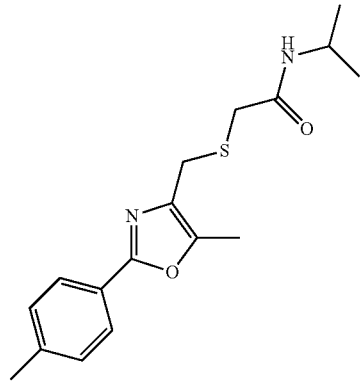 [SMILES: Cc1ccc(-c2nc(CSCC(=O)NC(C)C)c(C)o2)cc1] | 318.44 |
| IIa-1223 | 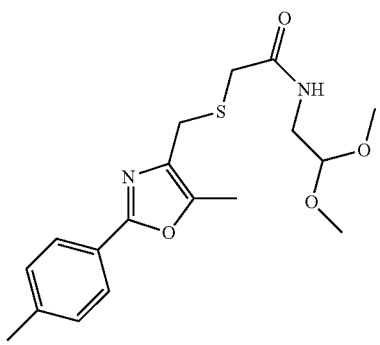 | 364.47 |
| IIa-1224 | 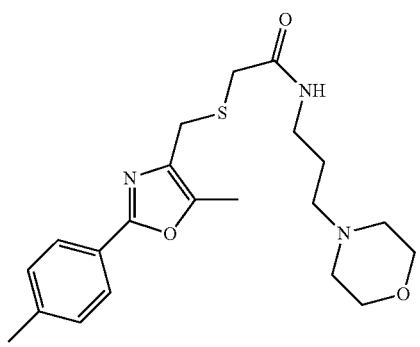 [SMILES: Cc1ccc(-c2nc(CSCC(=O)NCCCN3CCOCC3)c(C)o2)cc1] | 403.55 |

TABLE 5-continued
Oxazole amides (R³ = NH-C₃C₇cycloalkyl)
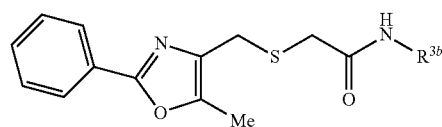
| ID | Structure | MW |
|---|---|---|
| IIa-1225 | 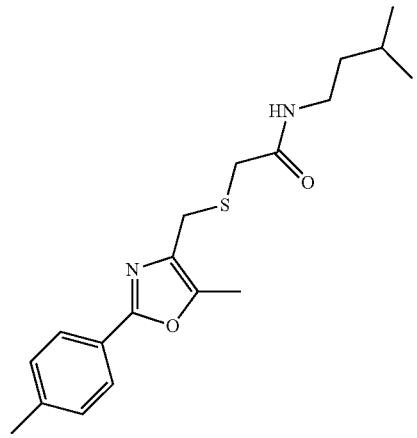 [SMILES: Cc1ccc(-c2nc(CSCC(=O)NCCC(C)C)c(C)o2)cc1] | 346.50 |
| IIa-1226 | 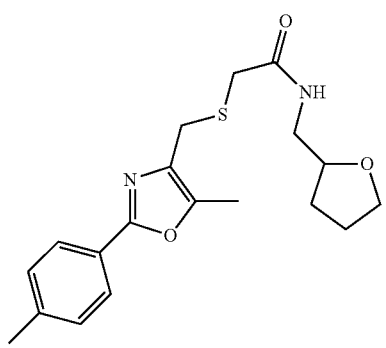 [SMILES: Cc1ccc(-c2nc(CSCC(=O)NCC3CCCO3)c(C)o2)cc1] | 360.48 |
| IIa-1227 | 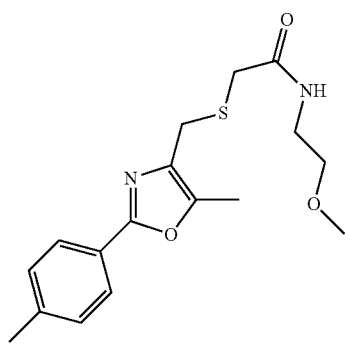 | 334.44 |

TABLE 5-continued
Oxazole amides (R³ = NH-C₃C₇cycloalkyl)
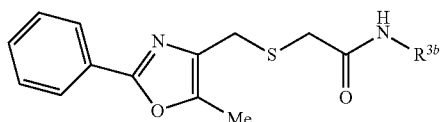
| ID | Structure | MW |
|---|---|---|
| IIa-1228 | | 372.51 |
| IIa-1229 | | 362.49 |
| IIa-1230 | | 408.57 |
| IIa-1231 | | 348.47 |

TABLE 5-continued
Oxazole amides (R³ = NH-C₃C₇cycloalkyl)
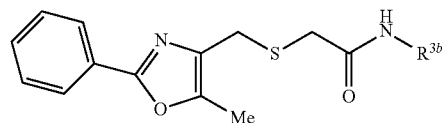
| ID | Structure | MW |
|---|---|---|
| IIa-1232 | 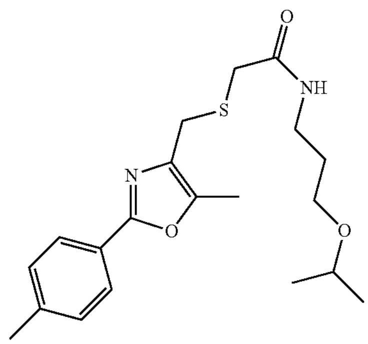 [SMILES: Cc1ccc(-c2nc(CSCC(=O)NCCCOC(C)C)c(C)o2)cc1] | 376.52 |
| IIa-1233 | 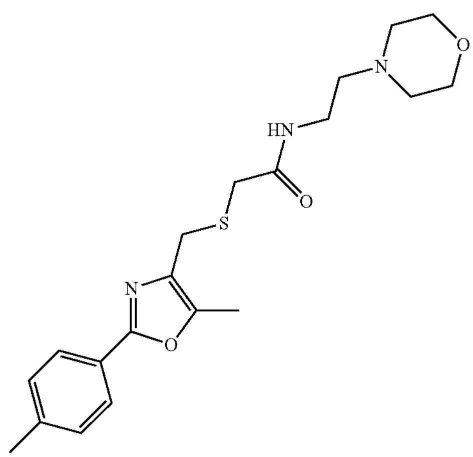 [SMILES: Cc1ccc(-c2nc(CSCC(=O)NCCN3CCOCC3)c(C)o2)cc1] | 389.52 |
| IIa-1234 | 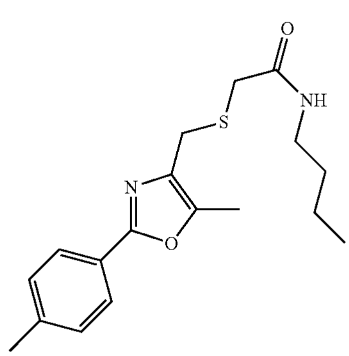 [SMILES: CCCCNC(=O)CSCc1nc(-c2ccc(C)cc2)oc1C] | 332.47 |

TABLE 5-continued
Oxazole amides (R³ = NH-C₃C₇cycloalkyl)
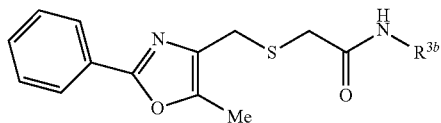
| ID | Structure | MW |
|---|---|---|
| IIa-1235 | | 373.52 |
| IIa-1236 | | 499.08 |

TABLE 5-continued
Oxazole amides (R³ = NH-C₃C₇cycloalkyl)
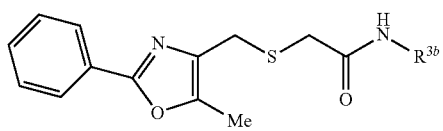
| ID | Structure | MW |
|---|---|---|
| IIa-1237 | 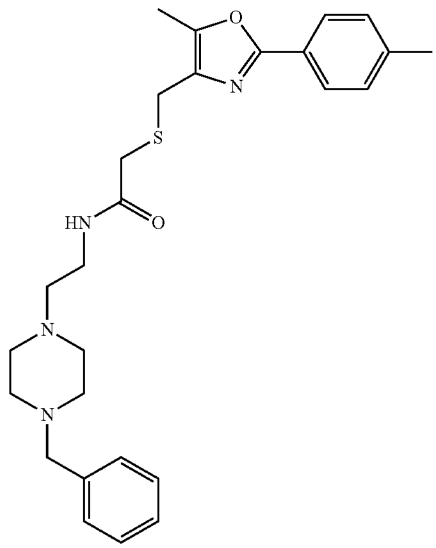 [SMILES: Cc1ccc(-c2nc(CSCC(=O)NCCN3CCN(Cc4ccccc4)CC3)c(C)o2)cc1] | 478.66 |
| IIa-1238 | 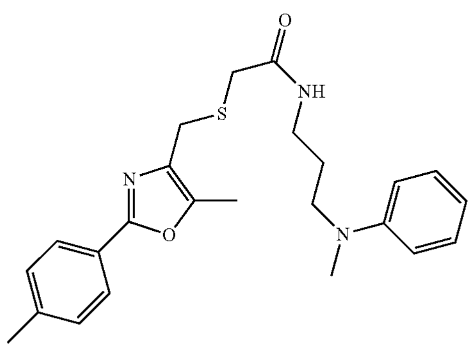 [SMILES: Cc1ccc(-c2nc(CSCC(=O)NCCCN(C)c3ccccc3)c(C)o2)cc1] | 423.58 |
| IIa-1239 | 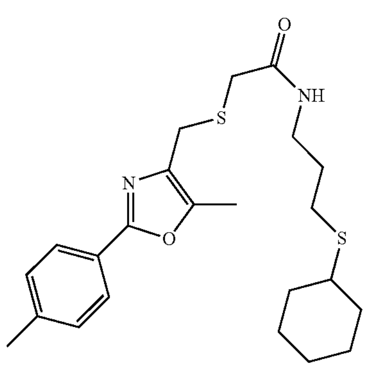 [SMILES: Cc1ccc(-c2nc(CSCC(=O)NCCCSC3CCCCC3)c(C)o2)cc1] | 432.65 |

TABLE 5-continued
Oxazole amides (R³ = NH-C₃C₇cycloalkyl)
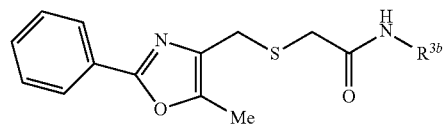
| ID | Structure | MW |
|---|---|---|
| IIa-1240 | | 463.56 |
| IIa-1241 | | 424.52 |

TABLE 5-continued
Oxazole amides (R³ = NH-C₃C₇cycloalkyl)
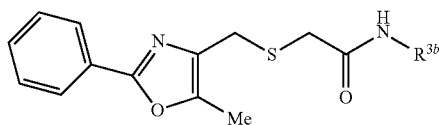
| ID | Structure | MW |
|---|---|---|
| IIa-1242 | 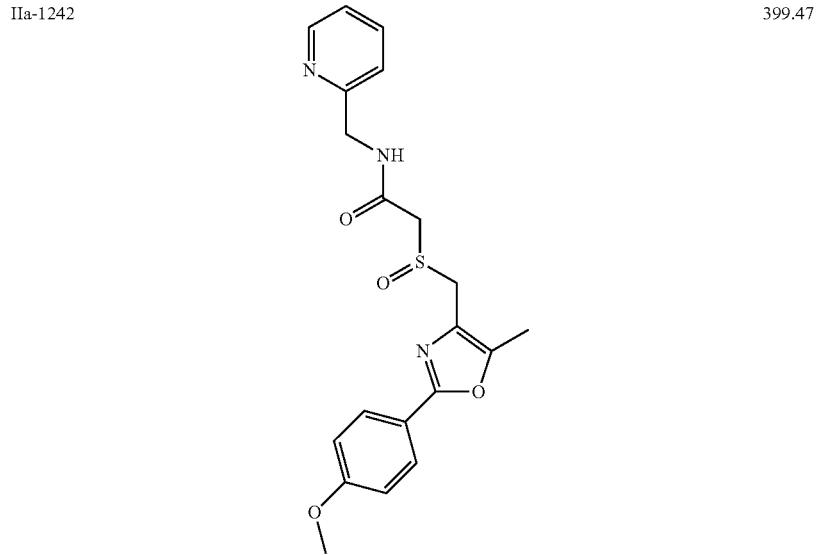 | 399.47 |
| IIa-1243 | 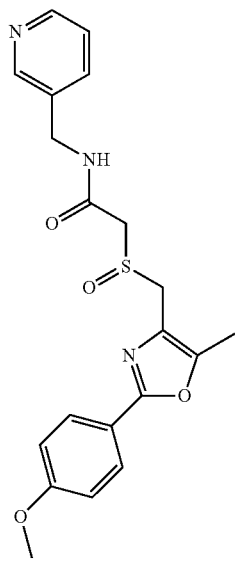 [SMILES: COc1ccc(-c2nc(CS(=O)CC(=O)NCc3cccnc3)c(C)o2)cc1] | 399.47 |

TABLE 5-continued
Oxazole amides (R³ = NH-C₃C₇cycloalkyl)
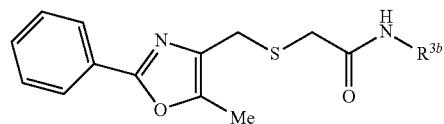
| ID | Structure | MW |
|---|---|---|
| IIa-1244 | 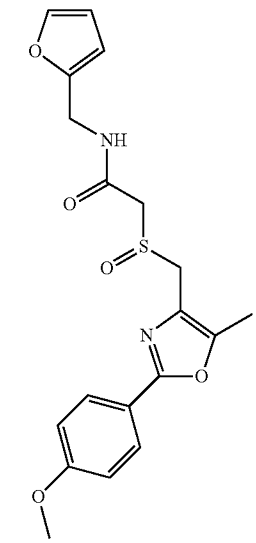 [SMILES: COc1ccc(-c2nc(CS(=O)CC(=O)NCc3ccco3)c(C)o2)cc1] | 388.45 |
| IIa-1245 | 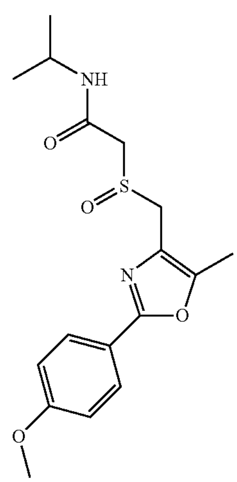 [SMILES: COc1ccc(-c2nc(CS(=O)CC(=O)NC(C)C)c(C)o2)cc1] | 350.44 |

TABLE 5-continued
Oxazole amides (R³ = NH-C₃C₇cycloalkyl)
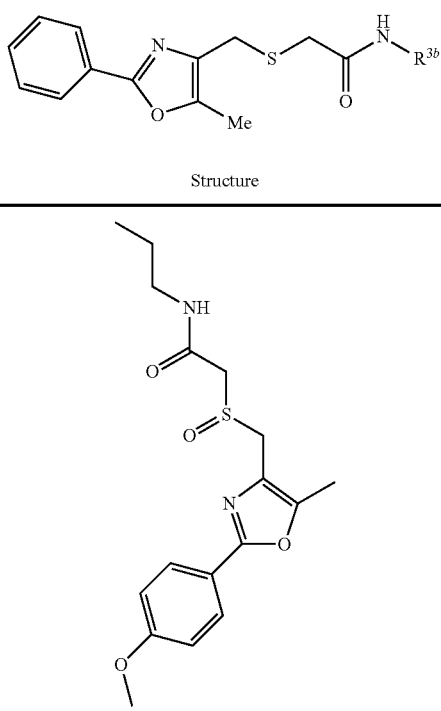
| ID | Structure | MW |
|---|---|---|
| IIa-1246 | 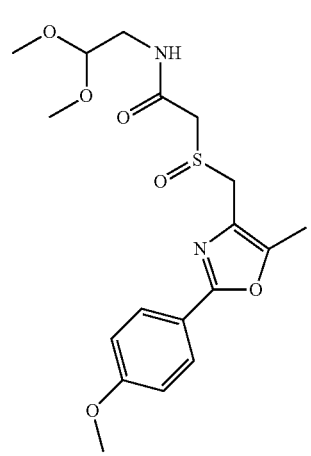 | 350.44 |
| IIa-1247 | | 396.47 |
| IIa-1248 | 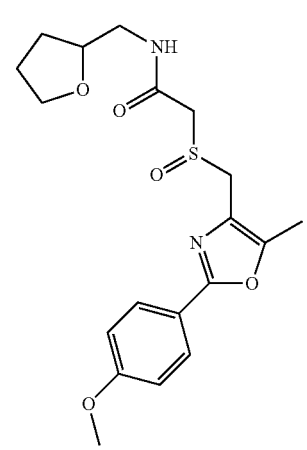 [SMILES: COc1ccc(-c2nc(CS(=O)CC(=O)NCC3CCCO3)c(C)o2)cc1] | 392.48 |

TABLE 5-continued

Oxazole amides (R³ = NH-C₃C₇cycloalkyl)

| ID | Structure | MW |
|---|---|---|
| IIa-1249 | 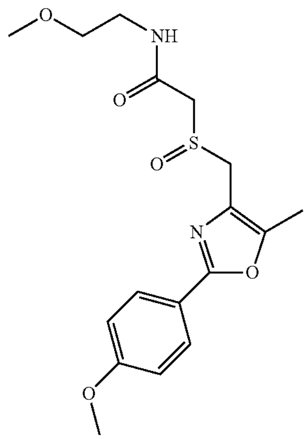 | 366.44 |
| IIa-1250 | 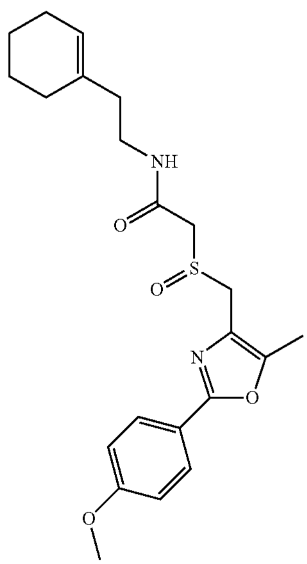 [SMILES: COc1ccc(-c2nc(CS(=O)CC(=O)NCCC3=CCCCC3)c(C)o2)cc1] | 416.54 |
| IIa-1251 | 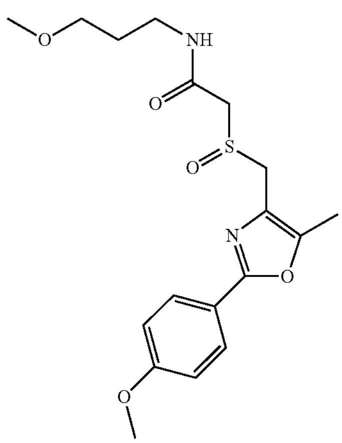 | 380.47 |

TABLE 5-continued
Oxazole amides (R³ = NH-C₃C₇cycloalkyl)
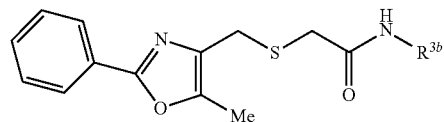
| ID | Structure | MW |
|---|---|---|
| IIa-1252 | 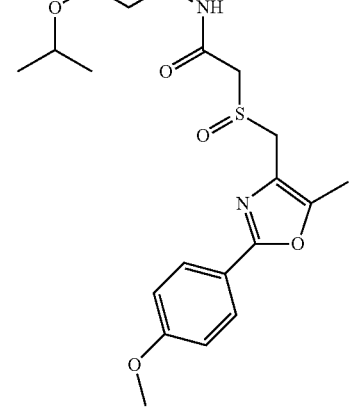 | 408.52 |
| IIa-1253 | 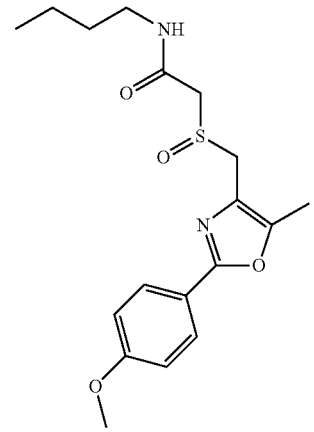 [SMILES: CCCCNC(=O)CS(=O)Cc1nc(-c2ccc(OC)cc2)oc1C] | 364.47 |

TABLE 5-continued

Oxazole amides (R³ = NH-C₃C₇cycloalkyl)

[Structure: phenyl-oxazole(Me)-CH₂-S-CH₂-C(=O)-NH-R^{3b}]

| ID | Structure | MW |
|---|---|---|
| IIa-1254 | [3-chlorophenyl-piperazine-ethyl-NH-C(=O)-CH₂-S(=O)-CH₂-(5-methyl-2-(4-methoxyphenyl)oxazol-4-yl)] | 531.08 |
| IIa-1255 | [propyl-NH-C(=O)-CH₂-S(=O)-CH₂-(5-methyl-2-(3-chlorophenyl)oxazol-4-yl)] | 354.86 |
| IIa-1256 | [methoxypropyl-NH-C(=O)-CH₂-S(=O)-CH₂-(5-methyl-2-(3-chlorophenyl)oxazol-4-yl)] | 384.88 |

TABLE 5-continued

Oxazole amides (R³ = NH-C₃C₇cycloalkyl)

| ID | Structure | MW |
|---|---|---|
| IIa-1257 | | 368.89 |
| IIa-1258 | | 451.52 |
| IIa-1259 | | 387.44 |

TABLE 5-continued
Oxazole amides (R³ = NH-C₃C₇cycloalkyl)
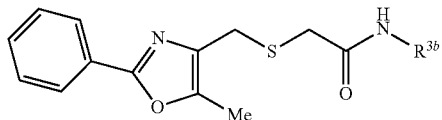
| ID | Structure | MW |
|---|---|---|
| IIa-1260 | | 387.44 |
| IIa-1261 | | 352.43 |
| IIa-1262 | | 338.40 |

TABLE 5-continued
Oxazole amides (R³ = NH-C₃C₇cycloalkyl)
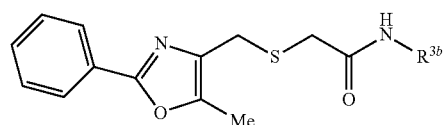
| ID | Structure | MW |
|---|---|---|
| IIa-1263 | | 384.43 |
| IIa-1264 | | 392.47 |
| IIa-1265 | | 368.43 |

TABLE 5-continued
Oxazole amides (R³ = NH-C₃C₇cycloalkyl)
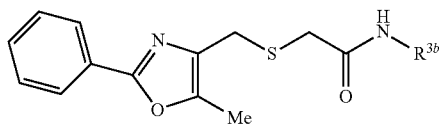
| ID | Structure | MW |
|---|---|---|
| IIa-1266 | | 396.48 |
| IIa-1267 | | 421.54 |
| IIa-1268 | | 383.47 |

TABLE 5-continued
Oxazole amides (R³ = NH-C₃C₇cycloalkyl)
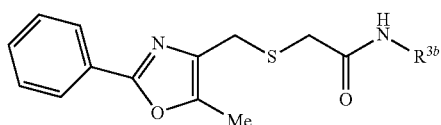
| ID | Structure | MW |
|---|---|---|
| IIa-1269 | 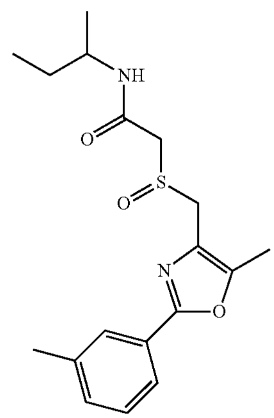 [SMILES: CCC(C)NC(=O)CS(=O)Cc1nc(-c2cccc(C)c2)oc1C] | 348.47 |
| IIa-1270 | 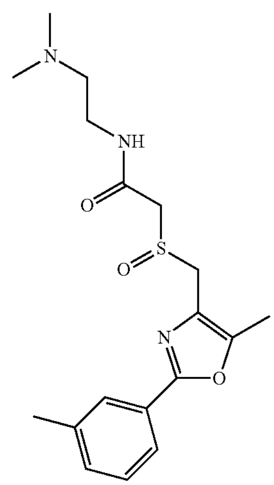 | 363.48 |
| IIa-1271 | 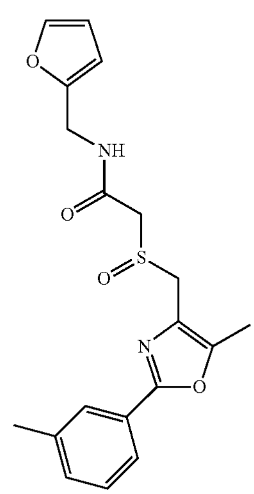 | 372.45 |

TABLE 5-continued
Oxazole amides (R³ = NH-C₃C₇cycloalkyl)
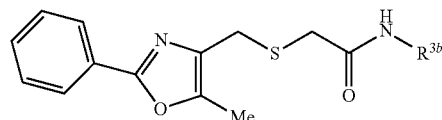
| ID | Structure | MW |
|---|---|---|
| IIa-1272 | 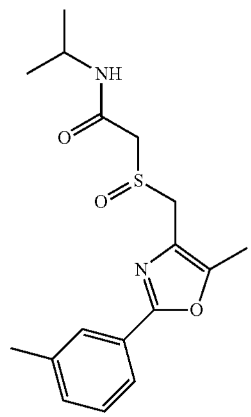 | 334.44 |
| IIa-1273 | 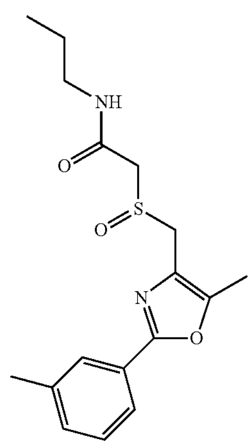 | 334.44 |
| IIa-1274 | 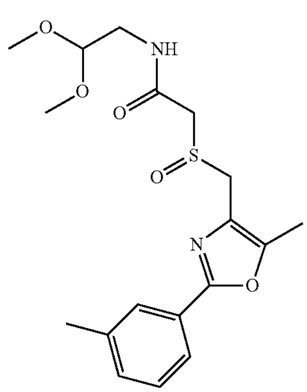 | 380.47 |

TABLE 5-continued

Oxazole amides (R³ = NH-C₃C₇cycloalkyl)

| ID | Structure | MW |
|----|-----------|-----|
| IIa-1275 | | 362.49 |
| IIa-1276 | | 376.48 |
| IIa-1277 | | 350.44 |

TABLE 5-continued
Oxazole amides (R³ = NH-C₃C₇cycloalkyl)
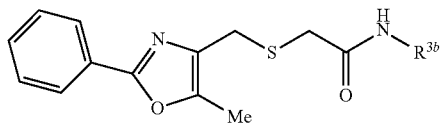
| ID | Structure | MW |
| --- | --- | --- |
| IIa-1278 | | 388.51 |
| IIa-1279 | | 378.49 |

TABLE 5-continued
Oxazole amides ($R^3$ = NH-$C_3C_7$cycloalkyl)
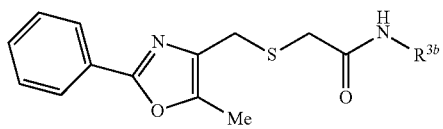
| ID | Structure | MW |
|---|---|---|
| IIa-1280 | | 424.57 |
| IIa-1281 | | 364.47 |
| IIa-1282 | | 348.47 |

TABLE 5-continued
Oxazole amides (R³ = NH-C₃C₇cycloalkyl)
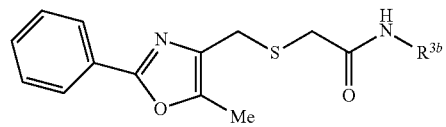
| ID | Structure | MW |
|---|---|---|
| IIa-1283 | 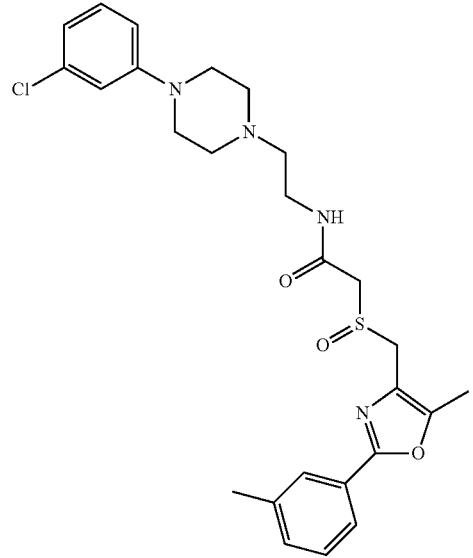 [SMILES: Cc1cccc(-c2nc(CS(=O)CC(=O)NCCN3CCN(c4cccc(Cl)c4)CC3)c(C)o2)c1] | 515.08 |
| IIa-1284 | 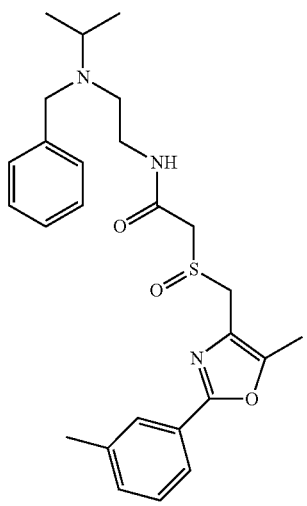 [SMILES: Cc1cccc(-c2nc(CS(=O)CC(=O)NCCN(Cc3ccccc3)C(C)C)c(C)o2)c1] | 467.64 |

TABLE 5-continued
Oxazole amides (R³ = NH-C₃C₇cycloalkyl)
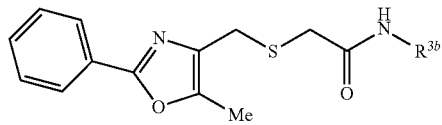
| ID | Structure | MW |
|---|---|---|
| IIa-1285 | | 453.61 |
| IIa-1286 | | 422.61 |

TABLE 5-continued
Oxazole amides (R³ = NH-C₃C₇cycloalkyl)
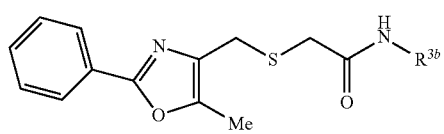
| ID | Structure | MW |
|---|---|---|
| IIa-1287 | 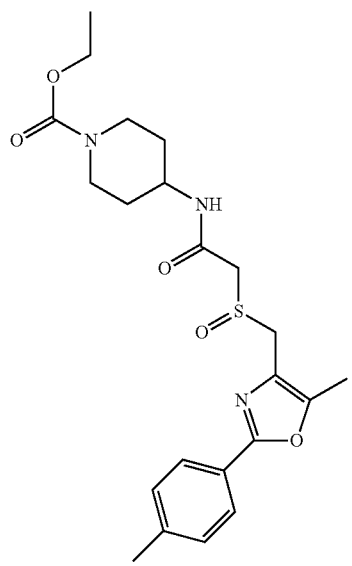 | 448.65 |
| IIa-1288 | 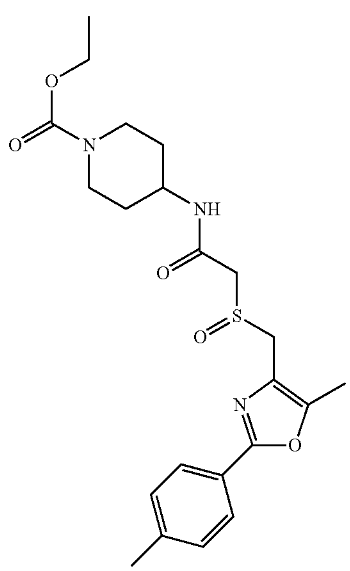 [SMILES: CCOC(=O)N1CCC(NC(=O)CS(=O)Cc2nc(-c3ccc(C)cc3)oc2C)CC1] | 447.56 |

TABLE 5-continued
Oxazole amides (R³ = NH-C₃C₇cycloalkyl)
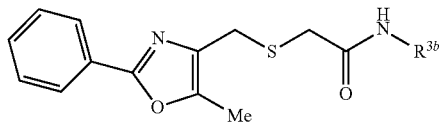
| ID | Structure | MW |
|---|---|---|
| IIa-1289 | 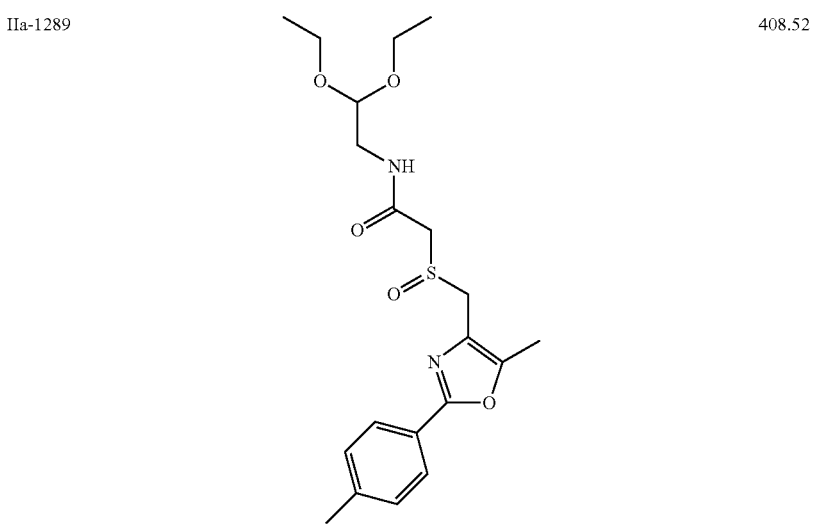 | 408.52 |
| IIa-1290 | 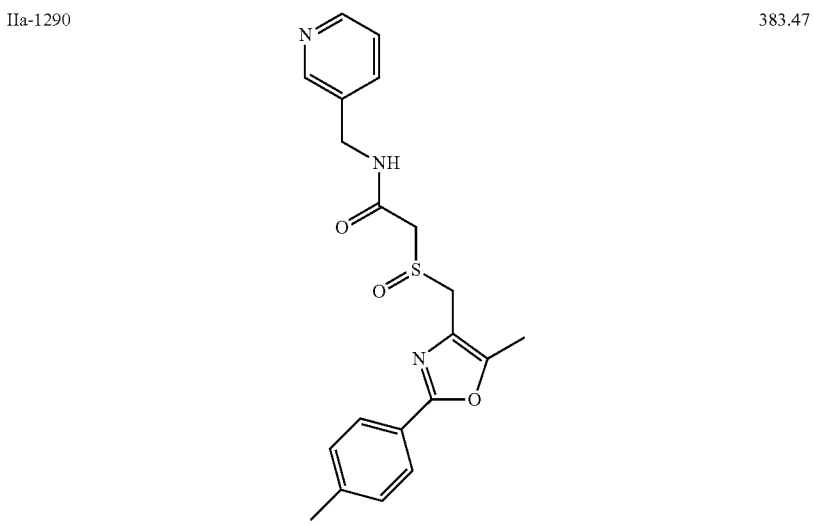 | 383.47 |

TABLE 5-continued
Oxazole amides (R³ = NH-C₃C₇cycloalkyl)
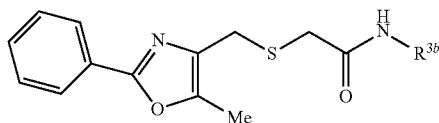
| ID | Structure | MW |
|---|---|---|
| IIa-1291 | 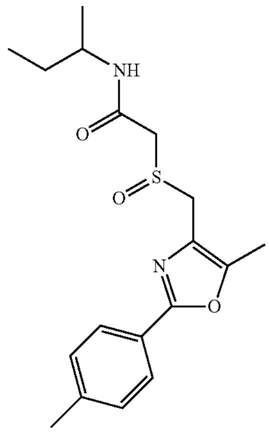 [SMILES: CCC(C)NC(=O)CS(=O)Cc1nc(-c2ccc(C)cc2)oc1C] | 348.47 |
| IIa-1292 | 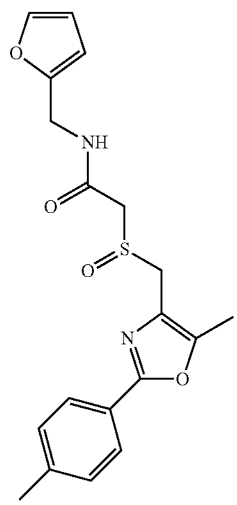 [SMILES: Cc1ccc(-c2nc(CS(=O)CC(=O)NCc3ccco3)c(C)o2)cc1] | 372.45 |
| IIa-1293 | 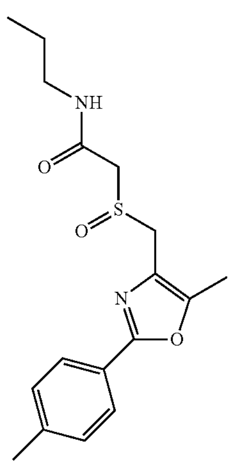 [SMILES: CCCNC(=O)CS(=O)Cc1nc(-c2ccc(C)cc2)oc1C] | 334.44 |

TABLE 5-continued
Oxazole amides (R³ = NH-C₃C₇cycloalkyl)
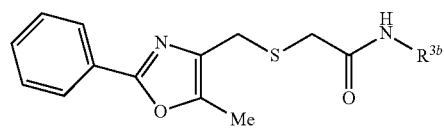
| ID | Structure | MW |
|---|---|---|
| IIa-1294 | | 391.54 |
| IIa-1295 | | 380.47 |
| IIa-1296 | | 362.49 |

TABLE 5-continued
Oxazole amides (R³ = NH-C₃C₇cycloalkyl)
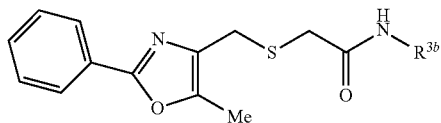
| ID | Structure | MW |
|---|---|---|
| IIa-1297 | 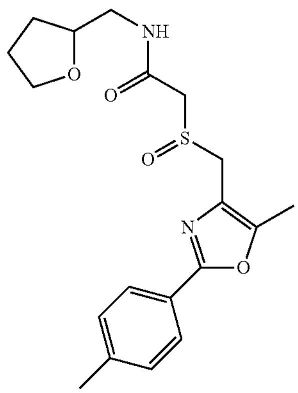 [SMILES: Cc1ccc(-c2nc(CS(=O)CC(=O)NCC3CCCO3)c(C)o2)cc1] | 376.48 |
| IIa-1298 | 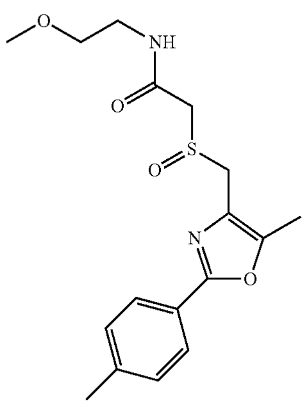 | 350.44 |
| IIa-1299 | 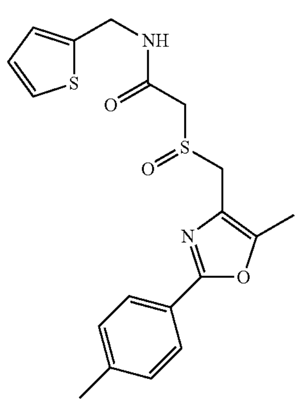 [SMILES: Cc1ccc(-c2nc(CS(=O)CC(=O)NCc3cccs3)c(C)o2)cc1] | 388.51 |

TABLE 5-continued
Oxazole amides (R³ = NH-C₃C₇cycloalkyl)
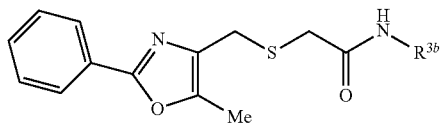
| ID | Structure | MW |
|---|---|---|
| IIa-1300 | | 378.49 |
| IIa-1301 | | 400.54 |

TABLE 5-continued

Oxazole amides (R³ = NH-C₃C₇cycloalkyl)

| ID | Structure | MW |
|---|---|---|
| IIa-1302 | | 424.57 |
| IIa-1303 | | 364.47 |
| IIa-1304 | | 392.52 |

TABLE 5-continued
Oxazole amides (R³ = NH-C₃C₇cycloalkyl)
| ID | Structure | MW |
|---|---|---|
| IIa-1305 | 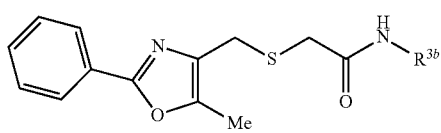 | 405.52 |
| IIa-1306 | 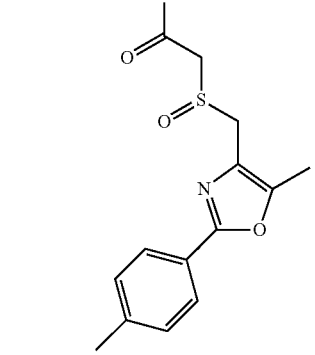 | 348.47 |
| IIa-1307 | 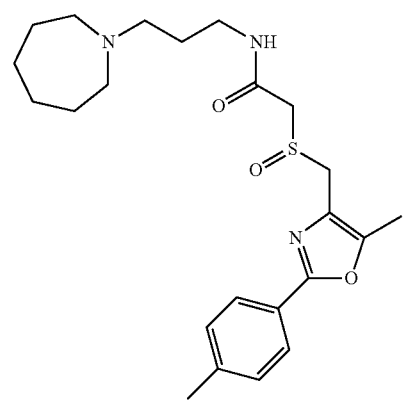 [SMILES: Cc1ccc(-c2nc(CS(=O)CC(=O)NCCCN3CCCCCC3)c(C)o2)cc1] | 431.60 |

TABLE 5-continued
Oxazole amides (R³ = NH-C₃C₇cycloalkyl)
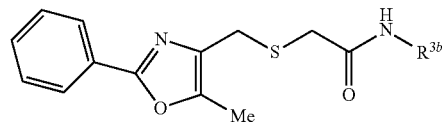
| ID | Structure | MW |
|---|---|---|
| IIa-1308 | | 417.57 |
| IIa-1309 | | 419.59 |

TABLE 5-continued
Oxazole amides (R³ = NH-C₃C₇cycloalkyl)
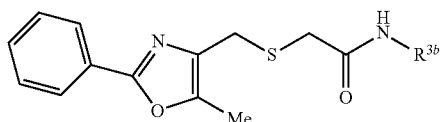
| ID | Structure | MW |
|---|---|---|
| IIa-1310 | 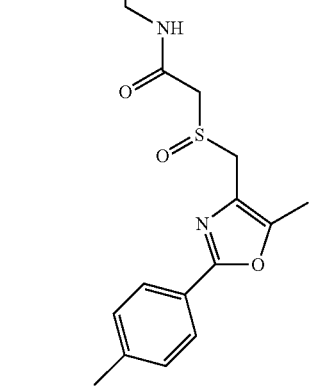 | 389.52 |
| IIa-1311 | 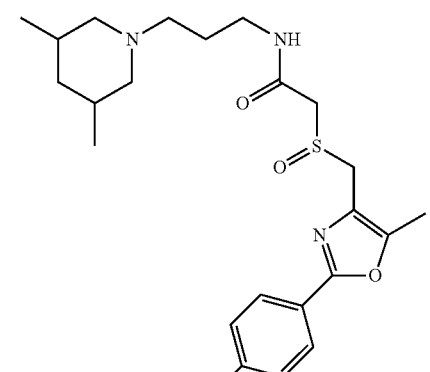 | 445.63 |
| IIa-1312 | 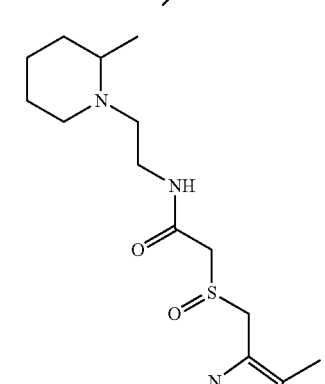 | 417.57 |

TABLE 5-continued
Oxazole amides (R³ = NH-C₃C₇cycloalkyl)
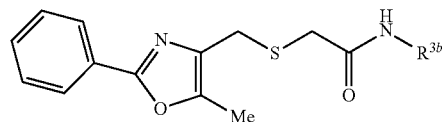
| ID | Structure | MW |
|---|---|---|
| IIa-1313 | 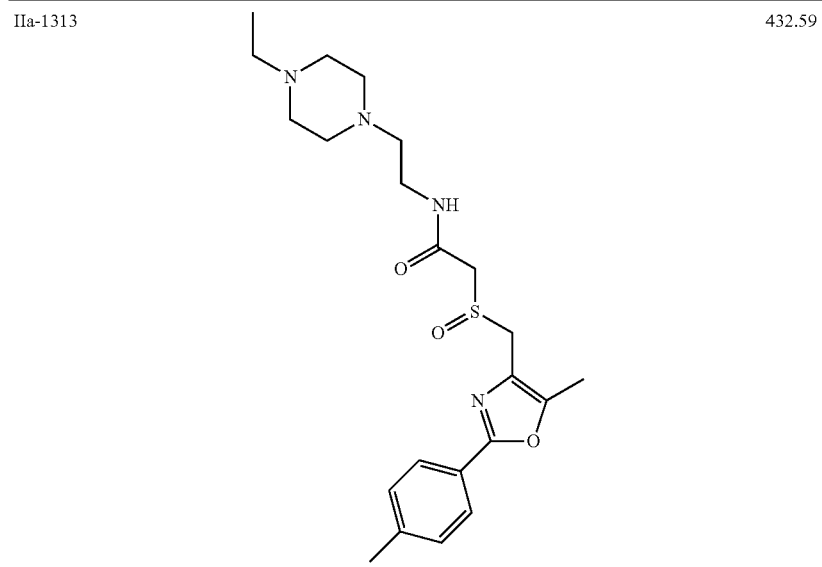 | 432.59 |
| IIa-1314 | 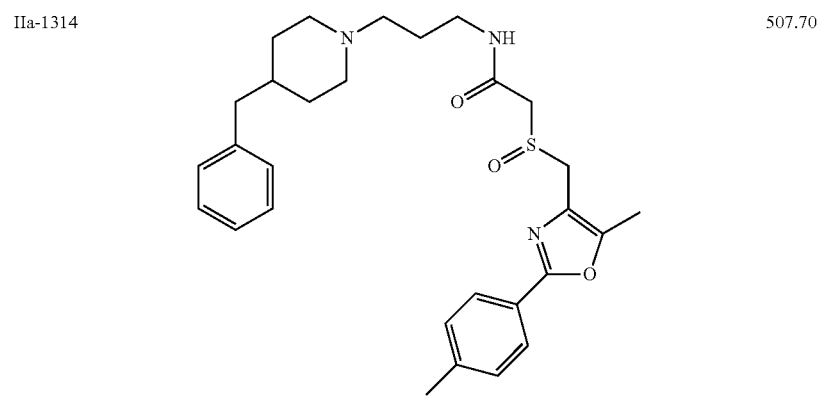 | 507.70 |

TABLE 5-continued
Oxazole amides (R³ = NH-C₃C₇cycloalkyl)
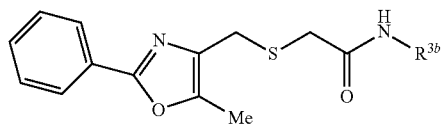
| ID | Structure | MW |
|---|---|---|
| IIa-1315 | 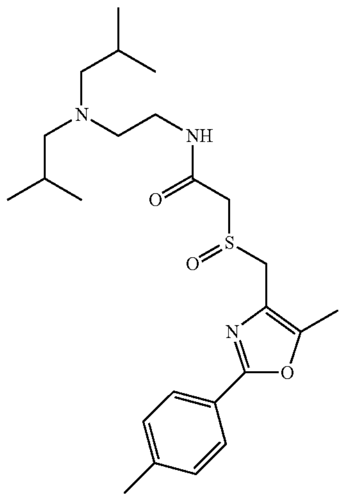 [SMILES: Cc1ccc(-c2nc(CS(=O)CC(=O)NCCN(CC(C)C)CC(C)C)c(C)o2)cc1] | 447.64 |
| IIa-1316 | 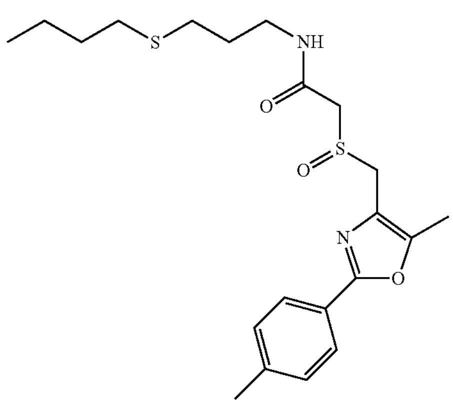 [SMILES: CCCCSCCCNC(=O)CS(=O)Cc1nc(-c2ccc(C)cc2)oc1C] | 422.61 |

TABLE 5-continued
Oxazole amides (R³ = NH-C₃C₇cycloalkyl)
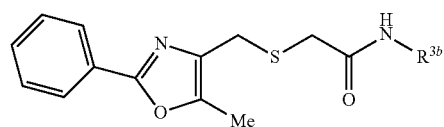
| ID | Structure | MW |
|---|---|---|
| IIa-1317 | | 448.65 |
| IIa-1318 | | 467.98 |

TABLE 5-continued
Oxazole amides ($R^3$ = NH-$C_3C_7$cycloalkyl)
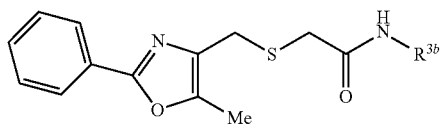
| ID | Structure | MW |
|---|---|---|
| IIa-1319 | | 428.94 |
| IIa-1320 | | 403.89 |

TABLE 5-continued
Oxazole amides (R³ = NH-C₃C₇cycloalkyl)
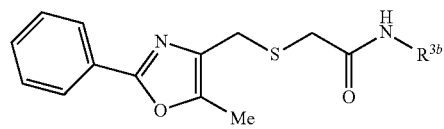
| ID | Structure | MW |
|---|---|---|
| IIa-1321 | | 392.86 |
| IIa-1322 | | 354.86 |

TABLE 5-continued
Oxazole amides (R³ = NH-C₃C₇cycloalkyl)
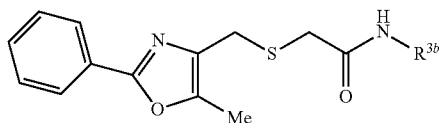
| ID | Structure | MW |
| --- | --- | --- |
| IIa-1323 | | 411.95 |
| IIa-1324 | | 439.96 |
| IIa-1325 | | 396.90 |

TABLE 5-continued

Oxazole amides (R³ = NH-C₃C₇cycloalkyl)

| ID | Structure | MW |
|---|---|---|
| IIa-1326 | | 370.86 |
| IIa-1327 | | 408.93 |
| IIa-1328 | | 398.91 |

TABLE 5-continued
Oxazole amides ($R^3$ = NH-$C_3C_7$cycloalkyl)
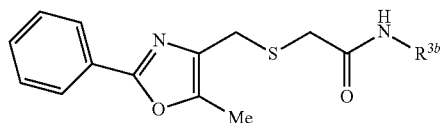
| ID | Structure | MW |
|---|---|---|
| IIa-1329 | 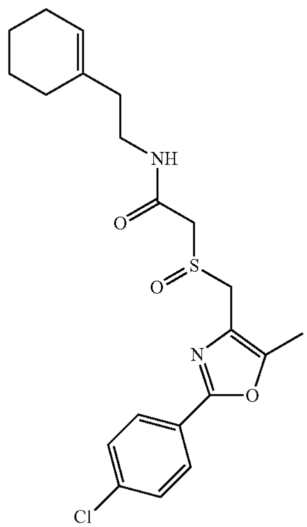 [SMILES: Cc1oc(-c2ccc(Cl)cc2)nc1CS(=O)CC(=O)NCCC1=CCCCC1] | 420.96 |
| IIa-1330 | 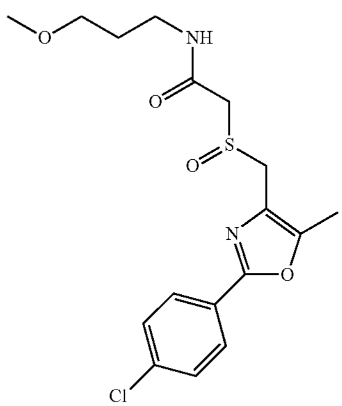 | 384.88 |
| IIa-1331 | 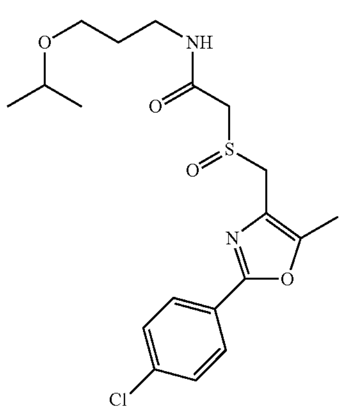 [SMILES: Cc1oc(-c2ccc(Cl)cc2)nc1CS(=O)CC(=O)NCCCOC(C)C] | 412.94 |

TABLE 5-continued
Oxazole amides (R³ = NH-C₃C₇cycloalkyl)
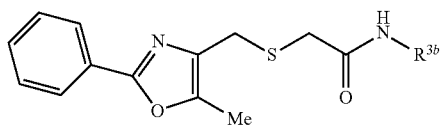
| ID | Structure | MW |
|---|---|---|
| IIa-1332 | 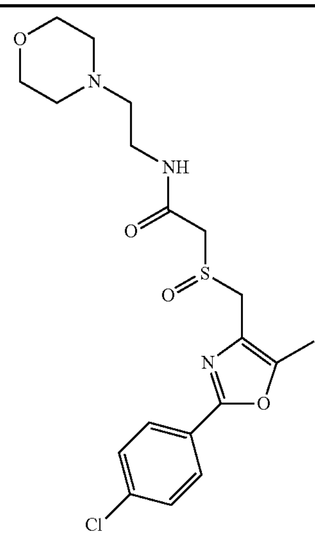 | 425.94 |
| IIa-1333 | 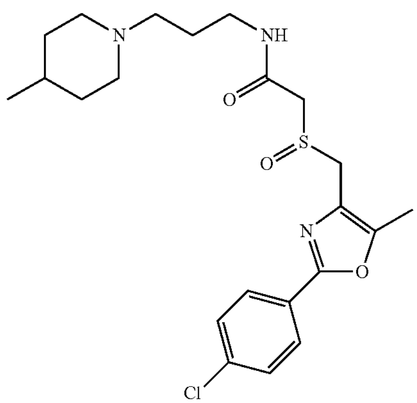 | 452.02 |
| IIa-1334 | 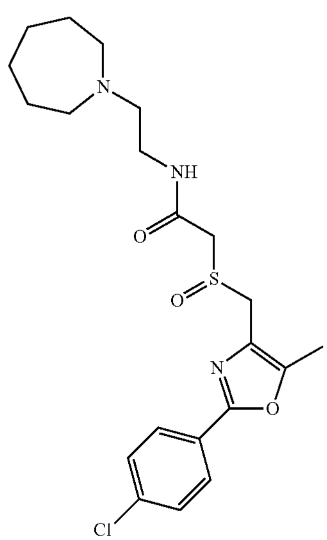 [SMILES: Cc1oc(-c2ccc(Cl)cc2)nc1CS(=O)CC(=O)NCCN1CCCCCC1] | 437.99 |

TABLE 5-continued
Oxazole amides ($R^3$ = NH-$C_3C_7$cycloalkyl)
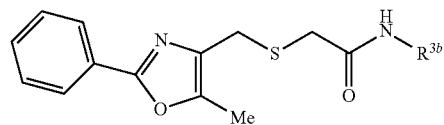
| ID | Structure | MW |
|---|---|---|
| IIa-1335 | | 409.94 |
| IIa-1336 | | 466.05 |

TABLE 5-continued
Oxazole amides (R³ = NH-C₃C₇cycloalkyl)
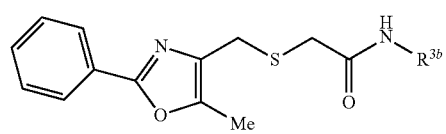
| ID | Structure | MW |
|---|---|---|
| IIa-1337 | | 453.01 |
| IIa-1338 | | 452.02 |

TABLE 5-continued

Oxazole amides (R³ = NH-C₃C₇cycloalkyl)

| ID | Structure | MW |
|---|---|---|
| IIa-1339 | 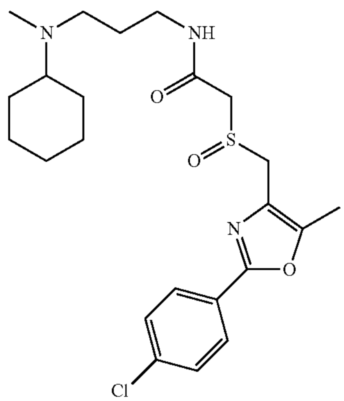 | 466.05 |
| IIa-1340 | 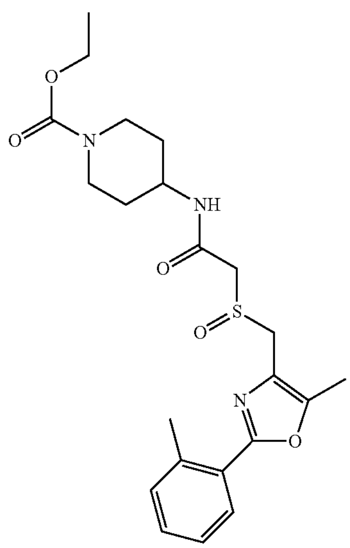 [SMILES: CCOC(=O)N1CCC(NC(=O)CS(=O)Cc2nc(-c3ccccc3C)oc2C)CC1] | 447.56 |
| IIa-1341 | 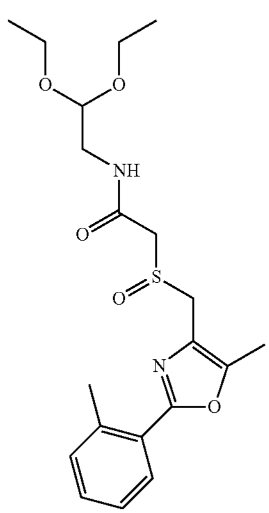 [SMILES: CCOC(CNC(=O)CS(=O)Cc1nc(-c2ccccc2C)oc1C)OCC] | 408.52 |

TABLE 5-continued
Oxazole amides (R³ = NH-C₃C₇cycloalkyl)
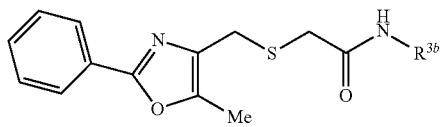
| ID | Structure | MW |
|---|---|---|
| IIa-1342 | 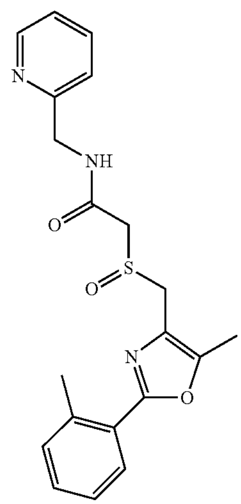 [SMILES: Cc1ccccc1-c1nc(CS(=O)CC(=O)NCc2ccccn2)c(C)o1] | 383.47 |
| IIa-1343 | 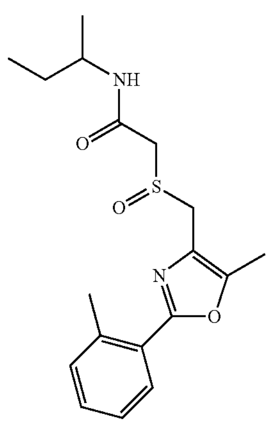 [SMILES: CCC(C)NC(=O)CS(=O)Cc1nc(-c2ccccc2C)oc1C] | 348.47 |
| IIa-1344 | 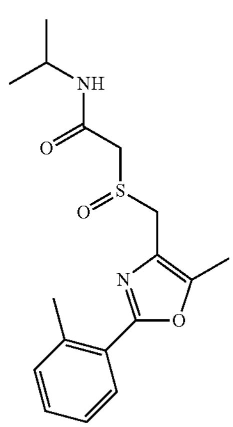 [SMILES: Cc1ccccc1-c1nc(CS(=O)CC(=O)NC(C)C)c(C)o1] | 334.44 |

TABLE 5-continued
Oxazole amides (R³ = NH-C₃C₇cycloalkyl)
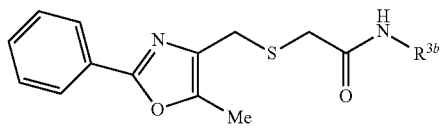
| ID | Structure | MW |
|---|---|---|
| IIa-1345 | | 334.44 |
| IIa-1346 | | 380.47 |
| IIa-1347 | | 419.55 |

TABLE 5-continued
Oxazole amides (R³ = NH-C₃C₇cycloalkyl)
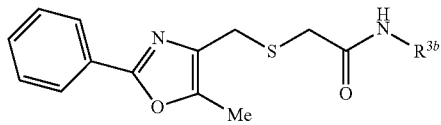
| ID | Structure | MW |
|---|---|---|
| IIa-1348 | 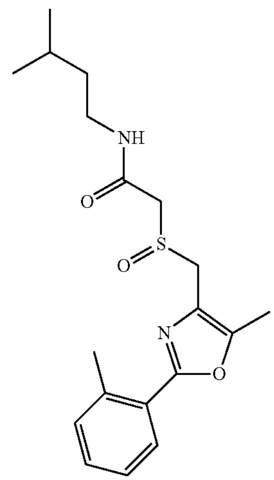 [SMILES: Cc1ccccc1-c1nc(CS(=O)CC(=O)NCCC(C)C)c(C)o1] | 362.49 |
| IIa-1349 | 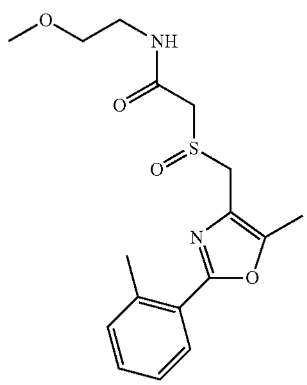 | 350.44 |
| IIa-1350 | 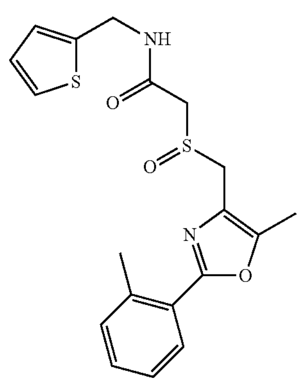 [SMILES: Cc1ccccc1-c1nc(CS(=O)CC(=O)NCc2cccs2)c(C)o1] | 388.51 |

TABLE 5-continued
Oxazole amides (R³ = NH-C₃C₇cycloalkyl)
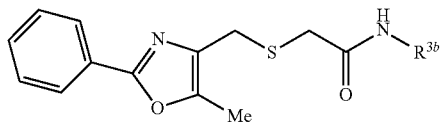
| ID | Structure | MW |
|---|---|---|
| IIa-1351 | 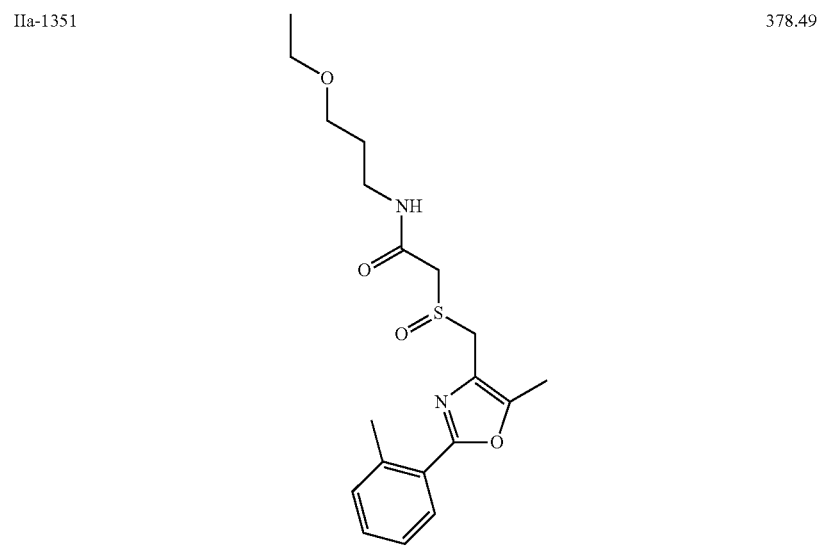 | 378.49 |
| IIa-1352 | 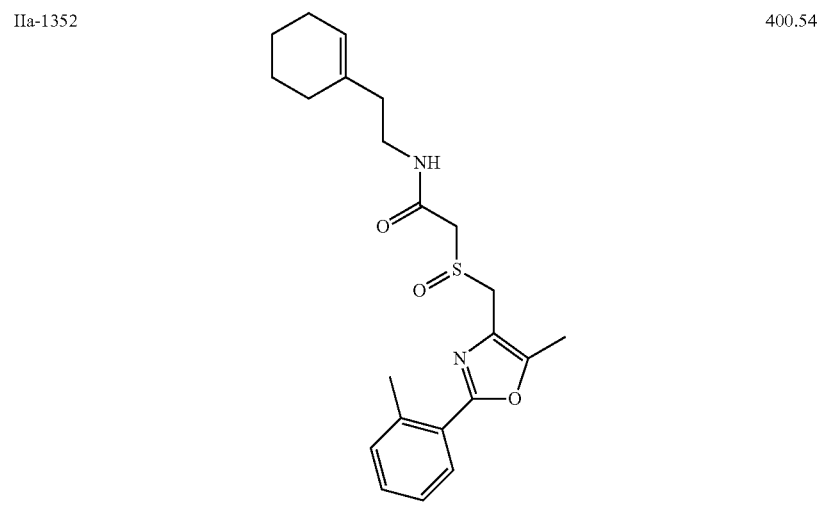 | 400.54 |

TABLE 5-continued

Oxazole amides (R³ = NH-C₃C₇cycloalkyl)

| ID | Structure | MW |
|---|---|---|
| IIa-1353 | 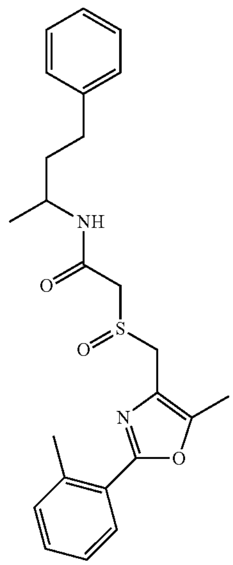 [SMILES: Cc1ccccc1-c1nc(CS(=O)CC(=O)NC(C)CCc2ccccc2)c(C)o1] | 424.57 |
| IIa-1354 | 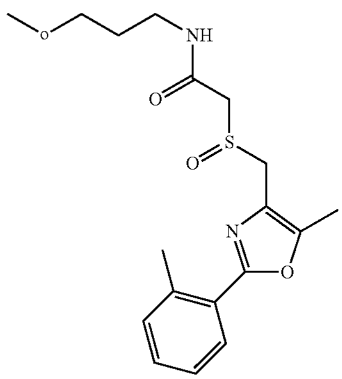 | 364.47 |
| IIa-1355 | 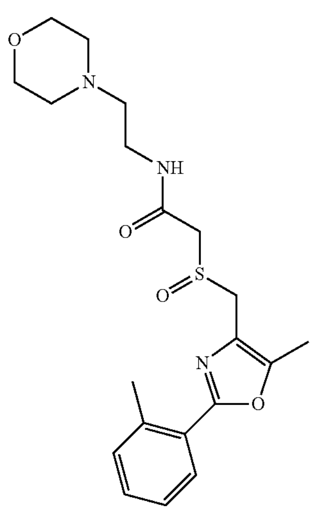 [SMILES: Cc1ccccc1-c1nc(CS(=O)CC(=O)NCCN2CCOCC2)c(C)o1] | 405.52 |

TABLE 5-continued
Oxazole amides ($R^3$ = NH-$C_3C_7$cycloalkyl)
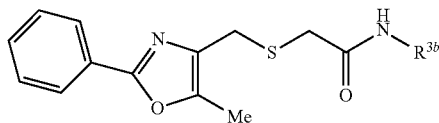
| ID | Structure | MW |
|---|---|---|
| IIa-1356 | | 348.47 |
| IIa-1357 | | 403.55 |
| IIa-1358 | | 515.08 |

TABLE 5-continued

Oxazole amides (R³ = NH-C₃C₇cycloalkyl)

| ID | Structure | MW |
|---|---|---|
| IIa-1359 | | 494.66 |
| IIa-1360 | | 439.58 |
| IIa-1361 | | 403.89 |

TABLE 5-continued
Oxazole amides (R³ = NH-C₃C₇cycloalkyl)
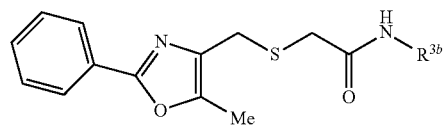
| ID | Structure | MW |
|---|---|---|
| IIa-1362 | 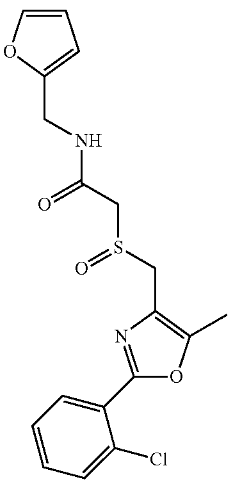 [SMILES: Cc1oc(-c2ccccc2Cl)nc1CS(=O)CC(=O)NCc1ccco1] | 392.86 |
| IIa-1363 | 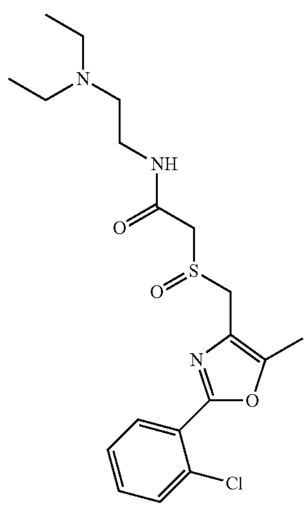 [SMILES: CCN(CC)CCNC(=O)CS(=O)Cc1nc(-c2ccccc2Cl)oc1C] | 411.95 |
| IIa-1364 | 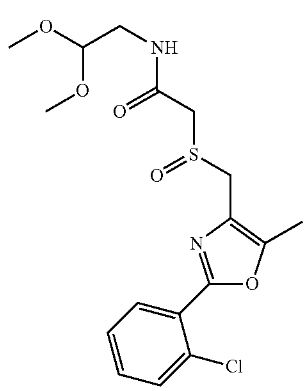 | 400.88 |

TABLE 5-continued
Oxazole amides (R³ = NH-C₃C₇cycloalkyl)
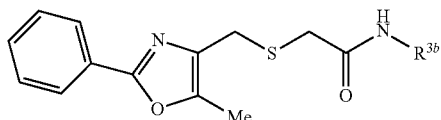
| ID | Structure | MW |
|---|---|---|
| IIa-1365 | | 382.91 |
| IIa-1366 | | 370.86 |
| IIa-1367 | | 408.93 |

TABLE 5-continued
Oxazole amides (R³ = NH-C₃C₇cycloalkyl)
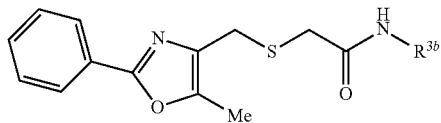
| ID | Structure | MW |
|---|---|---|
| IIa-1368 | | 368.89 |
| IIa-1369 | | 466.05 |
| IIa-1370 | | 463.56 |

TABLE 5-continued
Oxazole amides (R³ = NH-C₃C₇cycloalkyl)
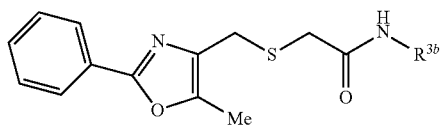
| ID | Structure | MW |
|---|---|---|
| IIa-1371 | 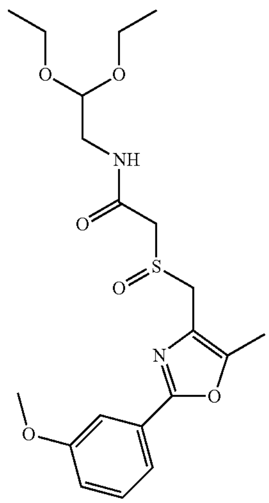 [SMILES: CCOC(CNC(=O)CS(=O)Cc1nc(-c2cccc(OC)c2)oc1C)OCC] | 424.52 |
| IIa-1372 | 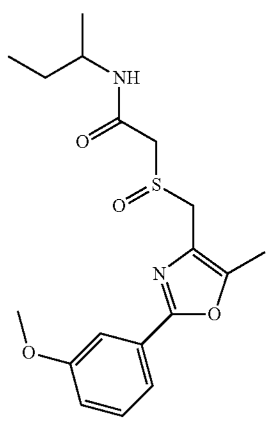 [SMILES: CCC(C)NC(=O)CS(=O)Cc1nc(-c2cccc(OC)c2)oc1C] | 364.47 |
| IIa-1373 | 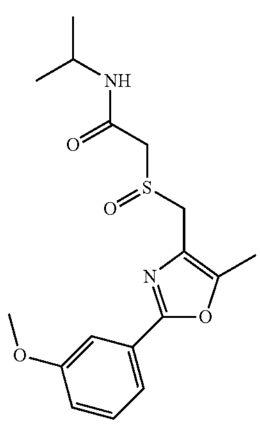 | 350.44 |

TABLE 5-continued
Oxazole amides (R³ = NH-C₃C₇cycloalkyl)
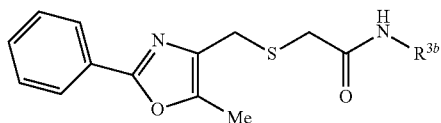
| ID | Structure | MW |
|---|---|---|
| IIa-1374 | 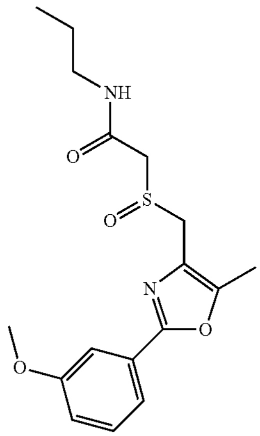 | 350.44 |
| IIa-1375 | 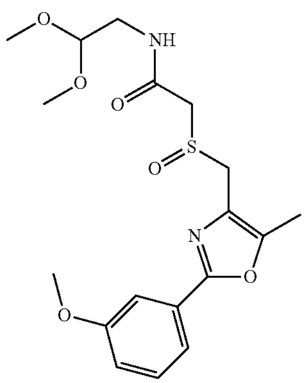 | 396.47 |
| IIa-1376 | 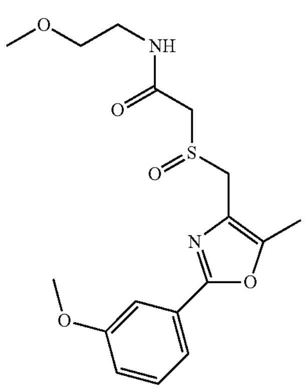 | 366.44 |

TABLE 5-continued
Oxazole amides ($R^3$ = NH-$C_3C_7$cycloalkyl)
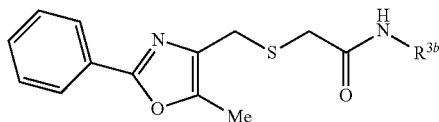
| ID | Structure | MW |
|---|---|---|
| IIa-1377 | 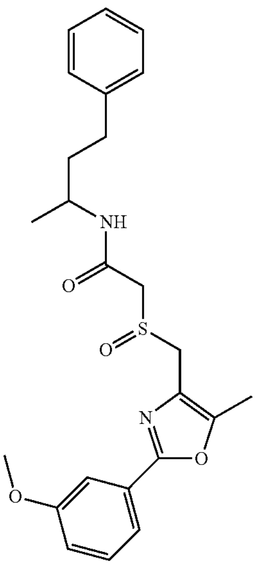 | 440.57 |
| IIa-1378 | 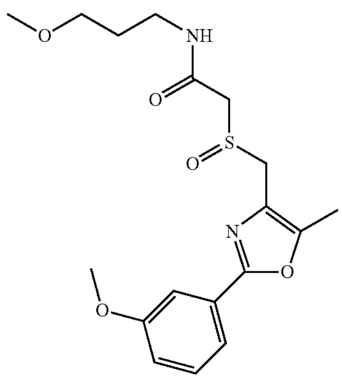 | 380.47 |
| IIa-1379 | 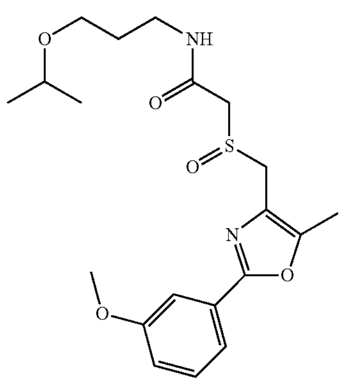 [SMILES: COc1cccc(-c2nc(CS(=O)CC(=O)NCCCOC(C)C)c(C)o2)c1] | 408.52 |

TABLE 5-continued
Oxazole amides ($R^3$ = NH-$C_3C_7$cycloalkyl)
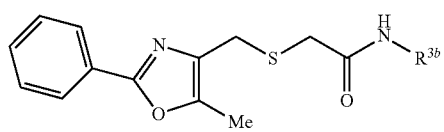
| ID | Structure | MW |
|---|---|---|
| IIa-1380 | | 364.47 |
| IIa-1381 | | 493.58 |

TABLE 5-continued
Oxazole amides (R³ = NH-C₃C₇cycloalkyl)
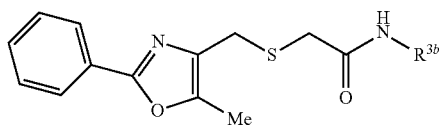
| ID | Structure | MW |
|---|---|---|
| IIa-1382 | | 454.55 |
| IIa-1383 | | 429.50 |

TABLE 5-continued
Oxazole amides (R³ = NH-C₃C₇cycloalkyl)
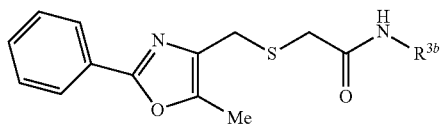
| ID | Structure | MW |
|---|---|---|
| IIa-1384 | 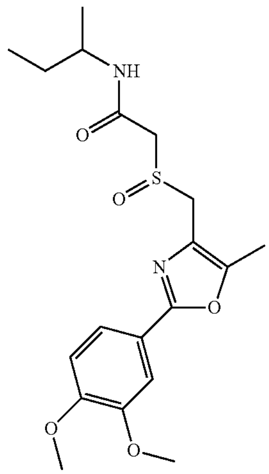 [SMILES: CCC(C)NC(=O)CS(=O)Cc1nc(-c2ccc(OC)c(OC)c2)oc1C] | 394.49 |
| IIa-1385 | 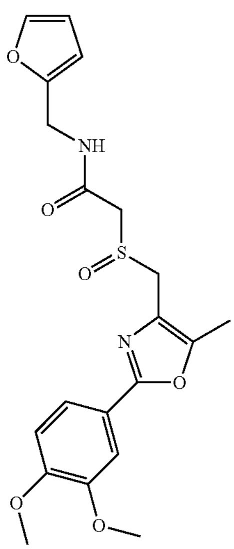 [SMILES: COc1ccc(-c2nc(CS(=O)CC(=O)NCc3ccco3)c(C)o2)cc1OC] | 418.47 |

TABLE 5-continued

Oxazole amides (R³ = NH-C₃C₇cycloalkyl)

| ID | Structure | MW |
|---|---|---|
| IIa-1386 | 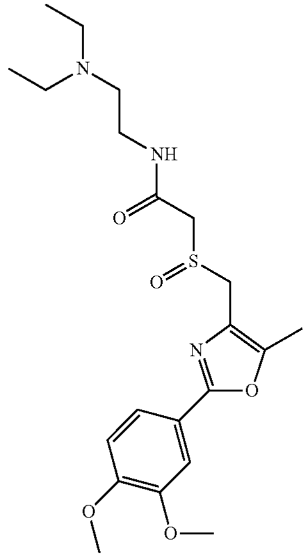 [SMILES: CCN(CC)CCNC(=O)CS(=O)Cc1nc(-c2ccc(OC)c(OC)c2)oc1C] | 437.56 |
| IIa-1387 | 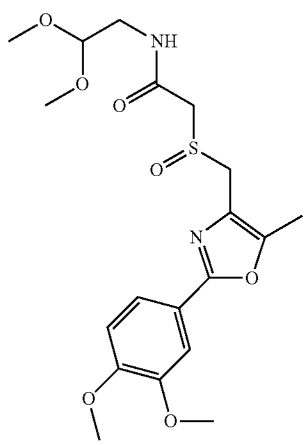 | 426.49 |
| IIa-1388 | 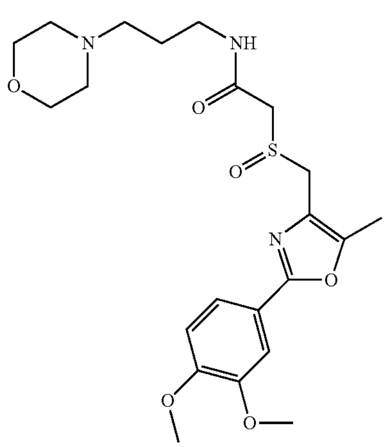 [SMILES: COc1ccc(-c2nc(CS(=O)CC(=O)NCCCN3CCOCC3)c(C)o2)cc1OC] | 465.57 |

TABLE 5-continued
Oxazole amides (R³ = NH-C₃C₇cycloalkyl)
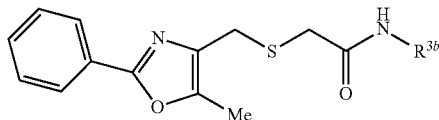
| ID | Structure | MW |
|---|---|---|
| IIa-1389 | | 408.52 |
| IIa-1390 | | 396.47 |

TABLE 5-continued
Oxazole amides (R³ = NH-C₃C₇cycloalkyl)
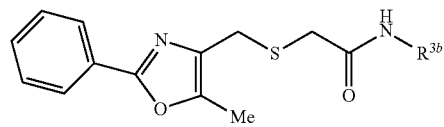
| ID | Structure | MW |
|---|---|---|
| IIa-1391 | | 449.57 |
| IIa-1392 | | 434.54 |

TABLE 5-continued
Oxazole amides (R³ = NH-C₃C₇cycloalkyl)
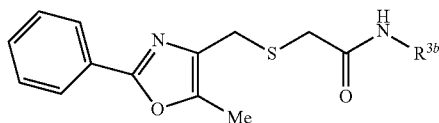
| ID | Structure | MW |
|---|---|---|
| IIa-1393 | | 424.52 |
| IIa-1394 | | 446.57 |

TABLE 5-continued
Oxazole amides (R³ = NH-C₃C₇cycloalkyl)
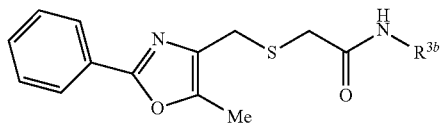
| ID | Structure | MW |
|---|---|---|
| IIa-1395 | | 470.59 |
| IIa-1396 | | 410.49 |

TABLE 5-continued
Oxazole amides (R³ = NH-C₃C₇cycloalkyl)
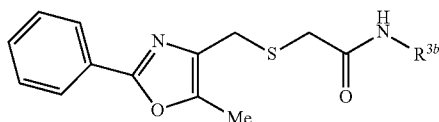
| ID | Structure | MW |
|---|---|---|
| IIa-1397 | | 438.55 |
| IIa-1398 | | 394.49 |
| IIa-1399 | | 491.65 |

TABLE 5-continued
Oxazole amides (R³ = NH-C₃C₇cycloalkyl)
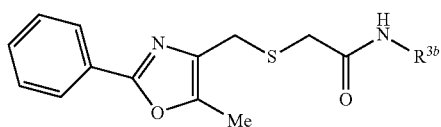
| ID | Structure | MW |
|---|---|---|
| IIa-1400 | 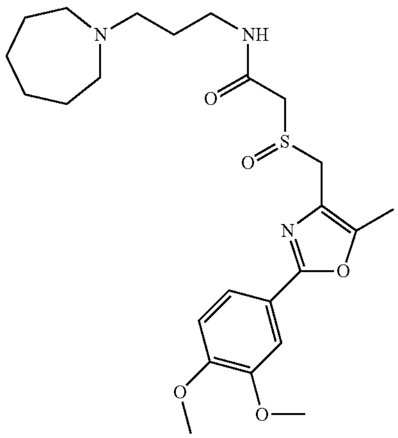 [SMILES: COc1ccc(-c2nc(CS(=O)CC(=O)NCCCN3CCCCCC3)c(C)o2)cc1OC] | 477.63 |
| IIa-1401 | 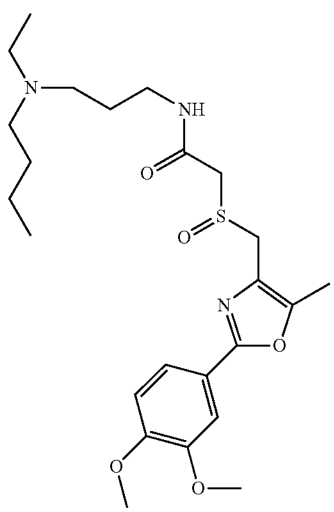 [SMILES: CCCCN(CC)CCCNC(=O)CS(=O)Cc1nc(-c2ccc(OC)c(OC)c2)oc1C] | 479.64 |
| IIa-1402 | 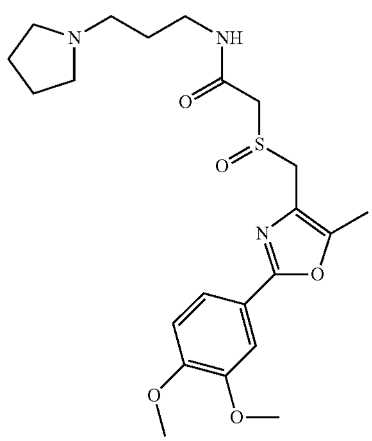 [SMILES: COc1ccc(-c2nc(CS(=O)CC(=O)NCCCN3CCCC3)c(C)o2)cc1OC] | 449.57 |

TABLE 5-continued
Oxazole amides ($R^3$ = NH-$C_3C_7$cycloalkyl)
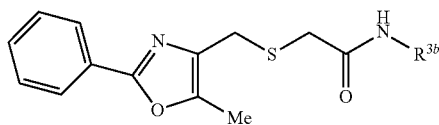
| ID | Structure | MW |
|---|---|---|
| IIa-1403 | | 463.60 |
| IIa-1404 | | 465.62 |

TABLE 5-continued
Oxazole amides ($R^3$ = NH-$C_3C_7$cycloalkyl)
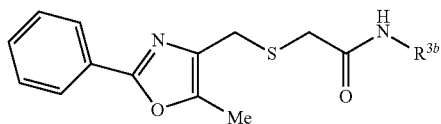
| ID | Structure | MW |
|---|---|---|
| IIa-1405 | 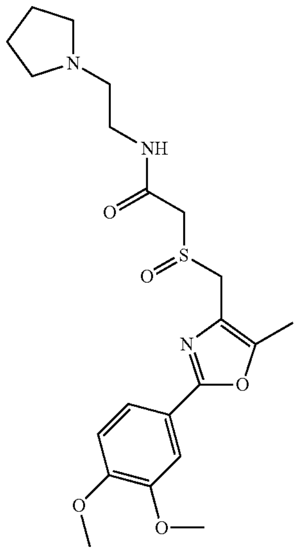 [SMILES: COc1ccc(-c2nc(CS(=O)CC(=O)NCCN3CCCC3)c(C)o2)cc1OC] | 435.55 |
| IIa-1406 | 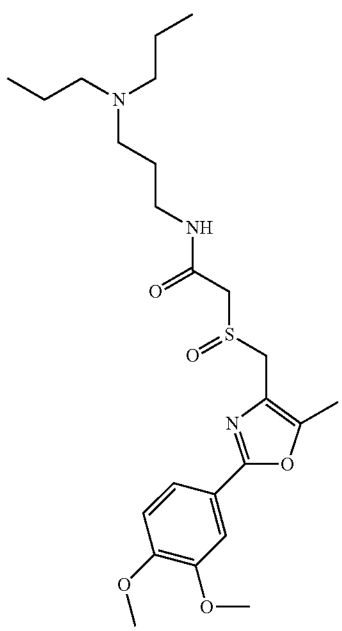 [SMILES: CCCN(CCC)CCCNC(=O)CS(=O)Cc1nc(-c2ccc(OC)c(OC)c2)oc1C] | 479.64 |

TABLE 5-continued
Oxazole amides ($R^3$ = NH-$C_3C_7$cycloalkyl)
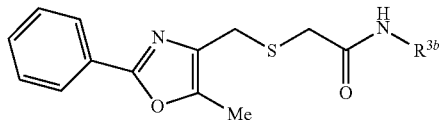
| ID | Structure | MW |
|---|---|---|
| IIa-1407 | 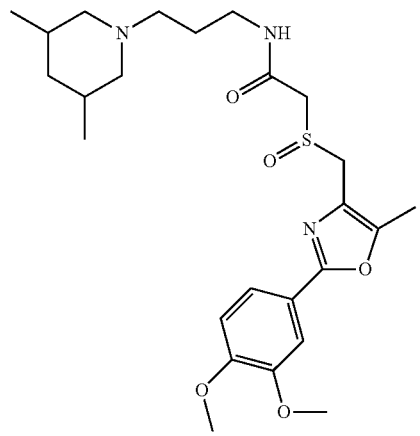 | 491.65 |
| IIa-1408 | 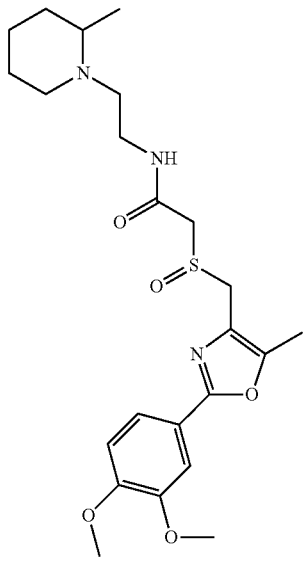 [SMILES: COc1ccc(-c2nc(CS(=O)CC(=O)NCCN3CCCCC3C)c(C)o2)cc1OC] | 463.60 |

TABLE 5-continued
Oxazole amides (R³ = NH-C₃C₇cycloalkyl)
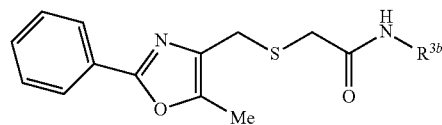
| ID | Structure | MW |
|---|---|---|
| IIa-1409 | | 478.62 |
| IIa-1410 | | 465.62 |

TABLE 5-continued
Oxazole amides (R³ = NH-C₃C₇cycloalkyl)
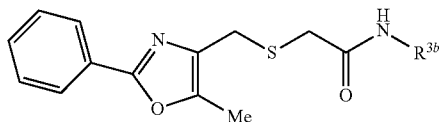
| ID | Structure | MW |
|---|---|---|
| IIa-1411 | 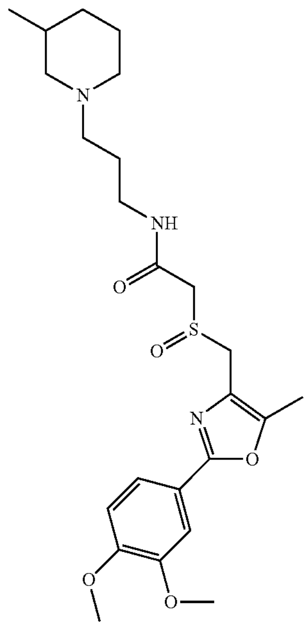 | 477.63 |
| IIa-1412 | 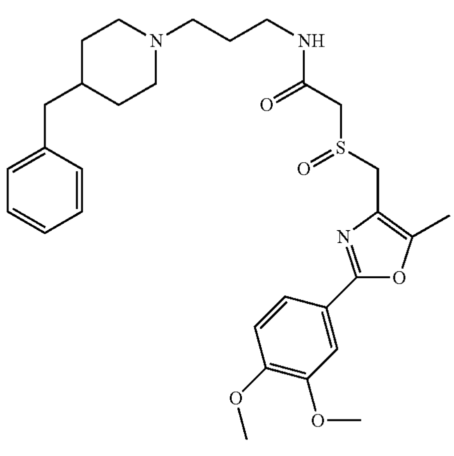 [SMILES: COc1ccc(-c2nc(CS(=O)CC(=O)NCCCN3CCC(Cc4ccccc4)CC3)c(C)o2)cc1OC] | 553.73 |

TABLE 5-continued
Oxazole amides (R³ = NH-C₃C₇cycloalkyl)
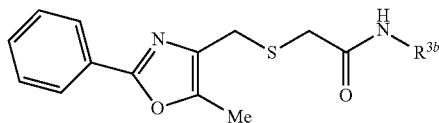
| ID | Structure | MW |
|---|---|---|
| IIa-1413 | | 507.70 |
| IIa-1414 | | 541.72 |

TABLE 5-continued
Oxazole amides (R³ = NH-C₃C₇cycloalkyl)
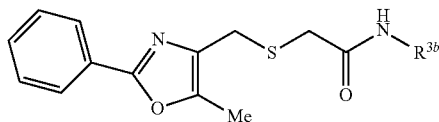
| ID | Structure | MW |
|---|---|---|
| IIa-1415 | | 561.10 |
| IIa-1416 | | 493.67 |

TABLE 5-continued
Oxazole amides (R³ = NH-C₃C₇cycloalkyl)
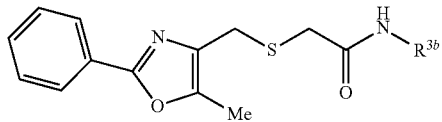
| ID | Structure | MW |
| --- | --- | --- |
| IIa-1417 | 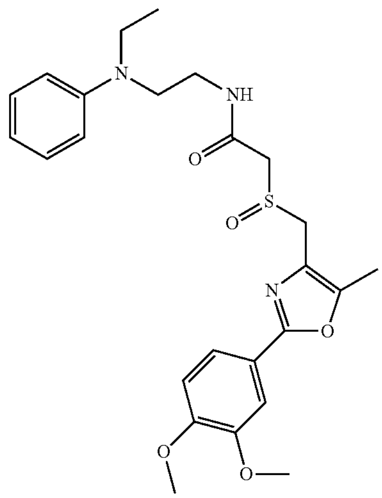 [SMILES: CCN(CCNC(=O)CS(=O)Cc1nc(-c2ccc(OC)c(OC)c2)oc1C)c1ccccc1] | 485.61 |
| IIa-1418 | 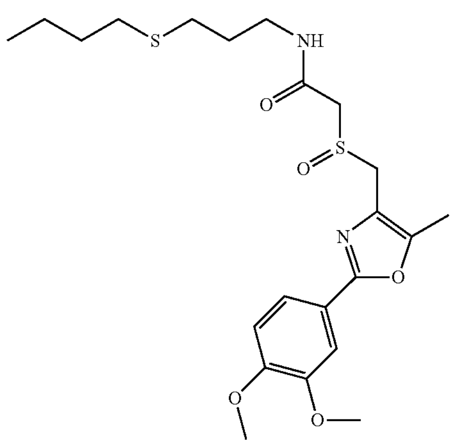 [SMILES: CCCCSCCCNC(=O)CS(=O)Cc1nc(-c2ccc(OC)c(OC)c2)oc1C] | 468.64 |

TABLE 5-continued
Oxazole amides (R³ = NH-C₃C₇cycloalkyl)
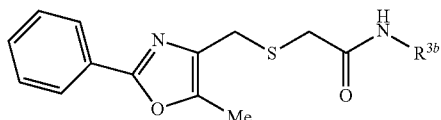
| ID | Structure | MW |
|---|---|---|
| IIa-1419 | 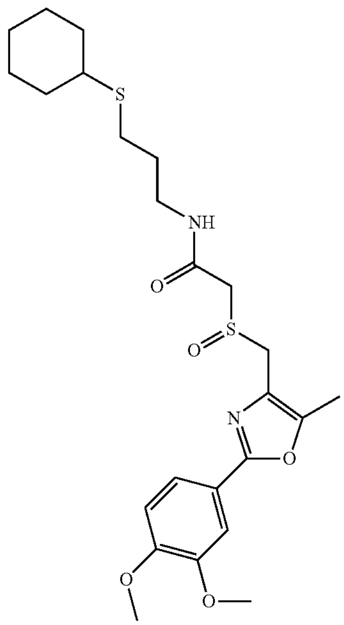 [SMILES: COc1ccc(-c2nc(CS(=O)CC(=O)NCCCSC3CCCCC3)c(C)o2)cc1OC] | 494.68 |
| IIa-1420 | 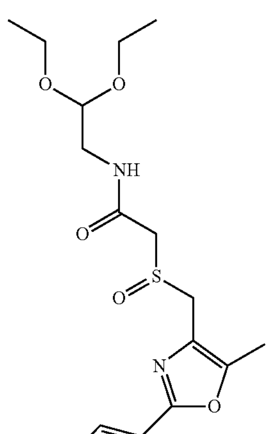 | 394.49 |

TABLE 5-continued
Oxazole amides ($R^3$ = NH-$C_3C_7$cycloalkyl)
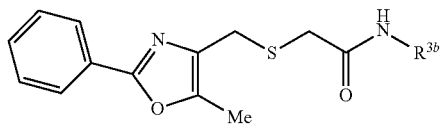
| ID | Structure | MW |
|---|---|---|
| IIa-1421 | | 369.45 |
| IIa-1422 | | 334.44 |
| IIa-1423 | | 349.46 |

TABLE 5-continued
Oxazole amides (R³ = NH-C₃C₇cycloalkyl)
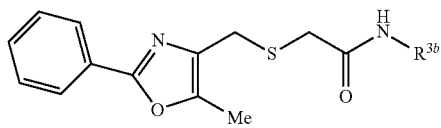
| ID | Structure | MW |
|---|---|---|
| IIa-1424 | 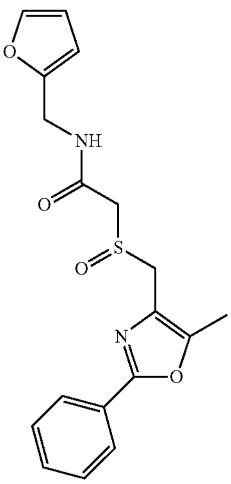 [SMILES: Cc1oc(-c2ccccc2)nc1CS(=O)CC(=O)NCc1ccco1] | 358.42 |
| IIa-1425 | 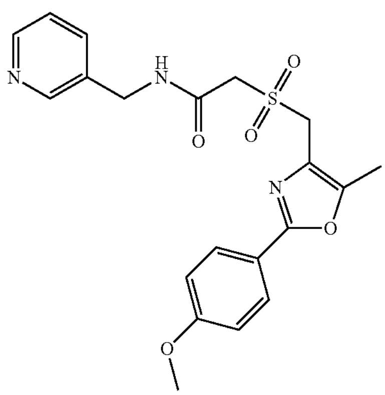 [SMILES: COc1ccc(-c2nc(CS(=O)(=O)CC(=O)NCc3cccnc3)c(C)o2)cc1] | 415.47 |
| IIa-1426 | 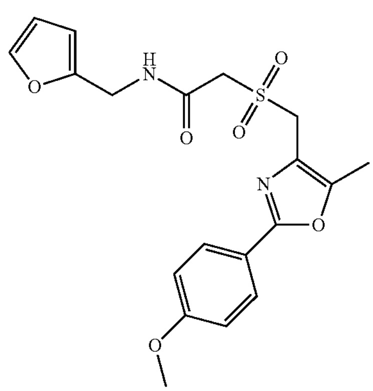 [SMILES: COc1ccc(-c2nc(CS(=O)(=O)CC(=O)NCc3ccco3)c(C)o2)cc1] | 404.45 |

TABLE 5-continued

Oxazole amides (R³ = NH-C₃C₇cycloalkyl)

| ID | Structure | MW |
|---|---|---|
| IIa-1427 | | 412.47 |
| IIa-1428 | | 394.49 |
| IIa-1429 | | 382.44 |
| IIa-1430 | | 432.54 |

TABLE 5-continued
Oxazole amides (R³ = NH-C₃C₇cycloalkyl)
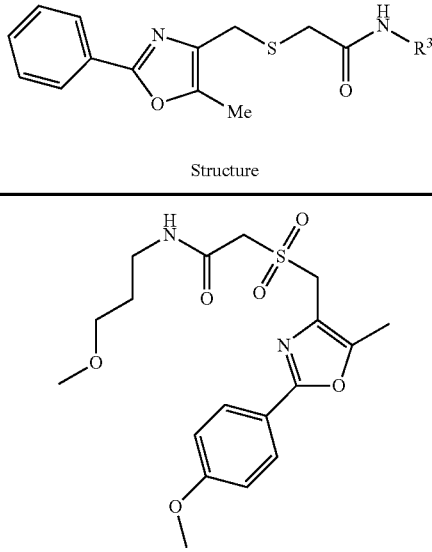
| ID | Structure | MW |
| --- | --- | --- |
| IIa-1431 | 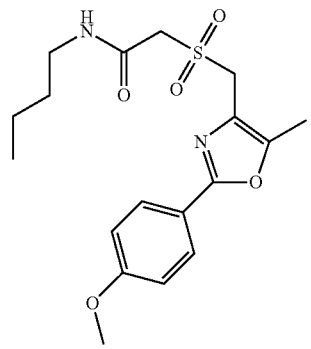 [SMILES: CCCCNC(=O)CS(=O)(=O)Cc1nc(-c2ccc(OC)cc2)oc1C] | 396.47 |
| IIa-1432 | | 380.47 |
| IIa-1433 | 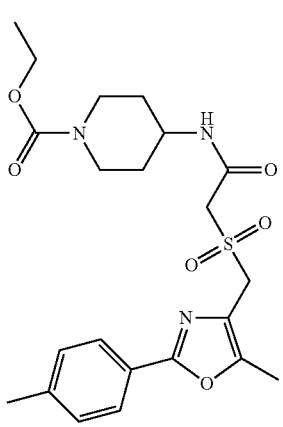 | 463.56 |

TABLE 5-continued
Oxazole amides ($R^3$ = NH-$C_3C_7$cycloalkyl)
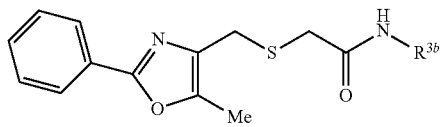
| ID | Structure | MW |
|---|---|---|
| IIa-1434 | 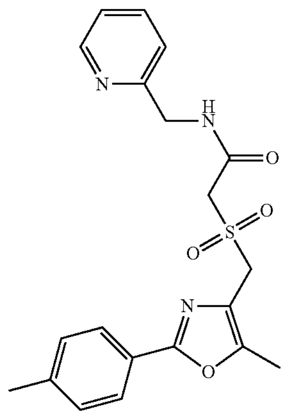 | 399.47 |
| IIa-1435 | 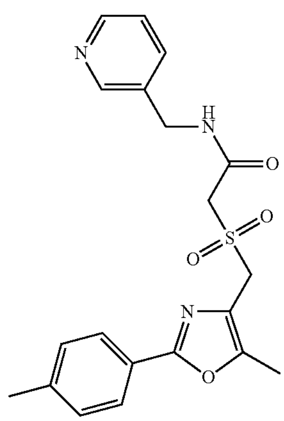 | 399.47 |
| IIa-1436 | 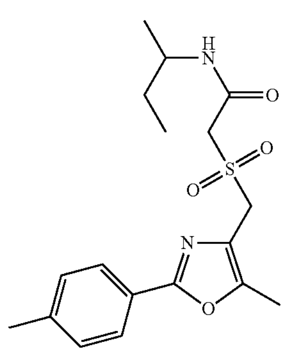 | 364.47 |

TABLE 5-continued
Oxazole amides (R³ = NH-C₃C₇cycloalkyl)
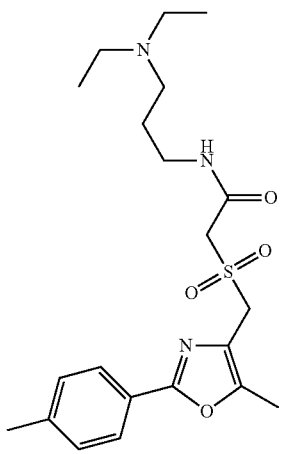
| ID | Structure | MW |
|---|---|---|
| IIa-1437 | 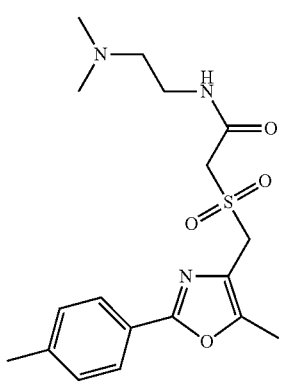 | 421.56 |
| IIa-1438 | | 379.48 |
| IIa-1439 | 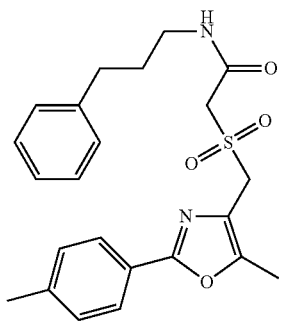 | 426.54 |

TABLE 5-continued
Oxazole amides (R³ = NH-C₃C₇cycloalkyl)
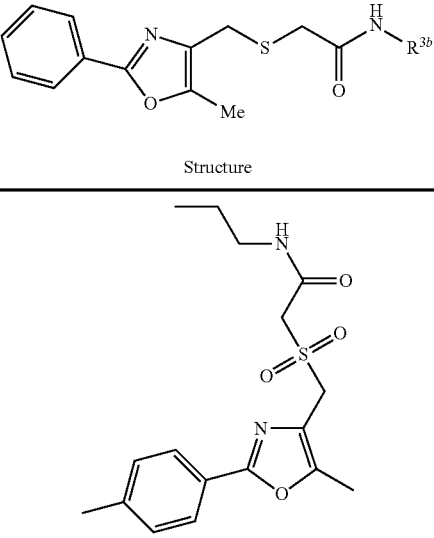
| ID | Structure | MW |
|---|---|---|
| IIa-1440 | 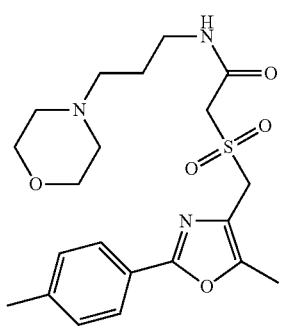 | 350.44 |
| IIa-1441 | 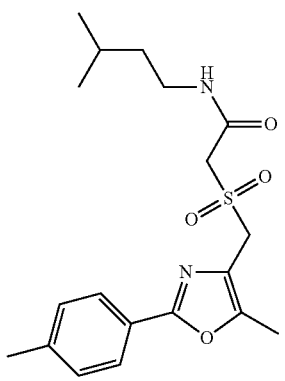 | 435.55 |
| IIa-1442 | 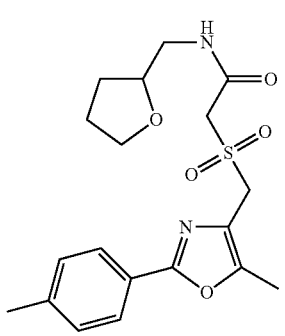 | 378.49 |
| IIa-1443 | 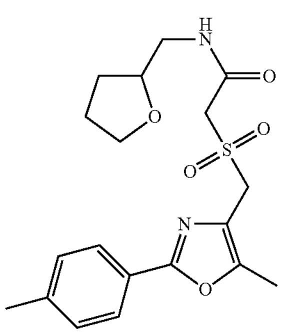 | 392.48 |

TABLE 5-continued

Oxazole amides (R³ = NH-C₃C₇cycloalkyl)

| ID | Structure | MW |
|---|---|---|
| IIa-1444 | | 366.44 |
| IIa-1445 | | 419.55 |
| IIa-1446 | | 451.55 |
| IIa-1447 | | 394.49 |

TABLE 5-continued
Oxazole amides (R³ = NH-C₃C₇cycloalkyl)
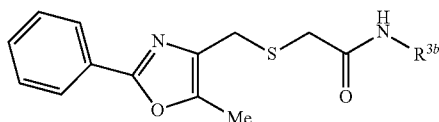
| ID | Structure | MW |
|---|---|---|
| IIa-1448 | 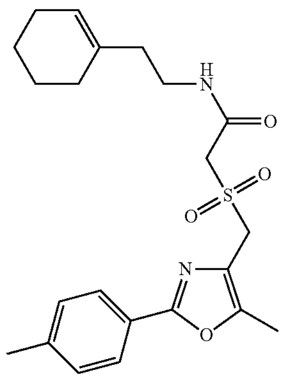 | 416.54 |
| IIa-1449 | 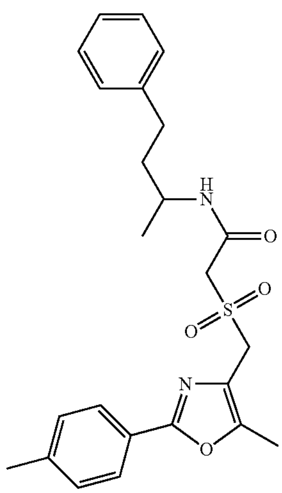 | 440.57 |
| IIa-1450 | 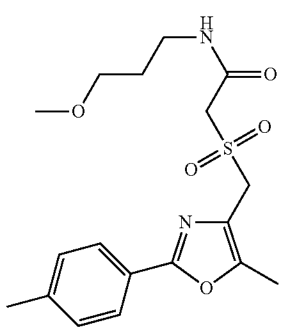 | 380.47 |

TABLE 5-continued
Oxazole amides (R³ = NH-C₃C₇cycloalkyl)
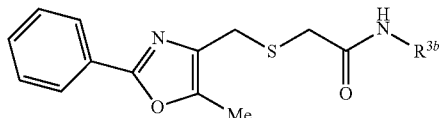
| ID | Structure | MW |
|---|---|---|
| IIa-1451 | | 408.52 |
| IIa-1452 | | 421.52 |
| IIa-1453 | | 470.64 |

TABLE 5-continued
Oxazole amides (R³ = NH-C₃C₇cycloalkyl)
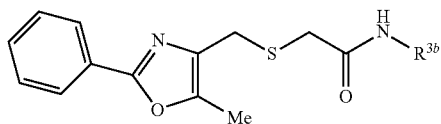
| ID | Structure | MW |
|---|---|---|
| IIa-1454 | | 448.59 |
| IIa-1455 | | 469.61 |
| IIa-1456 | | 449.62 |
| IIa-1457 | | 419.55 |

TABLE 5-continued

Oxazole amides (R³ = NH-C₃C₇cycloalkyl)

| ID | Structure | MW |
|---|---|---|
| IIa-1458 | | 435.59 |
| IIa-1459 | | 405.52 |
| IIa-1460 | | 461.63 |
| IIa-1461 | | 462.62 |

TABLE 5-continued
Oxazole amides (R³ = NH-C₃C₇cycloalkyl)
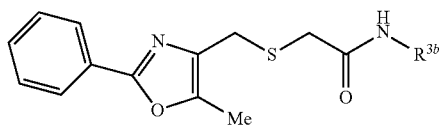
| ID | Structure | MW |
|---|---|---|
| IIa-1462 | 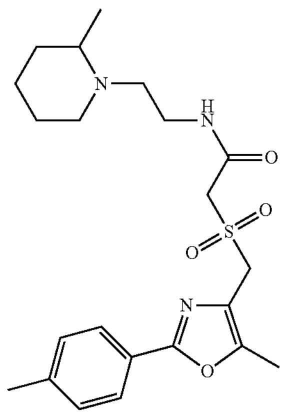 | 433.57 |
| IIa-1463 | 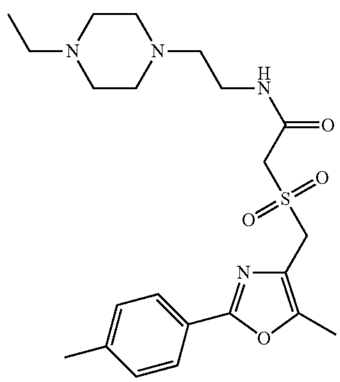 [SMILES: CCN1CCN(CCNC(=O)CS(=O)(=O)Cc2nc(-c3ccc(C)cc3)oc2C)CC1] | 448.59 |
| IIa-1464 | 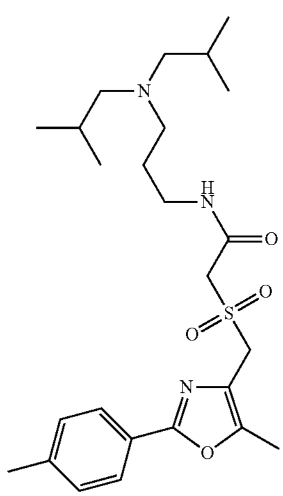 | 477.67 |

TABLE 5-continued
Oxazole amides (R³ = NH-C₃C₇cycloalkyl)
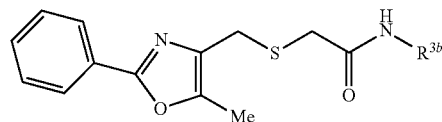
| ID | Structure | MW |
|---|---|---|
| IIa-1465 | | 477.67 |
| IIa-1466 | | 447.60 |

TABLE 5-continued

Oxazole amides (R³ = NH-C₃C₇cycloalkyl)

| ID | Structure | MW |
|---|---|---|
| IIa-1467 | | 463.64 |
| IIa-1468 | | 455.58 |
| IIa-1469 | | 497.66 |

TABLE 5-continued
Oxazole amides (R³ = NH-C₃C₇cycloalkyl)
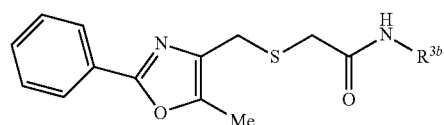
| ID | Structure | MW |
|---|---|---|
| IIa-1470 | | 424.59 |
| IIa-1471 | | 464.65 |
| IIa-1472 | | 489.68 |

TABLE 5-continued

Oxazole amides (R³ = NH-C₃C₇cycloalkyl)

| ID | Structure | MW |
|---|---|---|
| IIa-1473 | | 479.56 |
| IIa-1474 | | 440.52 |
| IIa-1475 | | 380.47 |

TABLE 5-continued
Oxazole amides (R³ = NH-C₃C₇cycloalkyl)
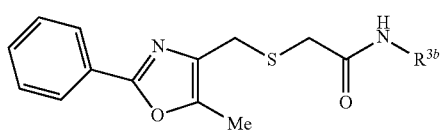
| ID | Structure | MW |
|---|---|---|
| IIa-1476 | | 395.48 |
| IIa-1477 | | 442.54 |
| IIa-1478 | | 423.54 |

TABLE 5-continued
Oxazole amides (R³ = NH-C₃C₇cycloalkyl)
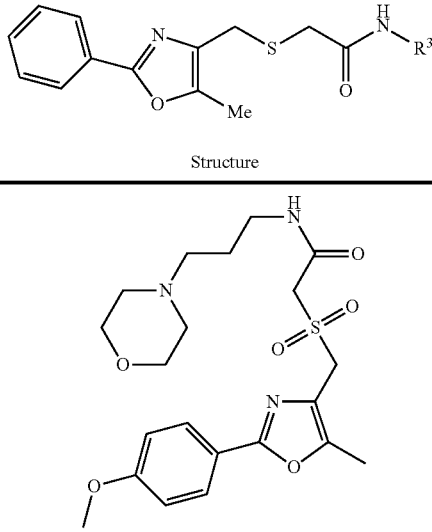
| ID | Structure | MW |
|---|---|---|
| IIa-1479 | 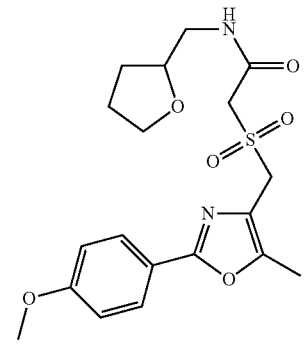 | 451.55 |
| IIa-1480 | 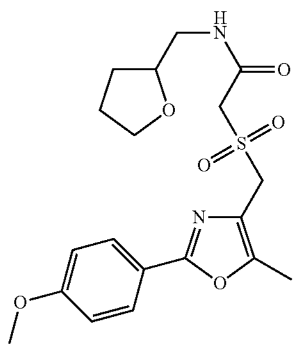 | 408.48 |
| IIa-1481 | 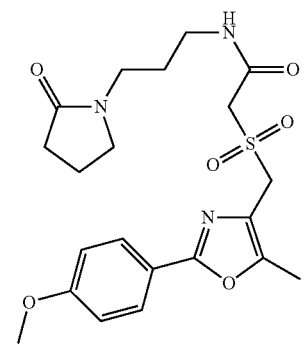 | 449.53 |

TABLE 5-continued
Oxazole amides (R³ = NH-C₃C₇cycloalkyl)
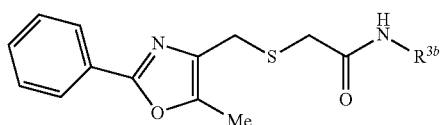
| ID | Structure | MW |
|---|---|---|
| IIa-1482 | 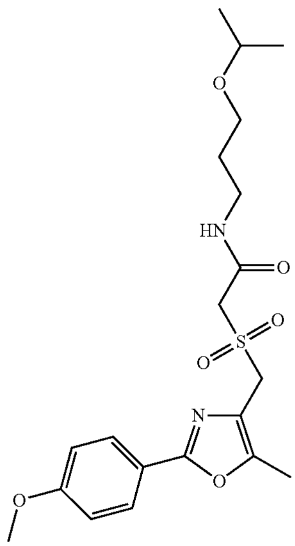 | 424.52 |
| IIa-1483 | 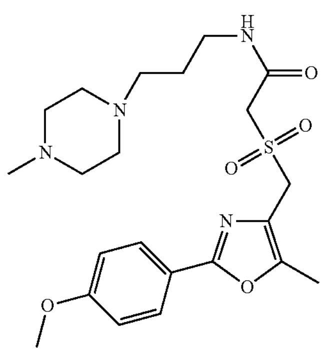 | 464.59 |
| IIa-1484 | 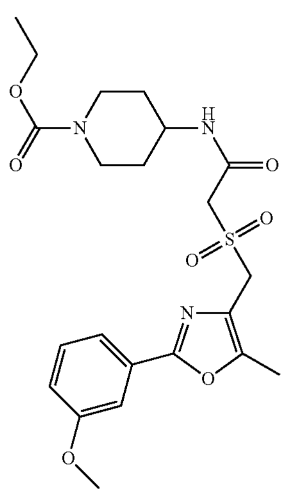 [SMILES: CCOC(=O)N1CCC(NC(=O)CS(=O)(=O)Cc2nc(-c3cccc(OC)c3)oc2C)CC1] | 479.56 |

TABLE 5-continued
Oxazole amides (R³ = NH-C₃C₇cycloalkyl)
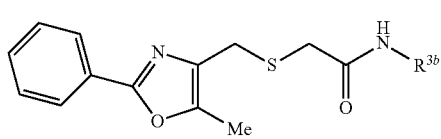
| ID | Structure | MW |
|---|---|---|
| IIa-1485 | 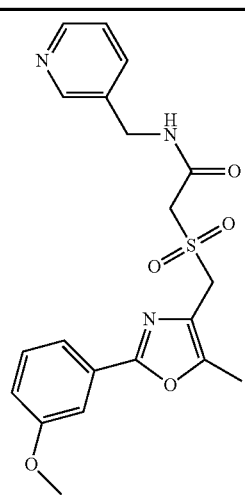 | 415.47 |
| IIa-1486 | | 380.47 |
| IIa-1487 | 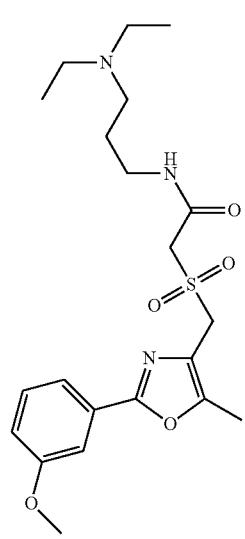 [SMILES: CCN(CC)CCCNC(=O)CS(=O)(=O)Cc1nc(-c2cccc(OC)c2)oc1C] | 437.56 |

TABLE 5-continued
Oxazole amides ($R^3$ = NH-$C_3C_7$cycloalkyl)
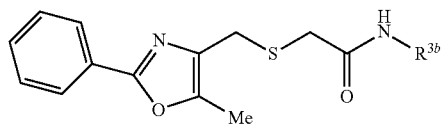
| ID | Structure | MW |
|---|---|---|
| IIa-1488 | | 395.48 |
| IIa-1489 | | 442.54 |
| IIa-1490 | | 366.44 |

TABLE 5-continued
Oxazole amides (R³ = NH-C₃C₇cycloalkyl)
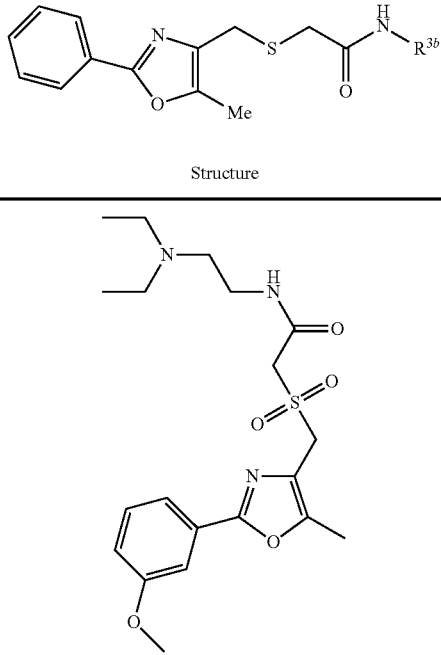
| ID | Structure | MW |
|---|---|---|
| IIa-1491 | 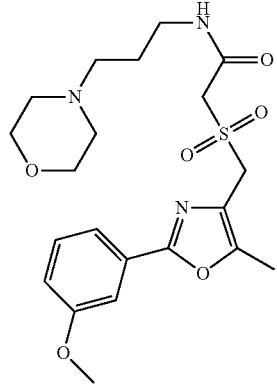 | 423.54 |
| IIa-1492 | 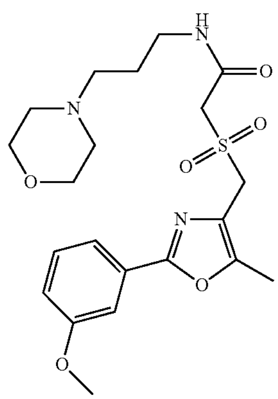 [SMILES: COc1cccc(-c2nc(CS(=O)(=O)CC(=O)NCCCN3CCOCC3)c(C)o2)c1] | 451.55 |
| IIa-1493 | 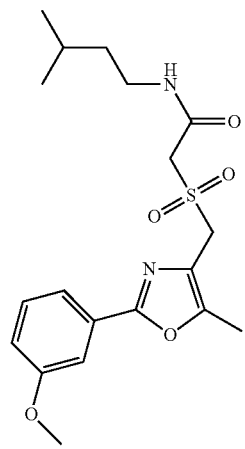 [SMILES: COc1cccc(-c2nc(CS(=O)(=O)CC(=O)NCCC(C)C)c(C)o2)c1] | 394.49 |

TABLE 5-continued
Oxazole amides (R³ = NH-C₃C₇cycloalkyl)
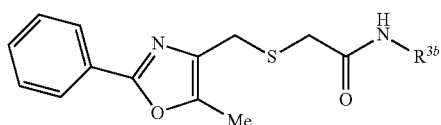
| ID | Structure | MW |
|---|---|---|
| IIa-1494 | | 449.53 |
| IIa-1495 | | 382.44 |
| IIa-1496 | | 420.51 |

TABLE 5-continued
Oxazole amides (R³ = NH-C₃C₇cycloalkyl)
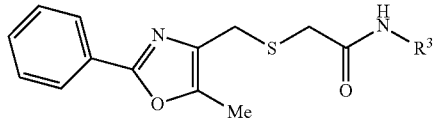
| ID | Structure | MW |
|---|---|---|
| IIa-1497 | 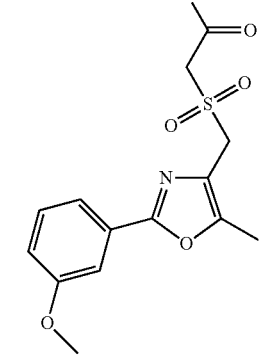 | 410.49 |
| IIa-1498 | 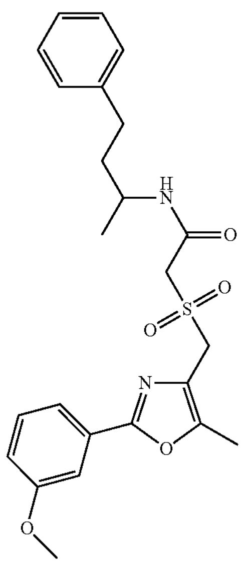 [SMILES: COc1cccc(-c2nc(CS(=O)(=O)CC(=O)NC(C)CCc3ccccc3)c(C)o2)c1] | 456.57 |
| IIa-1499 | 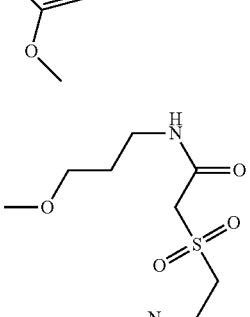 | 396.47 |

TABLE 5-continued
Oxazole amides ($R^3$ = NH-$C_3C_7$cycloalkyl)
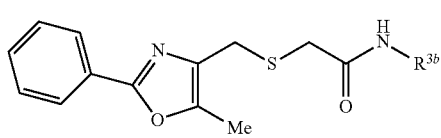
| ID | Structure | MW |
|---|---|---|
| IIa-1500 | | 424.52 |
| IIa-1501 | | 437.52 |

TABLE 5-continued
Oxazole amides (R³ = NH-C₃C₇cycloalkyl)
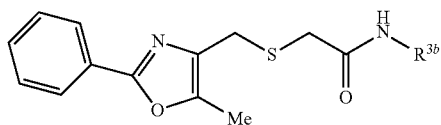
| ID | Structure | MW |
|---|---|---|
| IIa-1502 | 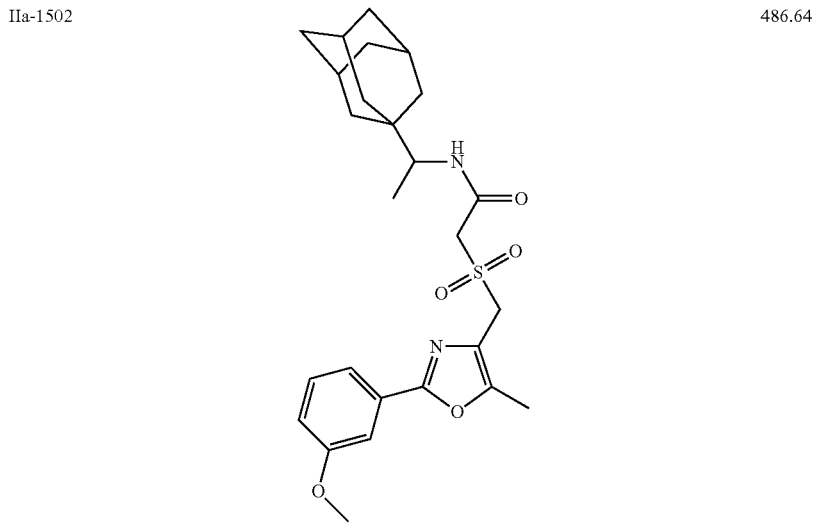 | 486.64 |
| IIa-1503 | 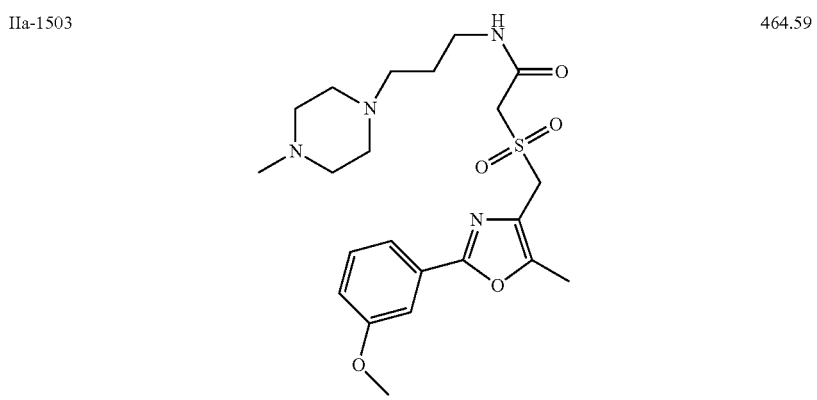 | 464.59 |

TABLE 5-continued
Oxazole amides (R³ = NH-C₃C₇cycloalkyl)
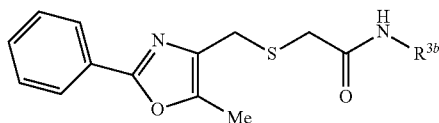
| ID | Structure | MW |
|---|---|---|
| IIa-1504 | | 485.61 |
| IIa-1505 | | 477.63 |

TABLE 5-continued

Oxazole amides (R³ = NH-C₃C₇cycloalkyl)

| ID | Structure | MW |
|---|---|---|
| IIa-1506 | 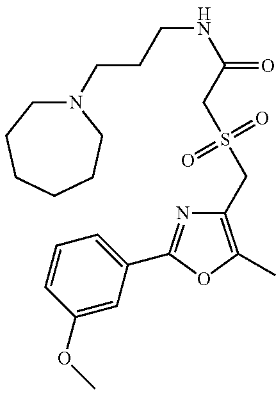 [SMILES: COc1cccc(-c2nc(CS(=O)(=O)CC(=O)NCCCN3CCCCCC3)c(C)o2)c1] | 463.60 |
| IIa-1507 | 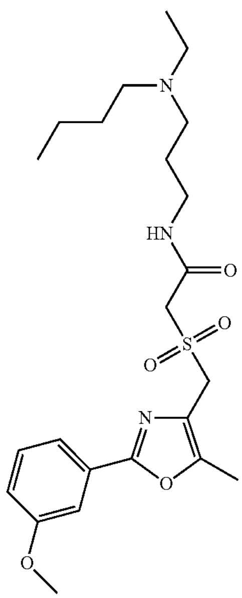 [SMILES: CCCCN(CC)CCCNC(=O)CS(=O)(=O)Cc1nc(-c2cccc(OC)c2)oc1C] | 465.62 |
| IIa-1508 | 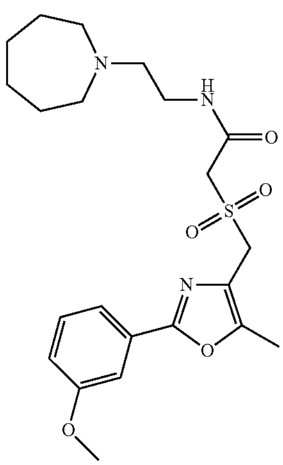 [SMILES: COc1cccc(-c2nc(CS(=O)(=O)CC(=O)NCCN3CCCCCC3)c(C)o2)c1] | 449.57 |

TABLE 5-continued

Oxazole amides (R³ = NH-C₃C₇cycloalkyl)

| ID | Structure | MW |
|---|---|---|
| IIa-1509 | | 451.59 |
| IIa-1510 | | 477.63 |
| IIa-1511 | | 478.62 |

TABLE 5-continued
Oxazole amides (R³ = NH-C₃C₇cycloalkyl)
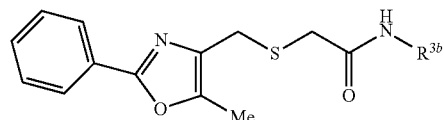
| ID | Structure | MW |
|---|---|---|
| IIa-1512 | | 493.67 |
| IIa-1513 | | 477.63 |

TABLE 5-continued
Oxazole amides (R³ = NH-C₃C₇cycloalkyl)
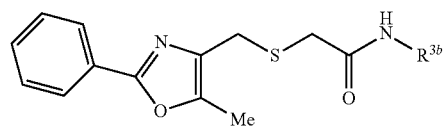
| ID | Structure | MW |
|---|---|---|
| IIa-1514 | 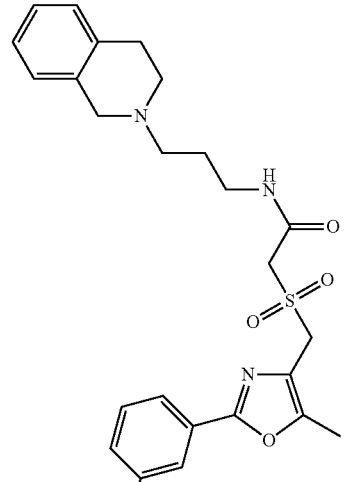 | 497.62 |
| IIa-1515 | | 479.64 |

TABLE 5-continued
Oxazole amides (R³ = NH-C₃C₇cycloalkyl)
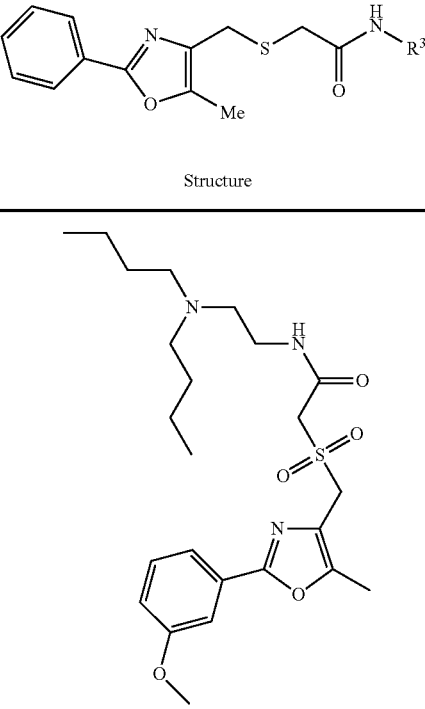
| ID | Structure | MW |
|---|---|---|
| IIa-1516 | 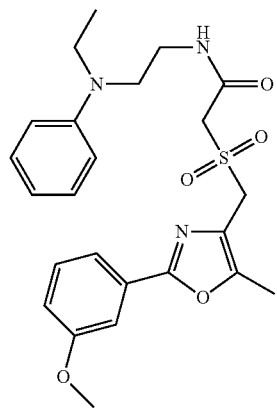 [SMILES: CCN(CCNC(=O)CS(=O)(=O)Cc1nc(-c2cccc(OC)c2)oc1C)c1ccccc1] | 479.64 |
| IIa-1517 | | 471.58 |
| IIa-1518 | 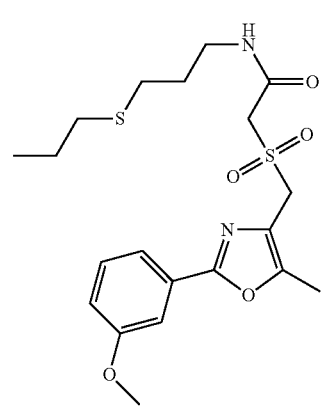 [SMILES: CCCSCCCNC(=O)CS(=O)(=O)Cc1nc(-c2cccc(OC)c2)oc1C] | 440.58 |

TABLE 5-continued
Oxazole amides (R³ = NH-C₃C₇cycloalkyl)
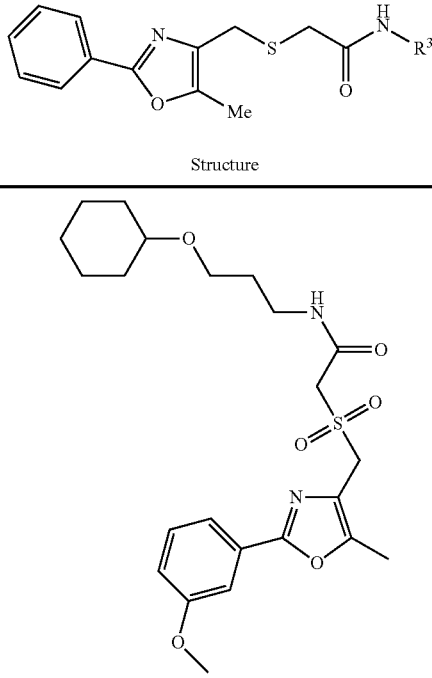
| ID | Structure | MW |
|---|---|---|
| IIa-1519 | 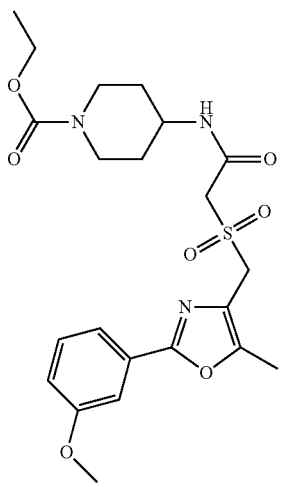 [SMILES: CCOC(=O)N1CCC(NC(=O)CS(=O)(=O)Cc2nc(-c3cccc(OC)c3)oc2C)CC1] | 480.65 |
| IIa-1520 | | 463.56 |
| IIa-1521 | 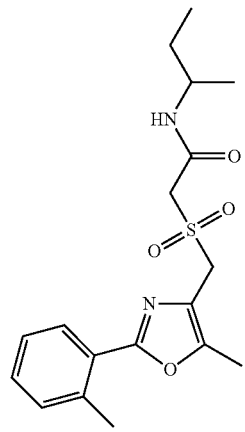 [SMILES: CCC(C)NC(=O)CS(=O)(=O)Cc1nc(-c2ccccc2C)oc1C] | 364.47 |

TABLE 5-continued
Oxazole amides (R³ = NH-C₃C₇cycloalkyl)
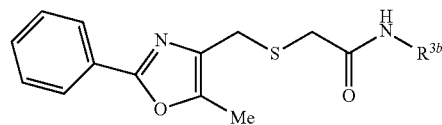
| ID | Structure | MW |
|----|-----------|-----|
| IIa-1522 | | 421.56 |
| IIa-1523 | | 379.48 |
| IIa-1524 | | 388.45 |

TABLE 5-continued
Oxazole amides (R³ = NH-C₃C₇cycloalkyl)
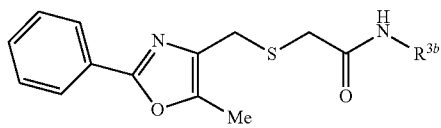
| ID | Structure | MW |
|---|---|---|
| IIa-1525 | | 426.54 |
| IIa-1526 | | 350.44 |
| IIa-1527 | | 407.54 |

TABLE 5-continued

Oxazole amides (R³ = NH-C₃C₇cycloalkyl)

| ID | Structure | MW |
|---|---|---|
| IIa-1528 | | 435.55 |
| IIa-1529 | | 378.49 |
| IIa-1530 | | 392.48 |
| IIa-1531 | | 433.53 |

TABLE 5-continued
Oxazole amides (R³ = NH-C₃C₇cycloalkyl)
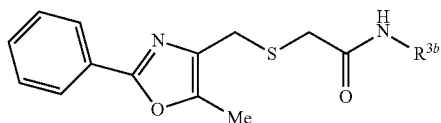
| ID | Structure | MW |
|---|---|---|
| IIa-1532 | | 366.44 |
| IIa-1533 | | 419.55 |
| IIa-1534 | | 440.57 |

TABLE 5-continued
Oxazole amides ($R^3$ = NH-$C_3C_7$cycloalkyl)
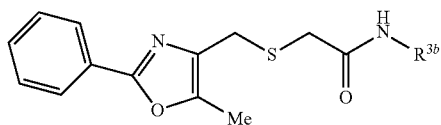
| ID | Structure | MW |
|---|---|---|
| IIa-1535 | | 380.47 |
| IIa-1536 | | 408.52 |
| IIa-1537 | | 421.52 |

TABLE 5-continued
Oxazole amides (R³ = NH-C₃C₇cycloalkyl)
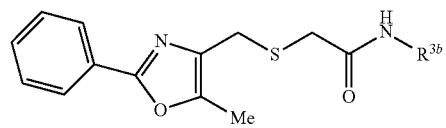
| ID | Structure | MW |
|---|---|---|
| IIa-1538 | | 364.47 |
| IIa-1539 | | 448.59 |
| IIa-1540 | | 419.55 |
| IIa-1541 | | 405.52 |

TABLE 5-continued
Oxazole amides (R³ = NH-C₃C₇cycloalkyl)
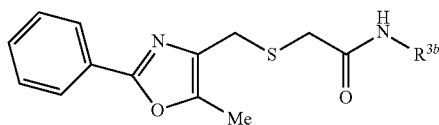
| ID | Structure | MW |
|---|---|---|
| IIa-1542 | | 461.63 |
| IIa-1543 | | 462.62 |
| IIa-1544 | | 477.67 |

TABLE 5-continued
Oxazole amides ($R^3$ = NH-$C_3C_7$cycloalkyl)
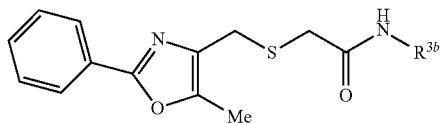
| ID | Structure | MW |
|---|---|---|
| IIa-1545 | | 461.63 |
| IIa-1546 | | 424.59 |
| IIa-1547 | | 383.44 |

TABLE 5-continued
Oxazole amides ($R^3$ = NH-$C_3C_7$cycloalkyl)
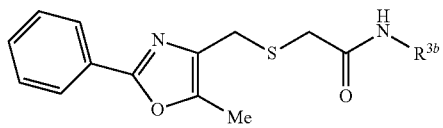
| ID | Structure | MW |
|---|---|---|
| IIa-1548 | | 392.41 |
| IIa-1549 | | 430.50 |
| IIa-1550 | | 400.43 |

TABLE 5-continued
Oxazole amides (R³ = NH-C₃C₇cycloalkyl)
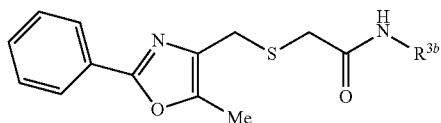
| ID | Structure | MW |
|---|---|---|
| IIa-1551 | | 439.51 |
| IIa-1552 | | 444.53 |
| IIa-1553 | | 452.55 |

TABLE 5-continued
Oxazole amides (R³ = NH-C₃C₇cycloalkyl)
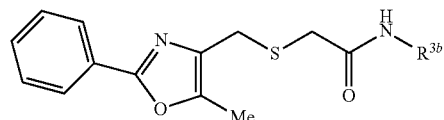
| ID | Structure | MW |
|---|---|---|
| IIa-1554 | | 439.55 |
| IIa-1555 | | 409.48 |
| IIa-1556 | | 465.59 |

TABLE 5-continued
Oxazole amides (R³ = NH-C₃C₇cycloalkyl)
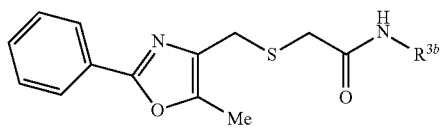
| ID | Structure | MW |
|---|---|---|
| IIa-1557 | | 465.59 |
| IIa-1558 | | 485.58 |
| IIa-1559 | | 451.56 |

TABLE 5-continued
Oxazole amides (R³ = NH-C₃C₇cycloalkyl)
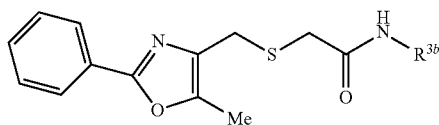
| ID | Structure | MW |
|---|---|---|
| IIa-1560 | 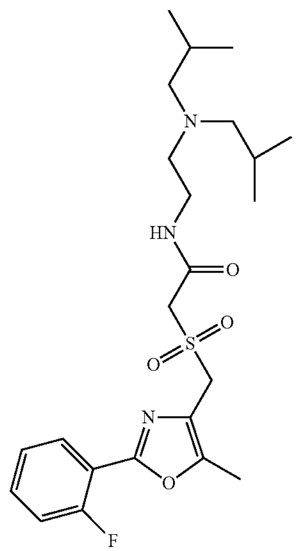 [SMILES: Cc1oc(-c2ccccc2F)nc1CS(=O)(=O)CC(=O)NCCN(CC(C)C)CC(C)C] | 467.61 |
| IIa-1561 | 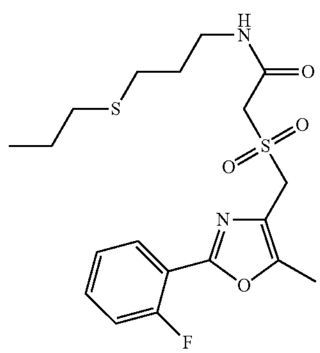 [SMILES: CCCSCCCNC(=O)CS(=O)(=O)Cc1nc(-c2ccccc2F)oc1C] | 428.55 |
| IIa-1562 | 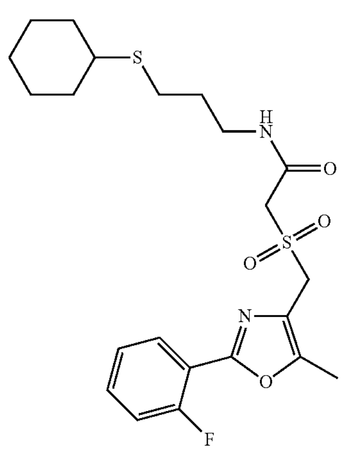 [SMILES: Cc1oc(-c2ccccc2F)nc1CS(=O)(=O)CC(=O)NCCCSC1CCCCC1] | 468.61 |

TABLE 5-continued
Oxazole amides ($R^3$ = NH-$C_3C_7$cycloalkyl)
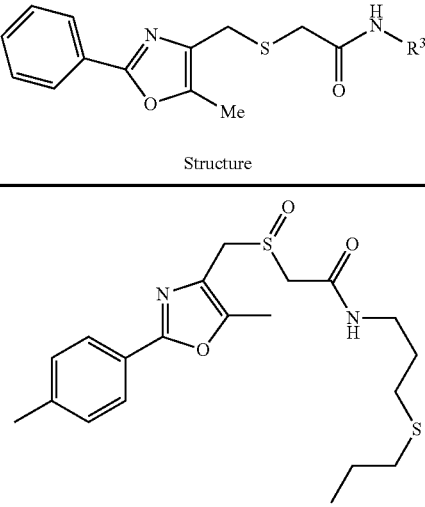
| ID | Structure | MW |
|---|---|---|
| IIa-1563 | 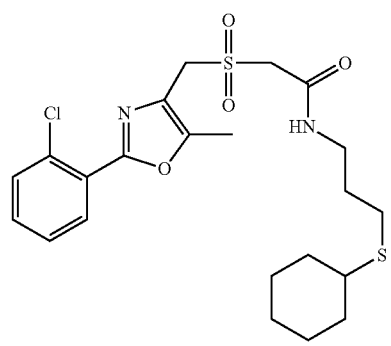 [SMILES: Cc1oc(-c2ccccc2Cl)nc1CS(=O)(=O)CC(=O)NCCCSC1CCCCC1] | 408.59 |
| IIa-1564 | 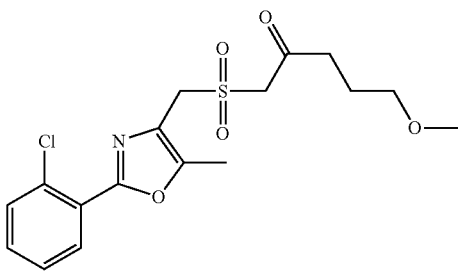 [SMILES: COCCCC(=O)CS(=O)(=O)Cc1nc(-c2ccccc2Cl)oc1C] | 485.07 |
| IIa-1565 | 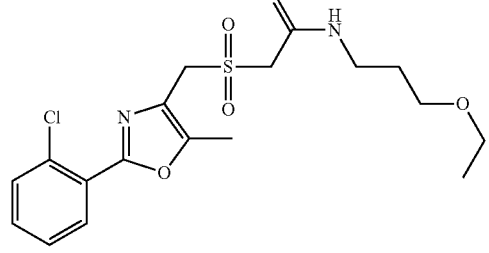 | 386.86 |
| IIa-1566 | | 414.91 |

TABLE 5-continued

Oxazole amides (R³ = NH-C₃C₇cycloalkyl)

| ID | Structure | MW |
|---|---|---|
| IIa-1567 | | 446.96 |
| IIa-1568 | | 408.86 |
| IIa-1569 | | 384.88 |
| IIa-1570 | | 561.10 |

TABLE 5-continued
Oxazole amides (R³ = NH-C₃C₇cycloalkyl)
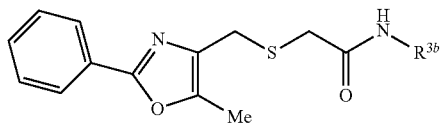
| ID | Structure | MW |
|---|---|---|
| IIa-1571 | 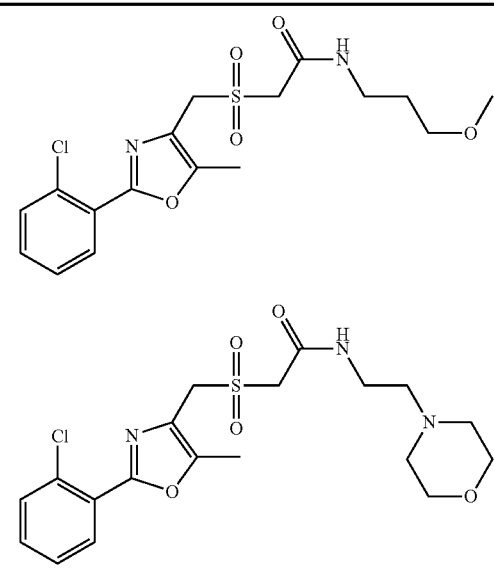 | 400.88 |
| IIa-1572 | 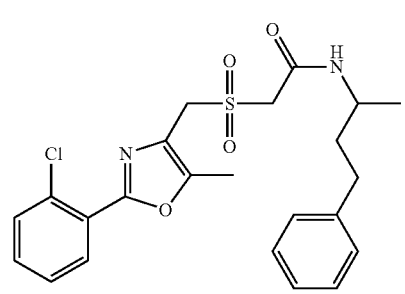 [SMILES: Cc1oc(-c2ccccc2Cl)nc1CS(=O)(=O)CC(=O)NC(C)CCc1ccccc1] | 441.94 |
| IIa-1573 | 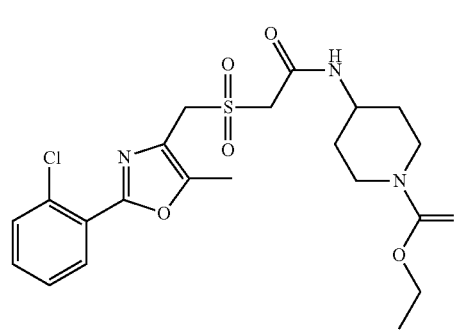 | 460.98 |
| IIa-1574 | 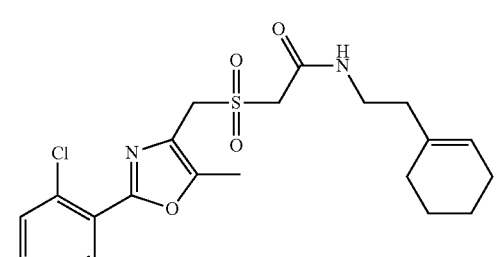 | 483.97 |
| IIa-1575 | | 436.96 |

TABLE 5-continued
Oxazole amides (R³ = NH-C₃C₇cycloalkyl)
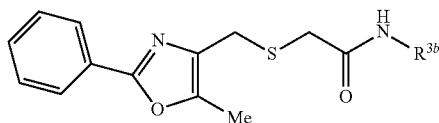
| ID | Structure | MW |
|---|---|---|
| IIa-1576 | | 370.86 |
| IIa-1577 | | 483.97 |
| IIa-1578 | | 446.96 |
| IIa-1579 | | 400.88 |
| IIa-1580 | | 428.94 |

TABLE 5-continued
Oxazole amides (R³ = NH-C₃C₇cycloalkyl)
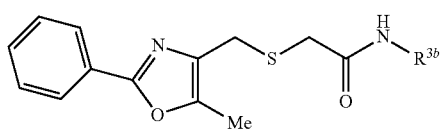
| ID | Structure | MW |
|---|---|---|
| IIa-1581 | 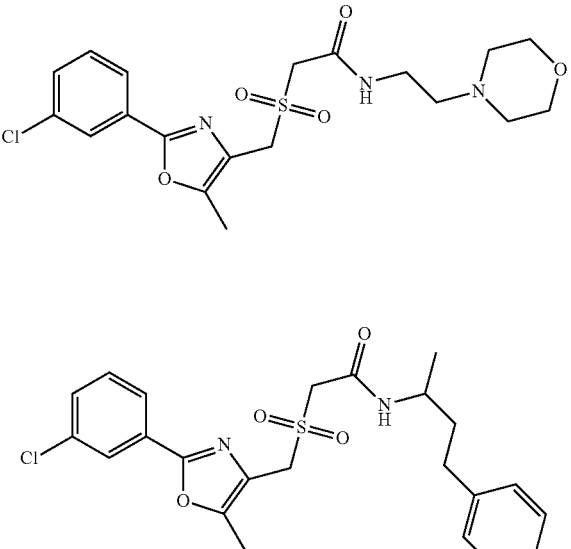 | 441.94 |
| IIa-1582 | 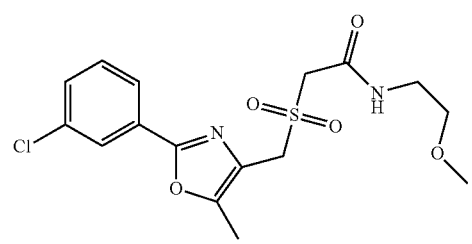 [SMILES: COCCNC(=O)CS(=O)(=O)Cc1nc(-c2cccc(Cl)c2)oc1C] | 460.98 |
| IIa-1583 | 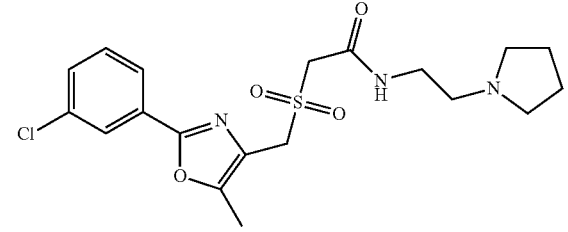 [SMILES: Cc1oc(-c2cccc(Cl)c2)nc1CS(=O)(=O)CC(=O)NCCN1CCCC1] | 386.86 |
| IIa-1584 | 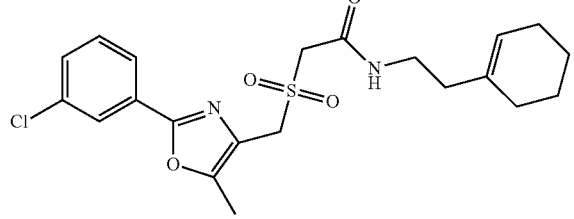 | 425.94 |
| IIa-1585 | 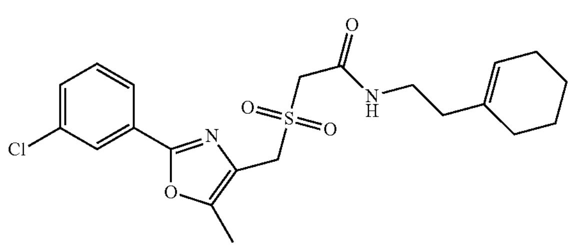 [SMILES: Cc1oc(-c2cccc(Cl)c2)nc1CS(=O)(=O)CC(=O)NCCC1=CCCCC1] | 436.96 |

TABLE 5-continued

Oxazole amides (R³ = NH-C₃C₇cycloalkyl)

| ID | Structure | MW |
|---|---|---|
| IIa-1586 | 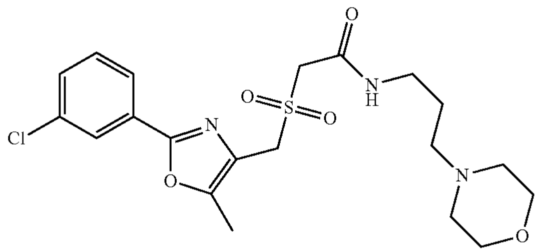 [SMILES: Cc1oc(-c2cccc(Cl)c2)nc1CS(=O)(=O)CC(=O)NCCCN1CCOCC1] | 455.96 |
| IIa-1587 | 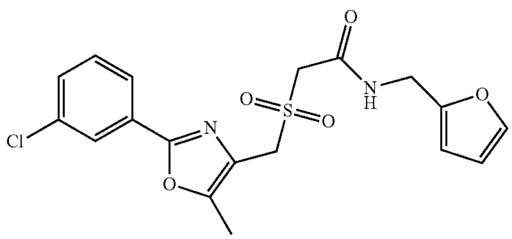 [SMILES: Cc1oc(-c2cccc(Cl)c2)nc1CS(=O)(=O)CC(=O)NCc1ccco1] | 408.86 |
| IIa-1588 | 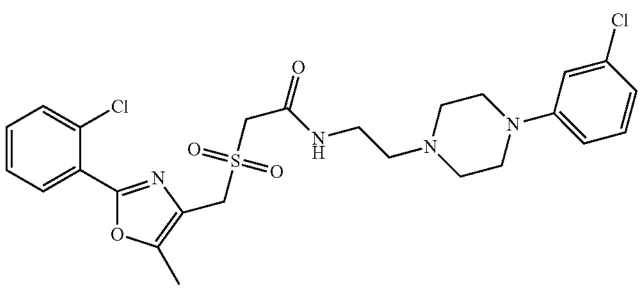 [SMILES: Cc1oc(-c2ccccc2Cl)nc1CS(=O)(=O)CC(=O)NCCN1CCN(c2cccc(Cl)c2)CC1] | 551.50 |
| IIa-1589 | 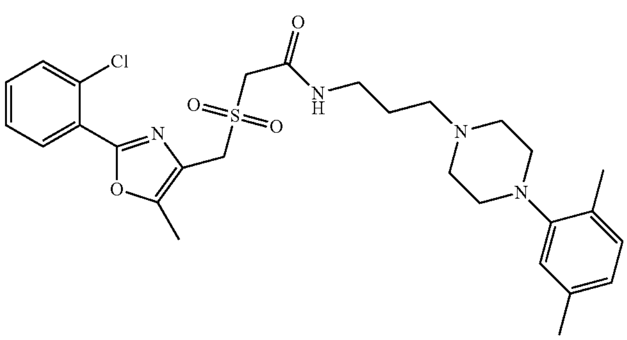 [SMILES: Cc1ccc(C)c(N2CCN(CCCNC(=O)CS(=O)(=O)Cc3nc(-c4ccccc4Cl)oc3C)CC2)c1] | 559.13 |
| IIa-1590 | 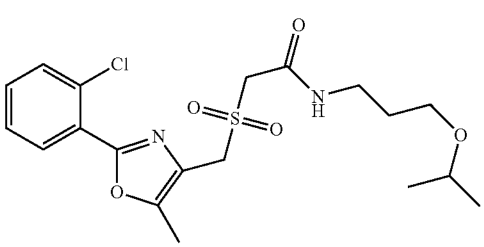 [SMILES: Cc1oc(-c2ccccc2Cl)nc1CS(=O)(=O)CC(=O)NCCCOC(C)C] | 428.94 |

TABLE 5-continued
Oxazole amides (R³ = NH-C₃C₇cycloalkyl)
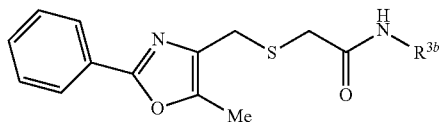
| ID | Structure | MW |
|---|---|---|
| IIa-1591 | | 334.44 |
| IIa-1592 | | 507.70 |

TABLE 5-continued
Oxazole amides (R³ = NH-C₃C₇cycloalkyl)
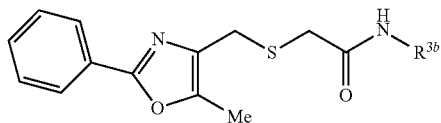
| ID | Structure | MW |
|---|---|---|
| IIa-1593 | 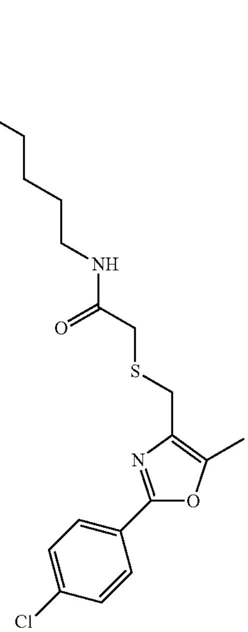 | 427.03 |
| IIa-1594 | 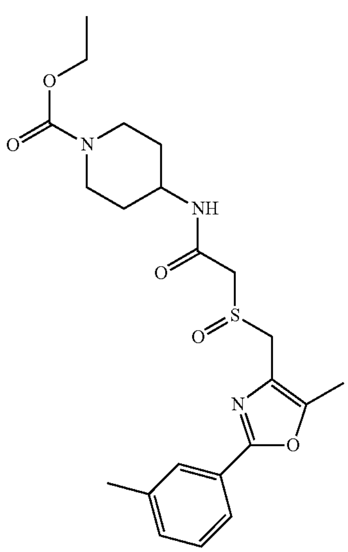 [SMILES: CCOC(=O)N1CCC(NC(=O)CS(=O)Cc2nc(-c3cccc(C)c3)oc2C)CC1] | 447.56 |

TABLE 5-continued

Oxazole amides (R³ = NH-C₃C₇cycloalkyl)

| ID | Structure | MW |
|---|---|---|
| IIa-1595 | | 403.89 |
| IIa-1596 | | 436.94 |
| IIa-1597 | | 408.31 |

TABLE 5-continued
Oxazole amides ($R^3$ = NH-C$_3$C$_7$cycloalkyl)
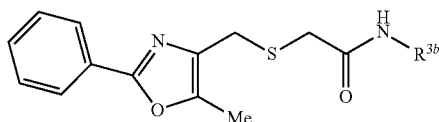
| ID | Structure | MW |
|---|---|---|
| IIa-1598 | | 377.85 |
| IIa-1599 | | 391.85 |
| IIa-1600 | | 361.40 |
| IIa-1601 | | 357.43 |

TABLE 5-continued
Oxazole amides ($R^3$ = NH-$C_3C_7$cycloalkyl)
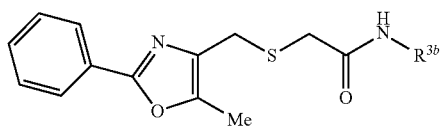
| ID | Structure | MW |
|---|---|---|
| IIa-1602 | | 387.89 |
| IIa-1603 | | 478.04 |
TABLE 6
Oxazole amides ($R^3$ = N-cyclo)
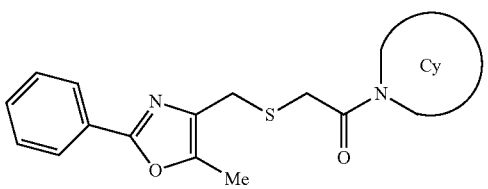
| ID | Structure | MW |
|---|---|---|
| IIa-2001 | | 330.45 |

TABLE 6-continued
Oxazole amides (R³ = N-cyclo)
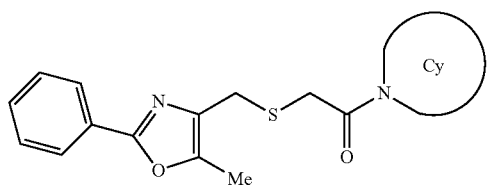 [SMILES: Cc1oc(-c2ccccc2)nc1CSCC(=O)N(C)C]
| ID | Structure | MW |
|---|---|---|
| IIa-2002 | 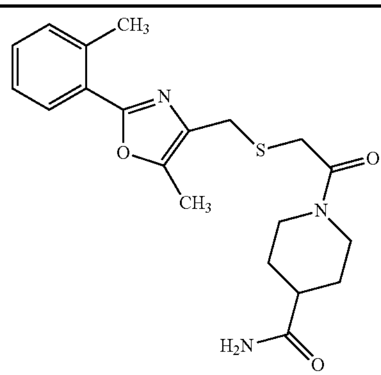 | 387.50 |
| IIa-2003 | 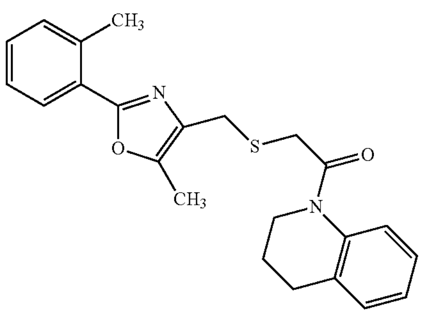 [SMILES: Cc1ccccc1-c1nc(CSCC(=O)N2CCCc3ccccc32)c(C)o1] | 392.52 |
| IIa-2004 | 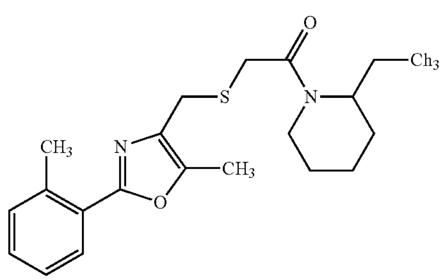 | 372.53 |
| IIa-2005 | 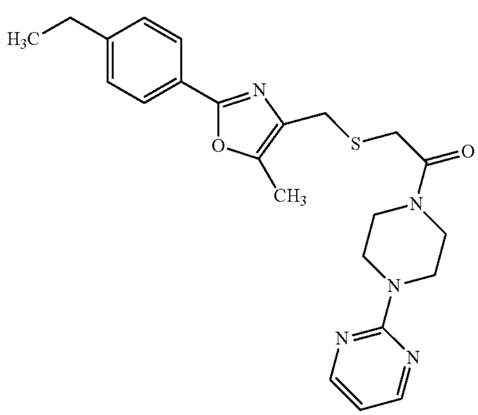 [SMILES: CCc1ccc(-c2nc(CSCC(=O)N3CCN(c4ncccn4)CC3)c(C)o2)cc1] | 437.57 |

TABLE 6-continued
Oxazole amides (R³ = N-cyclo)
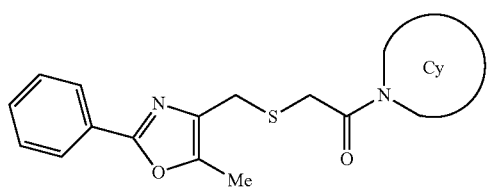
| ID | Structure | MW |
|---|---|---|
| IIa-2006 | 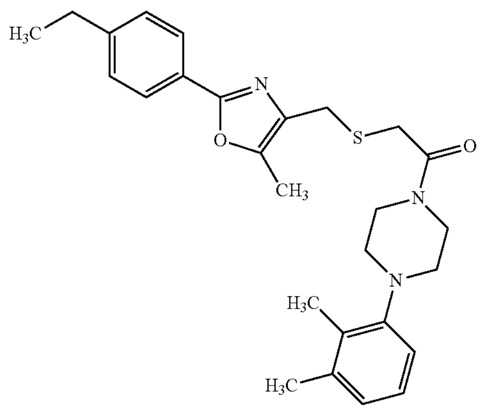 [SMILES: CCc1ccc(-c2nc(CSCC(=O)N3CCN(c4cccc(C)c4C)CC3)c(C)o2)cc1] | 463.65 |
| IIa-2007 | 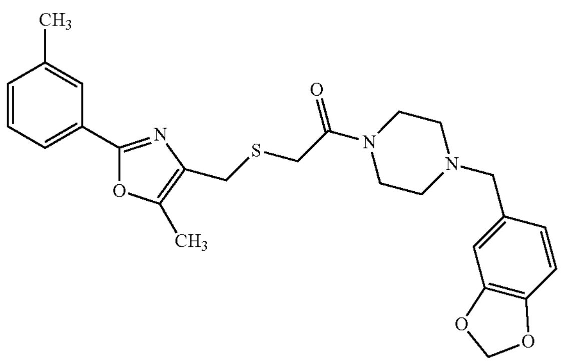 [SMILES: Cc1cccc(-c2nc(CSCC(=O)N3CCN(Cc4ccc5c(c4)OCO5)CC3)c(C)o2)c1] | 479.60 |
| IIa-2008 | 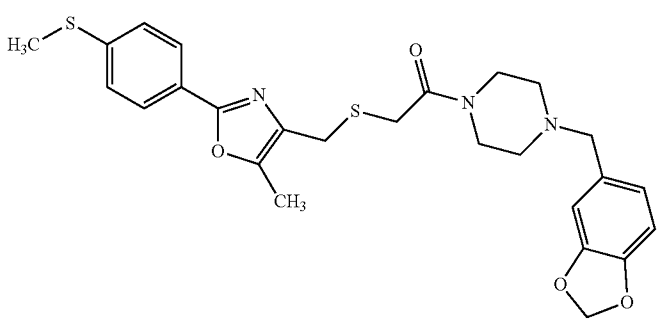 [SMILES: CSc1ccc(-c2nc(CSCC(=O)N3CCN(Cc4ccc5c(c4)OCO5)CC3)c(C)o2)cc1] | 511.67 |
| IIa-2009 | 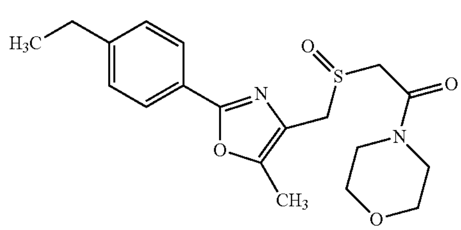 [SMILES: CCc1ccc(-c2nc(CS(=O)CC(=O)N3CCOCC3)c(C)o2)cc1] | 376.48 |

TABLE 6-continued

Oxazole amides (R³ = N-cyclo)

| ID | Structure | MW |
|---|---|---|
| IIa-2010 | 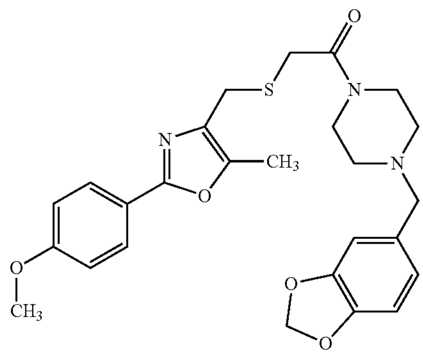 [SMILES: COc1ccc(-c2nc(CSCC(=O)N3CCN(Cc4ccc5c(c4)OCO5)CC3)c(C)o2)cc1] | 495.60 |
| IIa-2011 | 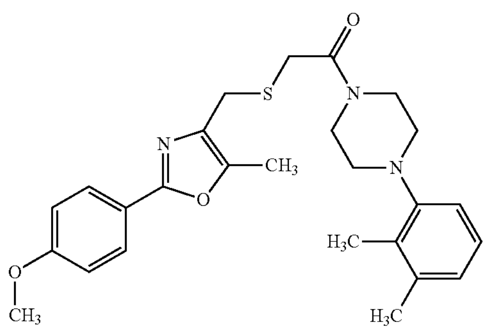 [SMILES: COc1ccc(-c2nc(CSCC(=O)N3CCN(c4cccc(C)c4C)CC3)c(C)o2)cc1] | 465.62 |
| IIa-2012 | 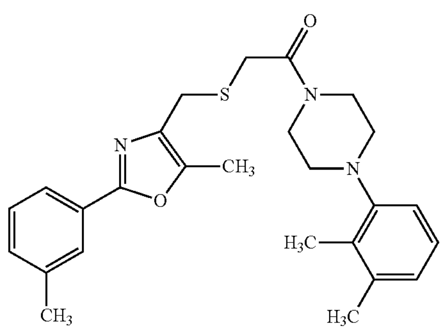 [SMILES: Cc1cccc(-c2nc(CSCC(=O)N3CCN(c4cccc(C)c4C)CC3)c(C)o2)c1] | 449.62 |
| IIa-2013 | 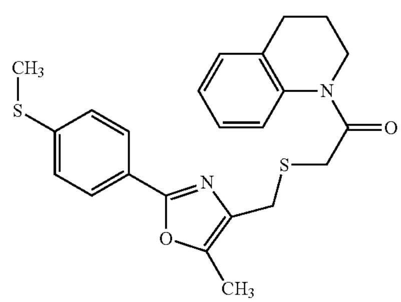 [SMILES: CSc1ccc(-c2nc(CSCC(=O)N3CCCc4ccccc43)c(C)o2)cc1] | 424.59 |

TABLE 6-continued
Oxazole amides (R³ = N-cyclo)
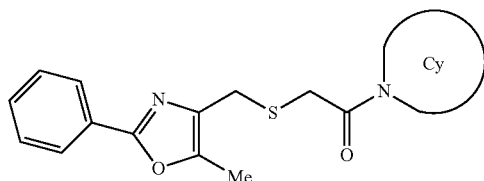
| ID | Structure | MW |
|---|---|---|
| IIa-2014 | 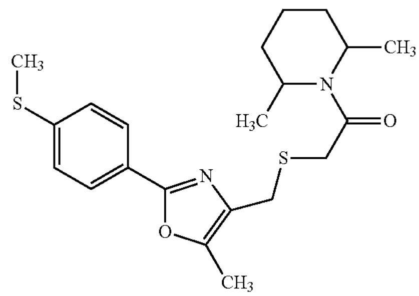 [SMILES: CSc1ccc(-c2nc(CSCC(=O)N3C(C)CCCC3C)c(C)o2)cc1] | 404.60 |
| IIa-2015 | 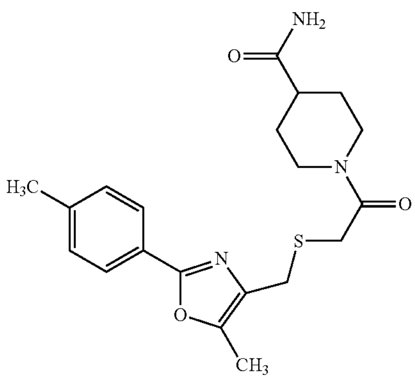 [SMILES: Cc1ccc(-c2nc(CSCC(=O)N3CCC(C(N)=O)CC3)c(C)o2)cc1] | 387.50 |
| IIa-2016 | 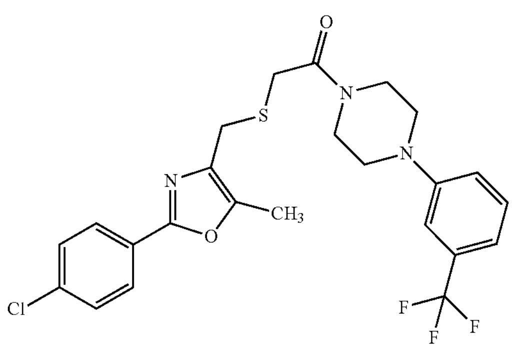 [SMILES: Cc1oc(-c2ccc(Cl)cc2)nc1CSCC(=O)N1CCN(c2cccc(C(F)(F)F)c2)CC1] | 509.98 |
| IIa-2017 | 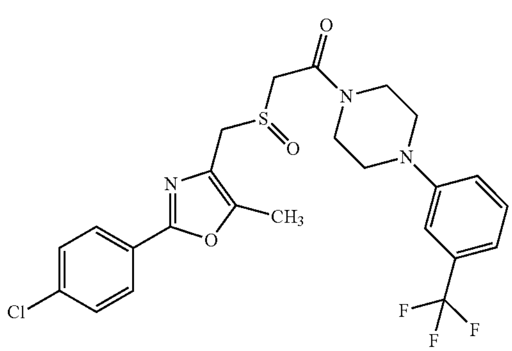 [SMILES: Cc1oc(-c2ccc(Cl)cc2)nc1CS(=O)CC(=O)N1CCN(c2cccc(C(F)(F)F)c2)CC1] | 525.98 |

TABLE 6-continued
Oxazole amides (R³ = N-cyclo)
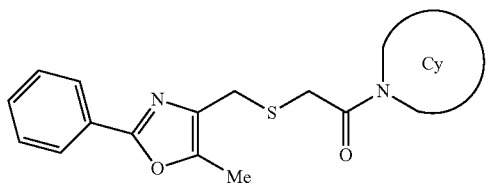
| ID | Structure | MW |
|---|---|---|
| IIa-2018 | | 521.56 |
| IIa-2019 | | 525.98 |
| IIa-2020 | | 505.56 |

TABLE 6-continued
Oxazole amides (R³ = N-cyclo)
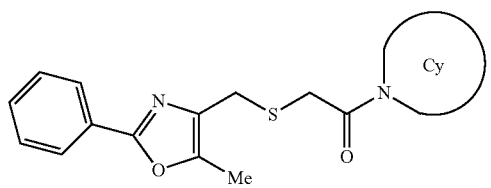
| ID | Structure | MW |
|---|---|---|
| IIa-2021 | | 432.54 |
| IIa-2022 | | 417.53 |
| IIa-2023 | | 446.57 |

TABLE 6-continued
Oxazole amides (R³ = N-cyclo)
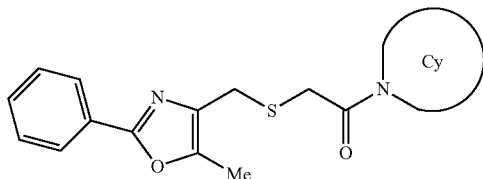
| ID | Structure | MW |
|---|---|---|
| IIa-2024 | 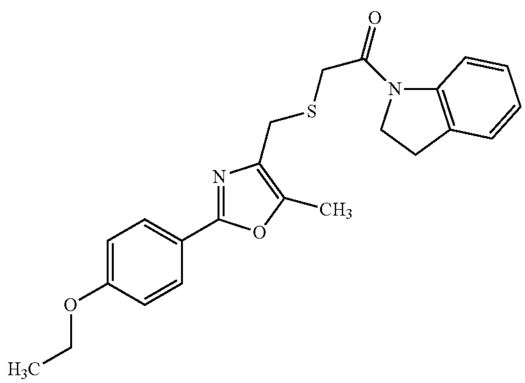 [SMILES: CCOc1ccc(-c2nc(CSCC(=O)N3CCc4ccccc43)c(C)o2)cc1] | 408.52 |
| IIa-2025 | 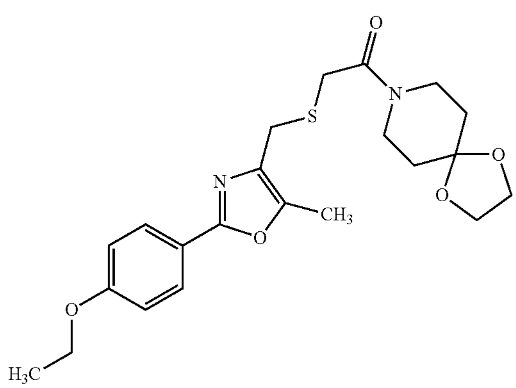 [SMILES: CCOc1ccc(-c2nc(CSCC(=O)N3CCC4(CC3)OCCO4)c(C)o2)cc1] | 432.54 |
| IIa-2026 | 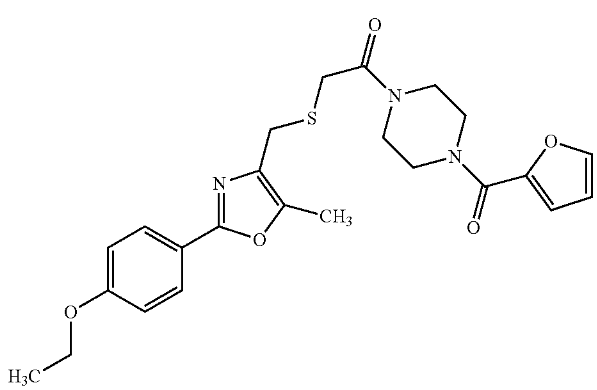 [SMILES: CCOc1ccc(-c2nc(CSCC(=O)N3CCN(C(=O)c4ccco4)CC3)c(C)o2)cc1] | 469.56 |

TABLE 6-continued
Oxazole amides (R³ = N-cyclo)
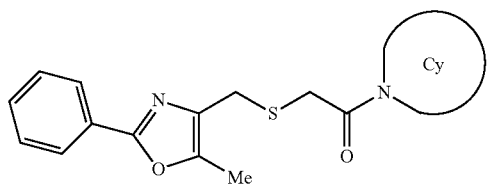
| ID | Structure | MW |
|---|---|---|
| IIa-2027 | 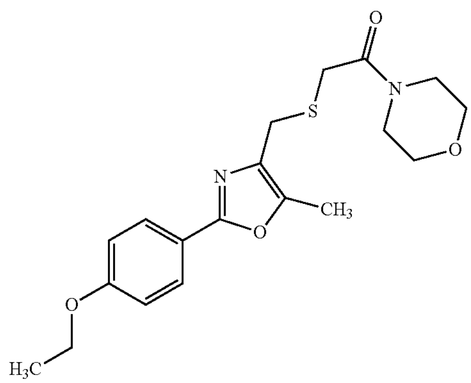 [SMILES: CCOc1ccc(-c2nc(CSCC(=O)N3CCOCC3)c(C)o2)cc1] | 376.48 |
| IIa-2028 | 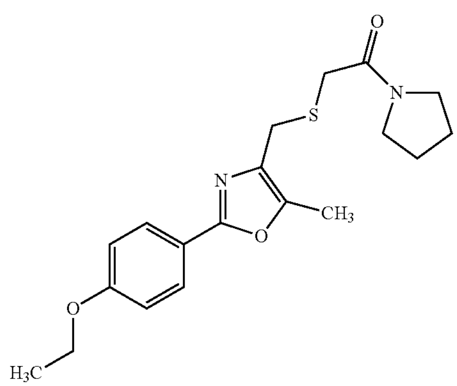 [SMILES: CCOc1ccc(-c2nc(CSCC(=O)N3CCCC3)c(C)o2)cc1] | 360.48 |
| IIa-2029 | 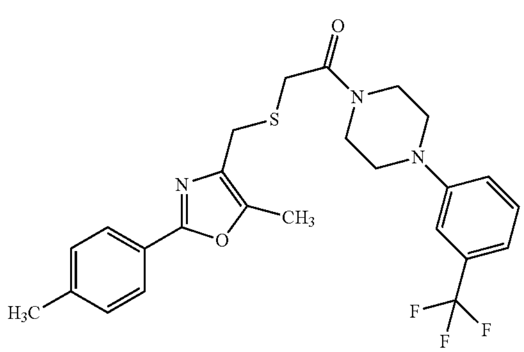 [SMILES: Cc1ccc(-c2nc(CSCC(=O)N3CCN(c4cccc(C(F)(F)F)c4)CC3)c(C)o2)cc1] | 489.56 |

TABLE 6-continued

Oxazole amides (R³ = N-cyclo)

| ID | Structure | MW |
|---|---|---|
| IIa-2030 | | 433.53 |
| IIa-2031 | | 473.64 |
| IIa-2032 | | 535.59 |

TABLE 6-continued
Oxazole amides (R³ = N-cyclo)
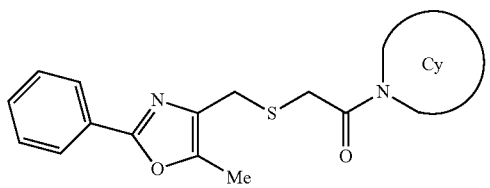
| ID | Structure | MW |
|---|---|---|
| IIa-2033 | | 495.65 |
| IIa-2034 | | 472.01 |
| IIa-2035 | | 439.54 |
| IIa-2036 | | 457.64 |

TABLE 6-continued
Oxazole amides (R³ = N-cyclo)
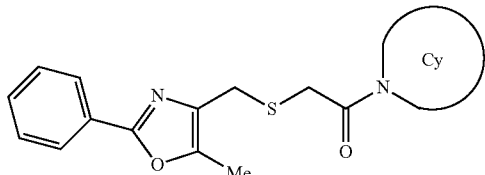
| ID | Structure | MW |
|---|---|---|
| IIa-2037 | 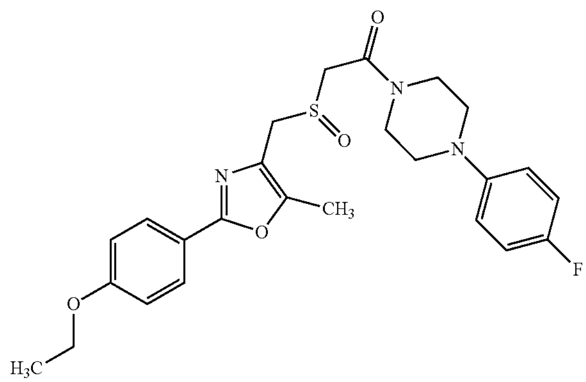 [SMILES: CCOc1ccc(-c2nc(CS(=O)CC(=O)N3CCN(c4ccc(F)cc4)CC3)c(C)o2)cc1] | 469.58 |
| IIa-2038 | 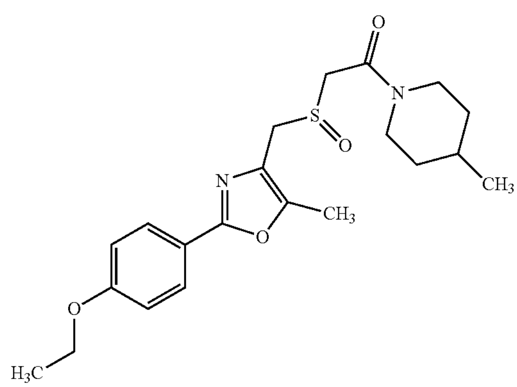 [SMILES: CCOc1ccc(-c2nc(CS(=O)CC(=O)N3CCC(C)CC3)c(C)o2)cc1] | 388.53 |
| IIa-2039 | 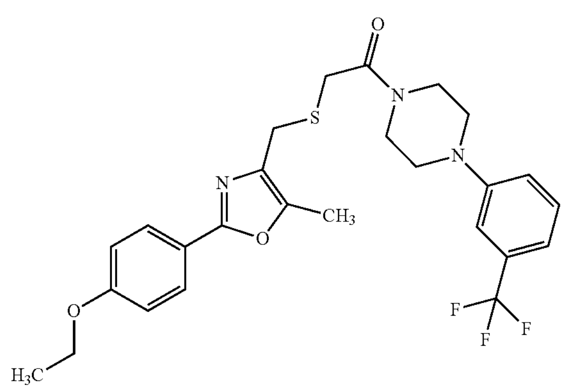 [SMILES: CCOc1ccc(-c2nc(CSCC(=O)N3CCN(c4cccc(C(F)(F)F)c4)CC3)c(C)o2)cc1] | 519.59 |

TABLE 6-continued
Oxazole amides (R³ = N-cyclo)
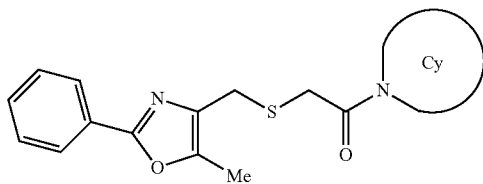
| ID | Structure | MW |
|---|---|---|
| IIa-2040 | 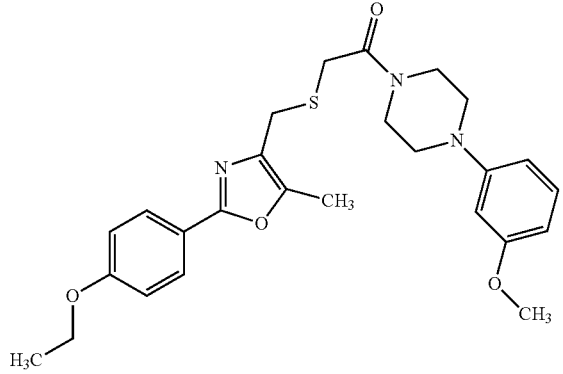 [SMILES: CCOc1ccc(-c2nc(CSCC(=O)N3CCN(c4cccc(OC)c4)CC3)c(C)o2)cc1] | 481.62 |
| IIa-2041 | 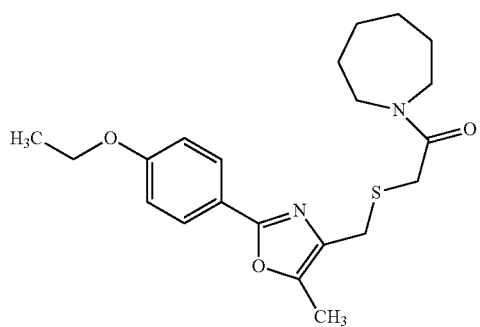 [SMILES: CCOc1ccc(-c2nc(CSCC(=O)N3CCCCCC3)c(C)o2)cc1] | 388.53 |
| IIa-2042 | 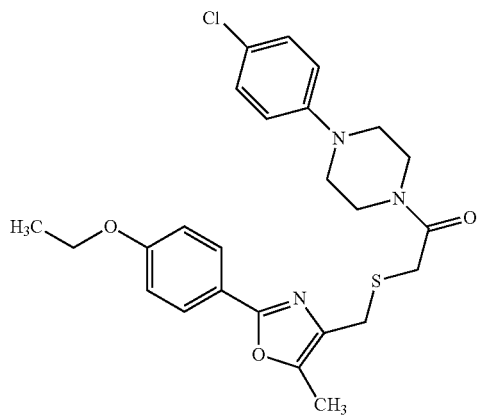 [SMILES: CCOc1ccc(-c2nc(CSCC(=O)N3CCN(c4ccc(Cl)cc4)CC3)c(C)o2)cc1] | 486.04 |

TABLE 6-continued
Oxazole amides (R³ = N-cyclo)
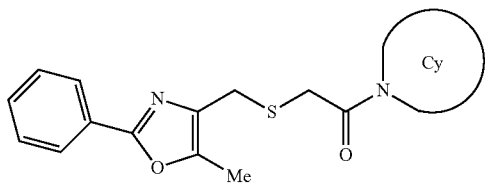
| ID | Structure | MW |
|---|---|---|
| IIa-2043 | | 523.61 |
| IIa-2044 | | 437.57 |
| IIa-2045 | | 346.45 |

TABLE 6-continued
Oxazole amides (R³ = N-cyclo)
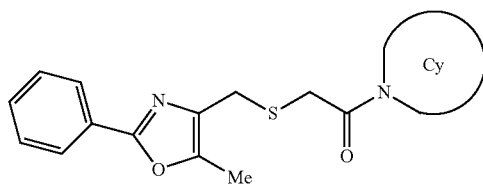
| ID | Structure | MW |
|---|---|---|
| IIa-2046 | 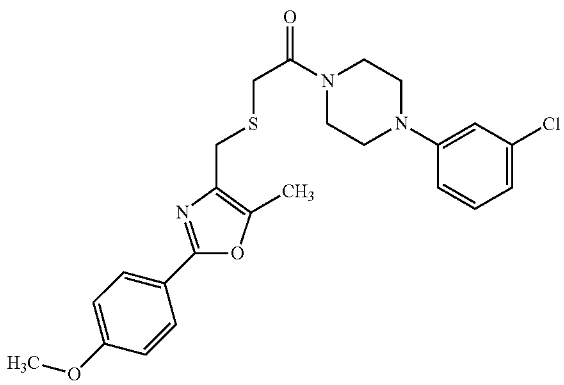 [SMILES: COc1ccc(-c2nc(CSCC(=O)N3CCN(c4cccc(Cl)c4)CC3)c(C)o2)cc1] | 472.01 |
| IIa-2047 | 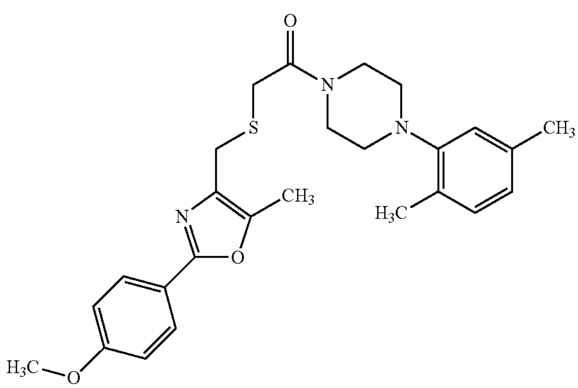 | 465.62 |
| IIa-2048 | 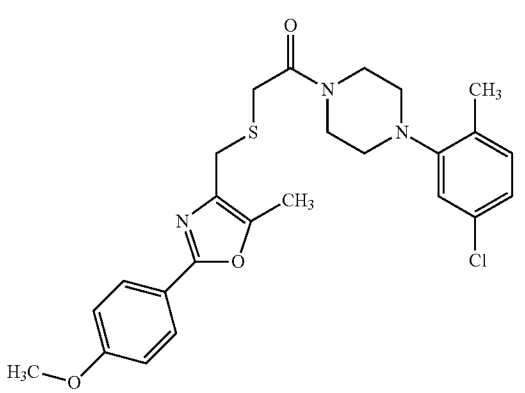 [SMILES: COc1ccc(-c2nc(CSCC(=O)N3CCN(c4cc(Cl)ccc4C)CC3)c(C)o2)cc1] | 486.04 |

TABLE 6-continued
Oxazole amides (R³ = N-cyclo)
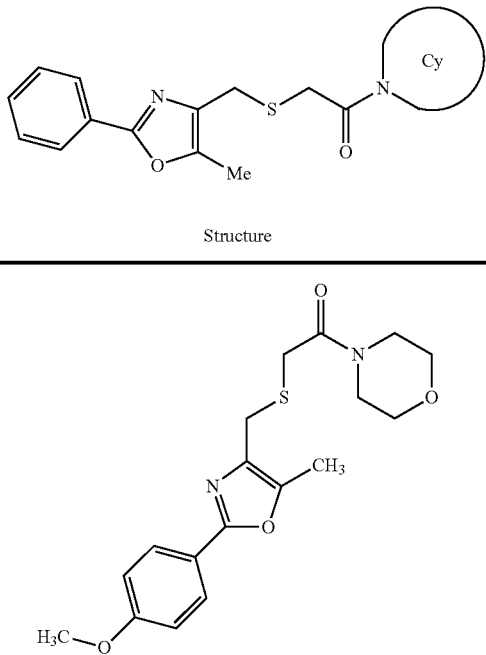
| ID | Structure | MW |
|---|---|---|
| IIa-2049 | 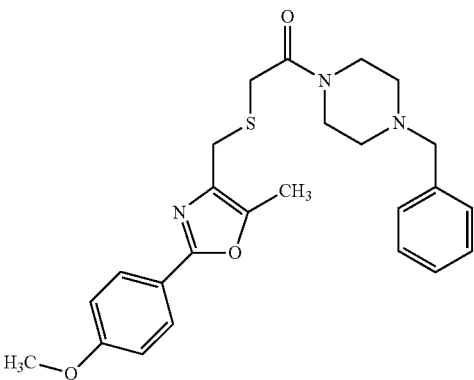 [SMILES: COc1ccc(-c2nc(CSCC(=O)N3CCN(Cc4ccccc4)CC3)c(C)o2)cc1] | 362.45 |
| IIa-2050 | 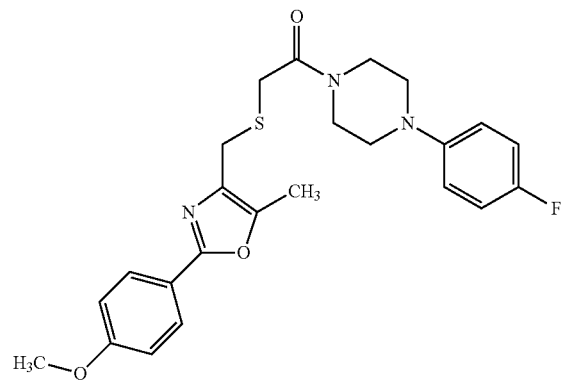 | 451.59 |
| IIa-2051 | 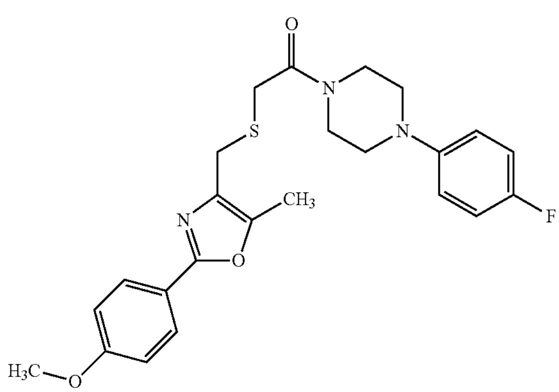 [SMILES: COc1ccc(-c2nc(CSCC(=O)N3CCN(c4ccc(F)cc4)CC3)c(C)o2)cc1] | 455.56 |

TABLE 6-continued
Oxazole amides (R³ = N-cyclo)
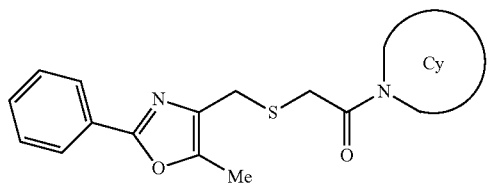
| ID | Structure | MW |
|---|---|---|
| IIa-2052 | 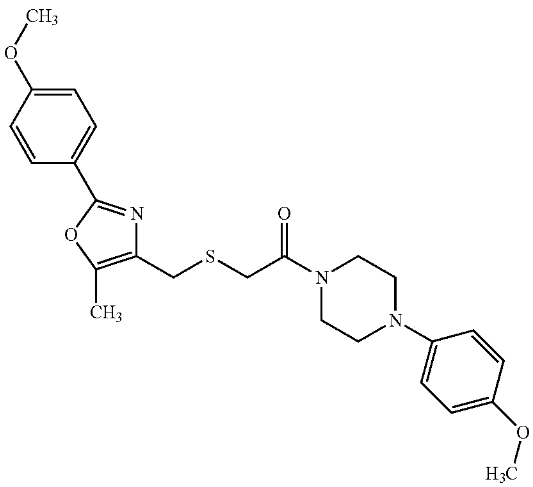 [SMILES: COc1ccc(-c2nc(CSCC(=O)N3CCN(c4ccc(OC)cc4)CC3)c(C)o2)cc1] | 467.59 |
| IIa-2053 | 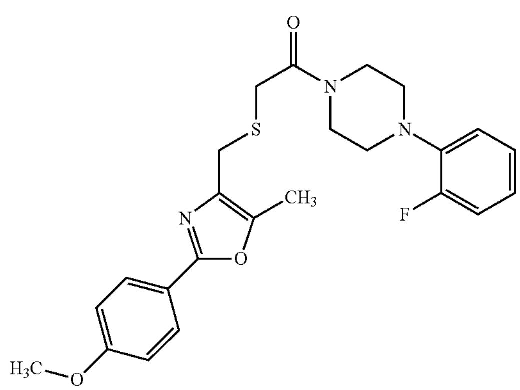 [SMILES: COc1ccc(-c2nc(CSCC(=O)N3CCN(c4ccccc4F)CC3)c(C)o2)cc1] | 455.56 |
| IIa-2054 | 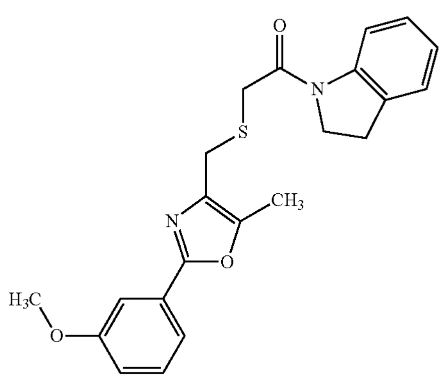 [SMILES: COc1cccc(-c2nc(CSCC(=O)N3CCc4ccccc43)c(C)o2)c1] | 394.50 |

TABLE 6-continued
Oxazole amides (R³ = N-cyclo)
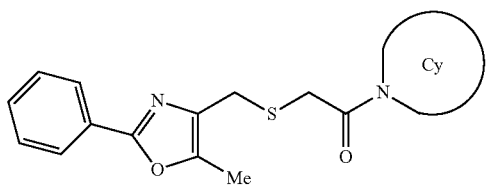
| ID | Structure | MW |
|---|---|---|
| IIa-2055 | | 346.45 |
| IIa-2056 | | 465.62 |
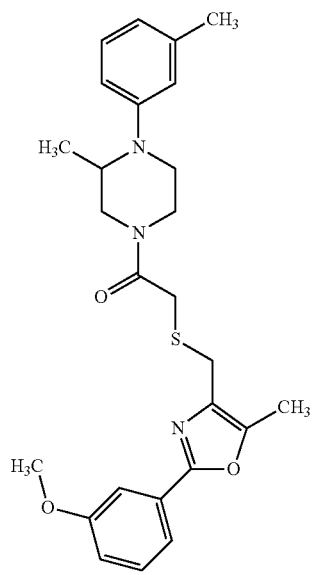

TABLE 6-continued

Oxazole amides (R³ = N-cyclo)

| ID | Structure | MW |
|---|---|---|
| IIa-2057 | | 426.54 |
| IIa-2058 | | 463.56 |
| IIa-2059 | | 424.52 |

TABLE 6-continued
Oxazole amides (R³ = N-cyclo)
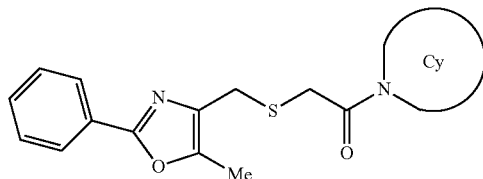
| ID | Structure | MW |
|---|---|---|
| IIa-2060 | 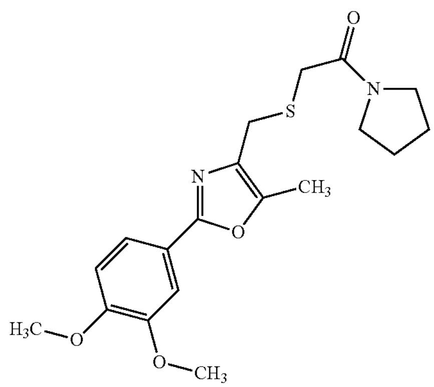 [SMILES: COc1ccc(-c2nc(CSCC(=O)N3CCCC3)c(C)o2)cc1OC] | 376.48 |
| IIa-2061 | 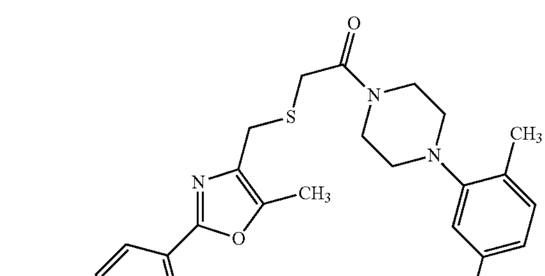 | 516.06 |
| IIa-2062 | 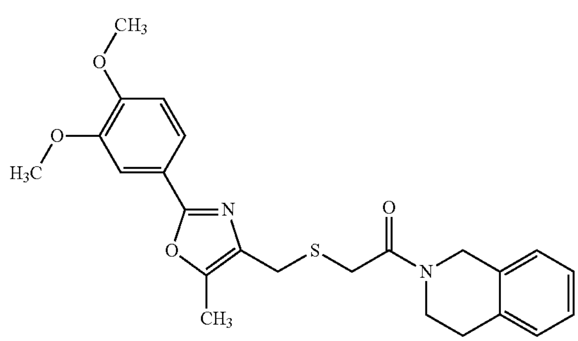 [SMILES: COc1ccc(-c2nc(CSCC(=O)N3CCc4ccccc4C3)c(C)o2)cc1OC] | 438.55 |

TABLE 6-continued
Oxazole amides (R³ = N-cyclo)
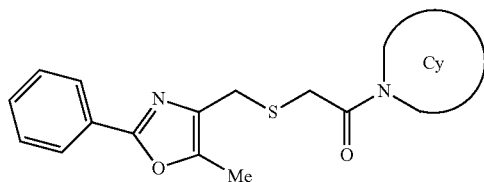
| ID | Structure | MW |
|---|---|---|
| IIa-2063 | | 495.65 |
| IIa-2064 | | 405.52 |
| IIa-2065 | | 392.48 |

TABLE 6-continued
Oxazole amides (R³ = N-cyclo)
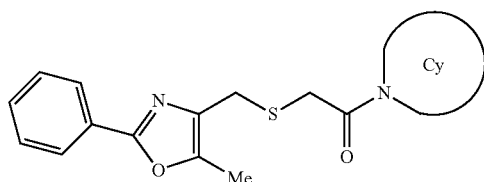
| ID | Structure | MW |
|---|---|---|
| IIa-2066 | 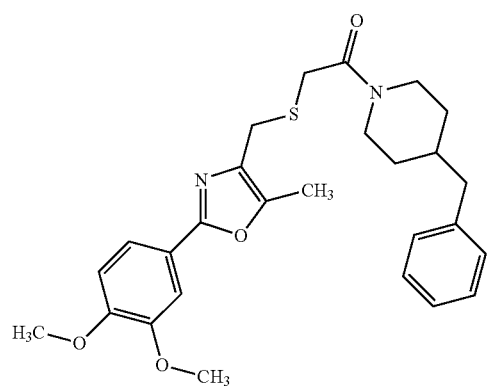 [SMILES: COc1ccc(-c2nc(CSCC(=O)N3CCC(Cc4ccccc4)CC3)c(C)o2)cc1OC] | 480.63 |
| IIa-2067 | 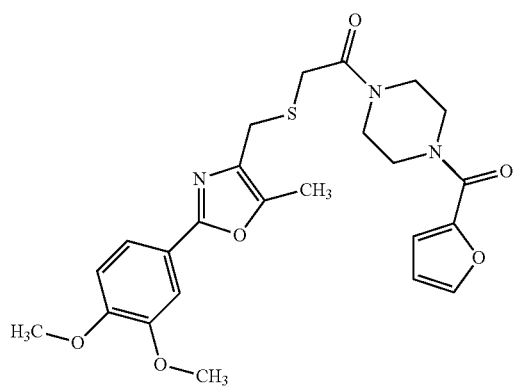 [SMILES: COc1ccc(-c2nc(CSCC(=O)N3CCN(C(=O)c4ccco4)CC3)c(C)o2)cc1OC] | 485.56 |
| IIa-2068 | 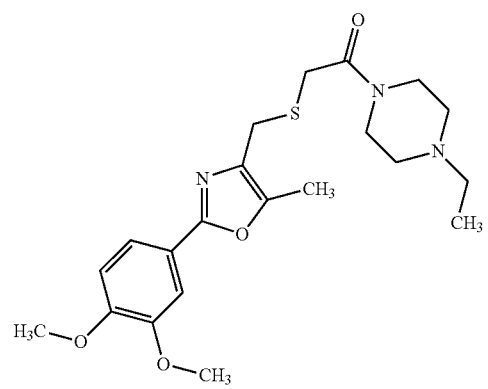 [SMILES: CCN1CCN(C(=O)CSCc2nc(-c3ccc(OC)c(OC)c3)oc2C)CC1] | 419.55 |

TABLE 6-continued
Oxazole amides (R³ = N-cyclo)
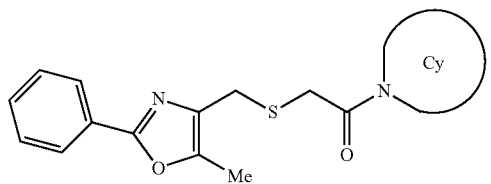
| ID | Structure | MW |
|---|---|---|
| IIa-2069 | 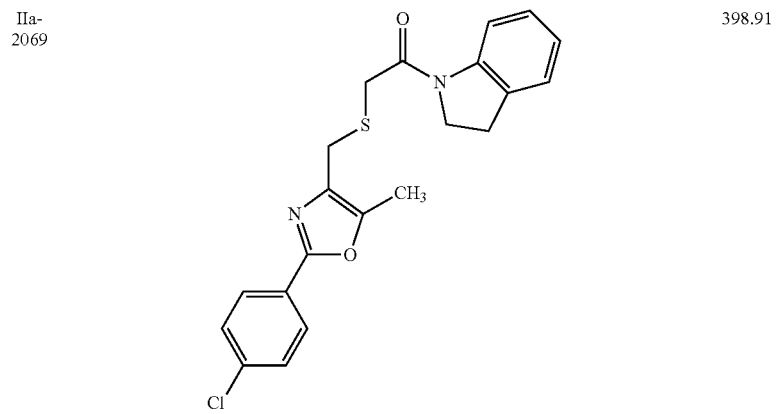 | 398.91 |
| IIa-2070 | 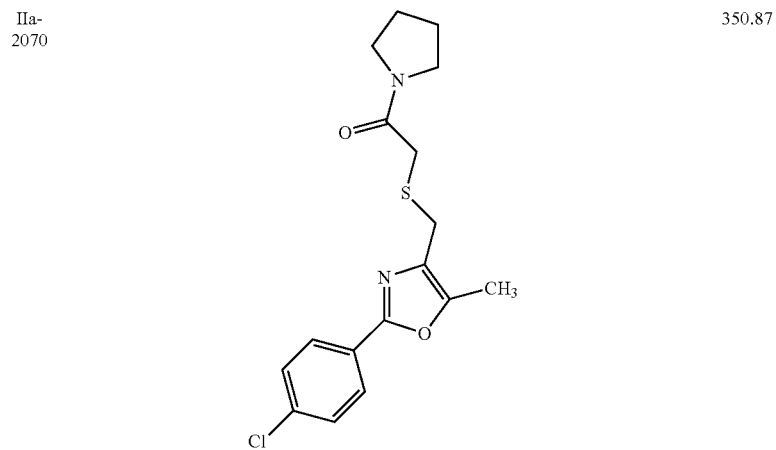 | 350.87 |

TABLE 6-continued
Oxazole amides (R³ = N-cyclo)
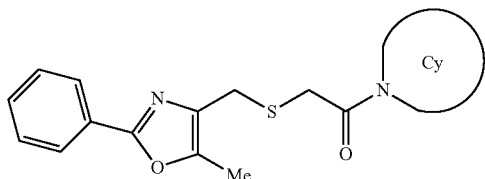
| ID | Structure | MW |
| --- | --- | --- |
| IIa-2071 | | 490.46 |
| IIa-2072 | | 436.96 |

TABLE 6-continued
Oxazole amides (R³ = N-cyclo)
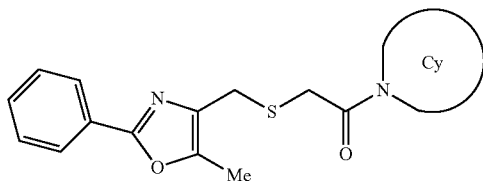
| ID | Structure | MW |
|---|---|---|
| IIa-2073 | | 380.51 |
| IIa-2074 | | 417.53 |
| IIa-2075 | | 421.57 |
| IIa-2076 | | 392.52 |

TABLE 6-continued
Oxazole amides (R³ = N-cyclo)
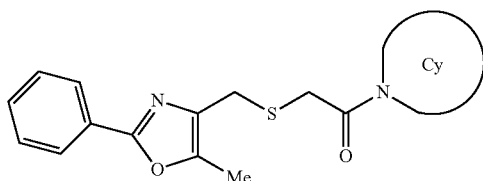
| ID | Structure | MW |
| --- | --- | --- |
| IIa-2077 | | 359.49 |
| IIa-2078 | | 346.45 |
| IIa-2079 | | 435.59 |
| IIa-2080 | | 422.55 |

TABLE 6-continued
Oxazole amides (R³ = N-cyclo)
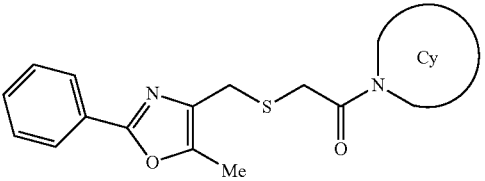
| ID | Structure | MW |
|---|---|---|
| IIa-2081 | 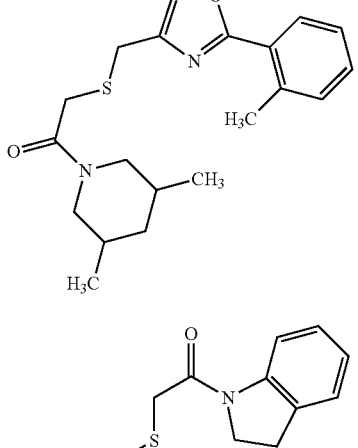 | 372.53 |
| IIa-2082 | 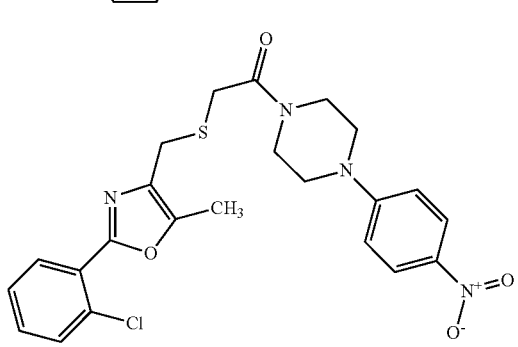 | 398.91 |
| IIa-2083 | 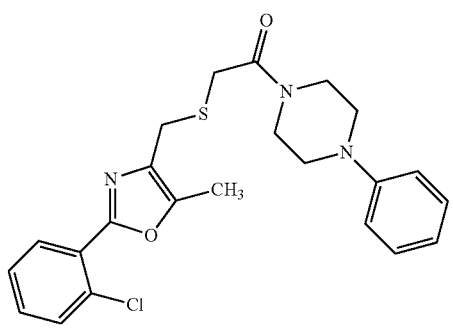 | 486.98 |
| IIa-2084 | 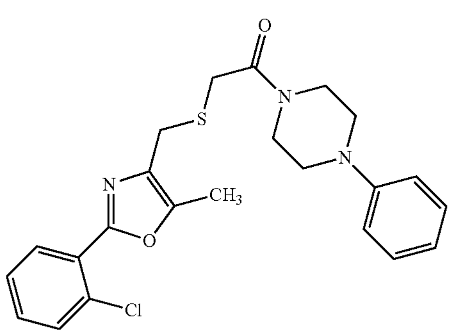 [SMILES: Cc1oc(-c2ccccc2Cl)nc1CSCC(=O)N1CCN(c2ccccc2)CC1] | 441.98 |

TABLE 6-continued
Oxazole amides (R³ = N-cyclo)
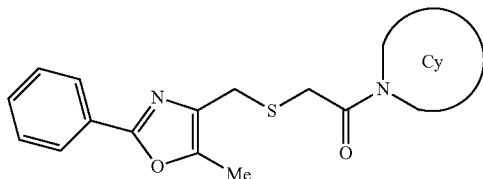
| ID | Structure | MW |
|---|---|---|
| IIa-2085 | | 350.87 |
| IIa-2086 | | 472.01 |
| IIa-2087 | | 412.58 |

937 938
TABLE 6-continued
Oxazole amides (R³ = N-cyclo)
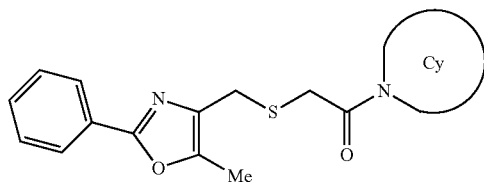
| ID | Structure | MW |
|---|---|---|
| IIa-2088 | 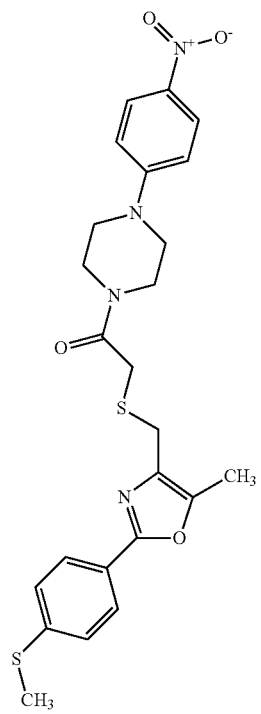 [SMILES: CSc1ccc(-c2nc(CSCC(=O)N3CCN(c4ccc([N+](=O)[O-])cc4)CC3)c(C)o2)cc1] | 498.63 |
| IIa-2089 | 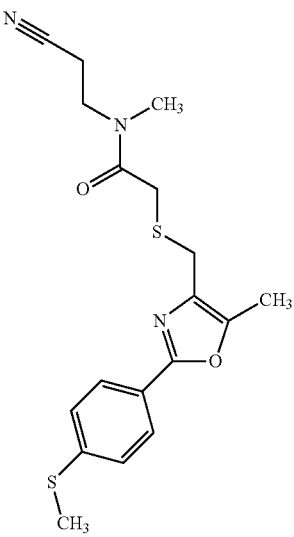 [SMILES: CSc1ccc(-c2nc(CSCC(=O)N(C)CCC#N)c(C)o2)cc1] | 375.51 |

TABLE 6-continued
Oxazole amides (R³ = N-cyclo)
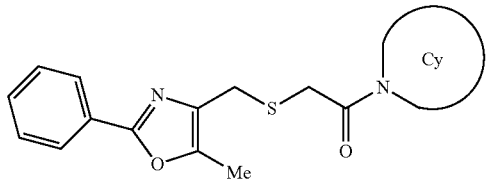
| ID | Structure | MW |
|---|---|---|
| IIa-2090 | | 362.52 |
| IIa-2091 | | 488.07 |

TABLE 6-continued
Oxazole amides (R³ = N-cyclo)
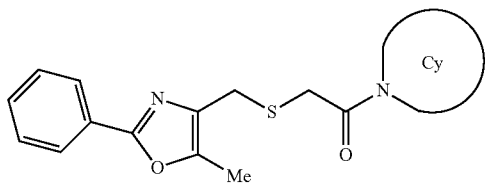
| ID | Structure | MW |
|---|---|---|
| IIa-2092 | 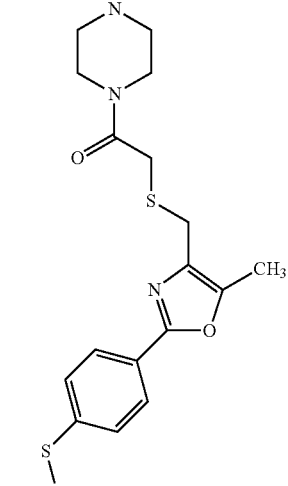 | 481.68 |
| IIa-2093 | 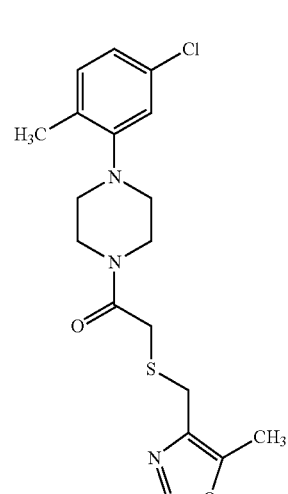 | 502.10 |

TABLE 6-continued
Oxazole amides (R³ = N-cyclo)
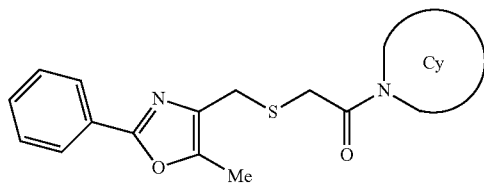
| ID | Structure | MW |
| --- | --- | --- |
| IIa-2094 | | 424.59 |
| IIa-2095 | | 391.56 |

TABLE 6-continued
Oxazole amides (R³ = N-cyclo)
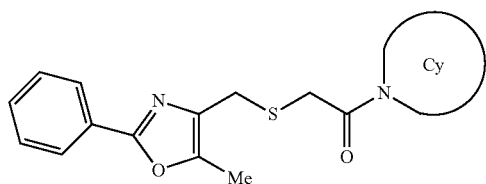
| ID | Structure | MW |
|---|---|---|
| IIa-2096 | | 378.52 |
| IIa-2097 | | 467.66 |

TABLE 6-continued
Oxazole amides (R³ = N-cyclo)
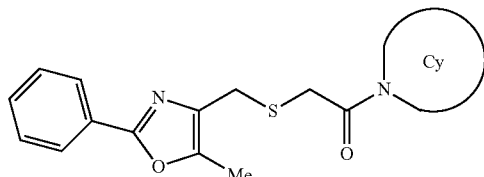
| ID | Structure | MW |
|---|---|---|
| IIa-2098 | | 466.67 |
| IIa-2099 | | 471.62 |

TABLE 6-continued
Oxazole amides (R³ = N-cyclo)
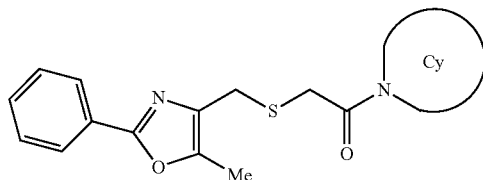
| ID | Structure | MW |
|---|---|---|
| IIa-2100 | 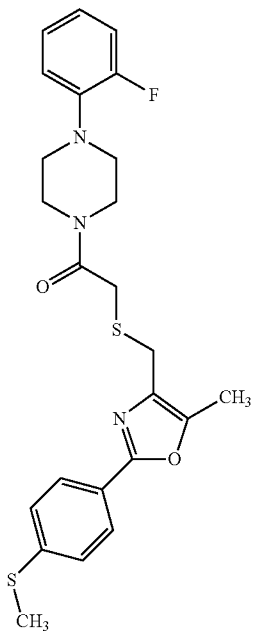 [SMILES: CSc1ccc(-c2nc(CSCC(=O)N3CCN(c4ccccc4F)CC3)c(C)o2)cc1] | 471.62 |
| IIa-2101 | 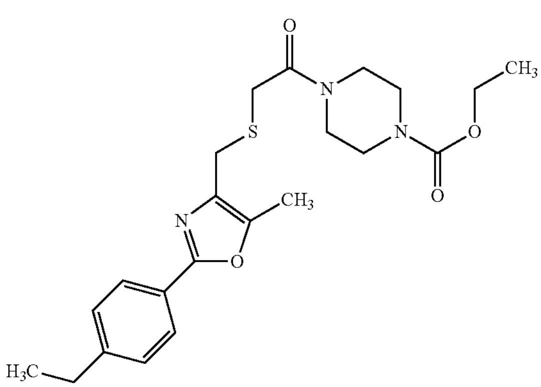 [SMILES: CCOC(=O)N1CCN(C(=O)CSCc2nc(-c3ccc(CC)cc3)oc2C)CC1] | 431.56 |

TABLE 6-continued
Oxazole amides (R³ = N-cyclo)
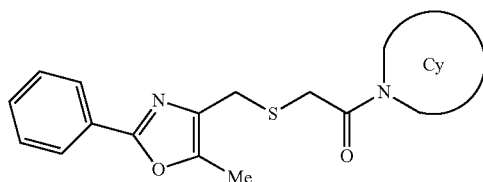
| ID | Structure | MW |
|---|---|---|
| IIa-2102 | | 392.52 |
| IIa-2103 | | 480.59 |
| IIa-2104 | | 435.59 |

TABLE 6-continued
Oxazole amides (R³ = N-cyclo)
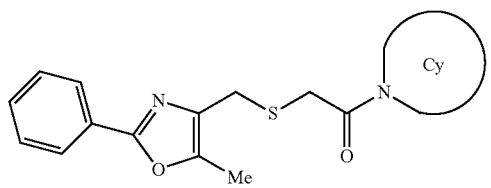
| ID | Structure | MW |
|---|---|---|
| IIa-2105 | 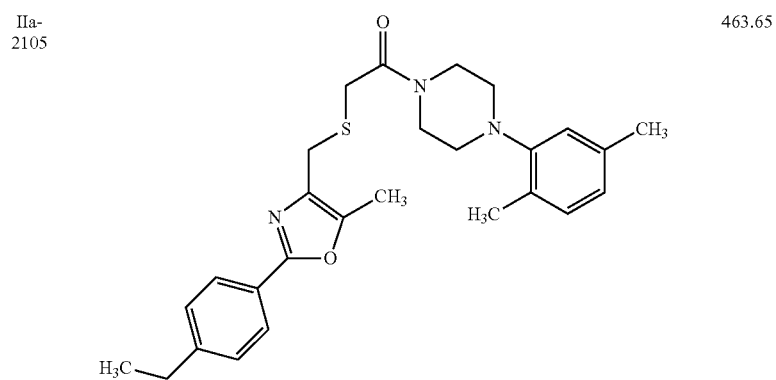 | 463.65 |
| IIa-2106 | 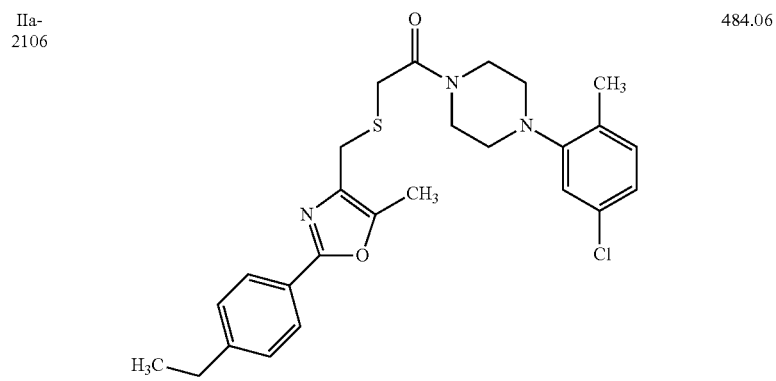 | 484.06 |
| IIa-2107 | 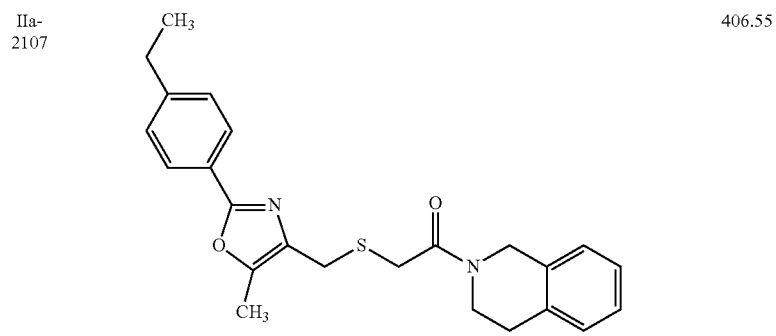 | 406.55 |

TABLE 6-continued
Oxazole amides (R³ = N-cyclo)
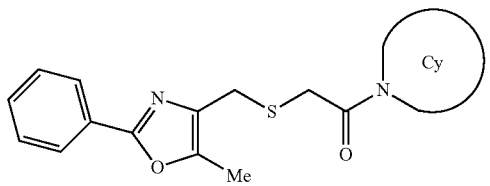
| ID | Structure | MW |
| --- | --- | --- |
| IIa-2108 | 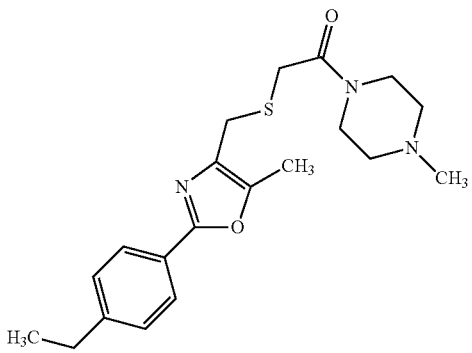 [SMILES: CCc1ccc(-c2nc(CSCC(=O)N3CCN(C)CC3)c(C)o2)cc1] | 373.52 |
| IIa-2109 | 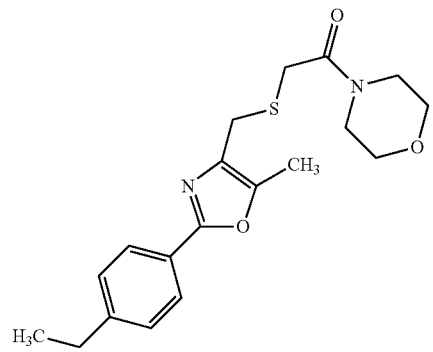 [SMILES: CCc1ccc(-c2nc(CSCC(=O)N3CCOCC3)c(C)o2)cc1] | 360.48 |
| IIa-2110 | 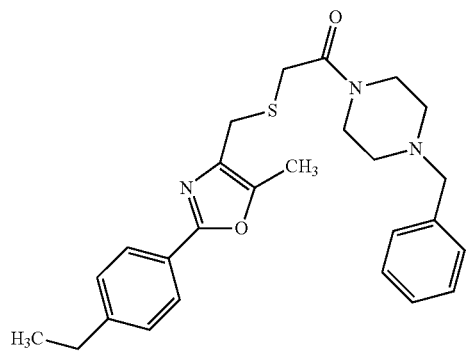 [SMILES: CCc1ccc(-c2nc(CSCC(=O)N3CCN(Cc4ccccc4)CC3)c(C)o2)cc1] | 449.62 |

TABLE 6-continued
Oxazole amides (R³ = N-cyclo)
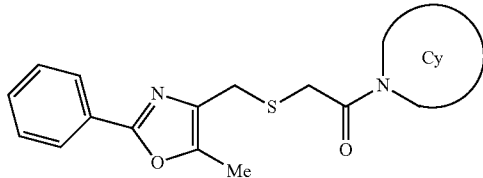
| ID | Structure | MW |
|---|---|---|
| IIa-2111 | 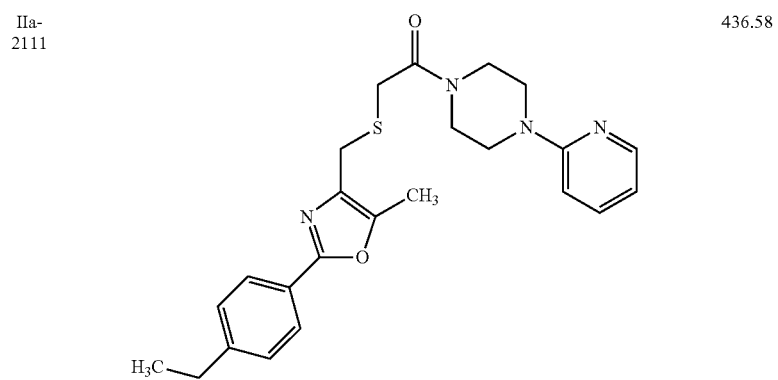 | 436.58 |
| IIa-2112 | 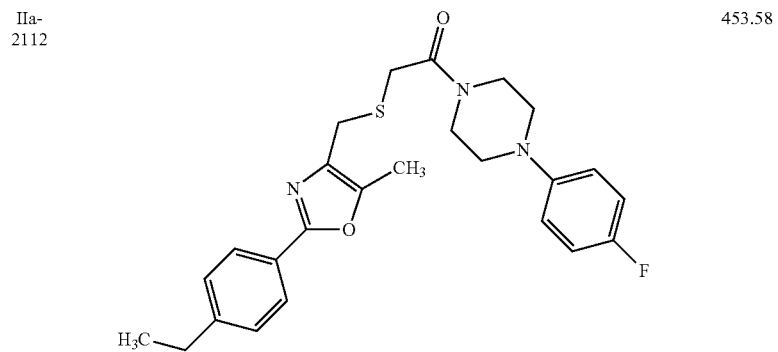 | 453.58 |
| IIa-2113 | 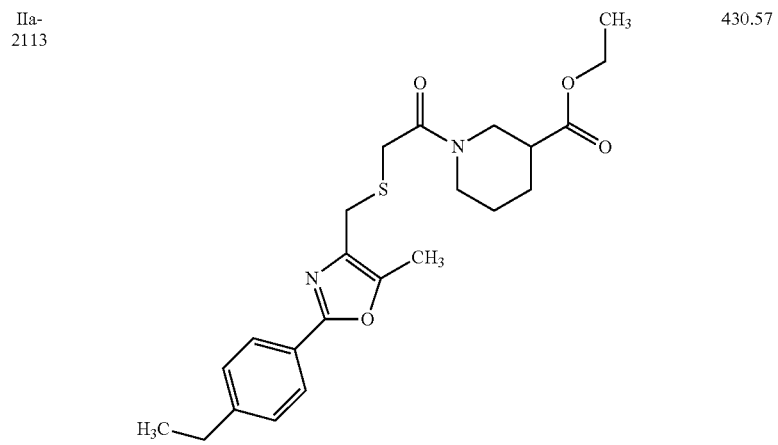 | 430.57 |

TABLE 6-continued

Oxazole amides (R³ = N-cyclo)

| ID | Structure | MW |
|---|---|---|
| IIa-2114 | 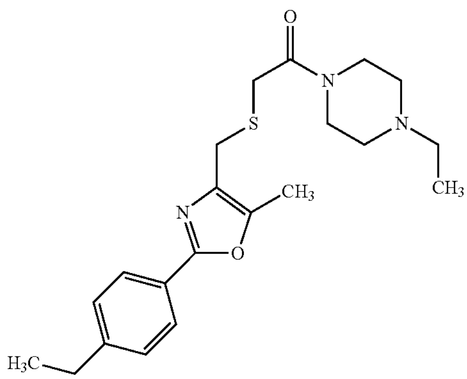 [SMILES: CCc1ccc(-c2nc(CSCC(=O)N3CCN(CC)CC3)c(C)o2)cc1] | 387.55 |
| IIa-2115 | 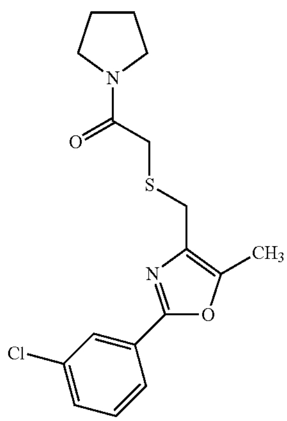 [SMILES: Cc1oc(-c2cccc(Cl)c2)nc1CSCC(=O)N1CCCC1] | 350.87 |
| IIa-2116 | 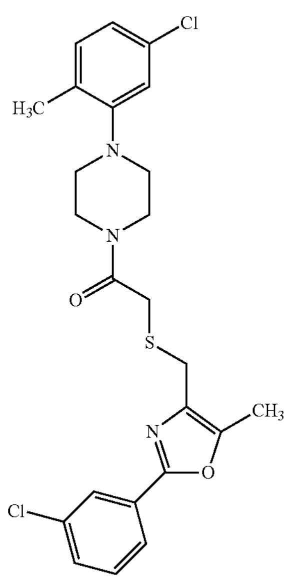 [SMILES: Cc1ccc(Cl)cc1N1CCN(C(=O)CSCc2nc(-c3cccc(Cl)c3)oc2C)CC1] | 490.46 |

TABLE 6-continued
Oxazole amides (R³ = N-cyclo)
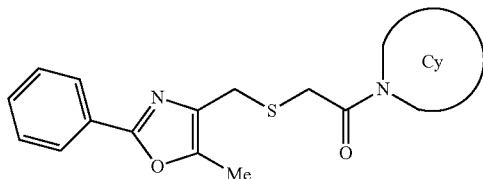
| ID | Structure | MW |
|---|---|---|
| IIa-2117 | | 459.97 |
| IIa-2118 | | 421.49 |
| IIa-2119 | | 470.53 |

TABLE 6-continued
Oxazole amides (R³ = N-cyclo)
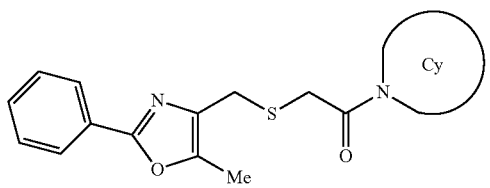
| ID | Structure | MW |
|---|---|---|
| IIa-2120 | 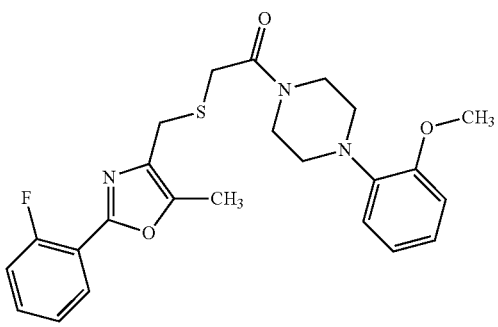 [SMILES: COc1ccccc1N1CCN(C(=O)CSCc2nc(-c3ccccc3F)oc2C)CC1] | 455.56 |
| IIa-2121 | 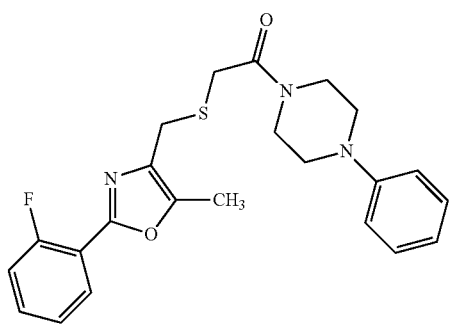 [SMILES: Cc1oc(-c2ccccc2F)nc1CSCC(=O)N1CCN(c2ccccc2)CC1] | 425.53 |
| IIa-2122 | 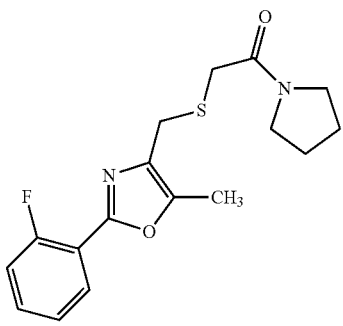 [SMILES: Cc1oc(-c2ccccc2F)nc1CSCC(=O)N1CCCC1] | 334.42 |
| IIa-2123 | 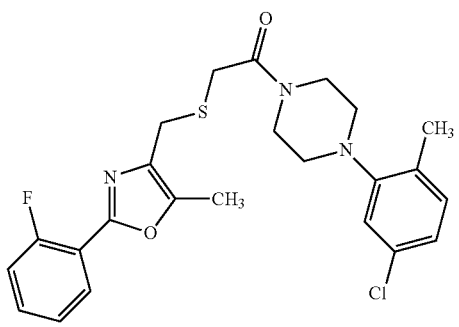 [SMILES: Cc1ccc(Cl)cc1N1CCN(C(=O)CSCc2nc(-c3ccccc3F)oc2C)CC1] | 474.00 |

TABLE 6-continued
Oxazole amides (R³ = N-cyclo)
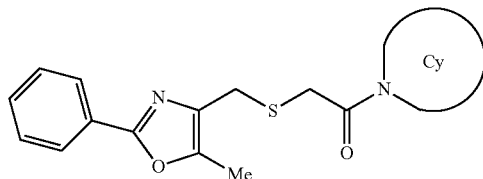
| ID | Structure | MW |
|---|---|---|
| IIa-2124 | | 443.52 |
| IIa-2125 | | 455.56 |

TABLE 6-continued
Oxazole amides (R³ = N-cyclo)
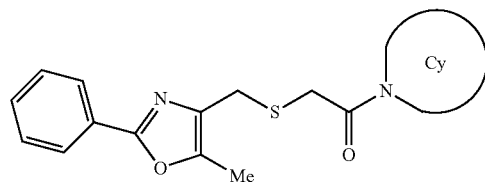
| ID | Structure | MW |
|---|---|---|
| IIa-2126 | 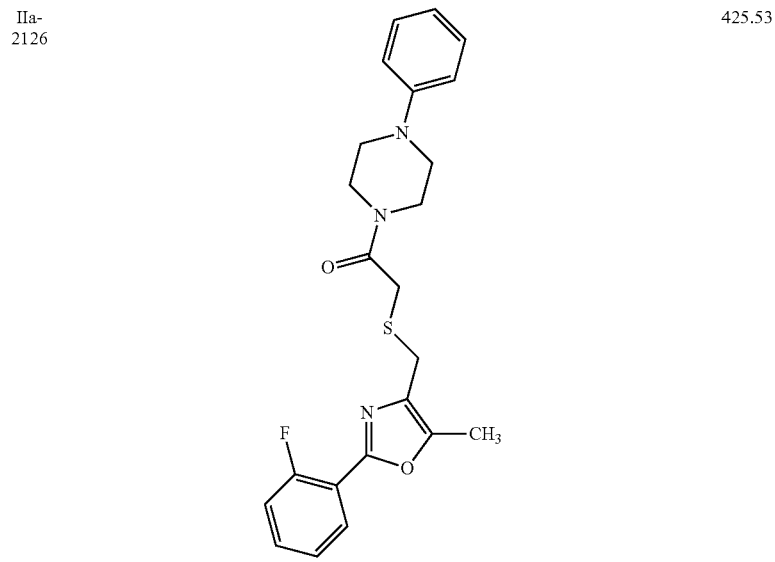 | 425.53 |
| IIa-2127 | 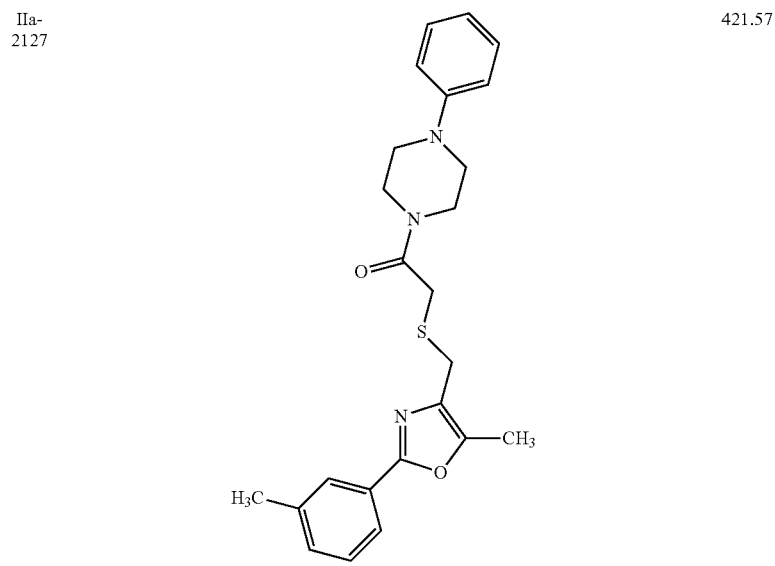 | 421.57 |

TABLE 6-continued
Oxazole amides (R³ = N-cyclo)
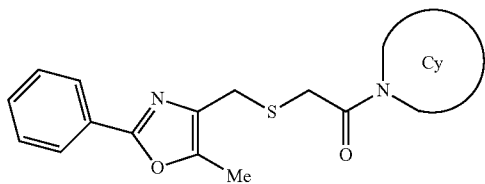
| ID | Structure | MW |
|---|---|---|
| IIa-2128 | | 392.52 |
| IIa-2129 | | 359.49 |
| IIa-2130 | | 346.45 |

TABLE 6-continued
Oxazole amides (R³ = N-cyclo)
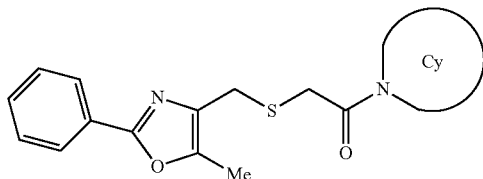
| ID | Structure | MW |
| --- | --- | --- |
| IIa-2131 | 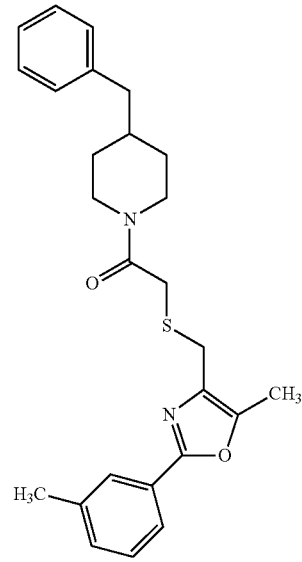 [SMILES: Cc1cccc(-c2nc(CSCC(=O)N3CCC(Cc4ccccc4)CC3)c(C)o2)c1] | 434.61 |
| IIa-2132 | 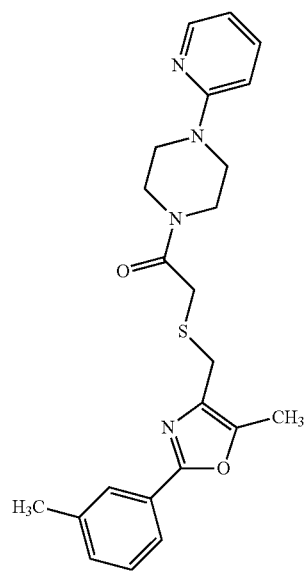 | 422.55 |

TABLE 6-continued
Oxazole amides (R³ = N-cyclo)
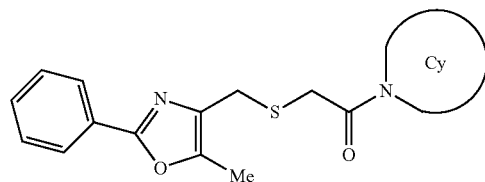
| ID | Structure | MW |
|---|---|---|
| IIa-2133 | | 439.56 |
| IIa-2134 | | 373.52 |

TABLE 6-continued
Oxazole amides (R³ = N-cyclo)
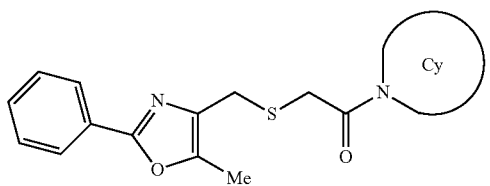
| ID | Structure | MW |
|---|---|---|
| IIa-2135 | 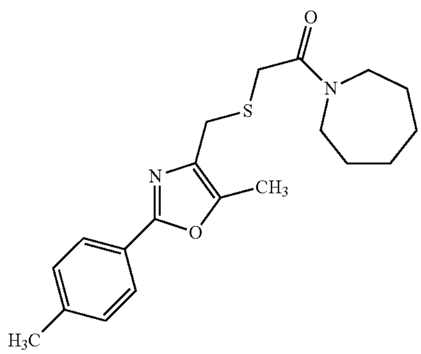 [SMILES: Cc1ccc(-c2nc(CSCC(=O)N3CCCCCC3)c(C)o2)cc1] | 358.51 |
| IIa-2136 | 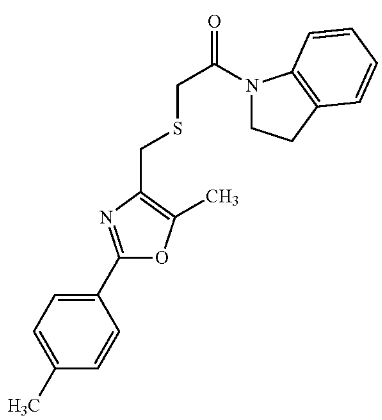 [SMILES: Cc1ccc(-c2nc(CSCC(=O)N3CCc4ccccc43)c(C)o2)cc1] | 378.50 |
| IIa-2137 | 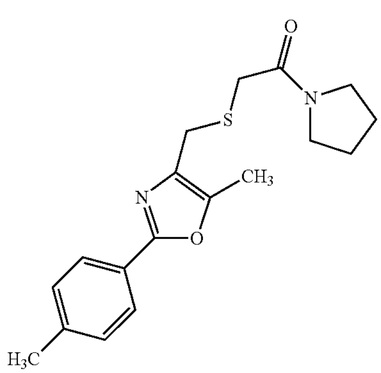 [SMILES: Cc1ccc(-c2nc(CSCC(=O)N3CCCC3)c(C)o2)cc1] | 330.45 |

TABLE 6-continued
Oxazole amides (R³ = N-cyclo)
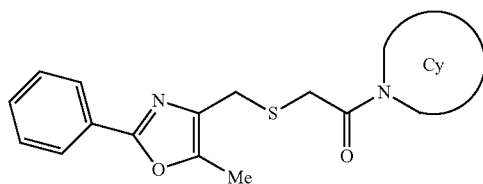
| ID | Structure | MW |
|---|---|---|
| IIa-2138 | 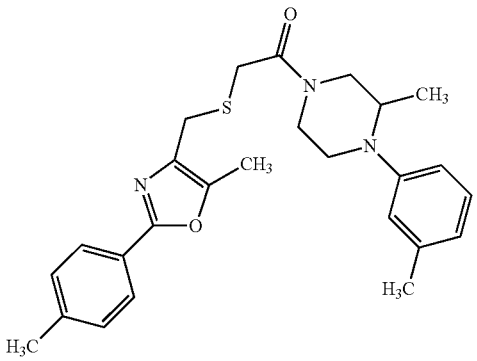 [SMILES: Cc1ccc(-c2nc(CSCC(=O)N3CCN(c4cccc(C)c4)C(C)C3)c(C)o2)cc1] | 449.62 |
| IIa-2139 | 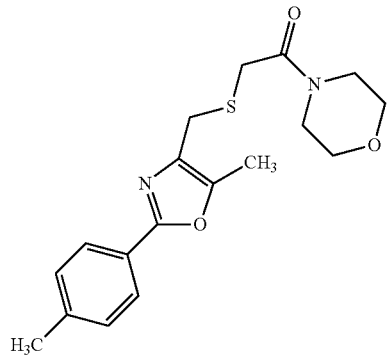 [SMILES: Cc1ccc(-c2nc(CSCC(=O)N3CCOCC3)c(C)o2)cc1] | 346.45 |
| IIa-2140 | 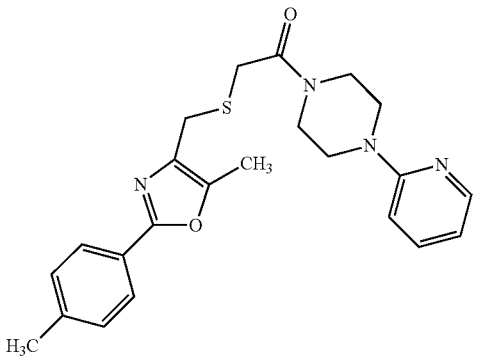 [SMILES: Cc1ccc(-c2nc(CSCC(=O)N3CCN(c4ccccn4)CC3)c(C)o2)cc1] | 422.55 |

TABLE 6-continued
Oxazole amides (R³ = N-cyclo)
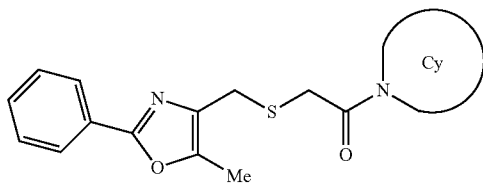
| ID | Structure | MW |
|---|---|---|
| IIa-2141 | | 402.52 |
| IIa-2142 | | 439.54 |
| IIa-2143 | | 392.52 |

TABLE 6-continued
Oxazole amides (R³ = N-cyclo)
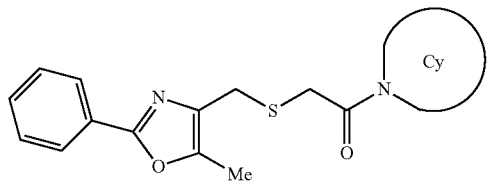
| ID | Structure | MW |
|---|---|---|
| IIa-2144 | 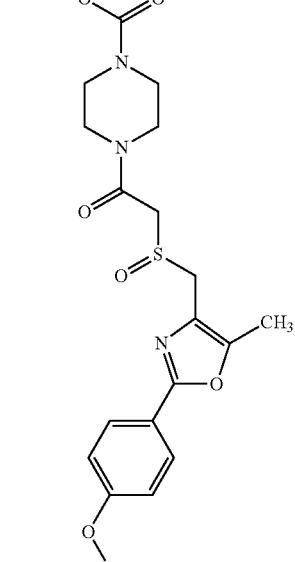 | 449.53 |
| IIa-2145 | 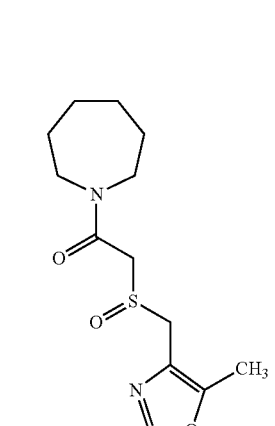 | 390.51 |

TABLE 6-continued
Oxazole amides (R³ = N-cyclo)
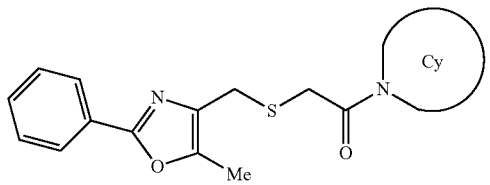
| ID | Structure | MW |
|---|---|---|
| IIa-2146 | | 362.45 |
| IIa-2147 | | 424.52 |

TABLE 6-continued
Oxazole amides (R³ = N-cyclo)
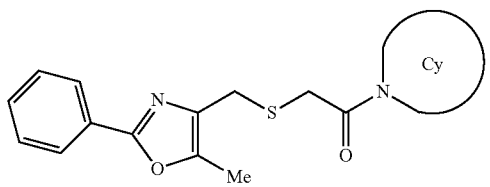
| ID | Structure | MW |
|---|---|---|
| IIa-2148 | 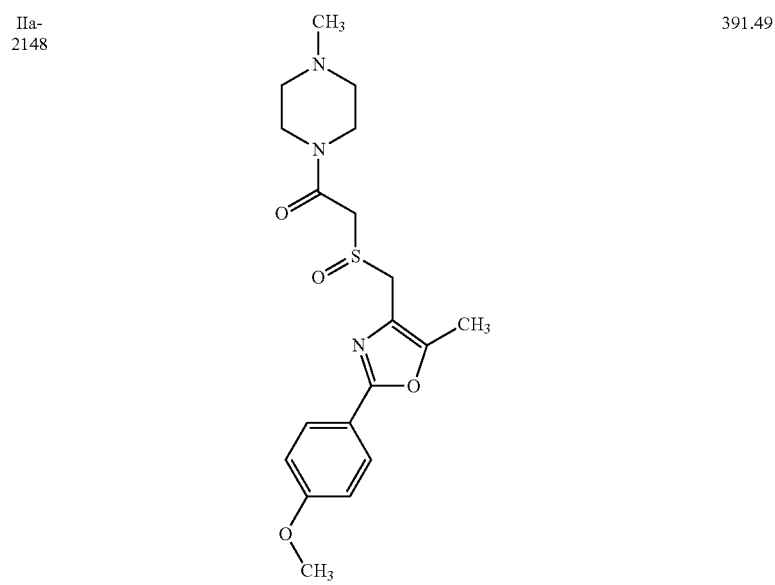 | 391.49 |
| IIa-2149 | 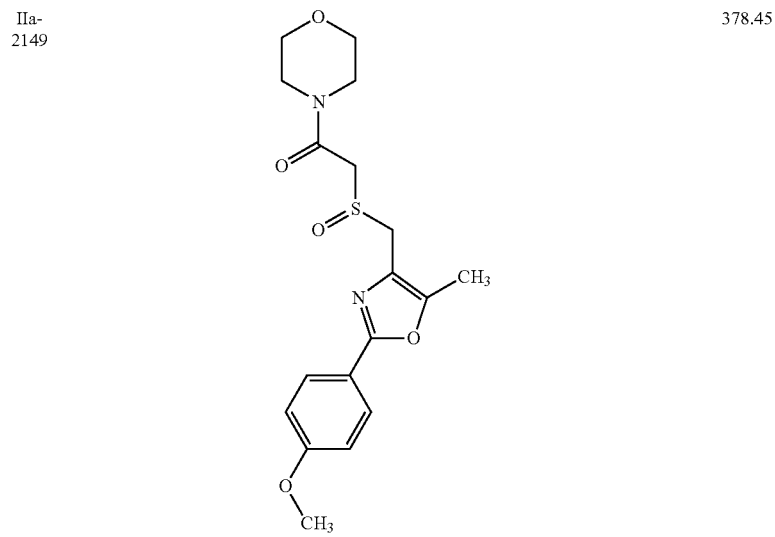 | 378.45 |

TABLE 6-continued
Oxazole amides (R³ = N-cyclo)
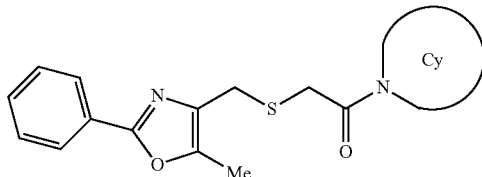
| ID | Structure | MW |
|---|---|---|
| IIa-2150 | 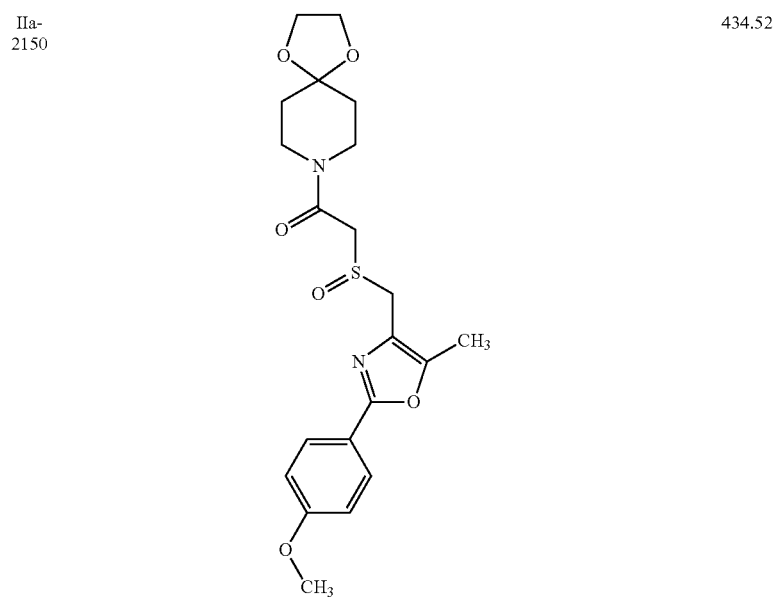 | 434.52 |
| IIa-2151 | 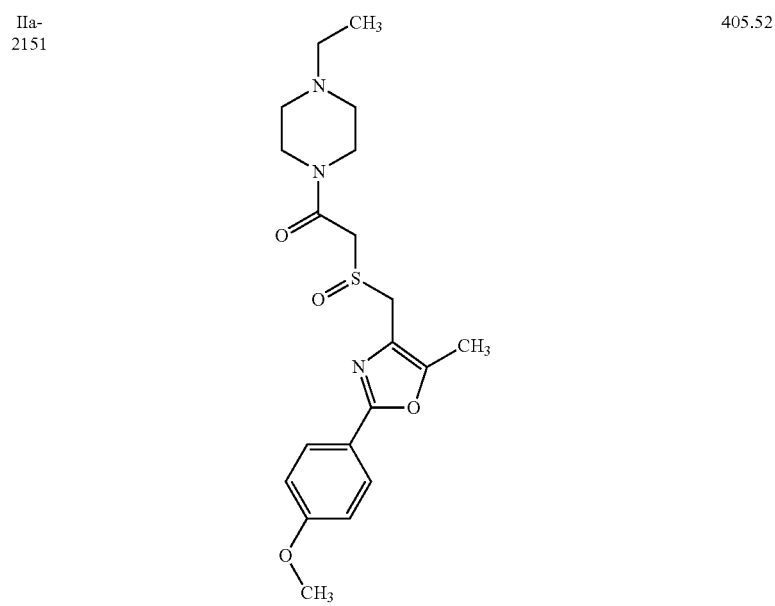 | 405.52 |

TABLE 6-continued
Oxazole amides (R³ = N-cyclo)
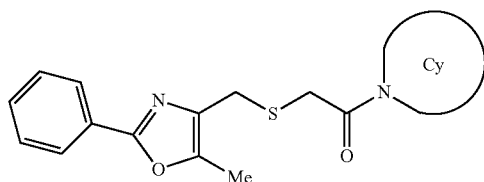
| ID | Structure | MW |
|---|---|---|
| IIa-2152 | | 376.48 |
| IIa-2153 | | 441.53 |

991
992
TABLE 6-continued
Oxazole amides (R³ = N-cyclo)
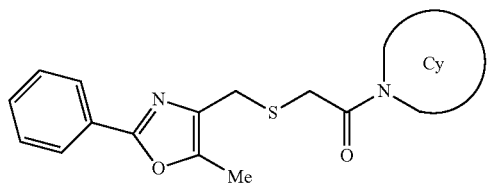
| ID | Structure | MW |
|---|---|---|
| IIa-2154 | | 376.52 |
| IIa-2155 | | 433.53 |

TABLE 6-continued
Oxazole amides (R³ = N-cyclo)
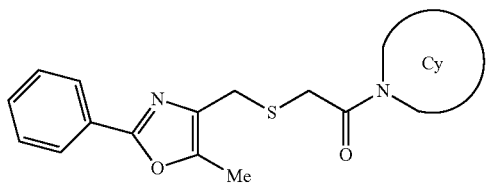
| ID | Structure | MW |
|---|---|---|
| IIa-2156 | | 374.51 |
| IIa-2157 | | 394.50 |
| IIa-2158 | | 359.45 |

TABLE 6-continued
Oxazole amides (R³ = N-cyclo)
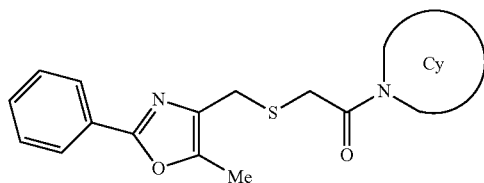
| ID | Structure | MW |
|---|---|---|
| IIa-2159 | 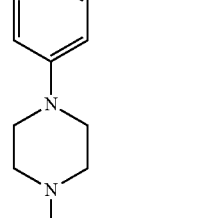 | 437.57 |
| IIa-2160 | 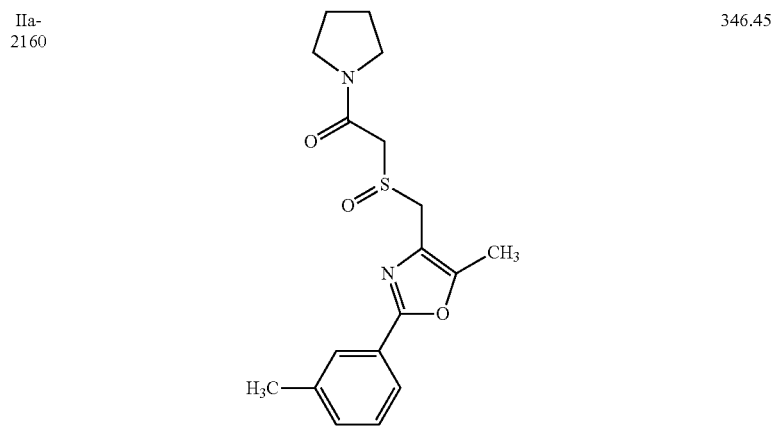 | 346.45 |

TABLE 6-continued
Oxazole amides (R³ = N-cyclo)
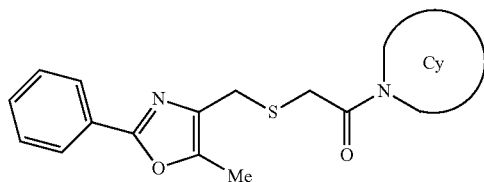
| ID | Structure | MW |
|---|---|---|
| IIa-2161 | | 486.04 |
| IIa-2162 | | 408.52 |

TABLE 6-continued
Oxazole amides (R³ = N-cyclo)
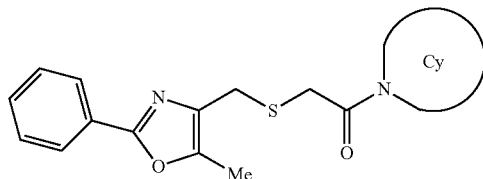
| ID | Structure | MW |
|---|---|---|
| IIa-2163 | | 375.49 |
| IIa-2164 | | 438.55 |

TABLE 6-continued
Oxazole amides (R³ = N-cyclo)
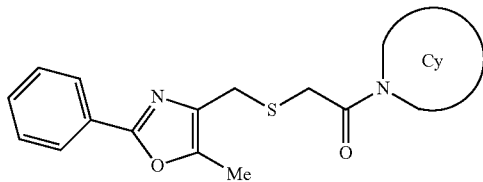
| ID | Structure | MW |
|---|---|---|
| IIa-2165 | | 388.53 |
| IIa-2166 | | 389.52 |

TABLE 6-continued
Oxazole amides (R³ = N-cyclo)
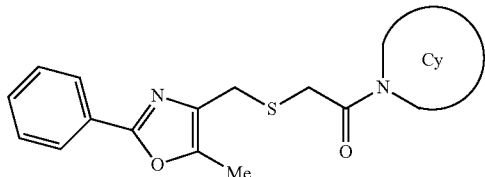
| ID | Structure | MW |
|---|---|---|
| IIa-2167 | | 360.48 |
| IIa-2168 | | 433.53 |

TABLE 6-continued
Oxazole amides (R³ = N-cyclo)
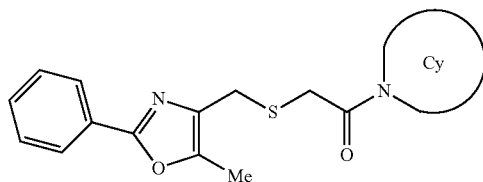
| ID | Structure | MW |
|---|---|---|
| IIa-2169 | 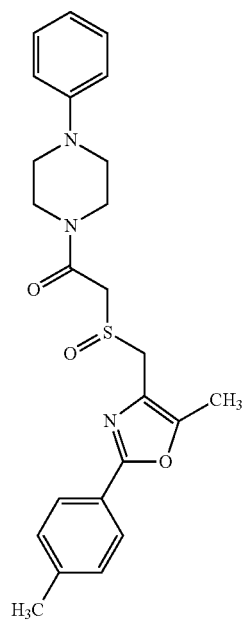 [SMILES: Cc1ccc(-c2nc(CS(=O)CC(=O)N3CCN(c4ccccc4)CC3)c(C)o2)cc1] | 437.57 |
| IIa-2170 | 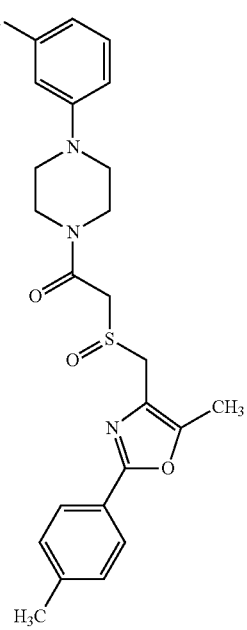 | 472.01 |

TABLE 6-continued
Oxazole amides (R³ = N-cyclo)
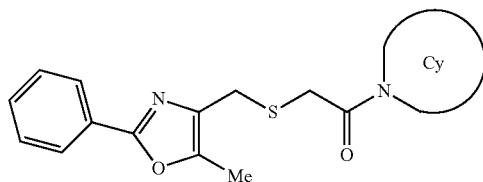
| ID | Structure | MW |
|---|---|---|
| IIa-2171 | | 408.52 |
| IIa-2172 | | 465.62 |

TABLE 6-continued
Oxazole amides (R³ = N-cyclo)
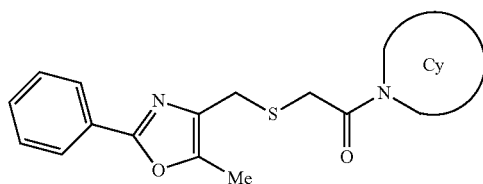
| ID | Structure | MW |
|---|---|---|
| IIa-2173 | 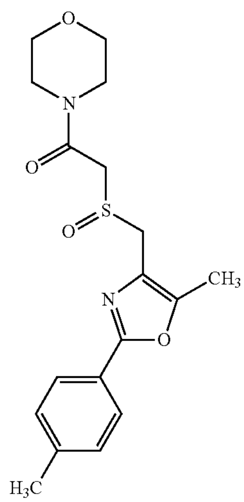 [SMILES: Cc1ccc(-c2nc(CS(=O)CC(=O)N3CCOCC3)c(C)o2)cc1] | 362.45 |
| IIa-2174 | 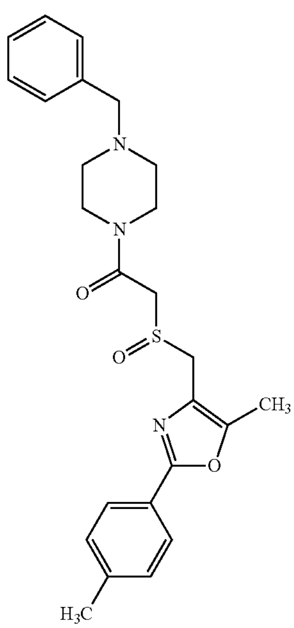 [SMILES: Cc1ccc(-c2nc(CS(=O)CC(=O)N3CCN(Cc4ccccc4)CC3)c(C)o2)cc1] | 451.59 |

TABLE 6-continued
Oxazole amides (R³ = N-cyclo)
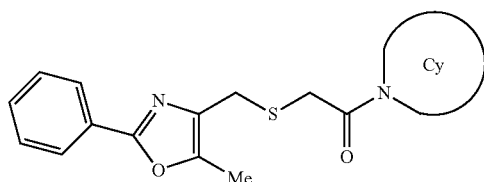
| ID | Structure | MW |
|---|---|---|
| IIa-2175 | | 418.52 |
| IIa-2176 | | 388.53 |

TABLE 6-continued
Oxazole amides (R³ = N-cyclo)
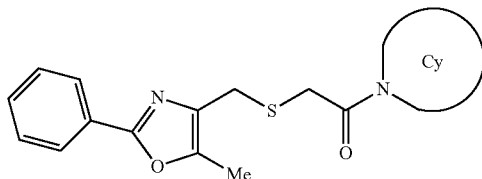
| ID | Structure | MW |
|---|---|---|
| IIa-2177 | 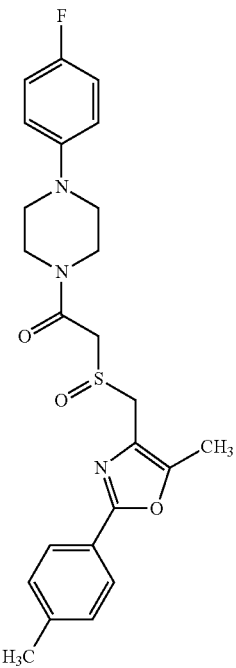 [SMILES: Cc1ccc(-c2nc(CS(=O)CC(=O)N3CCN(c4ccc(F)cc4)CC3)c(C)o2)cc1] | 455.56 |
| IIa-2178 | 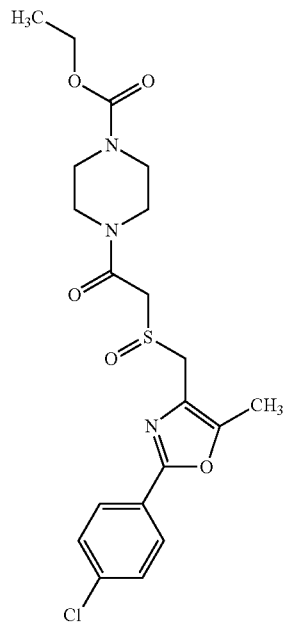 [SMILES: CCOC(=O)N1CCN(C(=O)CS(=O)Cc2nc(-c3ccc(Cl)cc3)oc2C)CC1] | 453.95 |

TABLE 6-continued
Oxazole amides (R³ = N-cyclo)
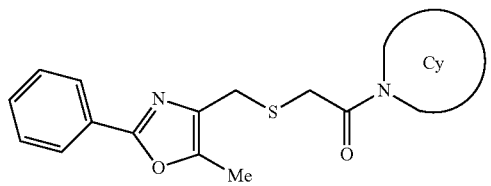
| ID | Structure | MW |
|---|---|---|
| IIa-2179 | | 438.93 |
| IIa-2180 | | 433.53 |

TABLE 6-continued
Oxazole amides (R³ = N-cyclo)
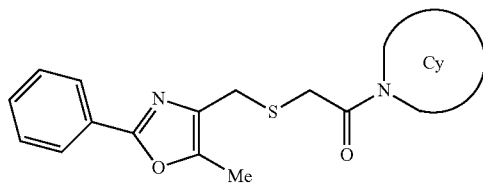
| ID | Structure | MW |
|---|---|---|
| IIa-2181 | 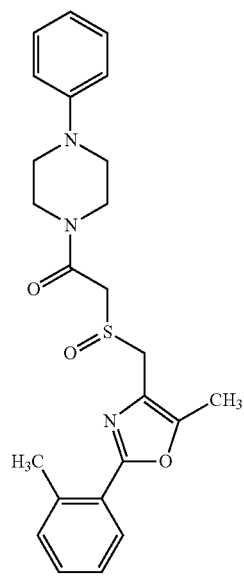 [SMILES: Cc1ccccc1-c1nc(CS(=O)CC(=O)N2CCN(c3ccccc3)CC2)c(C)o1] | 437.57 |
| IIa-2182 | 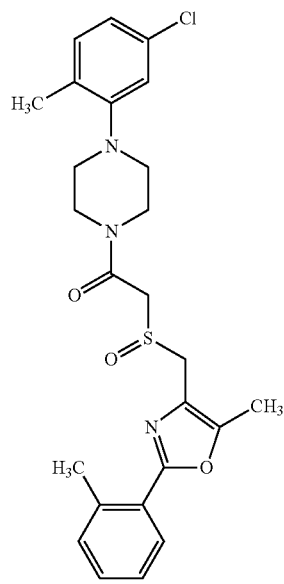 | 486.04 |

TABLE 6-continued
Oxazole amides (R³ = N-cyclo)
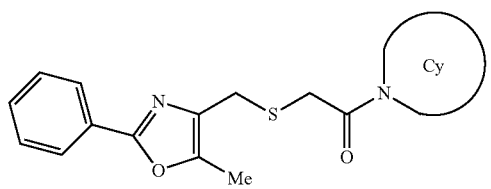
| ID | Structure | MW |
|---|---|---|
| IIa-2183 | | 362.45 |
| IIa-2184 | | 418.52 |

TABLE 6-continued
Oxazole amides (R³ = N-cyclo)
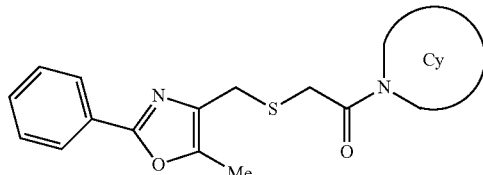
| ID | Structure | MW |
|---|---|---|
| IIa-2185 | 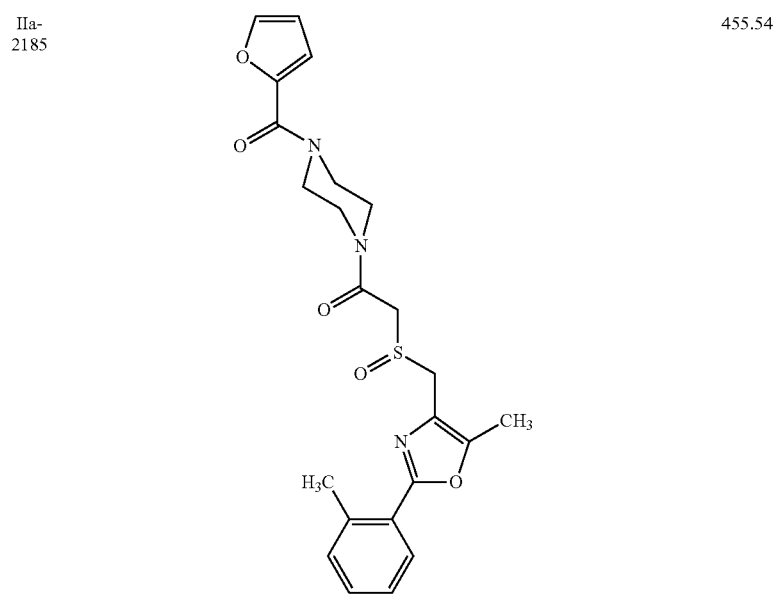 | 455.54 |
| IIa-2186 | 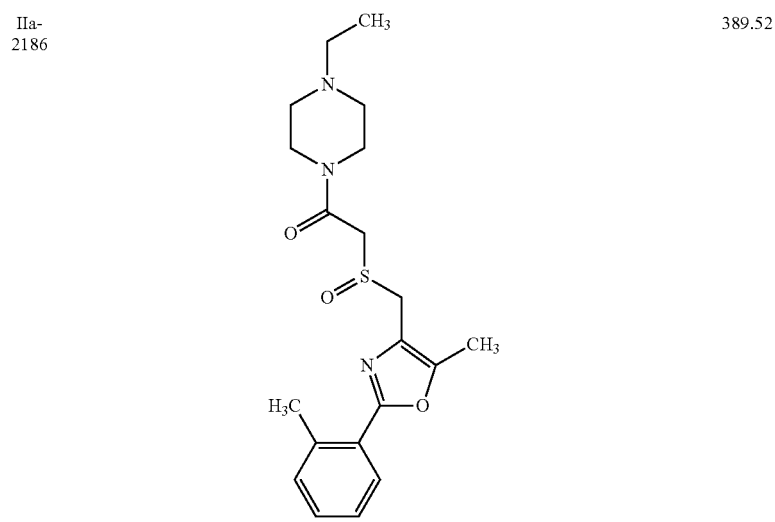 | 389.52 |

TABLE 6-continued
Oxazole amides (R³ = N-cyclo)
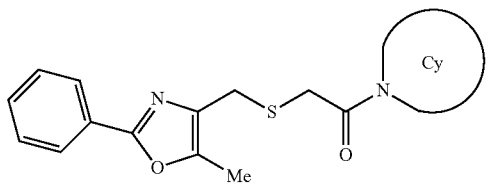
| ID | Structure | MW |
|---|---|---|
| IIa-2187 | | 360.48 |
| IIa-2188 | | 394.92 |

TABLE 6-continued
Oxazole amides (R³ = N-cyclo)
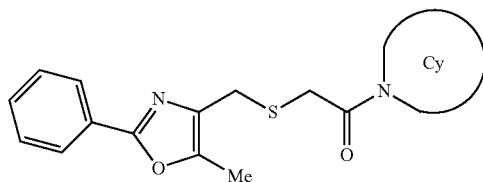
| ID | Structure | MW |
|---|---|---|
| IIa-2189 | | 457.98 |
| IIa-2190 | | 434.52 |

TABLE 6-continued
Oxazole amides (R³ = N-cyclo)
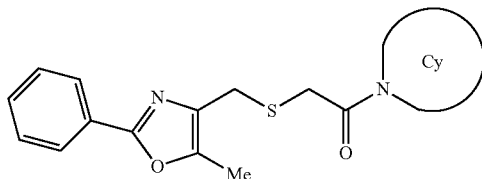
| ID | Structure | MW |
|---|---|---|
| IIa-2191 | | 479.56 |
| IIa-2192 | | 440.52 |

TABLE 6-continued
Oxazole amides (R³ = N-cyclo)
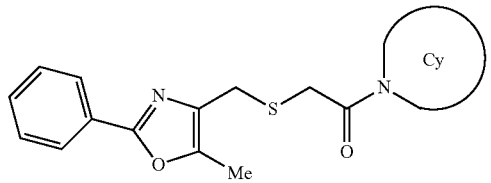
| ID | Structure | MW |
|---|---|---|
| IIa-2193 | | 511.65 |
| IIa-2194 | | 532.06 |

TABLE 6-continued
Oxazole amides (R³ = N-cyclo)
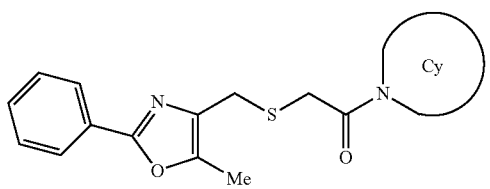
| ID | Structure | MW |
|---|---|---|
| IIa-2195 | 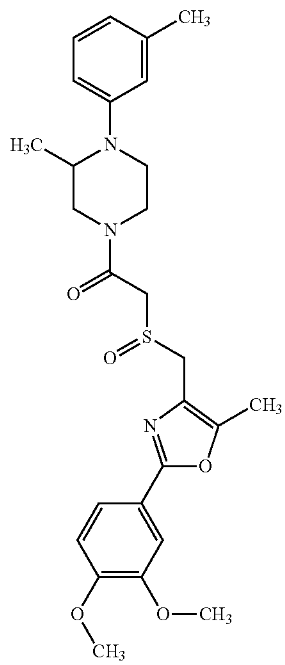 | 511.65 |
| IIa-2196 | 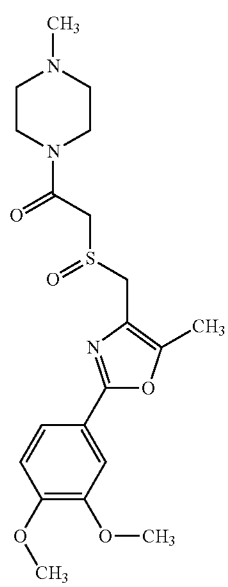 [SMILES: COc1ccc(-c2nc(CS(=O)CC(=O)N3CCN(C)CC3)c(C)o2)cc1OC] | 421.52 |

TABLE 6-continued
Oxazole amides (R³ = N-cyclo)
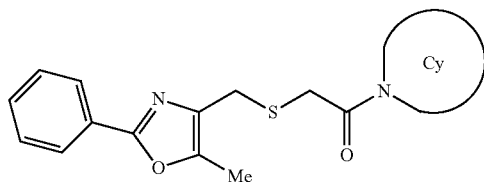
| ID | Structure | MW |
|---|---|---|
| IIa-2197 | 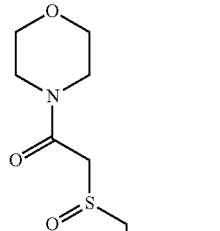 | 408.48 |
| IIa-2198 | 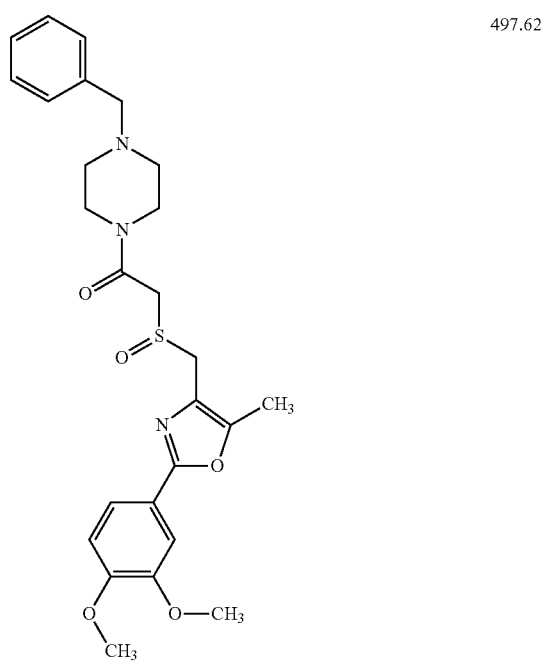 | 497.62 |

TABLE 6-continued
Oxazole amides (R³ = N-cyclo)
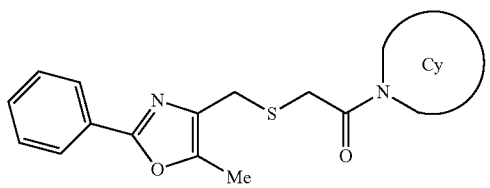
| ID | Structure | MW |
|---|---|---|
| IIa-2199 | 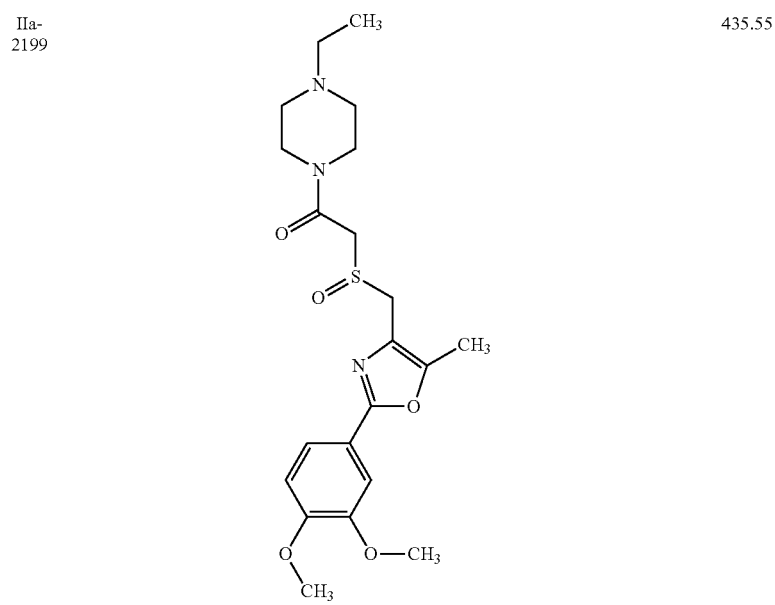 | 435.55 |
| IIa-2200 | 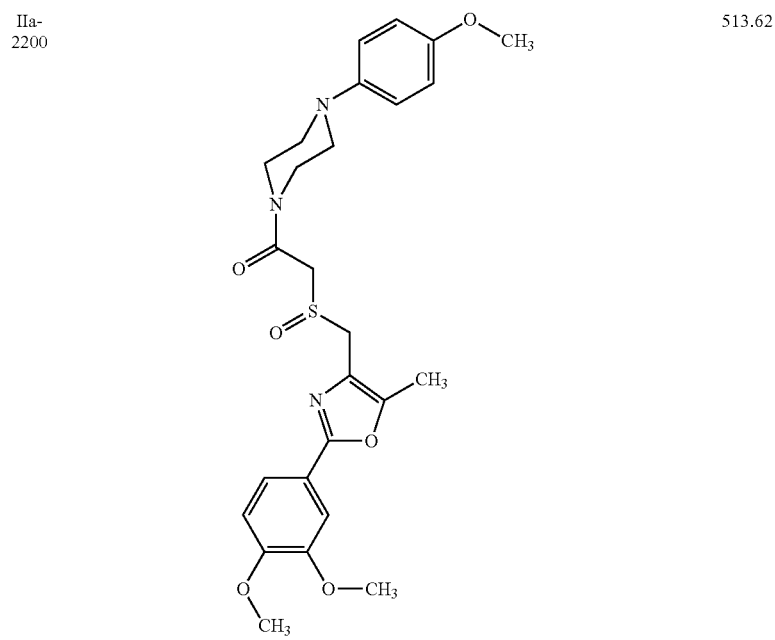 | 513.62 |

TABLE 6-continued

Oxazole amides (R³ = N-cyclo)

| ID | Structure | MW |
|---|---|---|
| IIa-2201 | | 382.49 |
| IIa-2202 | | 362.49 |
| IIa-2203 | | 380.47 |

TABLE 6-continued
Oxazole amides (R³ = N-cyclo)
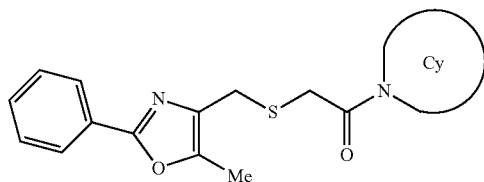
| ID | Structure | MW |
|---|---|---|
| IIa-2204 | | 423.54 |
| IIa-2205 | | 394.50 |

TABLE 6-continued

Oxazole amides (R³ = N-cyclo)

| ID | Structure | MW |
|---|---|---|
| IIa-2206 | 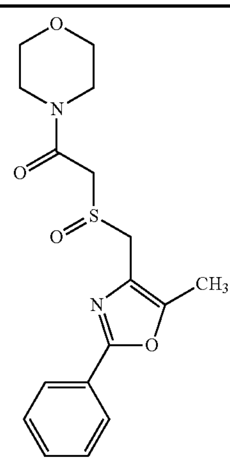 | 348.42 |
| IIa-2207 | 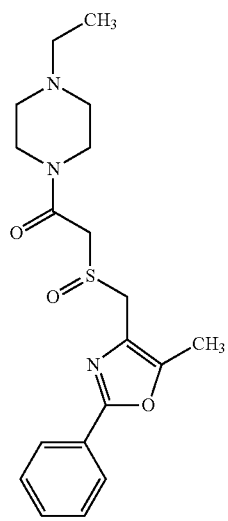 [SMILES: CCN1CCN(C(=O)CS(=O)Cc2nc(-c3ccccc3)oc2C)CC1] | 375.49 |
| IIa-2208 | 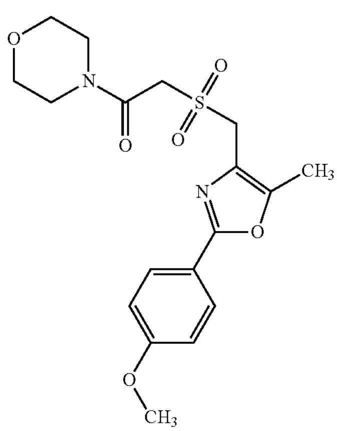 [SMILES: COc1ccc(-c2nc(CS(=O)(=O)CC(=O)N3CCOCC3)c(C)o2)cc1] | 394.45 |

TABLE 6-continued

Oxazole amides (R³ = N-cyclo)

| ID | Structure | MW |
|---|---|---|
| IIa-2209 | | 412.51 |
| IIa-2210 | | 392.52 |
| IIa-2211 | | 449.53 |

TABLE 6-continued
Oxazole amides (R³ = N-cyclo)
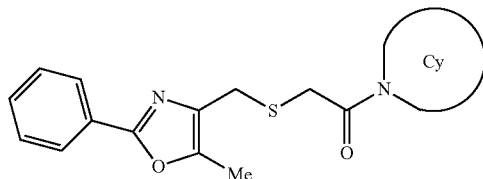
| ID | Structure | MW |
|---|---|---|
| IIa-2212 | 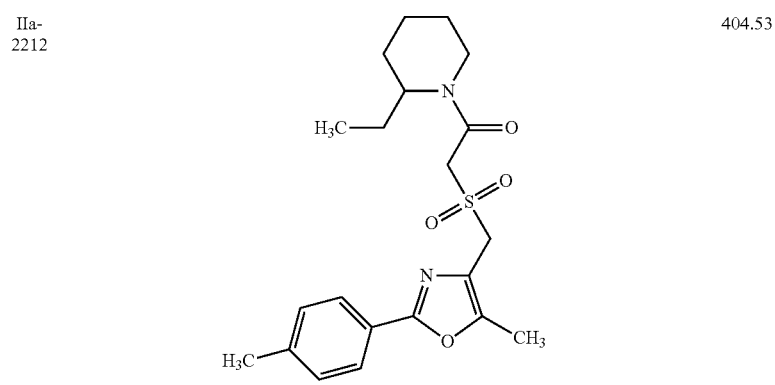 | 404.53 |
| IIa-2213 | 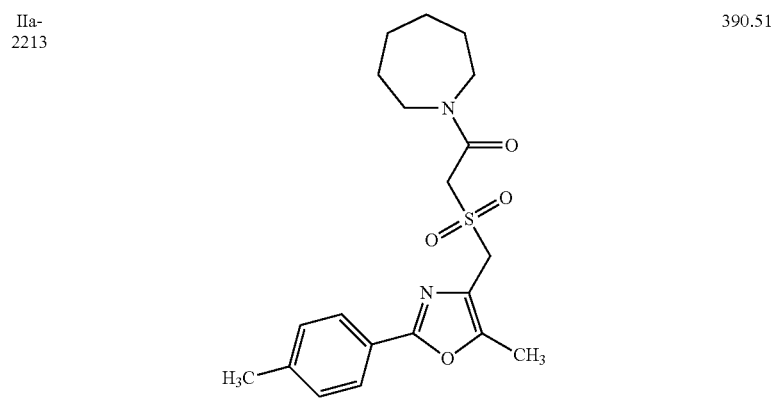 | 390.51 |
| IIa-2214 | 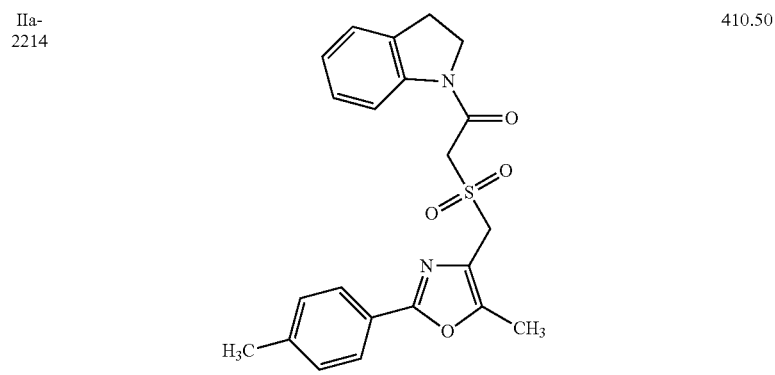 | 410.50 |

TABLE 6-continued
Oxazole amides (R³ = N-cyclo)
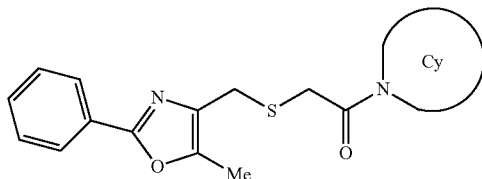
| ID | Structure | MW |
|---|---|---|
| IIa-2215 | 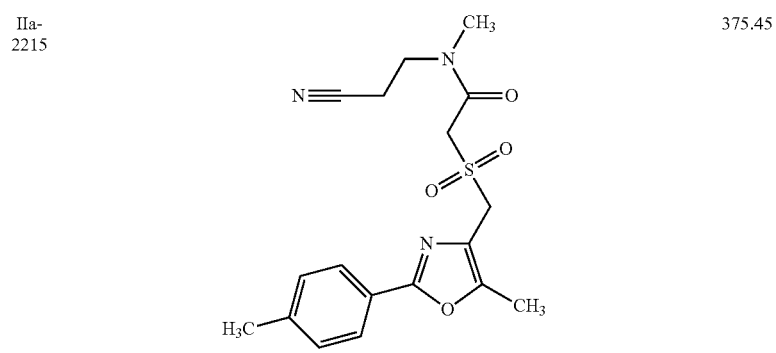 | 375.45 |
| IIa-2216 | 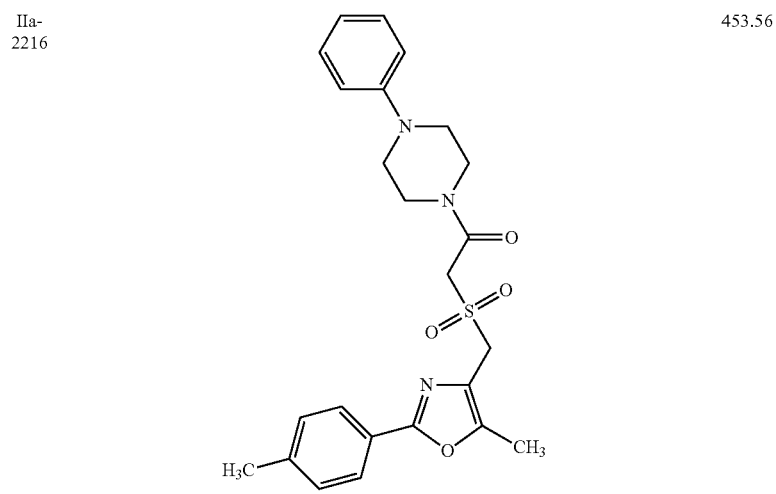 | 453.56 |
| IIa-2217 | 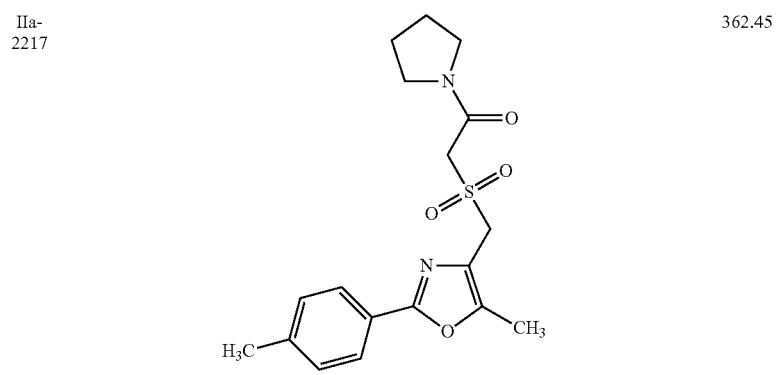 | 362.45 |

TABLE 6-continued
Oxazole amides (R³ = N-cyclo)
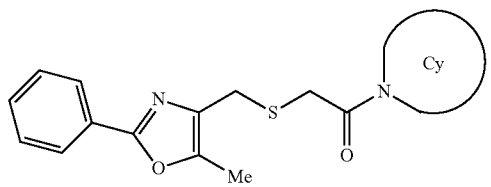
| ID | Structure | MW |
|---|---|---|
| IIa-2218 | 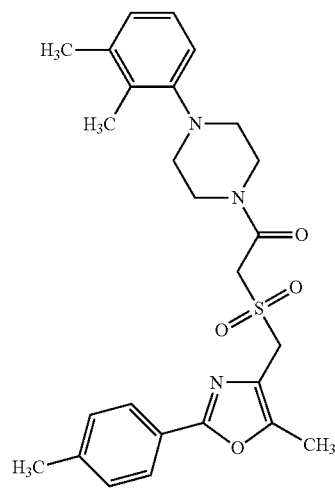 | 481.62 |
| IIa-2219 | 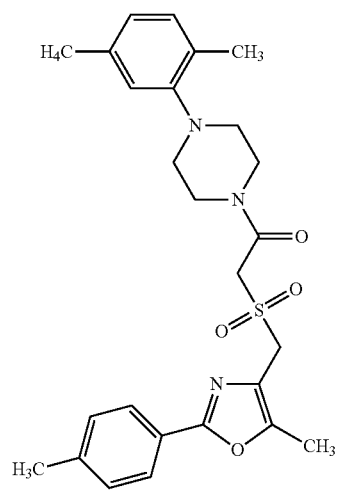 | 481.62 |

TABLE 6-continued

Oxazole amides (R³ = N-cyclo)

| ID | Structure | MW |
|---|---|---|
| IIa-2220 | | 424.52 |
| IIa-2221 | | 481.62 |
| IIa-2222 | | 391.49 |

TABLE 6-continued
Oxazole amides (R³ = N-cyclo)
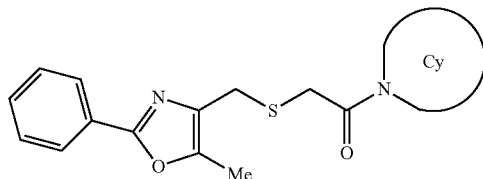
| ID | Structure | MW |
|---|---|---|
| IIa-2223 | | 378.45 |
| IIa-2224 | | 467.59 |
| IIa-2225 | | 404.53 |

TABLE 6-continued
Oxazole amides (R³ = N-cyclo)
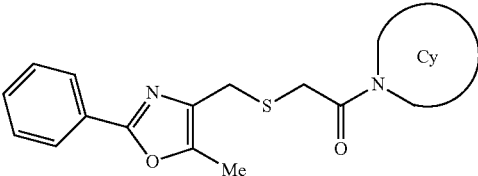
| ID | Structure | MW |
|---|---|---|
| IIa-2226 | 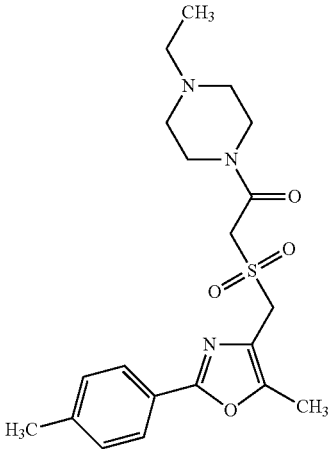 | 405.52 |
| IIa-2227 | | 428.51 |
| IIa-2228 | 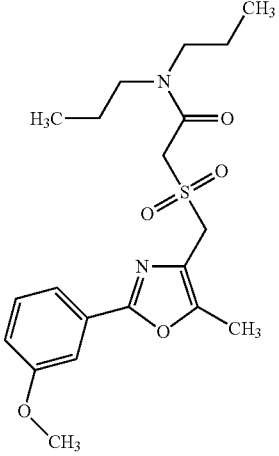 [SMILES: CCCN(CCC)C(=O)CS(=O)(=O)Cc1nc(-c2cccc(OC)c2)oc1C] | 408.52 |

TABLE 6-continued
Oxazole amides (R³ = N-cyclo)
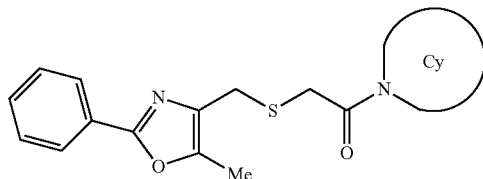
| ID | Structure | MW |
|---|---|---|
| IIa-2229 | | 465.53 |
| IIa-2230 | | 406.50 |

TABLE 6-continued
Oxazole amides (R³ = N-cyclo)
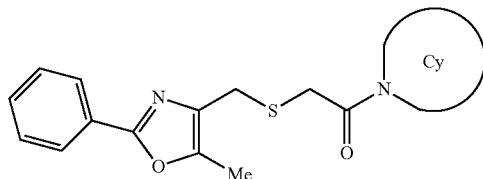
| ID | Structure | MW |
|---|---|---|
| IIa-2231 | | 426.50 |
| IIa-2232 | | 391.45 |

TABLE 6-continued
Oxazole amides (R³ = N-cyclo)
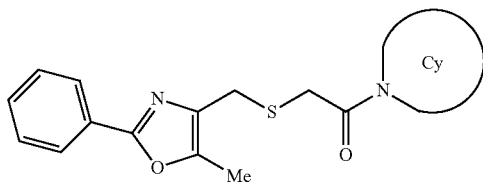
| ID | Structure | MW |
|---|---|---|
| IIa-2233 | 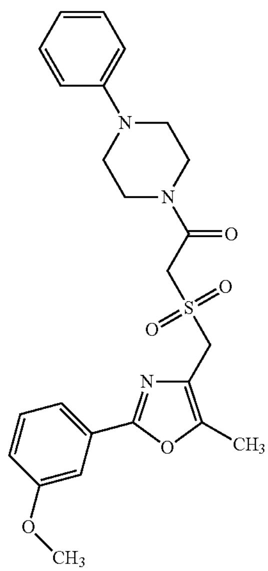 [SMILES: COc1cccc(-c2nc(CS(=O)(=O)CC(=O)N3CCN(c4ccccc4)CC3)c(C)o2)c1] | 469.56 |
| IIa-2234 | 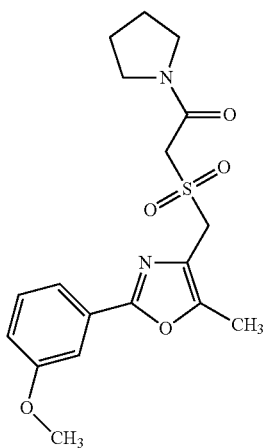 [SMILES: COc1cccc(-c2nc(CS(=O)(=O)CC(=O)N3CCCC3)c(C)o2)c1] | 378.45 |

TABLE 6-continued
Oxazole amides (R³ = N-cyclo)
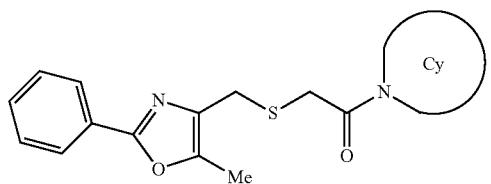
| ID | Structure | MW |
|---|---|---|
| IIa-2235 | | 475.61 |
| IIa-2236 | | 497.62 |

TABLE 6-continued
Oxazole amides (R³ = N-cyclo)
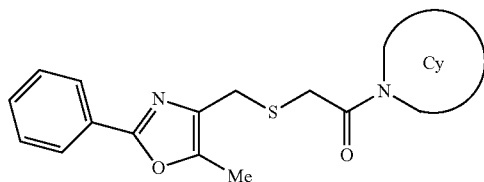
| ID | Structure | MW |
|---|---|---|
| IIa-2237 | 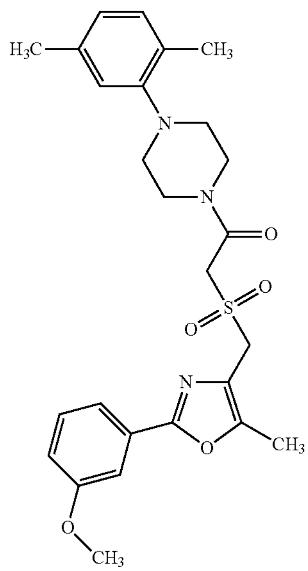 | 497.62 |
| IIa-2238 | 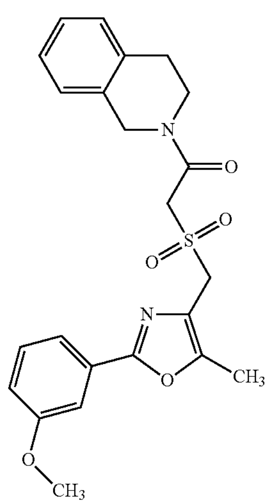 [SMILES: COc1cccc(-c2nc(CS(=O)(=O)CC(=O)N3CCc4ccccc4C3)c(C)o2)c1] | 440.52 |

TABLE 6-continued
Oxazole amides (R³ = N-cyclo)
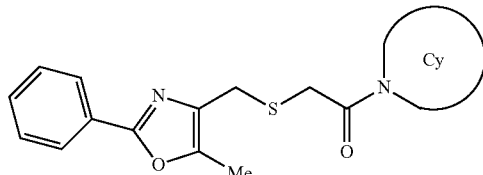
| ID | Structure | MW |
|---|---|---|
| IIa-2239 | 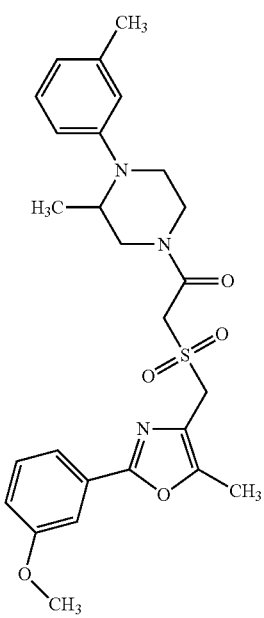 [SMILES: COc1cccc(-c2nc(CS(=O)(=O)CC(=O)N3CCN(c4cccc(C)c4)C(C)C3)c(C)o2)c1] | 497.62 |
| IIa-2240 | 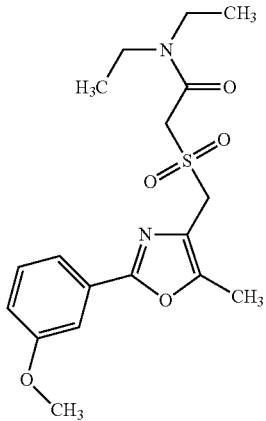 [SMILES: CCN(CC)C(=O)CS(=O)(=O)Cc1nc(-c2cccc(OC)c2)oc1C] | 380.47 |

TABLE 6-continued
Oxazole amides (R³ = N-cyclo)
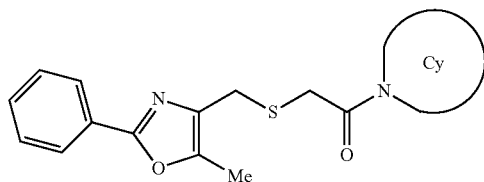
| ID | Structure | MW |
|---|---|---|
| IIa-2241 | | 407.49 |
| IIa-2242 | | 394.45 |

TABLE 6-continued
Oxazole amides (R³ = N-cyclo)
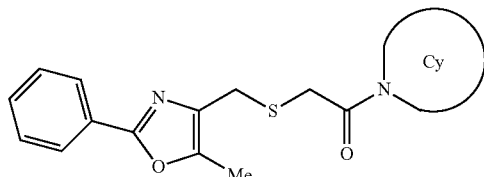
| ID | Structure | MW |
|---|---|---|
| IIa-2243 | | 483.59 |
| IIa-2244 | | 435.55 |

TABLE 6-continued
Oxazole amides (R³ = N-cyclo)
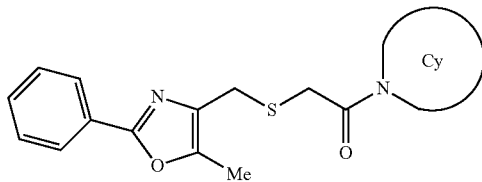
| ID | Structure | MW |
|---|---|---|
| IIa-2245 | 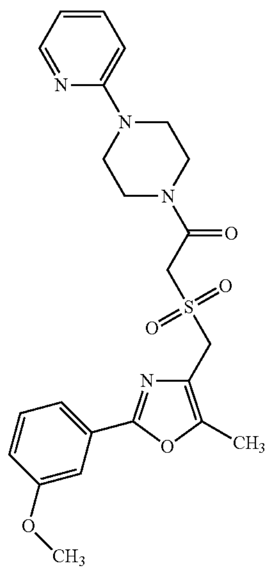 [SMILES: COc1cccc(-c2nc(CS(=O)(=O)CC(=O)N3CCN(c4ccccn4)CC3)c(C)o2)c1] | 470.55 |
| IIa-2246 | 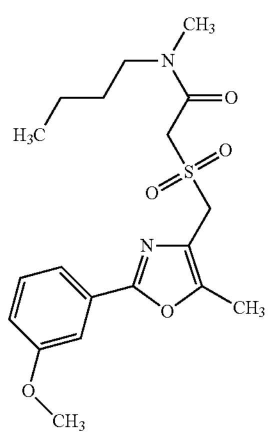 [SMILES: CCCCN(C)C(=O)CS(=O)(=O)Cc1nc(-c2cccc(OC)c2)oc1C] | 394.49 |

TABLE 6-continued
Oxazole amides (R³ = N-cyclo)
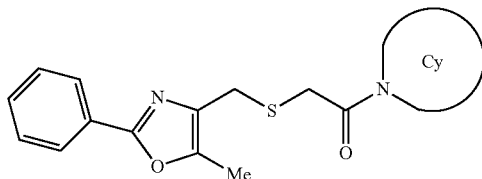
| ID | Structure | MW |
|---|---|---|
| IIa-2247 | 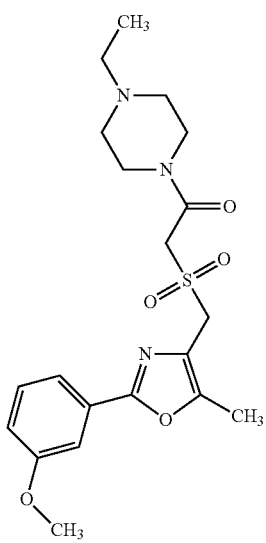 [SMILES: CCN1CCN(C(=O)CS(=O)(=O)Cc2nc(-c3cccc(OC)c3)oc2C)CC1] | 420.53 |
| IIa-2248 | | 421.52 |

TABLE 6-continued
Oxazole amides ($R^3$ = N-cyclo)
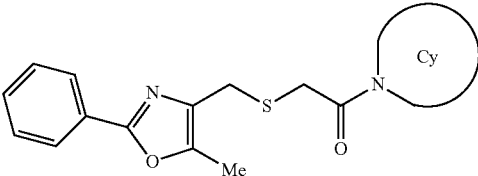
| ID | Structure | MW |
|---|---|---|
| IIa-2249 | 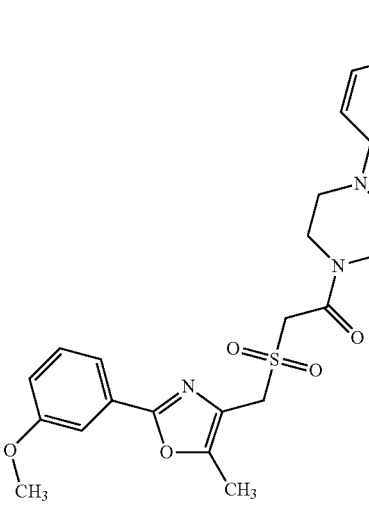 | 499.59 |
| IIa-2250 | 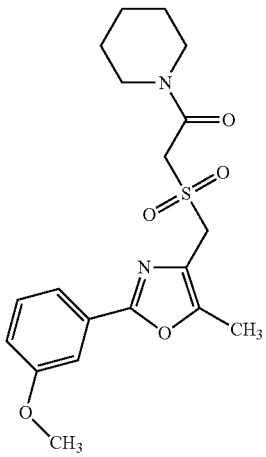 [SMILES: COc1cccc(-c2nc(CS(=O)(=O)CC(=O)N3CCCCC3)c(C)o2)c1] | 392.48 |
| IIa-2251 | 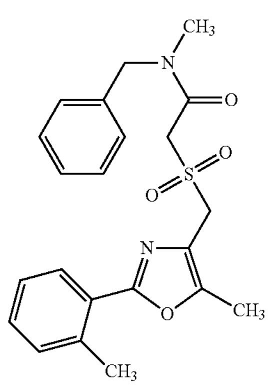 [SMILES: Cc1ccccc1-c1nc(CS(=O)(=O)CC(=O)N(C)Cc2ccccc2)c(C)o1] | 412.51 |

TABLE 6-continued
Oxazole amides (R³ = N-cyclo)
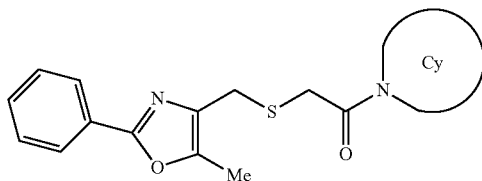
| ID | Structure | MW |
|---|---|---|
| IIa-2252 | 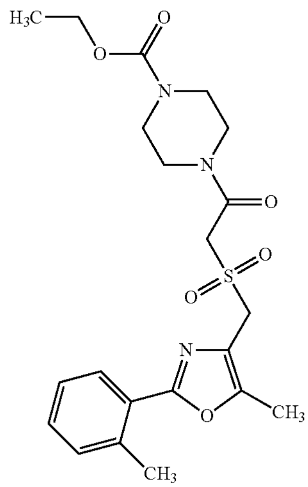 [SMILES: CCOC(=O)N1CCN(C(=O)CS(=O)(=O)Cc2nc(-c3ccccc3C)oc2C)CC1] | 449.53 |
| IIa-2253 | 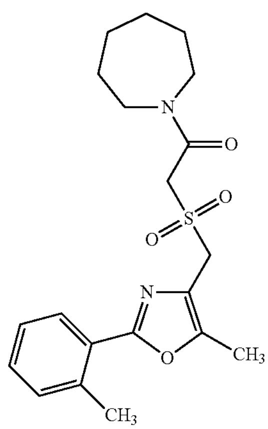 [SMILES: Cc1ccccc1-c1nc(CS(=O)(=O)CC(=O)N2CCCCCC2)c(C)o1] | 390.51 |
| IIa-2254 | 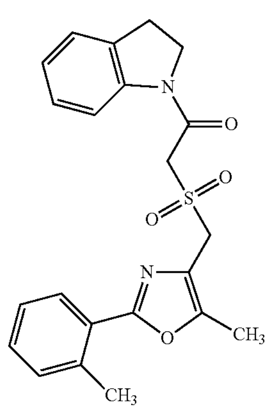 [SMILES: Cc1ccccc1-c1nc(CS(=O)(=O)CC(=O)N2CCc3ccccc32)c(C)o1] | 410.50 |

TABLE 6-continued
Oxazole amides (R³ = N-cyclo)
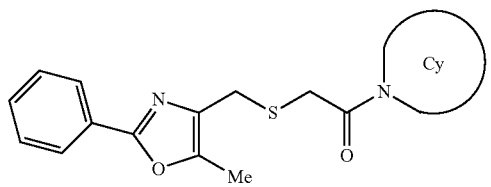
| ID | Structure | MW |
|---|---|---|
| IIa-2255 | | 375.45 |
| IIa-2256 | | 453.56 |
| IIa-2257 | | 362.45 |

TABLE 6-continued
Oxazole amides (R³ = N-cyclo)
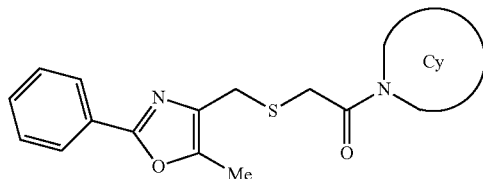
| ID | Structure | MW |
|---|---|---|
| IIa-2258 | | 424.52 |
| IIa-2259 | | 404.53 |

TABLE 6-continued
Oxazole amides (R³ = N-cyclo)
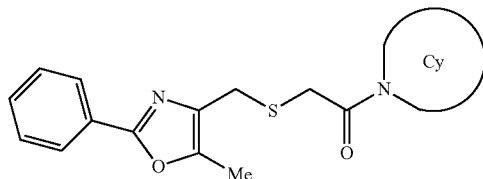
| ID | Structure | MW |
|---|---|---|
| IIa-2260 | 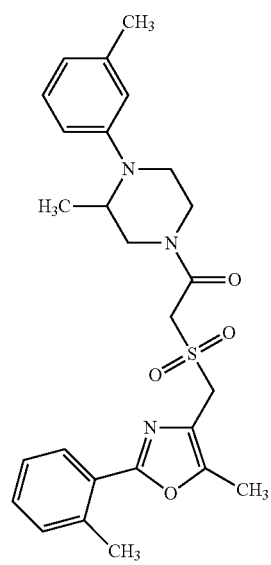 [SMILES: Cc1cccc(N2CCN(C(=O)CS(=O)(=O)Cc3nc(-c4ccccc4C)oc3C)CC2C)c1] | 481.62 |
| IIa-2261 | 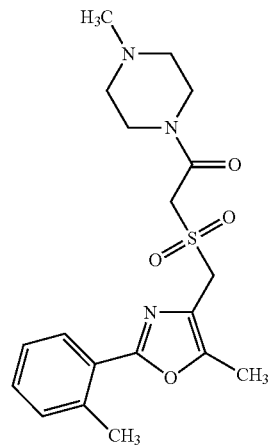 [SMILES: Cc1ccccc1-c1nc(CS(=O)(=O)CC(=O)N2CCN(C)CC2)c(C)o1] | 391.49 |

TABLE 6-continued
Oxazole amides (R³ = N-cyclo)
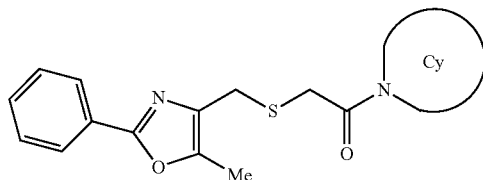
| ID | Structure | MW |
|---|---|---|
| IIa-2262 | 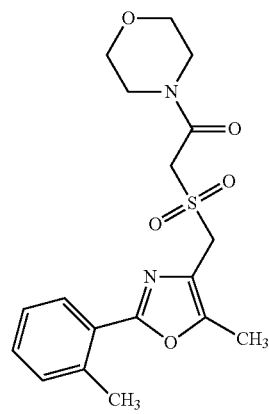 [SMILES: Cc1ccccc1-c1nc(CS(=O)(=O)CC(=O)N2CCOCC2)c(C)o1] | 378.45 |
| IIa-2263 | 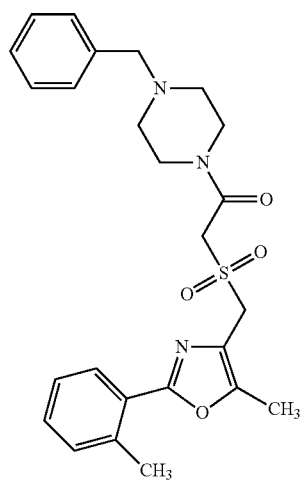 [SMILES: Cc1ccccc1-c1nc(CS(=O)(=O)CC(=O)N2CCN(Cc3ccccc3)CC2)c(C)o1] | 467.59 |

TABLE 6-continued
Oxazole amides (R³ = N-cyclo)
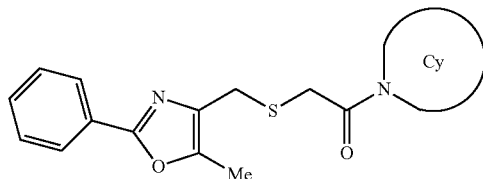
| ID | Structure | MW |
|---|---|---|
| IIa-2264 | 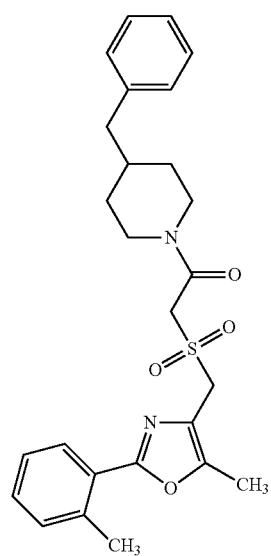 [SMILES: Cc1ccccc1-c1nc(CS(=O)(=O)CC(=O)N2CCC(Cc3ccccc3)CC2)c(C)o1] | 466.60 |
| IIa-2265 | 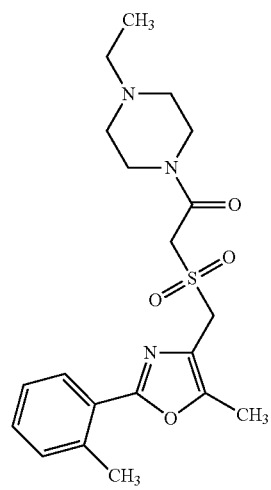 [SMILES: CCN1CCN(C(=O)CS(=O)(=O)Cc2nc(-c3ccccc3C)oc2C)CC1] | 405.52 |

TABLE 6-continued

Oxazole amides (R³ = N-cyclo)

| ID | Structure | MW |
|---|---|---|
| IIa-2266 | | 376.48 |
| IIa-2267 | | 491.97 |
| IIa-2268 | | 408.50 |

TABLE 6-continued
Oxazole amides (R³ = N-cyclo)
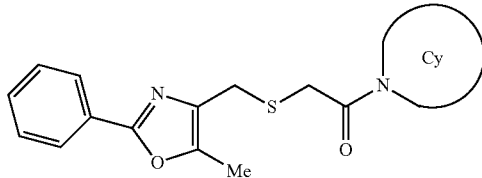
| ID | Structure | MW |
|---|---|---|
| IIa-2269 | 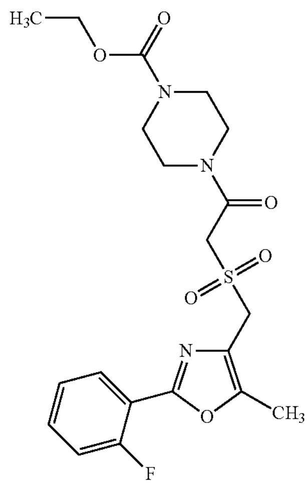 [SMILES: CCOC(=O)N1CCN(C(=O)CS(=O)(=O)Cc2nc(-c3ccccc3F)oc2C)CC1] | 453.49 |
| IIa-2270 | 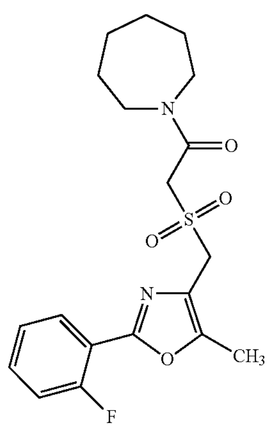 [SMILES: Cc1oc(-c2ccccc2F)nc1CS(=O)(=O)CC(=O)N1CCCCCC1] | 394.47 |
| IIa-2271 | 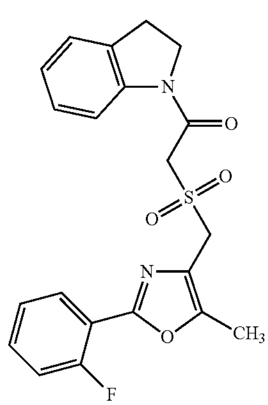 [SMILES: Cc1oc(-c2ccccc2F)nc1CS(=O)(=O)CC(=O)N1CCc2ccccc21] | 414.46 |

TABLE 6-continued
Oxazole amides (R³ = N-cyclo)
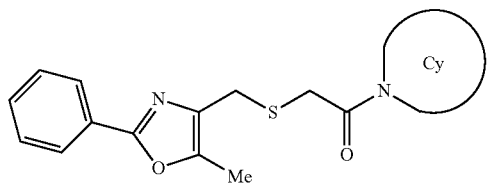
| ID | Structure | MW |
|---|---|---|
| IIa-2272 | | 457.53 |
| IIa-2273 | | 428.49 |

TABLE 6-continued
Oxazole amides (R³ = N-cyclo)
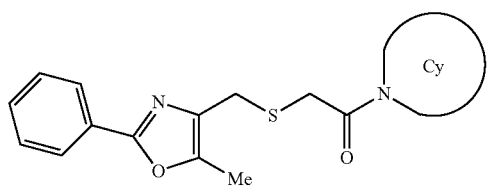
| ID | Structure | MW |
|---|---|---|
| IIa-2274 | | 486.58 |
| IIa-2275 | | 382.41 |

TABLE 6-continued

Oxazole amides (R³ = N-cyclo)

| ID | Structure | MW |
|---|---|---|
| IIa-2276 | 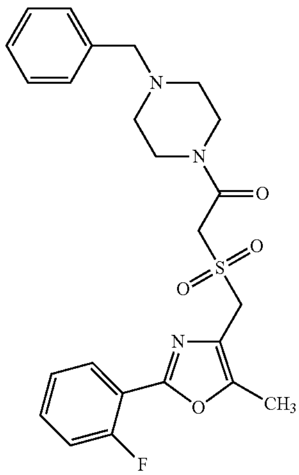 [SMILES: Cc1oc(-c2ccccc2F)nc1CS(=O)(=O)CC(=O)N1CCN(Cc2ccccc2)CC1] | 471.55 |
| IIa-2277 | 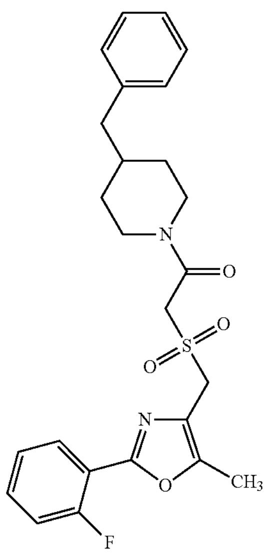 [SMILES: Cc1oc(-c2ccccc2F)nc1CS(=O)(=O)CC(=O)N1CCC(Cc2ccccc2)CC1] | 470.57 |
| IIa-2278 | 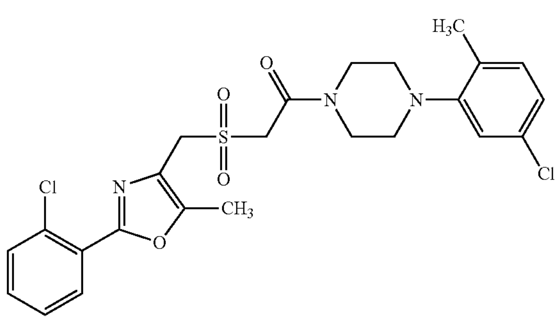 [SMILES: Cc1ccc(Cl)cc1N1CCN(C(=O)CS(=O)(=O)Cc2nc(-c3ccccc3Cl)oc2C)CC1] | 522.45 |

TABLE 6-continued

Oxazole amides (R³ = N-cyclo)

| ID | Structure | MW |
|---|---|---|
| IIa-2279 | | 430.91 |
| IIa-2280 | | 468.96 |
| IIa-2281 | | 398.87 |
| IIa-2282 | | 480.03 |

TABLE 6-continued
Oxazole amides ($R^3$ = N-cyclo)
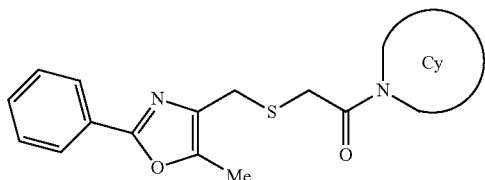
| ID | Structure | MW |
|---|---|---|
| IIa-2283 | 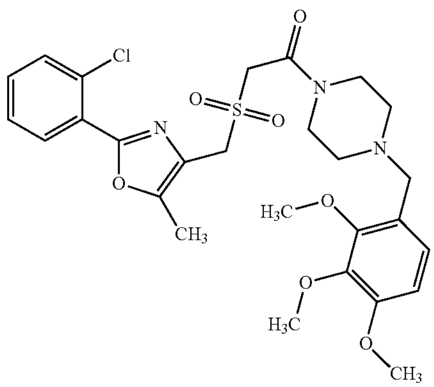 [SMILES: COc1ccc(CN2CCN(C(=O)CS(=O)(=O)Cc3nc(-c4ccccc4Cl)oc3C)CC2)c(OC)c1OC] | 578.09 |
| IIa-2284 | 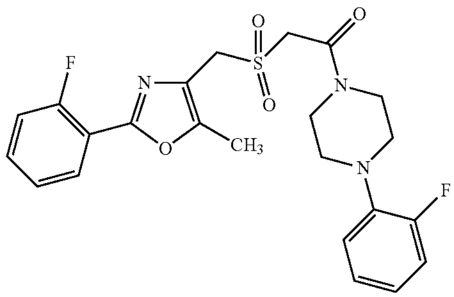 [SMILES: Cc1oc(-c2ccccc2F)nc1CS(=O)(=O)CC(=O)N1CCN(c2ccccc2F)CC1] | 475.52 |
| IIa-2285 | 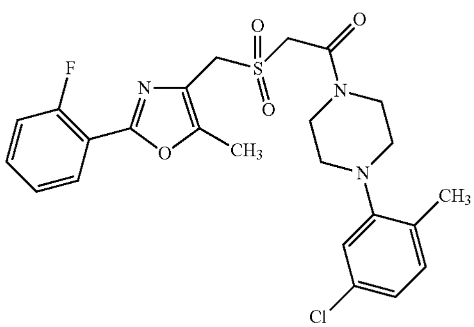 [SMILES: Cc1ccc(Cl)cc1N1CCN(C(=O)CS(=O)(=O)Cc2nc(-c3ccccc3F)oc2C)CC1] | 506.00 |
| IIa-2286 | 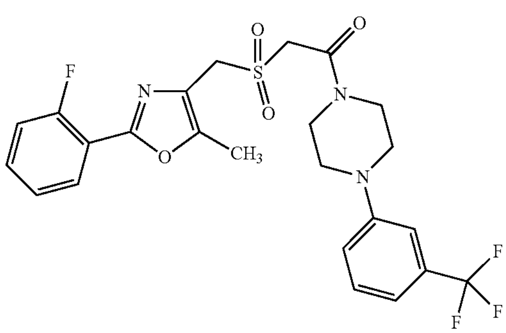 [SMILES: Cc1oc(-c2ccccc2F)nc1CS(=O)(=O)CC(=O)N1CCN(c2cccc(C(F)(F)F)c2)CC1] | 525.53 |

TABLE 6-continued
Oxazole amides (R³ = N-cyclo)
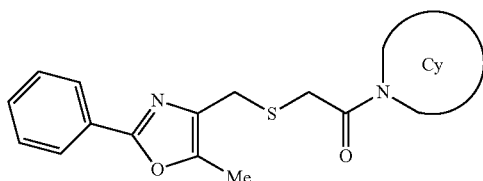
| ID | Structure | MW |
|---|---|---|
| IIa-2287 | | 514.62 |
| IIa-2288 | | 374.46 |
| IIa-2289 | | 441.60 |

TABLE 6-continued

Oxazole amides (R³ = N-cyclo)

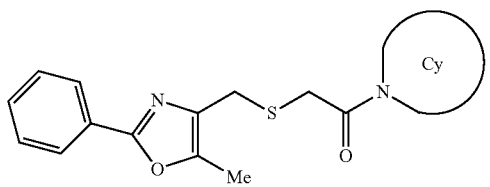

| ID | Structure | MW |
|---|---|---|
| IIa-2290 | (3-methylphenyl oxazole, S-CH2-C(O)-N-tetrahydroquinoline) | 392.52 |
| IIa-2291 | (3,4-dimethoxyphenyl oxazole, S-CH2-C(O)-piperazine-N-propyl) | 433.57 |

TABLE 7

Phenmethylene-Thiazole Alkanoic Acids (R³ = OH)

| ID | Structure | MW |
|---|---|---|
| IIb-1 | (4-methoxy-3-bromobenzylidene thiazolidinedione-propanoic acid) | 402.3 |
| IIb-2 | (4-pentyloxy-3-methoxybenzylidene thiazolidinedione-propanoic acid) | 409.5 |

TABLE 7-continued

Phenmethylene-Thiazole Alkanoic Acids ($R^3$ = OH)

| ID | Structure | MW |
|---|---|---|
| IIb-3 | 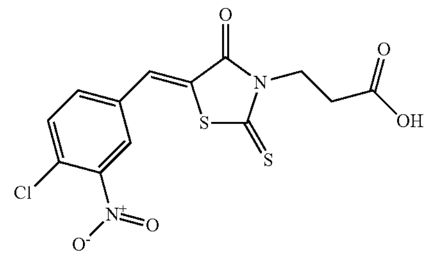 [SMILES: O=C(O)CCN1C(=O)/C(=C/c2ccc(Cl)c([N+](=O)[O-])c2)SC1=S] | 372.8 |
| IIb-4 | 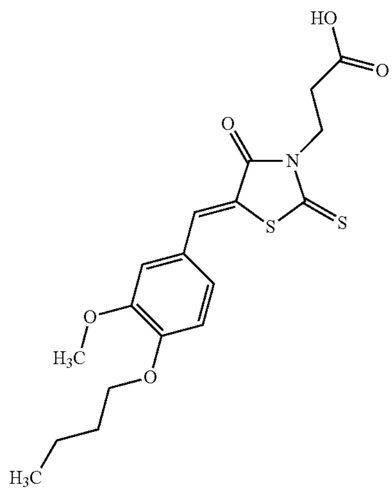 [SMILES: CCCCOc1ccc(/C=C2\SC(=S)N(CCC(=O)O)C2=O)cc1OC] | 395.5 |
| IIb-5 | 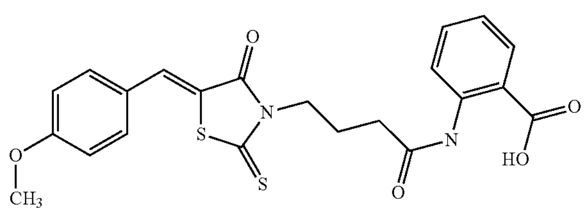 [SMILES: COc1ccc(/C=C2\SC(=S)N(CCCC(=O)Nc3ccccc3C(=O)O)C2=O)cc1] | 456.5 |
| IIb-6 | 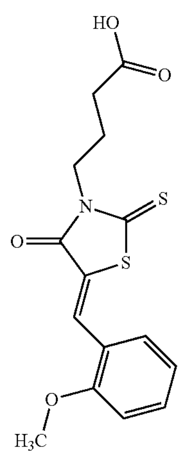 [SMILES: COc1ccccc1/C=C1\SC(=S)N(CCCC(=O)O)C1=O] | 337.4 |

TABLE 7-continued

| | Phenmethylene-Thiazole Alkanoic Acids ($R^3$ = OH) | |
|---|---|---|
| ID | Structure | MW |
| IIb-7 | | 423.6 |
| IIb-8 | | 442.5 |
| IIb-9 | | 426.5 |
| IIb-10 | | 343.4 |

TABLE 7-continued

Phenmethylene-Thiazole Alkanoic Acids (R³ = OH)

| ID | Structure | MW |
| --- | --- | --- |
| IIb-11 | 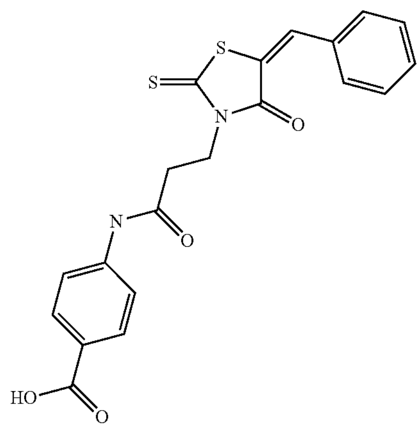 [SMILES: O=C(CCN1C(=O)/C(=C\c2ccccc2)SC1=S)Nc1ccc(C(=O)O)cc1] | 412.5 |
| IIb-12 | 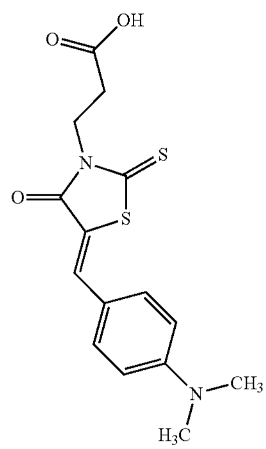 [SMILES: CN(C)c1ccc(/C=C2\SC(=S)N(CCC(=O)O)C2=O)cc1] | 336.4 |
| IIb-13 | 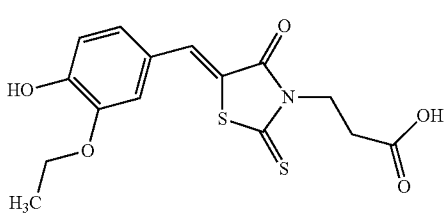 [SMILES: CCOc1cc(/C=C2\SC(=S)N(CCC(=O)O)C2=O)ccc1O] | 353.4 |
| IIb-14 | 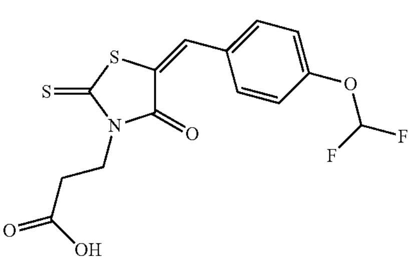 [SMILES: O=C(O)CCN1C(=O)/C(=C\c2ccc(OC(F)F)cc2)SC1=S] | 359.4 |

TABLE 7-continued

Phenmethylene-Thiazole Alkanoic Acids ($R^3$ = OH)

| ID | Structure | MW |
| --- | --- | --- |
| IIb-15 | 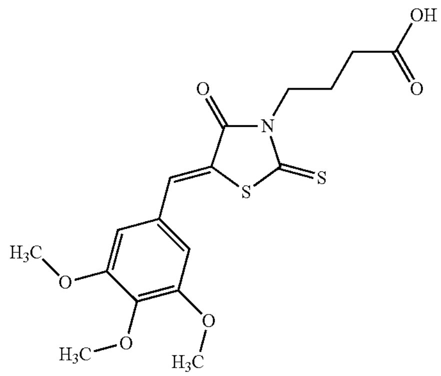 [SMILES: COc1cc(/C=C2\SC(=S)N(CCCC(=O)O)C2=O)cc(OC)c1OC] | 397.5 |
| IIb-16 | 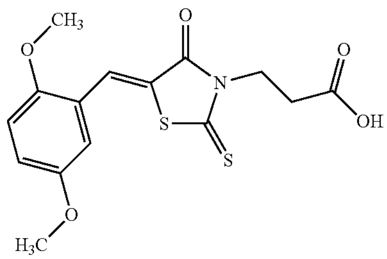 [SMILES: COc1ccc(OC)c(/C=C2\SC(=S)N(CCC(=O)O)C2=O)c1] | 353.4 |
| IIb-17 | 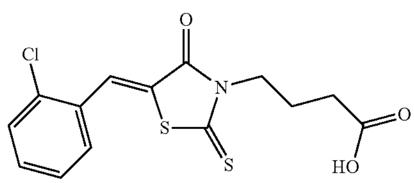 [SMILES: O=C(O)CCCN1C(=O)/C(=C/c2ccccc2Cl)SC1=S] | 341.8 |
| IIb-18 | 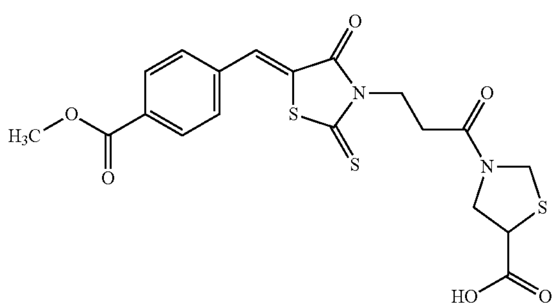 [SMILES: COC(=O)c1ccc(/C=C2\SC(=S)N(CCC(=O)N3CSC(C(=O)O)C3)C2=O)cc1] | 466.6 |
| IIb-19 | 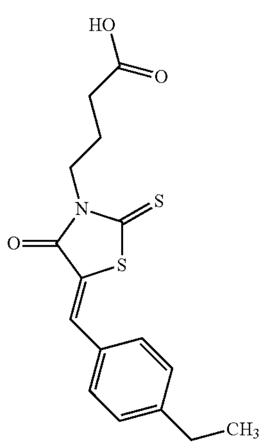 [SMILES: CCc1ccc(/C=C2\SC(=S)N(CCCC(=O)O)C2=O)cc1] | 335.4 |

TABLE 7-continued

Phenmethylene-Thiazole Alkanoic Acids ($R^3$ = OH)

| ID | Structure | MW |
|---|---|---|
| IIb-20 | 3-bromophenyl derivative | 372.3 |
| IIb-21 | 2,4-dichlorophenyl derivative | 362.3 |
| IIb-22 | 2,6-dichlorophenyl derivative | 362.3 |
| IIb-23 | benzo[1,3]dioxole derivative | 337.4 |
| IIb-24 | 2-fluorophenyl derivative | 311.4 |

TABLE 7-continued

Phenmethylene-Thiazole Alkanoic Acids ($R^3$ = OH)

| ID | Structure | MW |
|---|---|---|
| IIb-25 | 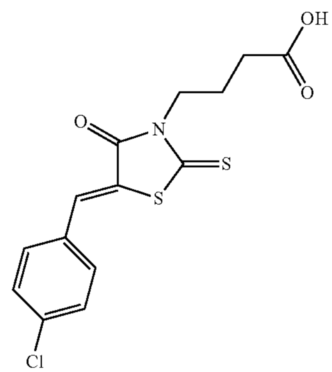 [SMILES: O=C(O)CCCN1C(=O)/C(=C/c2ccc(Cl)cc2)SC1=S] | 341.8 |
| IIb-26 | 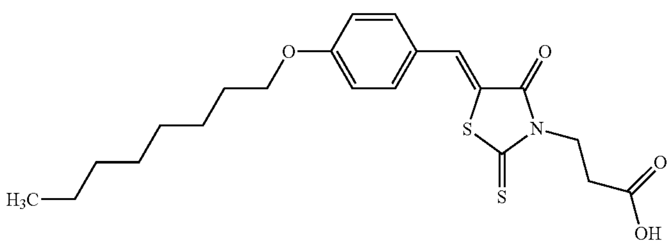 [SMILES: CCCCCCCCOc1ccc(/C=C2\SC(=S)N(CCC(=O)O)C2=O)cc1] | 421.6 |
| IIb-27 | 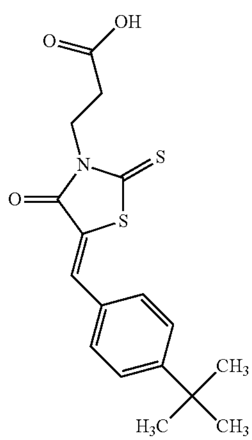 [SMILES: CC(C)(C)c1ccc(/C=C2\SC(=S)N(CCC(=O)O)C2=O)cc1] | 349.5 |
| IIb-28 | 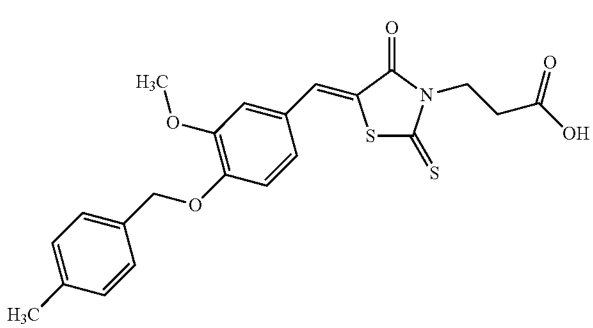 [SMILES: COc1cc(/C=C2\SC(=S)N(CCC(=O)O)C2=O)ccc1OCc1ccc(C)cc1] | 443.5 |

TABLE 7-continued

Phenmethylene-Thiazole Alkanoic Acids (R³ = OH)

| ID | Structure | MW |
|---|---|---|
| IIb-29 | 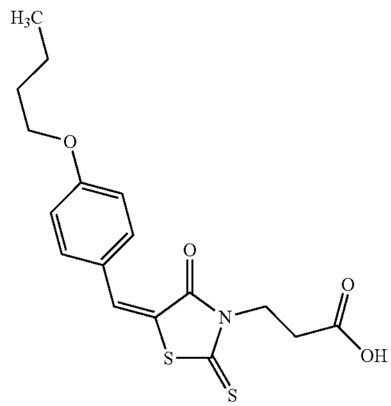 [SMILES: CCCCOc1ccc(/C=C2/SC(=S)N(CCC(=O)O)C2=O)cc1] | 365.5 |
| IIb-30 | 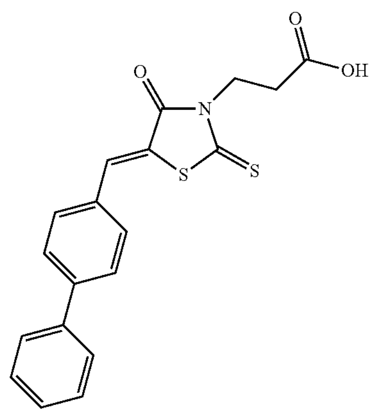 [SMILES: O=C(O)CCN1C(=O)/C(=C/c2ccc(-c3ccccc3)cc2)SC1=S] | 369.5 |
| IIb-31 | 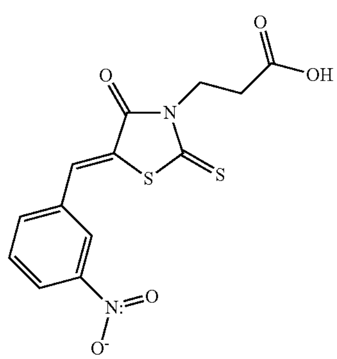 | 338.4 |
| IIb-32 | 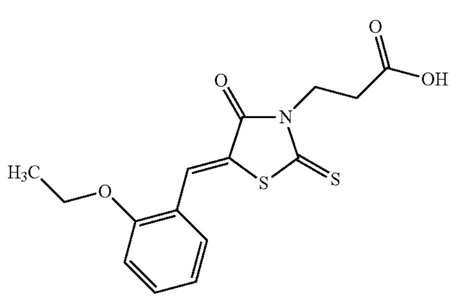 [SMILES: CCOc1ccccc1/C=C1\SC(=S)N(CCC(=O)O)C1=O] | 337.4 |

TABLE 7-continued

| | Phenmethylene-Thiazole Alkanoic Acids (R³ = OH) | |
|---|---|---|
| ID | Structure | MW |
| IIb-33 | | 399.5 |
| IIb-34 | | 339.5 |
| IIb-35 | | 335.4 |
| IIb-36 | | 397.4 |

TABLE 7-continued

Phenmethylene-Thiazole Alkanoic Acids ($R^3$ = OH)

| ID | Structure | MW |
|---|---|---|
| IIb-37 | 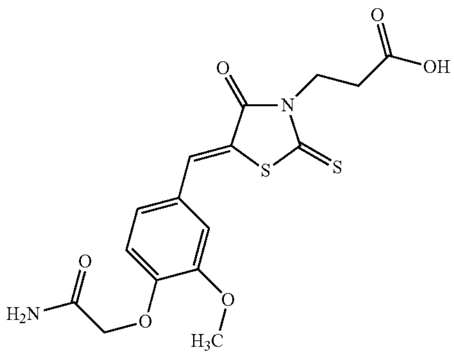 [SMILES: COc1cc(/C=C2\SC(=S)N(CCC(=O)O)C2=O)ccc1OCC(N)=O] | 396.4 |
| IIb-38 | 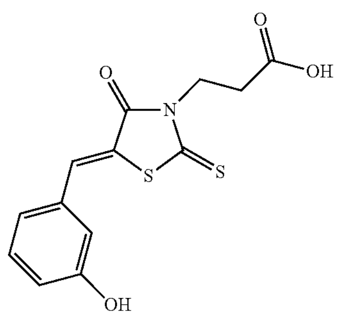 [SMILES: O=C(O)CCN1C(=O)/C(=C/c2cccc(O)c2)SC1=S] | 309.4 |
| IIb-39 | 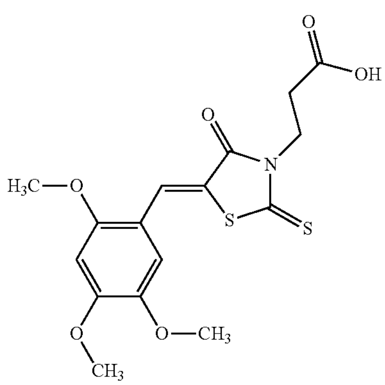 [SMILES: COc1cc(OC)c(OC)cc1/C=C1\SC(=S)N(CCC(=O)O)C1=O] | 383.4 |
| IIb-40 | 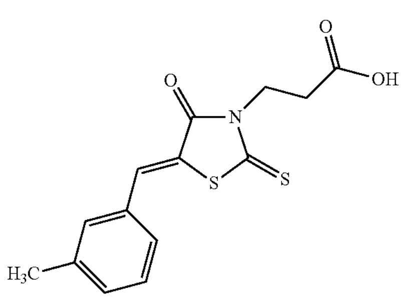 [SMILES: Cc1cccc(/C=C2\SC(=S)N(CCC(=O)O)C2=O)c1] | 307.4 |

TABLE 7-continued

Phenmethylene-Thiazole Alkanoic Acids (R³ = OH)

| ID | Structure | MW |
|---|---|---|
| IIb-41 | 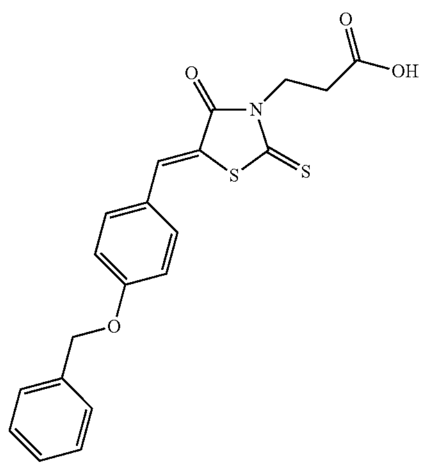 [SMILES: O=C(O)CCN1C(=O)/C(=C/c2ccc(OCc3ccccc3)cc2)SC1=S] | 399.5 |
| IIb-42 | 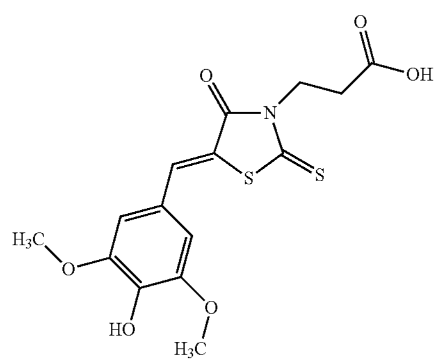 [SMILES: COc1cc(/C=C2\SC(=S)N(CCC(=O)O)C2=O)cc(OC)c1O] | 369.4 |
| IIb-43 | 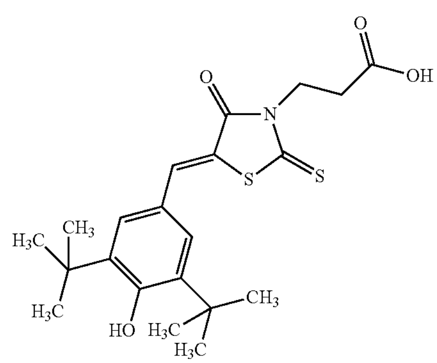 [SMILES: CC(C)(C)c1cc(/C=C2\SC(=S)N(CCC(=O)O)C2=O)cc(C(C)(C)C)c1O] | 421.6 |
| IIb-44 | 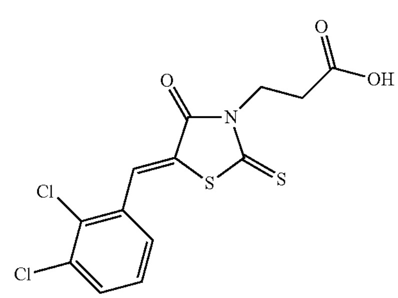 [SMILES: O=C(O)CCN1C(=O)/C(=C/c2cccc(Cl)c2Cl)SC1=S] | 362.3 |

TABLE 7-continued

Phenmethylene-Thiazole Alkanoic Acids ($R^3$ = OH)

| ID | Structure | MW |
| --- | --- | --- |
| IIb-45 | 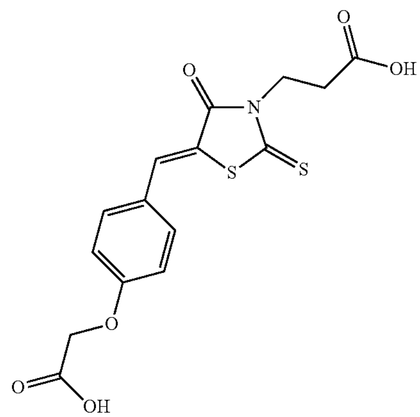 [SMILES: O=C(O)CCN1C(=O)/C(=C/c2ccc(OCC(=O)O)cc2)SC1=S] | 367.4 |
| IIb-46 | 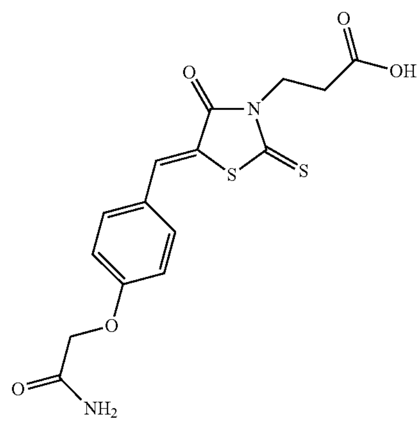 [SMILES: NC(=O)COc1ccc(/C=C2\SC(=S)N(CCC(=O)O)C2=O)cc1] | 366.4 |
| IIb-47 | 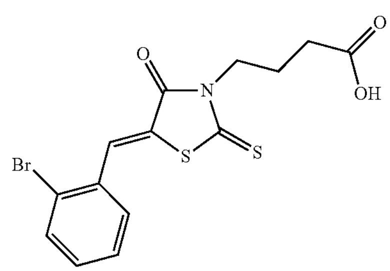 [SMILES: O=C(O)CCCN1C(=O)/C(=C/c2ccccc2Br)SC1=S] | 386.3 |
| IIb-48 | 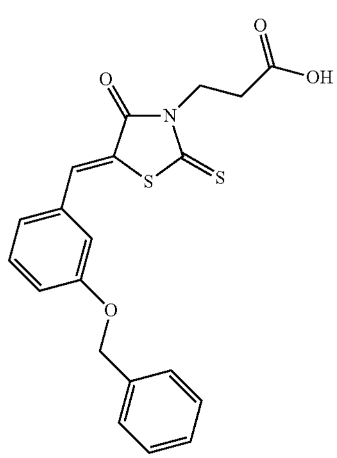 [SMILES: O=C(O)CCN1C(=O)/C(=C/c2cccc(OCc3ccccc3)c2)SC1=S] | 413.5 |

TABLE 7-continued

Phenmethylene-Thiazole Alkanoic Acids ($R^3$ = OH)

| ID | Structure | MW |
|---|---|---|
| IIb-49 | 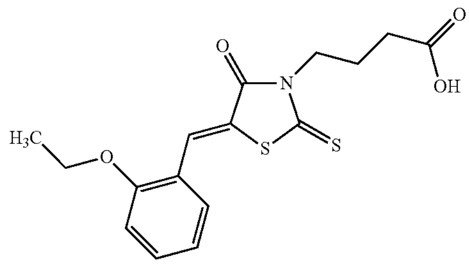 [SMILES: CCOc1ccccc1/C=C1\SC(=S)N(CCCC(=O)O)C1=O] | 351.4 |
| IIb-50 | 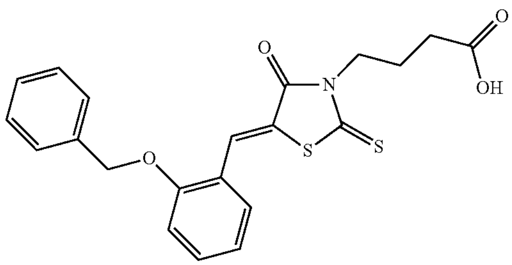 [SMILES: O=C(O)CCCN1C(=O)/C(=C/c2ccccc2OCc2ccccc2)SC1=S] | 413.5 |
| IIb-51 | 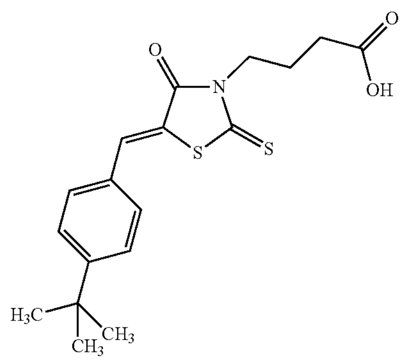 [SMILES: CC(C)(C)c1ccc(/C=C2\SC(=S)N(CCCC(=O)O)C2=O)cc1] | 363.5 |
| IIb-52 | 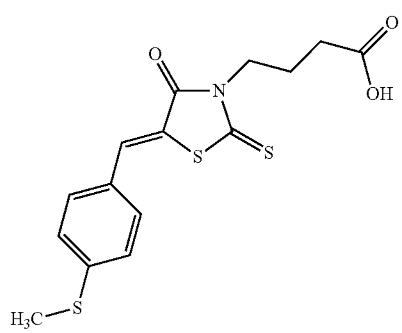 [SMILES: CSc1ccc(/C=C2\SC(=S)N(CCCC(=O)O)C2=O)cc1] | 353.5 |
| IIb-53 | 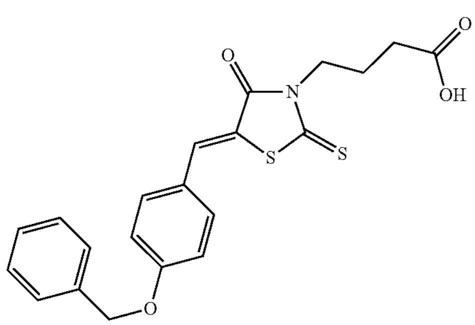 [SMILES: O=C(O)CCCN1C(=O)/C(=C/c2ccc(OCc3ccccc3)cc2)SC1=S] | 413.5 |

TABLE 7-continued

Phenmethylene-Thiazole Alkanoic Acids ($R^3$ = OH)

| ID | Structure | MW |
|---|---|---|
| IIb-54 | 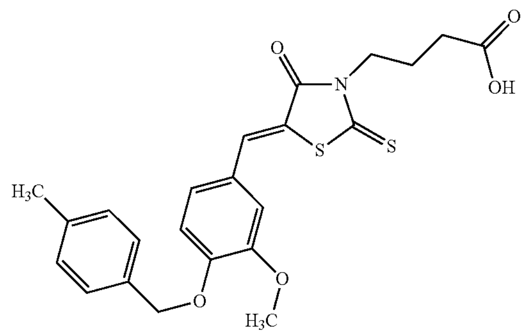 [SMILES: COc1cc(/C=C2\SC(=S)N(CCCC(=O)O)C2=O)ccc1OCc1ccc(C)cc1] | 457.6 |
| IIb-55 | 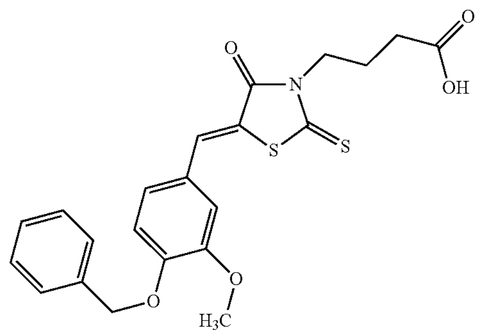 [SMILES: COc1cc(/C=C2\SC(=S)N(CCCC(=O)O)C2=O)ccc1OCc1ccccc1] | 443.5 |
| IIb-56 | 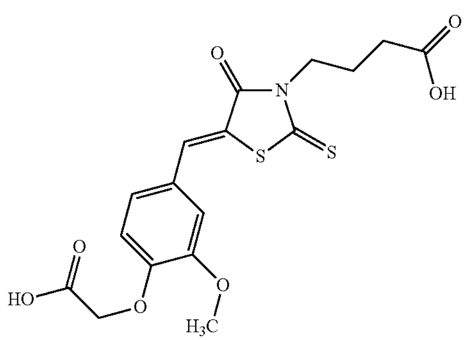 [SMILES: COc1cc(/C=C2\SC(=S)N(CCCC(=O)O)C2=O)ccc1OCC(=O)O] | 411.5 |
| IIb-57 | 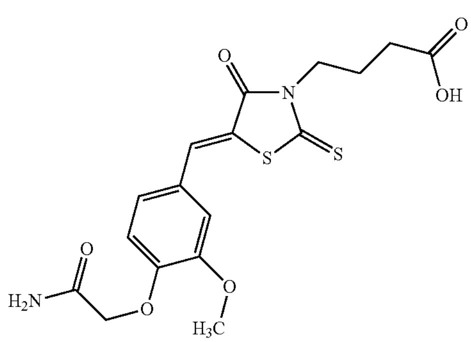 [SMILES: COc1cc(/C=C2\SC(=S)N(CCCC(=O)O)C2=O)ccc1OCC(N)=O] | 410.5 |

TABLE 7-continued
Phenmethylene-Thiazole Alkanoic Acids (R³ = OH)
| ID | Structure | MW |
| --- | --- | --- |
| IIb-58 | 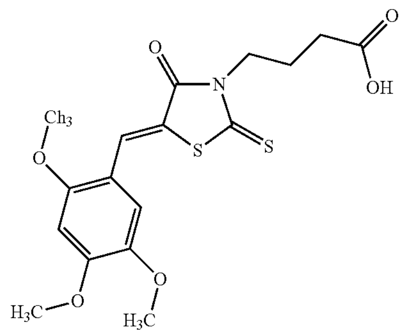 | 397.5 |
| IIb-59 | 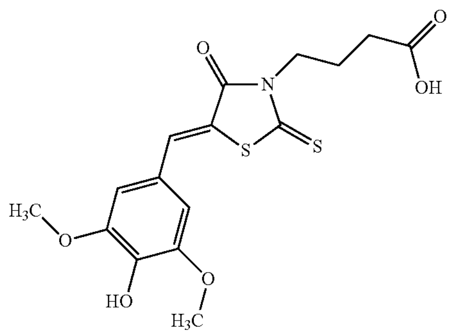 [SMILES: COc1cc(/C=C2\SC(=S)N(CCCC(=O)O)C2=O)cc(OC)c1O] | 383.4 |
| IIb-60 | 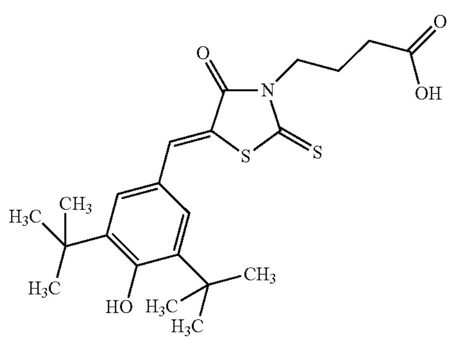 [SMILES: CC(C)(C)c1cc(/C=C2\SC(=S)N(CCCC(=O)O)C2=O)cc(C(C)(C)C)c1O] | 435.6 |
| IIb-61 | 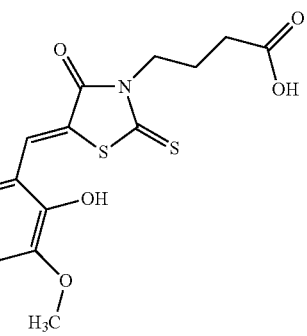 | 353.4 |

1137 1138

TABLE 7-continued

Phenmethylene-Thiazole Alkanoic Acids ($R^3$ = OH)

| ID | Structure | MW |
|---|---|---|
| IIb-62 | 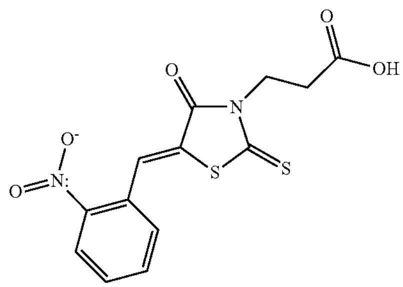 | 338.4 |
| IIb-63 | 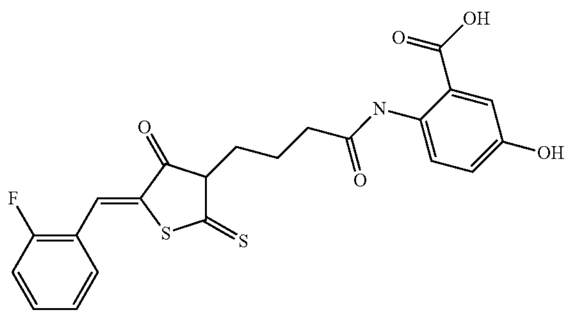 [SMILES: O=C(CCCC1C(=O)/C(=C/c2ccccc2F)SC1=S)Nc1ccc(O)cc1C(=O)O] | 460.5 |
| IIb-64 | 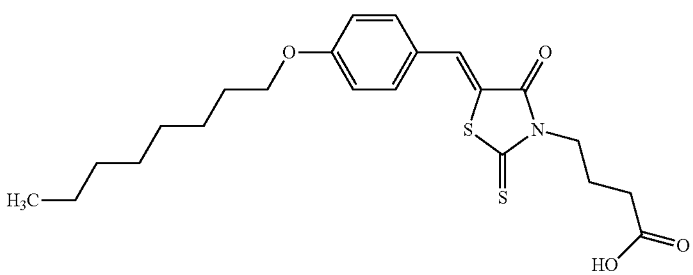 [SMILES: CCCCCCCCOc1ccc(/C=C2\SC(=S)N(CCCC(=O)O)C2=O)cc1] | 435.6 |
| IIb-65 | 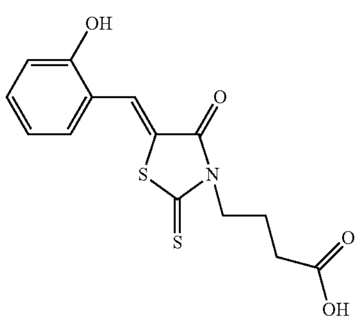 [SMILES: O=C(O)CCCN1C(=O)/C(=C/c2ccccc2O)SC1=S] | 323.4 |
| IIb-66 | 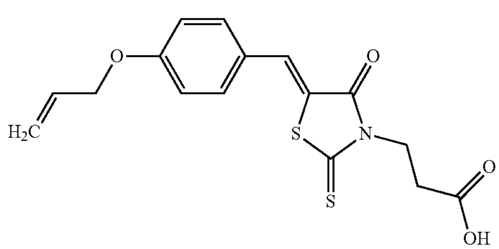 [SMILES: C=CCOc1ccc(/C=C2\SC(=S)N(CCC(=O)O)C2=O)cc1] | 349.4 |

TABLE 7-continued

Phenmethylene-Thiazole Alkanoic Acids ($R^3$ = OH)

| ID | Structure | MW |
|---|---|---|
| IIb-67 | 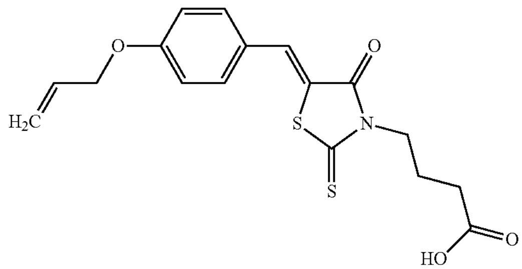 [SMILES: C=CCOc1ccc(/C=C2\SC(=S)N(CCCC(=O)O)C2=O)cc1] | 363.5 |
| IIb-68 | 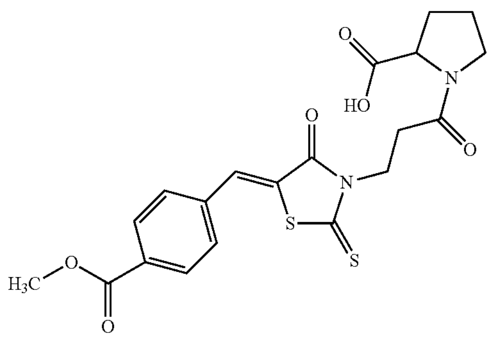 [SMILES: COC(=O)c1ccc(/C=C2\SC(=S)N(CCC(=O)N3CCCC3C(=O)O)C2=O)cc1] | 448.5 |
| IIb-69 | 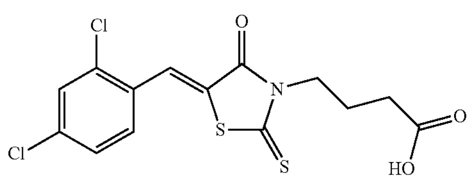 [SMILES: O=C(O)CCCN1C(=O)/C(=C/c2ccc(Cl)cc2Cl)SC1=S] | 376.3 |
| IIb-70 | 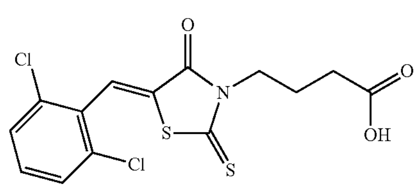 [SMILES: O=C(O)CCCN1C(=O)/C(=C/c2c(Cl)cccc2Cl)SC1=S] | 434.5 |
| IIb-71 | 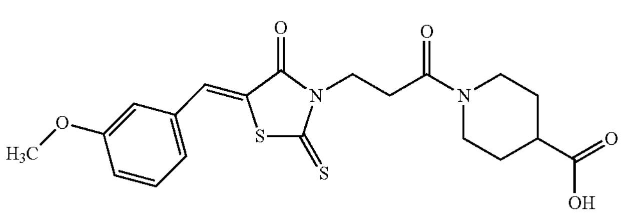 [SMILES: COc1cccc(/C=C2\SC(=S)N(CCC(=O)N3CCC(C(=O)O)CC3)C2=O)c1] | 434.5 |

TABLE 7-continued

Phenmethylene-Thiazole Alkanoic Acids (R³ = OH)

| ID | Structure | MW |
| --- | --- | --- |
| IIb-72 | 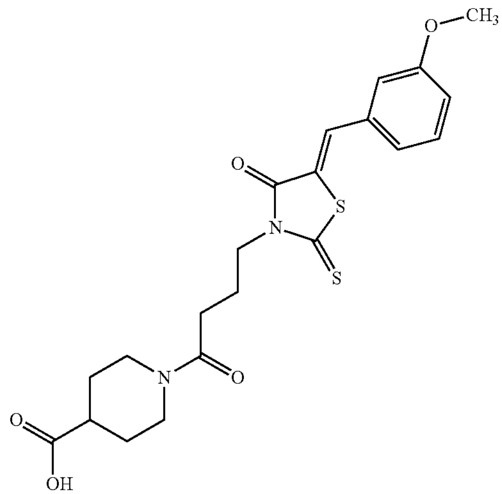 [SMILES: COc1cccc(/C=C2\SC(=S)N(CCCC(=O)N3CCC(C(=O)O)CC3)C2=O)c1] | 448.6 |
| IIb-73 | 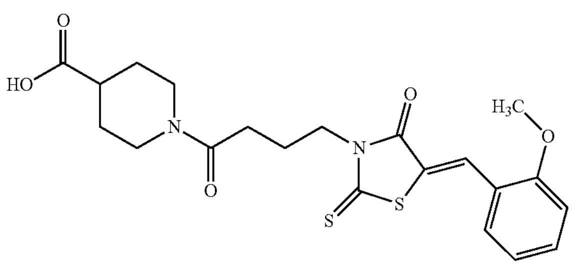 [SMILES: COc1ccccc1/C=C1\SC(=S)N(CCCC(=O)N2CCC(C(=O)O)CC2)C1=O] | 448.6 |
| IIb-74 | 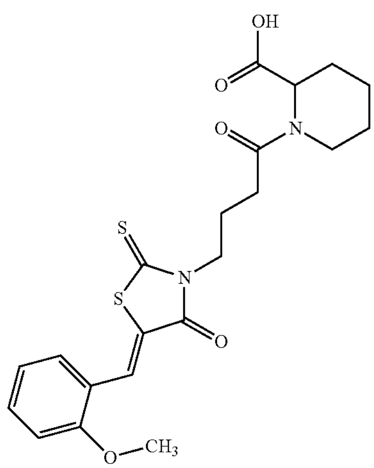 [SMILES: COc1ccccc1/C=C1\SC(=S)N(CCCC(=O)N2CCCCC2C(=O)O)C1=O] | 448.6 |
| IIb-75 | 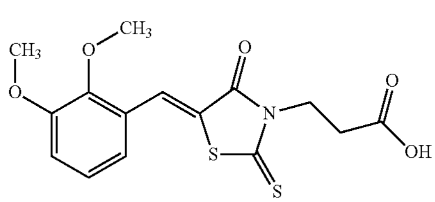 [SMILES: COc1cccc(/C=C2\SC(=S)N(CCC(=O)O)C2=O)c1OC] | 353.4 |

TABLE 7-continued

| | Phenmethylene-Thiazole Alkanoic Acids (R³ = OH) | |
|---|---|---|
| ID | Structure | MW |
| IIb-76 | | 364.5 |
| IIb-77 | | 478.9 |
| IIb-78 | | 344.4 |
| IIb-79 | | 358.4 |
| IIb-80 | | 344.4 |

TABLE 7-continued

| | Phenmethylene-Thiazole Alkanoic Acids ($R^3$ = OH) | |
|---|---|---|
| ID | Structure | MW |
| IIb-81 | | 345.4 |
| IIb-82 | | 358.4 |
| IIb-83 | | 359.4 |
| IIb-84 | | 339.4 |

TABLE 7-continued

Phenmethylene-Thiazole Alkanoic Acids ($R^3$ = OH)

| ID | Structure | MW |
|---|---|---|
| IIb-85 | 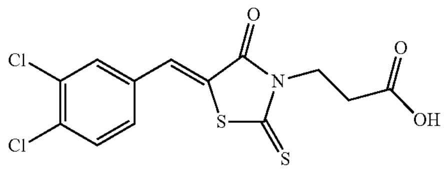 [SMILES: O=C(O)CCN1C(=O)/C(=C/c2ccc(Cl)c(Cl)c2)SC1=S] | 362.3 |
| IIb-86 | 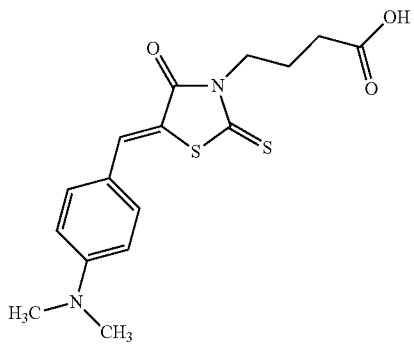 [SMILES: CN(C)c1ccc(/C=C2\SC(=S)N(CCCC(=O)O)C2=O)cc1] | 350.5 |
| IIb-87 | 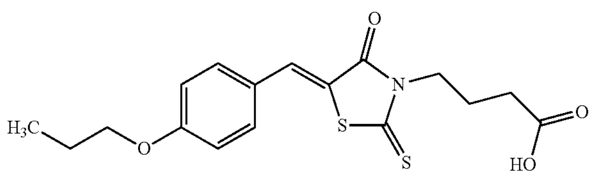 [SMILES: CCCOc1ccc(/C=C2\SC(=S)N(CCCC(=O)O)C2=O)cc1] | 365.5 |
| IIb-88 | 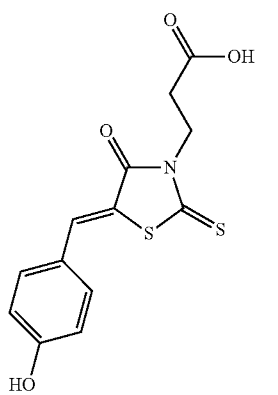 [SMILES: O=C(O)CCN1C(=O)/C(=C/c2ccc(O)cc2)SC1=S] | 309.4 |
| IIb-89 | 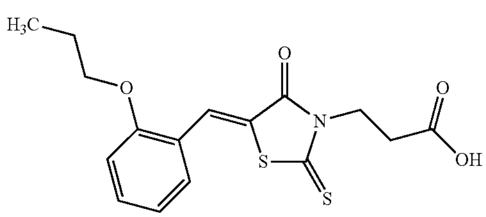 [SMILES: CCCOc1ccccc1/C=C1\SC(=S)N(CCC(=O)O)C1=O] | 351.4 |
| IIb-90 | 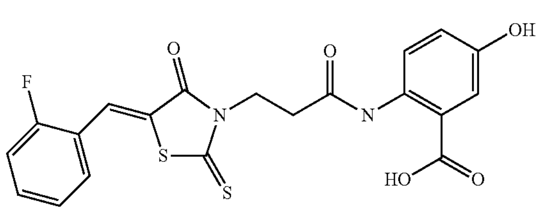 [SMILES: O=C(CCN1C(=O)/C(=C/c2ccccc2F)SC1=S)Nc1ccc(O)cc1C(=O)O] | 446.5 |

TABLE 7-continued

Phenmethylene-Thiazole Alkanoic Acids ($R^3$ = OH)

| ID | Structure | MW |
|---|---|---|
| IIb-91 | 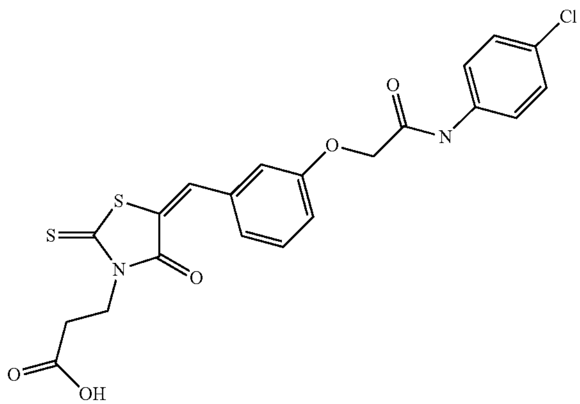 [SMILES: O=C(O)CCN1C(=O)/C(=C\c2cccc(OCC(=O)Nc3ccc(Cl)cc3)c2)SC1=S] | 477.0 |
| IIb-92 | 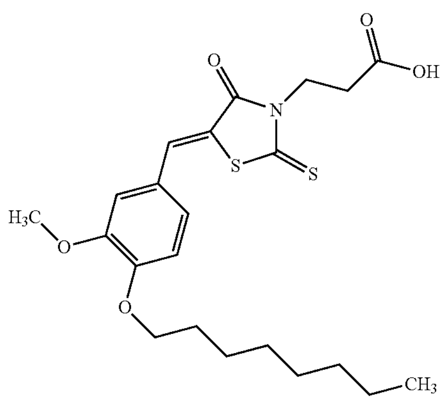 [SMILES: CCCCCCCCOc1ccc(/C=C2\SC(=S)N(CCC(=O)O)C2=O)cc1OC] | 451.6 |
| IIb-93 | 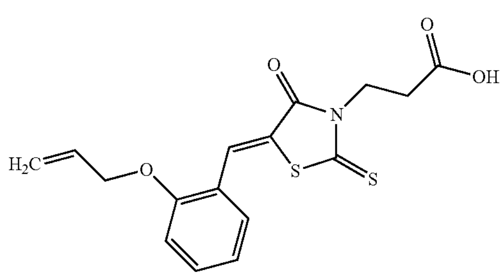 [SMILES: C=CCOc1ccccc1/C=C1\SC(=S)N(CCC(=O)O)C1=O] | 349.4 |
| IIb-94 | 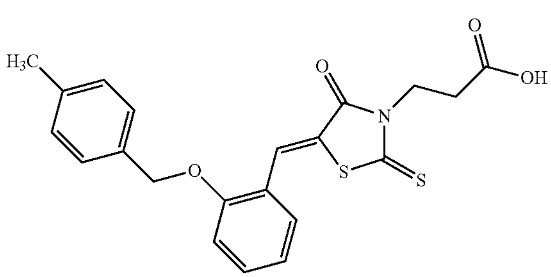 [SMILES: Cc1ccc(COc2ccccc2/C=C2\SC(=S)N(CCC(=O)O)C2=O)cc1] | 413.5 |

TABLE 7-continued

Phenmethylene-Thiazole Alkanoic Acids ($R^3$ = OH)

| ID | Structure | MW |
|---|---|---|
| IIb-95 | 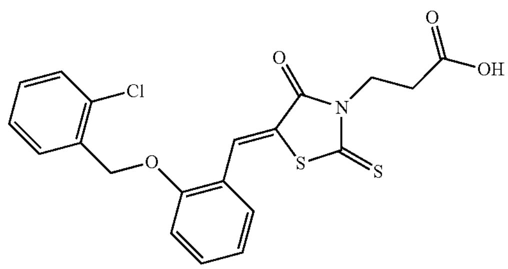 [SMILES: O=C(O)CCN1C(=O)/C(=C/c2ccccc2OCc2ccccc2Cl)SC1=S] | 433.9 |
| IIb-96 | 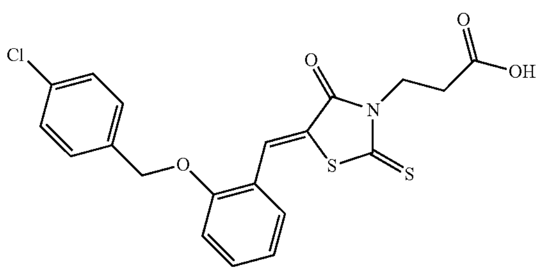 [SMILES: O=C(O)CCN1C(=O)/C(=C/c2ccccc2OCc2ccc(Cl)cc2)SC1=S] | 433.9 |
| IIb-97 | 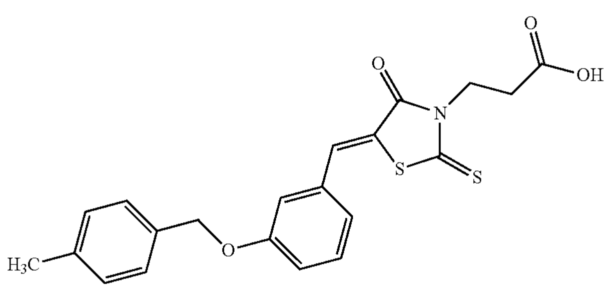 [SMILES: Cc1ccc(COc2cccc(/C=C3\SC(=S)N(CCC(=O)O)C3=O)c2)cc1] | 413.5 |
| IIb-98 | 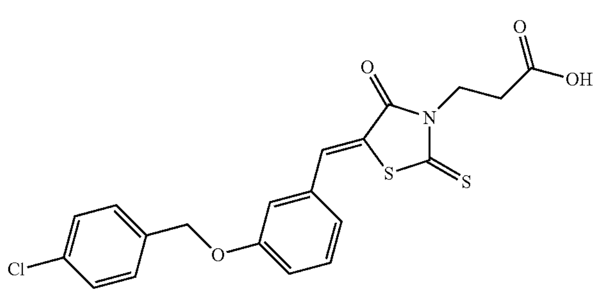 [SMILES: O=C(O)CCN1C(=O)/C(=C/c2cccc(OCc3ccc(Cl)cc3)c2)SC1=S] | 433.9 |

TABLE 7-continued
Phenmethylene-Thiazole Alkanoic Acids ($R^3$ = OH)
| ID | Structure | MW |
|---|---|---|
| IIb-99 | 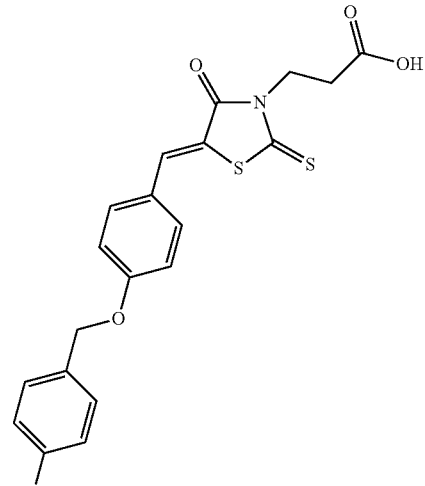 | 413.5 |
| IIb-100 | 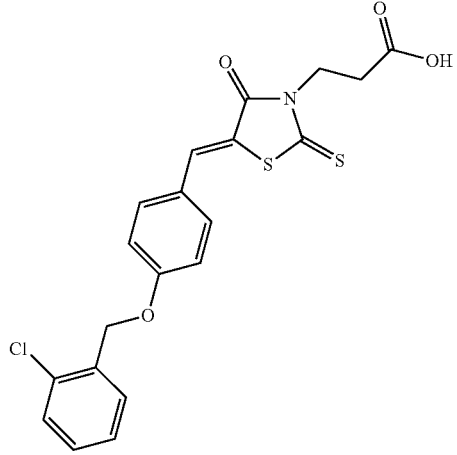 [SMILES: O=C(O)CCN1C(=O)/C(=C/c2ccc(OCc3ccccc3Cl)cc2)SC1=S] | 433.9 |
| IIb-101 | 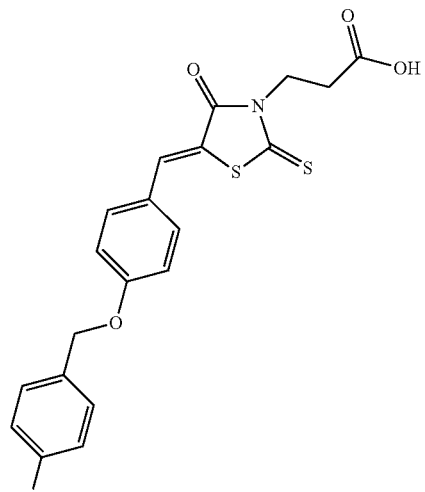 | 433.9 |

TABLE 7-continued
| | Phenmethylene-Thiazole Alkanoic Acids (R³ = OH) | |
|---|---|---|
| ID | Structure | MW |
| IIb-102 | 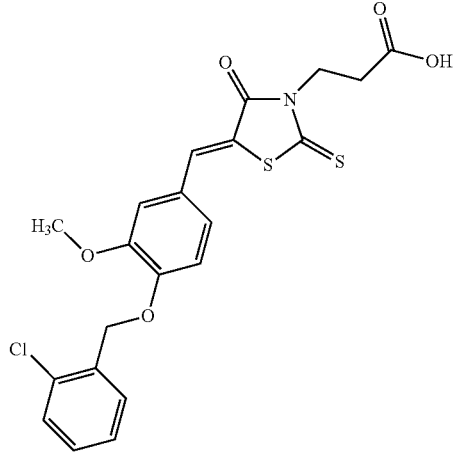 [SMILES: COc1cc(/C=C2\SC(=S)N(CCC(=O)O)C2=O)ccc1OCc1ccccc1Cl] | 464.0 |
| IIb-103 | 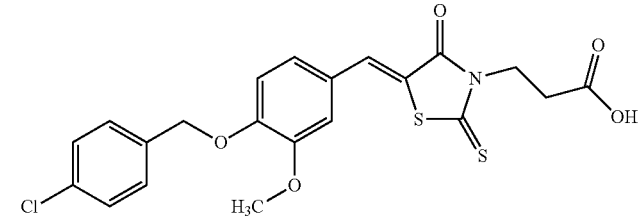 [SMILES: COc1cc(/C=C2\SC(=S)N(CCC(=O)O)C2=O)ccc1OCc1ccc(Cl)cc1] | 464.0 |
| IIb-104 | 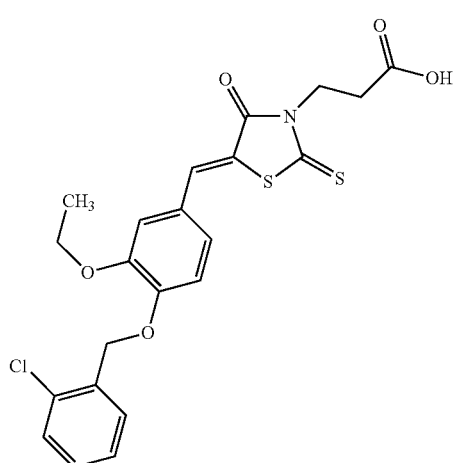 | 478.0 |

TABLE 7-continued

Phenmethylene-Thiazole Alkanoic Acids ($R^3$ = OH)

| ID | Structure | MW |
|---|---|---|
| IIb-105 | 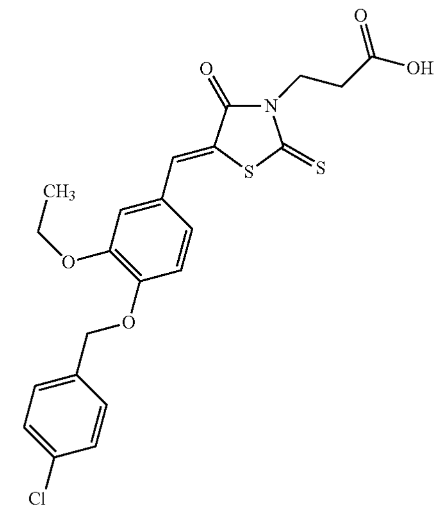 [SMILES: CCOc1cc(/C=C2\SC(=S)N(CCC(=O)O)C2=O)ccc1OCc1ccc(Cl)cc1] | 478.0 |
| IIb-106 | 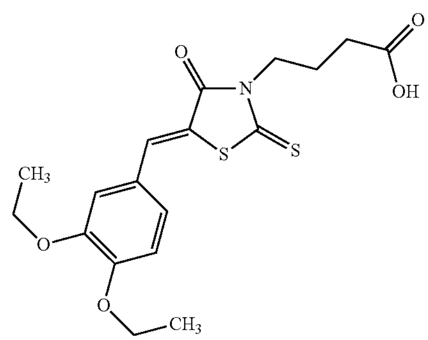 [SMILES: CCOc1ccc(/C=C2\SC(=S)N(CCCC(=O)O)C2=O)cc1OCC] | 395.5 |
| IIb-107 | 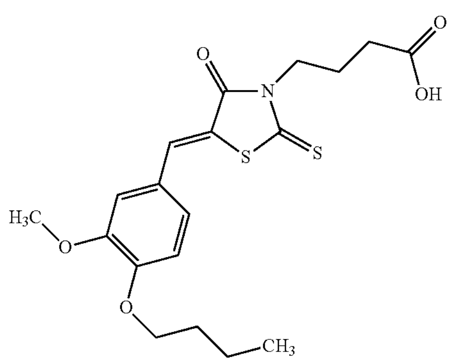 [SMILES: CCCCOc1ccc(/C=C2\SC(=S)N(CCCC(=O)O)C2=O)cc1OC] | 409.5 |
| IIb-108 | 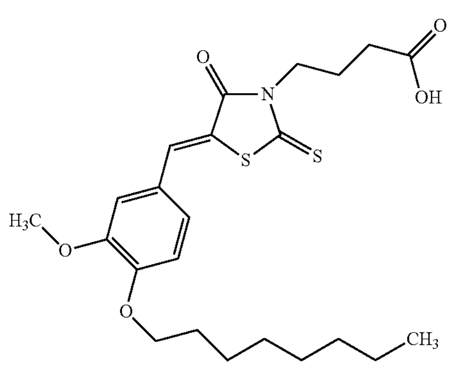 [SMILES: CCCCCCCCOc1ccc(/C=C2\SC(=S)N(CCCC(=O)O)C2=O)cc1OC] | 465.6 |

TABLE 7-continued

Phenmethylene-Thiazole Alkanoic Acids (R³ = OH)

| ID | Structure | MW |
|---|---|---|
| IIb-109 | 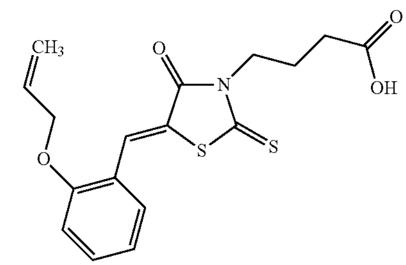 [SMILES: C=CCOc1ccccc1/C=C1\SC(=S)N(CCCC(=O)O)C1=O] | 363.5 |
| IIb-110 | 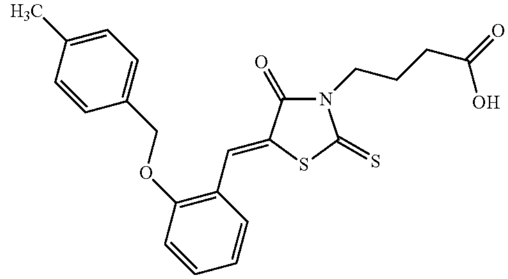 [SMILES: Cc1ccc(COc2ccccc2/C=C2\SC(=S)N(CCCC(=O)O)C2=O)cc1] | 427.5 |
| IIb-111 | 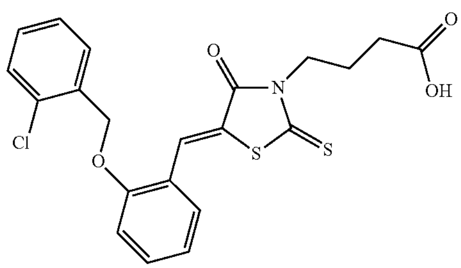 [SMILES: O=C(O)CCCN1C(=O)/C(=C/c2ccccc2OCc2ccccc2Cl)SC1=S] | 448.0 |
| IIb-112 | 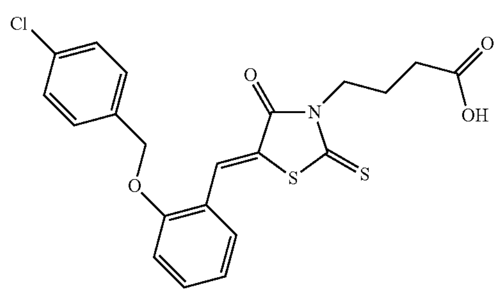 [SMILES: O=C(O)CCCN1C(=O)/C(=C/c2ccccc2OCc2ccc(Cl)cc2)SC1=S] | 448.0 |
| IIb-113 | 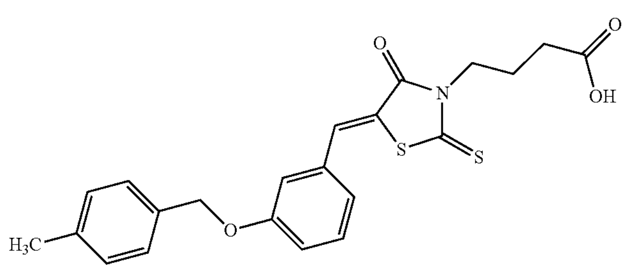 [SMILES: Cc1ccc(COc2cccc(/C=C3\SC(=S)N(CCCC(=O)O)C3=O)c2)cc1] | 427.5 |

TABLE 7-continued

Phenmethylene-Thiazole Alkanoic Acids ($R^3$ = OH)

| ID | Structure | MW |
|---|---|---|
| IIb-114 | 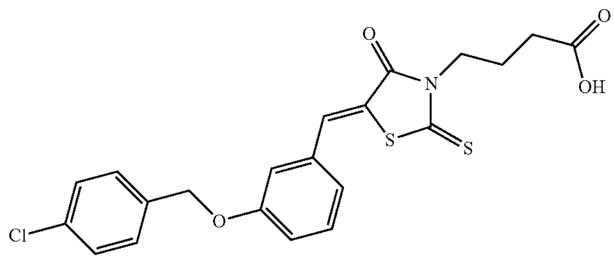 [SMILES: O=C(O)CCCN1C(=O)/C(=C/c2cccc(OCc3ccc(Cl)cc3)c2)SC1=S] | 448.0 |
| IIb-115 | 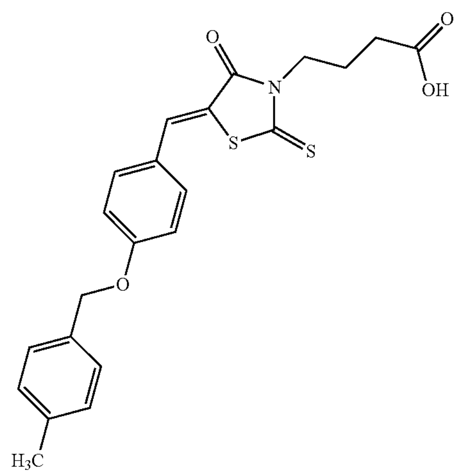 [SMILES: Cc1ccc(COc2ccc(/C=C3\SC(=S)N(CCCC(=O)O)C3=O)cc2)cc1] | 427.5 |
| IIb-116 | 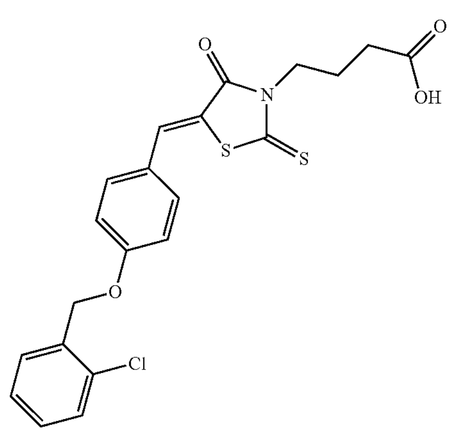 [SMILES: O=C(O)CCCN1C(=O)/C(=C/c2ccc(OCc3ccccc3Cl)cc2)SC1=S] | 448.0 |

TABLE 7-continued

| | Phenmethylene-Thiazole Alkanoic Acids (R³ = OH) | |
|---|---|---|
| ID | Structure | MW |
| IIb-117 | | 448.0 |
| IIb-118 | | 478.0 |
| IIb-119 | | 478.0 |

TABLE 7-continued

| | Phenmethylene-Thiazole Alkanoic Acids (R³ = OH) | |
|---|---|---|
| ID | Structure | MW |
| IIb-120 | | 492.0 |
| IIb-121 | | 492.0 |
| IIb-122 | | 418.3 |

TABLE 7-continued

Phenmethylene-Thiazole Alkanoic Acids ($R^3$ = OH)

| ID | Structure | MW |
|---|---|---|
| IIb-123 | 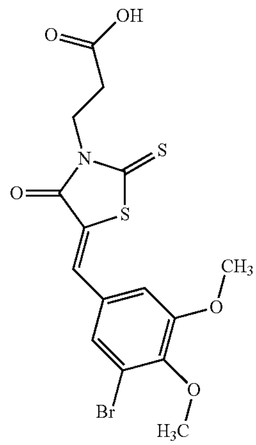 [SMILES: COc1cc(/C=C2\SC(=S)N(CCC(=O)O)C2=O)cc(Br)c1OC] | 432.3 |
| IIb-124 | 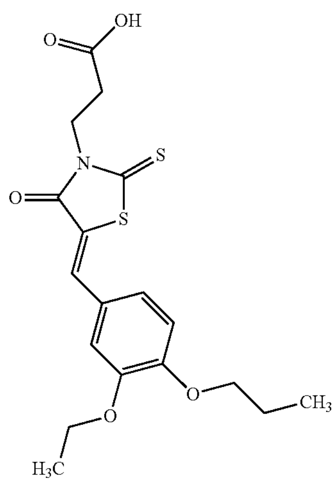 [SMILES: CCCOc1ccc(/C=C2\SC(=S)N(CCC(=O)O)C2=O)cc1OCC] | 395.5 |
| IIb-125 | 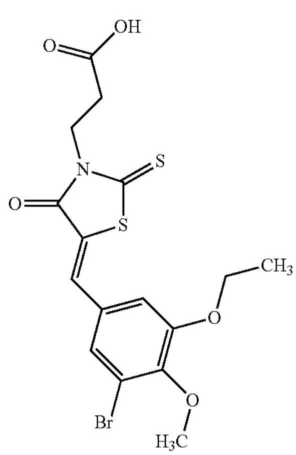 [SMILES: CCOc1cc(/C=C2\SC(=S)N(CCC(=O)O)C2=O)cc(Br)c1OC] | 446.3 |

TABLE 7-continued

Phenmethylene-Thiazole Alkanoic Acids ($R^3$ = OH)

| ID | Structure | MW |
|---|---|---|
| IIb-126 | 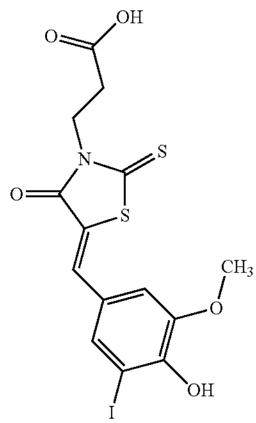 [SMILES: COc1cc(/C=C2\SC(=S)N(CCC(=O)O)C2=O)cc(I)c1O] | 465.3 |
| IIb-127 | 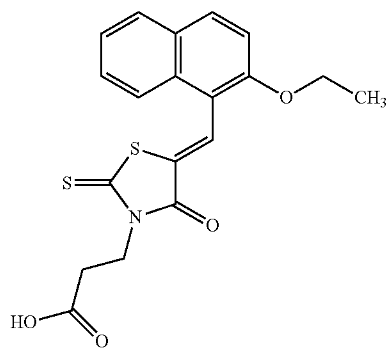 [SMILES: CCOc1ccc2ccccc2c1/C=C1\SC(=S)N(CCC(=O)O)C1=O] | 387.5 |
| IIb-128 | 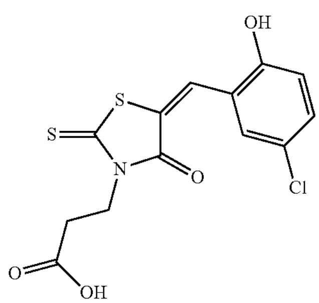 [SMILES: O=C(O)CCN1C(=O)/C(=C\c2cc(Cl)ccc2O)SC1=S] | 343.8 |
| IIb-129 | 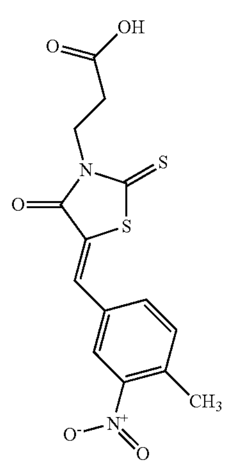 [SMILES: Cc1ccc(/C=C2\SC(=S)N(CCC(=O)O)C2=O)cc1[N+](=O)[O-]] | 352.4 |

TABLE 7-continued

Phenmethylene-Thiazole Alkanoic Acids ($R^3$ = OH)

| ID | Structure | MW |
| --- | --- | --- |
| IIb-130 | 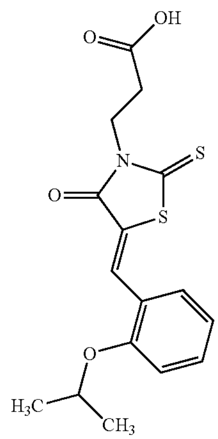 [SMILES: CC(C)Oc1ccccc1/C=C1\SC(=S)N(CCC(=O)O)C1=O] | 351.4 |
| IIb-131 | 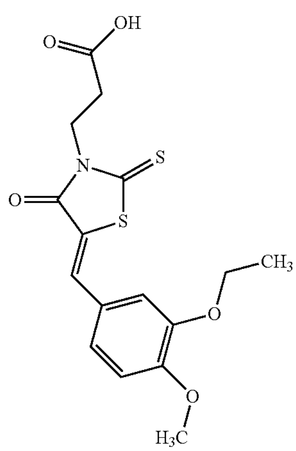 [SMILES: CCOc1cc(/C=C2\SC(=S)N(CCC(=O)O)C2=O)ccc1OC] | 367.4 |
| IIb-132 | 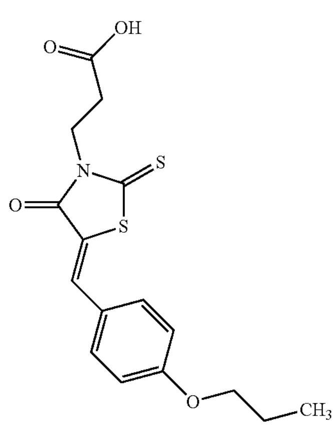 [SMILES: CCCOc1ccc(/C=C2\SC(=S)N(CCC(=O)O)C2=O)cc1] | 351.4 |

TABLE 7-continued

Phenmethylene-Thiazole Alkanoic Acids ($R^3$ = OH)

| ID | Structure | MW |
| --- | --- | --- |
| IIb-133 | 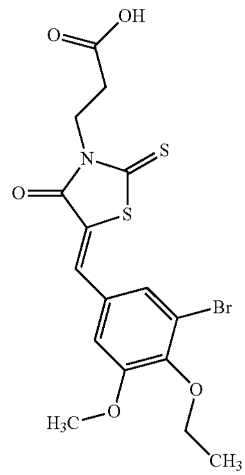 [SMILES: CCOc1c(Br)cc(/C=C2\SC(=S)N(CCC(=O)O)C2=O)cc1OC] | 446.3 |
| IIb-134 | 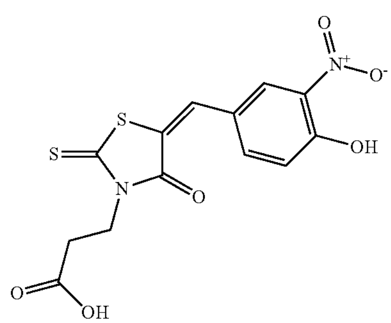 [SMILES: O=C(O)CCN1C(=O)/C(=C\c2ccc(O)c([N+](=O)[O-])c2)SC1=S] | 354.4 |
| IIb-135 | 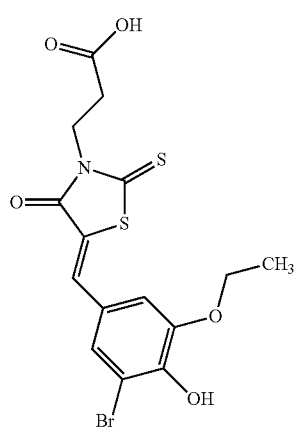 [SMILES: CCOc1cc(/C=C2\SC(=S)N(CCC(=O)O)C2=O)cc(Br)c1O] | 432.3 |

TABLE 7-continued

Phenmethylene-Thiazole Alkanoic Acids ($R^3$ = OH)

| ID | Structure | MW |
|---|---|---|
| IIb-136 | 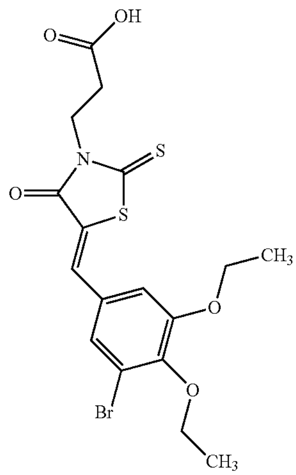 [SMILES: CCOc1cc(/C=C2\SC(=S)N(CCC(=O)O)C2=O)cc(Br)c1OCC] | 460.4 |
| IIb-137 | 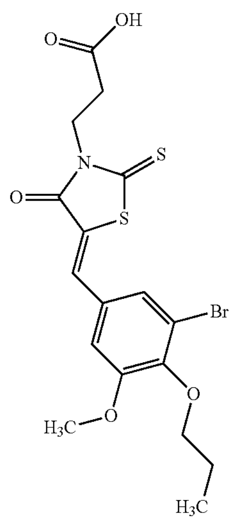 [SMILES: CCCOc1c(Br)cc(/C=C2\SC(=S)N(CCC(=O)O)C2=O)cc1OC] | 460.4 |
| IIb-138 | 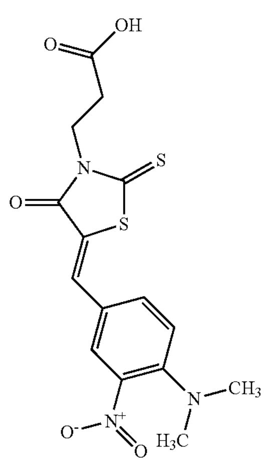 [SMILES: CN(C)c1ccc(/C=C2\SC(=S)N(CCC(=O)O)C2=O)cc1[N+](=O)[O-]] | 381.4 |

TABLE 7-continued

| | Phenmethylene-Thiazole Alkanoic Acids ($R^3$ = OH) | |
|---|---|---|
| ID | Structure | MW |
| IIb-139 | | 416.3 |
| IIb-140 | | 337.4 |
| IIb-141 | | 432.3 |
| IIb-142 | | 467.2 |

TABLE 7-continued
Phenmethylene-Thiazole Alkanoic Acids ($R^3$ = OH)
| ID | Structure | MW |
|---|---|---|
| IIIb-143 | 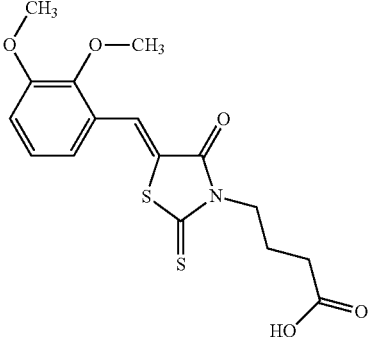 [SMILES: COc1cccc(/C=C2\SC(=S)N(CCCC(=O)O)C2=O)c1OC] | 367.4 |
| IIb-144 | 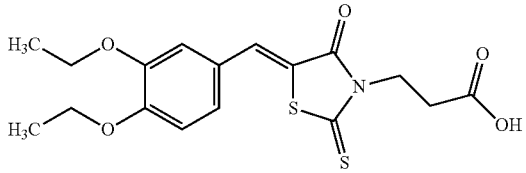 [SMILES: CCOc1ccc(/C=C2\SC(=S)N(CCC(=O)O)C2=O)cc1OCC] | 381.5 |
| IIb-145 | 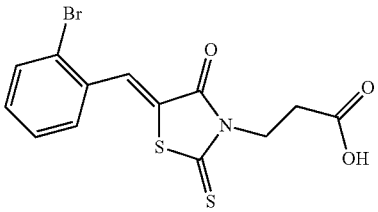 [SMILES: O=C(O)CCN1C(=O)/C(=C/c2ccccc2Br)SC1=S] | 372.3 |
| IIb-146 | 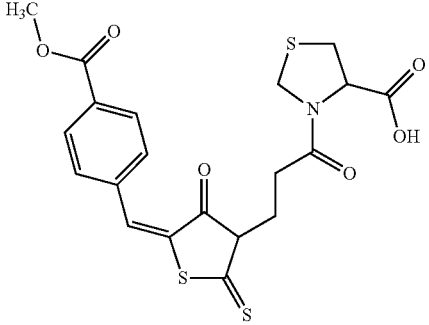 [SMILES: COC(=O)c1ccc(/C=C2/SC(=S)C(CCC(=O)N3CSCC3C(=O)O)C2=O)cc1] | 466.6 |
| IIb-147 | 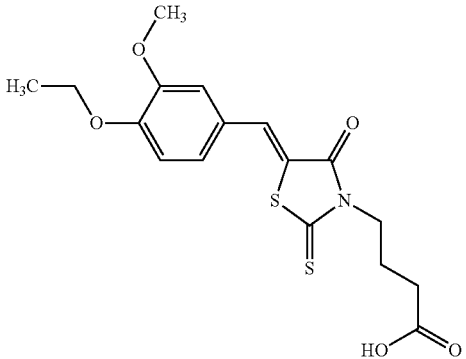 [SMILES: CCOc1ccc(/C=C2\SC(=S)N(CCCC(=O)O)C2=O)cc1OC] | 381.5 |

TABLE 7-continued

Phenmethylene-Thiazole Alkanoic Acids ($R^3$ = OH)

| ID | Structure | MW |
|---|---|---|
| IIb-148 | 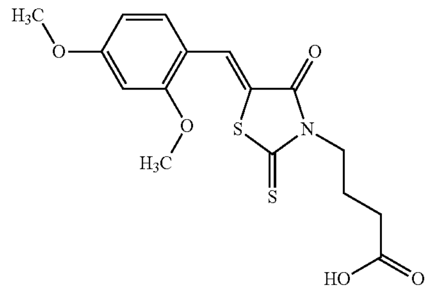 [SMILES: COc1ccc(/C=C2\SC(=S)N(CCCC(=O)O)C2=O)c(OC)c1] | 367.4 |
| IIb-149 | 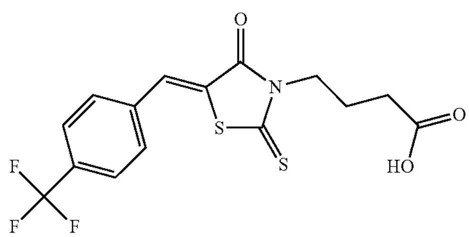 [SMILES: O=C(O)CCCN1C(=O)/C(=C/c2ccc(C(F)(F)F)cc2)SC1=S] | 375.4 |
| IIb-150 | 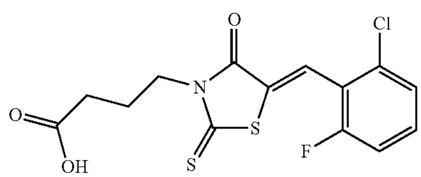 [SMILES: O=C(O)CCCN1C(=O)/C(=C/c2c(F)cccc2Cl)SC1=S] | 359.8 |
| IIb-151 | 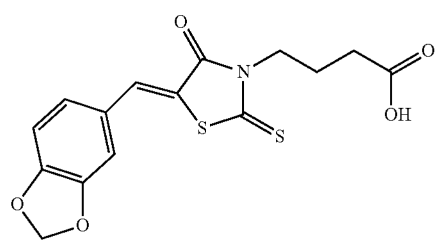 [SMILES: O=C(O)CCCN1C(=O)/C(=C/c2ccc3c(c2)OCO3)SC1=S] | 351.4 |
| IIb-152 | 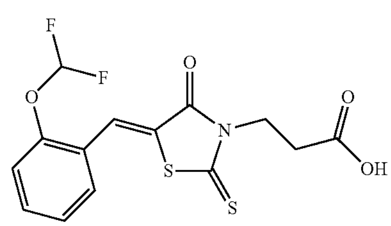 [SMILES: O=C(O)CCN1C(=O)/C(=C/c2ccccc2OC(F)F)SC1=S] | 359.4 |
| IIb-153 | 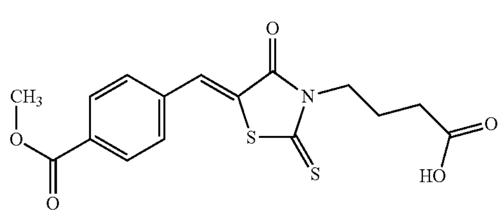 [SMILES: COC(=O)c1ccc(/C=C2\SC(=S)N(CCCC(=O)O)C2=O)cc1] | 365.4 |

TABLE 7-continued

Phenmethylene-Thiazole Alkanoic Acids ($R^3$ = OH)

| ID | Structure | MW |
|---|---|---|
| IIb-154 | 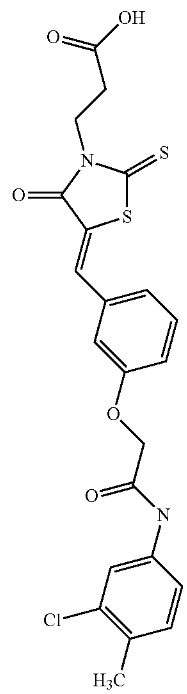 [SMILES: Cc1ccc(NC(=O)COc2cccc(/C=C3\SC(=S)N(CCC(=O)O)C3=O)c2)cc1Cl] | 491.0 |
| IIb-155 | 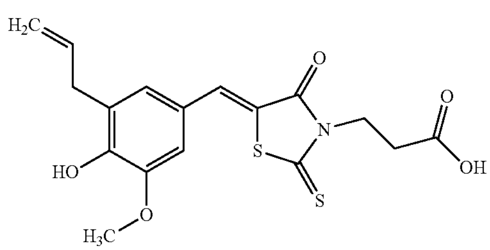 [SMILES: C=CCc1cc(/C=C2\SC(=S)N(CCC(=O)O)C2=O)cc(OC)c1O] | 379.5 |
| IIb-156 | 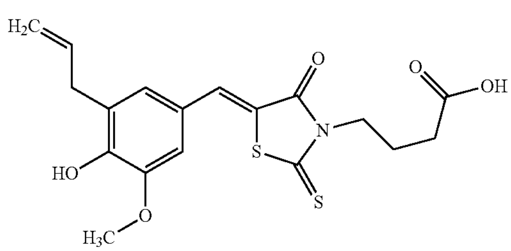 [SMILES: C=CCc1cc(/C=C2\SC(=S)N(CCCC(=O)O)C2=O)cc(OC)c1O] | 393.5 |
| IIb-157 | 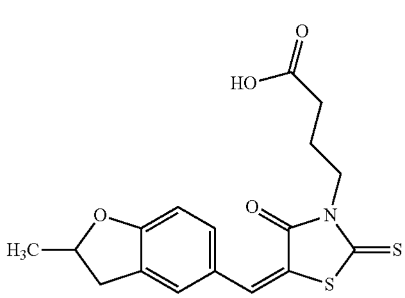 [SMILES: CC1Cc2cc(/C=C3/SC(=S)N(CCCC(=O)O)C3=O)ccc2O1] | 363.5 |

TABLE 7-continued

Phenmethylene-Thiazole Alkanoic Acids ($R^3$ = OH)

| ID | Structure | MW |
|---|---|---|
| IIb-158 | 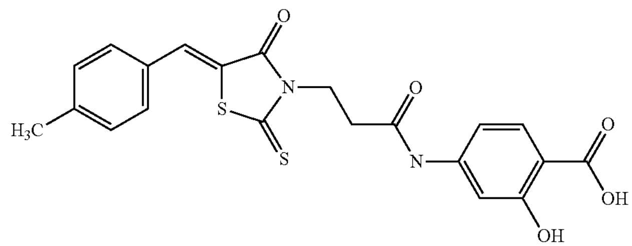 [SMILES: Cc1ccc(/C=C2\SC(=S)N(CCC(=O)Nc3ccc(C(=O)O)c(O)c3)C2=O)cc1] | 442.5 |
| IIb-159 | 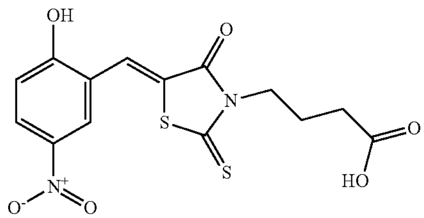 [SMILES: O=C(O)CCCN1C(=O)/C(=C/c2cc([N+](=O)[O-])ccc2O)SC1=S] | 368.4 |
| IIb-160 | 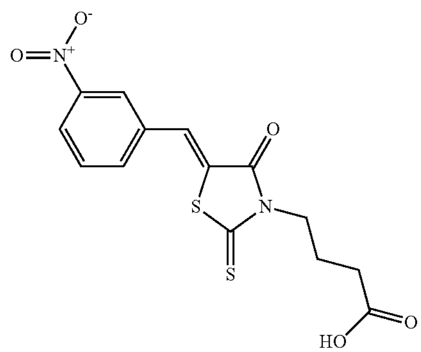 [SMILES: O=C(O)CCCN1C(=O)/C(=C/c2cccc([N+](=O)[O-])c2)SC1=S] | 352.4 |
| IIb-161 | 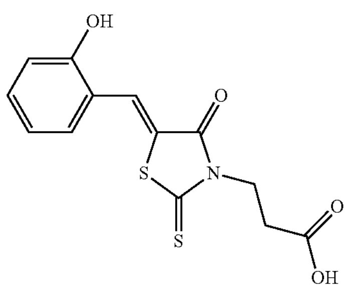 [SMILES: O=C(O)CCN1C(=O)/C(=C/c2ccccc2O)SC1=S] | 309.4 |
| IIb-162 | 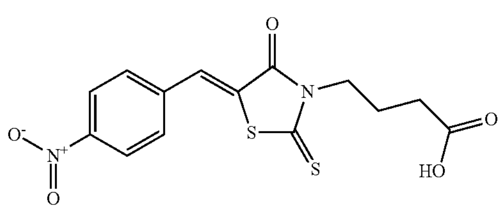 [SMILES: O=C(O)CCCN1C(=O)/C(=C/c2ccc([N+](=O)[O-])cc2)SC1=S] | 352.4 |
| IIb-163 | 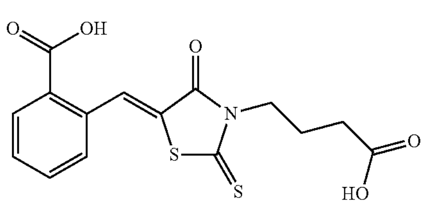 [SMILES: O=C(O)CCCN1C(=O)/C(=C/c2ccccc2C(=O)O)SC1=S] | 351.4 |

TABLE 7-continued

Phenmethylene-Thiazole Alkanoic Acids ($R^3$ = OH)

| ID | Structure | MW |
|---|---|---|
| IIb-164 | 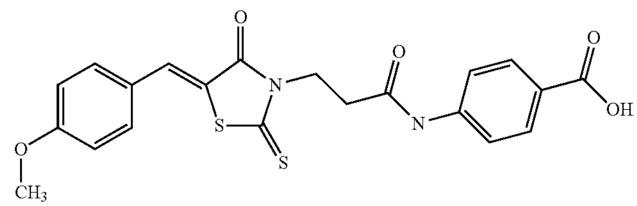 | 442.5 |
| IIb-165 | 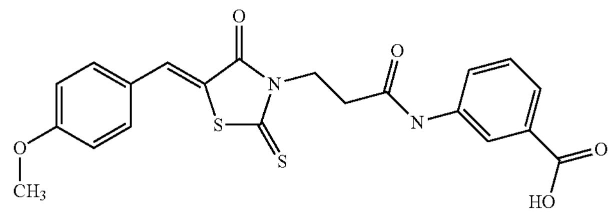 [SMILES: COc1ccc(/C=C2\SC(=S)N(CCC(=O)Nc3cccc(C(=O)O)c3)C2=O)cc1] | 442.5 |
| IIb-166 | 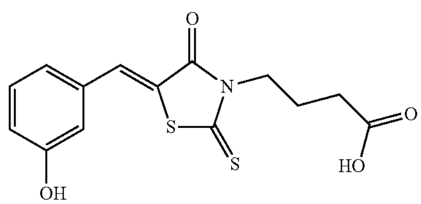 [SMILES: O=C(O)CCCN1C(=O)/C(=C/c2cccc(O)c2)SC1=S] | 323.4 |
| IIb-167 | 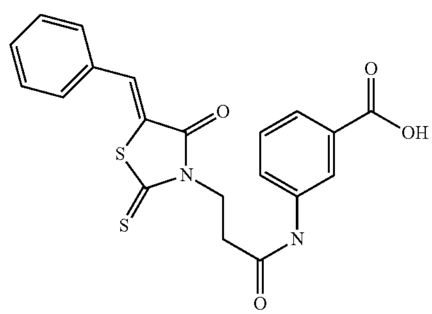 [SMILES: O=C(CCN1C(=O)/C(=C/c2ccccc2)SC1=S)Nc1cccc(C(=O)O)c1] | 412.5 |
| IIb-168 | 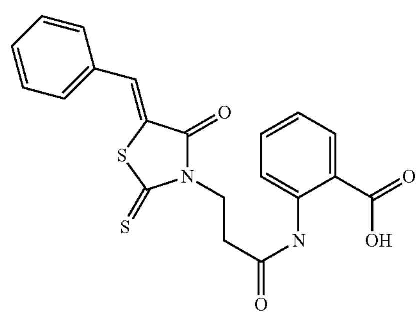 [SMILES: O=C(CCN1C(=O)/C(=C/c2ccccc2)SC1=S)Nc1ccccc1C(=O)O] | 412.5 |
| IIb-169 | 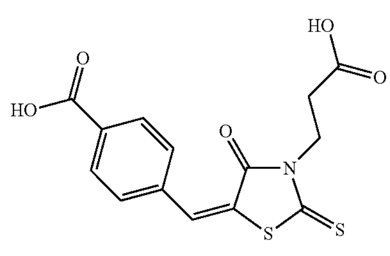 [SMILES: O=C(O)CCN1C(=O)/C(=C\c2ccc(C(=O)O)cc2)SC1=S] | 337.4 |

TABLE 7-continued

Phenmethylene-Thiazole Alkanoic Acids ($R^3$ = OH)

| ID | Structure | MW |
|---|---|---|
| IIb-170 | 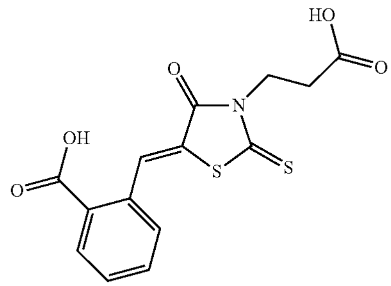 [SMILES: O=C(O)CCN1C(=O)/C(=C/c2ccccc2C(=O)O)SC1=S] | 337.4 |
| IIb-171 | 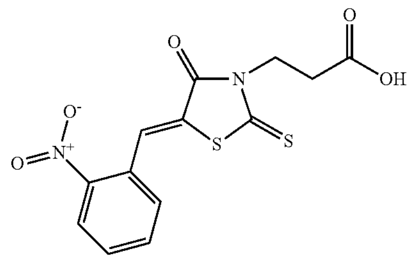 [SMILES: O=C(O)CCN1C(=O)/C(=C/c2ccccc2[N+](=O)[O-])SC1=S] | 338.4 |
| IIb-172 | 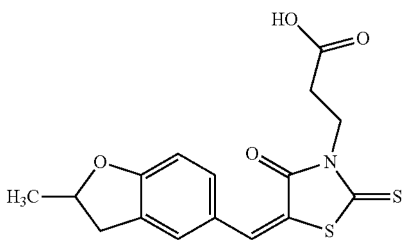 [SMILES: CC1Cc2cc(/C=C3/SC(=S)N(CCC(=O)O)C3=O)ccc2O1] | 349.4 |
| IIb-173 | 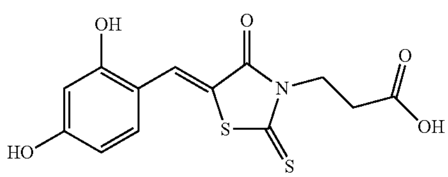 [SMILES: O=C(O)CCN1C(=O)/C(=C/c2ccc(O)cc2O)SC1=S] | 325.4 |
| IIb-174 | 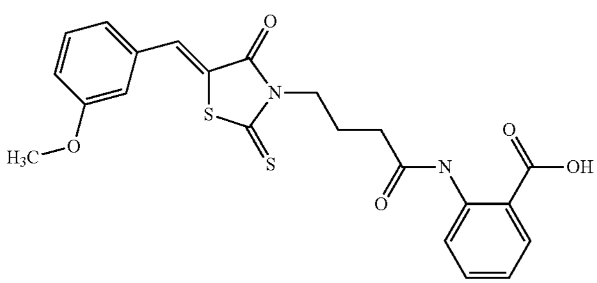 [SMILES: COc1cccc(/C=C2\SC(=S)N(CCCC(=O)Nc3ccccc3C(=O)O)C2=O)c1] | 456.5 |
| IIb-175 | 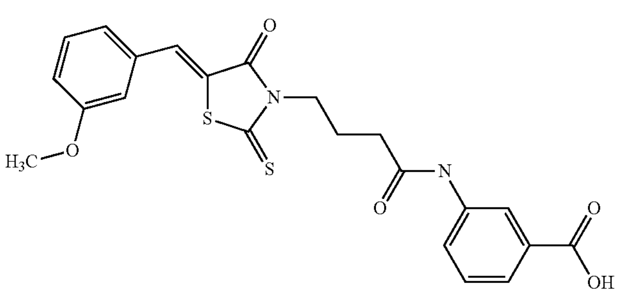 [SMILES: COc1cccc(/C=C2\SC(=S)N(CCCC(=O)Nc3cccc(C(=O)O)c3)C2=O)c1] | 456.5 |

TABLE 7-continued

Phenmethylene-Thiazole Alkanoic Acids ($R^3$ = OH)

| ID | Structure | MW |
|---|---|---|
| IIb-176 | 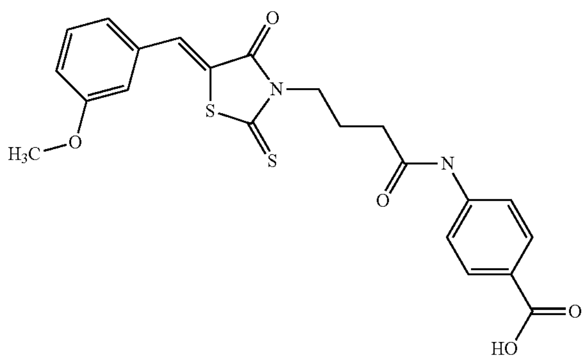 [SMILES: COc1cccc(/C=C2\SC(=S)N(CCCC(=O)Nc3ccc(C(=O)O)cc3)C2=O)c1] | 456.5 |
| IIb-177 | 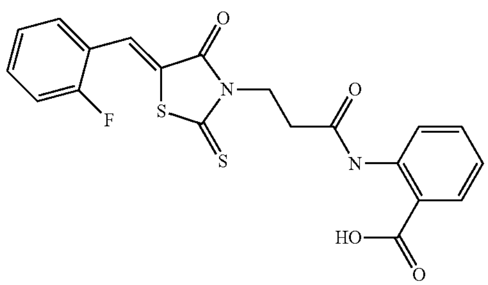 [SMILES: O=C(CCN1C(=O)/C(=C/c2ccccc2F)SC1=S)Nc1ccccc1C(=O)O] | 430.5 |
| IIb-178 | 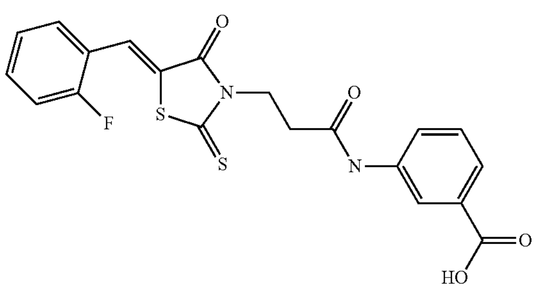 [SMILES: O=C(CCN1C(=O)/C(=C/c2ccccc2F)SC1=S)Nc1cccc(C(=O)O)c1] | 430.5 |
| IIb-179 | 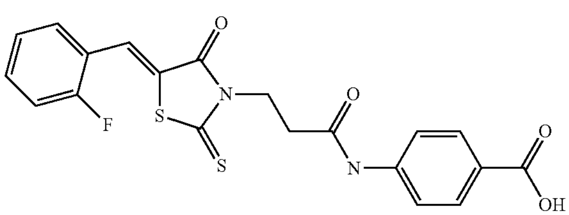 [SMILES: O=C(CCN1C(=O)/C(=C/c2ccccc2F)SC1=S)Nc1ccc(C(=O)O)cc1] | 430.5 |
| IIb-180 | 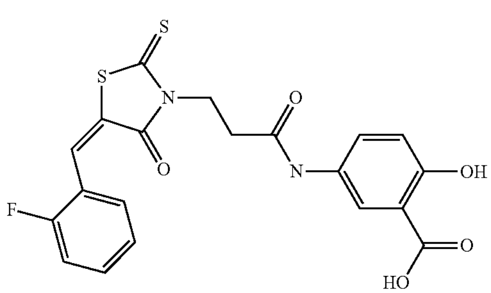 [SMILES: O=C(CCN1C(=O)/C(=C\c2ccccc2F)SC1=S)Nc1ccc(O)c(C(=O)O)c1] | 446.5 |

TABLE 7-continued

Phenmethylene-Thiazole Alkanoic Acids (R³ = OH)

| ID | Structure | MW |
|---|---|---|
| IIb-181 | 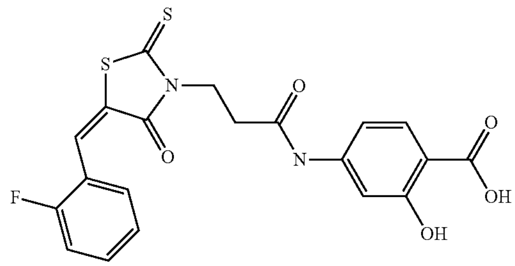 [SMILES: O=C(CCN1C(=O)/C(=C\c2ccccc2F)SC1=S)Nc1ccc(C(=O)O)c(O)c1] | 446.5 |
| IIb-182 | 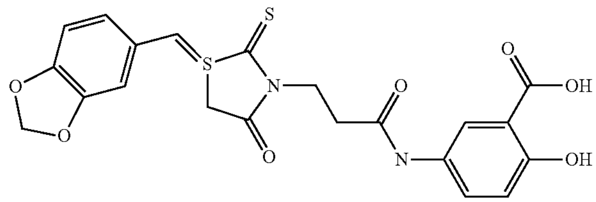 [SMILES: O=C(CCN1C(=O)C/S(=C\c2ccc3c(c2)OCO3)C1=S)Nc1ccc(O)c(C(=O)O)c1] | 472.5 |
| IIb-183 | 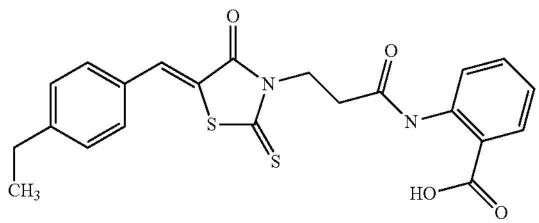 [SMILES: CCc1ccc(/C=C2\SC(=S)N(CCC(=O)Nc3ccccc3C(=O)O)C2=O)cc1] | 440.5 |
| IIb-184 | 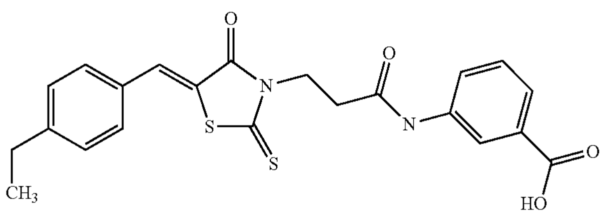 [SMILES: CCc1ccc(/C=C2\SC(=S)N(CCC(=O)Nc3cccc(C(=O)O)c3)C2=O)cc1] | 440.5 |
| IIb-185 | 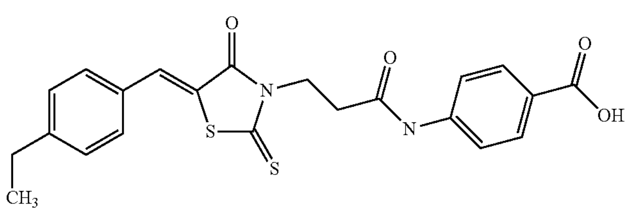 [SMILES: CCc1ccc(/C=C2\SC(=S)N(CCC(=O)Nc3ccc(C(=O)O)cc3)C2=O)cc1] | 440.5 |
| IIb-186 | 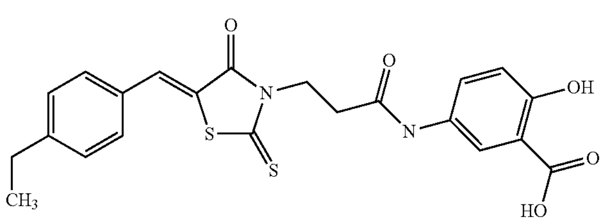 [SMILES: CCc1ccc(/C=C2\SC(=S)N(CCC(=O)Nc3ccc(O)c(C(=O)O)c3)C2=O)cc1] | 456.5 |
| IIb-187 | 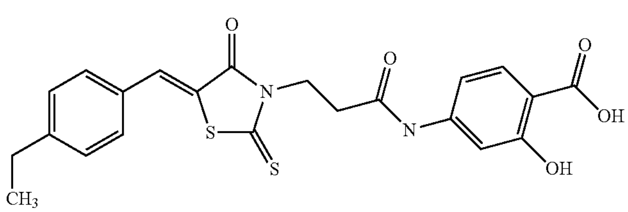 [SMILES: CCc1ccc(/C=C2\SC(=S)N(CCC(=O)Nc3ccc(C(=O)O)c(O)c3)C2=O)cc1] | 456.5 |

TABLE 7-continued

Phenmethylene-Thiazole Alkanoic Acids ($R^3$ = OH)

| ID | Structure | MW |
|---|---|---|
| IIb-188 | 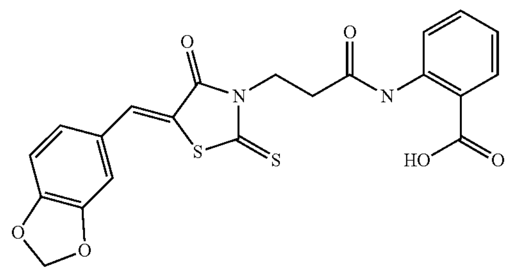 [SMILES: O=C(CCN1C(=O)/C(=C/c2ccc3c(c2)OCO3)SC1=S)Nc1ccccc1C(=O)O] | 456.5 |
| IIb-189 | 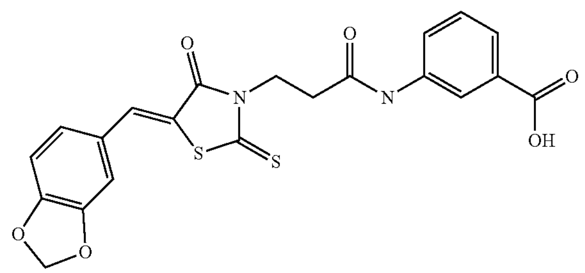 [SMILES: O=C(CCN1C(=O)/C(=C/c2ccc3c(c2)OCO3)SC1=S)Nc1cccc(C(=O)O)c1] | 456.5 |
| IIb-190 | 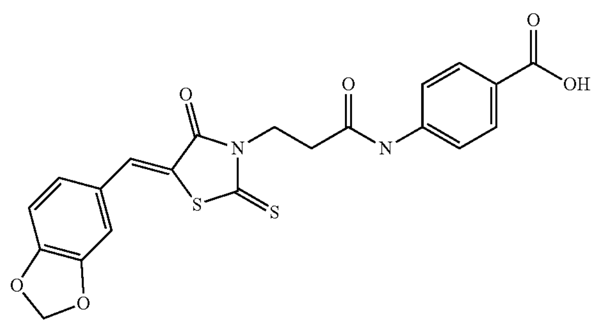 [SMILES: O=C(CCN1C(=O)/C(=C/c2ccc3c(c2)OCO3)SC1=S)Nc1ccc(C(=O)O)cc1] | 456.5 |
| IIb-191 | 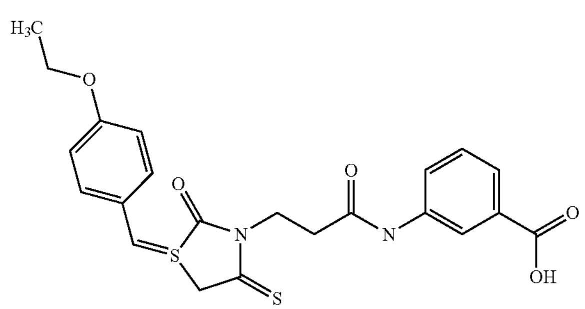 [SMILES: CCOc1ccc(/C=S2/CC(=S)N(CCC(=O)Nc3cccc(C(=O)O)c3)C2=O)cc1] | 456.5 |
| IIb-192 | 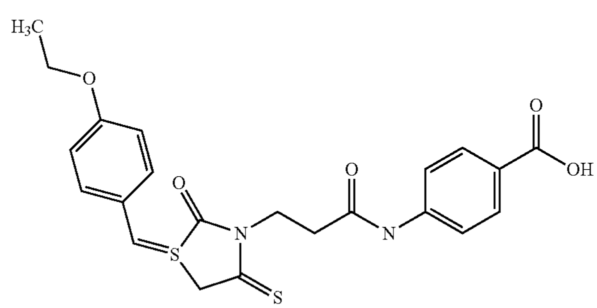 [SMILES: CCOc1ccc(/C=S2/CC(=S)N(CCC(=O)Nc3ccc(C(=O)O)cc3)C2=O)cc1] | 456.5 |

TABLE 7-continued

Phenmethylene-Thiazole Alkanoic Acids ($R^3$ = OH)

| ID | Structure | MW |
|---|---|---|
| IIb-193 | 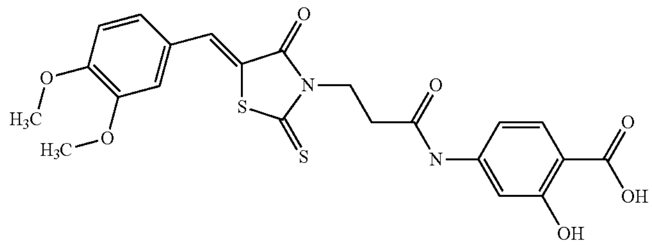 [SMILES: COc1ccc(/C=C2\SC(=S)N(CCC(=O)Nc3ccc(C(=O)O)c(O)c3)C2=O)cc1OC] | 488.5 |
| IIb-194 | 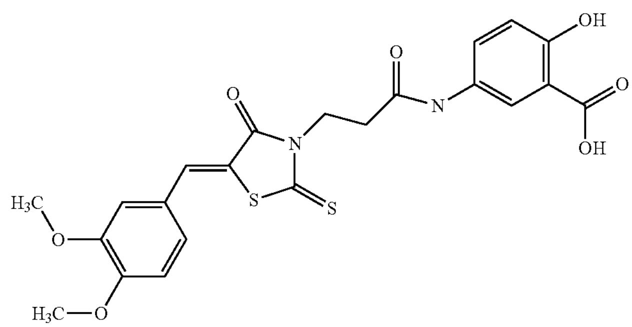 [SMILES: COc1ccc(/C=C2\SC(=S)N(CCC(=O)Nc3ccc(O)c(C(=O)O)c3)C2=O)cc1OC] | 488.5 |
| IIb-195 | 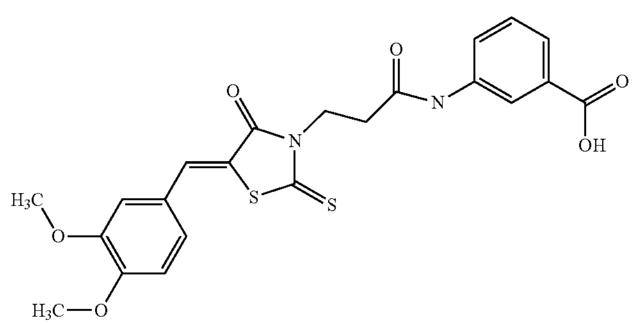 [SMILES: COc1ccc(/C=C2\SC(=S)N(CCC(=O)Nc3cccc(C(=O)O)c3)C2=O)cc1OC] | 472.5 |
| IIb-196 | 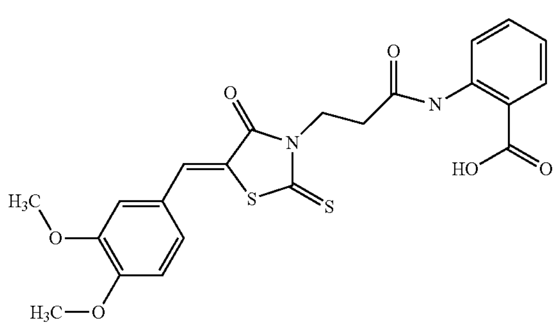 [SMILES: COc1ccc(/C=C2\SC(=S)N(CCC(=O)Nc3ccccc3C(=O)O)C2=O)cc1OC] | 472.5 |

TABLE 7-continued

Phenmethylene-Thiazole Alkanoic Acids ($R^3$ = OH)

| ID | Structure | MW |
|---|---|---|
| IIb-197 | 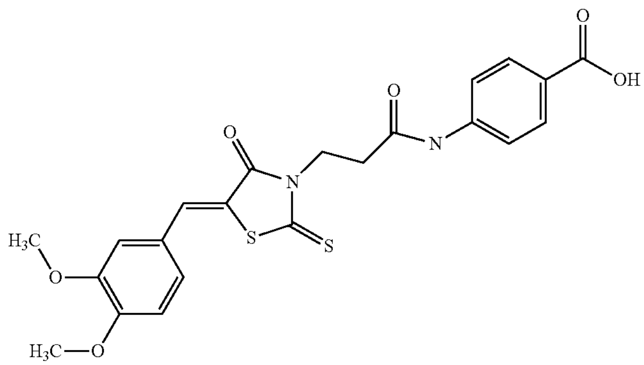 [SMILES: COc1ccc(/C=C2\SC(=S)N(CCC(=O)Nc3ccc(C(=O)O)cc3)C2=O)cc1OC] | 472.5 |
| IIb-198 | 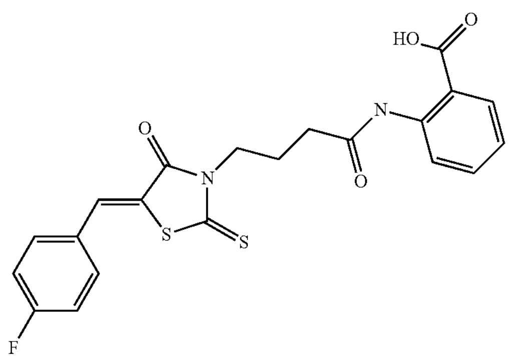 [SMILES: O=C(CCCN1C(=O)/C(=C/c2ccc(F)cc2)SC1=S)Nc1ccccc1C(=O)O] | 444.5 |
| IIb-199 | 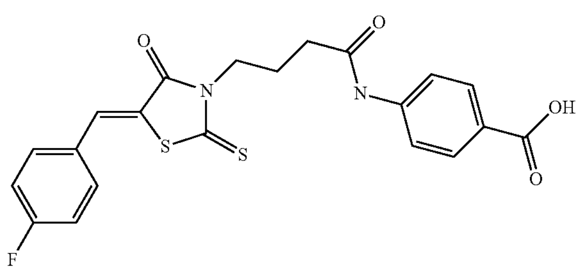 [SMILES: O=C(CCCN1C(=O)/C(=C/c2ccc(F)cc2)SC1=S)Nc1ccc(C(=O)O)cc1] | 444.5 |
| IIb-200 | 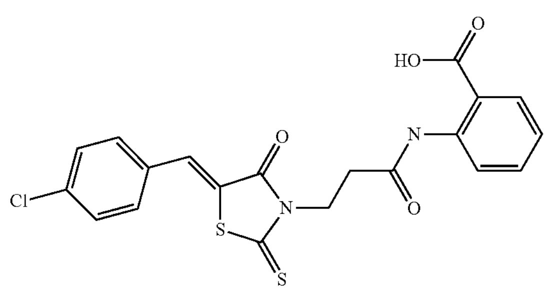 [SMILES: O=C(CCN1C(=O)/C(=C/c2ccc(Cl)cc2)SC1=S)Nc1ccccc1C(=O)O] | 446.9 |
| IIb-201 | 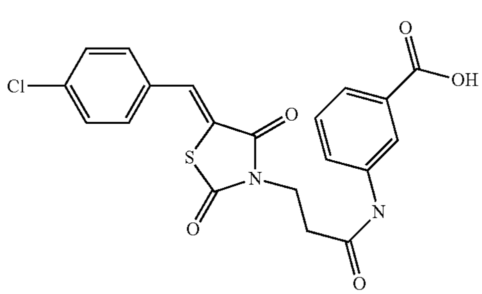 [SMILES: O=C(CCN1C(=O)S/C(=C\c2ccc(Cl)cc2)C1=O)Nc1cccc(C(=O)O)c1] | 446.9 |

TABLE 7-continued

Phenmethylene-Thiazole Alkanoic Acids ($R^3$ = OH)

| ID | Structure | MW |
|---|---|---|
| IIb-202 | 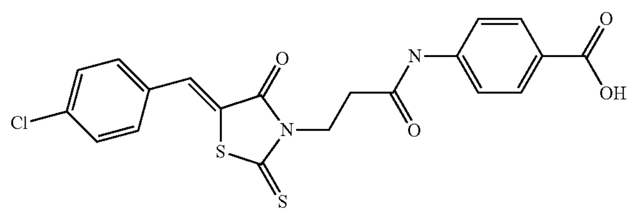 [SMILES: O=C(CCN1C(=O)/C(=C/c2ccc(Cl)cc2)SC1=S)Nc1ccc(C(=O)O)cc1] | 446.9 |
| IIb-203 | 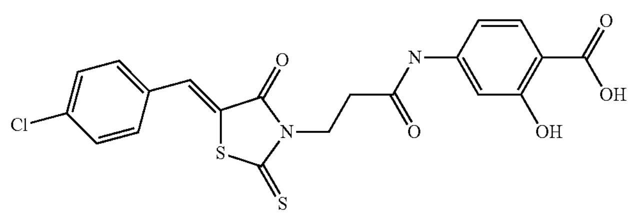 [SMILES: O=C(CCN1C(=O)/C(=C/c2ccc(Cl)cc2)SC1=S)Nc1ccc(C(=O)O)c(O)c1] | 462.9 |
| IIb-204 | 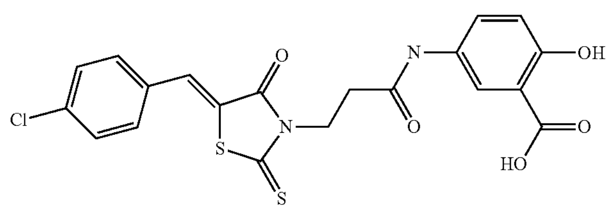 [SMILES: O=C(CCN1C(=O)/C(=C/c2ccc(Cl)cc2)SC1=S)Nc1ccc(O)c(C(=O)O)c1] | 462.9 |
| IIb-205 | 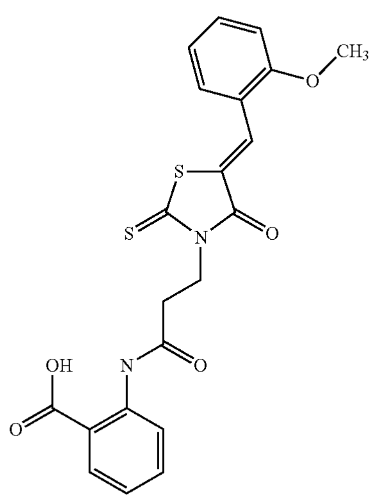 [SMILES: COc1ccccc1/C=C1\SC(=S)N(CCC(=O)Nc2ccccc2C(=O)O)C1=O] | 442.5 |

TABLE 7-continued
| Phenmethylene-Thiazole Alkanoic Acids ($R^3$ = OH) | | |
|---|---|---|
| ID | Structure | MW |
| IIb-206 | | 442.5 |
| IIb-207 | 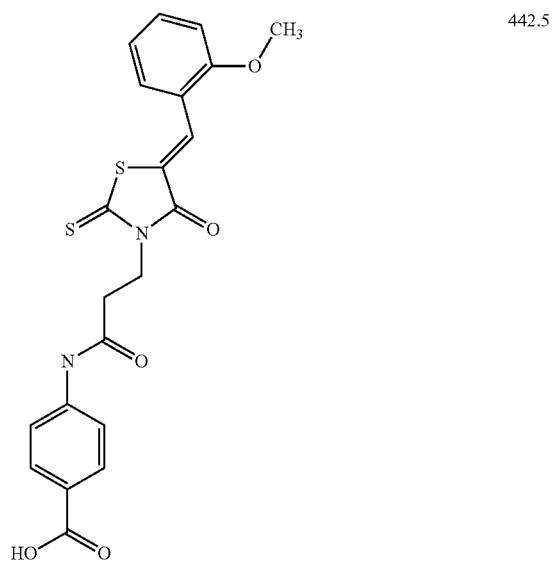 | 442.5 |

TABLE 7-continued
| | Phenmethylene-Thiazole Alkanoic Acids ($R^3$ = OH) | |
|---|---|---|
| ID | Structure | MW |
| IIb-208 | 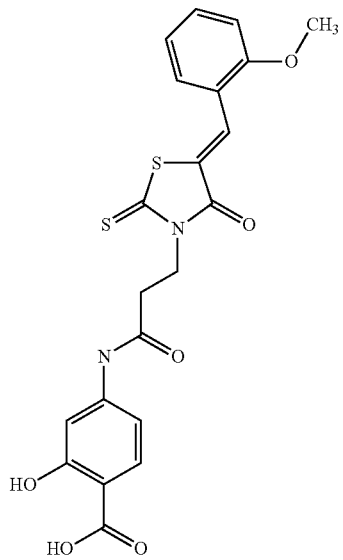 [SMILES: COc1ccccc1/C=C1\SC(=S)N(CCC(=O)Nc2ccc(C(=O)O)c(O)c2)C1=O] | 458.5 |
| IIb-209 | 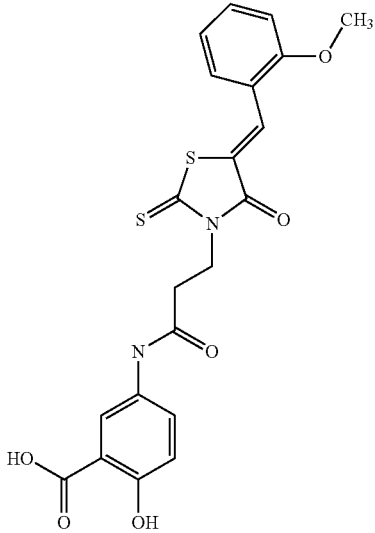 [SMILES: COc1ccccc1/C=C1\SC(=S)N(CCC(=O)Nc2ccc(O)c(C(=O)O)c2)C1=O] | 458.5 |
| IIb-210 | 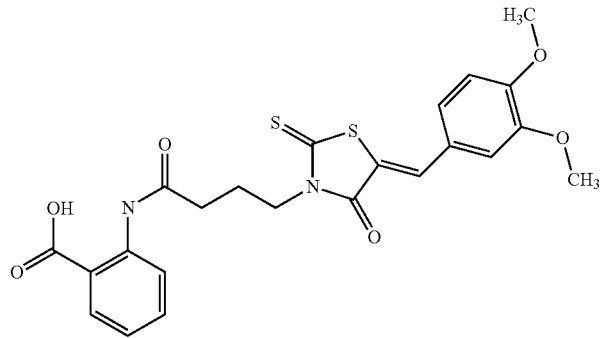 [SMILES: COc1ccc(/C=C2\SC(=S)N(CCCC(=O)Nc3ccccc3C(=O)O)C2=O)cc1OC] | 486.6 |

TABLE 7-continued

Phenmethylene-Thiazole Alkanoic Acids (R³ = OH)

| ID | Structure | MW |
|---|---|---|
| IIb-211 | 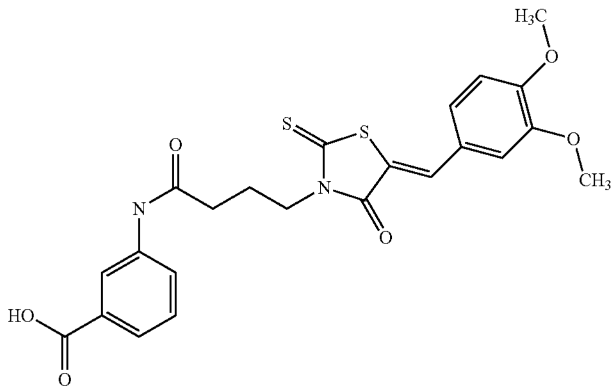 [SMILES: COc1ccc(/C=C2\SC(=S)N(CCCC(=O)Nc3cccc(C(=O)O)c3)C2=O)cc1OC] | 486.6 |
| IIb-212 | 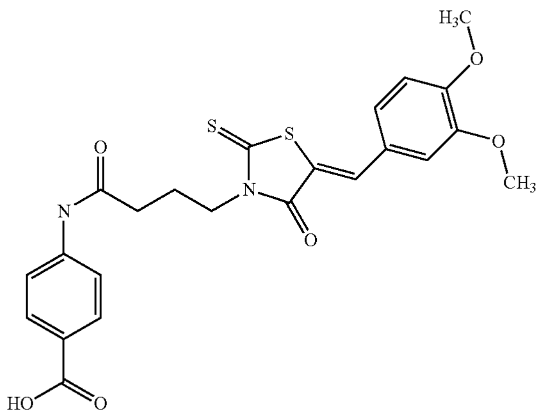 [SMILES: COc1ccc(/C=C2\SC(=S)N(CCCC(=O)Nc3ccc(C(=O)O)cc3)C2=O)cc1OC] | 486.6 |
| IIb-213 | 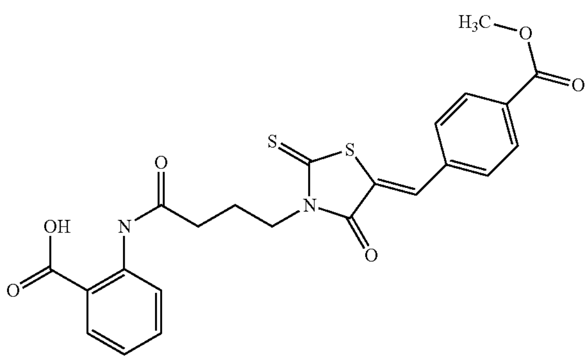 [SMILES: COC(=O)c1ccc(/C=C2\SC(=S)N(CCCC(=O)Nc3ccccc3C(=O)O)C2=O)cc1] | 484.6 |
| IIb-214 | 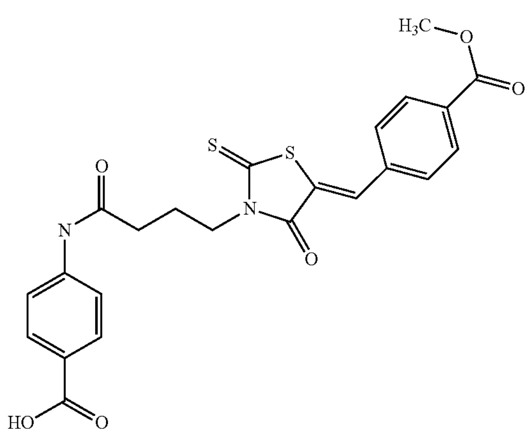 [SMILES: COC(=O)c1ccc(/C=C2\SC(=S)N(CCCC(=O)Nc3ccc(C(=O)O)cc3)C2=O)cc1] | 484.6 |

TABLE 7-continued

Phenmethylene-Thiazole Alkanoic Acids ($R^3$ = OH)

| ID | Structure | MW |
|---|---|---|
| IIb-215 | 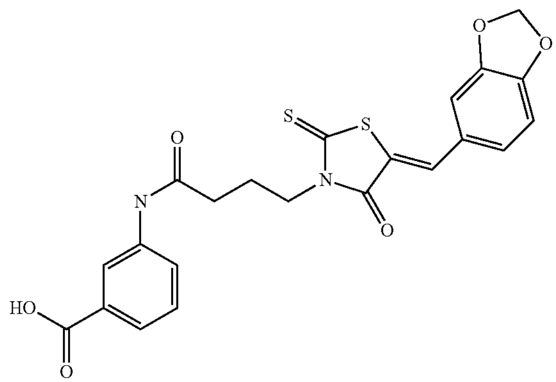 [SMILES: O=C(CCCN1C(=O)/C(=C/c2ccc3c(c2)OCO3)SC1=S)Nc1cccc(C(=O)O)c1] | 470.5 |
| IIb-216 | 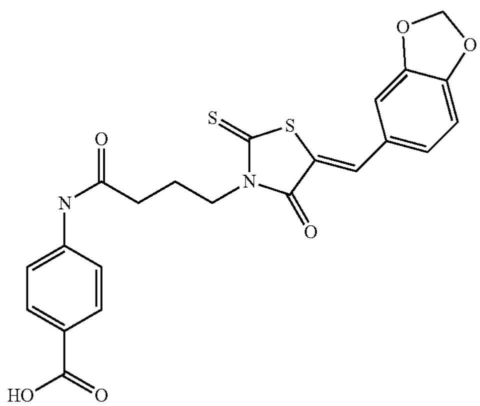 [SMILES: O=C(CCCN1C(=O)/C(=C/c2ccc3c(c2)OCO3)SC1=S)Nc1ccc(C(=O)O)cc1] | 470.5 |
| IIb-217 | 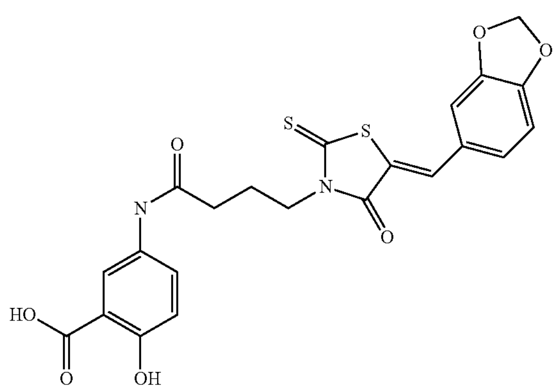 [SMILES: O=C(CCCN1C(=O)/C(=C/c2ccc3c(c2)OCO3)SC1=S)Nc1ccc(O)c(C(=O)O)c1] | 486.5 |
| IIb-218 | 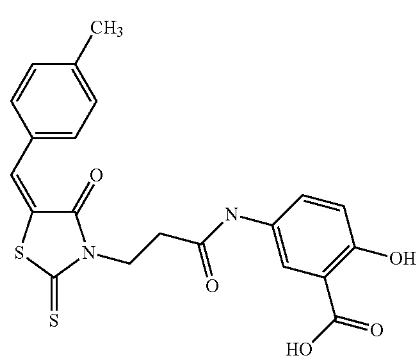 [SMILES: Cc1ccc(/C=C2/SC(=S)N(CCC(=O)Nc3ccc(O)c(C(=O)O)c3)C2=O)cc1] | 442.5 |

TABLE 7-continued
Phenmethylene-Thiazole Alkanoic Acids ($R^3$ = OH)
| ID | Structure | MW |
|---|---|---|
| IIb-219 | 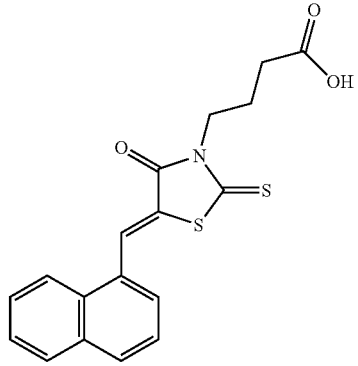 [SMILES: O=C(O)CCCN1C(=O)/C(=C/c2cccc3ccccc23)SC1=S] | 357.5 |
| IIb-220 | 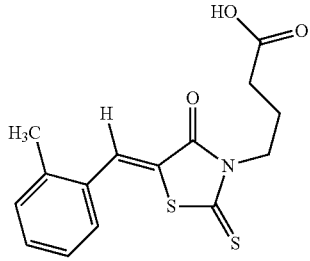 [SMILES: Cc1ccccc1/C=C1\SC(=S)N(CCCC(=O)O)C1=O] | 321.4 |
| IIb-221 | 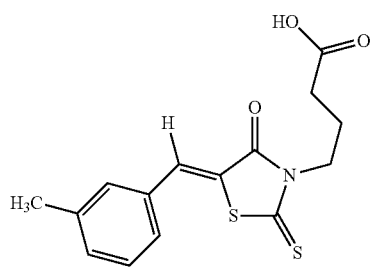 [SMILES: Cc1cccc(/C=C2\SC(=S)N(CCCC(=O)O)C2=O)c1] | 321.4 |
| IIb-222 | 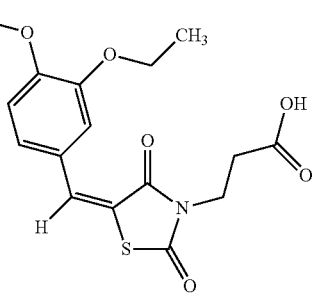 | 465.6 |

TABLE 7-continued
Phenmethylene-Thiazole Alkanoic Acids ($R^3$ = OH)
| ID | Structure | MW |
|---|---|---|
| IIb-223 | 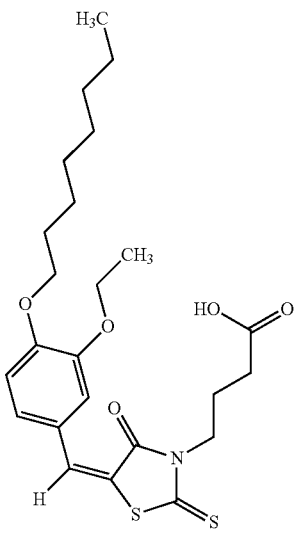 [SMILES: CCCCCCCCOc1ccc(/C=C2/SC(=S)N(CCCC(=O)O)C2=O)cc1OCC] | 479.7 |
| IIb-224 | 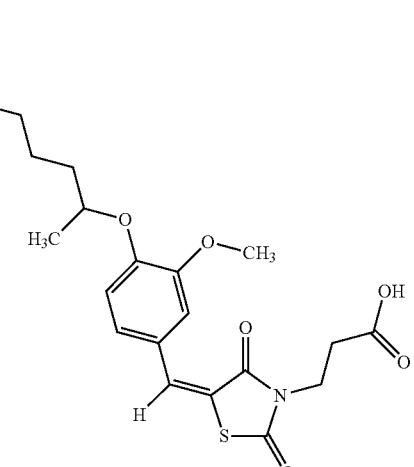 | 465.6 |
| IIb-225 | 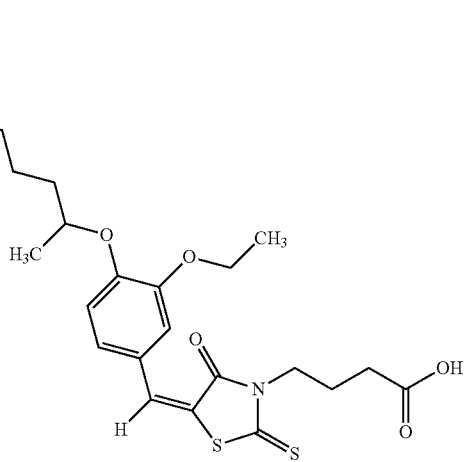 | 479.7 |

TABLE 7-continued
Phenmethylene-Thiazole Alkanoic Acids ($R^3$ = OH)
| ID | Structure | MW |
|---|---|---|
| IIb-226 | 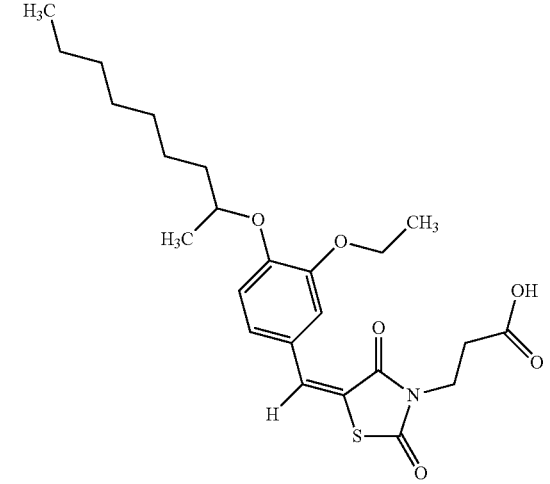 [SMILES: CCCCCCCC(C)Oc1ccc(/C=C2/SC(=O)N(CCC(=O)O)C2=O)cc1OCC] | 479.7 |
| IIb-227 | 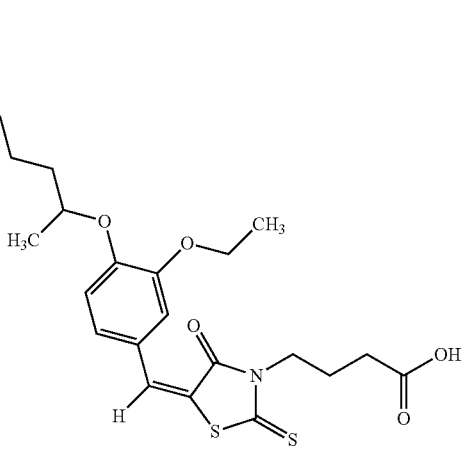 | 493.7 |
| IIb-228 | 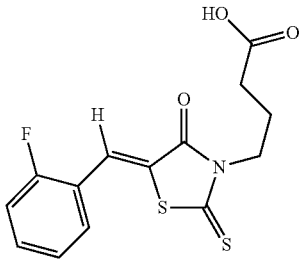 [SMILES: O=C(O)CCCN1C(=O)/C(=C/c2ccccc2F)SC1=S] | 325.4 |
| IIb-229 | 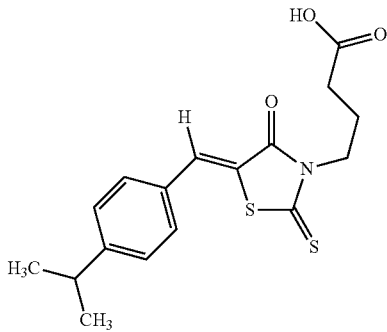 [SMILES: CC(C)c1ccc(/C=C2\SC(=S)N(CCCC(=O)O)C2=O)cc1] | 349.5 |

TABLE 7-continued
| Phenmethylene-Thiazole Alkanoic Acids (R³ = OH) | | |
|---|---|---|
| ID | Structure | MW |
| IIb-230 | 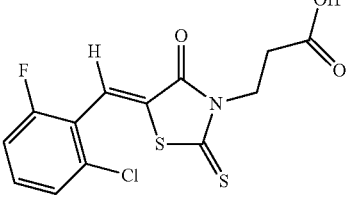 | 345.8 |
| IIb-231 | 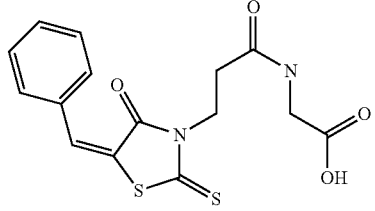 [SMILES: O=C(O)CNC(=O)CCN1C(=O)/C(=C\c2ccccc2)SC1=S] | 350.4 |
| IIb-232 | 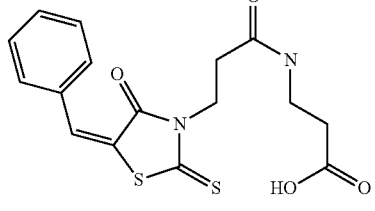 | 364.4 |
| IIb-233 | 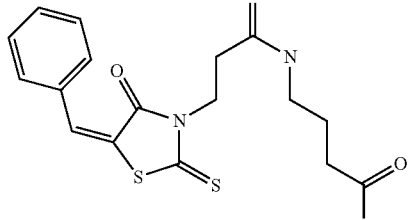 | 378.5 |
| IIb-234 | 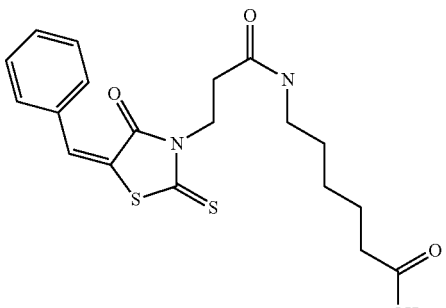 | 406.5 |
| IIb-235 | 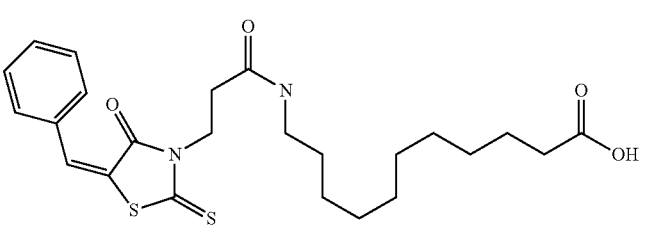 [SMILES: O=C(O)CCCCCCCCCCNC(=O)CCN1C(=O)/C(=C\c2ccccc2)SC1=S] | 476.7 |

TABLE 7-continued

Phenmethylene-Thiazole Alkanoic Acids ($R^3$ = OH)

| ID | Structure | MW |
|---|---|---|
| IIb-236 | 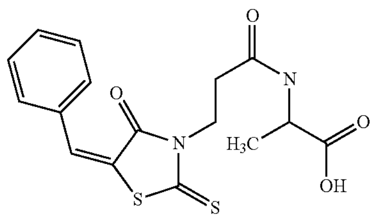 [SMILES: CC(NC(=O)CCN1C(=O)/C(=C\c2ccccc2)SC1=S)C(=O)O] | 364.4 |
| IIb-237 | 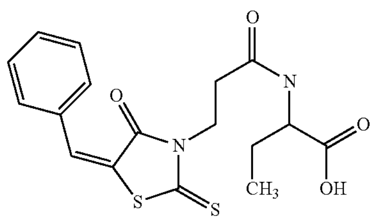 [SMILES: CCC(NC(=O)CCN1C(=O)/C(=C\c2ccccc2)SC1=S)C(=O)O] | 378.5 |
| IIb-238 | 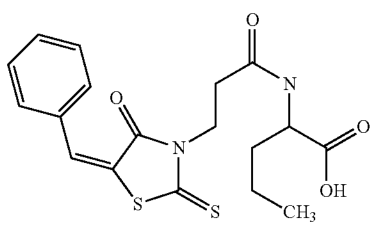 [SMILES: CCCC(NC(=O)CCN1C(=O)/C(=C\c2ccccc2)SC1=S)C(=O)O] | 392.5 |
| IIb-239 | 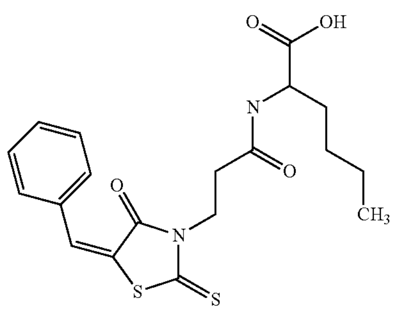 [SMILES: CCCCC(NC(=O)CCN1C(=O)/C(=C\c2ccccc2)SC1=S)C(=O)O] | 406.5 |
| IIb-240 | 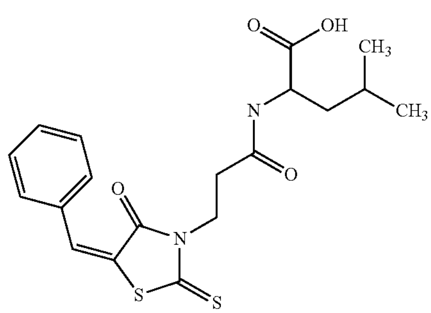 [SMILES: CC(C)CC(NC(=O)CCN1C(=O)/C(=C\c2ccccc2)SC1=S)C(=O)O] | 406.5 |

TABLE 7-continued

Phenmethylene-Thiazole Alkanoic Acids ($R^3$ = OH)

| ID | Structure | MW |
|---|---|---|
| IIb-241 | 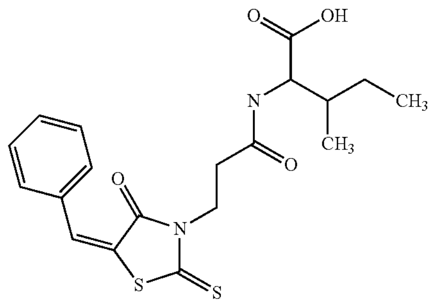 [SMILES: CCC(C)C(NC(=O)CCN1C(=O)/C(=C\c2ccccc2)SC1=S)C(=O)O] | 406.5 |
| IIb-242 | 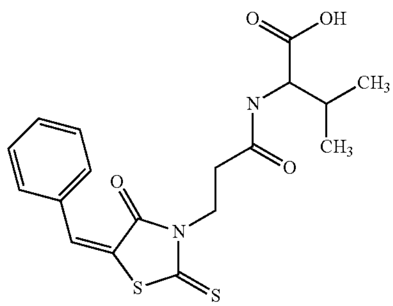 [SMILES: CC(C)C(NC(=O)CCN1C(=O)/C(=C\c2ccccc2)SC1=S)C(=O)O] | 392.5 |
| IIb-243 | 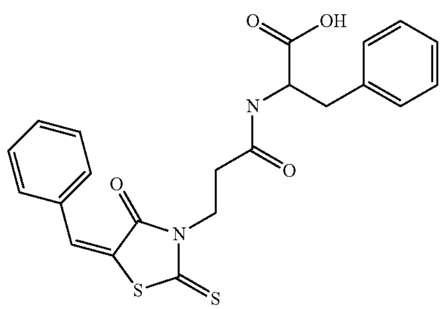 [SMILES: O=C(CCN1C(=O)/C(=C\c2ccccc2)SC1=S)NC(Cc1ccccc1)C(=O)O] | 440.5 |
| IIb-244 | 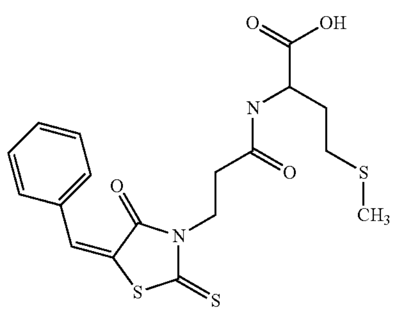 [SMILES: CSCCC(NC(=O)CCN1C(=O)/C(=C\c2ccccc2)SC1=S)C(=O)O] | 424.6 |
| IIb-245 | 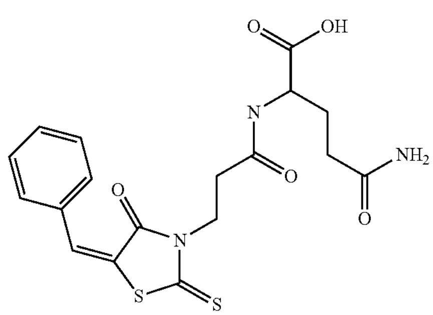 [SMILES: NC(=O)CCC(NC(=O)CCN1C(=O)/C(=C\c2ccccc2)SC1=S)C(=O)O] | 421.5 |

TABLE 7-continued
Phenmethylene-Thiazole Alkanoic Acids ($R^3$ = OH)
| ID | Structure | MW |
|---|---|---|
| IIb-246 | 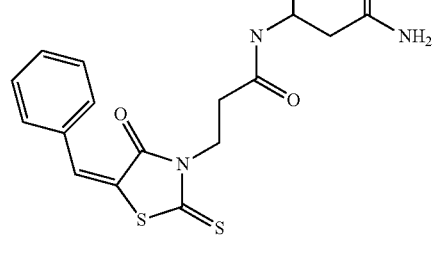 | 407.5 |
| IIb-247 | 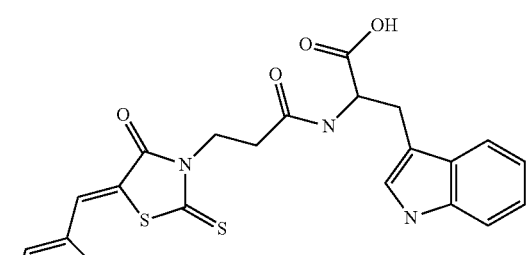 | 479.6 |
| IIb-248 | 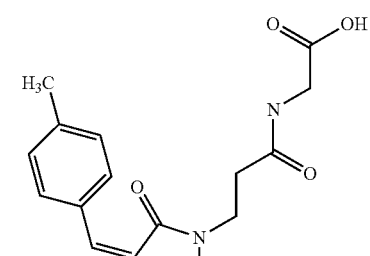 | 364.4 |
| IIb-249 | 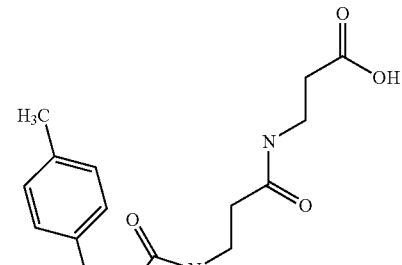 | 378.5 |

TABLE 7-continued

Phenmethylene-Thiazole Alkanoic Acids (R³ = OH)

| ID | Structure | MW |
|---|---|---|
| IIb-250 | 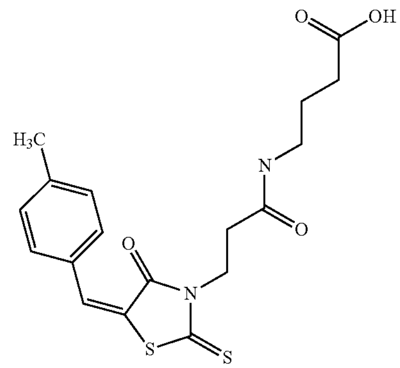 [SMILES: Cc1ccc(/C=C2/SC(=S)N(CCC(=O)NCCCC(=O)O)C2=O)cc1] | 392.5 |
| IIb-251 | 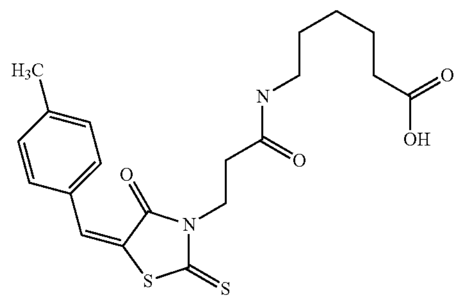 [SMILES: Cc1ccc(/C=C2/SC(=S)N(CCC(=O)NCCCCCC(=O)O)C2=O)cc1] | 420.6 |
| IIb-252 | 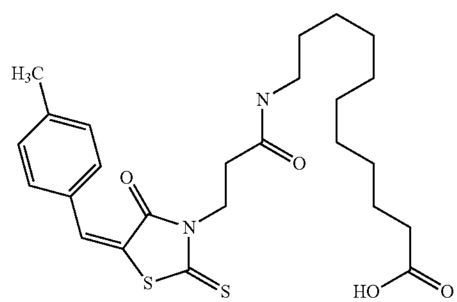 [SMILES: Cc1ccc(/C=C2/SC(=S)N(CCC(=O)NCCCCCCCCCCC(=O)O)C2=O)cc1] | 490.7 |
| IIb-253 | 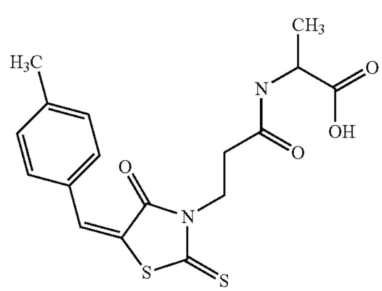 [SMILES: Cc1ccc(/C=C2/SC(=S)N(CCC(=O)NC(C)C(=O)O)C2=O)cc1] | 378.5 |
| IIb-254 | 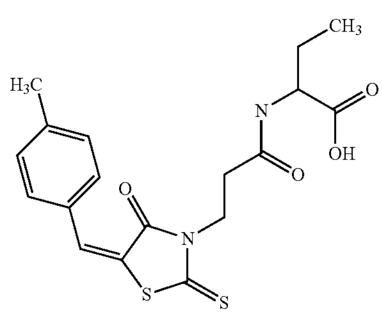 [SMILES: CCC(NC(=O)CCN1C(=O)/C(=C\c2ccc(C)cc2)SC1=S)C(=O)O] | 392.5 |

TABLE 7-continued

Phenmethylene-Thiazole Alkanoic Acids ($R^3$ = OH)

| ID | Structure | MW |
|---|---|---|
| IIb-255 | 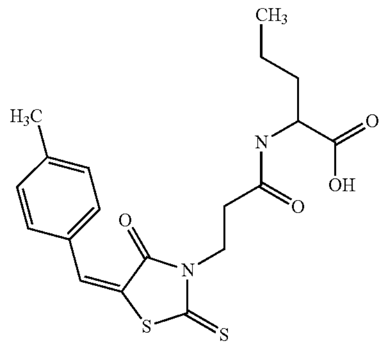 [SMILES: CCCC(NC(=O)CCN1C(=O)/C(=C\c2ccc(C)cc2)SC1=S)C(=O)O] | 406.5 |
| IIb-256 | 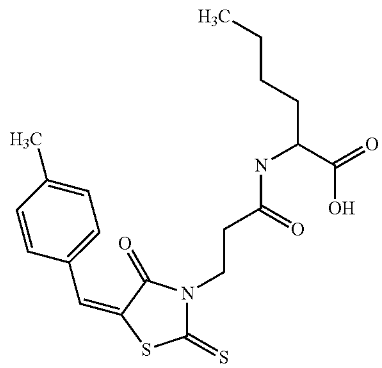 [SMILES: CCCCC(NC(=O)CCN1C(=O)/C(=C\c2ccc(C)cc2)SC1=S)C(=O)O] | 420.6 |
| IIb-257 | 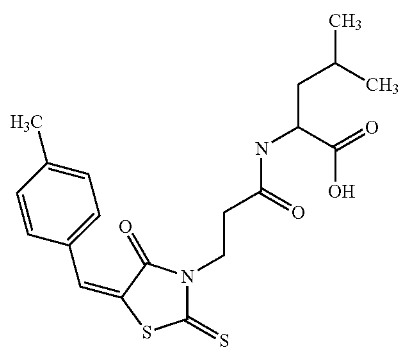 [SMILES: Cc1ccc(/C=C2/SC(=S)N(CCC(=O)NC(CC(C)C)C(=O)O)C2=O)cc1] | 420.6 |
| IIb-258 | 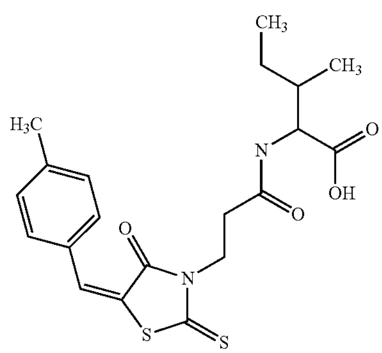 [SMILES: CCC(C)C(NC(=O)CCN1C(=O)/C(=C\c2ccc(C)cc2)SC1=S)C(=O)O] | 420.6 |

TABLE 7-continued

Phenmethylene-Thiazole Alkanoic Acids (R³ = OH)

| ID | Structure | MW |
|---|---|---|
| IIb-259 | 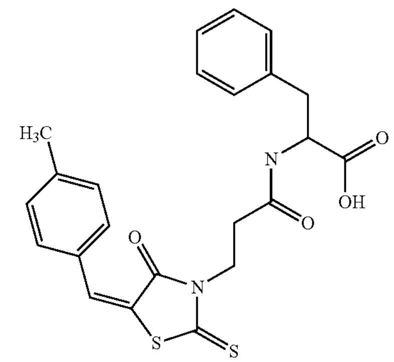 [SMILES: Cc1ccc(/C=C2/SC(=S)N(CCC(=O)NC(Cc3ccccc3)C(=O)O)C2=O)cc1] | 454.6 |
| IIb-260 | 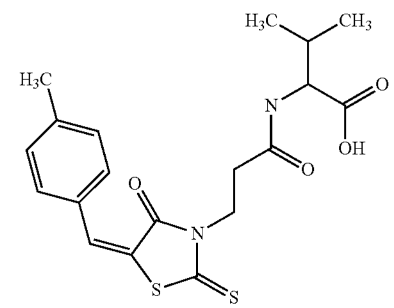 [SMILES: Cc1ccc(/C=C2/SC(=S)N(CCC(=O)NC(C(=O)O)C(C)C)C2=O)cc1] | 406.5 |
| IIb-261 | 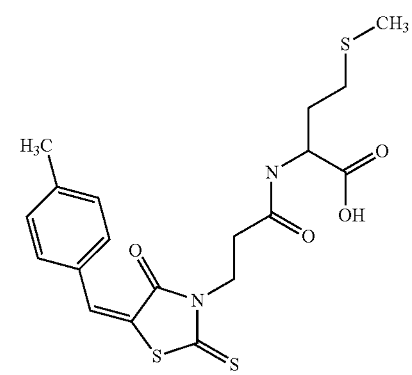 [SMILES: CSCCC(NC(=O)CCN1C(=O)/C(=C\c2ccc(C)cc2)SC1=S)C(=O)O] | 438.6 |
| IIb-262 | 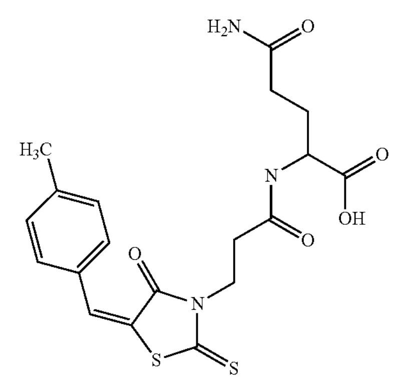 [SMILES: Cc1ccc(/C=C2/SC(=S)N(CCC(=O)NC(CCC(N)=O)C(=O)O)C2=O)cc1] | 435.5 |

TABLE 7-continued

Phenmethylene-Thiazole Alkanoic Acids ($R^3$ = OH)

| ID | Structure | MW |
| --- | --- | --- |
| IIb-263 | 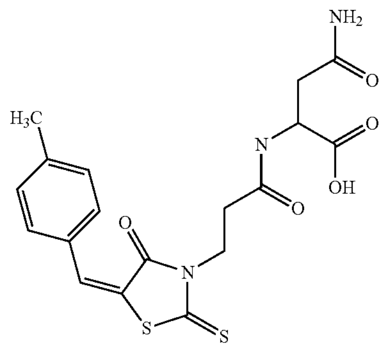 [SMILES: Cc1ccc(/C=C2/SC(=S)N(CCC(=O)NC(CC(N)=O)C(=O)O)C2=O)cc1] | 421.5 |
| IIb-264 | 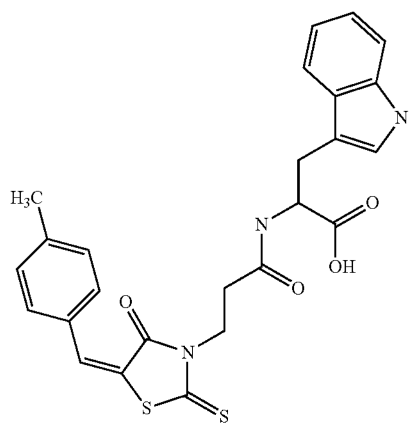 [SMILES: Cc1ccc(/C=C2/SC(=S)N(CCC(=O)NC(Cc3c[nH]c4ccccc34)C(=O)O)C2=O)cc1] | 493.6 |
| IIb-265 | 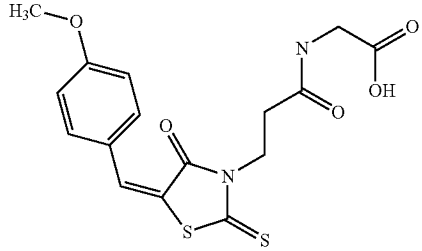 [SMILES: COc1ccc(/C=C2/SC(=S)N(CCC(=O)NCC(=O)O)C2=O)cc1] | 380.4 |
| IIb-266 | 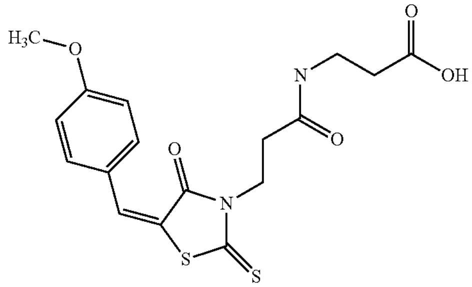 [SMILES: COc1ccc(/C=C2/SC(=S)N(CCC(=O)NCCC(=O)O)C2=O)cc1] | 394.5 |

TABLE 7-continued

Phenmethylene-Thiazole Alkanoic Acids ($R^3$ = OH)

| ID | Structure | MW |
|---|---|---|
| IIb-267 | 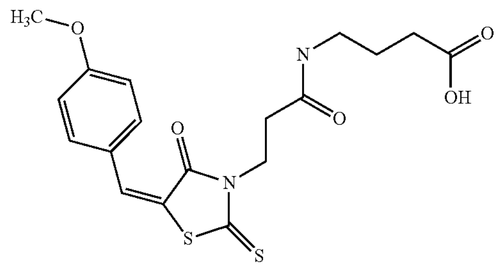 [SMILES: COc1ccc(/C=C2/SC(=S)N(CCC(=O)NCCCC(=O)O)C2=O)cc1] | 408.5 |
| IIb-268 | 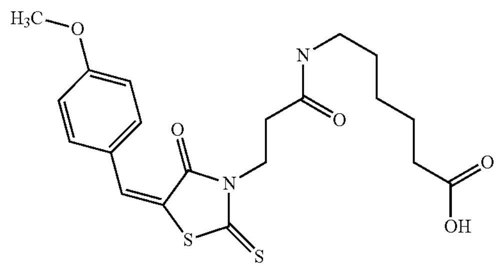 [SMILES: COc1ccc(/C=C2/SC(=S)N(CCC(=O)NCCCCCC(=O)O)C2=O)cc1] | 436.6 |
| IIb-269 | 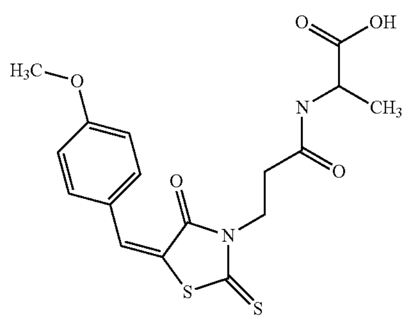 [SMILES: COc1ccc(/C=C2/SC(=S)N(CCC(=O)NC(C)C(=O)O)C2=O)cc1] | 394.5 |
| IIb-270 | 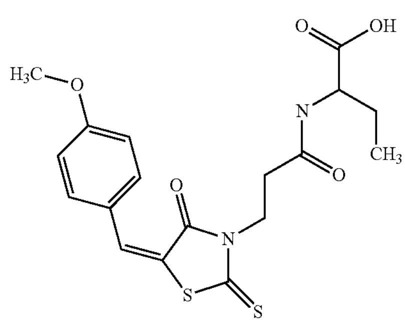 [SMILES: CCC(NC(=O)CCN1C(=O)/C(=C\c2ccc(OC)cc2)SC1=S)C(=O)O] | 408.5 |
| IIb-271 | 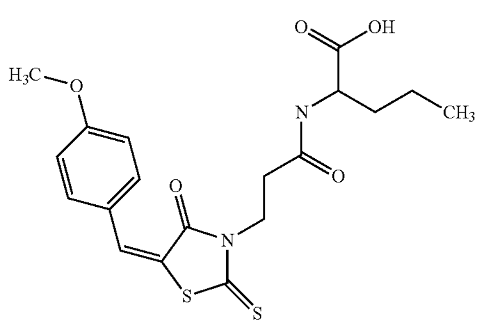 [SMILES: CCCC(NC(=O)CCN1C(=O)/C(=C\c2ccc(OC)cc2)SC1=S)C(=O)O] | 422.5 |

TABLE 7-continued

Phenmethylene-Thiazole Alkanoic Acids ($R^3$ = OH)

| ID | Structure | MW |
|---|---|---|
| IIb-272 | 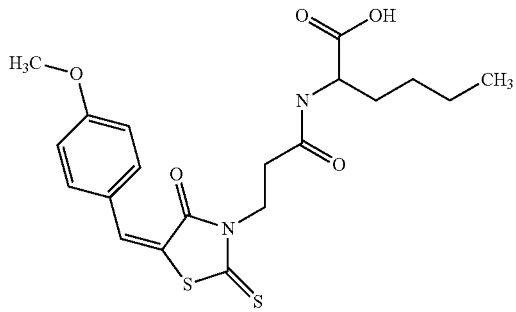 [SMILES: CCCCC(NC(=O)CCN1C(=O)/C(=C\c2ccc(OC)cc2)SC1=S)C(=O)O] | 436.6 |
| IIb-273 | 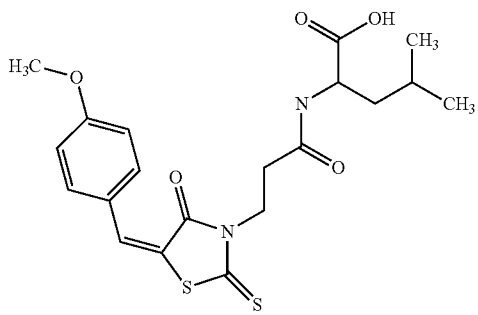 [SMILES: COc1ccc(/C=C2/SC(=S)N(CCC(=O)NC(CC(C)C)C(=O)O)C2=O)cc1] | 436.6 |
| IIb-274 | 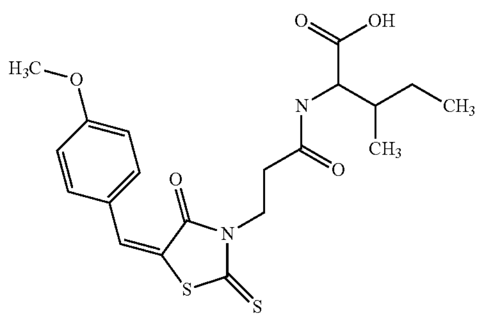 [SMILES: CCC(C)C(NC(=O)CCN1C(=O)/C(=C\c2ccc(OC)cc2)SC1=S)C(=O)O] | 436.6 |
| IIb-275 | 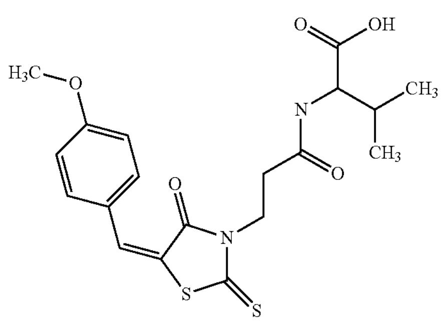 [SMILES: COc1ccc(/C=C2/SC(=S)N(CCC(=O)NC(C(=O)O)C(C)C)C2=O)cc1] | 422.5 |
| IIb-276 | 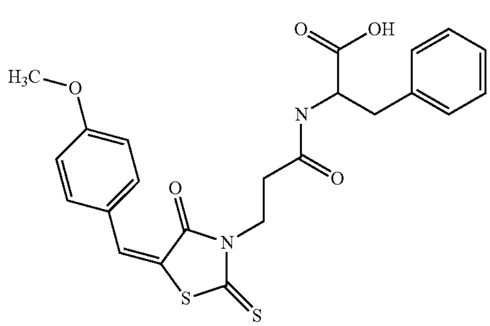 [SMILES: COc1ccc(/C=C2/SC(=S)N(CCC(=O)NC(Cc3ccccc3)C(=O)O)C2=O)cc1] | 470.6 |

TABLE 7-continued

Phenmethylene-Thiazole Alkanoic Acids ($R^3$ = OH)

| ID | Structure | MW |
| --- | --- | --- |
| IIb-277 | 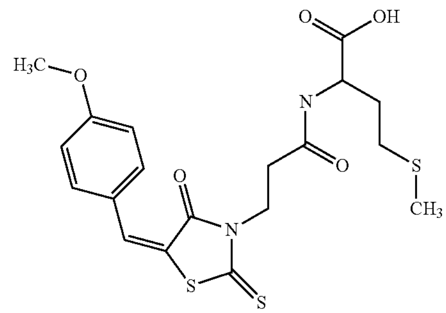 | 454.6 |
| IIb-278 | 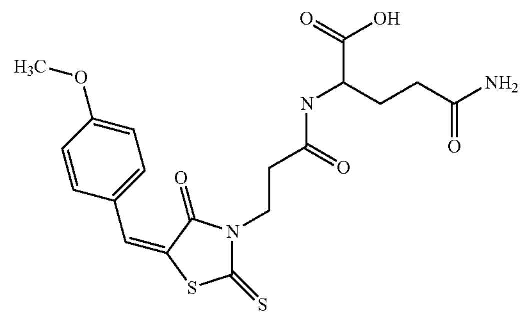 [SMILES: COc1ccc(/C=C2/SC(=S)N(CCC(=O)NC(CCC(N)=O)C(=O)O)C2=O)cc1] | 451.5 |
| IIb-279 | 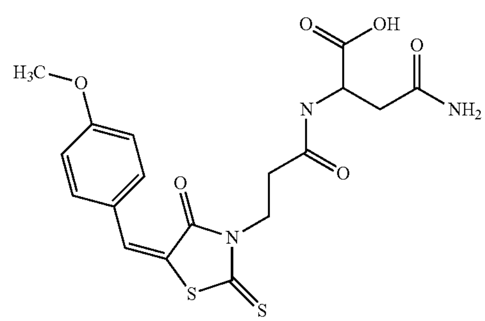 [SMILES: COc1ccc(/C=C2/SC(=S)N(CCC(=O)NC(CC(N)=O)C(=O)O)C2=O)cc1] | 437.5 |
| IIb-280 | 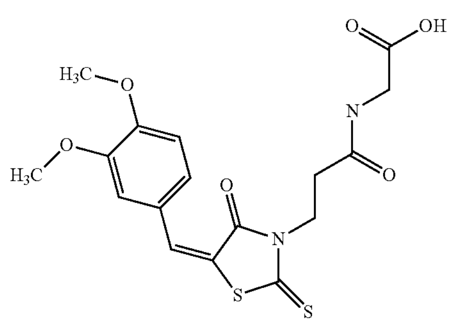 [SMILES: COc1ccc(/C=C2/SC(=S)N(CCC(=O)NCC(=O)O)C2=O)cc1OC] | 410.5 |

TABLE 7-continued

Phenmethylene-Thiazole Alkanoic Acids (R³ = OH)

| ID | Structure | MW |
|---|---|---|
| IIb-281 | 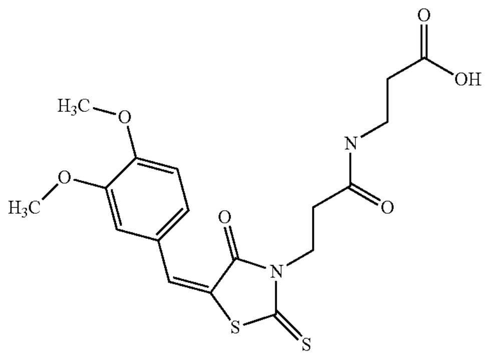 [SMILES: COc1ccc(/C=C2/SC(=S)N(CCC(=O)NCCC(=O)O)C2=O)cc1OC] | 424.5 |
| IIb-282 | 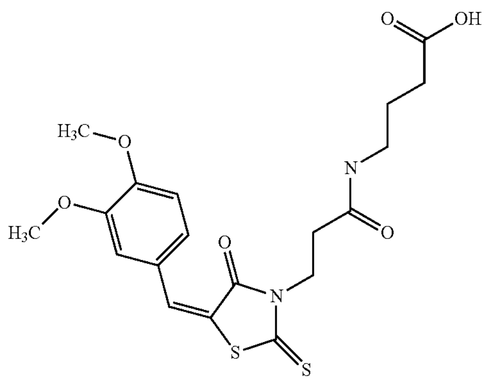 [SMILES: COc1ccc(/C=C2/SC(=S)N(CCC(=O)NCCCC(=O)O)C2=O)cc1OC] | 438.5 |
| IIb-283 | 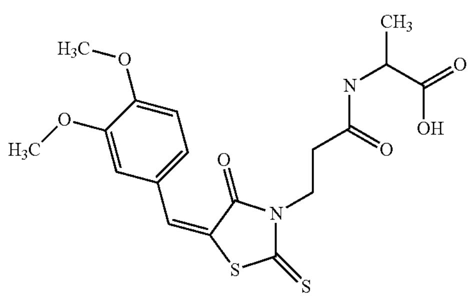 [SMILES: COc1ccc(/C=C2/SC(=S)N(CCC(=O)NC(C)C(=O)O)C2=O)cc1OC] | 424.5 |
| IIb-284 | 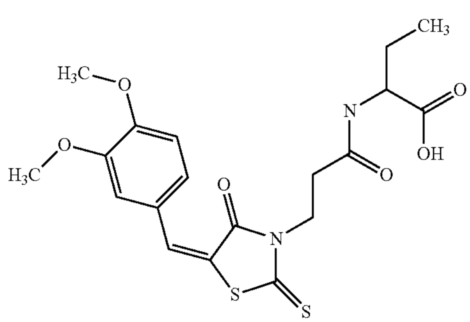 [SMILES: CCC(NC(=O)CCN1C(=O)/C(=C\c2ccc(OC)c(OC)c2)SC1=S)C(=O)O] | 438.5 |

TABLE 7-continued

Phenmethylene-Thiazole Alkanoic Acids (R³ = OH)

| ID | Structure | MW |
|----|-----------|-----|
| IIb-285 | 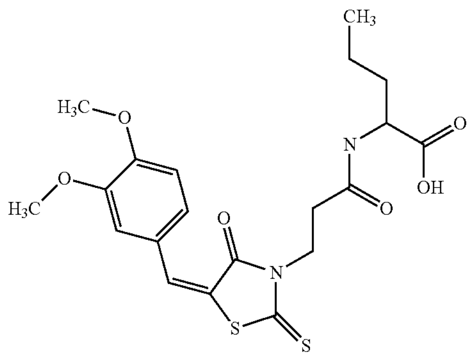 [SMILES: CCCC(NC(=O)CCN1C(=O)/C(=C\c2ccc(OC)c(OC)c2)SC1=S)C(=O)O] | 452.6 |
| IIb-286 | 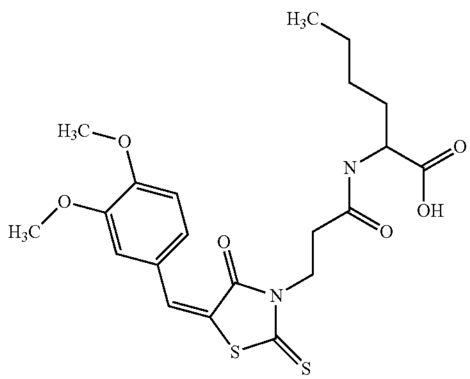 [SMILES: CCCCC(NC(=O)CCN1C(=O)/C(=C\c2ccc(OC)c(OC)c2)SC1=S)C(=O)O] | 466.6 |
| IIb-287 | 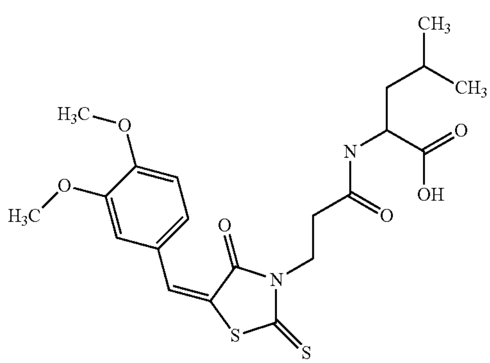 [SMILES: COc1ccc(/C=C2/SC(=S)N(CCC(=O)NC(CC(C)C)C(=O)O)C2=O)cc1OC] | 466.6 |
| IIb-288 | 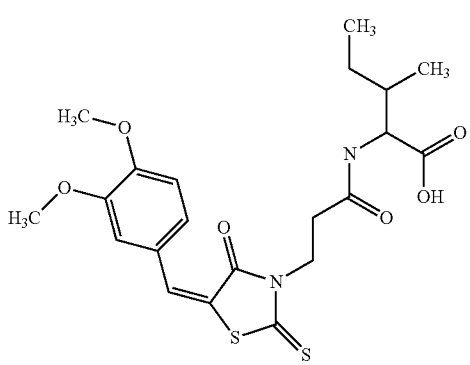 [SMILES: CCC(C)C(NC(=O)CCN1C(=O)/C(=C\c2ccc(OC)c(OC)c2)SC1=S)C(=O)O] | 466.6 |

TABLE 7-continued
Phenmethylene-Thiazole Alkanoic Acids ($R^3$ = OH)
| ID | Structure | MW |
|---|---|---|
| IIb-289 | 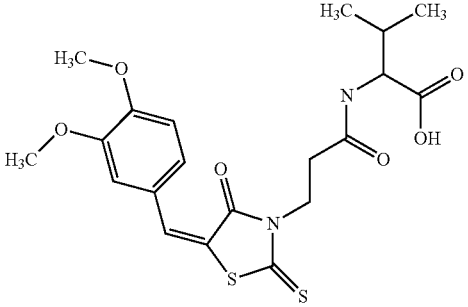 [SMILES: COc1ccc(/C=C2/SC(=S)N(CCC(=O)NC(C(=O)O)C(C)C)C2=O)cc1OC] | 452.6 |
| IIb-290 | 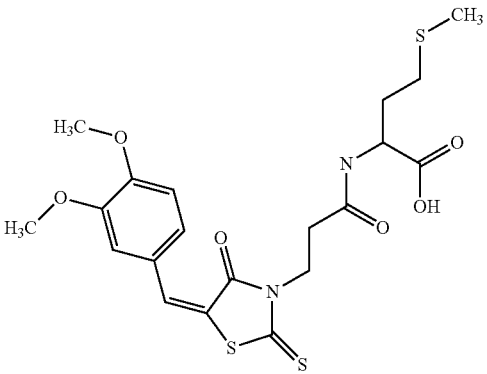 | 484.6 |
| IIb-291 | 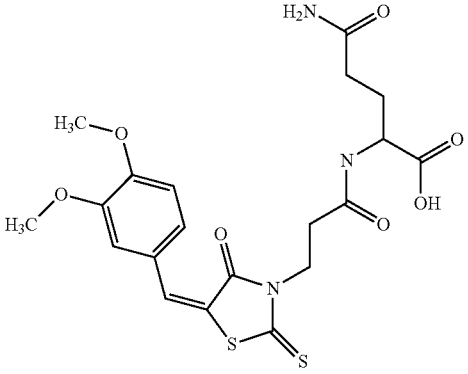 [SMILES: COc1ccc(/C=C2/SC(=S)N(CCC(=O)NC(CCC(N)=O)C(=O)O)C2=O)cc1OC] | 481.6 |
| IIb-292 | 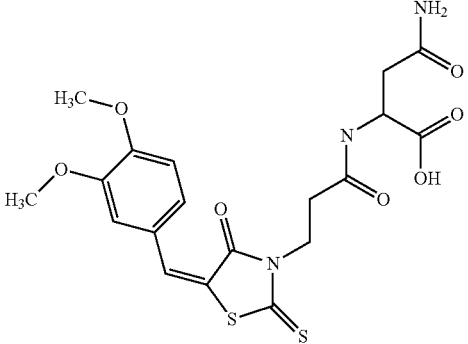 [SMILES: COc1ccc(/C=C2/SC(=S)N(CCC(=O)NC(CC(N)=O)C(=O)O)C2=O)cc1OC] | 467.5 |

TABLE 7-continued

Phenmethylene-Thiazole Alkanoic Acids (R³ = OH)

| ID | Structure | MW |
|---|---|---|
| IIb-293 | 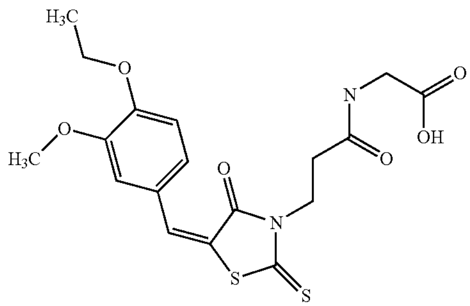 [SMILES: CCOc1ccc(/C=C2/SC(=S)N(CCC(=O)NCC(=O)O)C2=O)cc1OC] | 424.5 |
| IIb-294 | 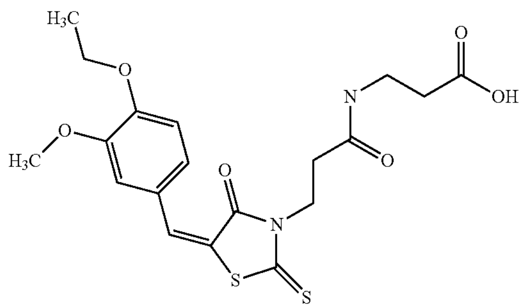 [SMILES: CCOc1ccc(/C=C2/SC(=S)N(CCC(=O)NCCC(=O)O)C2=O)cc1OC] | 438.5 |
| IIb-295 | 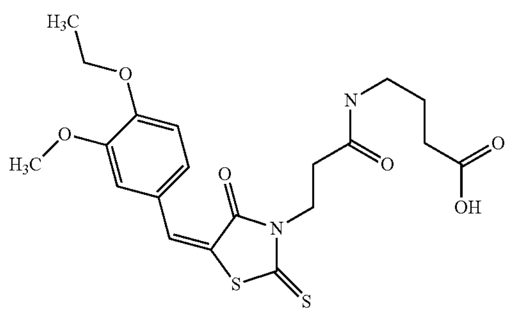 [SMILES: CCOc1ccc(/C=C2/SC(=S)N(CCC(=O)NCCCC(=O)O)C2=O)cc1OC] | 452.6 |
| IIb-296 | 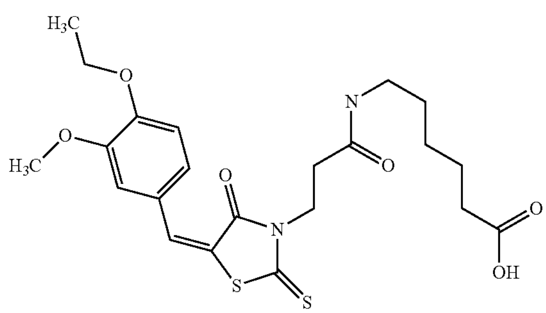 [SMILES: CCOc1ccc(/C=C2/SC(=S)N(CCC(=O)NCCCCCC(=O)O)C2=O)cc1OC] | 480.6 |
| IIb-297 | 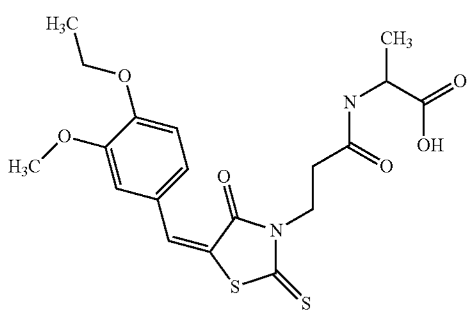 [SMILES: CCOc1ccc(/C=C2/SC(=S)N(CCC(=O)NC(C)C(=O)O)C2=O)cc1OC] | 438.5 |

TABLE 7-continued
| | Phenmethylene-Thiazole Alkanoic Acids ($R^3$ = OH) | |
|---|---|---|
| ID | Structure | MW |
| IIb-298 | 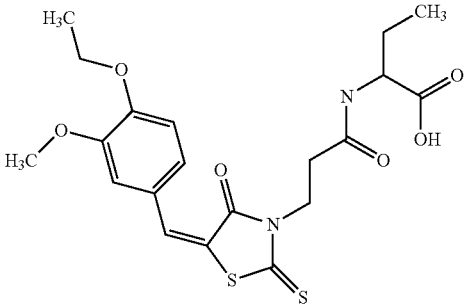 [SMILES: CCOc1ccc(/C=C2/SC(=S)N(CCC(=O)NC(CC)C(=O)O)C2=O)cc1OC] | 452.6 |
| IIb-299 | 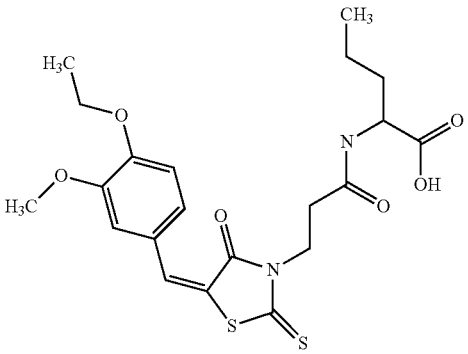 [SMILES: CCCC(NC(=O)CCN1C(=O)/C(=C\c2ccc(OCC)c(OC)c2)SC1=S)C(=O)O] | 466.6 |
| IIb-300 | 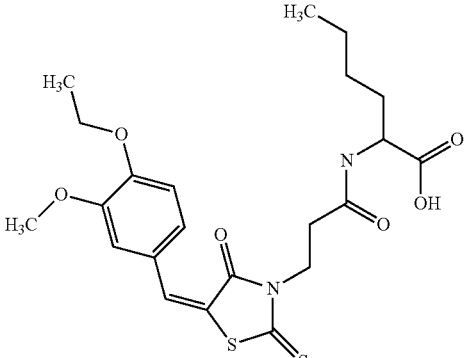 | 480.6 |
| IIb-301 | 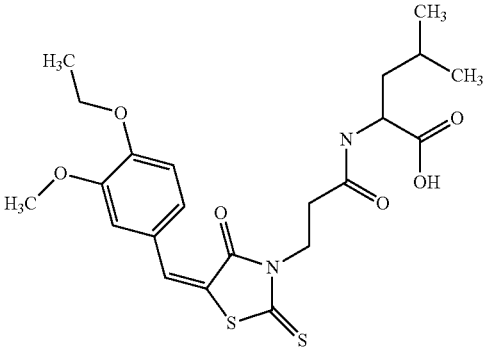 [SMILES: CCOc1ccc(/C=C2/SC(=S)N(CCC(=O)NC(CC(C)C)C(=O)O)C2=O)cc1OC] | 480.6 |

TABLE 7-continued

Phenmethylene-Thiazole Alkanoic Acids ($R^3$ = OH)

| ID | Structure | MW |
|---|---|---|
| IIb-302 | 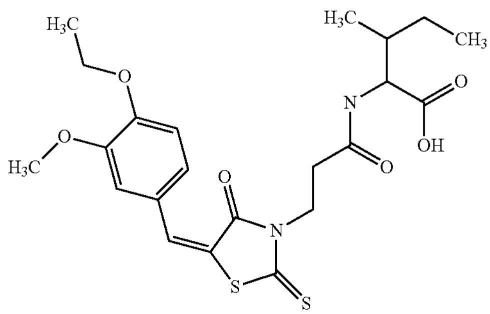 [SMILES: CCOc1ccc(/C=C2/SC(=S)N(CCC(=O)NC(C(=O)O)C(C)CC)C2=O)cc1OC] | 480.6 |
| IIb-303 | 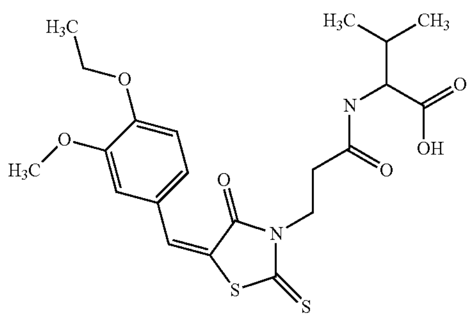 [SMILES: CCOc1ccc(/C=C2/SC(=S)N(CCC(=O)NC(C(=O)O)C(C)C)C2=O)cc1OC] | 466.6 |
| IIb-304 | 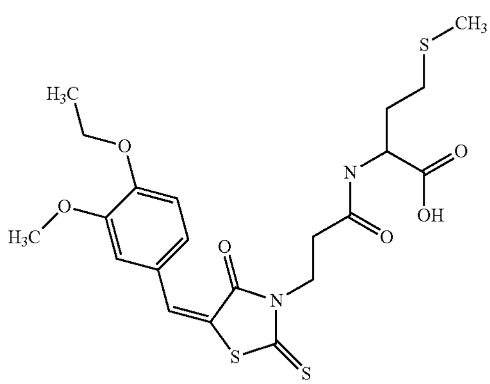 | 498.6 |
| IIb-305 | 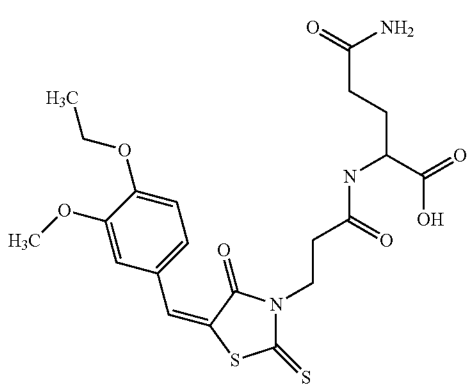 [SMILES: CCOc1ccc(/C=C2/SC(=S)N(CCC(=O)NC(CCC(N)=O)C(=O)O)C2=O)cc1OC] | 495.6 |

TABLE 7-continued

Phenmethylene-Thiazole Alkanoic Acids ($R^3$ = OH)

| ID | Structure | MW |
|---|---|---|
| IIb-306 | 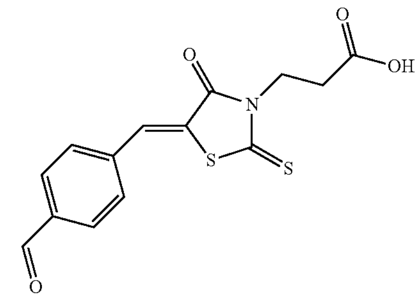 [SMILES: O=Cc1ccc(/C=C2\SC(=S)N(CCC(=O)O)C2=O)cc1] | 321.4 |
| IIb-307 | 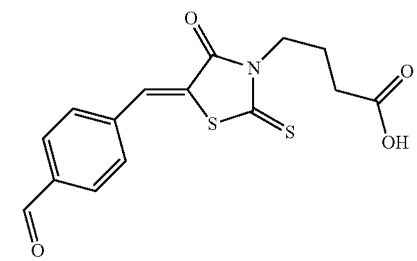 [SMILES: O=Cc1ccc(/C=C2\SC(=S)N(CCCC(=O)O)C2=O)cc1] | 335.4 |
| IIb-308 | 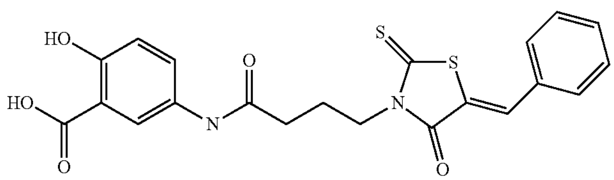 [SMILES: O=C(CCCN1C(=O)/C(=C/c2ccccc2)SC1=S)Nc1ccc(O)c(C(=O)O)c1] | 442.5 |
| IIb-309 | 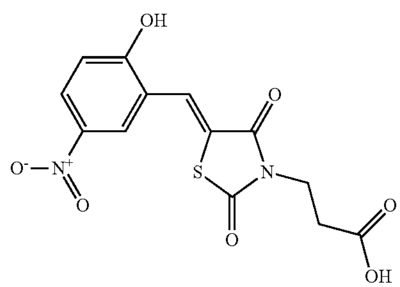 [SMILES: O=C(O)CCN1C(=O)S/C(=C\c2cc([N+](=O)[O-])ccc2O)C1=O] | 354.4 |
| IIb-310 | 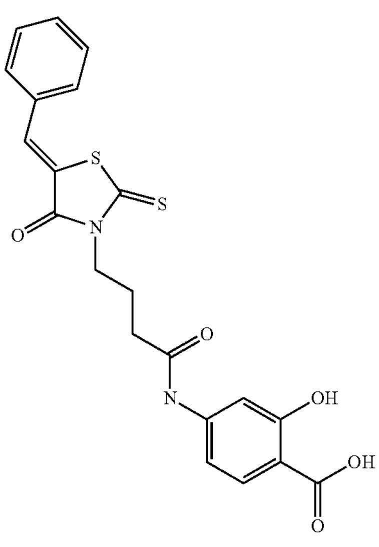 [SMILES: O=C(CCCN1C(=O)/C(=C/c2ccccc2)SC1=S)Nc1ccc(C(=O)O)c(O)c1] | 442.5 |

TABLE 7-continued

Phenmethylene-Thiazole Alkanoic Acids ($R^3$ = OH)

| ID | Structure | MW |
|---|---|---|
| IIb-311 | 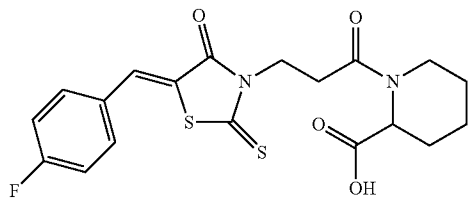 [SMILES: O=C(O)C1CCCCN1C(=O)CCN1C(=O)/C(=C/c2ccc(F)cc2)SC1=S] | 422.5 |
| IIb-312 | 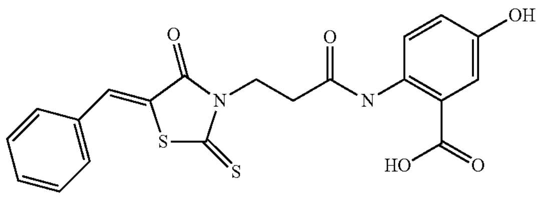 [SMILES: O=C(CCN1C(=O)/C(=C/c2ccccc2)SC1=S)Nc1ccc(O)cc1C(=O)O] | 428.5 |
| IIb-313 | 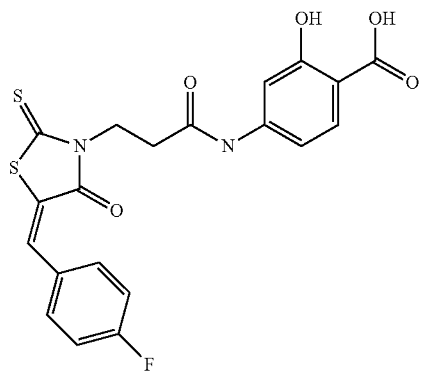 [SMILES: O=C(CCN1C(=O)/C(=C\c2ccc(F)cc2)SC1=S)Nc1ccc(C(=O)O)c(O)c1] | 446.5 |
| IIb-314 | 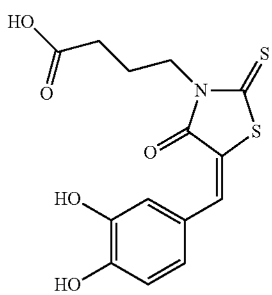 [SMILES: O=C(O)CCCN1C(=O)/C(=C\c2ccc(O)c(O)c2)SC1=S] | 339.4 |
| IIb-315 | 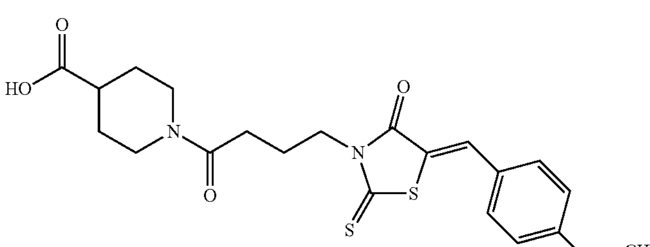 | 448.6 |
| IIb-316 | 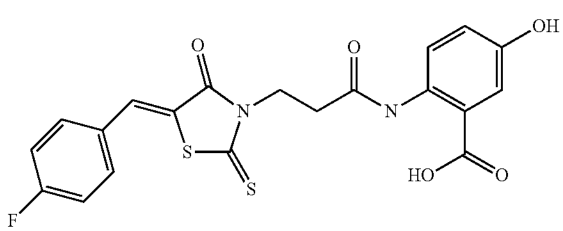 [SMILES: O=C(CCN1C(=O)/C(=C/c2ccc(F)cc2)SC1=S)Nc1ccc(O)cc1C(=O)O] | 446.5 |

TABLE 7-continued

Phenmethylene-Thiazole Alkanoic Acids ($R^3$ = OH)

| ID | Structure | MW |
|---|---|---|
| IIb-317 | 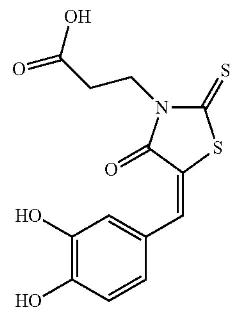 [SMILES: O=C(O)CCN1C(=O)/C(=C\c2ccc(O)c(O)c2)SC1=S] | 325.4 |
| IIb-318 | 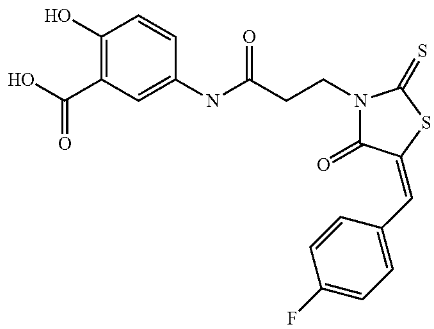 [SMILES: O=C(CCN1C(=O)/C(=C\c2ccc(F)cc2)SC1=S)Nc1ccc(O)c(C(=O)O)c1] | 446.5 |
| IIb-319 | 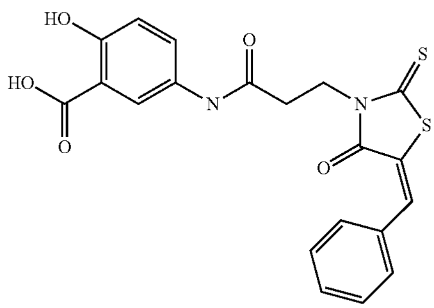 [SMILES: O=C(CCN1C(=O)/C(=C\c2ccccc2)SC1=S)Nc1ccc(O)c(C(=O)O)c1] | 428.5 |
| IIb-320 | 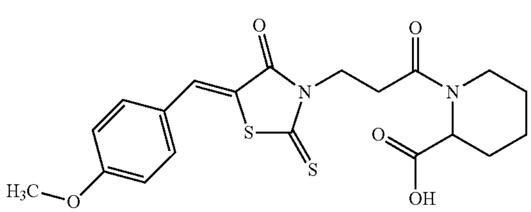 [SMILES: COc1ccc(/C=C2\SC(=S)N(CCC(=O)N3CCCCC3C(=O)O)C2=O)cc1] | 434.5 |
| IIb-321 | 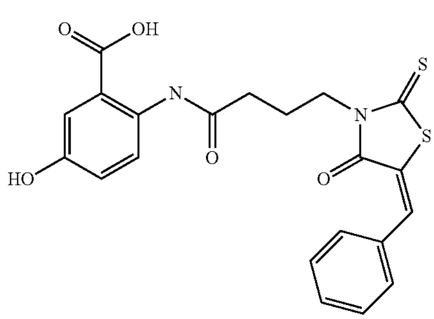 [SMILES: O=C(CCCN1C(=O)/C(=C\c2ccccc2)SC1=S)Nc1ccc(O)cc1C(=O)O] | 442.5 |

TABLE 7-continued

| | Phenmethylene-Thiazole Alkanoic Acids (R³ = OH) | |
|---|---|---|
| ID | Structure | MW |
| IIb-322 | | 434.5 |
| IIb-323 | | 428.5 |
| IIb-324 | | 377.5 |
| IIb-325 | | 363.5 |
| IIb-326 | | 373.4 |
| IIb-327 | | 378.5 |

TABLE 7-continued

Phenmethylene-Thiazole Alkanoic Acids ($R^3$ = OH)

| ID | Structure | MW |
| --- | --- | --- |
| IIb-328 | 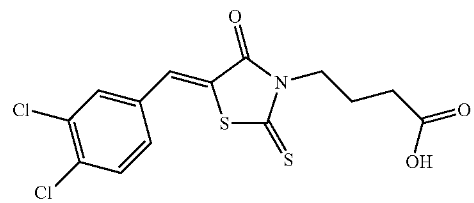 [SMILES: O=C(O)CCCN1C(=O)/C(=C/c2ccc(Cl)c(Cl)c2)SC1=S] | 376.3 |
| IIb-329 | 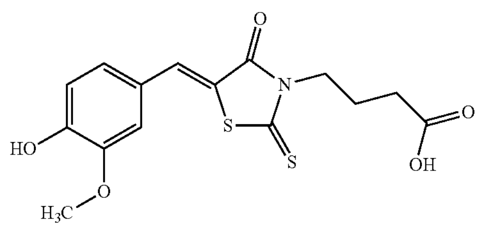 [SMILES: COc1cc(/C=C2\SC(=S)N(CCCC(=O)O)C2=O)ccc1O] | 353.4 |
| IIb-330 | 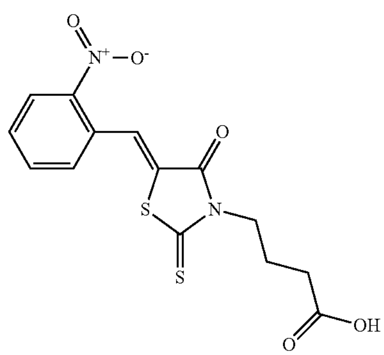 [SMILES: O=C(O)CCCN1C(=O)/C(=C/c2ccccc2[N+](=O)[O-])SC1=S] | 352.4 |
| IIb-331 | 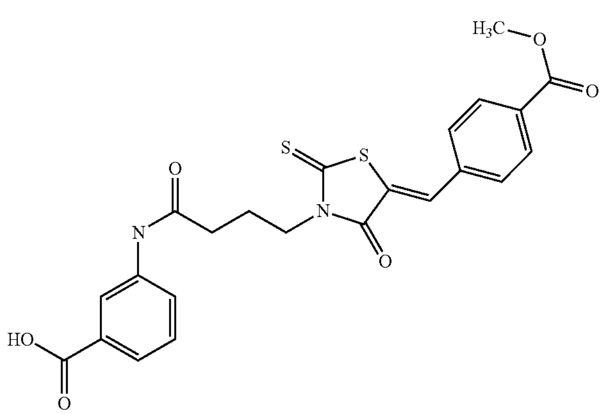 [SMILES: COC(=O)c1ccc(/C=C2\SC(=S)N(CCCC(=O)Nc3cccc(C(=O)O)c3)C2=O)cc1] | 484.6 |

TABLE 7-continued

Phenmethylene-Thiazole Alkanoic Acids ($R^3$ = OH)

| ID | Structure | MW |
| --- | --- | --- |
| IIb-332 | 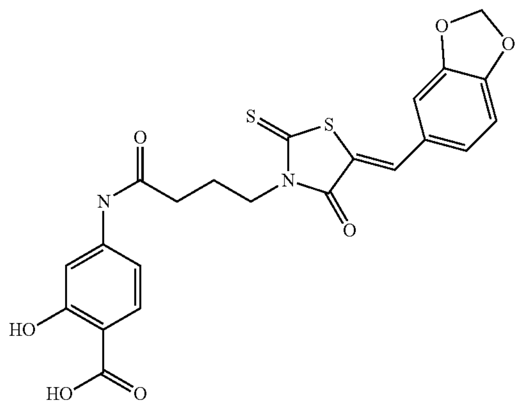 [SMILES: O=C(CCCN1C(=O)/C(=C/c2ccc3c(c2)OCO3)SC1=S)Nc1ccc(C(=O)O)c(O)c1] | 486.5 |
| IIb-333 | 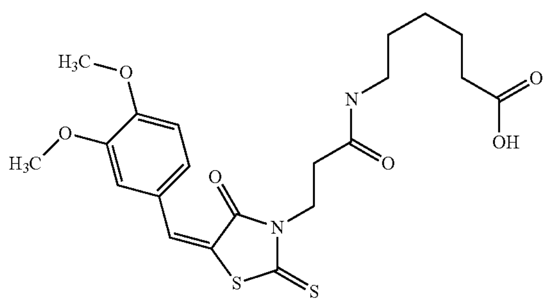 [SMILES: COc1ccc(/C=C2/SC(=S)N(CCC(=O)NCCCCCC(=O)O)C2=O)cc1OC] | 466.6 |
| IIb-334 | 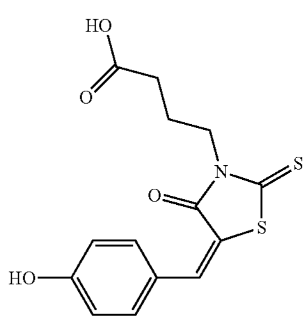 [SMILES: O=C(O)CCCN1C(=O)/C(=C\c2ccc(O)cc2)SC1=S] | 323.4 |
| IIb-335 | 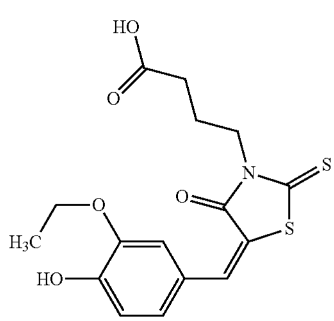 [SMILES: CCOc1cc(/C=C2/SC(=S)N(CCCC(=O)O)C2=O)ccc1O] | 367.4 |

TABLE 7-continued

| Phenmethylene-Thiazole Alkanoic Acids (R³ = OH) | | |
|---|---|---|
| ID | Structure | MW |
| IIb-336 | | 321.4 |
| IIb-337 | | 418.3 |
| IIb-338 | | 367.4 |
| IIb-339 | | 399.5 |
| IIb-340 | | 429.5 |

TABLE 7-continued

| | Phenmethylene-Thiazole Alkanoic Acids (R³ = OH) | |
|---|---|---|
| ID | Structure | MW |
| IIb-341 | | 422.5 |
| IIb-342 | | 457.6 |
| IIb-343 | | 338.4 |
| IIb-344 | | 338.4 |

TABLE 7-continued

Phenmethylene-Thiazole Alkanoic Acids (R³ = OH)

| ID | Structure | MW |
|---|---|---|
| IIb-345 | 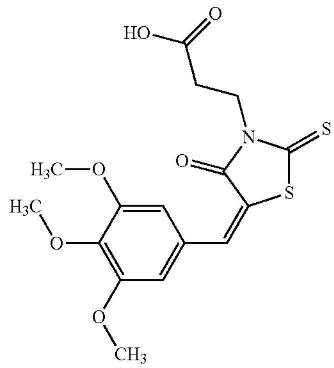 [SMILES: COc1cc(/C=C2/SC(=S)N(CCC(=O)O)C2=O)cc(OC)c1OC] | 383.4 |
| IIb-346 | 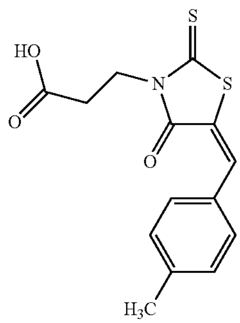 [SMILES: Cc1ccc(/C=C2/SC(=S)N(CCC(=O)O)C2=O)cc1] | 307.4 |
| IIb-347 | 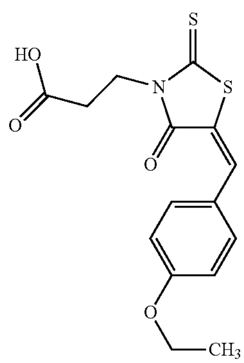 [SMILES: CCOc1ccc(/C=C2/SC(=S)N(CCC(=O)O)C2=O)cc1] | 337.4 |
| IIb-348 | 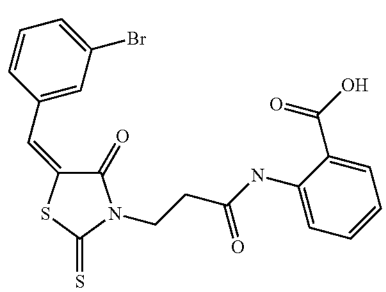 [SMILES: O=C(CCN1C(=O)/C(=C\c2cccc(Br)c2)SC1=S)Nc1ccccc1C(=O)O] | 491.4 |

TABLE 7-continued

Phenmethylene-Thiazole Alkanoic Acids ($R^3$ = OH)

| ID | Structure | MW |
|---|---|---|
| IIb-349 | 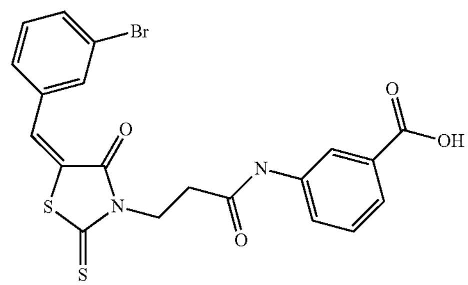 [SMILES: O=C(CCN1C(=O)/C(=C\c2cccc(Br)c2)SC1=S)Nc1cccc(C(=O)O)c1] | 491.4 |
| IIb-350 | 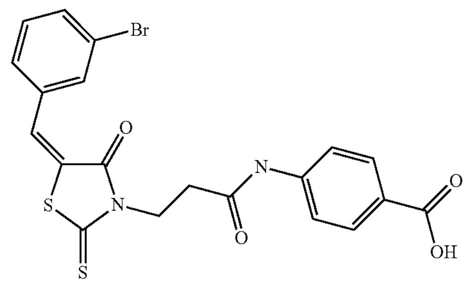 [SMILES: O=C(CCN1C(=O)/C(=C\c2cccc(Br)c2)SC1=S)Nc1ccc(C(=O)O)cc1] | 491.4 |
| IIb-351 | 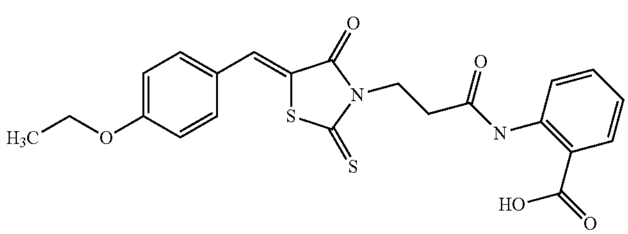 [SMILES: CCOc1ccc(/C=C2\SC(=S)N(CCC(=O)Nc3ccccc3C(=O)O)C2=O)cc1] | 456.5 |
| IIb-352 | 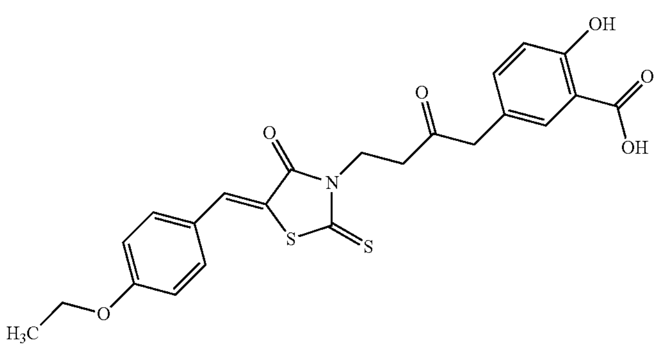 [SMILES: CCOc1ccc(/C=C2\SC(=S)N(CCC(=O)Cc3ccc(O)c(C(=O)O)c3)C2=O)cc1] | 472.5 |
| IIb-353 | 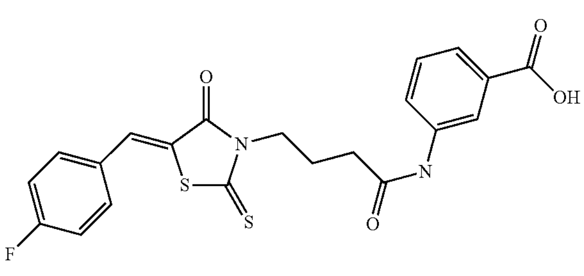 [SMILES: O=C(CCCN1C(=O)/C(=C/c2ccc(F)cc2)SC1=S)Nc1cccc(C(=O)O)c1] | 444.5 |

TABLE 7-continued

Phenmethylene-Thiazole Alkanoic Acids (R³ = OH)

| ID | Structure | MW |
|---|---|---|
| IIb-354 | 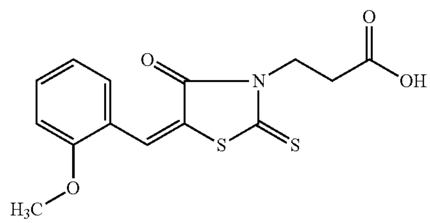 | 323.4 |
| IIb-355 | 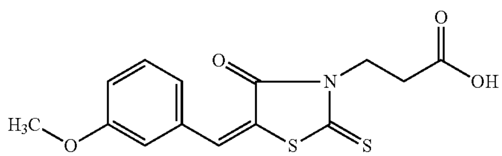 [SMILES: COc1cccc(/C=C2/SC(=S)N(CCC(=O)O)C2=O)c1] | 323.4 |
| IIb-356 | 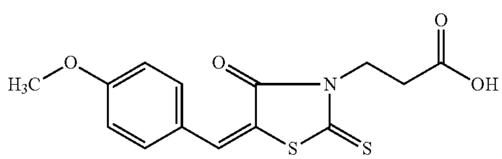 [SMILES: COc1ccc(/C=C2/SC(=S)N(CCC(=O)O)C2=O)cc1] | 323.4 |
| IIb-357 | 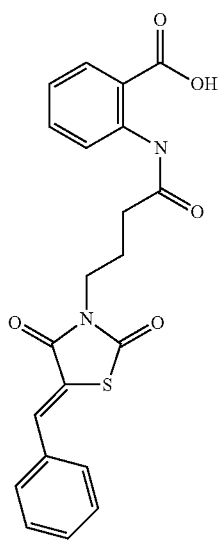 [SMILES: O=C(CCCN1C(=O)S/C(=C\c2ccccc2)C1=O)Nc1ccccc1C(=O)O] | 426.5 |
| IIb-358 | 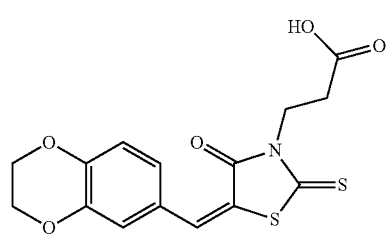 [SMILES: O=C(O)CCN1C(=O)/C(=C\c2ccc3c(c2)OCCO3)SC1=S] | 351.4 |

TABLE 7-continued

Phenmethylene-Thiazole Alkanoic Acids ($R^3$ = OH)

| ID | Structure | MW |
| --- | --- | --- |
| IIb-359 | 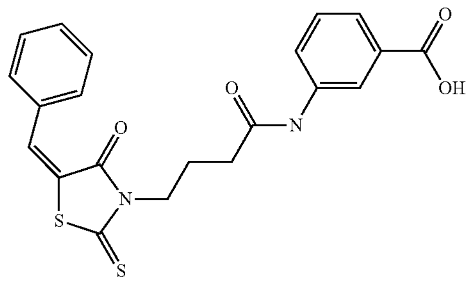 [SMILES: O=C(CCCN1C(=O)/C(=C\c2ccccc2)SC1=S)Nc1cccc(C(=O)O)c1] | 426.5 |
| IIb-360 | 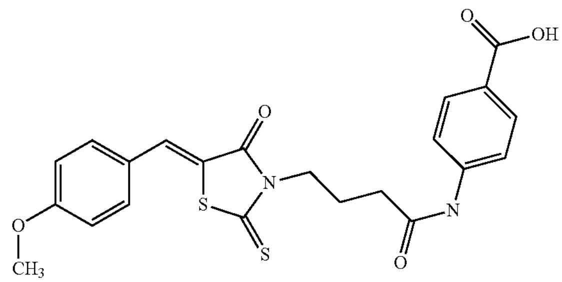 [SMILES: COc1ccc(/C=C2\SC(=S)N(CCCC(=O)Nc3ccc(C(=O)O)cc3)C2=O)cc1] | 456.5 |
| IIb-361 | 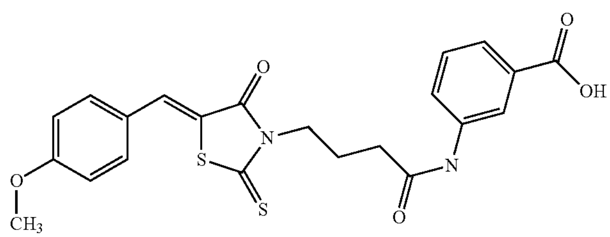 [SMILES: COc1ccc(/C=C2\SC(=S)N(CCCC(=O)Nc3cccc(C(=O)O)c3)C2=O)cc1] | 456.5 |
| IIb-362 | 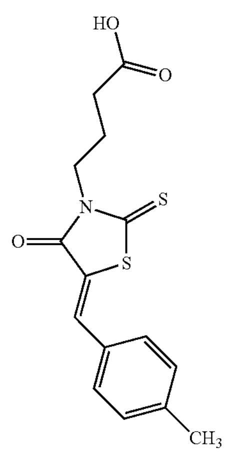 [SMILES: Cc1ccc(/C=C2\SC(=S)N(CCCC(=O)O)C2=O)cc1] | 321.4 |
| IIb-363 | 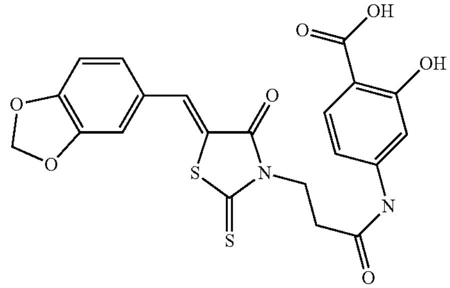 [SMILES: O=C(CCN1C(=O)/C(=C/c2ccc3c(c2)OCO3)SC1=S)Nc1ccc(C(=O)O)c(O)c1] | 472.5 |

TABLE 7-continued

Phenmethylene-Thiazole Alkanoic Acids ($R^3$ = OH)

| ID | Structure | MW |
|---|---|---|
| IIb-364 | 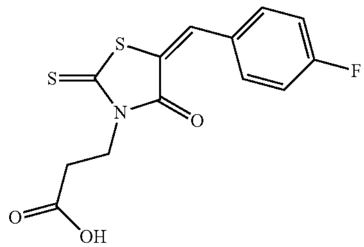 [SMILES: O=C(O)CCN1C(=O)/C(=C\c2ccc(F)cc2)SC1=S] | 311.4 |
| IIb-365 | 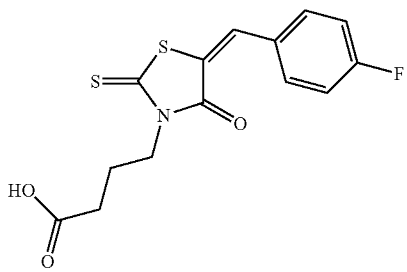 [SMILES: O=C(O)CCCN1C(=O)/C(=C\c2ccc(F)cc2)SC1=S] | 325.4 |
| IIb-366 | 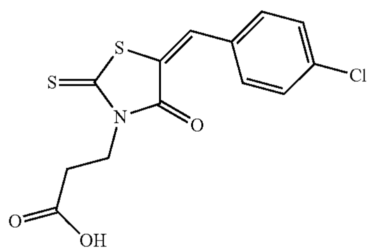 [SMILES: O=C(O)CCN1C(=O)/C(=C\c2ccc(Cl)cc2)SC1=S] | 327.8 |
| IIb-367 | 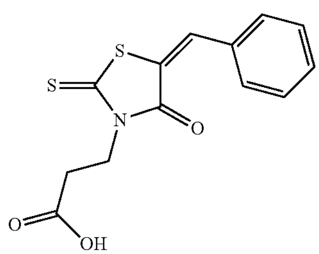 [SMILES: O=C(O)CCN1C(=O)/C(=C\c2ccccc2)SC1=S] | 293.4 |
| IIb-368 | 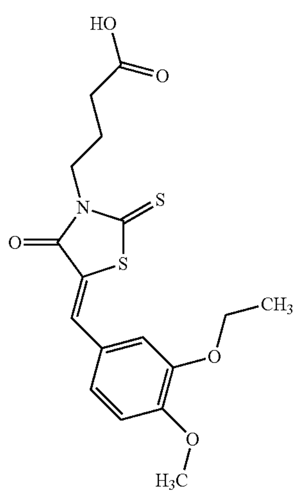 [SMILES: CCOc1cc(/C=C2\SC(=S)N(CCCC(=O)O)C2=O)ccc1OC] | 381.5 |

TABLE 7-continued
Phenmethylene-Thiazole Alkanoic Acids ($R^3$ = OH)
| ID | Structure | MW |
|---|---|---|
| IIb-369 | 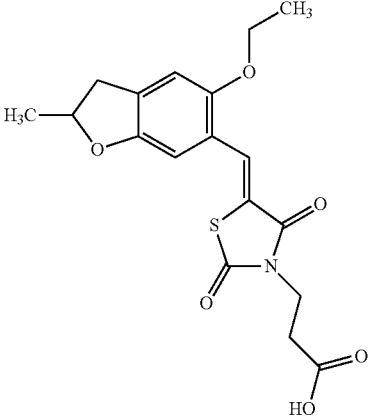 [SMILES: CCOc1cc2c(cc1/C=C1\SC(=O)N(CCC(=O)O)C1=O)OC(C)C2] | 393.5 |
| IIb-370 | 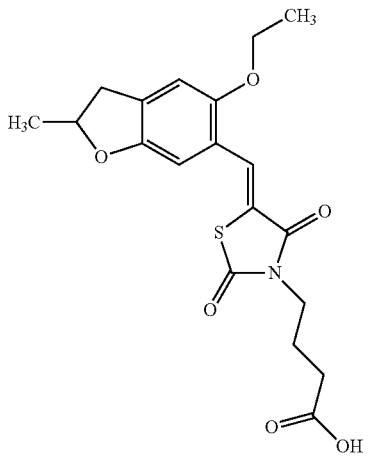 [SMILES: CCOc1cc2c(cc1/C=C1\SC(=O)N(CCCC(=O)O)C1=O)OC(C)C2] | 407.5 |
| IIb-371 | 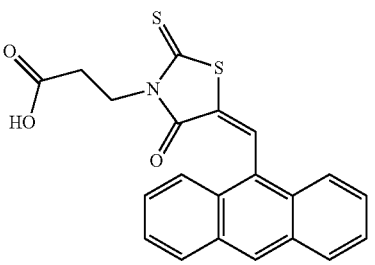 [SMILES: O=C(O)CCN1C(=O)/C(=C\c2c3ccccc3cc3ccccc23)SC1=S] | 393.5 |
| IIb-372 | 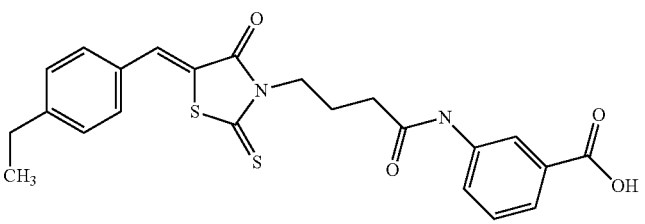 [SMILES: CCc1ccc(/C=C2\SC(=S)N(CCCC(=O)Nc3cccc(C(=O)O)c3)C2=O)cc1] | 454.6 |

TABLE 7-continued
Phenmethylene-Thiazole Alkanoic Acids ($R^3$ = OH)
| ID | Structure | MW |
|---|---|---|
| IIb-373 | 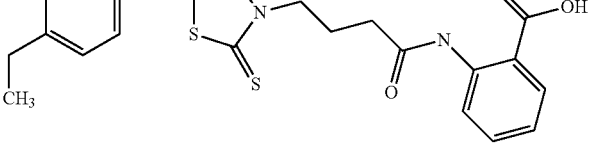 | 454.6 |
| IIb-374 | 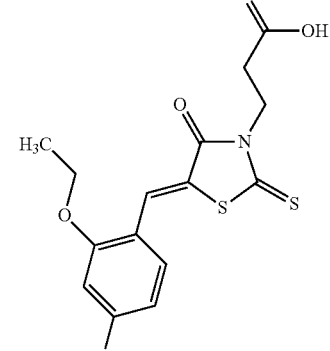 | 381.5 |
| IIb-375 | 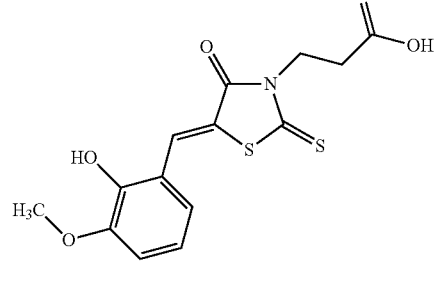 | 339.4 |
| IIb-376 | 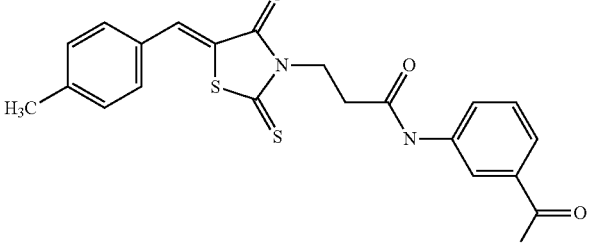 | 426.5 |

TABLE 7-continued

Phenmethylene-Thiazole Alkanoic Acids ($R^3$ = OH)

| ID | Structure | MW |
| --- | --- | --- |
| IIb-377 | 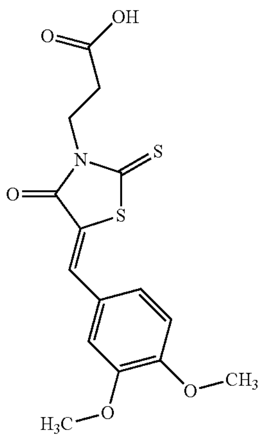 [SMILES: COc1ccc(/C=C2\SC(=S)N(CCC(=O)O)C2=O)cc1OC] | 353.4 |
| IIb-378 | 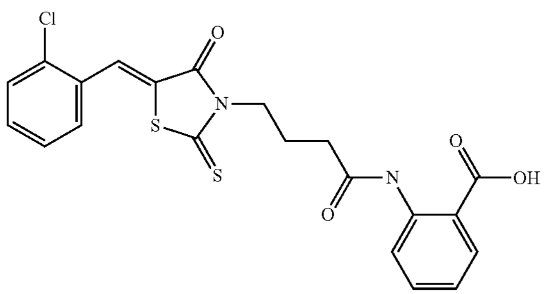 [SMILES: O=C(CCCN1C(=O)/C(=C/c2ccccc2Cl)SC1=S)Nc1ccccc1C(=O)O] | 461.0 |
| IIb-379 | 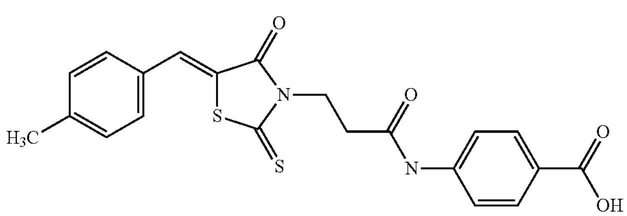 [SMILES: Cc1ccc(/C=C2\SC(=S)N(CCC(=O)Nc3ccc(C(=O)O)cc3)C2=O)cc1] | 426.5 |
| IIb-380 | 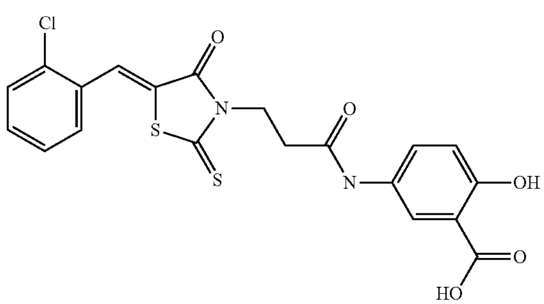 [SMILES: O=C(CCN1C(=O)/C(=C/c2ccccc2Cl)SC1=S)Nc1ccc(O)c(C(=O)O)c1] | 462.9 |
| IIb-381 | 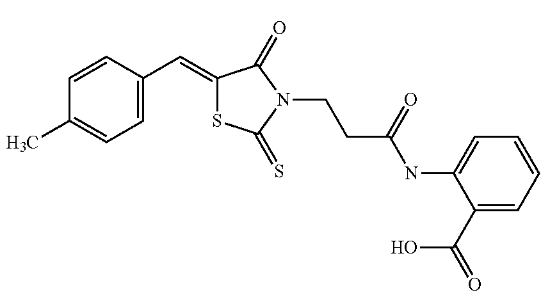 [SMILES: Cc1ccc(/C=C2\SC(=S)N(CCC(=O)Nc3ccccc3C(=O)O)C2=O)cc1] | 426.5 |

TABLE 7-continued

Phenmethylene-Thiazole Alkanoic Acids ($R^3$ = OH)

| ID | Structure | MW |
|---|---|---|
| IIb-382 | 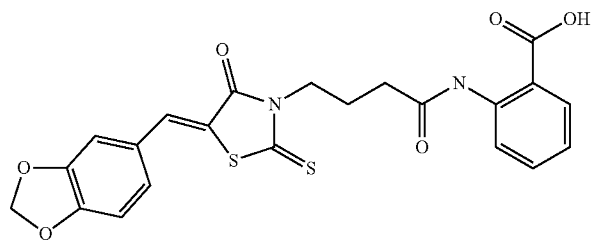 [SMILES: O=C(CCCN1C(=O)/C(=C/c2ccc3c(c2)OCO3)SC1=S)Nc1ccccc1C(=O)O] | 470.5 |
| IIb-383 | 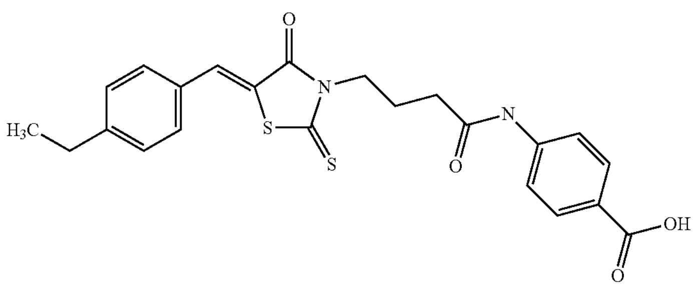 [SMILES: CCc1ccc(/C=C2\SC(=S)N(CCCC(=O)Nc3ccc(C(=O)O)cc3)C2=O)cc1] | 454.6 |
| IIb-384 | 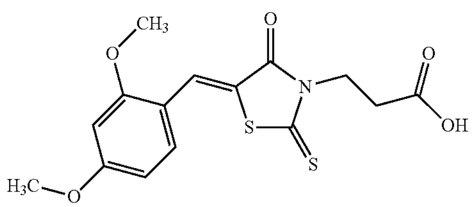 [SMILES: COc1ccc(/C=C2\SC(=S)N(CCC(=O)O)C2=O)c(OC)c1] | 353.4 |
| IIb-385 | 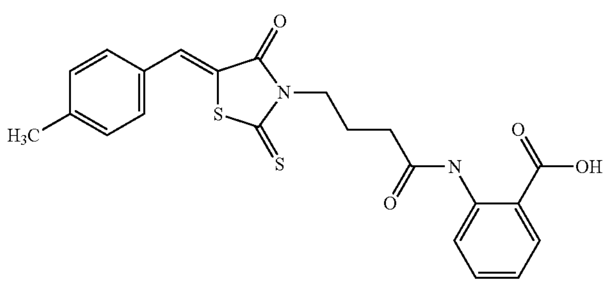 [SMILES: Cc1ccc(/C=C2\SC(=S)N(CCCC(=O)Nc3ccccc3C(=O)O)C2=O)cc1] | 440.5 |
| IIb-386 | 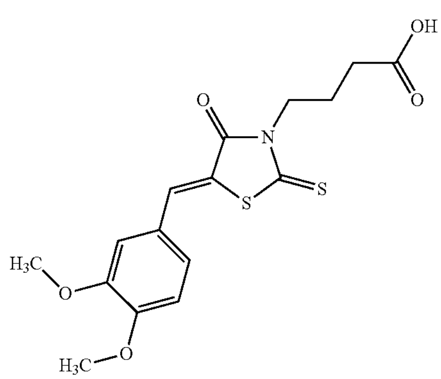 [SMILES: COc1ccc(/C=C2\SC(=S)N(CCCC(=O)O)C2=O)cc1OC] | 367.4 |

TABLE 7-continued

Phenmethylene-Thiazole Alkanoic Acids (R³ = OH)

| ID | Structure | MW |
|---|---|---|
| IIb-387 | 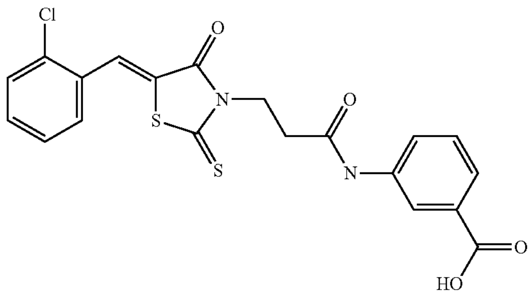 [SMILES: O=C(CCN1C(=O)/C(=C/c2ccccc2Cl)SC1=S)Nc1cccc(C(=O)O)c1] | 446.9 |
| IIb-388 | 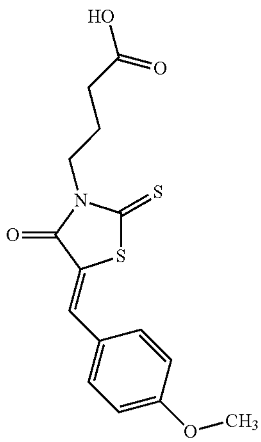 [SMILES: COc1ccc(/C=C2\SC(=S)N(CCCC(=O)O)C2=O)cc1] | 337.4 |
| IIb-389 | 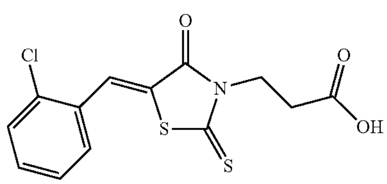 [SMILES: O=C(O)CCN1C(=O)/C(=C/c2ccccc2Cl)SC1=S] | 327.8 |
| IIb-390 | 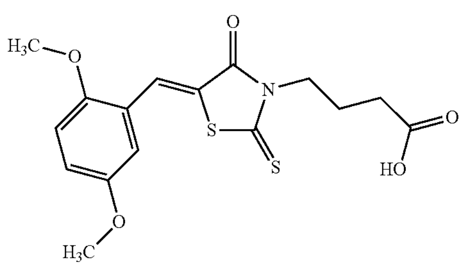 [SMILES: COc1ccc(OC)c(/C=C2\SC(=S)N(CCCC(=O)O)C2=O)c1] | 367.4 |
| IIb-391 | 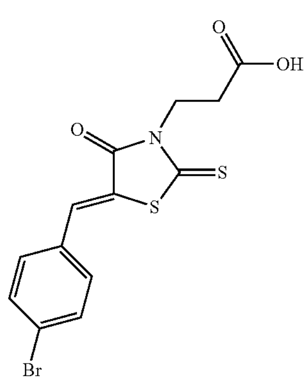 [SMILES: O=C(O)CCN1C(=O)/C(=C/c2ccc(Br)cc2)SC1=S] | 372.3 |

TABLE 7-continued

| Phenmethylene-Thiazole Alkanoic Acids ($R^3$ = OH) | | |
|---|---|---|
| ID | Structure | MW |
| IIb-392 | | 351.4 |
| IIb-393 | | 440.5 |
| IIb-394 | | 446.9 |
| IIb-395 | | 351.4 |
| IIb-396 | | 307.4 |

TABLE 7-continued

Phenmethylene-Thiazole Alkanoic Acids ($R^3$ = OH)

| ID | Structure | MW |
|---|---|---|
| IIb-397 | 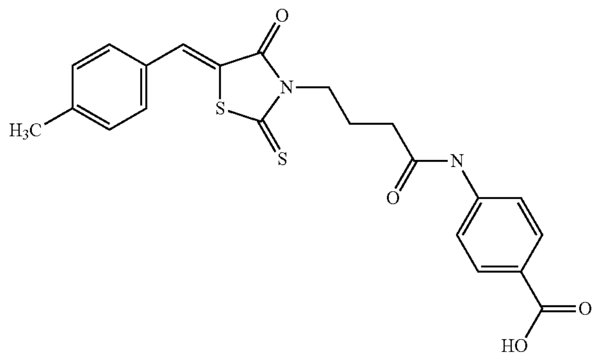 [SMILES: Cc1ccc(/C=C2\SC(=S)N(CCCC(=O)Nc3ccc(C(=O)O)cc3)C2=O)cc1] | 440.5 |
| IIb-398 | 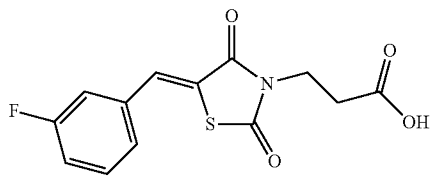 [SMILES: O=C(O)CCN1C(=O)S/C(=C\c2cccc(F)c2)C1=O] | 311.4 |
| IIb-399 | 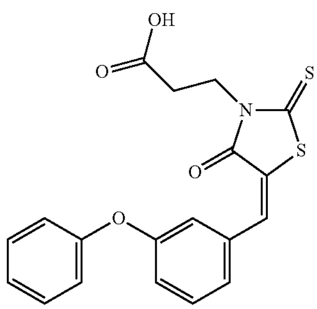 [SMILES: O=C(O)CCN1C(=O)/C(=C\c2cccc(Oc3ccccc3)c2)SC1=S] | 385.5 |
| IIb-400 | 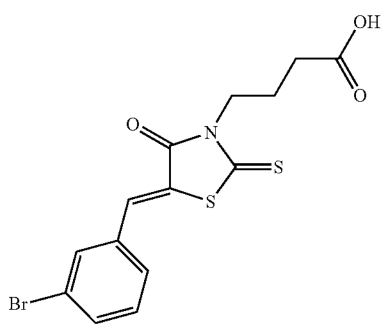 [SMILES: O=C(O)CCCN1C(=O)/C(=C/c2cccc(Br)c2)SC1=S] | 386.3 |
| IIb-401 | 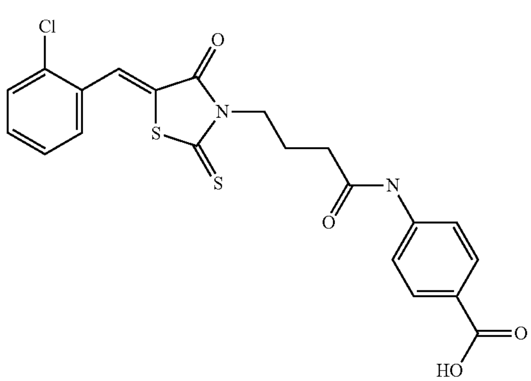 [SMILES: O=C(CCCN1C(=O)/C(=C/c2ccccc2Cl)SC1=S)Nc1ccc(C(=O)O)cc1] | 461.0 |

TABLE 7-continued

Phenmethylene-Thiazole Alkanoic Acids (R³ = OH)

| ID | Structure | MW |
|---|---|---|
| IIb-402 | 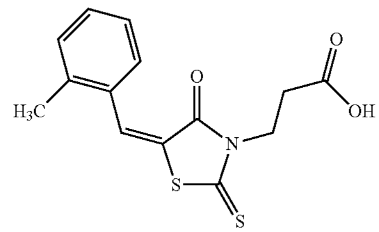 [SMILES: Cc1ccccc1/C=C1/SC(=S)N(CCC(=O)O)C1=O] | 307.4 |
| IIb-403 | 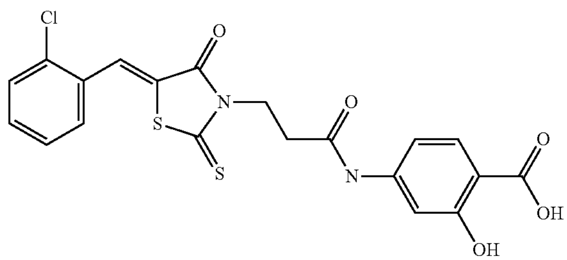 [SMILES: O=C(CCN1C(=O)/C(=C/c2ccccc2Cl)SC1=S)Nc1ccc(C(=O)O)c(O)c1] | 462.9 |
| IIb-404 | 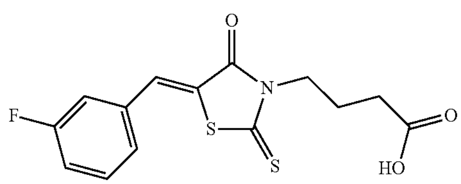 [SMILES: O=C(O)CCCN1C(=O)/C(=C/c2cccc(F)c2)SC1=S] | 325.4 |
| IIb-405 | 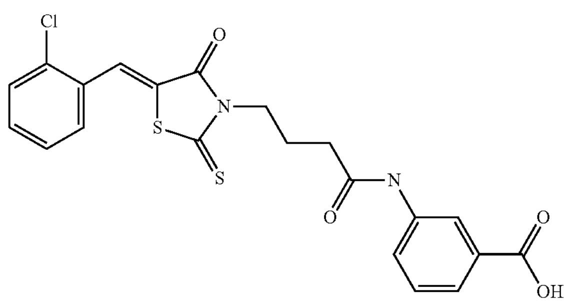 [SMILES: O=C(CCCN1C(=O)/C(=C/c2ccccc2Cl)SC1=S)Nc1cccc(C(=O)O)c1] | 461.0 |
| IIb-406 | 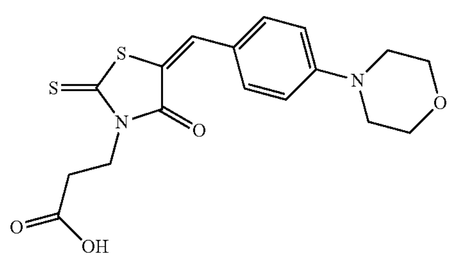 [SMILES: O=C(O)CCN1C(=O)/C(=C\c2ccc(N3CCOCC3)cc2)SC1=S] | 378.5 |
| IIb-407 | 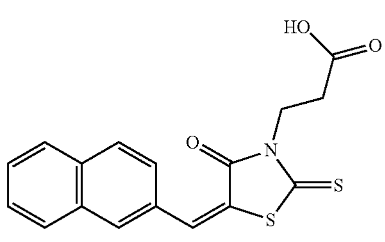 [SMILES: O=C(O)CCN1C(=O)/C(=C\c2ccc3ccccc3c2)SC1=S] | 343.4 |

TABLE 7-continued

Phenmethylene-Thiazole Alkanoic Acids (R³ = OH)

| ID | Structure | MW |
|---|---|---|
| IIb-408 | 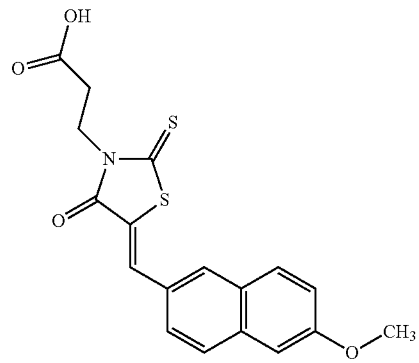 [SMILES: COc1ccc2cc(/C=C3\SC(=S)N(CCC(=O)O)C3=O)ccc2c1] | 373.5 |
| IIb-409 | 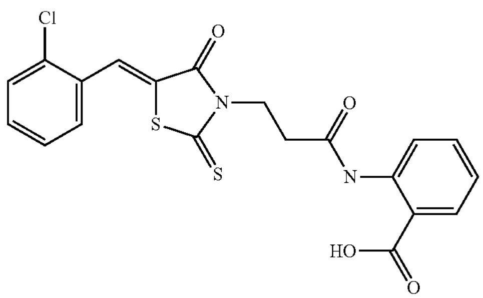 [SMILES: O=C(CCN1C(=O)/C(=C/c2ccccc2Cl)SC1=S)Nc1ccccc1C(=O)O] | 446.9 |
| IIb-410 | 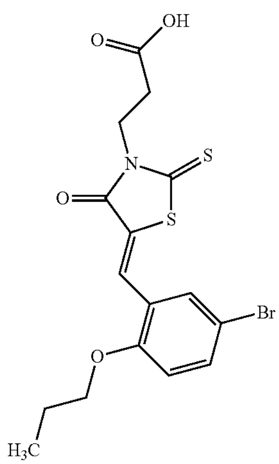 [SMILES: CCCOc1ccc(Br)cc1/C=C1\SC(=S)N(CCC(=O)O)C1=O] | 430.3 |
| IIb-411 | 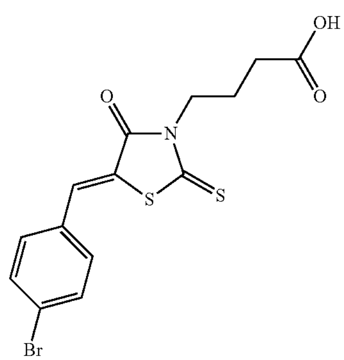 [SMILES: O=C(O)CCCN1C(=O)/C(=C/c2ccc(Br)cc2)SC1=S] | 386.3 |

TABLE 7-continued

Phenmethylene-Thiazole Alkanoic Acids ($R^3$ = OH)

| ID | Structure | MW |
|---|---|---|
| IIb-412 | 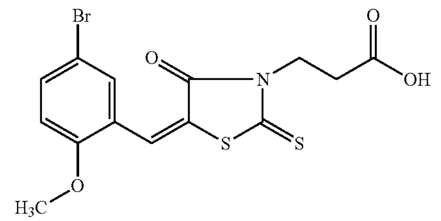 [SMILES: COc1ccc(Br)cc1/C=C1/SC(=S)N(CCC(=O)O)C1=O] | 402.3 |
| IIb-413 | 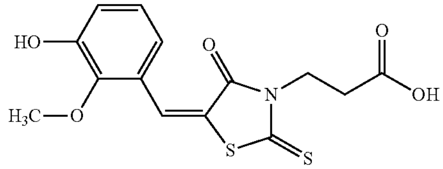 [SMILES: COc1c(O)cccc1/C=C1/SC(=S)N(CCC(=O)O)C1=O] | 339.4 |
| IIb-414 | 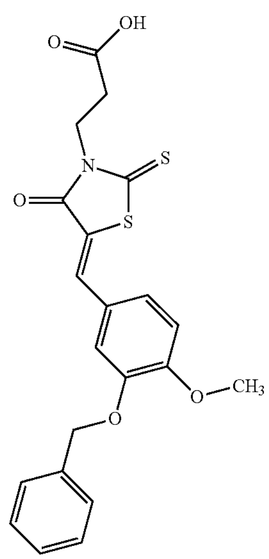 [SMILES: COc1ccc(/C=C2\SC(=S)N(CCC(=O)O)C2=O)cc1OCc1ccccc1] | 429.5 |
| IIb-415 | 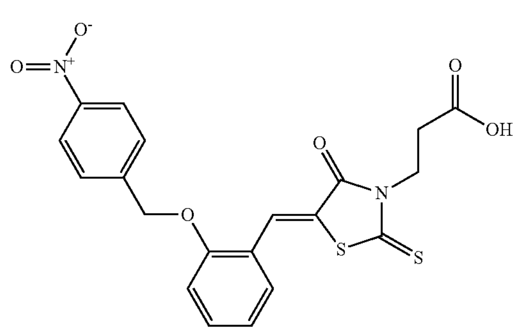 [SMILES: O=C(O)CCN1C(=O)/C(=C/c2ccccc2OCc2ccc([N+](=O)[O-])cc2)SC1=S] | 444.5 |

TABLE 8

Pyridyl And Quinolinyl Methylenyl Alkanoic Acids (R³ = OH)

| ID | Structure | MW |
|---|---|---|
| IIb-416 | 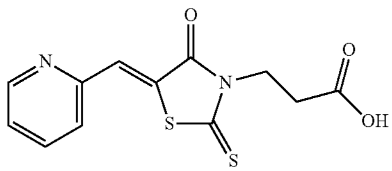 [SMILES: O=C(O)CCN1C(=O)/C(=C/c2ccccn2)SC1=S] | 294.4 |
| IIb-417 | 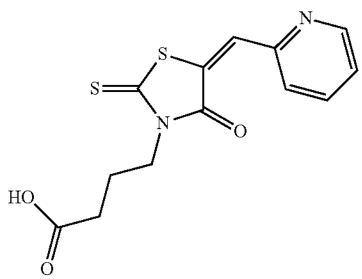 [SMILES: O=C(O)CCCN1C(=O)/C(=C\c2ccccn2)SC1=S] | 308.4 |
| IIb-418 | 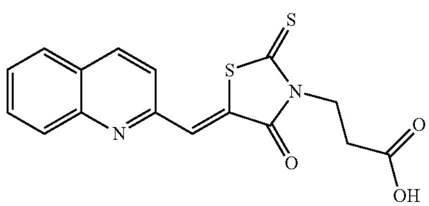 [SMILES: O=C(O)CCN1C(=O)/C(=C/c2ccc3ccccc3n2)SC1=S] | 344.4 |
| IIb-419 | 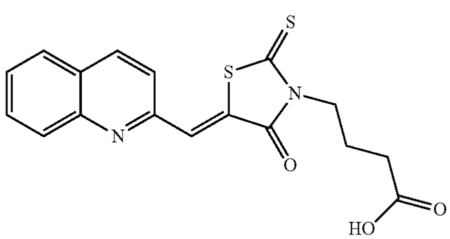 [SMILES: O=C(O)CCCN1C(=O)/C(=C/c2ccc3ccccc3n2)SC1=S] | 358.4 |
| IIb-420 | 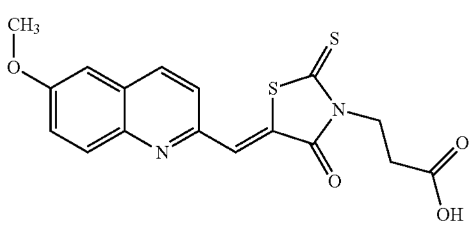 [SMILES: COc1ccc2nc(/C=C3\SC(=S)N(CCC(=O)O)C3=O)ccc2c1] | 374.4 |
| IIb-421 | 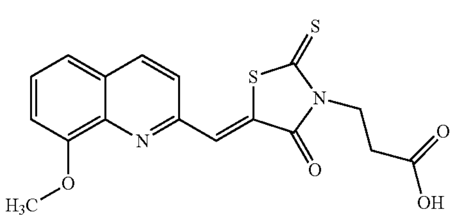 [SMILES: COc1cccc2ccc(/C=C3\SC(=S)N(CCC(=O)O)C3=O)nc12] | 374.4 |
| IIb-422 | 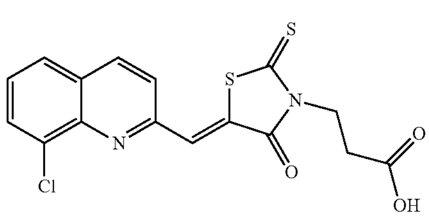 [SMILES: O=C(O)CCN1C(=O)/C(=C/c2ccc3cccc(Cl)c3n2)SC1=S] | 378.9 |
| IIb-423 | | 388.5 |
| IIb-424 | | 388.5 |
| IIb-425 | | 392.9 |
| IIb-426 | | 388.5 |
| IIb-427 | | 402.5 |

TABLE 8-continued
Pyridyl And Quinolinyl Methylenyl Alkanoic Acids (R³ = OH)
| ID | Structure | MW |
|---|---|---|
| IIb-428 | 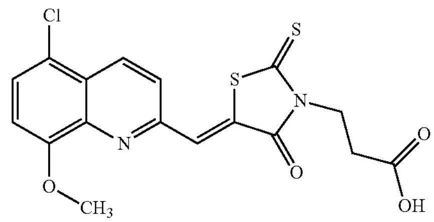 [SMILES: COc1ccc(Cl)c2ccc(/C=C3\SC(=S)N(CCC(=O)O)C3=O)nc12] | 408.9 |
| IIb-429 | 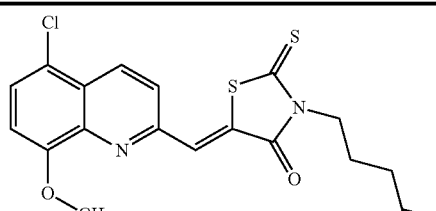 | 422.9 |
TABLE 9
Thiophenylmethylenyl Alkanoic Acids And Amides (R³ = O— And NH—)
| ID | Structure | MW |
|---|---|---|
| IIb-430 | | 327.4 |
| IIb-431 | | 446.6 |
| IIb-432 | | 404.5 |

TABLE 9-continued
Thiophenylmethylenyl Alkanoic Acids And Amides ($R^3$ = O— And NH—)
| | | |
|---|---|---|
| IIb-433 | 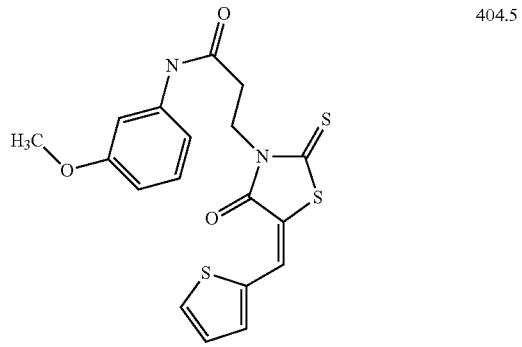 | 404.5 |
| IIb-434 | 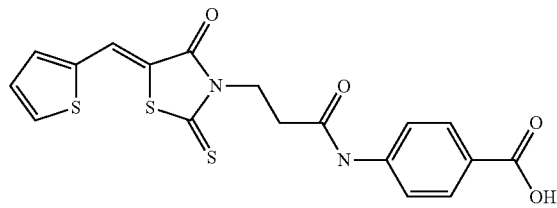 [SMILES: O=C(CCN1C(=O)/C(=C/c2cccs2)SC1=S)Nc1ccc(C(=O)O)cc1] | 418.5 |
| IIb-435 | 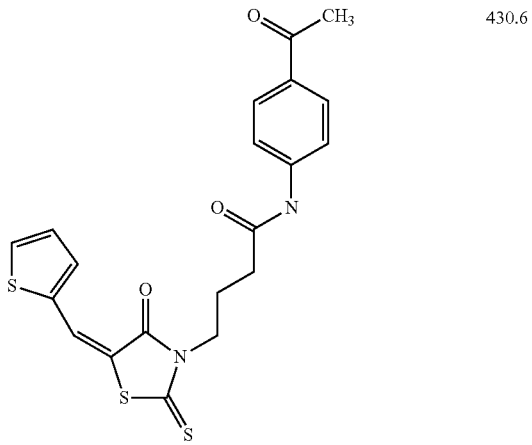 | 430.6 |
| IIb-436 | 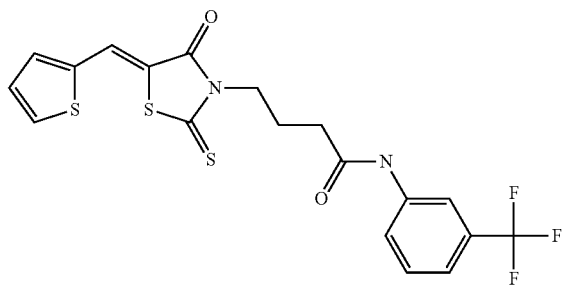 [SMILES: O=C(CCCN1C(=O)/C(=C/c2cccs2)SC1=S)Nc1cccc(C(F)(F)F)c1] | 456.5 |
| IIb-437 | 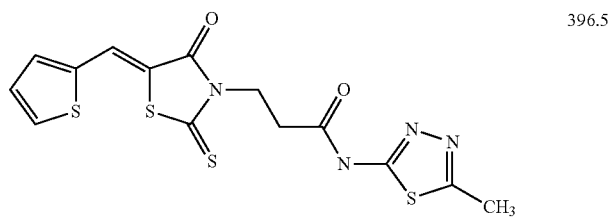 | 396.5 |

TABLE 9-continued
Thiophenylmethylenyl Alkanoic Acids And Amides ($R^3$ = O— And NH—)
| | | |
|---|---|---|
| IIb-438 | 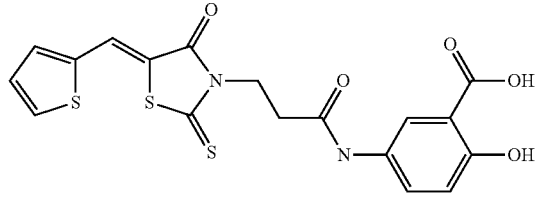 [SMILES: O=C(CCN1C(=O)/C(=C/c2cccs2)SC1=S)Nc1ccc(O)c(C(=O)O)c1] | 434.5 |
| IIb-439 | 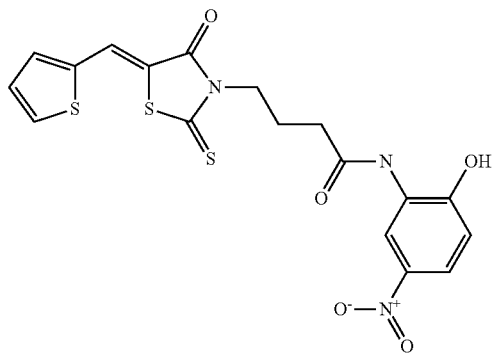 [SMILES: O=C(CCCN1C(=O)/C(=C/c2cccs2)SC1=S)Nc1cc([N+](=O)[O-])ccc1O] | 449.5 |
| IIb-440 | 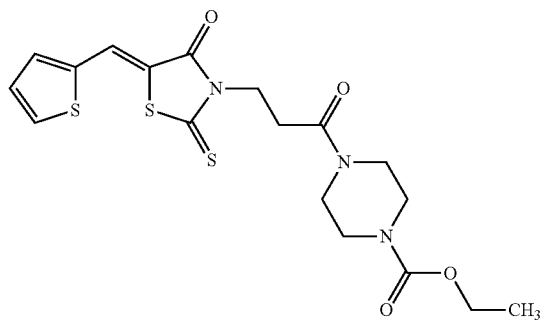 [SMILES: CCOC(=O)N1CCN(C(=O)CCN2C(=O)/C(=C/c3cccs3)SC2=S)CC1] | 439.6 |
| IIb-441 | 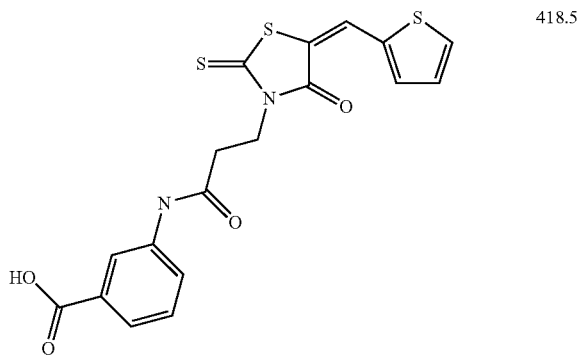 | 418.5 |
| IIb-442 | 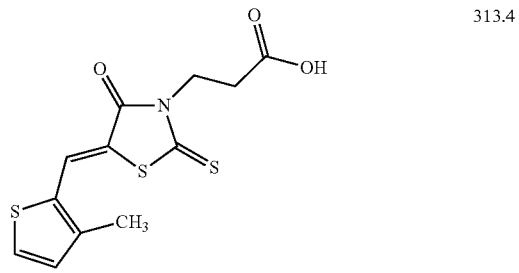 | 313.4 |

TABLE 9-continued
Thiophenylmethylenyl Alkanoic Acids And Amides ($R^3$ = O— And NH—)
| IIb-443 | 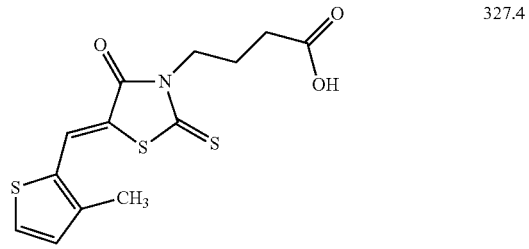 | 327.4 |
| IIb-444 | 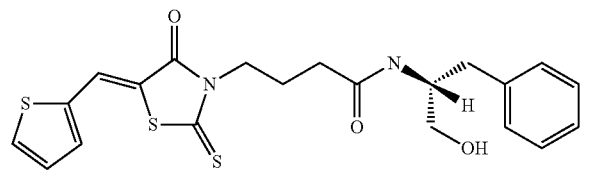 [SMILES: O=C(CCCN1C(=O)/C(=C/c2cccs2)SC1=S)N[C@@H](CO)Cc1ccccc1] | 446.6 |
| IIb-445 | 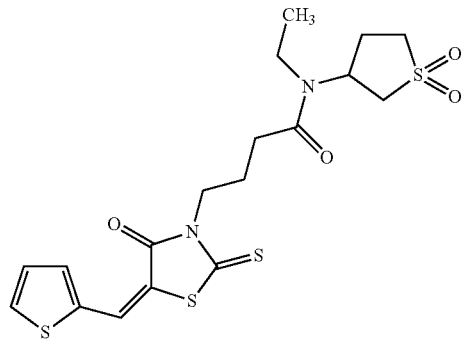 [SMILES: CCN(C(=O)CCCN1C(=O)/C(=C\c2cccs2)SC1=S)C1CCS(=O)(=O)C1] | 458.6 |
| IIb-446 | 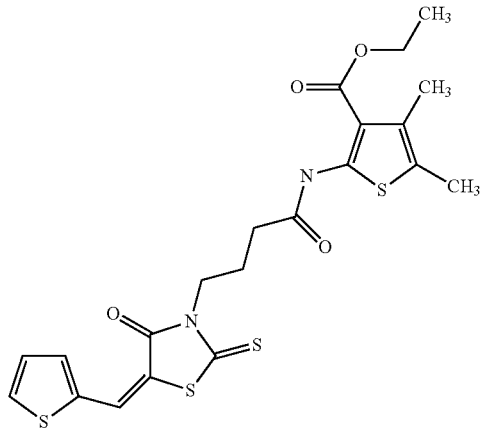 [SMILES: CCOC(=O)c1c(NC(=O)CCCN2C(=O)/C(=C\c3cccs3)SC2=S)sc(C)c1C] | 494.7 |
| IIb-447 | 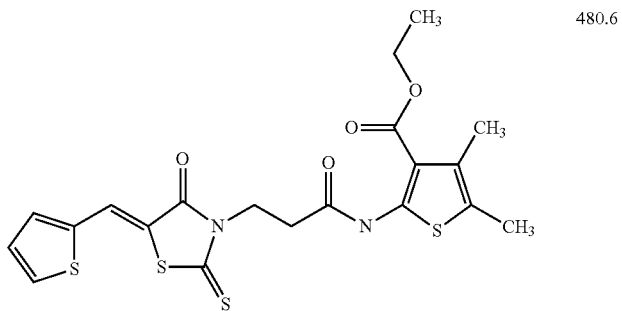 | 480.6 |

TABLE 9-continued
Thiophenylmethylenyl Alkanoic Acids And Amides ($R^3$ = O— And NH—)
IIb-448  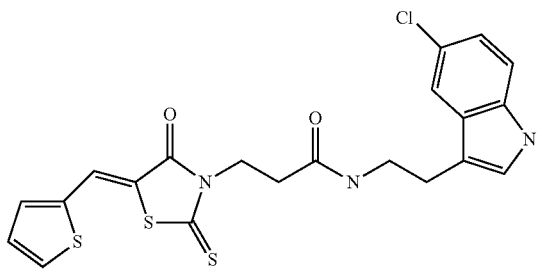 [SMILES: O=C(CCN1C(=O)/C(=C/c2cccs2)SC1=S)NCCc1c[nH]c2ccc(Cl)cc12]  476.0
IIb-449  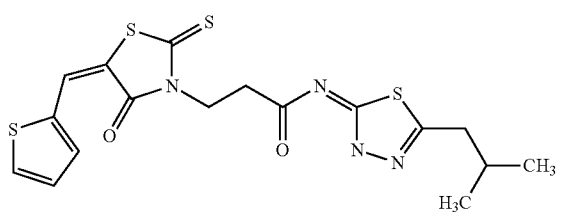 [SMILES: CC(C)Cc1n[nH]/c(=N\C(=O)CCN2C(=O)/C(=C\c3cccs3)SC2=S)s1]  438.6
IIb-450  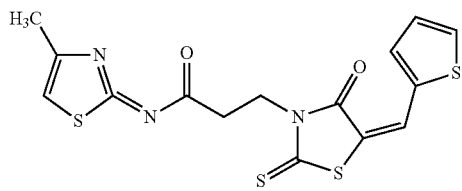  395.5
IIb-451  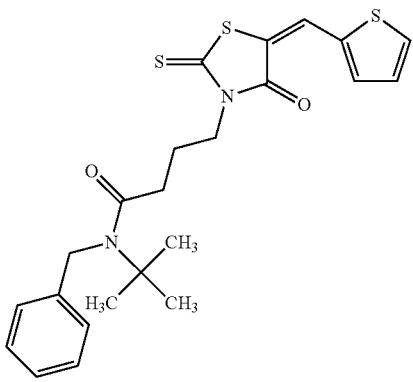 [SMILES: CC(C)(C)N(Cc1ccccc1)C(=O)CCCN1C(=O)/C(=C\c2cccs2)SC1=S]  458.7
IIb-452  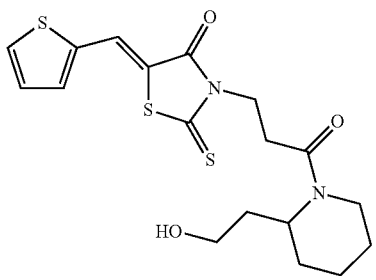 [SMILES: O=C1/C(=C/c2cccs2)SC(=S)N1CCC(=O)N1CCCCC1CCO]  410.6

TABLE 9-continued
Thiophenylmethylenyl Alkanoic Acids And Amides ($R^3$ = O— And NH—)
| IIb-453 | 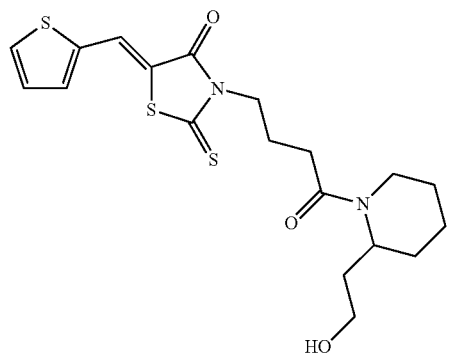 [SMILES: O=C1/C(=C/c2cccs2)SC(=S)N1CCCC(=O)N1CCCCC1CCO] | 424.6 |
| IIb-454 | 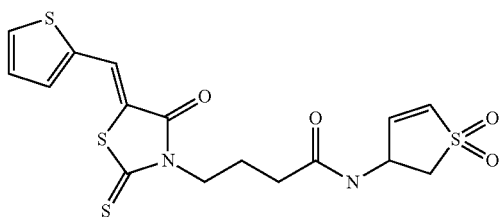 [SMILES: O=C(CCCN1C(=O)/C(=C/c2cccs2)SC1=S)NC1C=CS(=O)(=O)C1] | 428.6 |
| IIb-455 | 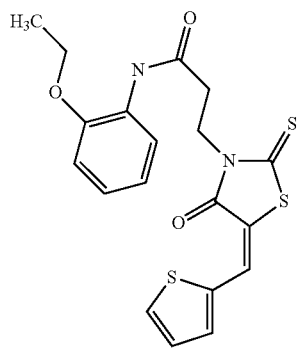 [SMILES: CCOc1ccccc1NC(=O)CCN1C(=O)/C(=C\c2cccs2)SC1=S] | 418.6 |
| IIb-456 | 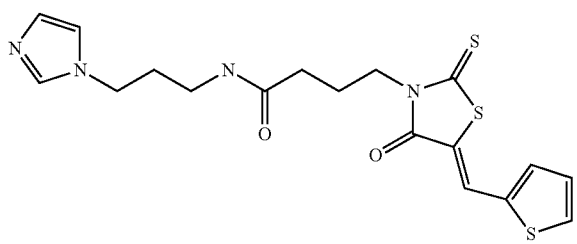 [SMILES: O=C(CCCN1C(=O)/C(=C/c2cccs2)SC1=S)NCCCn1ccnc1] | 420.6 |
| IIb-457 | 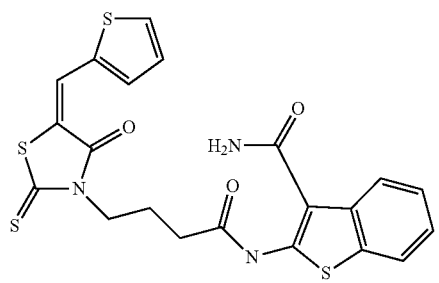 [SMILES: NC(=O)c1c(NC(=O)CCCN2C(=O)/C(=C\c3cccs3)SC2=S)sc2ccccc12] | 487.6 |

TABLE 9-continued

Thiophenylmethylenyl Alkanoic Acids And Amides ($R^3$ = O— And NH—)

| IIb-458 | | 457.6 |
| IIb-459 | | 398.6 |
| IIb-460 | | 380.6 |
| IIb-461 | | 412.6 |
| IIb-462 | | 456.5 |
| IIb-463 | | 432.6 |

TABLE 9-continued
Thiophenylmethylenyl Alkanoic Acids And Amides ($R^3$ = O— And NH—)
| | | |
|---|---|---|
| IIb-464 | 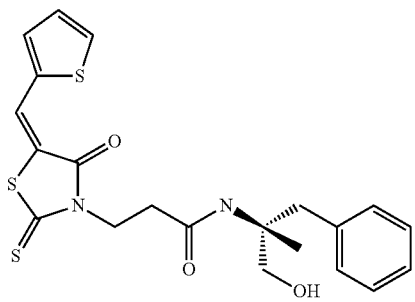 [SMILES: C[C@](CO)(Cc1ccccc1)NC(=O)CCN1C(=O)/C(=C\c2cccs2)SC1=S] | 432.6 |
| IIb-465 | 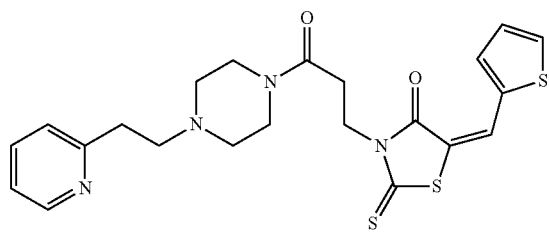 [SMILES: O=C(CCN1C(=O)/C(=C\c2cccs2)SC1=S)N1CCN(CCc2ccccn2)CC1] | 472.7 |
| IIb-466 | 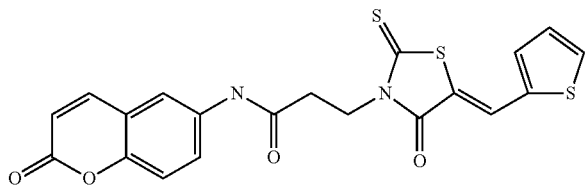 [SMILES: O=C(CCN1C(=O)/C(=C/c2cccs2)SC1=S)Nc1ccc2oc(=O)ccc2c1] | 442.5 |
| IIb-467 | 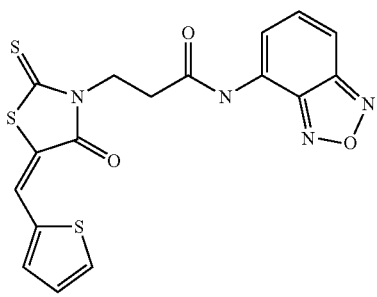 [SMILES: O=C(CCN1C(=O)/C(=C\c2cccs2)SC1=S)Nc1cccc2nonc12] | 416.5 |
| IIb-468 | 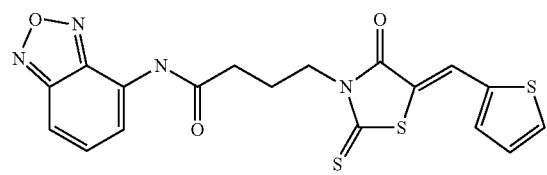 [SMILES: O=C(CCCN1C(=O)/C(=C/c2cccs2)SC1=S)Nc1cccc2nonc12] | 430.5 |
| IIb-469 | 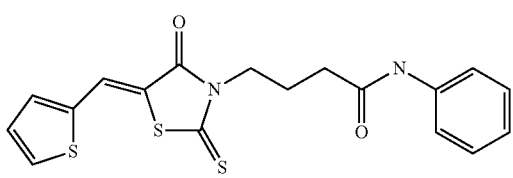 [SMILES: O=C(CCCN1C(=O)/C(=C/c2cccs2)SC1=S)Nc1ccccc1] | 388.5 |

TABLE 9-continued
Thiophenylmethylenyl Alkanoic Acids And Amides ($R^3$ = O— And NH—)
| | | |
|---|---|---|
| IIb-470 | 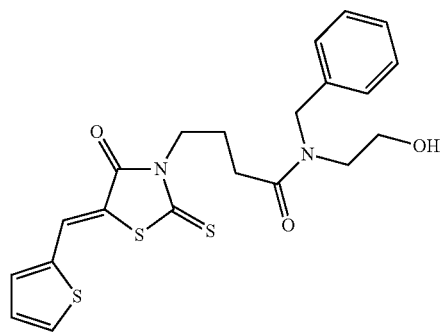 [SMILES: O=C(CCCN1C(=O)/C(=C/c2cccs2)SC1=S)N(CCO)Cc1ccccc1] | 446.6 |
| IIb-471 | 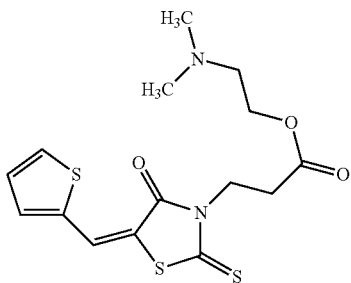 [SMILES: CN(C)CCOC(=O)CCN1C(=O)/C(=C\c2cccs2)SC1=S] | 370.5 |
| IIb-472 | 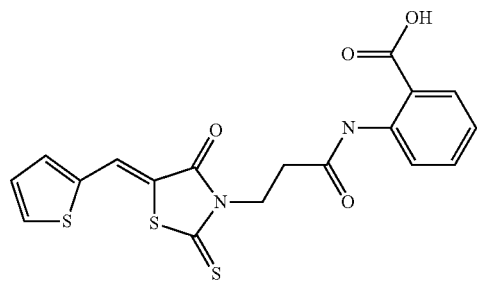 [SMILES: O=C(CCN1C(=O)/C(=C/c2cccs2)SC1=S)Nc1ccccc1C(=O)O] | 418.5 |
| IIb-473 | 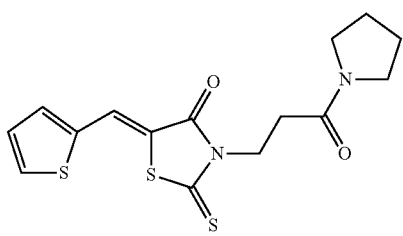 [SMILES: O=C(CCN1C(=O)/C(=C/c2cccs2)SC1=S)N1CCCC1] | 352.5 |
| IIb-474 | 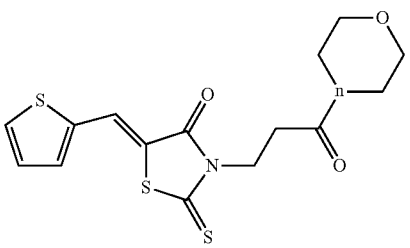 | 368.5 |
| IIb-475 | 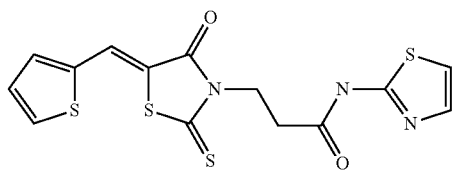 [SMILES: O=C(CCN1C(=O)/C(=C/c2cccs2)SC1=S)Nc1nccs1] | 381.5 |

TABLE 9-continued

Thiophenylmethylenyl Alkanoic Acids And Amides ($R^3$ = O— And NH—)

| | | |
|---|---|---|
| IIb-476 | | 383.5 |
| IIb-477 | | 379.5 |
| IIb-478 | | 375.5 |
| IIb-479 | | 375.5 |
| IIb-480 | | 432.6 |
| IIb-481 | | 341.5 |

TABLE 9-continued
Thiophenylmethylenyl Alkanoic Acids And Amides ($R^3$ = O— And NH—)
| IIb-482 | 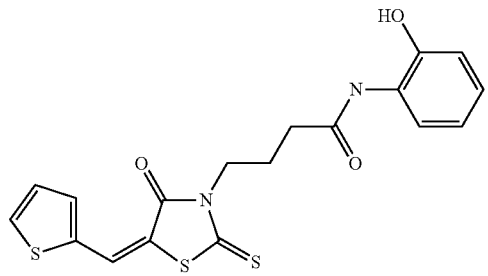 [SMILES: O=C(CCCN1C(=O)/C(=C\c2cccs2)SC1=S)Nc1ccccc1O] | 404.5 |
| IIb-483 | 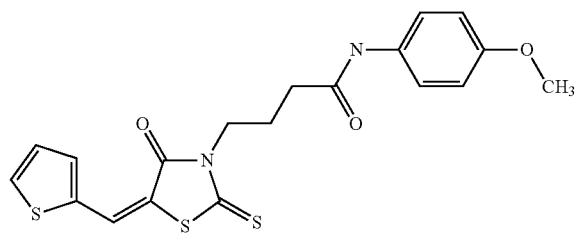 [SMILES: COc1ccc(NC(=O)CCCN2C(=O)/C(=C\c3cccs3)SC2=S)cc1] | 418.6 |
| IIb-484 | 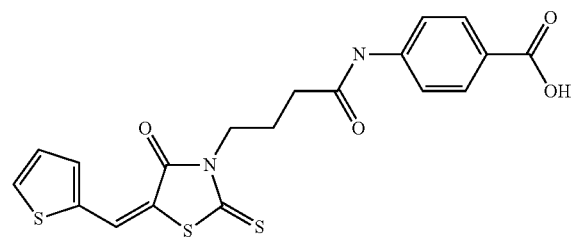 [SMILES: O=C(CCCN1C(=O)/C(=C\c2cccs2)SC1=S)Nc1ccc(C(=O)O)cc1] | 432.5 |
| IIb-485 | 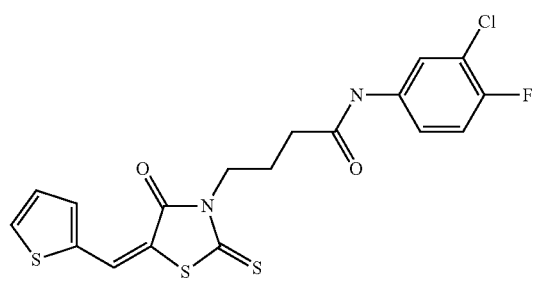 [SMILES: O=C(CCCN1C(=O)/C(=C\c2cccs2)SC1=S)Nc1ccc(F)c(Cl)c1] | 441.0 |
| IIb-486 | 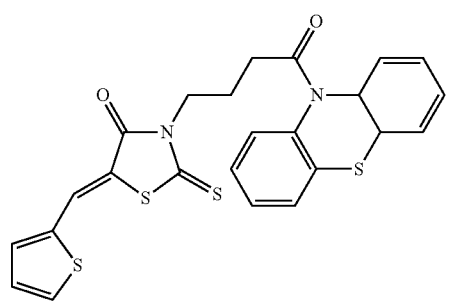 [SMILES: O=C1/C(=C/c2cccs2)SC(=S)N1CCCC(=O)N1c2ccccc2SC2C=CC=CC21] | 494.7 |

TABLE 9-continued
Thiophenylmethylenyl Alkanoic Acids And Amides ($R^3$ = O— And NH—)
IIb-487 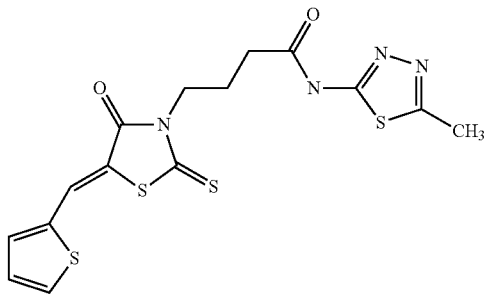 [SMILES: Cc1nnc(NC(=O)CCCN2C(=O)/C(=C/c3cccs3)SC2=S)s1] 410.6
IIb-488 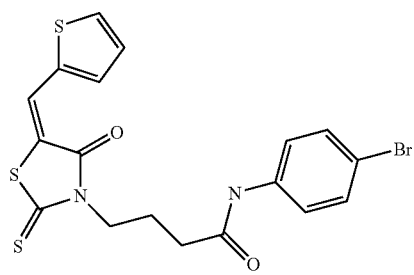 [SMILES: O=C(CCCN1C(=O)/C(=C\c2cccs2)SC1=S)Nc1ccc(Br)cc1] 467.4
IIb-489 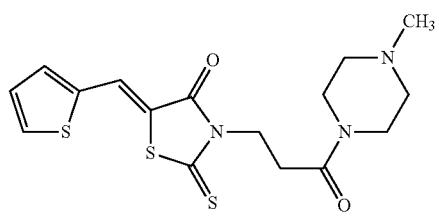 [SMILES: CN1CCN(C(=O)CCN2C(=O)/C(=C/c3cccs3)SC2=S)CC1] 381.5
IIb-490 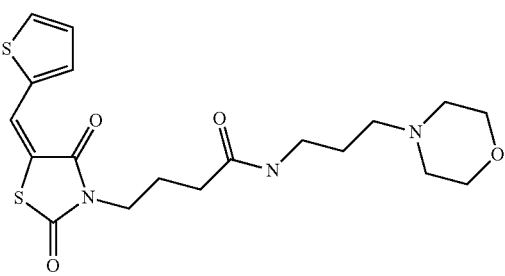 [SMILES: O=C(CCCN1C(=O)S/C(=C/c2cccs2)C1=O)NCCCN1CCOCC1] 439.6
IIb-491 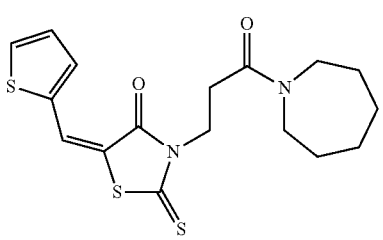 [SMILES: O=C(CCN1C(=O)/C(=C\c2cccs2)SC1=S)N1CCCCCC1] 380.6
IIb-492 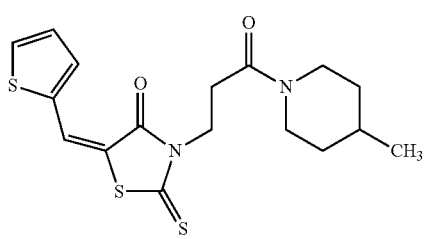 [SMILES: CC1CCN(C(=O)CCN2C(=O)/C(=C\c3cccs3)SC2=S)CC1] 380.6

TABLE 9-continued

Thiophenylmethylenyl Alkanoic Acids And Amides ($R^3$ = O— And NH—)

| | | |
|---|---|---|
| IIb-493 | | 416.6 |
| IIb-494 | | 354.5 |
| IIb-495 | | 384.5 |
| IIb-496 | | 380.6 |
| IIb-497 | | 477.6 |
| IIb-498 | | 445.6 |

TABLE 9-continued

Thiophenylmethylenyl Alkanoic Acids And Amides ($R^3$ = O— And NH—)

| | | |
|---|---|---|
| IIb-499 | | 416.6 |
| IIb-500 | | 406.5 |
| IIb-501 | | 439.0 |
| IIb-502 | | 397.6 |
| IIb-503 | | 457.6 |
| IIb-504 | | 416.6 |
| IIb-505 | | 430.6 |

TABLE 9-continued

Thiophenylmethylenyl Alkanoic Acids And Amides (R³ = O— And NH—)

| | | |
|---|---|---|
| IIb-506 | | 432.5 |
| IIb-507 | | 406.5 |
| IIb-508 | | 424.6 |
| IIb-509 | | 478.7 |
| IIb-510 | | 402.6 |
| IIb-511 | | 402.6 |
| IIb-512 | | 416.6 |

TABLE 9-continued

Thiophenylmethylenyl Alkanoic Acids And Amides ($R^3$ = O— And NH—)

| | | |
|---|---|---|
| IIb-513 | | 452.6 |
| IIb-514 | | 395.5 |
| IIb-515 | | 389.5 |
| IIb-516 | | 446.7 |
| IIb-517 | | 434.5 |
| IIb-518 | | 430.6 |
| IIb-519 | | 416.6 |

TABLE 9-continued

Thiophenylmethylenyl Alkanoic Acids And Amides ($R^3$ = O— And NH—)

| IIb-520 | [structure] | 444.6 |
| IIb-521 | [structure] | 448.5 |
| IIb-522 | [structure] | 444.6 |
| IIb-523 | [structure] | 441.6 |
| IIb-524 | [structure] | 434.5 |
| IIb-525 | [structure] | 430.6 |

TABLE 9-continued

Thiophenylmethylenyl Alkanoic Acids And Amides ($R^3$ = O— And NH—)

| IIb-526 | 414.5 |
| IIb-527 | 418.6 |
| IIb-528 | 406.6 |
| IIb-529 | 407.0 |
| IIb-530 | 428.6 |

TABLE 9-continued
Thiophenylmethylenyl Alkanoic Acids And Amides ($R^3$ = O— And NH—)
| | | |
|---|---|---|
| IIb-531 | 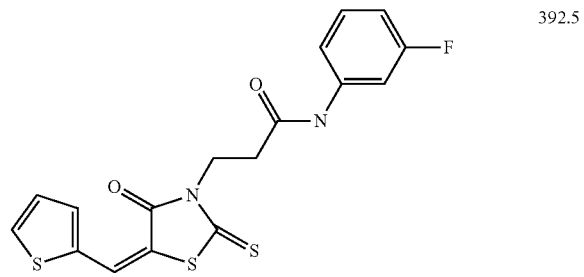 | 392.5 |
| IIb-532 | 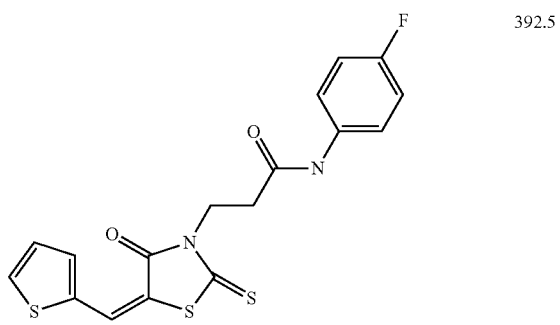 | 392.5 |
| IIb-533 | 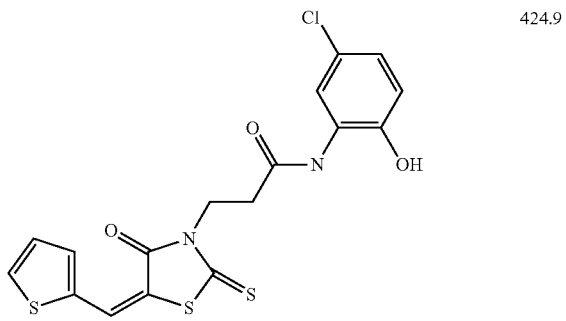 | 424.9 |
| IIb-534 | 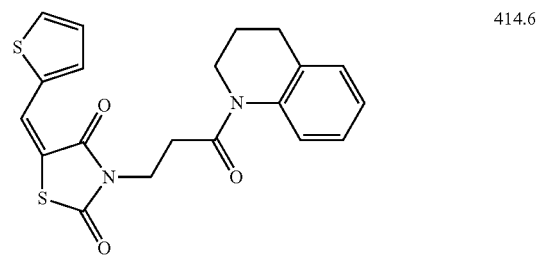 | 414.6 |
| IIb-535 | 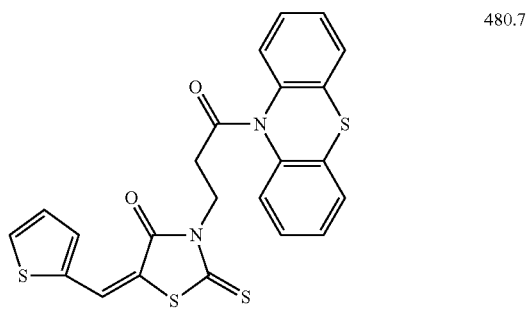 | 480.7 |

TABLE 9-continued

Thiophenylmethylenyl Alkanoic Acids And Amides (R³ = O— And NH—)

| IIb-536 | [structure] | 421.0 |
| IIb-537 | [structure] | 431.6 |
| IIb-538 | [structure] | 409.0 |
| IIb-539 | [structure] | 448.5 |
| IIb-540 | [structure] | 453.6 |

TABLE 9-continued
Thiophenylmethylenyl Alkanoic Acids And Amides ($R^3$ = O— And NH—)
| | | |
|---|---|---|
| IIb-541 | 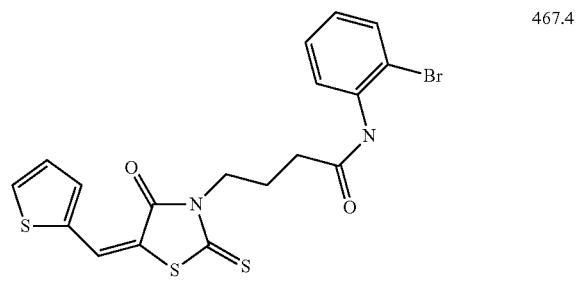 | 467.4 |
| IIb-542 | 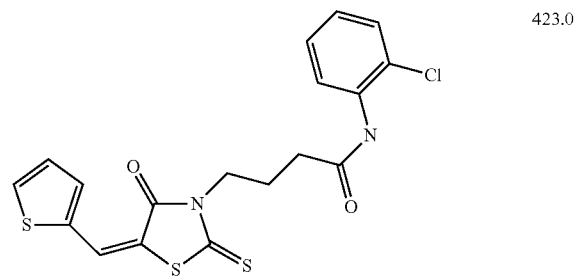 | 423.0 |
| IIb-543 | 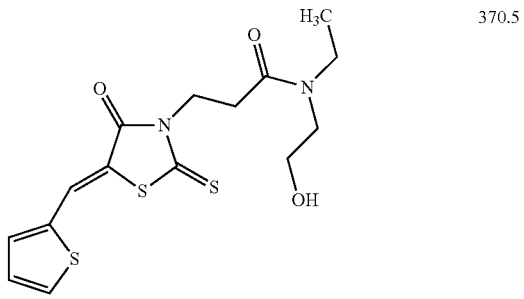 | 370.5 |
| IIb-544 | 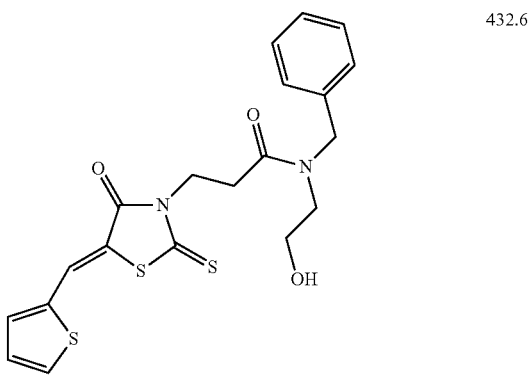 | 432.6 |
| IIb-545 | 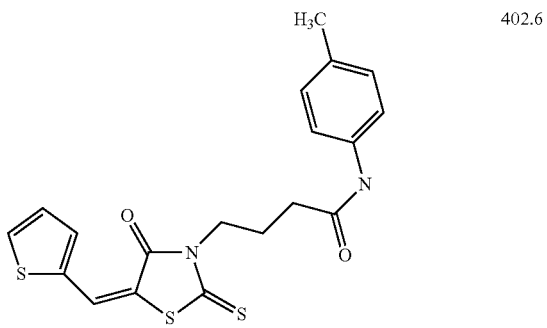 | 402.6 |

TABLE 9-continued
Thiophenylmethylenyl Alkanoic Acids And Amides ($R^3$ = O— And NH—)
| | | |
|---|---|---|
| IIb-546 | 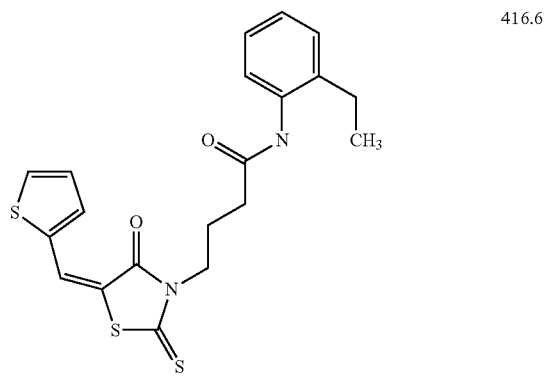 | 416.6 |
| IIb-547 | 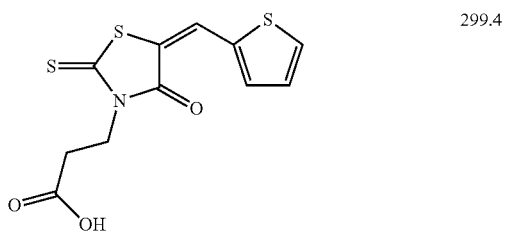 | 299.4 |
| IIb-548 | 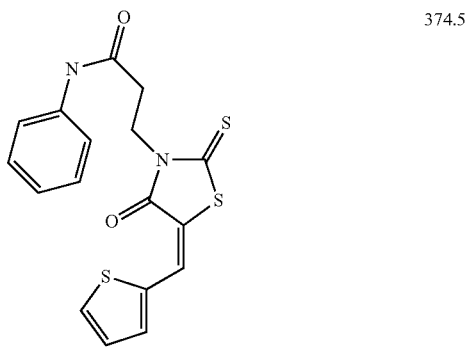 | 374.5 |
| IIb-549 | 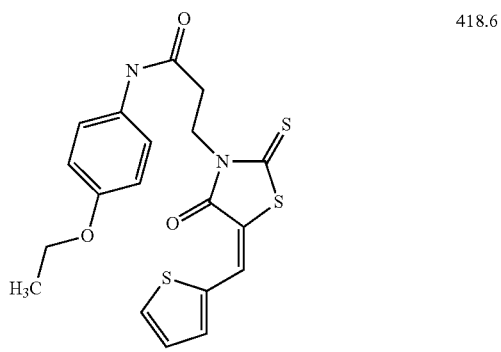 | 418.6 |

TABLE 9-continued
Thiophenylmethylenyl Alkanoic Acids And Amides ($R^3$ = O— And NH—)
IIb-550 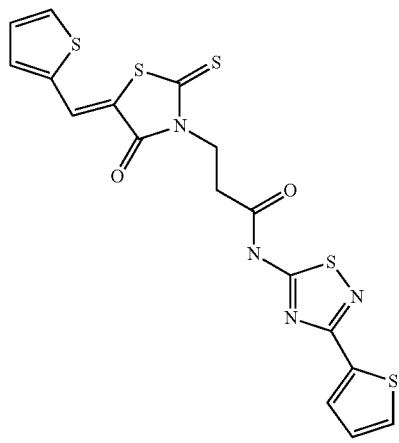 [SMILES: O=C(CCN1C(=O)/C(=C/c2cccs2)SC1=S)Nc1nc(-c2cccs2)ns1] 464.6
IIb-551 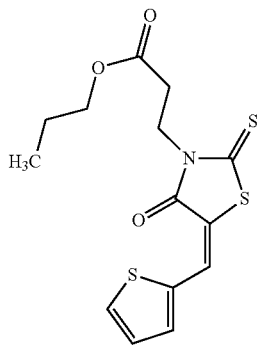 [SMILES: CCCOC(=O)CCN1C(=O)/C(=C\c2cccs2)SC1=S] 341.5
IIb-552 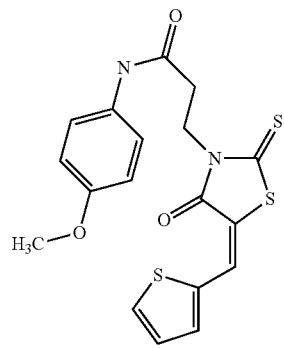 [SMILES: COc1ccc(NC(=O)CCN2C(=O)/C(=C\c3cccs3)SC2=S)cc1] 404.5
IIb-553 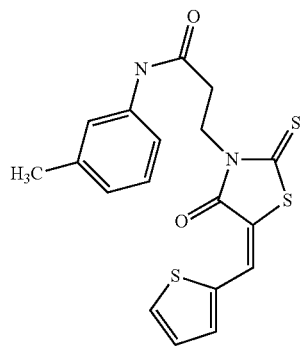 [SMILES: Cc1cccc(NC(=O)CCN2C(=O)/C(=C\c3cccs3)SC2=S)c1] 388.5

TABLE 9-continued

Thiophenylmethylenyl Alkanoic Acids And Amides ($R^3$ = O— And NH—)

| IIb-554 | | 407.0 |
| IIb-555 | | 313.4 |
| IIb-556 | | 388.5 |
| IIb-557 | | 388.5 |

TABLE 9-continued

Thiophenylmethylenyl Alkanoic Acids And Amides (R³ = O— And NH—)

| | | |
|---|---|---|
| IIb-558 | | 404.5 |
| IIb-559 | | 369.5 |
| IIb-560 | | 355.5 |
| IIb-561 | | 432.5 |

TABLE 9-continued
Thiophenylmethylenyl Alkanoic Acids And Amides ($R^3$ = O— And NH—)
| | | |
|---|---|---|
| IIb-562 | 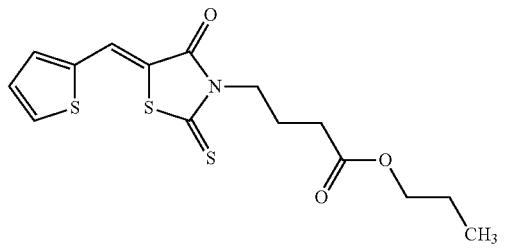 [SMILES: CCCOC(=O)CCCN1C(=O)/C(=C/c2cccs2)SC1=S] | 355.5 |
| IIb-563 | 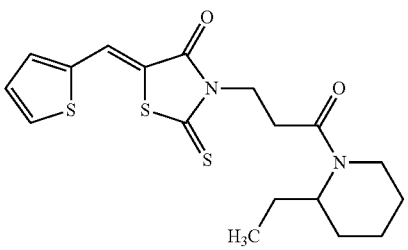 [SMILES: CCC1CCCCN1C(=O)CCN1C(=O)/C(=C/c2cccs2)SC1=S] | 394.6 |
| IIb-564 | 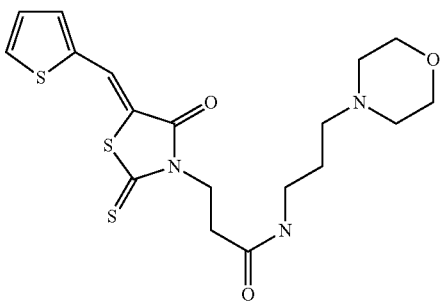 [SMILES: O=C(CCN1C(=O)/C(=C/c2cccs2)SC1=S)NCCCN1CCOCC1] | 425.6 |
| IIb-565 | 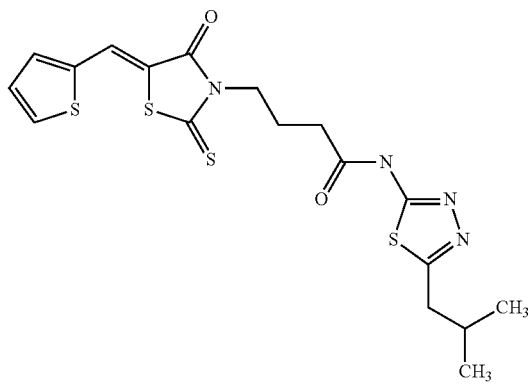 [SMILES: CC(C)Cc1nnc(NC(=O)CCCN2C(=O)/C(=C/c3cccs3)SC2=S)s1] | 452.6 |
| IIb-566 | 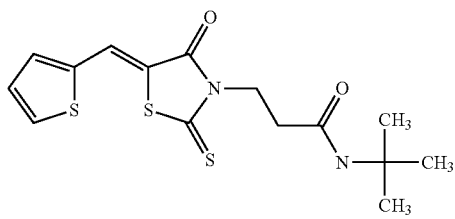 [SMILES: CC(C)(C)NC(=O)CCN1C(=O)/C(=C/c2cccs2)SC1=S] | 354.5 |

TABLE 9-continued

Thiophenylmethylenyl Alkanoic Acids And Amides ($R^3$ = O— And NH—)

| | | |
|---|---|---|
| IIb-567 | | 395.5 |
| IIb-568 | | 394.6 |
| IIb-569 | | 402.6 |
| IIb-570 | | 416.5 |
| IIb-571 | | 442.5 |

TABLE 9-continued
Thiophenylmethylenyl Alkanoic Acids And Amides ($R^3$ = O— And NH—)
| | | |
|---|---|---|
| IIb-572 | 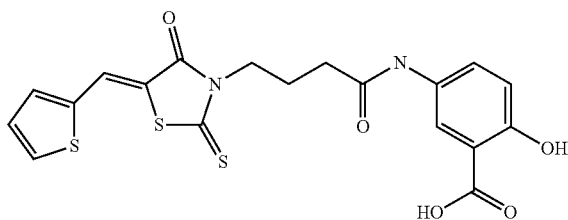 [SMILES: O=C(CCCN1C(=O)/C(=C/c2cccs2)SC1=S)Nc1ccc(O)c(C(=O)O)c1] | 448.5 |
| IIb-573 | 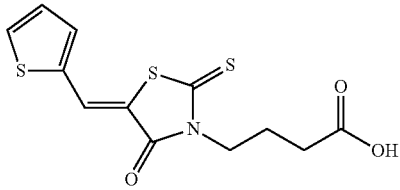 [SMILES: O=C(O)CCCN1C(=O)/C(=C/c2cccs2)SC1=S] | 313.4 |
| IIb-574 | 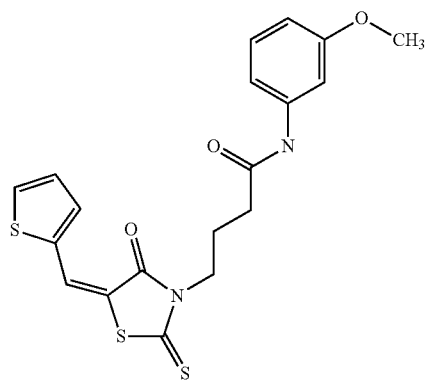 [SMILES: COc1cccc(NC(=O)CCCN2C(=O)/C(=C\c3cccs3)SC2=S)c1] | 418.6 |
| IIb-575 | 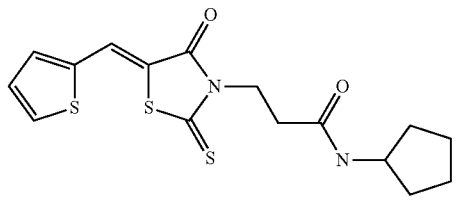 [SMILES: O=C(CCN1C(=O)/C(=C/c2cccs2)SC1=S)NC1CCCC1] | 366.5 |
| IIb-576 | 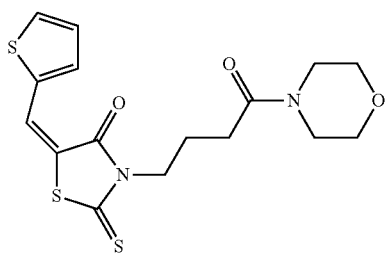 [SMILES: O=C(CCCN1C(=O)/C(=C\c2cccs2)SC1=S)N1CCOCC1] | 382.5 |
| IIb-577 | 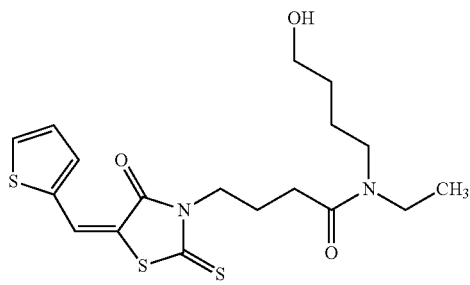 [SMILES: CCN(CCCCO)C(=O)CCCN1C(=O)/C(=C\c2cccs2)SC1=S] | 384.5 |

TABLE 9-continued

Thiophenylmethylenyl Alkanoic Acids And Amides ($R^3$ = O— And NH—)

| | | |
|---|---|---|
| IIb-578 | | 408.6 |
| IIb-579 | | 432.6 |
| IIb-580 | | 471.6 |
| IIb-581 | | 366.5 |
| IIb-582 | | 418.6 |
| IIb-583 | | 418.5 |

TABLE 9-continued

Thiophenylmethylenyl Alkanoic Acids And Amides ($R^3$ = O— And NH—)

| IIb-584 | | 421.0 |
| IIb-585 | | 380.6 |
| IIb-586 | | 327.4 |
| IIb-587 | | 402.6 |
| IIb-588 | | 389.5 |
| IIb-589 | | 410.6 |

TABLE 9-continued
Thiophenylmethylenyl Alkanoic Acids And Amides ($R^3$ = O— And NH—)
| | | |
|---|---|---|
| IIb-590 | 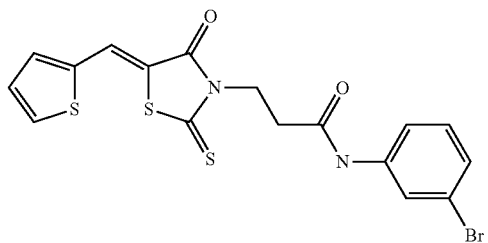 [SMILES: O=C(CCN1C(=O)/C(=C/c2cccs2)SC1=S)Nc1cccc(Br)c1] | 453.4 |
| IIb-591 | 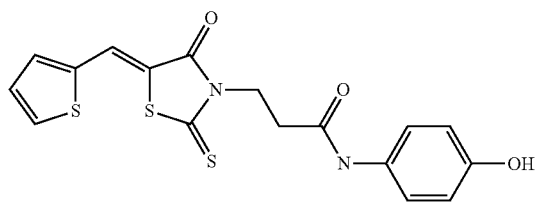 [SMILES: O=C(CCN1C(=O)/C(=C/c2cccs2)SC1=S)Nc1ccc(O)cc1] | 390.5 |
| IIb-592 | 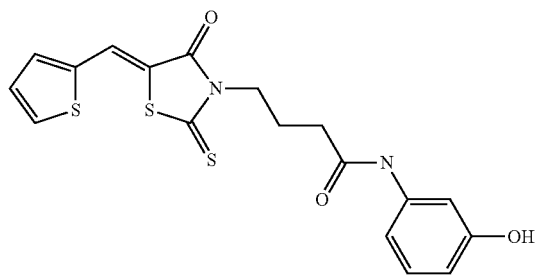 [SMILES: O=C(CCCN1C(=O)/C(=C/c2cccs2)SC1=S)Nc1cccc(O)c1] | 404.5 |
| IIb-593 | 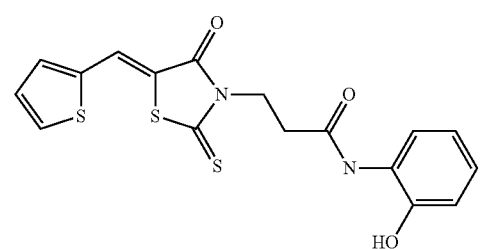 [SMILES: O=C(CCN1C(=O)/C(=C/c2cccs2)SC1=S)Nc1ccccc1O] | 390.5 |
| IIb-594 | 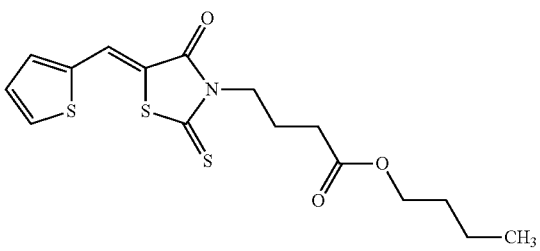 [SMILES: CCCCOC(=O)CCCN1C(=O)/C(=C/c2cccs2)SC1=S] | 369.5 |
| IIb-595 | 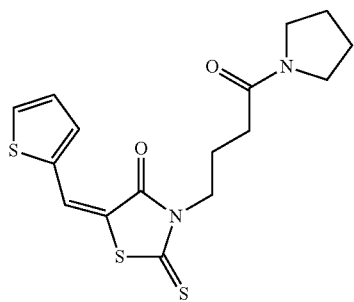 [SMILES: O=C(CCCN1C(=O)/C(=C\c2cccs2)SC1=S)N1CCCC1] | 366.5 |

TABLE 9-continued
Thiophenylmethylenyl Alkanoic Acids And Amides ($R^3$ = O— And NH—)
| | | |
|---|---|---|
| IIb-596 | 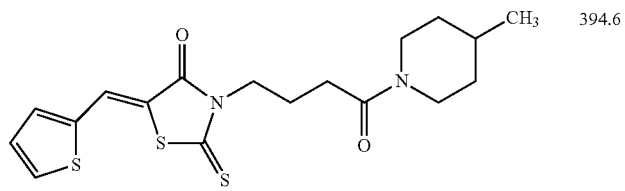 | 394.6 |
| IIb-597 | 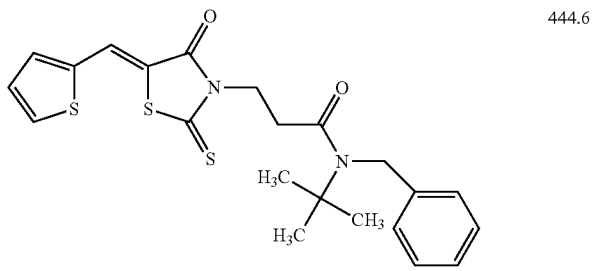 | 444.6 |
| IIb-598 | 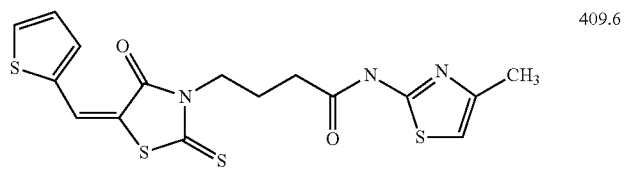 | 409.6 |
| IIb-599 | 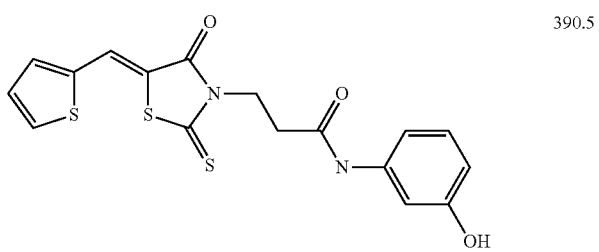 | 390.5 |
| IIb-600 | 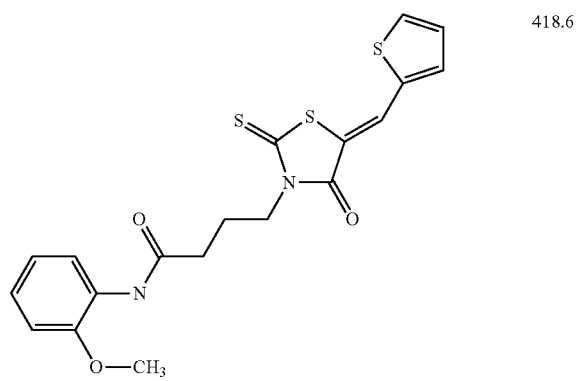 | 418.6 |
| IIb-601 | 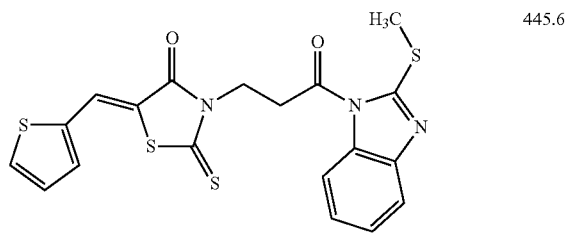 | 445.6 |

TABLE 9-continued
Thiophenylmethylenyl Alkanoic Acids And Amides ($R^3$ = O— And NH—)
| | | |
|---|---|---|
| IIb-602 | 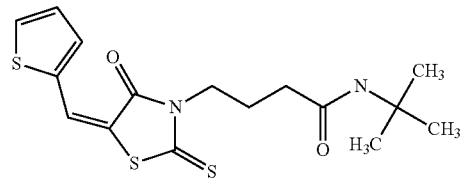 [SMILES: CC(C)(C)NC(=O)CCCN1C(=O)/C(=C\c2cccs2)SC1=S] | 368.5 |
| IIb-603 | 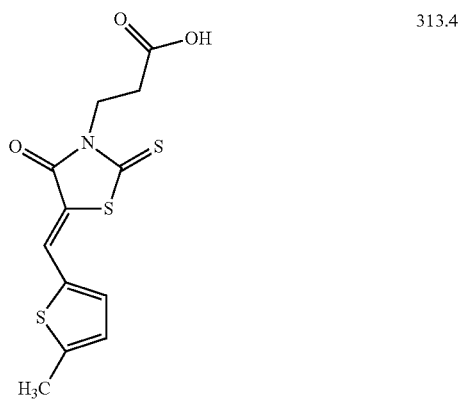 | 313.4 |
| IIb-604 | 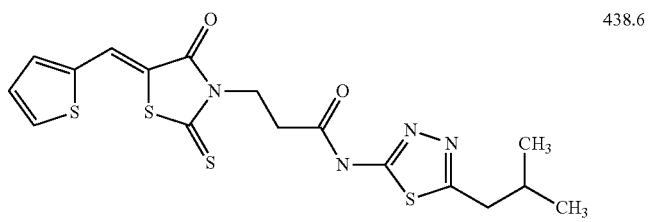 | 438.6 |
| IIb-605 | 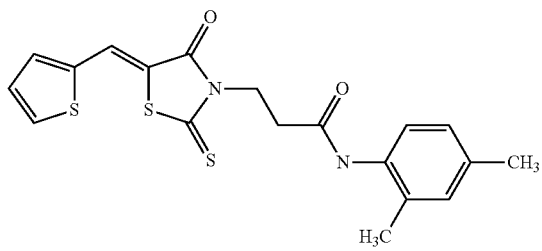 [SMILES: Cc1ccc(NC(=O)CCN2C(=O)/C(=C/c3cccs3)SC2=S)c(C)c1] | 402.6 |
| IIb-606 | 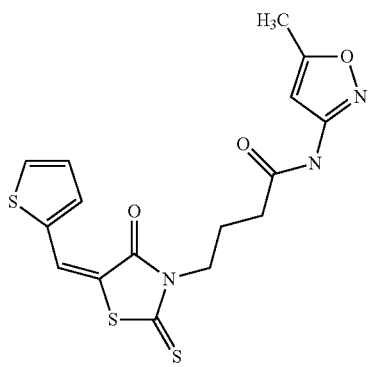 [SMILES: Cc1cc(NC(=O)CCCN2C(=O)/C(=C\c3cccs3)SC2=S)no1] | 393.5 |

TABLE 9-continued
Thiophenylmethylenyl Alkanoic Acids And Amides ($R^3$ = O— And NH—)
| | | |
|---|---|---|
| IIb-607 | 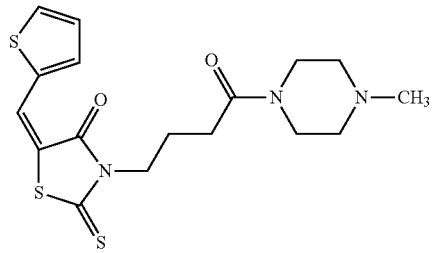 [SMILES: CN1CCN(C(=O)CCCN2C(=O)/C(=C\c3cccs3)SC2=S)CC1] | 395.6 |
| IIb-608 | 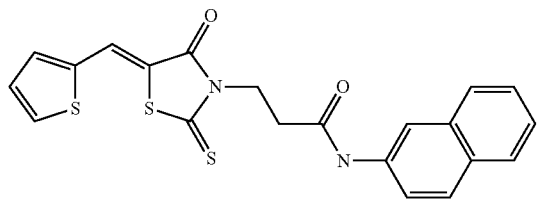 [SMILES: O=C(CCN1C(=O)/C(=C/c2cccs2)SC1=S)Nc1ccc2ccccc2c1] | 424.6 |
| IIb-609 | 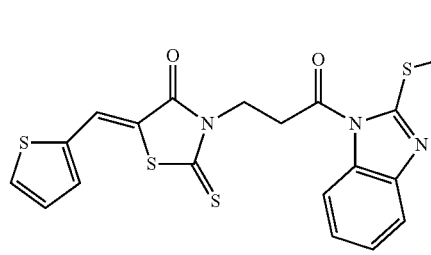 | 459.6 |
| IIb-610 | 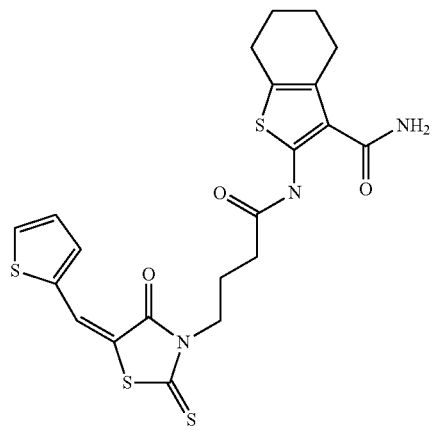 [SMILES: NC(=O)c1c(NC(=O)CCCN2C(=O)/C(=C\c3cccs3)SC2=S)sc2c1CCCC2] | 491.7 |
| IIb-611 | 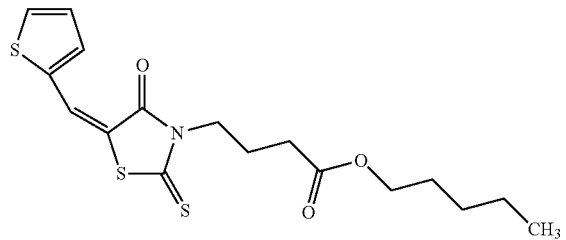 [SMILES: CCCCCOC(=O)CCCN1C(=O)/C(=C\c2cccs2)SC1=S] | 383.6 |

TABLE 9-continued
Thiophenylmethylenyl Alkanoic Acids And Amides (R³ = O— And NH—)
IIb-612 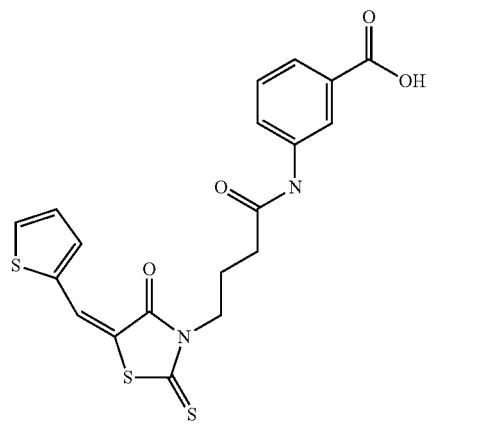 [SMILES: O=C(CCCN1C(=O)/C(=C\c2cccs2)SC1=S)Nc1cccc(C(=O)O)c1] 432.5
IIb-613 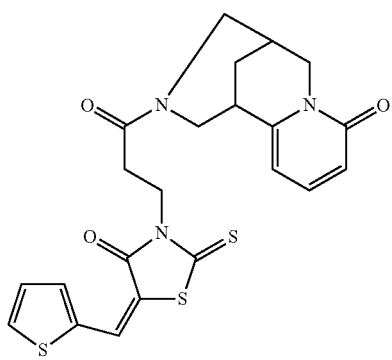 [SMILES: O=C(CCN1C(=O)/C(=C\c2cccs2)SC1=S)N1CC2CC(C1)c1cccc(=O)n1C2] 471.6
IIb-614 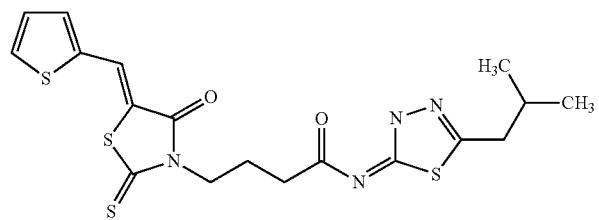 [SMILES: CC(C)Cc1n[nH]/c(=N\C(=O)CCCN2C(=O)/C(=C/c3cccs3)SC2=S)s1] 452.6
IIb-615 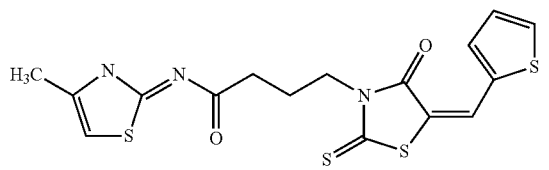 [SMILES: Cc1cs/c(=N\C(=O)CCCN2C(=O)/C(=C\c3cccs3)SC2=S)[nH]1] 409.6

TABLE 9-continued
Thiophenylmethylenyl Alkanoic Acids And Amides ($R^3$ = O— And NH—)
| ID | Structure | |
|---|---|---|
| IIb-616 | 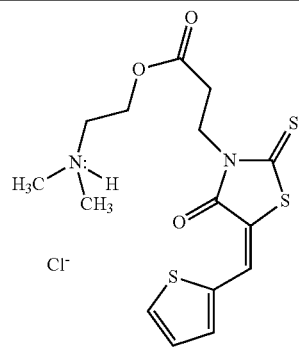 | 407.0 |
| IIb-617 | 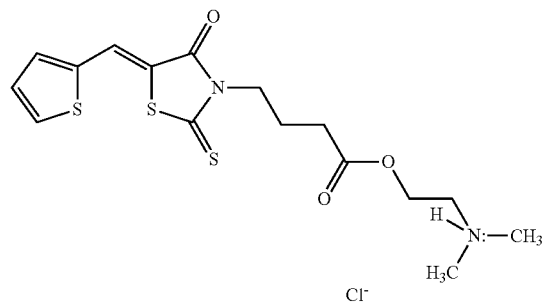 | 421.0 |
TABLE 10
5-[[2,5-Dimethyl-1H-Pyrrol-3-Yl]Methylene]-2,4-Thiazolidinediones
| ID | Structure |
|---|---|
| IIc-1 | 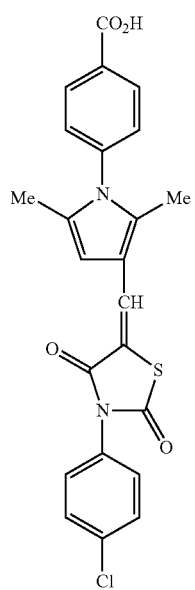 |
| IIc-2 | 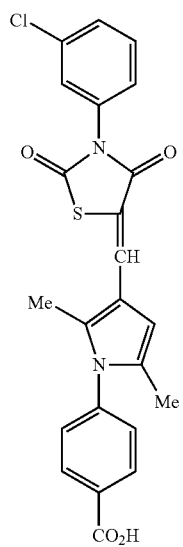 [SMILES: Cc1cc(C=C2SC(=O)N(c3cccc(Cl)c3)C2=O)c(C)n1-c1ccc(C(=O)O)cc1] |

TABLE 10-continued

5-[[2,5-Dimethyl-1H-Pyrrol-3-Yl]Methylene]-2,4-Thiazolidinediones

| ID | Structure |
|---|---|
| IIc-3 | 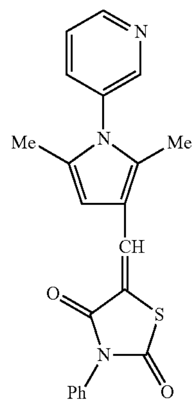 [SMILES: Cc1cc(C=C2SC(=O)N(c3ccccc3)C2=O)c(C)n1-c1cccnc1] |
| IIc-4 | 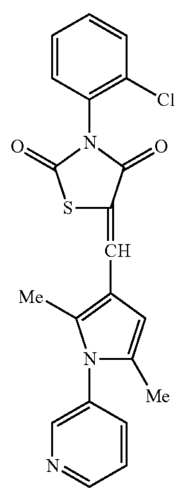 [SMILES: Cc1cc(C=C2SC(=O)N(c3ccccc3Cl)C2=O)c(C)n1-c1cccnc1] |
| IIc-5 | 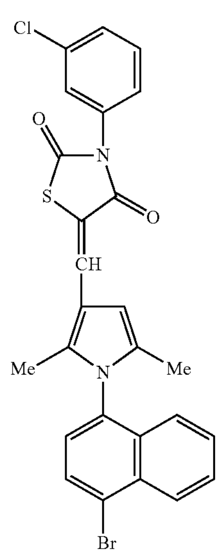 [SMILES: Cc1cc(C=C2SC(=O)N(c3cccc(Cl)c3)C2=O)c(C)n1-c1ccc(Br)c2ccccc12] |
| IIc-6 | |
| IIc-7 | |
| IIc-8 | |

TABLE 10-continued

5-[[2,5-Dimethyl-1H-Pyrrol-3-Yl]Methylene]-2,4-Thiazolidinediones

| ID | Structure |
|---|---|
| IIc-9 | 1-(4-methylpyridin-2-yl)-2,5-dimethylpyrrol-3-yl methylene, N-Ph thiazolidinedione |
| IIc-10 | 1-(pyridin-4-yl)-2,5-dimethylpyrrol-3-yl methylene, N-Ph thiazolidinedione |
| IIc-11 | 1-(4-cyanophenyl)-2,5-dimethylpyrrol-3-yl methylene, N-Ph thiazolidinedione |
| IIc-12 | 1-(2,4-dimethylphenyl)-2,5-dimethylpyrrol-3-yl methylene, N-(4-chlorophenyl) thiazolidinedione |
| IIc-13 | 1-(4-ethylphenyl)-2,5-dimethylpyrrol-3-yl methylene, N-(4-chlorophenyl) thiazolidinedione |

TABLE 10-continued
5-[[2,5-Dimethyl-1H-Pyrrol-3-Yl]Methylene]-2,4-Thiazolidinediones
| ID | Structure |
|---|---|
| IIc-14 | 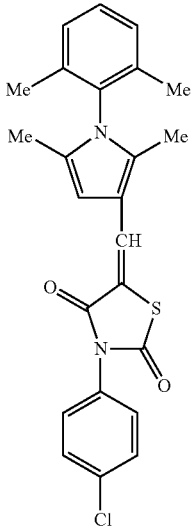 [SMILES: Cc1cccc(C)c1-n1c(C)cc(C=C2SC(=O)N(c3ccc(Cl)cc3)C2=O)c1C] |
| IIc-15 | 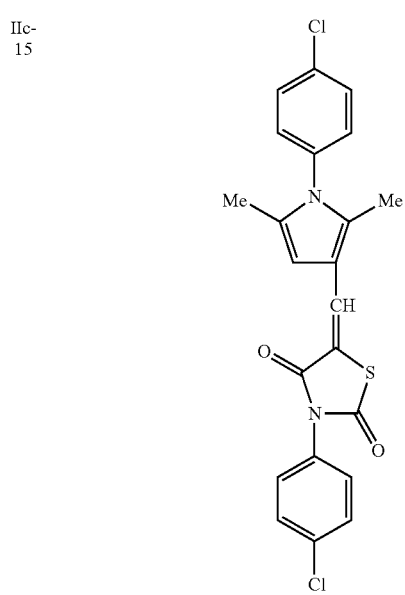 |
| IIc-16 | 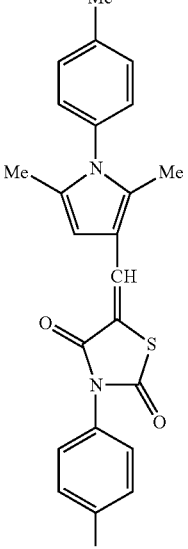 |
| IIc-17 | 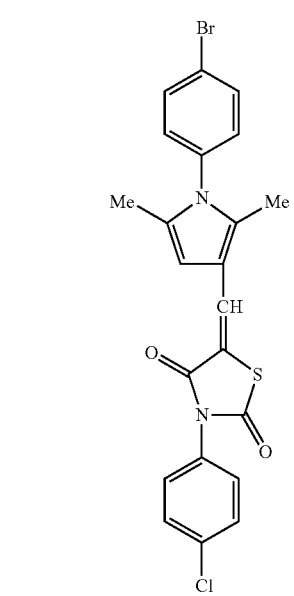 [SMILES: Cc1cc(C=C2SC(=O)N(c3ccc(Cl)cc3)C2=O)c(C)n1-c1ccc(Br)cc1] |

TABLE 10-continued
5-[[2,5-Dimethyl-1H-Pyrrol-3-Yl]Methylene]-2,4-Thiazolidinediones
| ID | Structure |
|---|---|
| IIc-18 | 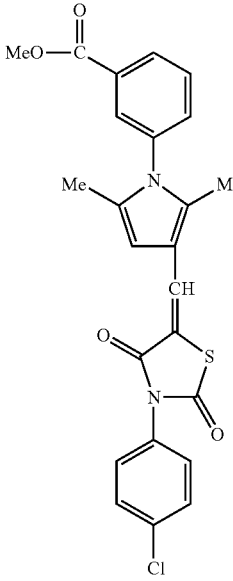 |
| IIc-19 | 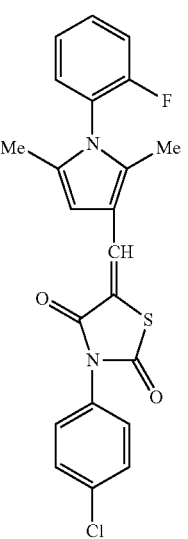 [SMILES: Cc1cc(C=C2SC(=O)N(c3ccc(Cl)cc3)C2=O)c(C)n1-c1ccccc1F] |
| IIc-20 | 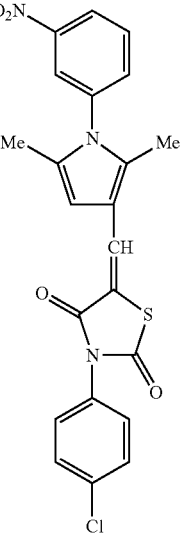 |
| IIc-21 | 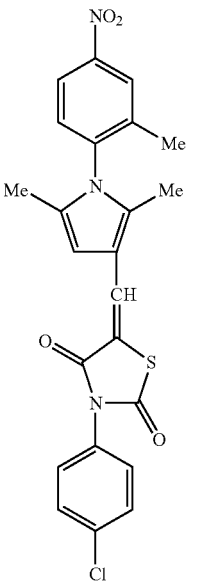 [SMILES: Cc1cc([N+](=O)[O-])ccc1-n1c(C)cc(C=C2SC(=O)N(c3ccc(Cl)cc3)C2=O)c1C] |
| IIc-22 | 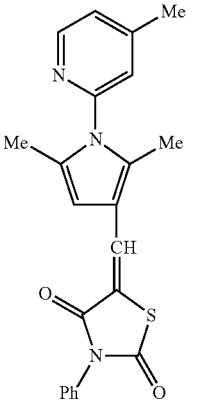 [SMILES: Cc1ccnc(-n2c(C)cc(C=C3SC(=O)N(c4ccccc4)C3=O)c2C)c1] |

TABLE 10-continued

5-[[2,5-Dimethyl-1H-Pyrrol-3-Yl]Methylene]-2,4-Thiazolidinediones

| ID | Structure |
|---|---|
| IIc-23 | *structure with 4-OMe phenyl on pyrrole N, phenyl on thiazolidinedione N* |
| IIc-24 | *structure with 4-Ph phenyl on pyrrole N, phenyl on thiazolidinedione N* |
| IIc-25 | *structure with 4-Et phenyl on pyrrole N, phenyl on thiazolidinedione N* |
| IIc-26 | *structure with 4-n-Bu phenyl on pyrrole N, phenyl on thiazolidinedione N* |
| IIc-27 | *structure with 4-OAc phenyl on pyrrole N, phenyl on thiazolidinedione N* |
| IIc-28 | *structure with 2,5-dimethylphenyl on pyrrole N, phenyl on thiazolidinedione N* |
| IIc-29 | *structure with benzo[1,3]dioxol-5-yl on pyrrole N, phenyl on thiazolidinedione N* |

TABLE 10-continued

5-[[2,5-Dimethyl-1H-Pyrrol-3-Yl]Methylene]-2,4-Thiazolidinediones

| ID | Structure |
|---|---|
| IIc-30 | 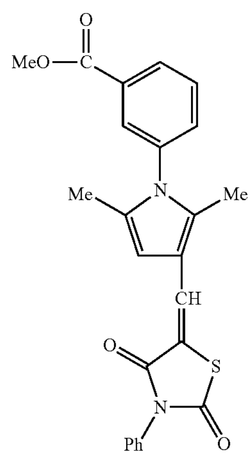 [SMILES: COC(=O)c1cccc(-n2c(C)cc(C=C3SC(=O)N(c4ccccc4)C3=O)c2C)c1] |
| IIc-31 | 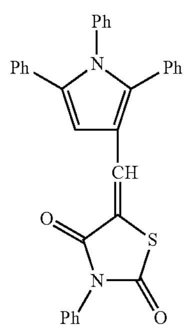 [SMILES: O=C1SC(=Cc2cc(-c3ccccc3)n(-c3ccccc3)c2-c2ccccc2)C(=O)N1c1ccccc1] |
| IIc-32 | 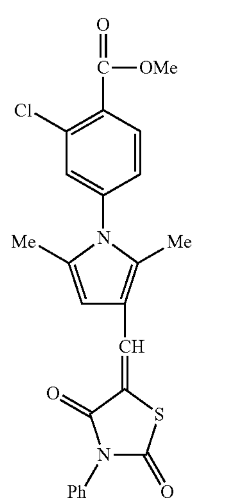 [SMILES: COC(=O)c1ccc(-n2c(C)cc(C=C3SC(=O)N(c4ccccc4)C3=O)c2C)cc1Cl] |
| IIc-33 | 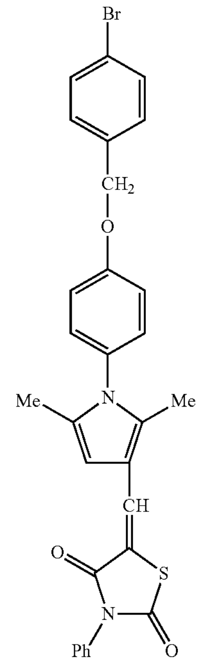 [SMILES: Cc1cc(C=C2SC(=O)N(c3ccccc3)C2=O)c(C)n1-c1ccc(OCc2ccc(Br)cc2)cc1] |
| IIc-34 | 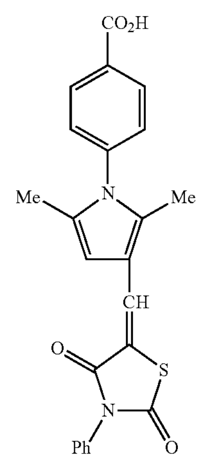 [SMILES: Cc1cc(C=C2SC(=O)N(c3ccccc3)C2=O)c(C)n1-c1ccc(C(=O)O)cc1] |
| IIc-35 | 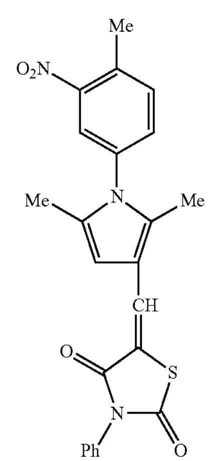 [SMILES: Cc1ccc(-n2c(C)cc(C=C3SC(=O)N(c4ccccc4)C3=O)c2C)cc1[N+](=O)[O-]] |

TABLE 10-continued
5-[[2,5-Dimethyl-1H-Pyrrol-3-Yl]Methylene]-2,4-Thiazolidinediones
| ID | Structure |
|---|---|
| IIc-36 | 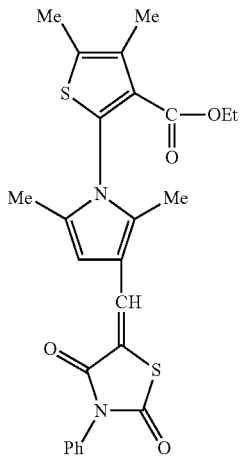 [SMILES: CCOC(=O)c1c(-n2c(C)cc(C=C3SC(=O)N(c4ccccc4)C3=O)c2C)sc(C)c1C] |
| IIc-37 | 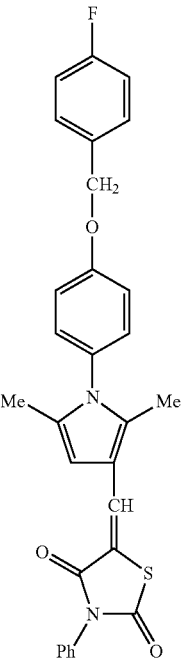 |
| IIc-38 | 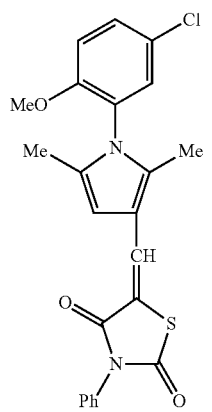 |
| IIc-39 | 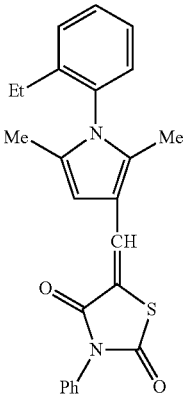 [SMILES: CCc1ccccc1-n1c(C)cc(C=C2SC(=O)N(c3ccccc3)C2=O)c1C] |
| IIc-40 | 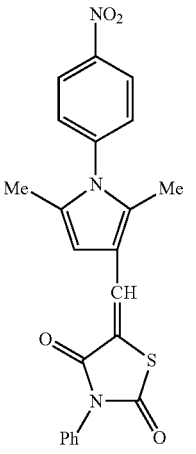 |
| IIc-41 | 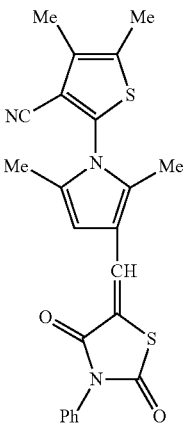 [SMILES: Cc1sc(-n2c(C)cc(C=C3SC(=O)N(c4ccccc4)C3=O)c2C)c(C#N)c1C] |

TABLE 10-continued
5-[[2,5-Dimethyl-1H-Pyrrol-3-Yl]Methylene]-2,4-Thiazolidinediones
| ID | Structure |
|---|---|
| IIc-42 | 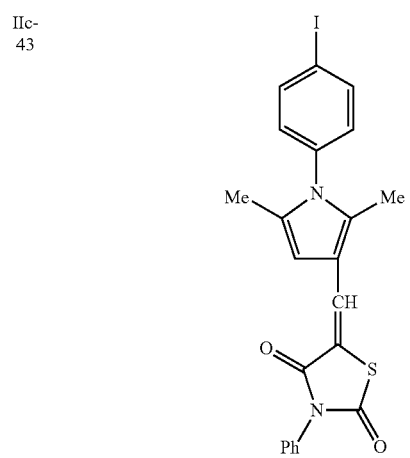 |
| IIc-43 | 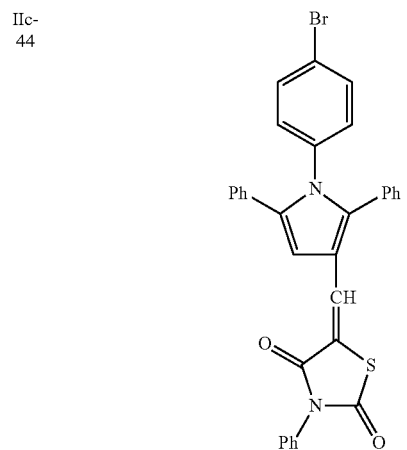 |
| IIc-44 | (structure with Br-phenyl, diphenyl pyrrole) |
TABLE 10-continued
5-[[2,5-Dimethyl-1H-Pyrrol-3-Yl]Methylene]-2,4-Thiazolidinediones
| ID | Structure |
|---|---|
| IIc-45 | 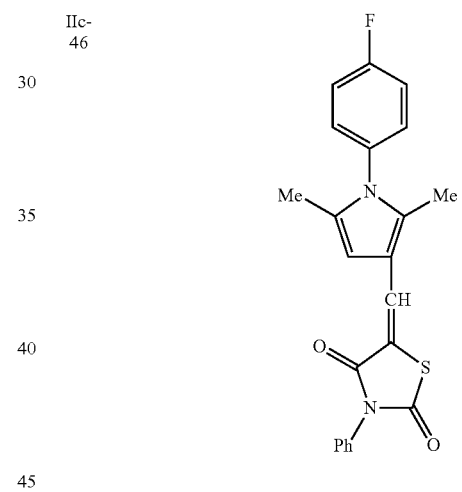 |
| IIc-46 | 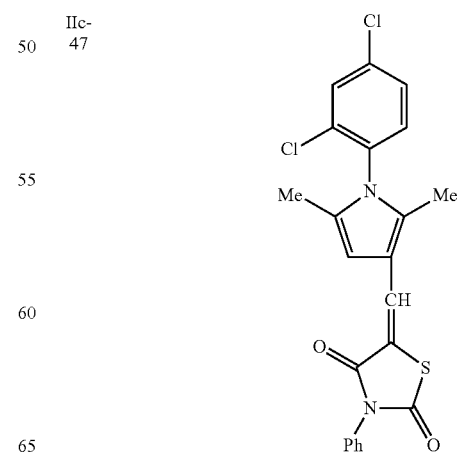 |
| IIc-47 | (2,4-dichlorophenyl structure) |

TABLE 10-continued
5-[[2,5-Dimethyl-1H-Pyrrol-3-Yl]Methylene]-2,4-Thiazolidinediones
| ID | Structure |
|---|---|
| IIc-48 | 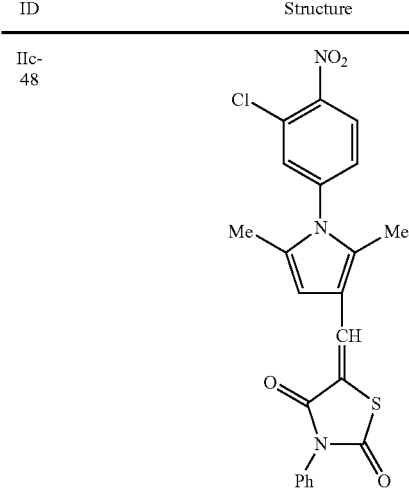 |
| IIc-49 | 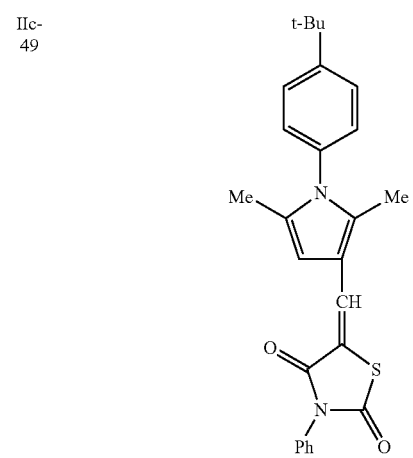 |
| IIc-50 | 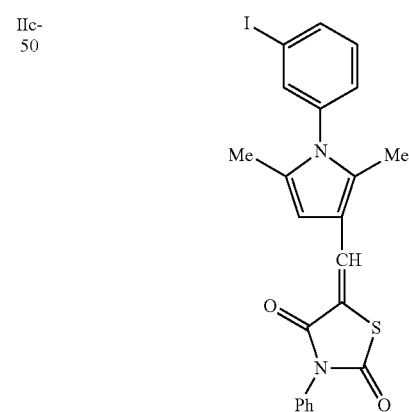 |
TABLE 10-continued
5-[[2,5-Dimethyl-1H-Pyrrol-3-Yl]Methylene]-2,4-Thiazolidinediones
| ID | Structure |
|---|---|
| IIc-51 | 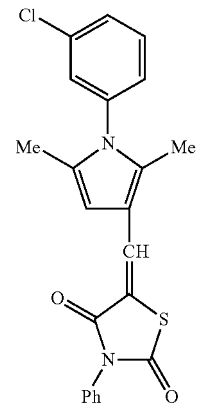 [SMILES: Cc1cc(C=C2SC(=O)N(c3ccccc3)C2=O)c(C)n1-c1cccc(Cl)c1] |
| IIc-52 | 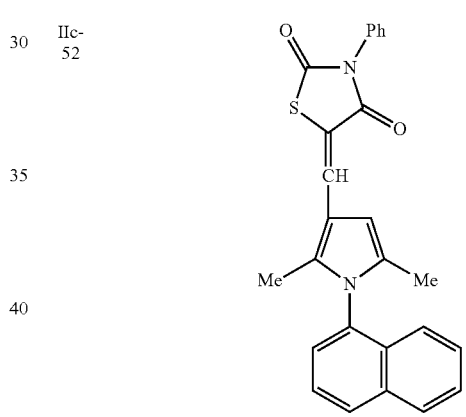 |
| IIc-53 | 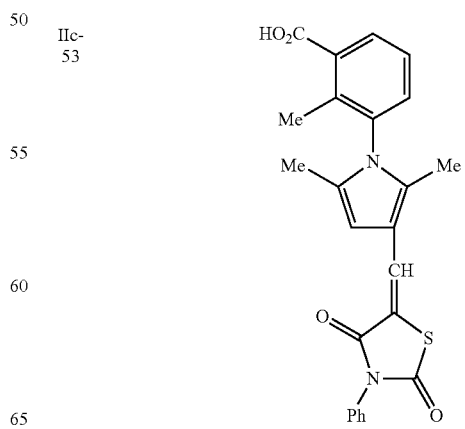 |

TABLE 10-continued
5-[[2,5-Dimethyl-1H-Pyrrol-3-Yl]Methylene]-2,4-Thiazolidinediones
| ID | Structure |
|---|---|
| IIc-54 | 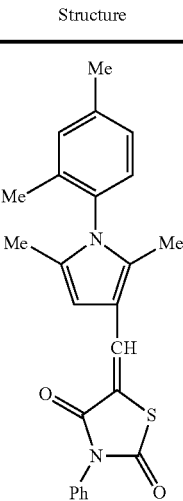 |
| IIc-55 | 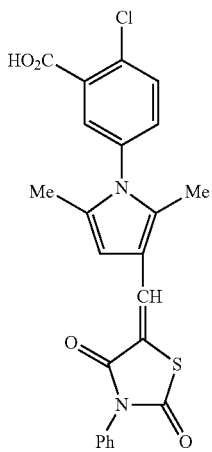 [SMILES: Cc1cc(C=C2SC(=O)N(c3ccccc3)C2=O)c(C)n1-c1ccc(Cl)c(C(=O)O)c1] |
| IIc-56 | 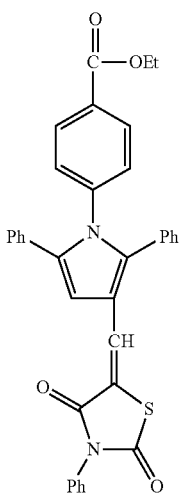 [SMILES: CCOC(=O)c1ccc(-n2c(-c3ccccc3)cc(C=C3SC(=O)N(c4ccccc4)C3=O)c2-c2ccccc2)cc1] |
| IIc-57 | 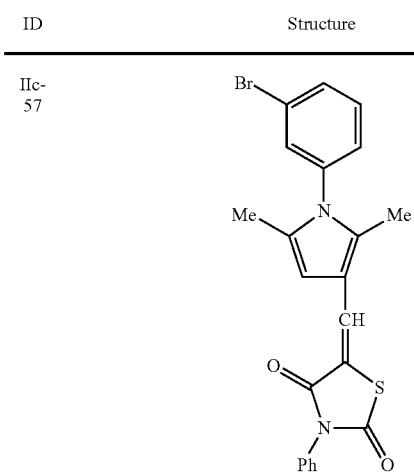 |
| IIc-58 | 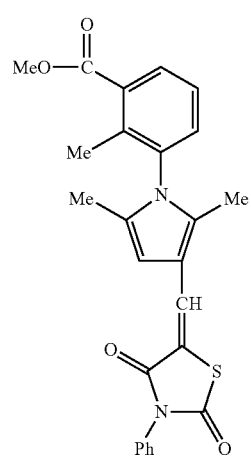 [SMILES: COC(=O)c1cccc(-n2c(C)cc(C=C3SC(=O)N(c4ccccc4)C3=O)c2C)c1C] |
| IIc-59 | 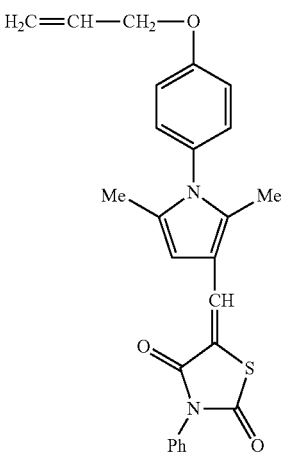 [SMILES: C=CCOc1ccc(-n2c(C)cc(C=C3SC(=O)N(c4ccccc4)C3=O)c2C)cc1] |

TABLE 10-continued

5-[[2,5-Dimethyl-1H-Pyrrol-3-Yl]Methylene]-2,4-Thiazolidinediones

| ID | Structure |
|---|---|
| IIc-60 | (2-cyanobenzyl)oxy-phenyl-pyrrole-thiazolidinedione structure |
| IIc-61 | 4-bromo-3-methylphenyl-pyrrole-thiazolidinedione structure |
| IIc-62 | 4-(ethoxycarbonyl)phenyl-pyrrole-thiazolidinedione structure |
| IIc-63 | 2,6-dimethylphenyl-pyrrole-thiazolidinedione structure |
| IIc-64 | (4-chlorobenzyl)oxy-phenyl-pyrrole-thiazolidinedione structure |
| IIc-65 | 4-methylphenyl-pyrrole-thiazolidinedione structure |

TABLE 10-continued

5-[[2,5-Dimethyl-1H-Pyrrol-3-Yl]Methylene]-2,4-Thiazolidinediones

| ID | Structure |
|---|---|
| IIc-66 | (4-nitrophenyl at N; 2,5-diphenyl pyrrole; N-Ph thiazolidinedione) |
| IIc-67 | (5-chloro-2-methylphenyl at N; 2,5-dimethyl pyrrole; N-Ph thiazolidinedione) |
| IIc-68 | (2-fluorobenzyloxy-phenyl at N; 2,5-dimethyl pyrrole; N-Ph thiazolidinedione) |
| IIc-69 | (3-carboxyphenyl at N; 2,5-dimethyl pyrrole; N-Ph thiazolidinedione) |
| IIc-70 | (4-acetamidophenyl at N; 2,5-dimethyl pyrrole; N-Ph thiazolidinedione) |
| IIc-71 | (4-nitrophenylthio-phenyl at N; 2,5-dimethyl pyrrole; N-Ph thiazolidinedione) |

TABLE 10-continued
5-[[2,5-Dimethyl-1H-Pyrrol-3-Yl]Methylene]-2,4-Thiazolidinediones
| ID | Structure |
|---|---|
| IIc-72 | 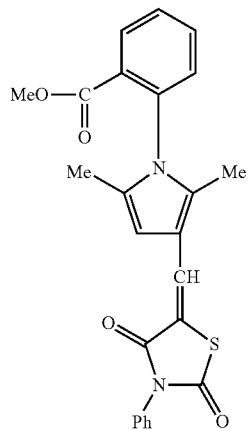 [SMILES: COC(=O)c1ccccc1-n1c(C)cc(C=C2SC(=O)N(c3ccccc3)C2=O)c1C] |
| IIc-73 | 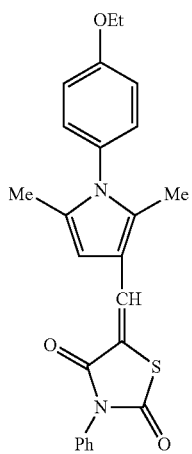 |
| IIc-74 | 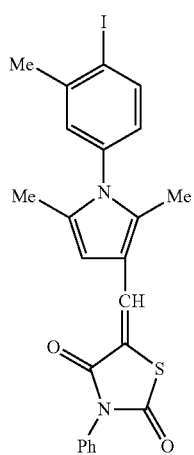 |
TABLE 10-continued
5-[[2,5-Dimethyl-1H-Pyrrol-3-Yl]Methylene]-2,4-Thiazolidinediones
| ID | Structure |
|---|---|
| IIc-75 | 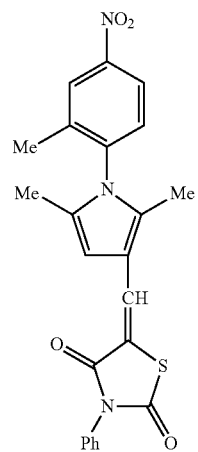 [SMILES: Cc1cc([N+](=O)[O-])ccc1-n1c(C)cc(C=C2SC(=O)N(c3ccccc3)C2=O)c1C] |
| IIc-76 | 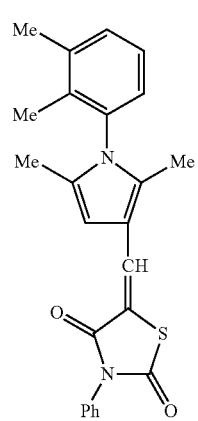 [SMILES: Cc1cccc(-n2c(C)cc(C=C3SC(=O)N(c4ccccc4)C3=O)c2C)c1C] |
| IIc-77 | 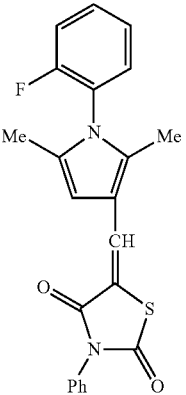 [SMILES: Cc1cc(C=C2SC(=O)N(c3ccccc3)C2=O)c(C)n1-c1ccccc1F] |

TABLE 10-continued

5-[[2,5-Dimethyl-1H-Pyrrol-3-Yl]Methylene]-2,4-Thiazolidinediones

| ID | Structure |
|---|---|
| IIc-78 | 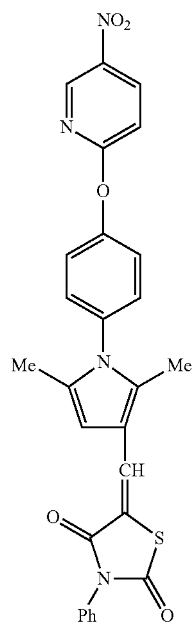 [SMILES: Cc1cc(C=C2SC(=O)N(c3ccccc3)C2=O)c(C)n1-c1ccc(Oc2ccc([N+](=O)[O-])cn2)cc1] |
| IIc-79 | 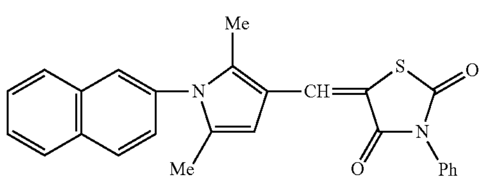 [SMILES: Cc1cc(C=C2SC(=O)N(c3ccccc3)C2=O)c(C)n1-c1ccc2ccccc2c1] |
| IIc-80 | 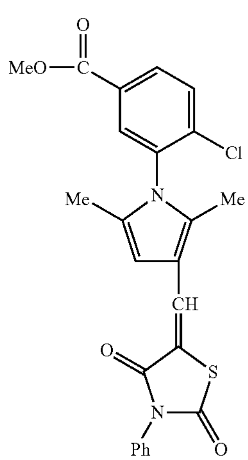 [SMILES: COC(=O)c1ccc(Cl)c(-n2c(C)cc(C=C3SC(=O)N(c4ccccc4)C3=O)c2C)c1] |
| IIc-81 | |
| IIc-82 | |
| IIc-83 | |

TABLE 10-continued
5-[[2,5-Dimethyl-1H-Pyrrol-3-Yl]Methylene]-2,4-Thiazolidinediones
| ID | Structure |
|---|---|
| IIc-84 | 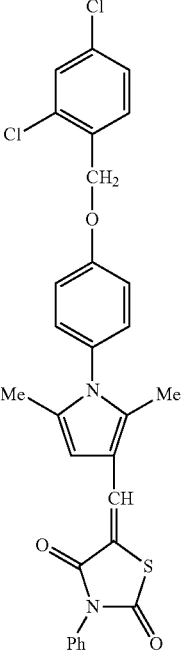 [SMILES: Cc1cc(C=C2SC(=O)N(c3ccccc3)C2=O)c(C)n1-c1ccc(OCc2ccc(Cl)cc2Cl)cc1] |
| IIc-85 | 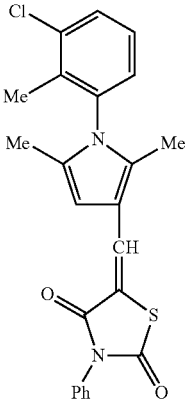 |
| IIc-86 | 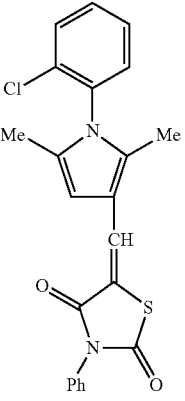 |
| IIc-87 | 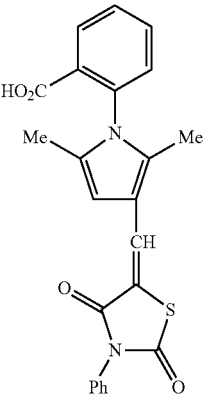 [SMILES: Cc1cc(C=C2SC(=O)N(c3ccccc3)C2=O)c(C)n1-c1ccccc1C(=O)O] |
| IIc-88 | 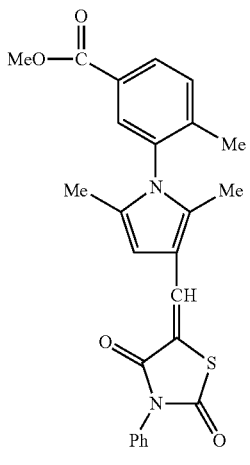 [SMILES: COC(=O)c1ccc(C)c(-n2c(C)cc(C=C3SC(=O)N(c4ccccc4)C3=O)c2C)c1] |
| IIc-89 | 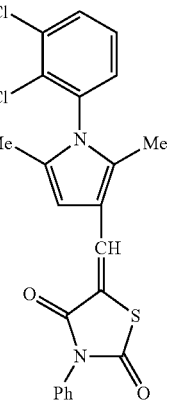 |

TABLE 10-continued

5-[[2,5-Dimethyl-1H-Pyrrol-3-Yl]Methylene]-2,4-Thiazolidinediones

| ID | Structure |
|---|---|
| IIc-90 | 3,4-dichlorophenyl on N of 2,5-dimethylpyrrole; pyrrole-3-CH= linked to 5-position of 3-phenyl-2,4-thiazolidinedione |
| IIc-91 | 4-(1-adamantyl)phenyl on N of 2,5-dimethylpyrrole; pyrrole-3-CH= linked to 5-position of 3-phenyl-2,4-thiazolidinedione |
| IIc-92 | 4-isopropylphenyl on N of 2,5-dimethylpyrrole; pyrrole-3-CH= linked to 5-position of 3-phenyl-2,4-thiazolidinedione |
| IIc-93 | 3-chloro-4-fluorophenyl on N of 2,5-dimethylpyrrole; pyrrole-3-CH= linked to 5-position of 3-phenyl-2,4-thiazolidinedione |
| IIc-94 | 4-(2-chlorobenzyloxy)phenyl on N of 2,5-dimethylpyrrole; pyrrole-3-CH= linked to 5-position of 3-phenyl-2,4-thiazolidinedione |
| IIc-95 | 4-hydroxyphenyl on N of 2,5-dimethylpyrrole; pyrrole-3-CH= linked to 5-position of 3-phenyl-2,4-thiazolidinedione |
| IIc-96 | 3-(ethoxycarbonyl)phenyl on N of 2,5-dimethylpyrrole; pyrrole-3-CH= linked to 5-position of 3-phenyl-2,4-thiazolidinedione |

TABLE 10-continued
5-[[2,5-Dimethyl-1H-Pyrrol-3-Yl]Methylene]-2,4-Thiazolidinediones
| ID | Structure |
|---|---|
| IIc-97 | 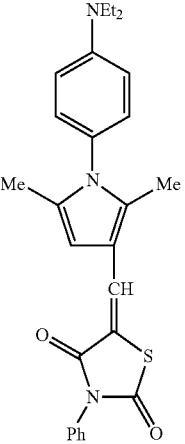 |
| IIc-98 | 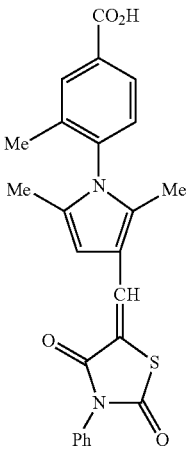 [SMILES: Cc1cc(C(=O)O)ccc1-n1c(C)cc(C=C2SC(=O)N(c3ccccc3)C2=O)c1C] |
| IIc-99 | 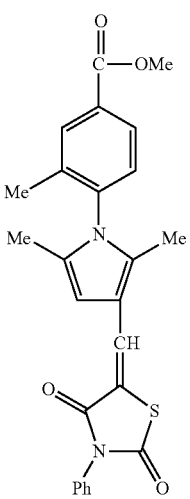 |
| IIc-100 | 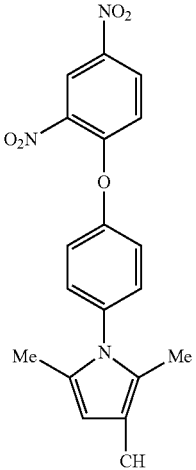 |
| IIc-101 | 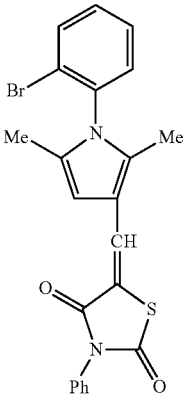 [SMILES: Cc1cc(C=C2SC(=O)N(c3ccccc3)C2=O)c(C)n1-c1ccccc1Br] |
| IIc-102 | 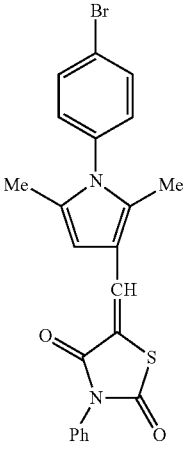 [SMILES: Cc1cc(C=C2SC(=O)N(c3ccccc3)C2=O)c(C)n1-c1ccc(Br)cc1] |

TABLE 10-continued
5-[[2,5-Dimethyl-1H-Pyrrol-3-Yl]Methylene]-2,4-Thiazolidinediones
| ID | Structure |
|---|---|
| IIc-103 | 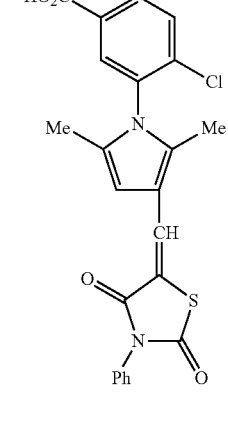 |
| IIc-104 | 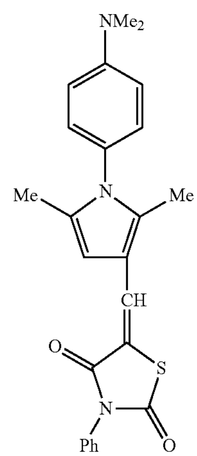 [SMILES: Cc1cc(C=C2SC(=O)N(c3ccccc3)C2=O)c(C)n1-c1ccc(N(C)C)cc1] |
| IIc-105 | 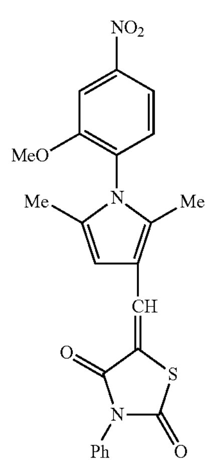 [SMILES: COc1cc([N+](=O)[O-])ccc1-n1c(C)cc(C=C2SC(=O)N(c3ccccc3)C2=O)c1C] |
| IIc-106 | 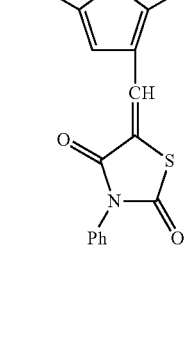 |
| IIc-107 | |
| IIc-108 | |

TABLE 10-continued

5-[[2,5-Dimethyl-1H-Pyrrol-3-Yl]Methylene]-2,4-Thiazolidinediones

| ID | Structure |
|---|---|
| IIc-109 | (2-methylphenyl on pyrrole N; pyrrole-CH=thiazolidinedione-N-Ph) |
| IIc-110 | (2-methoxy-5-nitrophenyl on pyrrole N; pyrrole-CH=thiazolidinedione-N-Ph) |
| IIc-111 | (4-(methoxycarbonyl)phenyl on pyrrole N; pyrrole-CH=thiazolidinedione-N-Ph) |
| IIc-112 | (3-nitrophenyl on pyrrole N; pyrrole-CH=thiazolidinedione-N-Ph) |
| IIc-113 | (3-methylphenyl on pyrrole N; pyrrole-CH=thiazolidinedione-N-Ph) |

A number of representative oxazoles and thiazole derivatives of this invention, as listed below in Table 11, were tested for their inhibitory activity and $IC_{50}$s were calculated. For the purpose of Table 11 below, activity of each compound is determined using the luciferase assay method in *Drosophila* Clone 8 cells.

TABLE 11

| | | IC$_{50}$ Values of Exemplary Compounds | | |
|---|---|---|---|---|
| ID | C#* | Structure | MW | IC$_{50}$ (μM) |
| IIa-66 | C6 | | 380.51 | 3.51 |
| IIa-333 | C3 | | 394.54 | 4.18 |
| IIa-719 | C1 | | 330.45 | 1.58 |

TABLE 11-continued
IC$_{50}$ Values of Exemplary Compounds
| ID | C#* | Structure | MW | IC$_{50}$ (µM) |
|---|---|---|---|---|
| IIa-722 | C13 | 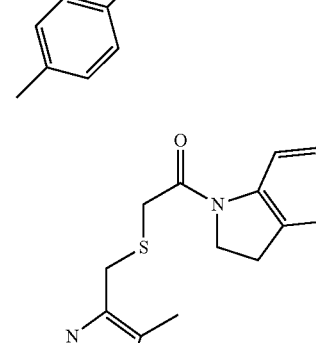 | 316.43 | 1259.72 |
| IIa-2102 | C8 | 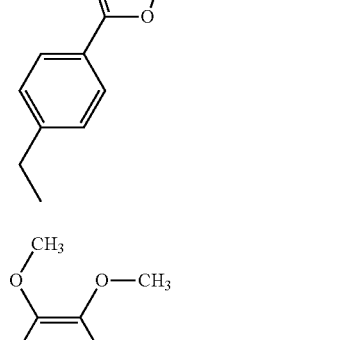 | 392.52 | 1.10 |
| IIa-143 | C5 | 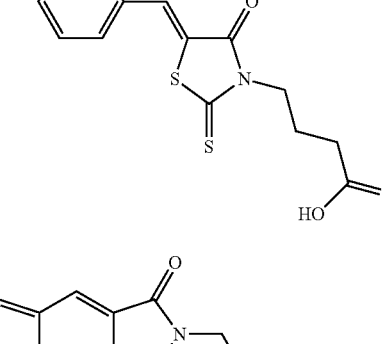 | 367.4 | 3.06 |
| IIa-432 | C10 | 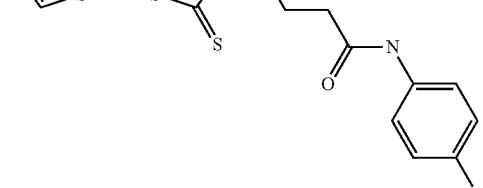 | 404.5 | 4.76 |

TABLE 11-continued

IC$_{50}$ Values of Exemplary Compounds

| ID | C#* | Structure | MW | IC$_{50}$ (µM) |
|---|---|---|---|---|
| IIc-3 | C14 | 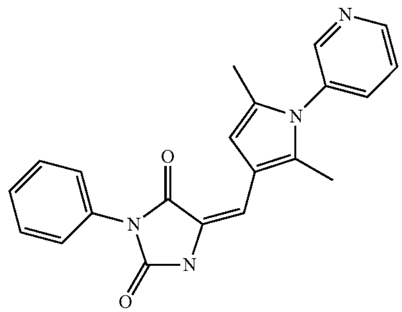 [SMILES: Cc1cc(/C=C2/NC(=O)N(c3ccccc3)C2=O)c(C)n1-c1cccnc1] | 375.4 | 3.24 |

*see FIGS. 3-12

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A method for treating or ameliorating in a mammal a disease or condition that is causally related to the aberrant activity of the Wnt signaling pathway in vivo, wherein the disease or condition is a cancer, which method comprises administering to the mammal an effective disease-treating or condition-treating amount of a compound according to formula I:

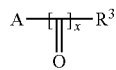
I wherein A is A$^1$;
A$^1$ is

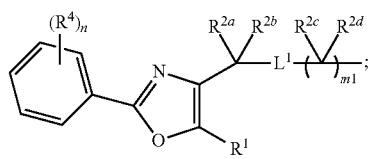

x is 1;
L$^1$ is S, SO or SO$_2$;
m1 is 1, 2 or 3; n is 1, 2, 3, 4 or 5;
each R$^1$, R$^{2a}$, R$^{2b}$, R$^{2c}$, and R$^{2d}$ is independently selected from hydrogen, halo, and substituted or unsubstituted C$_1$-C$_6$ alkyl;
R$^3$ is hydroxy, alkoxy, substituted or unsubstituted amino or cycloheteroalkyl;
each R$^4$ is independently selected from H, alkyl, substituted alkyl, acyl, substituted acyl, substituted or unsubstituted acylamino, substituted or unsubstituted alkylamino, substituted or unsubstituted alkythio, substituted or unsubstituted alkoxy, alkoxycarbonyl, substituted alkoxycarbonyl, substituted or unsubstituted alkylarylamino, arylalkyloxy, substituted arylalkyloxy, amino, aryl, substituted aryl, arylalkyl, substituted or unsubstituted sulfonyl, substituted or unsubstituted sulfinyl, substituted or unsubstituted sulfanyl, substituted or unsubstituted aminosulfonyl, substituted or unsubstituted arylsulfonyl, azido, carboxy, substituted or unsubstituted carbamoyl, cyano, substituted or unsubstituted cycloalkyl, substituted or unsubstituted cycloheteroalkyl, substituted or unsubstituted dialkylamino, halo, heteroaryloxy, substituted or unsubstituted heteroaryl, substituted or unsubstituted heteroalkyl, hydroxy, nitro, and thiol;
or a pharmaceutically acceptable salt, solvate or prodrug thereof;
and stereoisomers, isotopic variants and tautomers thereof.

2. The method according to claim 1, wherein the compound is according to formula IIa:

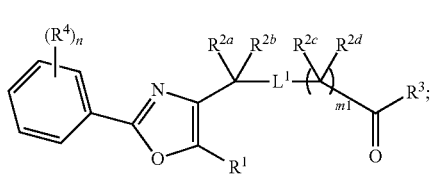

IIa and wherein $L^1$, m1, n, $R^1$, $R^{2a}$, $R^{2b}$, $R^{2c}$, $R^{2d}$, $R^3$ and $R^4$ are as in claim 1.

3. The method according to claim 2, wherein the compound is according to formula IVa:

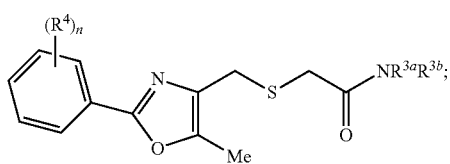

IVa wherein n, and $R^4$ are as stated, and each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ join together to form a cycloheteroalkyl heteroaryl ring.

4. The method according to claim 2, wherein the compound is according to formula VIIa, VIIb, VIIc or VIId:

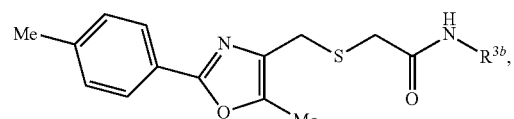

VIIa

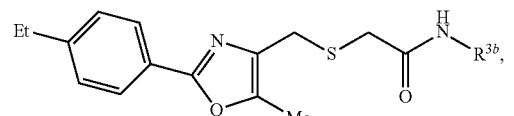

VIIb

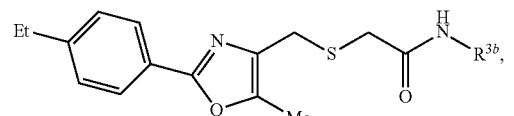

VIIc

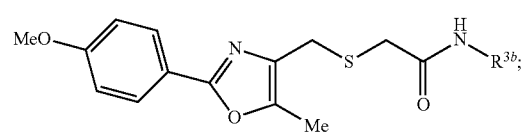

VIId wherein $R^{3b}$ is selected from H, substituted or unsubstituted alkyl, substituted or unsubstituted cycloalkyl, substituted or unsubstituted aryl, and substituted or unsubstituted heteroaryl; or $R^{3b}$ is joined together with $R^{3a}$ to form a cycloheteroalkyl heteroaryl ring.

5. The method according to claim 1, wherein the compound is according to formula VIIIa, VIIIb, VIIIc, or VIIId:

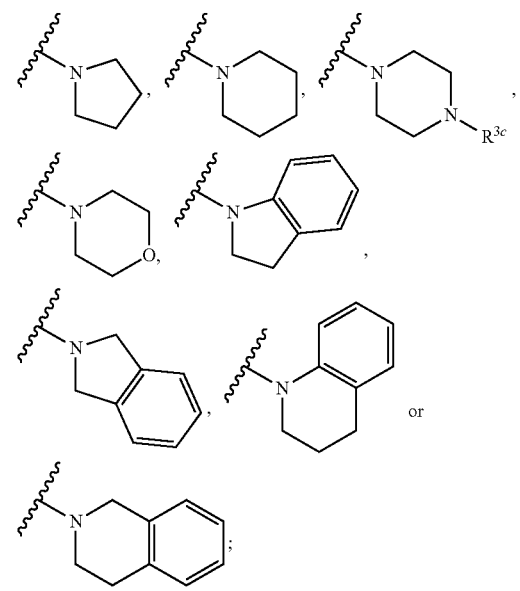

wherein Cy is

[structures shown]

and wherein $R^{3c}$ is H or alkyl.

6. The method according to claim 1, wherein the compound is according to formula IXa, IXb, IXc or IXd:

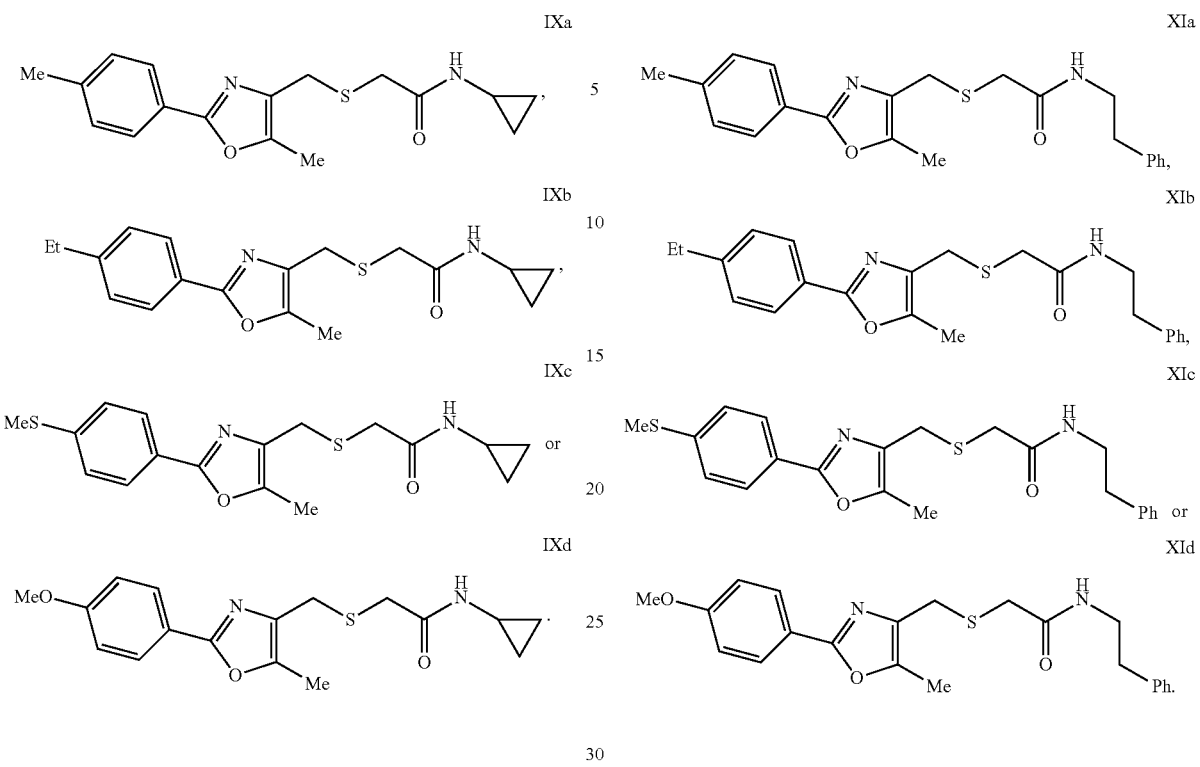
7. The method according to claim 1, wherein the compound is according to formula Xa, Xb, Xc or Xd:
8. The method according to claim 1, wherein the compound is according to formula XIa, XIb, XIc or XId:
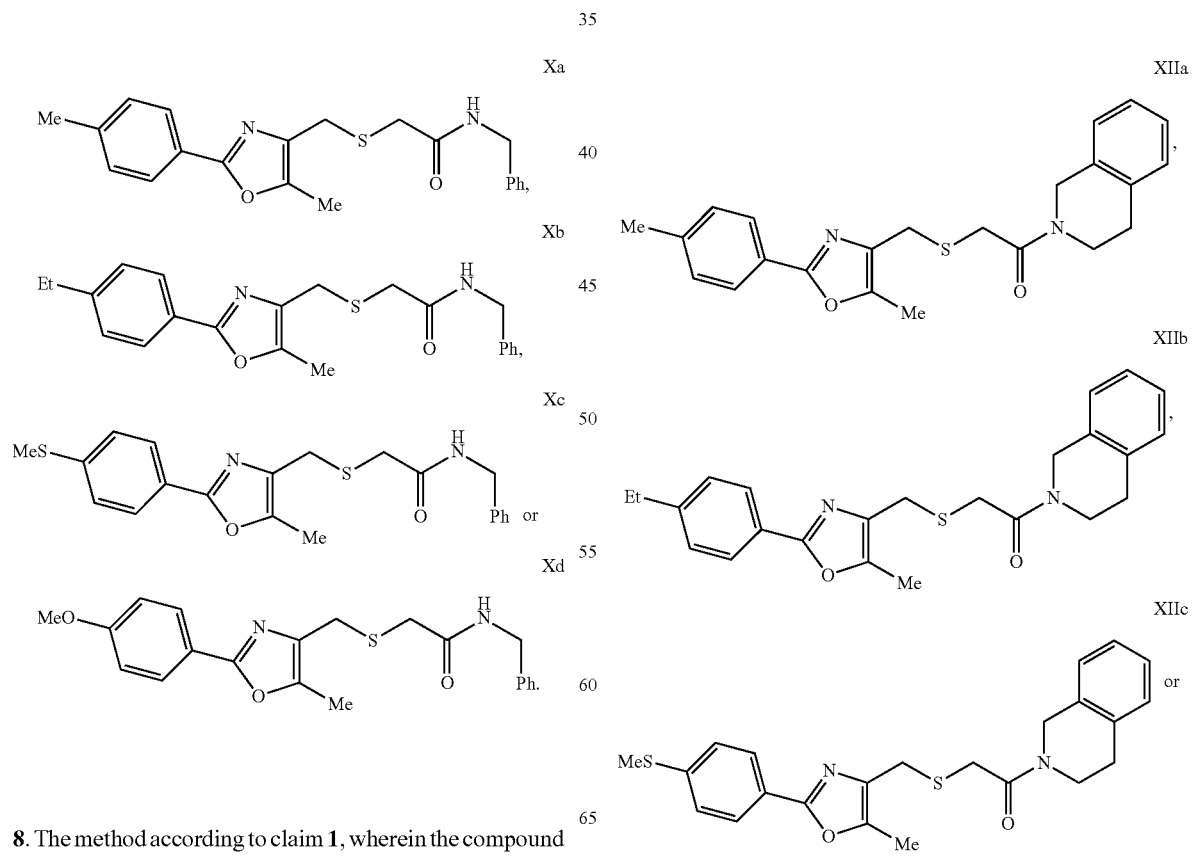
9. The method according to claim 1, wherein the compound is according to formula XIIa, XIIb, XIIc or XIId:

-continued

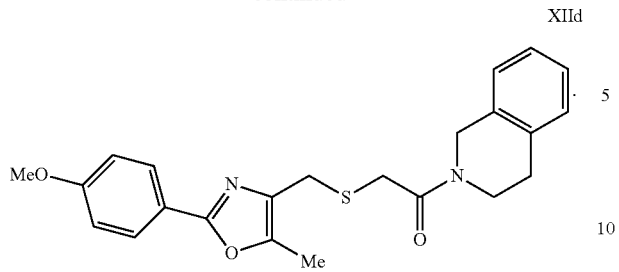

XIId

10. The method according to claim 1, wherein the compound is according to formula XIIIa, XIIIb, XIIIc or XIIId:

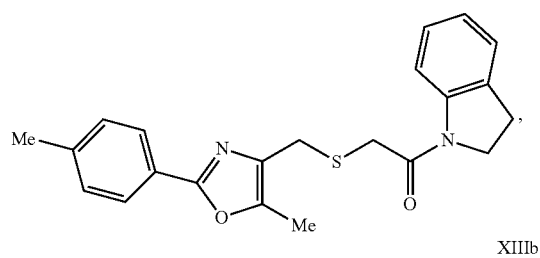

XIIIa

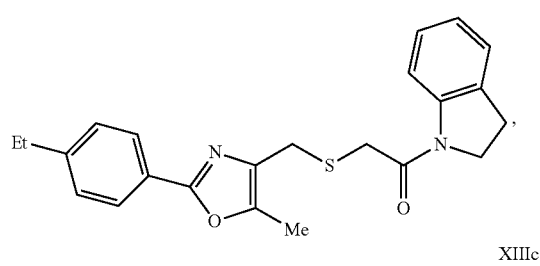

XIIIb

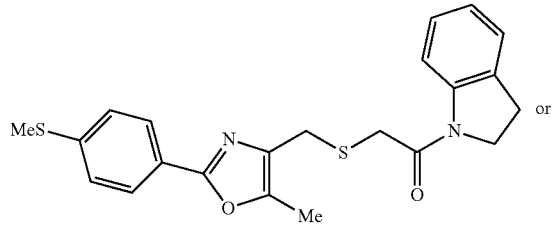

XIIIc

-continued

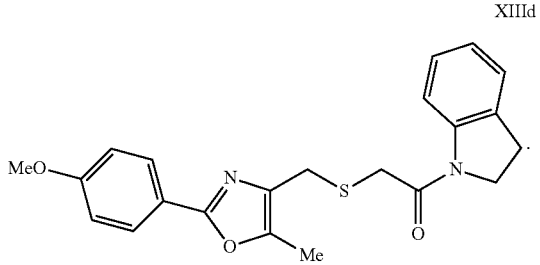

XIIId

11. The method according to claim 1, wherein the compound is selected from Tables 1-6.

12. The method of claim 1, wherein the cancer is prostate cancer, head and neck cancer, lung cancer, gastric cancer, mesothelioma, Barrett's esophagus, synovial sarcoma, cervical cancer, endometrial ovarian cancer, Wilm's tumor, bladder cancer or leukemia.

13. The method of claim 12, wherein the lung cancer is non-small cell lung cancer.

14. The method according to claim 2, wherein $L^1$ is S.

15. The method according to claim 2, wherein the subscript m1 is 1 or 2.

16. The method according to claim 2, wherein each of $R^{2a}$, $R^{2b}$, $R^{2c}$ and $R^{2d}$ is H.

17. The method according to claim 2, wherein $R^1$ is halo or Me.

18. The method according to claim 2, wherein n is 1 or 2; and $R^4$ is independently alkyl, alkoxy, haloalkyl, or halo.

19. The method according to claim 3, wherein one of $R^{3a}$ and $R^{3b}$ is substituted or unsubstituted alkyl, substituted or unsubstituted benzyl, substituted or unsubstituted phenethyl, substituted or unsubstituted cycloalkyl; and the other is H; or $R^{3a}$ and $R^{3b}$ join together to form a heterocycloalkyl or heteroaryl ring.

* * * * *